US009777332B2

(12) United States Patent
Campana et al.

(10) Patent No.: US 9,777,332 B2
(45) Date of Patent: Oct. 3, 2017

(54) METHODS AND COMPOSITIONS FOR IDENTIFYING MINIMAL RESIDUAL DISEASE IN ACUTE LYMPHOBLASTIC LEUKEMIA

(75) Inventors: Dario Campana, Kent Vale (SG); Elaine Coustan-Smith, Kent Vale (SG)

(73) Assignee: St. Jude Children's Research Hospital, Memphis, TN (US)

( * ) Notice: Subject to any disclaimer, the term of this patent is extended or adjusted under 35 U.S.C. 154(b) by 233 days.

(21) Appl. No.: 14/005,921

(22) PCT Filed: Mar. 14, 2012

(86) PCT No.: PCT/US2012/028993
§ 371 (c)(1),
(2), (4) Date: Oct. 2, 2013

(87) PCT Pub. No.: WO2012/134813
PCT Pub. Date: Oct. 4, 2012

(65) Prior Publication Data
US 2014/0148354 A1    May 29, 2014

Related U.S. Application Data

(60) Provisional application No. 61/470,056, filed on Mar. 31, 2011.

(51) Int. Cl.
C40B 30/04 (2006.01)
C40B 30/00 (2006.01)
C12Q 1/68 (2006.01)
G01N 33/574 (2006.01)

(52) U.S. Cl.
CPC ..... *C12Q 1/6886* (2013.01); *G01N 33/57426* (2013.01); *G01N 2333/705* (2013.01)

(58) Field of Classification Search
CPC .................................................. C12Q 1/6886
USPC ............................................................. 506/9
See application file for complete search history.

(56) References Cited

U.S. PATENT DOCUMENTS

| 2006/0240434 A1 | 10/2006 | Gabert et al. |
| 2007/0020670 A1 | 1/2007 | Loken et al. |
| 2012/0202202 A1 | 8/2012 | Wang et al. |

FOREIGN PATENT DOCUMENTS

| BR | WO 2010140885 A1 * | 12/2010 | ......... G01N 33/5094 |
| EP | 2 259 065 A1 | 8/2010 | |
| WO | WO 2007/008759 A2 | 1/2007 | |
| WO | WO 2010140885 A1 * | 12/2010 | |

OTHER PUBLICATIONS

Campana et al., Immunophenotyping of Leukemia, Journal of Immunological Methods, 2000, 243, 59-74.*
Campana, Minimal Residual Disease in Acute Lymphoblastic Leukemia, Hematology, 2010, 7-12.*
US Patent and Trademark Office (USPTO), Examples, Nature-Based Products, Interim Guidance, 2014, 1-17.*
Opinion of the United States Court of Appeals for the Federal Circuit, *Genetic Technologies Limited v. Merial LLC*, 2016, 1-20.*
Opinion of the United States Court of Appeals for the Federal Circuit, *Ariosa Diagnostics, Inc. v. Sequenom, Inc.*, 2015, 1-21.*
Stetler-Stevenson et al., Chapter 3, Flow Cytometry, Diagnostic Tehcniques in Hematological Malignancies, W. Erber ed., 2010, 51-63.*
Coustan-Smith, Elaine, et al., "Immunologic minimal residual diease detection in acute lymphoblastic leukemia: A comparative approach to molecular testing," *Best Practice & Research Clinical Haematology*, 2010, vol. 23(3), pp. 347-358.
Kato, K., et al., "Antibody arrays for quantitative immunophenotyping," *Biomaterials*, 2007, vol. 28(6), pp. 1289-1297.
Shehata, M., et al., "Partial Characterization and In Vitro Expansion of Putative CLL Precursor/Stem Cells Which Are Dependent on Bone Marrow Microenvironment for Survival," *Blood (Ash Annual Meeting Abstracts)*, 2010, vol. 116(21), pp. 1-2, Abstract 2433.

* cited by examiner

*Primary Examiner* — Amy M Bunker
(74) *Attorney, Agent, or Firm* — Womble Carlyle Sandridge & Rice LLP

(57) ABSTRACT

This invention provides methods and kits for diagnosing, ascertaining the clinical course of minimal residual disease associated with acute lymphoblastic leukemia (ALL). Specifically the invention provides methods and kits useful in the diagnosis and determination of clinical parameters associated with diseases associated with ALL based on patterns of surface marker expression unique to ALL.

10 Claims, 6 Drawing Sheets

METHODS AND COMPOSITIONS FOR IDENTIFYING MINIMAL RESIDUAL DISEASE IN ACUTE LYMPHOBLASTIC LEUKEMIA

CROSS-REFERENCE TO RELATED APPLICATIONS

This application is a 35 U.S.C. §273 U.S. National Stage of International Application PCT/US2012/028993 filed Mar. 14, 2012, which designates the U.S. and was published by the International Bureau in English on Oct. 4, 2012, and which claims the benefit of U.S. Provisional Application No. 61/470,056, filed Mar. 31, 2011, both of which are hereby incorporated by reference in their entirety.

STATEMENT REGARDING FEDERALLY SPONSORED RESEARCH OR DEVELOPMENT

This invention was made with support under United States Government Grant CA60419 awarded by the National Institutes of Health. The United States Government has certain rights in this invention.

REFERENCE TO SEQUENCE LISTING SUBMITTED ELECTRONICALLY

The official copy of the sequence listing is submitted electronically via EFS-Web as an ASCII formatted sequence listing with a file named 415313SEQLIST.txt, created on Mar. 6, 2012, and having a size of 225,858 bytes and is filed concurrently with the specification. The sequence listing contained in this ASCII formatted document is part of the specification and is herein incorporated by reference in its entirety.

FIELD OF THE INVENTION

This invention relates generally to the detection of minimal residual disease in patients with acute lymphoblastic leukemia (ALL) and, more specifically, to a method to improve minimal residual disease monitoring for risk assignment and selection of therapeutic regimens.

BACKGROUND OF THE INVENTION

Leukemia relapse is the major cause of treatment failure for patients with acute lymphoblastic leukemia (ALL) (Pui et al. (2009) *N Engl J Med.* 360:2730-2741; Gokbuget and Hoelzer (2009) *Semin. Hematol.* 46:64-75; and Faderl et al. (2010) *Cancer.* 116:1165-1176). Relapse originates from leukemic cells that are resistant to chemotherapy but become undetectable after initial treatment in most cases. Nevertheless, methods more sensitive than microscopic examination can demonstrate leukemic cells in a proportion of samples with no morphologic evidence of leukemia, a finding termed "minimal residual disease (MRD)" (Campana (2009) *Hematol. Oncol Clin North Am.* 23:1083-98, vii).

MRD is currently the most powerful prognostic indicator in childhood ALL (Cave et al. (1998) *N Engl J Med.* 339:591-598; Coustan-Smith et al. (1998) *Lancet.* 351:550-554; van Dongen et al. (1998) *Lancet.* 352:1731-1738; Coustan-Smith et al. (2000) *Blood.* 96:2691-2696; Dworzak et al. (2002) *Blood.* 99:1952-1958; Nyvold et al. (2002) *Blood.* 99:1253-1258; Zhou et al. (2007) *Blood.* 110:1607-1611; Borowitz et al. (2008) *Blood.* 111:5477-5485. Basso et al. (2009) *J Clin Oncol.* 27:5168-5174; Canter et al. (2010) *Blood.* 115:3206-3214; Stow et al. (2010) *Blood.* 115:4657-4663). There is strong evidence supporting its prognostic significance in adult ALL (Krampera et al. (2003) *Br J Haematol.* 120:74-79; Vidriales, et al. (2003) *Blood.* 101: 4695-4700; Raff et al. (2007) *Blood.* 109:910-915; Holowiecki et al. (2008) *Br. J. Haematol.* 142:227-237; Bassan et al. (2009) *Blood.* 113:4153-4162).

Thus, MRD monitoring has been introduced into many contemporary treatment protocols for risk assignment and selection of therapeutic regimens (Pui et al. (2009) *N Engl J Med.* 360:2730-2741; Gokbuget and Hoelzer. (2009) *Semin. Hematol.* 46:64-75; and Faderl et al. (2010) *Cancer.* 116:1165-1176). MRD measurements are also clinically useful in patients with relapsed ALL who achieve a second remission (Coustan-Smith et al. (2004) *Leukemia* 18:499-504; Paganin et al. (2008) *Leukemia.* 22:2193-2200; Raetz et al. (2008) *J Clin. Oncol.* 26:3971-3978), can help optimize the timing of hematopoietic stem cell transplantation (Bader et al. (2009) *J Clin Oncol.* 27:377-384), and guide decisions about donor lymphocyte infusion post-transplant (Lankester et al. (2010) *Leukemia.* 24:1462-1469).

Among methods for detecting MRD in ALL, PCR amplification of antigen-receptor genes has proven to be valuable and has been extensively standardized (Bruggemann, M., et al. (2010) *Leukemia.* 24:521-535) but the technical expertise and instrumentation required limit its application to specialized centers. PCR amplification of fusion transcripts may also provide useful clinical information but its applicability in ALL is restricted by the fact that molecular targets currently adaptable to routine MRD studies are present in only a minority of patients. Id. Flow cytometric detection of leukemia-specific markers has been shown to predict outcome in numerous clinical correlative studies (Coustan-Smith et al. (1998) *Lancet.* 351:550-554; Coustan-Smith et al. (2000) *Blood.* 96:2691-2696; Dworzak et al. (2002) *Blood.* 99:1952-1958; Borowitz, et al. (2008) *Blood.* 111: 5477-5485; Basso et al. (2009) *J Clin Oncol.* 27:5168-5174; Krampera et al. (2003) *Br J Haematol* 120:74-79; Vidriales et al. (2003) *Blood* 101:4695-4700; Holowiecki et al. (2008) *Br. J. Haematol.* 142:227-237). The method holds potential for wider applicability than molecular techniques because flow cytometric methods for leukemia diagnosis are already established at most cancer centers worldwide (Campana (2009) *Hematol. Oncol Clin North Am.* 23:1083-98, vii).

MRD studies by flow cytometry rely on panels of antibodies to define unique immunophenotypic signatures of leukemic cells which must distinguish leukemic blasts from their normal counterparts, the CD19+ CD10+ lymphoid progenitors of the bone marrow ("hematogones") (Campana (2009) *Hematol. Oncol Clin North Am.* 23:1083-98, vii; Bruggemann et al. (2010) *Leukemia.* 24:521-535; McKenna et al. (2001) *Blood.* 98:2498-2507; Lucio et al. (2001) *Leukemia.* 15:1185-1192).

Standard four-color flow cytometry can detect one leukemic cell in up to 10,000 normal bone marrow or peripheral blood cells but this task typically requires considerable interpretative expertise. Therefore, identification of new leukemia markers that are easily detectable and are stably expressed in a large proportion of ALL cases could simplify the application of MRD studies, and help extend their benefit to all patients and enhance the sensitivity of MRD detection.

BRIEF SUMMARY OF THE INVENTION

Methods and compositions are provided for identifying patients with minimal residual disease. The diagnostic methods generally comprise contacting a specimen from a patient with a plurality of probes, wherein each of said probes specifically binds to a distinct marker, wherein a first probe specifically binds to CD19, a second probe specifically binds to CD10, a third probe specifically binds to CD34, a fourth probe specifically binds to CD45, and at least two additional probes that specifically binds to any two of CD38, CD24, CD44, CD58, CD73, CD15, CD200, CD66c, CD123, CD86, CD72, CD13, CD33, CD79b, HSPB1, BCL2, CD164, CD304, CD97, CD99, CD102, or CD300a. The complex formed between each of the probes and their marker is detected and a value is generated corresponding to an expression level of each of said marker. An expression profile is generated by combining the expression level values. In such methods, the expression of CD19, CD10, CD34 and CD45 and a modulated level of at least two of CD38, CD24, CD44, CD58, CD73, CD15, CD200, CD66c, CD123, CD86, CD72, CD13, CD33, CD79b, HSPB1, BCL2, CD164, CD304, CD97, CD99, CD102, or CD300a relative to a normal control is indicative of minimal residual disease in acute lymphoblastic leukemia.

Additional methods for diagnosing minimal residual disease in a subject further include obtaining a specimen from a subject. The specimen is contacted with a plurality of probes, wherein each of the probes specifically binds to a distinct marker, wherein a first probe specifically binds to CD19 and a second probe specifically binds to CD10. A CD19+/CD10+ cell is isolated from the specimen. The expression level of at least two gene products expressed in said CD19+/CD10+ cell is determined, wherein the at least two gene products encode CD38, CD24, CD44, CD58, CD73, CD15, CD200, CD66c, CD123, CD86, CD72, CD13, CD33, CD79b, HSPB1, BCL2, CD164, CD304, CD97, CD99, CD102 or CD300a. An expression profile is generated by combining the values generated of the expression levels of the indicated markers. The expression of CD19 and CD10 and a modulated level of at least two gene products encoding CD38, CD24, CD44, CD58, CD73, CD15, CD200, CD66c, CD123, CD86, CD72, CD13, CD33, CD79b, HSPB1, BCL2, CD164, CD304, CD97, CD99, CD102, or CD300a relative to a normal control is indicative of minimal residual disease in acute lymphoblastic leukemia.

Kits for practicing the diagnostic methods of the invention are also provided, as well as, kits for evaluating the efficacy of a particular therapy for a subject with ALL.

DETAILED DESCRIPTION OF THE INVENTION

Figure 1:
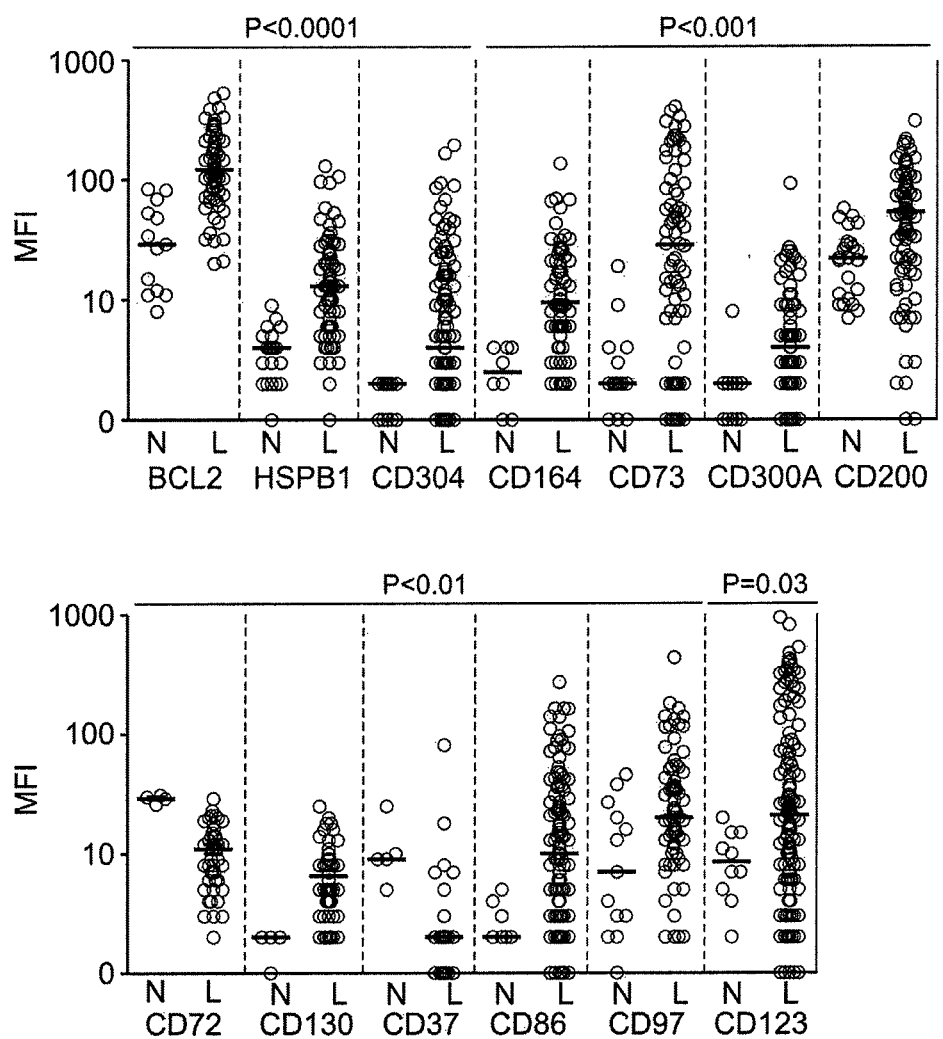
FIG. 1 shows a comparison of the relative mean fluorescence intensity of immunophenotypic markers expressed in ALL cells and in CD19$^+$CD10$^+$ B-cell progenitors as determined by flow cytometry.

The present invention will now be described more fully hereinafter with reference to the accompanying drawings, in which some, but not all embodiments of the inventions are shown. Indeed, these inventions may be embodied in many different forms and should not be construed as limited to the embodiments set forth herein; rather, these embodiments are provided so that this disclosure will satisfy applicable legal requirements. Like numbers refer to like elements throughout.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

Methods and compositions are provided for identifying patients with minimal residual disease in acute lymphoblastic leukemia (ALL). As discussed in further detail herein, genes expressed at different levels in ALL cells were compared to their normal counterparts. Using genome-wide gene analysis, expression profiles of 270 cases of newly diagnosed B-lineage ALL were compared to expression profiles of highly purified normal CD19+ CD10+ cells. Genes that had a substantially abnormal expression in leukemic cells were tested by flow cytometry to assess levels of protein expression. Promising molecules were examined in detail for optimization as MRD markers. Use of newly identified markers allows for the identification of unique leukemia profiles in ALL patients. Moreover, the compositions and methods disclosed herein allow for the detection of 1 leukemic cell in 100,000 normal bone marrow cells, thus significantly enhancing the power of flow cytometric monitoring of MRD in ALL.

Acute Lymphocytic Leukemia and Disease

Methods and compositions are provided herein directed to detection of minimal residual disease in acute B-lymphoblastic leukemia.

In specific methods, a specimen is taken from a subject with cancer, wherein the cancer is leukemia. Leukemia is a cancer of the bone marrow and blood. The four major types of leukemia are acute myeloid leukemia (AML), chronic myeloid leukemia (CML), acute lymphoblastic leukemia (ALL) and chronic lymphocytic leukemia (CLL). Acute leukemia is a rapidly progressing cancer that produces blood cells that are not fully developed. Acute lymphocytic leukemia is often referred to as "acute lymphoblastic leukemia" because the leukemic cell that replaces the normal marrow cell is the (leukemic) lymphoblast. There are two principal ALL subtypes including a) the B-lymphocyte subtype—identified by finding cell surface markers on the leukemic blast cells common to normal B lymphocytes; and b) the T lymphocyte subtypes—identified by finding cell surface markers on the leukemic blast cells common to normal T lymphocytes. About 15% of cases are of the T-lymphocyte, and 85% of cases are of the precursor B-cell subtype.

The effects of ALL include uncontrolled and exaggerated growth and accumulation of lymphoblasts which fail to function as normal blood cells, and blockage of the production of normal marrow cells. The lack of production of normal marrow cells often leads to a deficiency of red cells (anemia), platelets (thrombocytopenia) and normal white cells, especially neutrophils (neutropenia), in the blood. ALL progresses rapidly without treatment, therefore the methods and compositions provided herein can be employed to allow for the early detection of acute lymphocytic leukemia.

"Diagnosing ALL" and/or "detecting minimal residual disease (MRD)" or "diagnosing minimal residual disease (MRD)" is intended to include, for example, diagnosing or detecting the presence of acute lymphoblastic leukemia (ALL) by identifying or detecting cells and/or cell products in specimens that are indicative of ALL, monitoring the progression of the disease, monitoring and/or detecting the recurrence of ALL disease in patients who had been previously treated for ALL, and monitoring and/or detecting minimal residual disease. The terms "diagnosing," "detecting," and "identifying" when used with acute lymphoblastic leukemia or minimal residual disease (MRD) are used interchangeably herein to refer to the identifying or detecting cells and/or cell products in specimens that are indicative of disease.

One method disclosed herein is directed to monitoring remission of leukemia. Remission is defined as the absence of outward signs of cancer, or in the case of ALL, the absence of detectable cancer cells in the body after a course of therapy. Remission in ALL can be characterized, for example, as a lack of detectable abnormal cells in the blood, bone marrow, and/or cerebrospinal fluid, and less than 5% blast cells in the bone marrow. Embodiments of the invention seek to detect cancer cells in instances where there is a relatively minimal amount of disease (minimal residual disease (MDR)) by phenotypic analysis. Standard detection methods define minimal residual disease as an incidence of less than one leukemic cell in 10,000 normal bone marrow/blood cells. The methods and compositions of the instant invention can detect minimal residual disease with an incidence of less than one in 100,000 cells.

Most ALL patients achieve at least an initial remission. However, some patients have residual leukemic cells in their marrow. Other patients achieve remission then "relapse" wherein they have a decrease in normal blood cells and a return of leukemia cells in the marrow. Embodiments of the invention detect leukemia and can help evaluate the risk for relapse after initial treatment. In addition to the detection of evidence of minimal residual disease, embodiments of the invention can further help to evaluate treatment regimens. For example, the detection and characterization of MRD can be indicative of the efficacy of certain treatment regimes, e.g., stem cell transplant.

In other embodiments of the invention, detection or diagnosing MRD can help determine whether additional treatment may be necessary. One of skill in the art will recognize that in these methods the term "therapy" can include any therapy for treating ALL, including but not limited to chemotherapy, radiation therapy, stem cell transplantation, and biological therapy (e.g., monoclonal antibody therapy). Depending on the subtype, specific drugs or drug combinations, drug dosages, duration of treatment, and other types of treatment, may be indicated to achieve optimal results.

In still other embodiments of the invention, methods for evaluating the efficacy of a therapy for treating ALL in a subject are provided. Embodiments of the invention can also be used to test specimens taken from a subject during the course of therapy to monitor the effects of treatment. Such methods typically comprise comparing the level of expression of a plurality of markers of the invention in a first specimen procured prior to the initiation of therapy with that from a second sample obtained following administration of at least a portion of the therapy. In some embodiments, a significantly lower and/or an undetectable level of expression of a marker in the second specimen relative to that of the first specimen obtained prior to the initiation of the therapy can be a positive indication of the efficacy of the therapy. In other embodiments, a significantly higher level of expression of a marker in the second sample can be a negative indication of the efficacy of the therapy. A positive indication of the efficacy of the therapy can mean that the therapy is producing beneficial results in the treatment of ALL and no minimal residual disease is detected. A negative indication of the efficacy of the therapy can mean that the therapy is not having beneficial effects with respect to treatment of ALL and minimal residual disease is detected.

Specimens from Subjects

In embodiments of the invention, the method comprises obtaining a "specimen" from a subject. The term "specimen" is intended to include blood cells, bone marrow cells, and cellular products that are derived from blood and bone marrow cells. Cellular products can include, but are not limited to, expressed proteins, expressed RNA, and DNA. In embodiments of the invention, a specimen can include cells derived from a variety of sources including, but not limited to, single cells, a collection of cells, tissue, cell culture, bone marrow, blood, or other bodily fluids. A tissue or cell source may include a tissue biopsy sample, a cell sorted population, cell culture, or a single cell. Sources for the specimen of the present invention include cells from peripheral blood or bone marrow, such as blast cells from peripheral blood or bone marrow. The term "specimen" can be used interchangeably with the term "sample" or "patient sample."

A specimen may be processed in another embodiment to release or otherwise make available a nucleic acid or a protein for detection as described herein. Such processing may include, in one embodiment, steps of nucleic acid manipulation, e.g., preparing a cDNA by reverse transcription of RNA from the specimen. Thus, the nucleic acid to be amplified in one embodiment by the methods of the invention may be DNA or RNA. Isolation of protein, RNA, and DNA from the aforementioned sources is known to those of skill in the art, and is discussed herein.

In one embodiment, the method comprises obtaining a peripheral blood sample from a subject and analyzing the expression level of specific markers in leukocytes from the blood sample taken from the subject. To do blood tests, blood samples are generally taken from a vein in the subject's arm.

In another embodiment, the method comprises obtaining a bone marrow sample from a subject and analyzing the expression level of specific markers combinations in leukocytes from the blood sample taken from the subject. Specimens of marrow cells are obtained by bone marrow aspiration and biopsy.

The obtaining of a specimen uses methods well known in the art, as is the means to analyze leukocyte populations. For example, leukocyte populations can be prepared from whole blood by differential centrifugation, or for example, by density gradient centrifugation. The method can be conducted on leukocytes in blood samples which have not undergone any leukocyte enrichment, on whole blood samples, or where red blood cells have been lysed. In other embodiments the method can be conducted on enriched and purified subpopulations of cells, using methods well known in the art.

Analyzing Specimens

In embodiments of the invention, the method comprises "contacting" the specimen with a plurality of probes. In one embodiment, the term "contacting" is in reference to probes that are antibodies and generally referring to methods of "cell staining." In a method of the invention, an antibody is added to a specimen and the antibody recognizes and binds to a specific protein for example, on the surface of cells in the specimen. A complex is thereby formed between the probe and the expressed protein. The complex can be detected and visualized by various techniques, as will be discussed herein. Combinations of antibody probes can be collectively added to a specimen and thereby "stain" the cell for later analysis by visualization with a flow cytometer or microscope, for example. One of skill in the art could determine whether a cell expressed a specific protein based on the level of antibody that bound to the cell using standard methods.

In embodiments of the invention the term "contacting" in reference to probes that are nucleic acids, refers to methods of detecting expression of an mRNA of interest in a specimen. A detectable complex can be formed when a nucleic acid probe specific to an expressed gene of interest hybridizes and binds an mRNA/cDNA expressed by cells in a specimen. One of skill in the art could determine whether a cell expressed a specific mRNA based on the level of detectable PCR product, for example, using standard methods.

Detecting Expression of Markers for Minimal Residual Disease

As used herein a "marker" can be any gene or protein whose level of expression in a tissue or cell is used comparatively to evaluate the level of expression to that of a normal or healthy cell or tissue. In particular embodiments of the invention, antibodies are used to detect marker expression at the protein level. In other aspects of the invention, marker expression is detected at the nucleic acid level.

Markers of the invention may be referred to herein interchangeably as "markers," "immunophenotypic markers," "leukemia-associated phenotypic markers," "phenotypic markers," or "cell markers." "Leukemia-associated markers" can refer to particular combinations of markers used to diagnosis a particular leukemia, for example, an expression profile of different combinations of markers may be particular to a patient with ALL. In particular embodiments of the invention, markers can refer to "antigenic markers," "antigens," or "cell surface antigens," referring to proteins that are expressed on the cell surface. Combinations of markers of the invention are selective for ALL, and specifically minimal residual disease.

The various markers employed in the methods and compositions disclosed herein, can have a modulated level of expression when compared to an appropriate control. Alternatively, a given marker need not show a modulated level of expression, but rather must only be expressed in the given sample. Specific expression profiles of the given marker combinations that are predictive of the various states disclosed herein are discussed in further detail elsewhere herein.

As used herein, a "modulated level" of a marker can comprise any statistically significant increase (overexpression) or decrease (underexpression) of the given marker when compared to an appropriate control. The modulated level can be assayed by monitoring either the concentration of and/or activity of the marker polypeptide and/or the level of the mRNA encoding the marker polypeptide. In general, a modulate level of marker can include either an increase or a decrease of at least at least 1%, 5%, 10%, 20%, 30%, 40%, 50%, 60%, 70%, 80%, 90% or higher relative to an appropriate control.

By "overexpressed" it is intended that the marker of interest is overexpressed in ALL cells but is not overexpressed in conditions classified as nonmalignant, benign, and/or any conditions that are not considered to be indicative of clinical disease. In general, an overexpressed marker can include any statistically significant increase in expression when compared to an appropriate control, including for example, an increase of at least at least 1%, 5%, 10%, 20%, 30%, 40%, 50%, 60%, 70%, 80%, 90% or higher relative to an appropriate control.

By "underexpressed" it is intended that the marker of interest is underexpressed in ALL cells but is not underexpressed in conditions classified as nonmalignant, benign, and/or any conditions that are not considered to be indicative of clinical disease. Thus, detection of various combinations of markers of the invention permit the differentiation of specimens indicative of an increased likelihood of minimal residual disease associated with ALL as compared to those of normal control specimens that are indicative of nonmalignant and benign proliferation.

The level of expression of a particular marker that is sufficient to constitute "overexpression" will vary depending on the specific marker used. In particular embodiments of the invention, a "threshold level" of expression over a normal control is established for a particular marker, wherein expression levels above this value are deemed overexpression. Overexpression of a particular marker can refer to an increase in the percentage of a population detected as expressing a particular marker or marker combination. Overexpression can also refer to the level of expression on a population of cells as detected by an increase in the mean fluorescence intensity (MFI). For example, in one embodiment of the invention, "overexpression" may be determined if the marker MFI for the specimen is at least three-fold above the normal control, wherein a three-fold increase in MFI is the "threshold level." In other embodiments, an overexpressed marker can include any statistically significant decrease in expression when compared to an appropriate control, including for example, an increase of at least at least 1%, 5%, 10%, 20%, 30%, 40%, 50%, 60%, 70%, 80%, 90% or higher relative to an appropriate control or at least at least a 1 fold, 2 fold, 3 fold, 4 fold, 5 fold, 6 fold, 10 fold or higher expression level relative to an appropriate control.

The level of expression of a particular marker that is sufficient to constitute "underexpression" will vary depending on the specific marker used. In particular embodiments of the invention, a "threshold level" of expression is established for a particular marker, wherein expression levels below this value are deemed underexpression. Underexpression of a particular marker can refer to a decrease in the percentage of a population detected as expressing a particular marker or marker combination. Underexpression can also refer to the level of expression on a population of cells as detected by a decrease in the mean fluorescence intensity (MFI). For example, in one embodiment of the invention, "underexpression" may be determined for that particular marker if the marker MFI for the specimen is less than the normal control by at least half, wherein a 50% reduction MFI is the "threshold level". In other embodiments, an underexpressed marker can include any statistically significant decrease in expression when compared to an appropriate control, including for example, a decrease of at least at least 1%, 5%, 10%, 20%, 30%, 40%, 50%, 60%, 70%, 80%, 90% or lower relative to an appropriate control or at least at least a 1 fold, 2 fold, 3 fold, 4 fold, 5 fold, 6 fold, 10 fold or lower expression level relative to an appropriate control.

The methods of the invention comprise diagnosing minimal residual disease in a sample taken from a subject by detecting the expression of a plurality of markers that are modulated in ALL. Markers CD44, BCL2, HSPB1, CD73, CD24, CD123, CD72, CD86, CD200, CD79b, CD164, CD304, CD97, CD102, CD99, CD300a, CD130, PBX1, CTNNA1, ITGB7, CD69, and CD49f were analyzed and found differentially expressed in up to 81.4% of ALL cases. Embodiments of the invention can include, but are not limited to, compositions and methods related to new markers for the detection of minimal residual disease (MRD) comprising: CD44, BCL2, HSPB1, CD73, CD24, CD123, CD72, CD86, CD200, CD79b, CD164, CD304, CD97, CD102, CD99, CD300a, CD130, PBX1, CTNNA1, ITGB7, CD69, and CD49f.

In yet other embodiments, diagnosing minimal residual disease in a sample taken from a subject can comprise the detection of combinations of markers including, but not limited to markers CD19, CD10, CD34, and CD45, in combination with markers comprising: CD44, BCL2, HSPB1, CD73, CD24, CD123, CD72, CD86, CD200, CD79b, CD164, CD304, CD97, CD102, CD99, CD300a, CD130, PBX1, CTNNA1, ITGB7, CD69, or CD49f.

In yet other embodiments, diagnosing minimal residual disease in a sample taken from a subject can comprise the detection of combinations of markers including, but not limited to: CD19, CD10, CD34, and CD45, in combination with marker comprising: CD38, CD24, CD44, CD58, CD73, CD15, CD200, CD66c, CD123, CD86, CD72, CD13, CD33, CD79b, HSPB1, BCL2, CD164, CD304, CD97, CD99, CD102 or CD300a.

The methods of the invention can comprise MRD detection by flow cytometry with preferred combinations of probes to specific markers. MRD detection can be combined with at least 4 different probes, and can include in some embodiments at least 5, 6, 7, 8, 9, 10, 11, and 12 different probes. When incorporated with at least 6-probes, the new marker combinations afford the detection of one leukemic cell amongst $10^5$ bone marrow cells. These new markers allow MRD studies in all B-lineage ALL patients, and increase the sensitivity of detecting minimal residual disease.

Probes to Detect Markers of Minimal Residual Disease

The term "probe" refers to any molecule that is capable of specifically binding to an intended target molecule, for example, a nucleotide transcript or a protein encoded by a marker gene. RNA/DNA probes can be synthesized by one of skill in the art, or derived from appropriate biological preparations. Likewise, antibody probes to specific targets can be generated by one of skill in the art, or derived from appropriate sources. Probes may be specifically designed to be labeled. Examples of molecules that can be utilized as probes include, but are not limited to, RNA, DNA, proteins, antibodies, and organic molecules.

By "specifically binds," it is generally meant that an antibody binds to an epitope via its antigen binding domain, and that the binding entails some complementarity between the antigen binding domain and the epitope. An epitope is a site on an antigen or marker where the antibody binds via its variable region. The epitope is therefore a part of the antigen or marker, but the epitope is only a portion of the marker recognized by the antibody. According to this definition, an antibody is said to "specifically bind" to an epitope or have "antigen specificity" when it binds to that epitope, via its antigen binding domain more readily than it would bind to a random, unrelated epitope. As used herein, therefore, "specifically binds" is used interchangeably with recognition of a defined epitope on an antigen or marker, or any epitope contained in the antigen or marker. For example the term "specifically binds" when used in conjunction with a particular antibody is used to indicate that there is recognition of a certain epitope of the antigen and the interaction between the antibody and epitope is a non-random interaction indicative of the presence or "expression" of the certain epitope. The term "specifically binds" when used in conjunction with a particular marker is used to indicate that there is recognition of a certain antigen or marker and the interaction between the antibody and antigen or marker is a non-random interaction indicative of the presence or "expression" of the certain antigen or marker.

Embodiments of the invention, include methods and kits comprising probes to detect markers and combinations of markers in TABLE 1 comprising genes overexpressed in B-lineage ALL.

Embodiments of the invention, include methods and kits comprising probes to detect markers and combinations of markers in TABLE 2 comprising genes underexpressed in B-lineage ALL.

Embodiments of the invention include methods and kits comprising probes to detect markers and combinations of markers comprising CD44, BCL2, HSPB1, CD73, CD24, CD123, CD72, CD86, CD200, CD79b, CD164, CD304, CD97, CD102, CD99, CD300a, CD130, PBX1, CTNNA1, ITGB7, CD69, or CD49f.

Embodiments of the invention, include methods and kits comprising a plurality of probes to detect markers and combinations of markers comprising CD19, CD10, CD34, and CD45, and any two of CD38, CD24, CD44, CD58, CD73, CD15, CD200, CD66c, CD123, CD86, CD72, CD13, CD33, CD79b, HSPB1, BCL2, CD164, CD304, CD97, CD99, CD102 or CD300a (See TABLE 3).

Embodiments of the invention include methods and kits comprising contacting a specimen with a plurality of probes to detect expression levels of markers comprising CD19, CD10, CD34, and CD45, and any two of CD44, BCL2, HSPB1, CD73, CD24, CD123, CD72, CD86, CD200, CD79b, CD164, CD304, CD97, CD102, CD99, CD300a, CD130, PBX1, CTNNA1, ITGB7, CD69, or CD49f.

In one embodiment of the invention, a method comprises obtaining a specimen from a subject and contacting the specimen with plurality of probes to detect expression levels of markers. As a first step, the specimen is contacted by a plurality of probes to CD19, CD10, CD34 and CD45 wherein a first probe specifically binds to CD19, a second probe specifically binds to CD10, a third probe specifically binds to CD34, and a fourth probe specifically binds to CD45, and at least two additional probes specifically bind to any two of CD38, CD24, CD44, CD58, CD73, CD15, CD200, CD66c, CD123, CD86, CD72, CD13, CD33, CD79b, HSPB1, BCL2, CD164, CD304, CD97, CD99, CD102 or CD300a. As a third step, at least one complex formed between each of said probes and said markers is detected and a value generated, wherein the value corresponds to an expression level of each of said marker. As a fourth step, an expression profile is generated by combining said values generated. The expression profile displaying each of the markers from step one and those selected in step two is compared to a normal control expression profile. The expression of CD19 and CD10, a modulated level of CD34, and CD45, and a modulated level of at least one of CD38, CD24, CD44, CD58, CD73, CD15, CD200, CD66c, CD123, CD86, CD72, CD13, CD33, CD79b, HSPB1, BCL2, CD164, CD304, CD97, CD99, CD102 or CD300a is indicative of minimal residual disease in acute lymphoblastic leukemia.

In yet another embodiment of the invention, the method further comprises contacting the specimen with at least three, four, five, six, seven, or eight additional probes to detect expression levels of markers comprising CD38, CD24, CD44, CD58, CD73, CD15, CD200, CD66c, CD123, CD86, CD72, CD13, CD33, CD79b, HSPB1, BCL2, CD164, CD304, CD97, CD99, CD102 or CD300a.

In another embodiment of the invention, the method further comprises permeabilization of cells in the specimen prior to the contacting the specimen with a probe to detect expression levels of markers comprising CD38, CD24, CD44, CD58, CD73, CD15, CD200, CD66c, CD123, CD86, CD72, CD13, CD33, CD79b, HSPB1, BCL2, CD164, CD304, CD97, CD99, CD102 or CD300a.

In yet another embodiment of the invention, said plurality of probes specifically bind distinct markers comprising: (a) CD10, CD19, CD34, CD45, CD38, CD24, and CD44; (b) CD10, CD19, CD34, CD45, CD38, CD58, and CD44; (c) CD10, CD19, CD34, CD45, CD38, CD73, and CD15; (d) CD10, CD19, CD34, CD45, CD38, CD200, and CD44; (e) CD10, CD19, CD34, CD45, CD66c, CD123, and CD86; (f) CD10, CD19, CD34, CD45, CD72, CD13, and CD33; or (g) CD10, CD19, CD34, CD45, CD79b, HSPB1, and Bcl-2.

In another embodiment of the invention said modulated level comprises the expression of CD34 of CD45.

In yet another embodiment of the invention said modulated level comprises the overexpression of CD44, CD58, CD73, CD200, CD86, HSPB1, BCL2, CD164, CD97, CD99, or CD300a and/or the underexpression of CD38, CD72, or CD79b, relative to a normal control.

Generating Expression Profiles

As used herein, an "expression profile" comprises one or more values corresponding to a measurement of the relative abundance of a gene expression product (i.e., a marker). Such values may include measurements of RNA levels or protein abundance. Thus, an expression profile can comprise values representing the measurement of the transcriptional state or the translational state of the gene. As is known to those of skill in the art, the transcriptional state and translational state are related.

In embodiments of the invention, an "expression profile" of a specimen can include the identities and relative abundance, or "expression level," of the RNA species, especially mRNAs present in populations of cells in the specimen. Preferably, a sufficient fraction or mRNA is used generate an expression profile using combinations of markers predictive of minimal residual disease. An expression profile can be conveniently determined by measuring transcript abundance by any of several existing gene expression technologies.

In embodiments, an "expression profile" of a specimen can include the identities and relative abundance, or "expression level", of the constituent protein species expressed in populations of cells in the specimen. Expression profiles according to the invention comprise one or more values representing the expression level of a gene having differential expression in minimal residual disease as compared to a normal control specimen. Each expression profile can contain a sufficient number of values such that the profile can be used to distinguish samples containing a minimal number of leukemic cells or minimal residual disease as compared to specimens taken from normal controls. In some embodiments, an expression profile can comprise four values. In other embodiments, an expression profile can comprise more than four values corresponding to differentially expressed genes, for example at least 5, 6, 7, 8, 9, 10, 11, or 12 values.

In other embodiments of the invention, an expression profile can comprise values corresponding to mRNA expression levels as detected by nucleic acid probes. In exemplary embodiments, it may be advantageous to use a greater number of probes and therefore analyze the expression of a greater number of genes simultaneously. Therefore, in other embodiments of the invention 10, 20, 30, 40, 50, 60, 70, 80, 90, 100, 120, 130, 140, 150, 160, 170. 180, 190, 200, or >200 probes are reasonable. Embodiments of the invention, can include, but are not limited to, the detection of mRNA expression with probe sets shown in TABLE 1 comprising genes overexpressed in B-lineage ALL. Other embodiments of the invention, can include, but are not limited to, the detection of mRNA expression with probe sets shown in TABLE 2 comprising genes underexpressed in B-lineage ALL.

TABLE 1

Probe sets overexpressed in 25% of more of B-lineage ALL cases (n = 270) as compared to normal bone marrow CD19+CD10+ cells from 4 healthy donors

| probe set ID | CD10+ CD19+ max | CD10+ CD19+ min | ALL max | ALL min | % ALL over expressed | Title | Symbol |
| --- | --- | --- | --- | --- | --- | --- | --- |
| 205270_s_at | 63.1 | 12.7 | 2315.9 | 175.2 | 100.0 | lymphocyte cytosolic protein 2 (SH2 domain containing leukocyte protein of 76 kDa) | LCP2 |
| 213915_at | 23.3 | 7.7 | 3934.2 | 11.6 | 98.1 | natural killer cell group 7 sequence | NKG7 |
| 211745_x_at | 907.2 | 271.5 | 267381.8 | 226.1 | 97.4 | hemoglobin, alpha 1 /// hemoglobin, alpha 1 | HBA1 |
| 214414_x_at | 615.5 | 165.5 | 196027.6 | 18.1 | 97.4 | hemoglobin, alpha 2 /// hemoglobin, alpha 2 | HBA2 |
| 209458_x_at | 1028.1 | 164.7 | 274466.9 | 252.3 | 97.0 | hemoglobin, alpha 1 ///hemoglobin, alpha 2 | HBA1 /// HBA2 |
| 211699_x_at | 795.5 | 176 | 224904.8 | 286.1 | 97.0 | hemoglobin, alpha 1 ///hemoglobin, alpha 2 | HBA1 /// HBA2 |
| 215411_s_at | 280 | 87.6 | 7183.4 | 88.9 | 97.0 | TRAF3 interacting protein 2 | TRAF3IP2 |
| 217414_x_at | 445.7 | 33.4 | 158800.9 | 23.6 | 97.0 | hemoglobin, alpha 2 | HBA2 |
| 209116_x_at | 941.1 | 229.3 | 313970.9 | 235.5 | 96.7 | hemoglobin, beta | HBB |
| 211696_x_at | 1594.2 | 428.4 | 334867.9 | 455.7 | 96.7 | hemoglobin, beta | HBB |
| 204018_x_at | 1005.5 | 299.1 | 283177.3 | 26.8 | 96.7 | hemoglobin, alpha 1 /// hemoglobin, alpha 2 | HBA1 /// HBA2 |
| 212901_s_at | 47.5 | 36.6 | 930.7 | 44.5 | 96.3 | cleavage stimulation factor, 3' pre-RNA, subunit 2, 64 kDa, tau variant | CSTF2T |

TABLE 1-continued

Probe sets overexpressed in 25% of more of B-lineage ALL cases (n = 270) as compared to normal bone marrow CD19+CD10+ cells from 4 healthy donors

| probe set ID | CD10+ CD19+ max | CD10+ CD19+ min | ALL max | ALL min | % ALL over expressed | Title | Symbol |
|---|---|---|---|---|---|---|---|
| 217232_x_at | 1632.4 | 439.5 | 318351.3 | 441.5 | 96.3 | hemoglobin, beta | HBB |
| 212195_at | 166 | 116.4 | 4130.3 | 211.7 | 95.9 | MRNA; cDNA DKFZp564F053 (from clone DKFZp564F053) | — |
| 208469_s_at | 33.4 | 25.9 | 517.3 | 14.1 | 94.8 | palmitoyl-protein thioesterase 2 /// EGF-like-domain, multiple 8 | PPT2 /// EGFL8 |
| 208820_at | 18.3 | 5.4 | 1678 | 6.5 | 94.8 | PTK2 protein tyrosine kinase 2 | PTK2 |
| 212812_at | 247.8 | 122.3 | 13345.6 | 70.7 | 94.8 | CDNA: FLJ22642 fis, clone HSI06970 | — |
| 214617_at | 130.8 | 94.1 | 6399.6 | 159.5 | 94.4 | perforin 1 (pore forming protein) /// perforin 1 (pore forming protein) | PRF1 |
| 204848_x_at | 50.9 | 16.5 | 120790.8 | 19.7 | 94.1 | hemoglobin, gamma A /// hemoglobin, gamma G | HBG1 /// HBG2 |
| 213515_x_at | 356.4 | 139.2 | 88491.2 | 58.9 | 94.1 | hemoglobin, gamma A /// hemoglobin, gamma G | HBG1 /// HBG2 |
| 219243_at | 37.3 | 8.5 | 3807.4 | 14.9 | 93.0 | GTPase, IMAP family member 4 | GIMAP4 |
| 206834_at | 252.4 | 49.8 | 105121.3 | 49.3 | 92.2 | hemoglobin, delta /// hemoglobin, delta | HBD |
| 218805_at | 108.4 | 57.2 | 4940.9 | 80.9 | 92.2 | GTPase, IMAP family member 5 /// GTPase, IMAP family member 5 | GIMAP5 |
| 215806_x_at | 114.2 | 99.1 | 8980 | 33.2 | 92.2 | T cell receptor gamma constant 2 /// T cell receptor gamma variable 9 /// | TRGC2 /// TRGV9 /// |
| 204419_x_at | 277.7 | 152.9 | 124214.1 | 48.5 | 92.2 | hemoglobin, gamma A /// hemoglobin, gamma G | HBG1 /// HBG2 |
| 209200_at | 605.5 | 306.8 | 8617.6 | 49.7 | 92.2 | MADS box transcription enhancer factor 2, polypeptide C (myocyte enhancer factor 2C) | MEF2C |
| 200770_s_at | 62.9 | 33.2 | 793 | 25.7 | 91.5 | laminin, gamma 1 (formerly LAMB2) | LAMC1 |
| 204497_at | 12.9 | 7.2 | 3587.5 | 8.1 | 91.5 | adenylate cyclase 9 | ADCY9 |
| 213095_x_at | 40.2 | 29 | 3845.6 | 28 | 91.5 | allograft inflammatory factor 1 | AIF1 |
| 203745_at | 132.4 | 83.6 | 1181.3 | 77.4 | 90.7 | holocytochrome c synthase (cytochrome c heme-lyase) | HCCS |
| 205950_s_at | 223.3 | 39.9 | 70148.2 | 131 | 90.7 | carbonic anhydrase I | CA1 |
| 210031_at | 60.9 | 26.7 | 4613.9 | 22.6 | 90.7 | CD3Z antigen, zeta polypeptide (TiT3 complex) | CD3Z |
| 208923_at | 349.8 | 238 | 7825.2 | 220.5 | 90.4 | cytoplasmic FMR1 interacting protein 1 | CYFIP1 |
| 212136_at | 369.4 | 317.4 | 3062.7 | 228.2 | 90.4 | ATPase, Ca++ transporting, plasma membrane 4 | ATP2B4 |
| 218589_at | 179.1 | 114.7 | 11915.5 | 71.2 | 90.4 | purinergic receptor P2Y, G-protein coupled, 5 | P2RY5 |
| 220992_s_at | 63.6 | 42.9 | 664.5 | 16.6 | 90.4 | chromosome 1 open reading frame 25 /// chromosome 1 open reading frame 25 | C1orf25 |
| 205898_at | 69.3 | 11.1 | 4165.5 | 6.9 | 90.0 | chemokine (C—X3—C motif) receptor 1 | CX3CR1 |
| 213539_at | 160.4 | 53 | 7872.8 | 89.4 | 90.0 | CD3D antigen, delta polypeptide (TiT3 complex) | CD3D |
| 203685_at | 229 | 149.1 | 5203.8 | 150.1 | 89.6 | B-cell CLL/lymphoma 2 | BCL2 |
| 209813_x_at | 19.8 | 9.6 | 8796.6 | 11.2 | 88.9 | T cell receptor gamma constant 2 /// T cell receptor gamma variable 9 /// | TRGC2 /// TRGV9 /// |
| 205269_at | 99.5 | 58.2 | 1135.6 | 60.5 | 88.5 | lymphocyte cytosolic protein 2 (SH2 domain containing leukocyte protein of 76 kDa) | LCP2 |
| 212560_at | 629 | 507.9 | 13410.1 | 337.8 | 88.1 | chromosome 11 open reading frame 32 | C11orf32 |
| 215051_x_at | 110.9 | 60.4 | 8954.9 | 40.8 | 88.1 | allograft inflammatory factor 1 | AIF1 |
| 218244_at | 284.7 | 193.9 | 2035.2 | 146.7 | 88.1 | nucleolar protein 8 | NOL8 |
| 65585_at | 62.8 | 19.8 | 610.3 | 26.2 | 87.8 | family with sequence similarity 86, member B1 | FAM86B1 |
| 205592_at | 70.1 | 24.9 | 36020.7 | 26.5 | 87.4 | Solute carrier family 4, anion exchanger, member 1 (erythrocyte membrane protein band 3, Diego blood group) | SLC4A1 |
| 215920_s_at | 46.3 | 21.2 | 631 | 9.7 | 87.4 | hypothetical protein LOC283970 /// similar to nuclear pore complex interacting protein | LOC283970 /// LOC440350 |
| 213500_at | 47.6 | 12.2 | 836.8 | 15.8 | 87.0 | Mitochondrial ribosomal protein S22 | MRPS22 |
| 201841_s_at | 302 | 15.6 | 8938.9 | 36.4 | 86.7 | heat shock 27 kDa protein 1 | HSPB1 |
| 215967_s_at | 46.2 | 15.6 | 1629.1 | 15.5 | 86.7 | lymphocyte antigen 9 | LY9 |
| 204774_at | 305.5 | 167.7 | 6766.7 | 297.7 | 86.3 | ecotropic viral integration site 2A | EVI2A |
| 202771_at | 211.8 | 40.7 | 4946.6 | 19.9 | 86.3 | family with sequence similarity 38, member A | FAM38A |
| 217865_at | 188.7 | 14.9 | 3581.1 | 11.3 | 85.9 | ring finger protein 130 | RNF130 |
| 202615_at | 551.3 | 390.3 | 4195 | 16.1 | 85.9 | Guanine nucleotide binding protein (G protein), q polypeptide | GNAQ |
| 219654_at | 160.3 | 106.9 | 4702.9 | 17.2 | 85.9 | protein tyrosine phosphatase-like (proline instead of catalytic arginine), member a | PTPLA |
| 1405j_at | 22 | 5.7 | 2700.9 | 7.6 | 85.6 | chemokine (C-C motif) ligand 5 | CCL5 |
| 200696_s_at | 510.4 | 417 | 11239.7 | 359.9 | 84.8 | gelsolin (amyloidosis, Finnish type) | GSN |
| 204547_at | 19.3 | 5.2 | 885.8 | 4.4 | 84.8 | RAB40B, member RAS oncogene family | RAB40B |
| 209901_x_at | 47.7 | 36.8 | 4211 | 22.6 | 84.8 | allograft inflammatory factor 1 | AIF1 |
| 207643_s_at | 234.7 | 94.4 | 3029.5 | 28 | 84.1 | tumor necrosis factor receptor superfamily, member 1A | TNFRSF1A |
| 210933_s_at | 7.4 | 2.6 | 785.5 | 3.3 | 83.7 | fascin homolog 1, actin-bundling protein (Strongylocentrotus purpuratus) | FSCN1 |
| 211821_x_at | 26.2 | 13.7 | 32574.5 | 6.5 | 83.7 | glycophorin A (includes MN blood group) | GYPA |
| 32625_at | 50.2 | 34.8 | 1977.7 | 13.2 | 83.7 | natriuretic peptide receptor A/guanylate cyclase A (atrionatriuretic peptide receptor A) | NPR1 |
| 203388_at | 365.8 | 102.9 | 3514.3 | 116.3 | 83.3 | arrestin, beta 2 | ARRB2 |
| 203372_s_at | 1002.4 | 316.3 | 13986.4 | 31.5 | 83.3 | suppressor of cytokine signaling 2 | SOCS2 |
| 213541_s_at | 631 | 253.7 | 9628.5 | 89.7 | 82.6 | v-ets erythroblastosis virus E26 oncogene like (avian) | ERG |
| 214181_x_at | 171.8 | 56.6 | 11593.5 | 15.6 | 82.2 | leukocyte specific transcript 1 | LST1 |
| 215633_x_at | 233.3 | 128.3 | 11473.5 | 22.7 | 82.2 | leukocyte specific transcript 1 | LST1 |
| 203373_at | 1943.6 | 895.5 | 26597.2 | 73.1 | 82.2 | suppressor of cytokine signaling 2 | SOCS2 |

TABLE 1-continued

Probe sets overexpressed in 25% of more of B-lineage ALL cases (n = 270) as compared to normal bone marrow CD19+CD10+ cells from 4 healthy donors

| probe set ID | CD10+ CD19+ max | CD10+ CD19+ min | ALL max | ALL min | % ALL over expressed | Title | Symbol |
|---|---|---|---|---|---|---|---|
| 202594_at | 453.3 | 354.8 | 2346.8 | 399.3 | 81.9 | leptin receptor overlapping transcript-like 1 | LEPROTL1 |
| 205173_x_at | 604 | 304.7 | 7457.7 | 227.5 | 81.9 | CD58 antigen, (lymphocyte function-associated antigen 3) | CD58 |
| 214761_at | 244.1 | 157.3 | 3051.9 | 6.8 | 81.9 | zinc finger protein 423 | ZNF423 |
| 201280_s_at | 16.7 | 7.8 | 647.9 | 7.8 | 81.5 | disabled homolog 2, mitogen-responsive phosphoprotein (*Drosophila*) | DAB2 |
| 201906_s_at | 37.3 | 16 | 2193.9 | 12.8 | 81.1 | CTD (carboxy-terminal domain, RNA polymerase II, polypeptide A) small phosphatase-like | CTDSPL |
| 213123_at | 165.8 | 55.4 | 1188.1 | 20.9 | 81.1 | Microfibrillar-associated protein 3 | MFAP3 |
| 201681_s_at | 25.7 | 7.4 | 685.1 | 3.8 | 80.7 | discs, large homolog 5 (*Drosophila*) | DLG5 |
| 203596_s_at | 97.2 | 22.5 | 2083.3 | 34.8 | 80.7 | interferon-induced protein with tetratricopeptide repeats 5 | IFIT5 |
| 209409_at | 203.3 | 102.3 | 2142.6 | 97 | 80.7 | growth factor receptor-bound protein 10 | GRB10 |
| 209933_s_at | 126.1 | 59.1 | 1481.7 | 29.3 | 80.7 | CD300A antigen | CD300A |
| 218831_s_at | 55.9 | 42.5 | 4423.1 | 18.8 | 80.7 | Fc fragment of IgG, receptor, transporter, alpha | FCGRT |
| 218689_at | 42.1 | 20 | 997.9 | 13.5 | 80.4 | Fanconi anemia, complementation group F | FANCF |
| 202910_s_at | 303.4 | 149.2 | 6537 | 31.5 | 80.4 | CD97 antigen | CD97 |
| 216942_s_at | 275.1 | 129.2 | 4763 | 48.2 | 80.4 | CD58 antigen, (lymphocyte function-associated antigen 3) | CD58 |
| 210202_s_at | 141.1 | 45.9 | 2799.5 | 18.1 | 80.4 | bridging integrator 1 | BIN1 |
| 202426_s_at | 12.4 | 10.1 | 1492.4 | 6.3 | 80.0 | retinoid X receptor, alpha | RXRA |
| 209568_s_at | 371.5 | 262.5 | 4854.8 | 163.5 | 80.0 | ral guanine nucleotide dissociation stimulator-like 1 | RGL1 |
| 212298_at | 10.6 | 5.6 | 2155.1 | 3.3 | 80.0 | neuropilin 1 | NRP1 |
| 216050_at | 9.3 | 4.5 | 2263.8 | 0.9 | 80.0 | CDNA: FLJ20931 fis, clone ADSE01282 | — |
| 208010_s_at | 15.4 | 6.4 | 550.2 | 2.9 | 80.0 | protein tyrosine phosphatase, non-receptor type 22 (lymphoid) | PTPN22 |
| 215836_s_at | 220.6 | 114.5 | 4999.1 | 75.2 | 79.6 | protocadherin gamma subfamily A1 | PCDHGA1 |
| 219777_at | 45 | 2.4 | 3845.4 | 1.2 | 79.6 | GTPase, IMAP family member 6 | GIMAP6 |
| 221879_at | 67.6 | 32.7 | 1584.5 | 13.1 | 79.6 | calmodulin-like 4 | CALML4 |
| 219349_s_at | 123 | 63.1 | 709.7 | 12.8 | 79.6 | SEC5-like 1 (*S. cerevisiae*) | SEC5L1 |
| 219938_s_at | 67.1 | 43.3 | 1226.2 | 10.9 | 79.6 | proline-serine-threonine phosphatase interacting protein 2 | PSTPIP2 |
| 211582_x_at | 295.3 | 27.2 | 9348.4 | 23.1 | 79.3 | leukocyte specific transcript 1 | LST1 |
| 212070_at | 179.3 | 13.7 | 7815.2 | 33.7 | 79.3 | G protein-coupled receptor 56 | GPR56 |
| 203427_at | 262.2 | 115.7 | 1968.9 | 47 | 79.3 | ASF1 anti-silencing function 1 homolog A (*S. cerevisiae*) | ASF1A |
| 201105_at | 33.8 | 10.7 | 24467.4 | 7.8 | 78.9 | lectin, galactoside-binding, soluble, 1 (galectin 1) | LGALS1 |
| 205099_s_at | 17.7 | 8.1 | 958.1 | 7.1 | 78.9 | chemokine (C-C motif) receptor 1 | CCR1 |
| 202917_s_at | 379.2 | 230.5 | 76685.5 | 107.5 | 78.9 | S100 calcium binding protein A8 (calgranulin A) | S100A8 |
| 200953_s_at | 556.9 | 302.6 | 15144.4 | 183.6 | 78.5 | cyclin D2 | CCND2 |
| 204563_at | 415.7 | 288.1 | 16680.8 | 205 | 78.5 | selectin L (lymphocyte adhesion molecule 1) | SELL |
| 211560_s_at | 32.4 | 17.8 | 59803.8 | 11.7 | 78.1 | aminolevulinate, delta-, synthase 2 (sideroblastic/hypochromic anemia) | ALAS2 |
| 212267_at | 177.1 | 117.9 | 2050.8 | 127.1 | 78.1 | KIAA0261 | KIAA0261 |
| 222116_s_at | 65.2 | 11.5 | 991.4 | 9.7 | 78.1 | TBC1 domain family, member 16 | TBC1D16 |
| 57715_at | 138.8 | 41.2 | 1448.5 | 48.3 | 78.1 | family with sequence similarity 26, member B | FAM26B |
| 210916_s_at | 109.2 | 40.8 | 4864.2 | 18.8 | 78.1 | CD44 antigen (homing function and Indian blood group system) | CD44 |
| 209199_s_at | 1762.1 | 1338.9 | 12199.4 | 66.6 | 78.1 | MADS box transcription enhancer factor 2, polypeptide C (myocyte enhancer factor 2C) | MEF2C |
| 203232_s_at | 7.8 | 4.1 | 916.3 | 4 | 77.8 | ataxin 1 | ATXN1 |
| 222061_at | 60.7 | 6.9 | 864.5 | 13.9 | 77.8 | CD58 antigen, (lymphocyte function-associated antigen 3) | CD58 |
| 209129_at | 186.6 | 102.1 | 1556.4 | 77.3 | 77.4 | thyroid hormone receptor interactor 6 | TRIP6 |
| 211986_at | 187.8 | 24.6 | 7591.2 | 30.9 | 77.4 | AHNAK nucleoprotein (desmoyokin) | AHNAK |
| 212135_s_at | 881.2 | 583.9 | 6848.7 | 471.1 | 77.4 | ATPase, Ca++ transporting, plasma membrane 4 | ATP2B4 |
| 212349_at | 32.2 | 14.1 | 413.8 | 11.1 | 77.4 | protein O-fucosyltransferase 1 | POFUT1 |
| 209163_at | 64.7 | 37.7 | 1725.6 | 9.9 | 77.4 | cytochrome b-561 | CYB561 |
| 210164_at | 56.7 | 5.5 | 1828.8 | 6.5 | 77.0 | granzyme B (granzyme 2, cytotoxic T-lymphocyte-associated serine esterase 1) /// | GZMB |
| 212602_at | 79.7 | 18.9 | 1360.4 | 9.6 | 76.7 | WD repeat and FYVE domain containing 3 | WDFY3 |
| 200878_at | 23.4 | 9.6 | 1992 | 6.1 | 76.3 | endothelial PAS domain protein 1 | EPAS1 |
| 209195_s_at | 228.5 | 65.3 | 2349.2 | 62.6 | 76.3 | adenylate cyclase 6 | ADCY6 |
| 210629_x_at | 374.2 | 216.5 | 6073.9 | 65.3 | 76.3 | leukocyte specific transcript 1 | LST1 |
| 222101_s_at | 98.5 | 31.8 | 1276 | 15.3 | 76.3 | dachsous 1 (*Drosophila*) | DCHS1 |
| 218199_s_at | 72 | 66.6 | 632.1 | 28.1 | 76.3 | nucleolar protein family 6 (RNA-associated) | NOL6 |
| 215543_s_at | 281.5 | 56 | 1778.6 | 25.9 | 75.9 | like-glycosyltransferase | LARGE |
| 217730_at | 151.8 | 114.9 | 1923.4 | 34.6 | 75.9 | transmembrane BAX inhibitor motif containing 1 | TMBIM1 |
| 219161_s_at | 370.4 | 214.7 | 4079.9 | 48.4 | 75.9 | chemokine-like factor | CKLF |
| 201666_at | 287.5 | 234.5 | 6650.2 | 156.8 | 75.6 | TIMP metallopeptidase inhibitor 1 | TIMP1 |
| 203186_s_at | 545.5 | 147.1 | 14516.7 | 171.2 | 75.6 | calvasculin, metastasin, murine placental homolog) | S100A4 |
| 203508_at | 145.6 | 13.6 | 2176.2 | 28.1 | 75.6 | tumor necrosis factor receptor superfamily, member 1B | TNFRSF1B |
| 205354_at | 49.1 | 25 | 799.3 | 13.2 | 75.6 | guanidinoacetate N-methyltransferase | GAMT |

TABLE 1-continued

Probe sets overexpressed in 25% of more of B-lineage ALL cases (n = 270) as compared to normal bone marrow CD19+CD10+ cells from 4 healthy donors

| probe set ID | CD10+ CD19+ max | CD10+ CD19+ min | ALL max | ALL min | % ALL over expressed | Title | Symbol |
|---|---|---|---|---|---|---|---|
| 210784_x_at | 64.6 | 35.1 | 1105.8 | 21.4 | 75.6 | leukocyte immunoglobulin-like receptor, subfamily B (with TM and ITIM domains), member 2 /// leukocyte immunoglobulin-like receptor, subfamily B (with TM and ITIM domains), member 3 | LILRB2 /// LILRB3 |
| 211744_s_at | 428.3 | 296.5 | 5561.2 | 148.4 | 75.6 | CD58 antigen, (lymphocyte function-associated antigen 3) /// CD58 antigen, (lymphocyte function-associated antigen 3) | CD58 |
| 219672_at | 212.5 | 68.3 | 31465.9 | 32.8 | 75.6 | erythroid associated factor | ERAF |
| 202535_at | 134.1 | 94.1 | 756.6 | 21.9 | 75.2 | Fas (TNFRSF6)-associated via death domain | FADD |
| 205488_at | 133.2 | 17.6 | 8624.2 | 18.7 | 74.8 | granzyme A (granzyme 1, cytotoxic T-lymphocyte-associated serine esterase 3) | GZMA |
| 205708_s_at | 237.2 | 32 | 2798.1 | 131.5 | 74.8 | transient receptor potential cation channel, subfamily M, member 2 | TRPM2 |
| 214574_x_at | 530.6 | 84 | 10726.8 | 34.4 | 74.8 | leukocyte specific transcript 1 | LST1 |
| 215177_s_at | 145.9 | 31.5 | 12400.9 | 14.6 | 74.8 | integrin, alpha 6 | ITGA6 |
| 211101_x_at | 604.8 | 512.8 | 5777.6 | 123.3 | 74.8 | leukocyte immunoglobulin-like receptor, subfamily A (with TM domain), member 2 | LILRA2 |
| 208634_s_at | 1744.4 | 1323.4 | 8823.5 | 766 | 74.4 | microtubule-actin crosslinking factor 1 | MACF1 |
| 209949_at | 177.6 | 37 | 3712.2 | 28.7 | 74.4 | neutrophil cytosolic factor 2 (65 kDa, chronic granulomatous disease, autosomal 2) | NCF2 |
| 212678_at | 181.2 | 55.4 | 902.4 | 70 | 74.4 | Neurofibromin 1 (neurofibromatosis, von Recklinghausen disease, Watson disease) | NF1 |
| 219837_s_at | 43.5 | 15.8 | 8209.4 | 9.7 | 74.4 | cytokine-like 1 | CYTL1 |
| 202269_x_at | 70.2 | 15 | 4634.3 | 4.2 | 74.4 | guanylate binding protein 1, interferon-inducible, 67 kDa /// guanylate binding protein 1, interferon-inducible, 67 kDa | GBP1 |
| 202481_at | 170.6 | 37.7 | 3015.7 | 23.6 | 74.1 | dehydrogenase/reductase (SDR family) member 3 | DHRS3 |
| 220206_at | 62.6 | 20.4 | 507.2 | 7.4 | 74.1 | zinc finger, MYM-type 1 | ZMYM1 |
| 219753_at | 462.7 | 331.5 | 29780.3 | 31 | 74.1 | stromal antigen 3 | STAG3 |
| 217728_at | 358.4 | 166.7 | 11349.1 | 220.3 | 73.7 | S100 calcium binding protein A6 (calcyclin) | S100A6 |
| 222217_s_at | 459.8 | 324.6 | 4162.3 | 181.3 | 73.7 | solute carrier family 27 (fatty acid transporter), member 3 | SLC27A3 |
| 210146_x_at | 144.2 | 20.9 | 2389.3 | 12.7 | 73.3 | leukocyte immunoglobulin-like receptor, subfamily B (with TM and ITIM domains), member 2 | LILRB2 |
| 210225_x_at | 74.9 | 39 | 1132.5 | 21.1 | 73.3 | leukocyte immunoglobulin-like receptor, subfamily B (with TM and ITIM domains), member 2 /// leukocyte immunoglobulin-like receptor, subfamily B (with TM and ITIM domains), member 3 | LILRB2 /// LILRB3 |
| 217188_s_at | 44.3 | 31.3 | 866.3 | 21.9 | 73.3 | chromosome 14 open reading frame 1 | C14orf1 |
| 207338_s_at | 158.2 | 115.3 | 967.9 | 20.4 | 73.3 | zinc finger protein 200 | ZNF200 |
| 201301_s_at | 149.8 | 88.7 | 3595.6 | 11.2 | 73.3 | annexin A4 | ANXA4 |
| 203591_s_at | 55.4 | 21.3 | 2647.9 | 6.6 | 73.0 | colony stimulating factor 3 receptor (granulocyte) /// colony stimulating factor 3 receptor (granulocyte) | CSF3R |
| 204344_s_at | 60.7 | 28.2 | 753.9 | 24 | 72.6 | Sec23 homolog A (S. cerevisiae) | SEC23A |
| 212501_at | 158.1 | 115.9 | 7067.4 | 15.6 | 72.6 | CCAAT/enhancer binding protein (C/EBP), beta | CEBPB |
| 204249_s_at | 863.3 | 418.4 | 19159.9 | 415.6 | 71.9 | LIM domain only 2 (rhombotin-like 1) | LMO2 |
| 219326_s_at | 671.4 | 509.7 | 4219.2 | 395.1 | 71.9 | UDP-GlcNAc:betaGal beta-1,3-N-acetylglucosaminyltransferase 1 | B3GNT1 |
| 202894_at | 182 | 58.6 | 1507.8 | 27.6 | 71.9 | EPH receptor B4 | EPHB4 |
| 218988_at | 352.1 | 173.3 | 12424.3 | 59.3 | 71.9 | solute carrier family 35, member E3 | SLC35E3 |
| 209583_s_at | 423.9 | 313.2 | 3955.4 | 42.3 | 71.9 | CD200 antigen | CD200 |
| 213817_at | 111.9 | 9.6 | 1451.4 | 2 | 71.9 | MRNA; cDNA DKFZp586B0220 (from clone DKFZp586B0220) | — |
| 208047_s_at | 40.8 | 4 | 714.4 | 4.9 | 71.5 | NGFI-A binding protein 1 (EGR1 binding protein 1) | NAB1 |
| 216920_s_at | 169 | 132.3 | 9679.7 | 22.7 | 71.5 | T cell receptor gamma constant 2 /// T cell receptor gamma variable 9 | TRGC2 /// TRGV9 |
| 204959_at | 26.5 | 7.5 | 8089.4 | 3.1 | 71.5 | myeloid cell nuclear differentiation antigen /// myeloid cell nuclear differentiation antigen | MNDA |
| 204438_at | 114.4 | 83.8 | 12305 | 5.7 | 71.5 | mannose receptor, C type 1 /// mannose receptor, C type 1-like 1 | MRC1 /// MRC1L1 |
| 203948_s_at | 66.5 | 15.8 | 53188 | 9.1 | 71.1 | myeloperoxidase | MPO |
| 209365_s_at | 416.3 | 51.2 | 10277.5 | 46.2 | 70.7 | extracellular matrix protein 1 | ECM1 |
| 214407_x_at | 207 | 13.6 | 29217.6 | 7.7 | 70.7 | alycophorin B (includes Ss blood group) | GYPB |
| 221756_at | 235.7 | 94.4 | 3467.9 | 56.7 | 70.7 | HGFL gene /// HGFL gene | MGC17330 |
| 216511_s_at | 239.9 | 89 | 2129.1 | 12.7 | 70.7 | transcription factor 7-like 2 (T-cell specific, HMG-box) | TCF7L2 |
| 206207_at | 51.8 | 26.6 | 10212 | 7.2 | 70.7 | Charcot-Leyden crystal protein /// Charcot-Leyden crystal protein | CLC |
| 210547_x_at | 39.2 | 12.8 | 665.6 | 13.8 | 70.4 | islet cell autoantigen 1, 69 kDa | ICA1 |
| 213056_at | 257.6 | 173.8 | 3516 | 11.2 | 70.4 | FERM domain containing 4B | FRMD4B |
| 219530_at | 137.7 | 45.3 | 759 | 31.1 | 70.0 | hypothetical protein FLJ21816 | FLJ21816 |
| 222079_at | 159.9 | 99.5 | 1043.2 | 38.1 | 70.0 | — | — |
| 207788_s_at | 93.1 | 58.2 | 2250.2 | 12.5 | 70.0 | sorbin and SH3 domain containing 3 | SORBS3 |
| 212196_at | 258.2 | 132.8 | 3733.9 | 106 | 69.6 | MRNA; cDNA DKFZp564F053 (from clone DKFZp564F053) | — |

TABLE 1-continued

Probe sets overexpressed in 25% of more of B-lineage ALL cases (n = 270) as compared to normal bone marrow CD19+CD10+ cells from 4 healthy donors

| probe set ID | CD10+ CD19+ max | CD10+ CD19+ min | ALL max | ALL min | % ALL over expressed | Title | Symbol |
|---|---|---|---|---|---|---|---|
| 215844_at | 21.6 | 10.7 | 305.1 | 7 | 69.6 | transportin 2 (importin 3, karyopherin beta 2b) | TNPO2 |
| 215706_x_at | 363.3 | 176.5 | 3611.6 | 78.6 | 69.6 | zyxin | ZYX |
| 201564_s_at | 24.6 | 9.8 | 895.5 | 8.1 | 69.3 | fascin homolog 1, actin-bundling protein (Strongylocentrotus purpuratus) | FSCN1 |
| 208683_at | 362.3 | 288.9 | 5110.1 | 178 | 69.3 | calpain 2, (m/II) large subunit | CAPN2 |
| 221861_at | 202.8 | 34.1 | 1381.3 | 46 | 69.3 | MRNA; cDNA DKFZp762M127 (from clone DKFZp762M127) | — |
| 200951_s_at | 27.7 | 15.2 | 2127.3 | 6 | 69.3 | cyclin D2 | CCND2 |
| 201328_at | 751.6 | 331.4 | 7886.4 | 286.8 | 68.9 | v-ets erythroblastosis virus E26 oncogene homolog 2 (avian) | ETS2 |
| 209344_at | 630.8 | 208.5 | 7920.4 | 383.3 | 68.9 | tropomyosin 4 | TPM4 |
| 222303_at | 604.5 | 422 | 8580.9 | 42 | 68.9 | — | — |
| 211160_x_at | 41.3 | 19.1 | 1744.4 | 10.3 | 68.5 | actinin, alpha 1 | ACTN1 |
| 204083_s_at | 84.2 | 9.9 | 1854.6 | 7.3 | 68.1 | tropomyosin 2 (beta) | TPM2 |
| 211100_x_at | 604.9 | 372.9 | 6014.8 | 326.2 | 68.1 | leukocyte immunoglobulin-like receptor, subfamily A (with TM domain), member 2 | LILRA2 |
| 221679_s_at | 24.6 | 5.4 | 479 | 2.9 | 68.1 | abhydrolase domain containing 6 | ABHD6 |
| 218729_at | 227 | 131.9 | 5414.4 | 61.7 | 68.1 | latexin | LXN |
| 221773_at | 864.6 | 342.2 | 11369.1 | 83.4 | 68.1 | ELK3, ETS-domain protein (SRF accessory protein 2) | ELK3 |
| 200808_s_at | 336.8 | 99.6 | 3372.4 | 243 | 67.8 | zyxin | ZYX |
| 205837_s_at | 18.2 | 1.6 | 5044 | 1.6 | 67.8 | glycophorin A (includes MN blood group) | GYPA |
| 222062_at | 16.1 | 8.9 | 674.4 | 6.8 | 67.8 | interleukin 27 receptor, alpha | IL27RA |
| 218820_at | 151 | 83.1 | 2129.3 | 27.9 | 67.8 | chromosome 14 open reading frame 132 | C14orf132 |
| 204648_at | 71.3 | 15.4 | 1100 | 10 | 67.4 | natriuretic peptide receptor A/guanylate cyclase A (atrionatriuretic peptide receptor A) | NPR1 |
| 205289_at | 81.6 | 5.2 | 3030 | 5.3 | 67.4 | bone morphogenetic protein 2 | BMP2 |
| 211066_x_at | 362.3 | 258.9 | 7663.5 | 115.2 | 67.4 | protocadherin gamma subfamily A1 | PCDHGA1 |
| 205067_at | 698.3 | 430.6 | 6951.6 | 85.9 | 67.4 | interleukin 1, beta | IL1B |
| 202878_s_at | 348.1 | 242.3 | 3646.4 | 147.1 | 67.0 | complement component 1, q subcomponent, receptor 1 | C1QR1 |
| 211581_x_at | 485.2 | 62.8 | 6222.2 | 32.4 | 67.0 | leukocyte specific transcript 1 | LST1 |
| 212772_s_at | 208.1 | 171.5 | 1656.3 | 86.3 | 67.0 | ATP-binding cassette, sub-family A (ABC1), member 2 | ABCA2 |
| 218522_s_at | 241.8 | 148.4 | 1323.8 | 151.3 | 67.0 | BPY2 interacting protein 1 | BPY2IP1 |
| 221188_s_at | 257.9 | 146.8 | 1620.6 | 76 | 67.0 | cell death-inducing DFFA-like effector b | CIDEB |
| 216850_at | 23.1 | 14.9 | 437.5 | 4.5 | 67.0 | small nuclear ribonucleoprotein polypeptide N | SNRPN |
| 218532_s_at | 220 | 175.4 | 3786.7 | 11.2 | 67.0 | hypothetical protein FLJ20152 | FLJ20152 |
| 203370_s_at | 118.2 | 45.6 | 1223 | 24.7 | 66.7 | PDZ and LIM domain 7 (enigma) | PDLIM7 |
| 206337_at | 256 | 77.9 | 7065.2 | 126.8 | 66.7 | chemokine (C-C motif) receptor 7 /// chemokine (C-C motif) receptor 7 | CCR7 |
| 219411_at | 35.5 | 17.4 | 554.2 | 11.3 | 66.7 | engulfment and cell motility 3 (ced-12 homolog, C. elegans) | ELMO3 |
| 203939_at | 121.1 | 54.3 | 5133.9 | 5 | 66.7 | 5'-nucleotidase, ecto (CD73) | NT5E |
| 206769_at | 43.1 | 15.2 | 740.5 | 10.2 | 66.3 | thymosin, beta 4, Y-linked | TMSB4Y |
| 215076_s_at | 18.8 | 10.3 | 618.7 | 7.8 | 66.3 | collagen, type III, alpha 1 (Ehlers-Danlos syndrome type IV, autosomal dominant) | COL3A1 |
| 202711_at | 77.2 | 35.2 | 769.5 | 10.5 | 66.3 | ephrin-B1 | EFNB1 |
| 201976_s_at | 76.5 | 12 | 3468 | 10 | 65.9 | myosin X | MYO10 |
| 209468_at | 35.5 | 9 | 518.6 | 9.5 | 65.9 | low density lipoprotein receptor-related protein 5 | LRP5 |
| 213589_s_at | 13.2 | 8.1 | 555.7 | 8.5 | 65.9 | hypothetical protein LOC146712 /// UDP-GlcNAc:betaGal beta-1,3-N-acetylglucosaminyltransferase-like 1 | LOC146712 /// B3GNTL1 |
| 216352_x_at | 21.4 | 12.4 | 635.4 | 7 | 65.9 | protocadherin gamma subfamily A, 3 | PCDHGA3 |
| 212364_at | 56.6 | 15.9 | 1780.2 | 6.8 | 65.9 | myosin IB | MYO1B |
| 209101_at | 428 | 135.6 | 25930.7 | 14.5 | 65.9 | connective tissue growth factor | CTGF |
| 201295_s_at | 97.5 | 48.6 | 1881.2 | 32.4 | 65.6 | WD repeat and SOCS box-containing 1 | WSB1 |
| 203470_s_at | 138.4 | 59.7 | 2050.7 | 27.3 | 65.6 | pleckstrin | PLEK |
| 209079_x_at | 370.2 | 206.7 | 7185.2 | 78.4 | 65.6 | protocadherin gamma subfamily A1 | PCDHGA1 |
| 219539_at | 116.7 | 24.4 | 771.3 | 10.8 | 65.6 | gem (nuclear organelle) associated protein 6 | GEMIN6 |
| 210299_s_at | 280.5 | 132.8 | 4488.4 | 28 | 65.6 | four and a half LIM domains 1 | FHL1 |
| 210298_x_at | 363.7 | 190.1 | 7144.3 | 24.8 | 65.6 | four and a half LIM domains 1 | FHL1 |
| 207857_at | 394.5 | 181.8 | 4403.8 | 146.9 | 65.2 | leukocyte immunoglobulin-like receptor, subfamily A (with TM domain), member 2 | LILRA2 |
| 209930_s_at | 133.8 | 7.8 | 10314 | 6 | 65.2 | nuclear factor (erythroid-derived 2), 45 kDa | NFE2 |
| 213694_at | 301.2 | 211.7 | 3478.4 | 133.6 | 65.2 | round spermatid basic protein 1 | RSBN1 |
| 214880_x_at | 22.8 | 6.3 | 610 | 3.6 | 65.2 | caldesmon 1 | CALD1 |
| 211126_s_at | 411.4 | 157.2 | 4771.5 | 35.4 | 65.2 | cysteine and glycine-rich protein 2 | CSRP2 |
| 208146_s_at | 25.5 | 18.8 | 1653.4 | 7.6 | 65.2 | carboxypeptidase, vitellogenic-like /// carboxypeptidase, vitellogenic-like | CPVL |
| 213620_s_at | 983 | 871.1 | 7321.1 | 233.8 | 65.2 | intercellular adhesion molecule 2 | ICAM2 |
| 219667_s_at | 709.4 | 360.7 | 6837.7 | 12.4 | 65.2 | B-cell scaffold protein with ankyrin repeats 1 | BANK1 |
| 203957_at | 45.1 | 21.8 | 893.1 | 14.2 | 64.8 | E2F transcription factor 6 | E2F6 |
| 216035_x_at | 254.4 | 26.8 | 1646.6 | 26.1 | 64.8 | transcription factor 7-like 2 (T-cell specific, HMG-box) | TCF7L2 |
| 207827_x_at | 199.3 | 183 | 30767.9 | 21.7 | 64.8 | synuclein, alpha (non A4 component of amyloid precursor) | SNCA |
| 212158_at | 35.5 | 9.5 | 3320.4 | 4 | 64.8 | syndecan 2 (heparan sulfate proteoglycan 1, cell surface-associated, fibroglycan) | SDC2 |

TABLE 1-continued

Probe sets overexpressed in 25% of more of B-lineage ALL cases (n = 270) as compared to normal bone marrow CD19+CD10+ cells from 4 healthy donors

| probe set ID | CD10+ CD19+ max | CD10+ CD19+ min | ALL max | ALL min | % ALL over expressed | Title | Symbol |
|---|---|---|---|---|---|---|---|
| 204422_s_at | 9.3 | 6.5 | 388.3 | 2.3 | 64.8 | fibroblast growth factor 2 (basic) | FGF2 |
| 211031_s_at | 554.3 | 418.8 | 4347.1 | 103.8 | 64.8 | cytoplasmic linker 2 /// cytoplasmic linker 2 | CYLN2 |
| 214022_s_at | 886.2 | 395.4 | 26636.7 | 334.7 | 64.4 | interferon induced transmembrane protein 1 (9-27) | IFITM1 |
| 204466_s_at | 374.1 | 223 | 72280.7 | 90.1 | 64.4 | synuclein, alpha (non A4 component of amyloid precursor) | SNCA |
| 204683_at | 740.3 | 498.1 | 4022.8 | 292.4 | 64.1 | intercellular adhesion molecule 2 | ICAM2 |
| 210116_at | 14.8 | 3.6 | 1595.3 | 4.4 | 64.1 | SH2 domain protein 1A, Duncan's disease (lymphoproliferative syndrome) | SH2D1A |
| 202023_at | 54.6 | 31.9 | 1763.8 | 9.4 | 64.1 | ephrin-A1 | EFNA1 |
| 204845_s_at | 23.5 | 5.7 | 406.1 | 1.2 | 64.1 | glutamyl aminopeptidase (aminopeptidase A) | ENPEP |
| 207979_s_at | 120.4 | 38.6 | 2307.3 | 20.4 | 63.7 | CD8 antigen, beta polypeptide 1 (p37) | CD8B1 |
| 210140_at | 178.3 | 40.7 | 5369.7 | 30.9 | 63.7 | cystatin F (leukocystatin) | CST7 |
| 211135_x_at | 81.3 | 25.3 | 984.1 | 27.2 | 63.7 | leukocyte immunoglobulin-like receptor, subfamily B (with TM and ITIM domains), member 2 /// leukocyte immunoglobulin-like receptor, subfamily B (with TM and ITIM domains), member 3 | LILRB2 /// LILRB3 |
| 208871_at | 55.3 | 20.9 | 836.6 | 9.7 | 63.7 | atrophin 1 | ATN1 |
| 209683_at | 217.1 | 49.1 | 2479.7 | 14 | 63.7 | Family with sequence similarity 49, member A | FAM49A |
| 201944_at | 759.8 | 517 | 3132.4 | 663.7 | 63.3 | hexosaminidase B (beta polypeptide) | HEXB |
| 213103_at | 56.2 | 12.6 | 763.7 | 10.9 | 63.3 | START domain containing 13 | STARD13 |
| 202893_at | 134.7 | 39.5 | 1480.8 | 15.9 | 63.3 | unc-13 homolog B (C. elegans) | UNC13B |
| 207651_at | 42.2 | 20.3 | 8734.2 | 8 | 63.3 | G protein-coupled receptor 171 | GPR171 |
| 207075_at | 23.2 | 10.2 | 638.2 | 8.8 | 63.0 | cold autoinflammatory syndrome 1 | CIAS1 |
| 212728_at | 85.7 | 26.5 | 958 | 27 | 63.0 | discs, large homolog 3 (neuroendocrine-dig, Drosophila) | DLG3 |
| 212063_at | 733.2 | 361.3 | 15874.7 | 140.4 | 63.0 | CD44 antigen (homing function and Indian blood group system) | CD44 |
| 201508_at | 139.5 | 45.9 | 2084.8 | 20.8 | 63.0 | insulin-like growth factor binding protein 4 | IGFBP4 |
| 218025_s_at | 296.9 | 257.9 | 1696.4 | 72.7 | 63.0 | peroxisomal D3,D2-enoyl-CoA isomerase | PECI |
| 202270_at | 62.8 | 14.1 | 1821.4 | 4.4 | 63.0 | guanylate binding protein 1, interferon-inducible, 67 kDa /// guanylate binding protein 1, interferon-inducible, 67 kDa | GBP1 |
| 214551_s_at | 14.1 | 5.8 | 1524.8 | 3.8 | 62.6 | CD7 antigen (p41) | CD7 |
| 220146_at | 26.7 | 3.5 | 1010.1 | 2.1 | 62.6 | toll-like receptor 7 | TLR7 |
| 221786_at | 214.2 | 173.5 | 1433.7 | 16.9 | 62.6 | chromosome 6 open reading frame 120 | C6orf120 |
| 206584_at | 99.8 | 78.1 | 1102.1 | 13 | 62.6 | lymphocyte antigen 96 | LY96 |
| 201601_x_at | 604.7 | 162.7 | 22080.6 | 147 | 62.2 | interferon induced transmembrane protein 1 (9-27) | IFITM1 |
| 208130_s_at | 30.5 | 11.4 | 714.8 | 7.5 | 62.2 | thromboxane A synthase 1 (platelet, cytochrome P450, family 5, subfamily A) | TBXAS1 |
| 210370_s_at | 193.2 | 9 | 1151.2 | 11.5 | 62.2 | lymphocyte antigen 9 | LY9 |
| 218607_s_at | 446.2 | 365 | 1711.3 | 254.7 | 62.2 | SDA1 domain containing 1 | SDAD1 |
| 218613_at | 251.9 | 109.2 | 2485 | 44.6 | 62.2 | pleckstrin and Sec7 domain containing 3 | PSD3 |
| 212975_at | 687.4 | 618.3 | 10417.7 | 23 | 62.2 | DENN/MADD domain containing 3 | DENND3 |
| 207697_x_at | 402.5 | 221.4 | 4154.4 | 31.9 | 62.2 | leukocyte immunoglobulin-like receptor, subfamily B (with TM and ITIM domains), member 2 | LILRB2 |
| 203192_at | 85.8 | 61 | 1923.4 | 18 | 61.9 | ATP-binding cassette, sub-family B (MDR/TAP), member 6 | ABCB6 |
| 200660_at | 38.2 | 13.9 | 2700.3 | 7.8 | 61.5 | S100 calcium binding protein A11 (calgizzarin) | S100A11 |
| 202747_s_at | 82.5 | 46.5 | 7009.4 | 39.7 | 61.5 | integral membrane protein 2A | ITM2A |
| 203061_s_at | 59.9 | 34 | 667.2 | 17.6 | 61.5 | mediator of DNA damage checkpoint 1 | MDC1 |
| 214450_at | 30.1 | 16.7 | 2250.8 | 16.9 | 61.5 | cathepsin W (lymphopain) /// cathepsin W (lymphopain) | CTSW |
| 204304_s_at | 115.5 | 22 | 13206.2 | 6.9 | 61.5 | prominin 1 | PROM1 |
| 218999_at | 116.1 | 33.7 | 811.4 | 10.4 | 61.5 | hypothetical protein FLJ11000 | FLJ11000 |
| 220230_s_at | 162.6 | 11.7 | 7143.3 | 4.2 | 61.5 | cytochrome b5 reductase 2 | CYB5R2 |
| 202242_at | 318.5 | 109 | 4053.5 | 17.3 | 61.5 | tetraspanin 7 | TSPAN7 |
| 214505_s_at | 632 | 262.1 | 9639.8 | 188.3 | 61.1 | four and a half LIM domains 1 | FHL1 |
| 200771_at | 309.6 | 153.2 | 1480.6 | 18.1 | 61.1 | laminin, gamma 1 (formerly LAMB2) | LAMC1 |
| 220640_at | 29.3 | 13.3 | 665.2 | 5.6 | 61.1 | casein kinase 1, gamma 1 | CSNK1G1 |
| 201809_s_at | 398.3 | 237.2 | 7012.1 | 84.2 | 61.1 | endoglin (Osler-Rendu-Weber syndrome 1) | ENG |
| 206718_at | 54.8 | 32.7 | 691 | 9.3 | 61.1 | LIM domain only 1 (rhombotin 1) | LMO1 |
| 39402_at | 495.8 | 318.6 | 4822.3 | 44.9 | 61.1 | interleukin 1, beta | IL1B |
| 201858_s_at | 619.5 | 277.2 | 69794.9 | 28.2 | 61.1 | proteoglycan 1, secretory granule | PRG1 |
| 202371_at | 217.8 | 113.5 | 2896.9 | 9.1 | 61.1 | transcription elongation factor A (SII)-like 4 | TCEAL4 |
| 218569_s_at | 54.1 | 43.4 | 610.7 | 21.8 | 60.7 | ketch repeat and BTB (POZ) domain containing 4 | KBTBD4 |
| 32502_at | 128.3 | 52.3 | 758.7 | 38.5 | 60.7 | glycerophosphodiester phosphodiesterase domain containing 5 | GDPD5 |
| 218764_at | 696.6 | 275.3 | 8459 | 79 | 60.7 | protein kinase C, eta | PRKCH |
| 219686_at | 796.9 | 90 | 8383 | 15.6 | 60.7 | serine/threonine kinase 32B | STK32B |
| 220770_s_at | 52.6 | 12.1 | 360.7 | 2.5 | 60.4 | transposon-derived Buster3 transposase-like | LOC63920 |
| 202664_at | 976.9 | 593.1 | 6117.3 | 314.8 | 60.0 | Wiskott-Aldrich syndrome protein interacting protein | WASPIP |
| 219865_at | 142.4 | 71.9 | 1295.9 | 40.9 | 60.0 | HSPC157 protein | HSPC157 |
| 202430_s_at | 120.4 | 26.3 | 3812.6 | 8.4 | 60.0 | phospholipid scramblase 1 | PLSCR1 |
| 209234_at | 97.8 | 28.5 | 926.3 | 9.7 | 60.0 | kinesin family member 1B | KIF1B |
| 222201_s_at | 245.9 | 136.7 | 1241.3 | 48.4 | 60.0 | CASP8 associated protein 2 | CASP8AP2 |
| 209360_s_at | 704.4 | 281 | 4550 | 124.2 | 60.0 | runt-related transcription factor 1 (acute myeloid leukemia 1; aml1 oncogene) | RUNX1 |

TABLE 1-continued

Probe sets overexpressed in 25% of more of B-lineage ALL cases (n = 270) as compared to normal bone marrow CD19+CD10+ cells from 4 healthy donors

| probe set ID | CD10+ CD19+ max | CD10+ CD19+ min | ALL max | ALL min | % ALL over expressed | Title | Symbol |
|---|---|---|---|---|---|---|---|
| 210895_s_at | 106.9 | 31.9 | 1392.7 | 13.6 | 60.0 | CD86 antigen (CD28 antigen ligand 2, B7-2 antigen) | CD86 |
| 209035_at | 195.8 | 41.2 | 4059.5 | 10.9 | 60.0 | midkine (neurite growth-promoting factor 2) | MDK |
| 208370_s_at | 726.8 | 529.7 | 10489.7 | 85.9 | 60.0 | Down syndrome critical region gene 1 | DSCR1 |
| 203535_at | 311.5 | 255.2 | 52168.5 | 24.2 | 60.0 | S100 calcium binding protein A9 (calgranulin B) | S100A9 |
| 201656_at | 136.6 | 3.2 | 6443.6 | 1.7 | 59.6 | integrin, alpha 6 | ITGA6 |
| 221523_s_at | 177.2 | 83.5 | 1807.4 | 64.7 | 59.6 | Ras-related GTP binding D | RRAGD |
| 221565_s_at | 167.9 | 33.8 | 1912.9 | 20.9 | 59.6 | family with sequence similarity 26, member B | FAM26B |
| 206434_at | 12.7 | 2.4 | 810.5 | 0.7 | 59.6 | sparc/osteonectin, cwcv and kazal-like domains proteoglycan (testican) 3 | SPOCK3 |
| 206506_s_at | 190.3 | 45.2 | 2364.9 | 19 | 59.6 | suppressor of Ty 3 homolog (S. cerevisiae) | SUPT3H |
| 208891_at | 997 | 526.4 | 13003.4 | 128.7 | 59.6 | dual specificity phosphatase 6 | DUSP6 |
| 207785_s_at | 445.7 | 232.5 | 5173.6 | 231 | 59.3 | recombining binding protein suppressor of hairless (Drosophila) | RBPSUH |
| 212154_at | 129.4 | 6.7 | 4850.1 | 6.7 | 59.3 | syndecan 2 (heparan sulfate proteoglycan 1, cell surface-associated, fibroglycan) | SDC2 |
| 221797_at | 76.7 | 17.6 | 562.9 | 9.9 | 59.3 | hypothetical protein LOC339229 | LOC339229 |
| 202663_at | 272.6 | 108.1 | 1844.3 | 50.5 | 59.3 | Wiskott-Aldrich syndrome protein interacting protein | WASPIP |
| 206991_s_at | 87.3 | 60.1 | 1388.1 | 29 | 59.3 | chemokine (C-C motif) receptor 5 | CCR5 |
| 207735_at | 228.9 | 162.1 | 2162.1 | 21.7 | 59.3 | ring finger protein 125 | RNF125 |
| 211144_x_at | 179.3 | 73.4 | 7308.1 | 11.8 | 59.3 | T cell receptor gamma constant 2 | TRGC2 |
| 201315_x_at | 2600.3 | 1198.3 | 27908.8 | 1041.3 | 58.9 | interferon induced transmembrane protein 2 (1-8D) | IFITM2 |
| 202524_s_at | 393.7 | 350.1 | 4971.7 | 235 | 58.9 | sparc/osteonectin, cwcv and kazal-like domains proteoglycan (testican) 2 | SPOCK2 |
| 209728_at | 22 | 16.3 | 20171.1 | 9.5 | 58.9 | major histocompatibility complex, class II, DR beta 4 | HLA-DRB4 |
| 209892_at | 228.2 | 110.3 | 3825.8 | 173.9 | 58.9 | fucosyltransferase 4 (alpha (1,3) fucosyltransferase, myeloid-specific) | FUT4 |
| 212768_s_at | 8.8 | 2.4 | 6175.5 | 1.6 | 58.9 | olfactomedin 4 | OLFM4 |
| 214966_at | 42.2 | 11.3 | 563.1 | 5.9 | 58.9 | glutamate receptor, ionotropic, kainate 5 | GRIK5 |
| 217078_s_at | 16 | 4.5 | 519.5 | 2.4 | 58.9 | CD300A antigen | CD300A |
| 206582_s_at | 54.3 | 43.6 | 2710.8 | 14.3 | 58.9 | G protein-coupled receptor 56 | GPR56 |
| 214467_at | 154.9 | 77.3 | 1080.3 | 55.8 | 58.5 | G protein-coupled receptor 65 | GPR65 |
| 205571_at | 237.2 | 172.1 | 1201.6 | 71.9 | 58.5 | lipoyltransferase 1 | LIPT1 |
| 220134_x_at | 84.4 | 22.9 | 803.2 | 9 | 58.5 | chromosome 1 open reading frame 78 | C1orf78 |
| 203680_at | 168.3 | 39.3 | 2787.8 | 6.3 | 58.5 | protein kinase, cAMP-dependent, regulatory, type II, beta | PRKAR2B |
| 217800_s_at | 168.2 | 122.5 | 2297.2 | 7.4 | 58.5 | Nedd4 family interacting protein 1 | NDFIP1 |
| 203828_s_at | 18.5 | 8.1 | 3620.8 | 8.2 | 58.1 | interleukin 32 /// interleukin 32 | IL32 |
| 217321_x_at | 11.7 | 3.3 | 310.1 | 2.2 | 58.1 | Ataxin 3 | ATXN3 |
| 219423_x_at | 103.9 | 11.1 | 1087.9 | 14.1 | 58.1 | tumor necrosis factor receptor superfamily, member 25 | TNFRSF25 |
| 220187_at | 6.4 | 3 | 200.6 | 1.7 | 58.1 | STEAP family member 4 | STEAP4 |
| 204944_at | 6.1 | 5.3 | 368.8 | 2.2 | 58.1 | protein tyrosine phosphatase, receptor type, G | PTPRG |
| 204277_at | 19.9 | 11.2 | 342.4 | 11.4 | 57.8 | thymidine kinase 2, mitochondrial | TK2 |
| 205685_at | 76.9 | 7.2 | 1077.2 | 5 | 57.8 | CD86 antigen (CD28 antigen ligand 2, B7-2 antigen) | CD86 |
| 215933_s_at | 1121.5 | 787.7 | 11058 | 214.8 | 57.8 | hematopoietically expressed homeobox | HHEX |
| 218751_s_at | 339.1 | 208 | 8267.8 | 45 | 57.8 | F-box and WD-40 domain protein 7 (archipelago homolog, Drosophila) | FBXW7 |
| 211796_s_at | 382.6 | 210.2 | 13295.6 | 10.4 | 57.8 | T cell receptor beta variable 21-1 /// T cell receptor beta variable 19 /// T cell receptor beta variable 5-4 /// T cell receptor beta variable 3-1 /// T cell receptor beta constant 1 | TRBV21-1 /// TRBV19 /// TRBV5-4 /// TRBV3-1 /// TRBC1 |
| 206666_at | 123.4 | 33.3 | 5218.3 | 20.4 | 57.4 | granzyme K (granzyme 3; tryptase II) /// granzyme K (granzyme 3; tryptase II) | GZMK |
| 212671_s_at | 1304.7 | 118.8 | 18591.5 | 149 | 57.4 | major histocompatibility complex, class II, DQ alpha 1 /// DQ alpha 2 | HLA-DQA1 /// HLA-DQA2 |
| 213262_at | 154.3 | 93.2 | 1110 | 21.5 | 57.4 | spastic ataxia of Charlevoix-Saguenay (sacsin) | SACS |
| 218627_at | 347.9 | 213.1 | 4194.7 | 69.3 | 57.4 | hypothetical protein FLJ11259 | FLJ11259 |
| 203354_s_at | 37.7 | 20.5 | 814.1 | 8.2 | 57.4 | pleckstrin and Sec7 domain containing 3 | PSD3 |
| 217572_at | 24.3 | 12.9 | 2948 | 4.9 | 57.4 | Transcribed locus, strongly similar to NP_032244.1 hemoglobin alpha 1 chain [Mus musculus] | — |
| 213993_at | 15.3 | 8.7 | 815 | 2.8 | 57.4 | spondin 1, extracellular matrix protein | SPON1 |
| 212170_at | 164.8 | 106.1 | 770.6 | 12.4 | 57.4 | RNA binding motif protein 12 | RBM12 |
| 205786_s_at | 168.7 | 50.4 | 5191.4 | 29.6 | 57.0 | integrin, alpha M | ITGAM |
| 221748_s_at | 281.6 | 132.5 | 11141.1 | 85.8 | 57.0 | tensin 1 /// tensin 1 | TNS1 |
| 222155_s_at | 158.3 | 39.8 | 1291.3 | 23.6 | 57.0 | G protein-coupled receptor 172A | GPR172A |
| 200665_s_at | 101.3 | 17.2 | 3081.6 | 6.6 | 57.0 | secreted protein, acidic, cysteine-rich (osteonectin) /// secreted protein, acidic, cysteine-rich (osteonectin) | SPARC |
| 211795_s_at | 118.4 | 40.8 | 2108 | 20.1 | 57.0 | FYN binding protein (FYB-120/130) | FYB |
| 201212_at | 34.6 | 14.8 | 1137 | 4.4 | 57.0 | legumain | LGMN |
| 218695_at | 49.5 | 32.4 | 816.6 | 13 | 57.0 | exosome component 4 | EXOSC4 |
| 208886_at | 582.5 | 77.7 | 15547 | 11.8 | 57.0 | H1 histone family, member 0 | H1F0 |
| 218136_s_at | 409 | 344.1 | 18019.6 | 205.2 | 56.7 | solute carrier family 25, member 37 | SLC25A37 |
| 206734_at | 113.3 | 42.2 | 701.8 | 13.9 | 56.7 | jerky homolog-like (mouse) | JRKL |
| 209651_at | 114.5 | 58 | 865.7 | 6.7 | 56.7 | transforming growth factor beta 1 induced transcript 1 | TGFB1I1 |

TABLE 1-continued

Probe sets overexpressed in 25% of more of B-lineage ALL cases (n = 270) as compared to normal bone marrow $CD19^+CD10^+$ cells from 4 healthy donors

| probe set ID | CD10+ CD19+ max | CD10+ CD19+ min | ALL max | ALL min | % ALL over expressed | Title | Symbol |
|---|---|---|---|---|---|---|---|
| 214690_at | 13.1 | 8.5 | 360.6 | 2.8 | 56.7 | TATA box binding protein (TBP)-associated factor, RNA polymerase I, B, 63 kDa | TAF1B |
| 201279_s_at | 106.6 | 14.2 | 1243.9 | 7.6 | 56.3 | disabled homolog 2, mitogen-responsive phosphoprotein (*Drosophila*) | DAB2 |
| 210999_s_at | 224.7 | 70.5 | 3092.9 | 70.1 | 56.3 | growth factor receptor-bound protein 10 | GRB10 |
| 212498_at | 912.7 | 724.8 | 4480.2 | 570.3 | 56.3 | CDNA FLJ31636 fis, clone NT2RI2003481 | — |
| 206229_x_at | 46.9 | 20.7 | 548.4 | 8.7 | 56.3 | paired box gene 2 | PAX2 |
| 219945_at | 21.8 | 13.4 | 261.9 | 5.4 | 56.3 | DEAD (Asp-Glu-Ala-Asp) box polypeptide 25 | DDX25 |
| 206852_at | 57.4 | 10 | 1522.9 | 1.8 | 56.3 | EPH receptor A7 | EPHA7 |
| 209485_s_at | 28.9 | 12.4 | 1427.2 | 3.8 | 56.3 | oxysterol binding protein-like 1A | OSBPL1A |
| 204457_s_at | 19 | 7.9 | 3486.7 | 4.9 | 55.9 | growth arrest-specific 1 | GAS1 |
| 206498_at | 62.6 | 26.2 | 1115.7 | 18.8 | 55.9 | oculocutaneous albinism II (pink-eye dilution homolog, mouse) | OCA2 |
| 209691_s_at | 42.9 | 11 | 706.7 | 8 | 55.9 | docking protein 4 | DOK4 |
| 202446_s_at | 557.8 | 361 | 16437.5 | 52.3 | 55.9 | phospholipid scramblase 1 | PLSCR1 |
| 206674_at | 496.6 | 291.7 | 11241.8 | 143.6 | 55.9 | fms-related tyrosine kinase 3 | FLT3 |
| 217983_s_at | 2911.2 | 1695.5 | 23933.1 | 798.4 | 55.9 | ribonuclease T2 | RNASET2 |
| 219812_at | 398.9 | 90.5 | 5223.7 | 44.7 | 55.9 | hypothetical protein MGC2463 | MGC2463 |
| 205285_s_at | 92.8 | 32.2 | 933.9 | 8.6 | 55.9 | FYN binding protein (FYB-120/130) | FYB |
| 202688_at | 217.4 | 76.5 | 3385.9 | 50.9 | 55.6 | tumor necrosis factor (ligand) superfamily, member 10 | TNFSF10 |
| 202710_at | 258.9 | 138.5 | 1342.8 | 82.5 | 55.6 | BET1 homolog (*S. cerevisiae*) | BET1 |
| 204116_at | 1213.2 | 604 | 8123.4 | 574.9 | 55.6 | interleukin 2 receptor, gamma (severe combined immunodeficiency) | IL2RG |
| 206332_s_at | 2150.8 | 1433.4 | 10919.1 | 739.6 | 55.6 | interferon, gamma-inducible protein 16 | IFI16 |
| 206752_at | 83.6 | 13.6 | 681.7 | 10.6 | 55.6 | DNA fragmentation factor, 40 kDa, beta polypeptide (caspase-activated DNase) | DFFB |
| 208657_s_at | 138.4 | 25.5 | 3249.4 | 25.4 | 55.6 | septin 9 | SEPT9 |
| 219487_at | 59.7 | 1.6 | 551.4 | 3.1 | 55.6 | hypothetical protein FLJ23560 | FLJ23560 |
| 203386_at | 193.2 | 109 | 1626.1 | 18.5 | 55.6 | TBC1 domain family, member 4 | TBC1D4 |
| 205640_at | 56.9 | 35.6 | 1153 | 15.1 | 55.6 | aldehyde dehydrogenase 3 family, member B1 | ALDH3B1 |
| 203069_at | 66.8 | 19 | 844.4 | 13 | 55.2 | synaptic vesicle glycoprotein 2A | SV2A |
| 204302_s_at | 68.2 | 26.7 | 944.7 | 21.1 | 55.2 | KIAA0427 | KIAA0427 |
| 205290_s_at | 176.5 | 13.9 | 9212 | 8.5 | 55.2 | bone morphogenetic protein 2 | BMP2 |
| 205881_at | 117.4 | 11.6 | 790.2 | 25.2 | 55.2 | zinc finger protein 74 (Cos52) | ZNF74 |
| 215574_at | 78.3 | 19.4 | 2858 | 12.2 | 55.2 | CDNA FLJ11454 fis, clone HEMBA1001463 | — |
| 215471_s_at | 45.3 | 17 | 1245.8 | 15.9 | 54.8 | microtubule-associated protein 7 | MAP7 |
| 217936_at | 251.3 | 158.7 | 1327.8 | 122.5 | 54.8 | Rho GTPase activating protein 5 | ARHGAP5 |
| 203264_s_at | 75.9 | 25.6 | 513.6 | 9.9 | 54.8 | Cdc42 guanine nucleotide exchange factor (GEF) 9 | ARHGEF9 |
| 221058_s_at | 279.4 | 210.1 | 2060.4 | 24.2 | 54.8 | chemokine-like factor | CKLF |
| 202845_s_at | 663.8 | 459.5 | 2955 | 268.7 | 54.4 | ralA binding protein 1 | RALBP1 |
| 202931_x_at | 553.1 | 343.6 | 3782.7 | 233.6 | 54.4 | bridging integrator 1 | BIN1 |
| 209555_s_at | 81.9 | 8.9 | 8745.9 | 6.3 | 54.4 | CD36 antigen (collagen type I receptor, thrombospondin receptor) | CD36 |
| 210201_x_at | 795.6 | 608.4 | 5732.9 | 359.2 | 54.4 | bridging integrator 1 | BIN1 |
| 211627_x_at | 10.8 | 4.1 | 257 | 2.9 | 54.4 | estrogen receptor 1 /// estrogen receptor 1 | ESR1 |
| 213193_x_at | 720.7 | 601.7 | 16080.3 | 353.1 | 54.4 | T cell receptor beta variable 19 /// T cell receptor beta variable 19 /// T cell receptor beta constant 1 /// T cell receptor beta constant 1 | TRBV19 /// TRBC1 |
| 218510_x_at | 249.7 | 41.2 | 4634.1 | 20.6 | 54.4 | hypothetical protein FLJ20152 | FLJ20152 |
| 218706_s_at | 22.8 | 5.6 | 759.6 | 4 | 54.4 | HCV NS3-transactivated protein 2 | NS3TP2 |
| 212905_at | 250.8 | 141.5 | 1185.6 | 50.5 | 54.4 | cleavage stimulation factor, 3' pre-RNA, subunit 2, 64 kDa, tau variant | CSTF2T |
| 206234_s_at | 105.2 | 27.5 | 839 | 12.8 | 54.4 | matrix metallopeptidase 17 (membrane-inserted) | MMP17 |
| 203678_at | 352.4 | 188.6 | 1567.1 | 175.4 | 54.1 | KIAA1018 protein | KIAA1018 |
| 204720_s_at | 31.5 | 7.3 | 1142.5 | 4.4 | 54.1 | DnaJ (Hsp40) homolog, subfamily C, member 6 | DNAJC6 |
| 210061_at | 74.6 | 27.7 | 511.4 | 14.1 | 54.1 | zinc finger protein 589 | ZNF589 |
| 220974_x_at | 30.1 | 15.8 | 1382.3 | 10.7 | 54.1 | sideroflexin 3 /// sideroflexin 3 | SFXN3 |
| 204067_at | 191.3 | 43.9 | 958.5 | 21.1 | 54.1 | sulfite oxidase | SUOX |
| 200670_at | 2422.4 | 1523 | 17638.7 | 508.3 | 54.1 | X-box binding protein 1 | XBP1 |
| 212731_at | 220.1 | 158.7 | 830.8 | 14.9 | 54.1 | ankyrin repeat domain 46 | ANKRD46 |
| 221527_s_at | 136.3 | 40.6 | 694.5 | 10.4 | 54.1 | par-3 partitioning defective 3 homolog (*C. elegans*) | PARD3 |
| 211339_s_at | 193 | 76.6 | 4748.8 | 110.2 | 53.7 | IL2-inducible T-cell kinase | ITK |
| 220969_s_at | 122.5 | 79.9 | 614.7 | 58.2 | 53.7 | — | — |
| 219130_at | 264.9 | 180.4 | 1083.9 | 47.7 | 53.7 | hypothetical protein FLJ10287 | FLJ10287 |
| 219335_at | 165.2 | 77.7 | 1285 | 34.2 | 53.7 | armadillo repeat containing, X-linked 5 | ARMCX5 |
| 206275_s_at | 35.9 | 9.6 | 506.5 | 3.2 | 53.7 | microtubule associated monoxygenase, calponin and LIM domain containing 2 | MICAL2 |
| 219871_at | 36.5 | 11.9 | 819.2 | 4.3 | 53.7 | hypothetical protein FLJ13197 | FLJ13197 |
| 209213_at | 80 | 41.3 | 944.1 | 8.2 | 53.7 | carbonyl reductase 1 | CBR1 |
| 210746_s_at | 51.5 | 22.9 | 22040.8 | 16.6 | 53.3 | erythrocyte membrane protein band 4.2 /// erythrocyte membrane protein band 4.2 | EPB42 |
| 219528_s_at | 139.2 | 37.1 | 1828.1 | 42.7 | 53.3 | B-cell CLL/lymphoma 11B (zinc finger protein) | BCL11B |
| 202336_s_at | 22.2 | 10.3 | 4372.9 | 4.8 | 53.3 | peptidylglycine alpha-amidating monooxygenase | PAM |

TABLE 1-continued

Probe sets overexpressed in 25% of more of B-lineage ALL cases (n = 270) as compared to normal bone marrow CD19+CD10+ cells from 4 healthy donors

| probe set ID | CD10+ CD19+ max | CD10+ CD19+ min | ALL max | ALL min | % ALL over expressed | Title | Symbol |
|---|---|---|---|---|---|---|---|
| 210215_at | 54.2 | 13.4 | 2653.7 | 5.7 | 53.3 | transferrin receptor 2 | TFR2 |
| 216321_s_at | 756.7 | 523.2 | 10606.3 | 260.3 | 53.3 | nuclear receptor subfamily 3, group C, member 1 (glucocorticoid receptor) | NR3C1 |
| 202932_at | 96.3 | 14 | 1478.6 | 3.4 | 53.3 | v-yes-1 Yamaguchi sarcoma viral oncogene homolog 1 | YES1 |
| 221920_s_at | 275.2 | 71.1 | 16582.5 | 15.1 | 53.3 | solute carrier family 25, member 37 | SLC25A37 |
| 208071_s_at | 465.6 | 298.2 | 3598.8 | 36.7 | 53.3 | leukocyte-associated Ig-like receptor 1 | LAIR1 |
| 201061_s_at | 426 | 245.6 | 17977.3 | 186.3 | 53.0 | stomatin | STOM |
| 212408_at | 828.7 | 649.6 | 4117 | 668.9 | 53.0 | torsin A interacting protein 1 | TOR1AIP1 |
| 221005_s_at | 38.9 | 14.8 | 491.4 | 11.5 | 53.0 | phosphatidylserine synthase 2 /// phosphatidylserine synthase 2 | PTDSS2 |
| 212956_at | 276.4 | 23.5 | 5870 | 4.7 | 53.0 | KIAA0882 protein | KIAA0882 |
| 217948_at | 27.1 | 19.1 | 371.1 | 5.9 | 53.0 | DKFZP564B147 protein | DKFZP564B147 |
| 216011_at | 47.5 | 26.8 | 508 | 7.3 | 53.0 | Solute carrier family 39 (zinc transporter), member 9 | SLC39A9 |
| 202949_s_at | 33.3 | 13.6 | 1345.9 | 7.5 | 52.6 | four and a half LIM domains 2 | FHL2 |
| 203387_s_at | 266.9 | 209.8 | 1701.4 | 132.2 | 52.6 | TBC1 domain family, member 4 | TBC1D4 |
| 201540_at | 1847.7 | 885.4 | 22279.2 | 224 | 52.6 | four and a half LIM domains 1 | FHL1 |
| 219315_s_at | 171.4 | 63.4 | 2139.8 | 19.8 | 52.6 | chromosome 16 open reading frame 30 | C16orf30 |
| 205739_x_at | 409.9 | 270.6 | 4446.8 | 95.8 | 52.6 | zinc finger protein 588 | ZNF588 |
| 211909_x_at | 7.6 | 3.7 | 231 | 1 | 52.6 | prostaglandin E receptor 3 (subtype EP3) /// prostaglandin E receptor 3 (subtype EP3) | PTGER3 |
| 212488_at | 794.1 | 481.3 | 6100.5 | 39.7 | 52.6 | collagen, type V, alpha 1 | COL5A1 |
| 211368_s_at | 187.8 | 104.4 | 1699.1 | 4.5 | 52.6 | caspase 1, apoptosis-related cysteine peptidase (interleukin 1, beta, convertase) | CASP1 |
| 203349_s_at | 218.6 | 56.9 | 3919.9 | 36.4 | 52.2 | ets variant gene 5 (ets-related molecule) | ETV5 |
| 206099_at | 521.1 | 140.5 | 6649.5 | 98 | 52.2 | protein kinase C, eta | PRKCH |
| 209176_at | 78.5 | 12.3 | 645.9 | 10.5 | 52.2 | — | — |
| 215111_s_at | 486.3 | 376.5 | 8516 | 194.7 | 52.2 | TSC22 domain family, member 1 | TSC22D1 |
| 218086_at | 26 | 10.9 | 3310.3 | 8.8 | 52.2 | neural proliferation, differentiation and control, 1 | NPDC1 |
| 217977_at | 88.7 | 35.5 | 4936.5 | 15.4 | 52.2 | selenoprotein X, 1 | SEPX1 |
| 212473_s_at | 118.4 | 85.5 | 10655.4 | 6.7 | 52.2 | microtubule associated monoxygenase, calponin and LIM domain containing 2 | MICAL2 |
| 205717_x_at | 452.2 | 265.9 | 4246.6 | 159.1 | 51.9 | protocadherin gamma subfamily A, 1 | PCDHGA1 |
| 212343_at | 43.5 | 20.4 | 580.2 | 13.2 | 51.9 | Yip1 domain family, member 6 | YIPF6 |
| 202342_s_at | 66.7 | 9.5 | 492.8 | 3.4 | 51.9 | tripartite motif-containing 2 | TRIM2 |
| 216913_s_at | 24.9 | 19.3 | 1027.2 | 9.6 | 51.9 | KIAA0690 | KIAA0690 |
| 211546_x_at | 238.6 | 220.9 | 24574.6 | 38.4 | 51.9 | synuclein, alpha (non A4 component of amyloid precursor) | SNCA |
| 220330_s_at | 76.6 | 55.8 | 1219.5 | 1.9 | 51.9 | SAM domain, SH3 domain and nuclear localisation signals, 1 | SAMSN1 |
| 201313_at | 59.3 | 11.7 | 806.8 | 8.4 | 51.5 | enolase 2 (gamma, neuronal) | ENO2 |
| 209677_at | 59.3 | 10 | 494.2 | 6.6 | 51.5 | protein kinase C, iota | PRKCI |
| 208534_s_at | 60.8 | 12.2 | 1464.6 | 6 | 51.5 | RAS p21 protein activator 4 /// hypothetical protein FLJ21767 | RASA4 /// FLJ21767 |
| 212504_at | 241.7 | 71.4 | 2483.2 | 32 | 51.5 | KIAA0934 | KIAA0934 |
| 201329_s_at | 863.4 | 379.9 | 7961 | 122.2 | 51.5 | v-ets erythroblastosis virus E26 oncogene homolog 2 (avian) | ETS2 |
| 209146_at | 118.9 | 64.6 | 825.4 | 6.9 | 51.5 | sterol-C4-methyl oxidase-like | SC4MOL |
| 221526_x_at | 245.3 | 109.5 | 1393 | 29.7 | 51.5 | par-3 partitioning defective 3 homolog (C. elegans) | PARD3 |
| 214156_at | 42.4 | 17.2 | 1686.2 | 3.8 | 51.5 | myosin VIIA and Rab interacting protein | MYRIP |
| 219014_at | 1928.5 | 1774.4 | 18056.6 | 300 | 51.5 | placenta-specific 8 | PLAC8 |
| 200050_at | 747.8 | 270.7 | 2799 | 232.9 | 51.1 | zinc finger protein 146 /// zinc finger protein 146 | ZNF146 |
| 201790_s_at | 103.8 | 21.9 | 1309.1 | 15.1 | 51.1 | 7-dehydrocholesterol reductase | DHCR7 |
| 203611_at | 1976.8 | 1120.4 | 37006.1 | 737.2 | 51.1 | telomeric repeat binding factor 2 | TERF2 |
| 209835_x_at | 477.3 | 245.5 | 9995.9 | 168.9 | 51.1 | CD44 antigen (homing function and Indian blood group system) | CD44 |
| 212183_at | 100.8 | 17 | 1555.8 | 18.8 | 51.1 | nudix (nucleoside diphosphate linked moiety X)-type motif 4 | NUDT4 |
| 212598_at | 41.3 | 12 | 536.8 | 6.1 | 51.1 | WD repeat and FYVE domain containing 3 | WDFY3 |
| 218113_at | 229 | 70 | 1840 | 54.7 | 51.1 | transmembrane protein 2 | TMEM2 |
| 218486_at | 132.3 | 10.8 | 3794.5 | 4.8 | 51.1 | Kruppel-like factor 11 | KLF11 |
| 54037_at | 362.6 | 285.4 | 2749.7 | 98.4 | 51.1 | Hermansky-Pudlak syndrome 4 | HPS4 |
| 207813_s_at | 34.9 | 27 | 288.2 | 8 | 51.1 | ferredoxin reductase | FDXR |
| 207120_at | 22.2 | 11 | 322.9 | 2.7 | 51.1 | zinc finger protein 667 | ZNF667 |
| 214321_at | 35.5 | 22.5 | 3390.7 | 3.4 | 51.1 | nephroblastoma overexpressed gene | NOV |
| 204546_at | 60.8 | 16 | 772.7 | 8 | 50.7 | KIAA0513 | KIAA0513 |
| 205467_at | 194.7 | 41.4 | 1696.3 | 27.4 | 50.7 | caspase 10, apoptosis-related cysteine peptidase | CASP10 |
| 210176_at | 198.1 | 109.2 | 1127.4 | 115.6 | 50.7 | toll-like receptor 1 | TLR1 |
| 211828_s_at | 25 | 7.9 | 521.9 | 7.4 | 50.7 | TRAF2 and NCK interacting kinase | TNIK |
| 200999_s_at | 220.7 | 113.6 | 3758.8 | 26.4 | 50.7 | cytoskeleton-associated protein 4 | CKAP4 |
| 206011_at | 183.1 | 75.1 | 1908.8 | 12.4 | 50.7 | caspase 1, apoptosis-related cysteine peptidase (interleukin 1, beta, convertase) | CASP1 |
| 202517_at | 273.9 | 170.4 | 6850.3 | 28.3 | 50.7 | collapsin response mediator protein 1 | CRMP1 |
| 204747_at | 282.2 | 196.5 | 5497.8 | 129.3 | 50.4 | interferon-induced protein with tetratricopeptide repeats 3 | IFIT3 |
| 205838_at | 28.5 | 9.3 | 8663.8 | 6.7 | 50.4 | glycophorin A (includes MN blood group) | GYPA |

TABLE 1-continued

Probe sets overexpressed in 25% of more of B-lineage ALL cases (n = 270) as compared to normal bone marrow CD19+CD10+ cells from 4 healthy donors

| probe set ID | CD10+ CD19+ max | CD10+ CD19+ min | ALL max | ALL min | % ALL over expressed | Title | Symbol |
|---|---|---|---|---|---|---|---|
| 206098_at | 35.9 | 3.4 | 206 | 2.4 | 50.4 | zinc finger protein 482 | ZNF482 |
| 218825_at | 270.2 | 16.8 | 3402.2 | 15.1 | 50.4 | EGF-like-domain, multiple 7 | EGFL7 |
| 209215_at | 294 | 224.3 | 2545 | 82 | 50.4 | tetracycline transporter-like protein | TETRAN |
| 212077_at | 70.8 | 60.4 | 5341.6 | 3.6 | 50.4 | caldesmon 1 | CALD1 |
| 207723_s_at | 14 | 6.5 | 1469.8 | 3.3 | 50.0 | killer cell lectin-like receptor subfamily C, member 3 | KLRC3 |
| 219743_at | 71.1 | 15.2 | 2565.5 | 7.9 | 50.0 | hairy/enhancer-of-split related with YRPW motif 2 | HEY2 |
| 201422_at | 434.5 | 286.1 | 6636.6 | 46.9 | 50.0 | interferon, gamma-inducible protein 30 | IFI30 |
| 201859_at | 820.4 | 406.8 | 24186.7 | 181.1 | 50.0 | proteoglycan 1, secretory granule | PRG1 |
| 206232_s_at | 140.2 | 32 | 1423.6 | 8.3 | 50.0 | UDP-Gal:betaGlcNAc beta 1,4-galactosyltransferase, polypeptide 6 | B4GALT6 |
| 200762_at | 1427.6 | 1083.2 | 10880.8 | 344.9 | 50.0 | dihydropyrimidinase-like 2 | DPYSL2 |
| 209679_s_at | 361 | 105.6 | 2891.8 | 34.3 | 50.0 | small trans-membrane and glycosylated protein | LOC57228 |
| 203153_at | 46 | 5.9 | 4357.9 | 7 | 49.6 | interferon-induced protein with tetratricopeptide repeats 1 | IFIT1 |
| 204310_s_at | 24.1 | 10.3 | 346.6 | 5.8 | 49.6 | natriuretic peptide receptor B/guanylate cyclase B (atrionatriuretic peptide receptor B) | NPR2 |
| 206866_at | 38.8 | 11.3 | 1138.2 | 6 | 49.6 | cadherin 4, type 1, R-cadherin (retinal) | CDH4 |
| 211133_x_at | 167.6 | 48.7 | 831.3 | 33.3 | 49.6 | leukocyte immunoglobulin-like receptor, subfamily B (with TM and ITIM domains), member 2 /// leukocyte immunoglobulin-like receptor, subfamily B (with TM and ITIM domains), member 3 | LILRB2 /// LILRB3 |
| 212605_s_at | 456.6 | 387.3 | 2803.4 | 247.1 | 49.6 | Nudix (nucleoside diphosphate linked moiety X)-type motif 3 | NUDT3 |
| 213273_at | 114.6 | 12.6 | 2460 | 10.9 | 49.6 | odz, odd Oz/ten-m homolog 4 (Drosophila) | ODZ4 |
| 218983_at | 90.8 | 24.9 | 833.9 | 10.5 | 49.6 | complement component 1, r subcomponent-like | C1RL |
| 201028_s_at | 2047.8 | 1148.8 | 19384.2 | 325.4 | 49.6 | CD99 antigen | CD99 |
| 211429_s_at | 128.8 | 61.2 | 4692.5 | 21.8 | 49.6 | serpin peptidase inhibitor, clade A (alpha-1 antiproteinase, antitrypsin), member 1 | SERPINA1 |
| 205041_s_at | 8.5 | 3.2 | 1537.4 | 2.6 | 49.3 | orosomucoid 1 /// orosomucoid 2 | ORM1 /// ORM2 |
| 205418_at | 133.4 | 15.3 | 890.2 | 11.3 | 49.3 | feline sarcoma oncogene | FES |
| 205495_s_at | 165.1 | 14.8 | 3464.4 | 14.4 | 49.3 | granulysin /// granulysin | GNLY |
| 210314_x_at | 176.8 | 16.3 | 1177.3 | 20.7 | 49.3 | tumor necrosis factor (ligand) superfamily, member 13 /// tumor necrosis factor (ligand) superfamily, member 12-member 13 | TNFSF13 /// TNFSF12-TNFSF13 |
| 209241_x_at | 205.9 | 152.8 | 1195.2 | 26.5 | 49.3 | misshapen-like kinase 1 (zebrafish) | MINK1 |
| 202145_at | 160.4 | 71.4 | 2972.7 | 28.1 | 49.3 | lymphocyte antigen 6 complex, locus E | LY6E |
| 204352_at | 516.8 | 346.2 | 3368.9 | 89.5 | 49.3 | TNF receptor-associated factor 5 | TRAF5 |
| 213233_s_at | 508.3 | 399.2 | 2437.2 | 33.5 | 49.3 | kelch-like 9 (Drosophila) | KLHL9 |
| 211367_s_at | 177.9 | 76.1 | 1385.3 | 6.2 | 49.3 | caspase 1, apoptosis-related cysteine peptidase (interleukin 1, beta, convertase) | CASP1 |
| 218690_at | 84 | 56.9 | 637.1 | 17.8 | 49.3 | PDZ and LIM domain 4 | PDLIM4 |
| 220448_at | 169.6 | 93.8 | 5928.5 | 4.3 | 49.3 | potassium channel, subfamily K, member 12 | KCNK12 |
| 201012_at | 202.4 | 40.4 | 15217.5 | 79.3 | 48.9 | annexin A1 | ANXA1 |
| 201325_s_at | 41.6 | 9.2 | 2026.9 | 7.8 | 48.9 | epithelial membrane protein 1 | EMP1 |
| 206871_at | 33.4 | 11.3 | 43391 | 8.5 | 48.9 | elastase 2, neutrophil | ELA2 |
| 204489_s_at | 491.6 | 46.5 | 6193.8 | 22.5 | 48.9 | CD44 antigen (homing function and Indian blood group system) | CD44 |
| 212675_s_at | 649.7 | 387.7 | 3942.6 | 127.4 | 48.9 | — | — |
| 207733_x_at | 133.5 | 44.8 | 804.2 | 11.6 | 48.9 | pregnancy specific beta-1-glycoprotein 9 | PSG9 |
| 215469_at | 9.1 | 6 | 491 | 2.4 | 48.9 | CDNA FLJ11627 fis, clone HEMBA1004225 | — |
| 202052_s_at | 113.2 | 17 | 783.9 | 9 | 48.5 | retinoic acid induced 14 | RAI14 |
| 211571_s_at | 20.8 | 5.6 | 6316.7 | 4.8 | 48.5 | chondroitin sulfate proteoglycan 2 (versican) | CSPG2 |
| 221942_s_at | 495.9 | 272.4 | 6805.3 | 76.1 | 48.5 | guanylate cyclase 1, soluble, alpha 3 | GUCY1A3 |
| 208636_at | 475.1 | 235 | 5700.3 | 22 | 48.5 | Actinin, alpha 1 | ACTN1 |
| 212503_s_at | 243.6 | 152.1 | 2682.6 | 52.9 | 48.5 | KIAA0934 | KIAA0934 |
| 213746_s_at | 181.5 | 133.1 | 2479.4 | 15.3 | 48.5 | filamin A, alpha (actin binding protein 280) | FLNA |
| 210262_at | 18.9 | 11.2 | 1040.7 | 3.6 | 48.5 | cysteine-rich secretory protein 2 | CRISP2 |
| 206082_at | 517.7 | 281.3 | 3082.3 | 26.6 | 48.5 | — | — |
| 203814_s_at | 45.7 | 11.7 | 1307.6 | 6.4 | 48.1 | NAD(P)H dehydrogenase, quinone 2 | NQO2 |
| 207426_s_at | 405.2 | 164.3 | 4003.1 | 88.9 | 48.1 | tumor necrosis factor (ligand) superfamily, member 4 (tax-transcriptionally activated glycoprotein 1, 34 kDa) | TNFSF4 |
| 217382_at | 27.6 | 2.8 | 671.1 | 1.5 | 48.1 | similar to Chloride intracellular channel protein 1 (Nuclear chloride ion channel 27) (NCC27) (p64 CLCP) (Chloride channel ABP) | LOC390363 |
| 218152_at | 397.3 | 264.4 | 2145.1 | 196.1 | 48.1 | high-mobility group 20A | HMG20A |
| 219570_at | 98.5 | 13.1 | 722.8 | 12.4 | 48.1 | chromosome 20 open reading frame 23 | C20orf23 |
| 214439_x_at | 738.3 | 423.3 | 5005.2 | 34.9 | 48.1 | bridging integrator 1 | BIN1 |
| 219956_at | 150.6 | 83.3 | 1080.7 | 16.4 | 48.1 | UDP-N-acetyl-alpha-D-galactosamine:polypeptide N-acetylgalactosaminyltransferase 6 (GalNAc-T6) | GALNT6 |
| 212820_at | 167.8 | 54.4 | 2069.3 | 11.1 | 48.1 | Dmx-like 2 | DMXL2 |
| 218694_at | 175.4 | 122.2 | 1524.5 | 24.4 | 48.1 | armadillo repeat containing, X-linked 1 | ARMCX1 |
| 205653_at | 99.7 | 74.7 | 24713.5 | 17 | 48.1 | cathepsin G | CTSG |
| 205804_s_at | 239.2 | 196.7 | 1677.1 | 25.1 | 48.1 | TRAF3 interacting protein 3 | TRAF3IP3 |
| 203167_at | 27.5 | 21.2 | 755.1 | 11.8 | 47.8 | TIMP metallopeptidase inhibitor 2 | TIMP2 |

TABLE 1-continued

Probe sets overexpressed in 25% of more of B-lineage ALL cases (n = 270) as compared to normal bone marrow CD19+CD10+ cells from 4 healthy donors

| probe set ID | CD10+ CD19+ max | CD10+ CD19+ min | ALL max | ALL min | % ALL over expressed | Title | Symbol |
|---|---|---|---|---|---|---|---|
| 209286_at | 109.6 | 17.3 | 3085.9 | 13.9 | 47.8 | CDC42 effector protein (Rho GTPase binding) 3 | CDC42EP3 |
| 218758_s_at | 122.6 | 44 | 901.4 | 17.9 | 47.8 | DNA segment on chromosome 21 (unique) 2056 expressed sequence | D21S2056E |
| 220618_s_at | 78.8 | 35.1 | 864.5 | 14 | 47.8 | zinc finger, CW type with PWWP domain 1 | ZCWPW1 |
| 216056_at | 37.5 | 20.4 | 1647.5 | 6.6 | 47.8 | CD44 antigen (Indian blood group) | CD44 |
| 204122_at | 194.7 | 37.7 | 4519.8 | 38.5 | 47.4 | TYRO protein tyrosine kinase binding protein | TYROBP |
| 211820_x_at | 154 | 9.9 | 16977.4 | 10.9 | 47.4 | glycophorin A (includes MN blood group) | GYPA |
| 213975_s_at | 385.3 | 20.4 | 11329.4 | 7.7 | 47.4 | lysozyme (renal amyloidosis) /// leukocyte immunoglobulin-like receptor, subfamily B (with TM and ITIM domains), member 1 | LYZ /// LILRB1 |
| 203305_at | 477 | 331.4 | 17615.2 | 50.6 | 47.4 | coagulation factor XIII, A1 polypeptide | F13A1 |
| 203923_s_at | 307.5 | 200.6 | 2691.8 | 94.1 | 47.4 | cytochrome b-245, beta polypeptide (chronic granulomatous disease) | CYBB |
| 207705_s_at | 244.4 | 101.3 | 1962.5 | 21 | 47.4 | KIAA0980 protein | KIAA0980 |
| 218935_at | 225.6 | 98.8 | 1666.1 | 18.2 | 47.4 | EH-domain containing 3 | EHD3 |
| 214433_s_at | 176.1 | 92.2 | 37065.6 | 8.9 | 47.4 | selenium binding protein 1 /// selenium binding protein 1 | SELENBP1 |
| 202382_s_at | 27.2 | 13.3 | 709.5 | 6.9 | 47.0 | glucosamine-6-phosphate deaminase 1 | GNPDA1 |
| 210589_s_at | 50.6 | 33.4 | 1138.1 | 22.4 | 47.0 | glucosidase, beta; acid (includes glucosylceramidase) /// glucosidase, beta; acid, pseudogene | GBA /// GBAP |
| 221709_s_at | 59.4 | 16.6 | 632 | 15.8 | 47.0 | chromosome 14 open reading frame 131 /// chromosome 14 open reading frame 131 | C14orf131 |
| 218276_s_at | 222.1 | 153.4 | 1251.9 | 51.4 | 47.0 | salvador homolog 1 (Drosophila) | SAV1 |
| 216155_at | 107.9 | 19 | 814.4 | 5 | 47.0 | Neuron navigator 1 | NAV1 |
| 219691_at | 139 | 37.5 | 921.3 | 10 | 47.0 | sterile alpha motif domain containing 9 | SAMD9 |
| 215449_at | 65.7 | 45.5 | 6842.1 | 16 | 47.0 | benzodiazapine receptor (peripheral)-like 1 | BZRPL1 |
| 201372_s_at | 37.6 | 12.1 | 384.9 | 4.6 | 47.0 | cullin 3 | CUL3 |
| 207104_x_at | 116.2 | 21.1 | 980.6 | 14.4 | 46.7 | leukocyte immunoglobulin-like receptor, subfamily B (with TM and ITIM domains), member 1 | LILRB1 |
| 209370_s_at | 401.4 | 81.6 | 4041.7 | 110.9 | 46.7 | SH3-domain binding protein 2 | SH3BP2 |
| 219359_at | 272.8 | 98 | 4034.5 | 56.4 | 46.7 | hypothetical protein FLJ22635 | FLJ22635 |
| 37145_at | 188.7 | 20.9 | 2719.6 | 16.5 | 46.7 | granulysin | GNLY |
| 213117_at | 176.9 | 40.6 | 1268 | 13.6 | 46.7 | kelch-like 9 (Drosophila) | KLHL9 |
| 210321_at | 33.3 | 16.6 | 1557.9 | 6.2 | 46.7 | granzyme H (cathepsin G-like 2, protein h-CCPX) /// granzyme H (cathepsin G-like 2, protein h-CCPX) | GZMH |
| 212509_s_at | 874.8 | 669.9 | 16097.8 | 208.4 | 46.7 | matrix-remodelling associated 7 | MXRA7 |
| 206518_at | 35.2 | 14.3 | 1009.6 | 2.9 | 46.7 | regulator of G-protein signalling 9 | RGS9 |
| 205899_at | 81.3 | 41.1 | 5746.4 | 6.7 | 46.7 | cyclin A1 | CCNA1 |
| 219952_s_at | 44.5 | 10.4 | 1155.8 | 14.4 | 46.3 | mucolipin 1 | MCOLN1 |
| 220734_at | 86.1 | 20.6 | 492.2 | 15.8 | 46.3 | hypothetical protein MGC10334 | MGC10334 |
| 221014_s_at | 150.6 | 5.4 | 789.2 | 61.9 | 46.3 | RAB33B, member RAS oncogene family /// RAB33B, member RAS oncogene family | RAB33B |
| 220615_s_at | 206.2 | 22.1 | 2746.1 | 9.3 | 46.3 | male sterility domain containing 1 | MLSTD1 |
| 200615_s_at | 283.8 | 215.7 | 2222.3 | 31.7 | 46.3 | adaptor-related protein complex 2, beta 1 subunit | AP2B1 |
| 218954_s_at | 51.1 | 31.2 | 548.7 | 8 | 46.3 | BRF2, subunit of RNA polymerase III transcription initiation factor, BRF1-like | BRF2 |
| 221724_s_at | 32.3 | 26.6 | 1445.2 | 9.7 | 46.3 | C-type lectin domain family 4, member A | CLEC4A |
| 212013_at | 1198.6 | 779.5 | 6768.7 | 10.4 | 46.3 | peroxidasin homolog (Drosophila) | PXDN |
| 201060_x_at | 351.6 | 243.5 | 9900.6 | 143.4 | 45.9 | stomatin | STOM |
| 204928_s_at | 26.6 | 16.4 | 605.2 | 12.6 | 45.9 | solute carrier family 10 (sodium/bile acid cotransporter family), member 3 | SLC10A3 |
| 205758_at | 251.6 | 28.5 | 2296.3 | 26.2 | 45.9 | CD8 antigen, alpha polypeptide (p32) /// D8 antigen, alpha polypeptide (p32) | CD8A |
| 214692_s_at | 36.8 | 18.8 | 697.7 | 12.1 | 45.9 | jerky homolog (mouse) | JRK |
| 217904_s_at | 54.5 | 20 | 988.3 | 7.2 | 45.9 | beta-site APP-cleaving enzyme 1 | BACE1 |
| 205391_x_at | 97.2 | 24.1 | 5144.8 | 10.1 | 45.9 | ankyrin 1, erythrocytic /// ankyrin 1, erythrocytic | ANK1 |
| 215666_at | 10.4 | 4 | 4868.5 | 1.7 | 45.9 | major histocompatibility complex, class II, DR beta 4 | HLA-DRB4 |
| 32042_at | 93.3 | 75.7 | 657 | 18.1 | 45.9 | cytosolic ovarian carcinoma antigen 1 | COVA1 |
| 221485_at | 159.7 | 88.1 | 2565.1 | 13.4 | 45.9 | UDP-Gal:betaGlcNAc beta 1,4-galactosyltransferase, polypeptide 5 | B4GALT5 |
| 219504_s_at | 74.9 | 32.1 | 647.3 | 5.1 | 45.9 | chromosome 1 open reading frame 82 | C1orf82 |
| 219154_at | 139.2 | 34.7 | 1223.9 | 32.3 | 45.6 | ras homolog gene family, member F (in filopodia) | RHOF |
| 201964_at | 592.6 | 317.4 | 2559.5 | 146.2 | 45.6 | amyotrophic lateral sclerosis 4 | ALS4 |
| 206414_s_at | 172.8 | 30.4 | 1356.5 | 12.5 | 45.6 | development and differentiation enhancing factor 2 | DDEF2 |
| 209297_at | 64.6 | 28.3 | 2212.4 | 12.9 | 45.6 | intersectin 1 (SH3 domain protein) | ITSN1 |
| 221040_at | 31.9 | 7.5 | 818.7 | 3.6 | 45.6 | calpain 10 | CAPN10 |
| 211474_s_at | 583.1 | 390.7 | 2625.8 | 126.3 | 45.6 | serpin peptidase inhibitor, clade B (ovalbumin), member 6 | SERPINB6 |
| 204924_at | 164.9 | 53.5 | 1519.3 | 16.7 | 45.6 | toll-like receptor 2 | TLR2 |
| 218625_at | 309.9 | 197.7 | 7686.5 | 59.9 | 45.6 | neuritin 1 | NRN1 |
| 64408_s_at | 69.9 | 34.2 | 431.4 | 7.2 | 45.6 | calmodulin-like 4 | CALML4 |
| 204030_s_at | 777.4 | 335.9 | 5350.9 | 17.8 | 45.6 | schwannomin interacting protein 1 | SCHIP1 |
| 206048_at | 26.8 | 6 | 296.3 | 6 | 45.2 | ovo-like 2 (Drosophila) | OVOL2 |
| 207417_s_at | 179.2 | 129.8 | 960.4 | 71.8 | 45.2 | zinc finger protein 177 | ZNF177 |
| 221682_s_at | 55.4 | 3.5 | 615.7 | 2.5 | 45.2 | protocadherin gamma subfamily B, 6 | PCDHGB6 |

TABLE 1-continued

Probe sets overexpressed in 25% of more of B-lineage ALL cases (n = 270) as compared to normal bone marrow CD19⁺CD10⁺ cells from 4 healthy donors

| probe set ID | CD10+ CD19+ max | CD10+ CD19+ min | ALL max | ALL min | % ALL over expressed | Title | Symbol |
|---|---|---|---|---|---|---|---|
| 217143_s_at | 148.2 | 47 | 2102.9 | 22.5 | 45.2 | T cell receptor alpha locus /// T cell receptor delta locus | TRA@ /// TRD@ |
| 219200_at | 193.1 | 136.2 | 791 | 40.9 | 45.2 | hypothetical protein MGC5297 | MGC5297 |
| 203952_at | 98 | 67.6 | 671.4 | 26.8 | 45.2 | activating transcription factor 6 | ATF6 |
| 205878_at | 39.3 | 19.3 | 420.9 | 6.1 | 45.2 | POU domain, class 6, transcription factor 1 | POU6F1 |
| 212062_at | 18.9 | 10.9 | 2294.2 | 4.1 | 45.2 | ATPase, Class II, type 9A | ATP9A |
| 221788_at | 76.1 | 20.4 | 718.2 | 4.8 | 45.2 | Phosphoglucomutase 3 | PGM3 |
| 207821_s_at | 245.4 | 65 | 1131.2 | 54.3 | 44.8 | PTK2 protein tyrosine kinase 2 | PTK2 |
| 222312_s_at | 50.8 | 9 | 422.6 | 8.3 | 44.8 | CDNA clone IMAGE: 6186815 | — |
| 207459_x_at | 272.7 | 55.5 | 20138.4 | 19.3 | 44.8 | glycophorin B (includes Ss blood group) | GYPB |
| 218298_s_at | 440.3 | 284.8 | 2624.6 | 118.3 | 44.8 | chromosome 14 open reading frame 159 | C14orf159 |
| 202202_s_at | 47.6 | 9.8 | 586.4 | 2.7 | 44.8 | laminin, alpha 4 | LAMA4 |
| 215354_s_at | 147.9 | 86.6 | 605 | 23.4 | 44.8 | proline-, glutamic acid-, leucine-rich protein 1 | PELP1 |
| 203355_s_at | 319.3 | 149.7 | 2993.9 | 23.7 | 44.8 | pleckstrin and Sec7 domain containing 3 | PSD3 |
| 207030_s_at | 394.1 | 147.2 | 4873.1 | 24.3 | 44.8 | cysteine and glycine-rich protein 2 | CSRP2 |
| 215807_s_at | 69 | 40.2 | 1184.6 | 13.1 | 44.8 | plexin B1 | PLXNB1 |
| 212235_at | 152.9 | 16.9 | 1270 | 13.7 | 44.4 | plexin D1 | PLXND1 |
| 218608_at | 170.7 | 14.9 | 1358.1 | 12.8 | 44.4 | ATPase type 13A2 | ATP13A2 |
| 34726_at | 210.8 | 91.9 | 901.7 | 87 | 44.4 | calcium channel, voltage-dependent, beta 3 subunit | CACNB3 |
| 202201_at | 261.3 | 56.9 | 23262.7 | 27.3 | 44.4 | biliverdin reductase B (flavin reductase (NADPH)) | BLVRB |
| 203148_s_at | 276.3 | 157.7 | 1480.8 | 42.5 | 44.4 | tripartite motif-containing 14 | TRIM14 |
| 215719_x_at | 61.1 | 13.9 | 1175.1 | 5.9 | 44.4 | Fas (TNF receptor superfamily, member 6) | FAS |
| 222126_at | 161 | 95 | 1827.7 | 26 | 44.4 | Insulin receptor substrate 3-like | HRBL |
| 212372_at | 618.7 | 397.6 | 4614.1 | 115.8 | 44.4 | myosin, heavy polypeptide 10, non-muscle | MYH10 |
| 221994_at | 36.1 | 13.4 | 347.7 | 3.8 | 44.4 | PDZ and LIM domain 5 | PDLIM5 |
| 215028_at | 97.8 | 15.6 | 1792.1 | 2.9 | 44.4 | sema domain, transmembrane domain (TM), and cytoplasmic domain, (semaphorin) 6A | SEMA6A |
| 212192_at | 127.9 | 35.5 | 3244.7 | 2.6 | 44.4 | potassium channel tetramerisation domain containing 12 | KCTD12 |
| 203325_s_at | 265.4 | 137.3 | 2845.4 | 11.5 | 44.4 | collagen, type V, alpha 1 | COL5A1 |
| 200699_at | 294.6 | 228 | 1197.6 | 124.3 | 44.1 | KDEL (Lys-Asp-Glu-Leu) endoplasmic reticulum protein retention receptor 2 | KDELR2 |
| 218899_s_at | 164.5 | 10.8 | 3140.6 | 10.1 | 44.1 | brain and acute leukemia, cytoplasmic | BAALC |
| 217519_at | 30.4 | 4.6 | 285 | 2.2 | 44.1 | Microtubule-actin crosslinking factor 1 | MACF1 |
| 218807_at | 562.5 | 419.2 | 4141.9 | 204.2 | 44.1 | vav 3 oncogene | VAV3 |
| 210151_s_at | 365.9 | 274.5 | 1788.9 | 42.5 | 44.1 | dual-specificity tyrosine-(Y)-phosphorylation regulated kinase 3 | DYRK3 |
| 215894_at | 82.6 | 6.9 | 1987 | 2.1 | 44.1 | prostaglandin D2 receptor (DP) | PTGDR |
| 210783_x_at | 163 | 40.1 | 1631.4 | 13 | 44.1 | C-type lectin domain family 11, member A | CLEC11A |
| 205154_at | 38 | 17.4 | 1093.7 | 11.5 | 43.7 | leucine rich repeat neuronal 5 | LRRN5 |
| 210430_x_at | 45.3 | 24.4 | 5655.9 | 16.2 | 43.7 | Rhesus blood group, D antigen | RHD |
| 211148_s_at | 10.3 | 4.4 | 593 | 4.2 | 43.7 | angiopoietin 2 | ANGPT2 |
| 222144_at | 28.4 | 13 | 709.7 | 10.4 | 43.7 | kinesin family member 17 | KIF17 |
| 210613_s_at | 450.3 | 135.3 | 2720.5 | 25.2 | 43.7 | synaptogyrin 1 | SYNGR1 |
| 204929_s_at | 343.3 | 181 | 2094.2 | 33.4 | 43.7 | vesicle-associated membrane protein 5 (myobrevin) | VAMP5 |
| 201807_at | 874.5 | 680.8 | 4594.7 | 473.5 | 43.3 | vacuolar protein sorting 26 homolog A (yeast) | VPS26A |
| 207846_at | 9.9 | 1.7 | 407.8 | 0.9 | 43.3 | POU domain, class 1, transcription factor 1 (Pit1, growth hormone factor 1) | POU1F1 |
| 200923_at | 674.8 | 262.5 | 6976.3 | 63.3 | 43.3 | lectin, galactoside-binding, soluble, 3 binding protein | LGALS3BP |
| 211419_s_at | 38.7 | 9.4 | 731 | 4 | 43.3 | chimerin (chimaerin) 2 | CHN2 |
| 209582_s_at | 413.4 | 242.1 | 2897.2 | 106.3 | 43.3 | CD200 antigen | CD200 |
| 205131_x_at | 255 | 36.1 | 2512.6 | 11.9 | 43.3 | C-type lectin domain family 11, member A | CLEC11A |
| 208322_s_at | 188 | 60.7 | 2898.8 | 15.2 | 43.3 | ST3 beta-galactoside alpha-2,3-sialyltransferase 1 | ST3GAL1 |
| 208198_x_at | 73.6 | 66.4 | 647.4 | 21.5 | 43.3 | killer cell immunoglobulin-like receptor, two domains, short cytoplasmic tail, 1 | KIR2DS1 |
| 217584_at | 61.9 | 28.2 | 750.6 | 4.8 | 43.3 | Niemann-Pick disease, type C1 | NPC1 |
| 205330_at | 200.9 | 114.6 | 3525.1 | 24.7 | 43.3 | meningioma (disrupted in balanced translocation) 1 | MN1 |
| 214475_x_at | 190.4 | 85.4 | 4205.9 | 10.1 | 43.3 | calpain 3, (p94) | CAPN3 |
| 211709_s_at | 559.3 | 441.1 | 5273.2 | 17.1 | 43.3 | C-type lectin domain family 11, member A /// C-type lectin domain family 11, member A | CLEC11A |
| 204032_at | 75.1 | 13.4 | 409.7 | 7.3 | 43.0 | breast cancer anti-estrogen resistance 3 | BCAR3 |
| 205109_s_at | 96.9 | 8.6 | 2788.5 | 5.2 | 43.0 | Rho guanine nucleotide exchange factor (GEF) 4 | ARHGEF4 |
| 218525_s_at | 191.5 | 59.4 | 973.3 | 40.3 | 43.0 | hypoxia-inducible factor 1, alpha subunit inhibitor | HIF1AN |
| 221771_s_at | 414.5 | 191.6 | 1621.4 | 150.2 | 43.0 | M-phase phosphoprotein, mpp8 | HSMPP8 |
| 221933_at | 30.4 | 5.8 | 1889.4 | 3.6 | 43.0 | neuroligin 4, X-linked | NLGN4X |
| 202826_at | 43.2 | 36.7 | 620.2 | 12.9 | 43.0 | serine peptidase inhibitor, Kunitz type 1 | SPINT1 |
| 213618_at | 578.7 | 308 | 2951.3 | 141.6 | 43.0 | centaurin, delta 1 | CENTD1 |
| 219376_at | 112.3 | 45.6 | 439 | 22.2 | 43.0 | zinc finger protein 322B | ZNF322B |
| 220986_s_at | 22.1 | 2.9 | 250.7 | 0.9 | 43.0 | tigger transposable element derived 6 /// tigger transposable element derived 6 | TIGD6 |
| 205349_at | 542.8 | 279.4 | 9728.6 | 79.3 | 43.0 | guanine nucleotide binding protein (G protein), alpha 15 (Gq class) | GNA15 |
| 206001_at | 1156.7 | 435.3 | 13016 | 73.3 | 43.0 | neuropeptide Y | NPY |
| 201617_x_at | 30.9 | 6.3 | 1133.6 | 1.6 | 43.0 | caldesmon 1 | CALD1 |
| 205407_at | 153.9 | 62.7 | 1103.5 | 6.8 | 43.0 | reversion-inducing-cysteine-rich protein with kazal motifs | RECK |

TABLE 1-continued

Probe sets overexpressed in 25% of more of B-lineage ALL cases (n = 270) as compared to normal bone marrow CD19+CD10+ cells from 4 healthy donors

| probe set ID | CD10+ CD19+ max | CD10+ CD19+ min | ALL max | ALL min | % ALL over expressed | Title | Symbol |
|---|---|---|---|---|---|---|---|
| 214920_at | 71.5 | 13.9 | 7696.6 | 1 | 43.0 | hypothetical protein LOC221981 | LOC221981 |
| 203509_at | 1408.7 | 987.3 | 19247.5 | 644.6 | 42.6 | sortilin-related receptor, L(DLR class) A repeats-containing | SORL1 |
| 203756_at | 63.4 | 33.9 | 985.4 | 17.2 | 42.6 | Rho guanine nucleotide exchange factor (GEF) 17 | ARHGEF17 |
| 215247_at | 37 | 14.1 | 505.1 | 8.8 | 42.6 | hypothetical protein LOC339692 | LOC339692 |
| 204490_s_at | 358.2 | 177 | 6178.3 | 80.2 | 42.6 | CD44 antigen (homing function and Indian blood group system) | CD44 |
| 202990_at | 129.3 | 80.2 | 2758.5 | 19.8 | 42.6 | phosphorylase, glycogen; liver (Hers disease, glycogen storage disease type VI) | PYGL |
| 209617_s_at | 68.7 | 23.3 | 424.5 | 6 | 42.6 | catenin (cadherin-associated protein), delta 2 (neural plakophilin-related arm-repeat protein) | CTNND2 |
| 210432_s_at | 126 | 7 | 8051.5 | 3 | 42.6 | sodium channel, voltage-gated, type III, alpha | SCN3A |
| 202786_at | 516.7 | 381.8 | 3315.8 | 115.1 | 42.6 | serine threonine kinase 39 (STE20/SPS1 homolog, yeast) | STK39 |
| 203595_s_at | 211.8 | 106.6 | 2067.3 | 39.1 | 42.6 | interferon-induced protein with tetratricopeptide repeats 5 | IFIT5 |
| 201375_s_at | 570.8 | 376.1 | 3830.3 | 343.5 | 42.2 | protein phosphatase 2 (formerly 2A), catalytic subunit, beta isoform | PPP2CB |
| 201640_x_at | 90.8 | 14.3 | 542.2 | 14.8 | 42.2 | cleft lip and palate associated transmembrane protein 1 | CLPTM1 |
| 201894_s_at | 782.9 | 494.9 | 3984.2 | 463.8 | 42.2 | signal sequence receptor, alpha (translocon-associated protein alpha) | SSR1 |
| 210854_x_at | 157.5 | 33 | 5300.7 | 25.1 | 42.2 | solute carrier family 6 (neurotransmitter transporter, creatine), member 8 | SLC6A8 |
| 212014_x_at | 406.8 | 193.4 | 8862.5 | 103.3 | 42.2 | CD44 antigen (homing function and Indian blood group system) | CD44 |
| 212366_at | 238.2 | 143.6 | 1029.8 | 72.6 | 42.2 | zinc finger protein 292 | ZNF292 |
| 212606_at | 216.6 | 9.2 | 1437.3 | 6.1 | 42.2 | WD repeat and FYVE domain containing 3 | WDFY3 |
| 218676_s_at | 240.6 | 17.7 | 3374.1 | 9.2 | 42.2 | phosphatidylcholine transfer protein | PCTP |
| 219485_s_at | 568.5 | 437.9 | 3387.7 | 256.5 | 42.2 | proteasome (prosome, macropain) 26S subunit, non-ATPase, 10 | PSMD10 |
| 219491_at | 33.9 | 14 | 393.9 | 10.4 | 42.2 | leucine rich repeat and fibronectin type III domain containing 4 | LRFN4 |
| 219521_at | 24.7 | 17.2 | 731.3 | 12.4 | 42.2 | beta-1,3-glucuronyltransferase 1 (glucuronosyltransferase P) | B3GAT1 |
| 49111_at | 242.1 | 150.9 | 1265 | 107.9 | 42.2 | MRNA; cDNA DKFZp762M127 (from clone DKFZp762M127) | — |
| 206676_at | 25.6 | 8.4 | 11672.8 | 2.9 | 42.2 | carcinoembryonic antigen-related cell adhesion molecule 8 | CEACAM8 |
| 209970_x_at | 558.3 | 425.2 | 3740.3 | 162.5 | 42.2 | caspase 1, apoptosis-related cysteine peptidase (interleukin 1, beta, convertase) | CASP1 |
| 216392_s_at | 288.4 | 175.1 | 1390.9 | 40.1 | 42.2 | SEC23 interacting protein | SEC23IP |
| 201539_s_at | 357.3 | 328.8 | 6236.3 | 98.9 | 42.2 | four and a half LIM domains 1 | FHL1 |
| 204066_s_at | 99.5 | 53.6 | 13416.6 | 8.8 | 42.2 | centaurin, gamma 2 | CENTG2 |
| 202392_s_at | 197.9 | 91.7 | 971.1 | 29.9 | 42.2 | phosphatidylserine decarboxylase | PISD |
| 204914_s_at | 68 | 22.8 | 6617.3 | 4.2 | 42.2 | SRY (sex determining region Y)-box 11 | SOX11 |
| 213050_at | 85.5 | 61.6 | 2104.7 | 18.4 | 42.2 | cordon-bleu homolog (mouse) | COBL |
| 202797_at | 512.7 | 296.4 | 2519.2 | 230.9 | 41.9 | SAC1 suppressor of actin mutations 1-like (yeast) | SACM1L |
| 205844_at | 44.7 | 3.2 | 2772.1 | 2.6 | 41.9 | vanin 1 /// vanin 1 | VNN1 |
| 221023_s_at | 46.3 | 6 | 655.1 | 4.1 | 41.9 | potassium voltage-gated channel, subfamily H (eag-related), member 6 /// potassium voltage-gated channel, subfamily H (eag-related), member 6 | KCNH6 |
| 219799_s_at | 198.1 | 82 | 2562.8 | 30.6 | 41.9 | dehydrogenase/reductase (SDR family) member 9 | DHRS9 |
| 202803_s_at | 827.9 | 622.5 | 7958.6 | 236.1 | 41.9 | integrin, beta 2 (antigen CD18 (p95), lymphocyte function-associated antigen 1; macrophage antigen 1 (mac-1) beta subunit) | ITGB2 |
| 221157_s_at | 25.8 | 14.7 | 294.4 | 5 | 41.9 | F-box protein 24 | FBXO24 |
| 202411_at | 184.7 | 70.5 | 20733 | 10.7 | 41.9 | interferon, alpha-inducible protein 27 | IFI27 |
| 206986_at | 35.2 | 16.2 | 238.3 | 5.6 | 41.9 | fibroblast growth factor 18 | FGF18 |
| 203550_s_at | 191 | 73.5 | 1361.8 | 46.2 | 41.5 | chromosome 1 open reading frame 2 | C1orf2 |
| 210586_x_at | 69.6 | 27.6 | 8076.6 | 14 | 41.5 | Rhesus blood group, D antigen | RHD |
| 215874_at | 144.7 | 31.8 | 1354 | 54.7 | 41.5 | ST3 beta-galactoside alpha-2,3-sialyltransferase 1 | ST3GAL1 |
| 219201_s_at | 12.2 | 6.1 | 317.3 | 5.3 | 41.5 | twisted gastrulation homolog 1 (Drosophila) | TWSG1 |
| 219363_s_at | 245.9 | 138.9 | 938.5 | 70.7 | 41.5 | MTERF domain containing 1 | MTERFD1 |
| 222134_at | 23.2 | 8.2 | 453.2 | 6.7 | 41.5 | D-aspartate oxidase | DDO |
| 202431_s_at | 1088.3 | 130.1 | 8590.2 | 54.6 | 41.5 | v-myc myelocytomatosis viral oncogene homolog (avian) | MYC |
| 219913_s_at | 297.8 | 220.7 | 1053.6 | 40.1 | 41.5 | Cm, crooked neck-like 1 (Drosophila) | CRNKL1 |
| 202196_s_at | 8.5 | 3.5 | 592.6 | 0.8 | 41.5 | dickkopf homolog 3 (Xenopus laevis) | DKK3 |
| 217559_at | 143.2 | 78.6 | 819.1 | 28.8 | 41.5 | ribosomal protein L10-like | RPL10L |
| 205442_at | 23.3 | 7.8 | 1395.9 | 2.4 | 41.5 | microfibrillar-associated protein 3-like | MFAP3L |
| 212915_at | 12 | 5.1 | 653.8 | 1 | 41.5 | PDZ domain containing RING finger 3 | PDZRN3 |
| 205424_at | 91.1 | 72.1 | 711.9 | 20.3 | 41.5 | ProSAPiP2 protein | ProSAPiP2 |
| 204288_s_at | 30.9 | 16.4 | 1075.6 | 8.8 | 41.1 | sorbin and SH3 domain containing 2 | SORBS2 |
| 211250_s_at | 123.7 | 10.2 | 1289.1 | 9.9 | 41.1 | SH3-domain binding protein 2 | SH3BP2 |
| 211565_at | 111.6 | 8 | 1229.6 | 11.1 | 41.1 | SH3-domain GRB2-like 3 | SH3GL3 |
| 212759_s_at | 50.3 | 20 | 1354.5 | 11.1 | 41.1 | transcription factor 7-like 2 (T-cell specific, HMG-box) | TCF7L2 |

TABLE 1-continued

Probe sets overexpressed in 25% of more of B-lineage ALL cases (n = 270) as compared to normal bone marrow CD19+CD10+ cells from 4 healthy donors

| probe set ID | CD10+ CD19+ max | CD10+ CD19+ min | ALL max | ALL min | % ALL over expressed | Title | Symbol |
|---|---|---|---|---|---|---|---|
| 213269_at | 161.6 | 26.4 | 990 | 13.7 | 41.1 | zinc finger protein 248 | ZNF248 |
| 202933_s_at | 87.6 | 7.7 | 1307.2 | 3 | 41.1 | v-yes-1 Yamaguchi sarcoma viral oncogene homolog 1 | YES1 |
| 204319_s_at | 323.1 | 27 | 3182.8 | 9.5 | 41.1 | regulator of G-protein signalling 10 | RGS10 |
| 206179_s_at | 33.8 | 13.5 | 280.9 | 6.4 | 41.1 | brain-specific protein p25 alpha | TPPP |
| 202694_at | 23.1 | 10.3 | 411.9 | 4.7 | 41.1 | serine/threonine kinase 17a (apoptosis-inducing) | STK17A |
| 213317_at | 62.8 | 11.5 | 4466.4 | 1.6 | 41.1 | Chloride intracellular channel 5 | CLIC5 |
| 221790_s_at | 153.6 | 46.8 | 3617.7 | 12.9 | 41.1 | low density lipoprotein receptor adaptor protein 1 | LDLRAP1 |
| 209168_at | 202.8 | 133.5 | 2043.8 | 18.8 | 41.1 | glycoprotein M6B | GPM6B |
| 204430_s_at | 433.8 | 96.8 | 8380.8 | 16.8 | 41.1 | solute carrier family 2 (facilitated glucose/fructose transporter), member 5 | SLC2A5 |
| 203111_s_at | 266.2 | 23.4 | 2421.3 | 22.9 | 40.7 | PTK2B protein tyrosine kinase 2 beta | PTK2B |
| 204011_at | 238.2 | 32.7 | 4642.4 | 23.3 | 40.7 | sprouty homolog 2 (Drosophila) | SPRY2 |
| 206077_at | 98.8 | 27.1 | 3637.6 | 19.7 | 40.7 | Kell blood group | KEL |
| 208460_at | 116.9 | 25.4 | 674.9 | 13.3 | 40.7 | gap junction protein, alpha 7, 45 kDa (connexin 45) | GJA7 |
| 210401_at | 875.3 | 442.5 | 5542.9 | 273.2 | 40.7 | purinergic receptor P2X, ligand-gated ion channel, 1 | P2RX1 |
| 212186_at | 66.1 | 36.6 | 986.1 | 28.3 | 40.7 | acetyl-Coenzyme A carboxylase alpha | ACACA |
| 212199_at | 654.1 | 450.9 | 2384.1 | 261.7 | 40.7 | Morf4 family associated protein 1-like 1 | MRFAP1L1 |
| 201887_at | 159.2 | 81.2 | 2829.5 | 30.4 | 40.7 | interleukin 13 receptor, alpha 1 | IL13RA1 |
| 205259_at | 116.8 | 12.2 | 2391.5 | 4 | 40.7 | nuclear receptor subfamily 3, group C, member 2 | NR3C2 |
| 206150_at | 440.2 | 65.5 | 5428.4 | 25.6 | 40.7 | tumor necrosis factor receptor superfamily, member 7 | TNFRSF7 |
| 214298_x_at | 1264.2 | 1096.3 | 7522.7 | 184.1 | 40.7 | septin 6 | SEPT6 |
| 210390_s_at | 39.8 | 11.9 | 314.9 | 3.3 | 40.7 | chemokine (C-C motif) ligand 14 /// chemokine (C-C motif) ligand 15 | CCL14 /// CCL15 |
| 202746_at | 186.5 | 152.4 | 9006.6 | 24.9 | 40.7 | integral membrane protein 2A | ITM2A |
| 211286_x_at | 39.9 | 21.4 | 331.6 | 7.4 | 40.7 | colony stimulating factor 2 receptor, alpha, low-affinity (granulocyte-macrophage) | CSF2RA |
| 220089_at | 63.8 | 22.6 | 573.9 | 6 | 40.7 | L-2-hydroxyglutarate dehydrogenase | L2HGDH |
| 200736_s_at | 2887.8 | 1921.6 | 31355.7 | 1488.8 | 40.4 | glutathione peroxidase 1 | GPX1 |
| 204468_s_at | 12.2 | 5.1 | 736.9 | 3.6 | 40.4 | tyrosine kinase with immunoglobulin-like and EGF-like domains 1 | TIE1 |
| 210094_s_at | 165 | 41.8 | 1041.4 | 27.5 | 40.4 | par-3 partitioning defective 3 homolog (C. elegans) | PARD3 |
| 217984_at | 1991.8 | 1242.4 | 15329.1 | 851.9 | 40.4 | ribonuclease T2 | RNASET2 |
| 219829_at | 31.7 | 12.6 | 379.4 | 9.6 | 40.4 | integrin beta 1 binding protein (melusin) 2 | ITGB1BP2 |
| 64064_at | 439.2 | 266.2 | 4543.4 | 171.3 | 40.4 | GTPase, IMAP family member 5 | GIMAP5 |
| 208966_x_at | 3288.9 | 1811.3 | 12809.7 | 786.3 | 40.4 | interferon, gamma-inducible protein 16 | IFI16 |
| 213888_s_at | 336 | 144.1 | 2671.9 | 10.8 | 40.4 | TRAF3 interacting protein 3 | TRAF3IP3 |
| 203104_at | 156.1 | 81.9 | 4853.9 | 20.2 | 40.4 | colony stimulating factor 1 receptor, formerly McDonough feline sarcoma viral (v-fms) oncogene homolog /// colony stimulating factor 1 receptor, formerly McDonough feline sarcoma viral (v-fms) oncogene homolog | CSF1R |
| 202668_at | 282.8 | 98.6 | 4724.3 | 7.1 | 40.4 | ephrin-B2 | EFNB2 |
| 203110_at | 942.9 | 657.8 | 4194.4 | 419.8 | 40.0 | PTK2B protein tyrosine kinase 2 beta | PTK2B |
| 203688_at | 756.1 | 258 | 5245.7 | 177 | 40.0 | polycystic kidney disease 2 (autosomal dominant) | PKD2 |
| 207358_x_at | 775.4 | 601.9 | 3134.2 | 315.2 | 40.0 | microtubule-actin crosslinking factor 1 | MACF1 |
| 209631_s_at | 9.4 | 2.2 | 423.1 | 1.3 | 40.0 | G protein-coupled receptor 37 (endothelin receptor type B-like) | GPR37 |
| 210066_at | 8.2 | 4.2 | 183.1 | 1.1 | 40.0 | aquaporin 4 | AQP4 |
| 213848_at | 330.6 | 78.2 | 2652.2 | 24.4 | 40.0 | Dual specificity phosphatase 7 | DUSP7 |
| 220850_at | 12.6 | 3.9 | 357.8 | 1.1 | 40.0 | MORC family CW-type zinc finger 1 | MORC1 |
| 218816_at | 33.6 | 13.1 | 422.8 | 6.1 | 40.0 | leucine rich repeat containing 1 | LRRC1 |
| 203817_at | 196.6 | 124 | 1401.8 | 10.1 | 40.0 | — | — |
| 204915_s_at | 63 | 13.8 | 2637.5 | 4 | 40.0 | SRY (sex determining region Y)-box 11 | SOX11 |
| 218966_at | 1090.3 | 549.8 | 4844.8 | 343.3 | 39.6 | myosin VC | MYO5C |
| 51146_at | 86.5 | 10.7 | 414.5 | 8.2 | 39.6 | phosphatidylinositol glycan, class V | PIGV |
| 205528_s_at | 17 | 3.2 | 436 | 1.4 | 39.6 | runt-related transcription factor 1; translocated to, 1 (cyclin D-related) | RUNX1T1 |
| 215388_s_at | 5.7 | 3.2 | 626 | 1.4 | 39.6 | complement factor H /// complement factor H-related 1 | CFH /// CFHL1 |
| 215672_s_at | 114.2 | 49 | 643.7 | 18.7 | 39.6 | KIAA0828 protein | KIAA0828 |
| 202178_at | 49.4 | 16.9 | 9160.2 | 6.6 | 39.6 | protein kinase C, zeta | PRKCZ |
| 209670_at | 561.5 | 298 | 15751.4 | 97.6 | 39.6 | T cell receptor alpha constant /// T cell receptor alpha constant | TRAC |
| 200986_at | 142.2 | 25.8 | 1035.7 | 8.5 | 39.6 | serpin peptidase inhibitor, clade G (C1 inhibitor), member 1, (angioedema, hereditary) | SERPING1 |
| 217440_at | 26.3 | 4 | 796.2 | 0.5 | 39.6 | MRNA; cDNA DKFZp566A193 (from clone DKFZp566A193) | — |
| 213920_at | 47.8 | 18.4 | 592.2 | 5.6 | 39.6 | cut-like 2 (Drosophila) | CUTL2 |
| 212489_at | 390.1 | 192 | 2846.1 | 5.9 | 39.6 | collagen, type V, alpha 1 | COL5A1 |
| 213831_at | 519.5 | 80.8 | 9979.3 | 8.5 | 39.6 | major histocompatibility complex, class II, DQ alpha 1 | HLA-DQA1 |
| 201811_x_at | 1176.8 | 559 | 14168.3 | 14 | 39.6 | SH3-domain binding protein 5 (BTK-associated) | SH3BP5 |
| 203116_s_at | 499.9 | 411.2 | 22232 | 218.8 | 39.3 | ferrochelatase (protoporphyria) | FECH |
| 213280_at | 326 | 39.5 | 2453.6 | 21.7 | 39.3 | GTPase activating Rap/RanGAP domain-like 4 | GARNL4 |

TABLE 1-continued

Probe sets overexpressed in 25% of more of B-lineage ALL cases (n = 270) as compared to normal bone marrow CD19+CD10+ cells from 4 healthy donors

| probe set ID | CD10+ CD19+ max | CD10+ CD19+ min | ALL max | ALL min | % ALL over expressed | Title | Symbol |
|---|---|---|---|---|---|---|---|
| 213737_x_at | 599.4 | 466 | 12405.3 | 237.8 | 39.3 | hypothetical LOC283768 /// similar to hypothetical protein /// similar to hypothetical protein /// golgi autoantigen, golgin family member /// similar to hypothetical protein /// similar to hypothetical protein /// hypothetical protein DKFZp434P162 | LOC283768 /// LOC388080 /// LOC388189 /// LOC390535 /// LOC400304 /// LOC440234 /// DKFZp434P162 |
| 218864_at | 47.5 | 11.1 | 3993.7 | 10.3 | 39.3 | tensin 1 | TNS1 |
| 218980_at | 24.5 | 6.5 | 632.6 | 5.8 | 39.3 | formin homology 2 domain containing 3 | FHOD3 |
| 208613_s_at | 185.1 | 40.9 | 4202.2 | 15.4 | 39.3 | filamin B, beta (actin binding protein 278) | FLNB |
| 218536_at | 202.7 | 131.6 | 826.2 | 7.1 | 39.3 | MRS2-like, magnesium homeostasis factor (S. cerevisiae) | MRS2L |
| 208303_s_at | 47.2 | 25.1 | 2971.8 | 6.9 | 39.3 | cytokine receptor-like factor 2 | CRLF2 |
| 216620_s_at | 192.7 | 27.7 | 3588.2 | 12.3 | 39.3 | Rho guanine nucleotide exchange factor (GEF) 10 | ARHGEF10 |
| 205715_at | 26.5 | 18.8 | 1743.7 | 7.5 | 39.3 | bone marrow stromal cell antigen 1 | BST1 |
| 215017_s_at | 148.3 | 71.4 | 866.3 | 2.2 | 39.3 | formin binding protein 1-like | FNBP1L |
| 207218_at | 63 | 24.6 | 565.5 | 3.5 | 39.3 | coagulation factor IX (plasma thromboplastic component, Christmas disease, hemophilia B) | F9 |
| 208654_s_at | 1274.4 | 754.9 | 15234.8 | 667.6 | 38.9 | CD164 antigen, sialomucin | CD164 |
| 209638_x_at | 41.2 | 3.4 | 532.9 | 1.8 | 38.9 | regulator of G-protein signalling 12 | RGS12 |
| 214049_x_at | 38.7 | 15.3 | 2222.3 | 7.7 | 38.9 | CD7 antigen (p41) | CD7 |
| 218965_s_at | 75.9 | 13.5 | 397.8 | 9.5 | 38.9 | RNA binding motif protein 21 | RBM21 |
| 220751_s_at | 52 | 19.2 | 4567.8 | 11.3 | 38.9 | chromosome 5 open reading frame 4 | C5orf4 |
| 202275_at | 226.8 | 115 | 4046.1 | 45.6 | 38.9 | glucose-6-phosphate dehydrogenase | G6PD |
| 219191_s_at | 67.1 | 28.6 | 1955.3 | 9.7 | 38.9 | bridging integrator 2 | BIN2 |
| 218328_at | 119.6 | 97.9 | 861.5 | 16.1 | 38.9 | coenzyme Q4 homolog (yeast) | COQ4 |
| 206622_at | 58.4 | 45.3 | 3374 | 7.6 | 38.9 | thyrotropin-releasing hormone | TRH |
| 203854_at | 56 | 18.2 | 406.4 | 12.2 | 38.5 | I factor (complement) | IF |
| 204462_s_at | 207.7 | 42.5 | 1528.7 | 26.5 | 38.5 | solute carrier family 16 (monocarboxylic acid transporters), member 2 | SLC16A2 |
| 218361_at | 251.4 | 34.4 | 1506.7 | 22.1 | 38.5 | golgi phosphoprotein 3-like | GOLPH3L |
| 204187_at | 133 | 21.5 | 10704.9 | 10.7 | 38.5 | guanosine monophosphate reductase /// guanosine monophosphate reductase | GMPR |
| 209705_at | 774.4 | 659.1 | 3152.7 | 307.1 | 38.5 | metal response element binding transcription factor 2 | MTF2 |
| 220232_at | 570.7 | 370.1 | 6663.3 | 133 | 38.5 | stearoyl-CoA desaturase 5 | SCD5 |
| 222273_at | 172.6 | 109.8 | 752.1 | 30.5 | 38.5 | poly(A) polymerase gamma | PAPOLG |
| 200885_at | 301.6 | 195.1 | 1938.3 | 60.7 | 38.5 | ras homolog gene family, member C | RHOC |
| 205372_at | 87.9 | 9.5 | 860 | 2.2 | 38.5 | pleiomorphic adenoma gene 1 | PLAG1 |
| 215702_s_at | 19 | 9.1 | 222 | 2.4 | 38.5 | cystic fibrosis transmembrane conductance regulator, ATP-binding cassette (sub-family C, member 7) | CFTR |
| 216123_x_at | 78.6 | 43.1 | 655.2 | 4.4 | 38.5 | CDNA FLJ14096 fis, clone MAMMA1000752 | — |
| 214745_at | 214.1 | 99.5 | 2085.9 | 2.2 | 38.5 | phospholipase C-like 3 | PLCL3 |
| 206995_x_at | 112.9 | 6.8 | 541.1 | 6.5 | 38.1 | scavenger receptor class F, member 1 | SCARF1 |
| 210644_s_at | 2023.5 | 1311.6 | 9630.6 | 700 | 38.1 | leukocyte-associated Ig-like receptor 1 | LAIR1 |
| 213518_at | 198.1 | 59.3 | 773.3 | 47.3 | 38.1 | protein kinase C, iota | PRKCI |
| 216407_at | 61.4 | 13.9 | 526.8 | 8.7 | 38.1 | Vac14 homolog (S. cerevisiae) | VAC14 |
| 204297_at | 424.7 | 357.1 | 9590.8 | 156.3 | 38.1 | phosphoinositide-3-kinase, class 3 | PIK3C3 |
| 205174_s_at | 23.2 | 5.5 | 712.9 | 1.9 | 38.1 | glutaminyl-peptide cyclotransferase (glutaminyl cyclase) | QPCT |
| 218989_x_at | 175.4 | 115 | 603 | 19.2 | 38.1 | solute carrier family 30 (zinc transporter), member 5 | SLC30A5 |
| 204759_at | 484.7 | 307 | 9086.3 | 34.2 | 38.1 | regulator of chromosome condensation (RCC1) and BTB (POZ) domain containing protein 2 | RCBTB2 |
| 206479_at | 17.1 | 5.8 | 214.2 | 1.8 | 38.1 | transient receptor potential cation channel, subfamily M, member 1 | TRPM1 |
| 214012_at | 126.4 | 71 | 1014.4 | 7.5 | 38.1 | type 1 tumor necrosis factor receptor shedding aminopeptidase regulator | ARTS-1 |
| 202451_at | 260.2 | 193.2 | 861.3 | 16.8 | 38.1 | general transcription factor IIH, polypeptide 1, 62 kDa | GTF2H1 |
| 219797_at | 103.8 | 72.9 | 686.8 | 4.2 | 38.1 | mannosyl (alpha-1,3-)-glycoprotein beta-1,4-N-acetylglucosaminyltransferase, isoenzyme A | MGAT4A |
| 206637_at | 298.6 | 54.2 | 4668.9 | 1.6 | 38.1 | purinergic receptor P2Y, G-protein coupled, 14 | P2RY14 |
| 203585_at | 219.3 | 174 | 2221.3 | 40.4 | 38.1 | zinc finger protein 185 (LIM domain) | ZNF185 |
| 204700_x_at | 158.8 | 78.3 | 747 | 43.7 | 37.8 | chromosome 1 open reading frame 107 | C1orf107 |
| 211924_s_at | 184.9 | 27.2 | 2286.6 | 32.1 | 37.8 | plasminogen activator, urokinase receptor /// plasminogen activator, urokinase receptor | PLAUR |
| 212977_at | 93.2 | 5 | 1209.6 | 4.3 | 37.8 | chemokine orphan receptor 1 | CMKOR1 |
| 206177_s_at | 130.3 | 68.7 | 3199 | 26.4 | 37.8 | arginase, liver | ARG1 |
| 201302_at | 300 | 203.7 | 2835.2 | 21.2 | 37.8 | annexin A4 | ANXA4 |
| 208343_s_at | 7.2 | 3 | 2604.5 | 1.1 | 37.8 | nuclear receptor subfamily 5, group A, member 2 | NR5A2 |
| 209615_s_at | 92.3 | 24.5 | 507.8 | 6.3 | 37.8 | p21/Cdc42/Rac1-activated kinase 1 (STE20 homolog, yeast) | PAK1 |
| 220646_s_at | 79.7 | 23 | 801.8 | 5 | 37.8 | killer cell lectin-like receptor subfamily F, member 1 | KLRF1 |
| 204811_s_at | 112 | 50.8 | 1771.5 | 12.1 | 37.8 | calcium channel, voltage-dependent, alpha 2/delta subunit 2 | CACNA2D2 |
| 205462_s_at | 310.4 | 171.9 | 2565.1 | 18.5 | 37.8 | hippocalcin-like 1 | HPCAL1 |
| 213096_at | 320.3 | 249.8 | 14744.9 | 27.6 | 37.8 | transmembrane and coiled-coil domain family 2 | TMCC2 |

TABLE 1-continued

Probe sets overexpressed in 25% of more of B-lineage ALL cases (n = 270) as compared to normal bone marrow CD19$^+$CD10$^+$ cells from 4 healthy donors

| probe set ID | CD10+ CD19+ max | CD10+ CD19+ min | ALL max | ALL min | % ALL over expressed | Title | Symbol |
|---|---|---|---|---|---|---|---|
| 217901_at | 110.4 | 74.5 | 1631 | 5.4 | 37.8 | Desmoglein 2 | DSG2 |
| 204204_at | 87.5 | 26.1 | 918.5 | 13.1 | 37.4 | solute carrier family 31 (copper transporters), member 2 | SLC31A2 |
| 208073_x_at | 2070.2 | 1406.9 | 13227.3 | 1120.5 | 37.4 | tetratricopeptide repeat domain 3 | TTC3 |
| 208799_at | 545.7 | 302.9 | 2235 | 353.8 | 37.4 | proteasome (prosome, macropain) subunit, beta type, 5 | PSMB5 |
| 214040_s_at | 41.5 | 10.3 | 2140.6 | 9 | 37.4 | gelsolin (amyloidosis, Finnish type) | GSN |
| 218417_s_at | 107.6 | 23.1 | 990.5 | 14.8 | 37.4 | hypothetical protein FLJ20489 | FLJ20489 |
| 218659_at | 2636.3 | 1222.8 | 19916.5 | 736.9 | 37.4 | additional sex combs like 2 (Drosophila) | ASXL2 |
| 220178_at | 140.7 | 11.2 | 1510.2 | 11.3 | 37.4 | chromosome 19 open reading frame 28 | C19orf28 |
| 221350_at | 53.8 | 15.1 | 917.6 | 11.3 | 37.4 | homeo box C8 | HOXC8 |
| 205945_at | 97.8 | 7 | 1113.7 | 3.3 | 37.4 | interleukin 6 receptor /// interleukin 6 receptor | IL6R |
| 205614_x_at | 85.9 | 47.3 | 694.9 | 20.6 | 37.4 | macrophage stimulating 1 (hepatocyte growth factor-like) | MST1 |
| 202628_s_at | 27.6 | 18.9 | 1056.7 | 8 | 37.4 | serpin peptidase inhibitor, clade E (nexin, plasminogen activator inhibitor type 1), member 1 | SERPINE1 |
| 205952_at | 88.1 | 19.7 | 2026.6 | 8.6 | 37.4 | potassium channel, subfamily K, member 3 | KCNK3 |
| 210504_at | 181.5 | 109 | 11394.7 | 31.4 | 37.4 | Kruppel-like factor 1 (erythroid) | KLF1 |
| 46665_at | 83.8 | 45.2 | 1801.6 | 15.5 | 37.4 | sema domain, immunoglobulin domain (Ig), transmembrane domain (TM) and short cytoplasmic domain, (semaphorin) 4C | SEMA4C |
| 209543_s_at | 704.3 | 328.5 | 11548 | 98.4 | 37.4 | CD34 antigen | CD34 |
| 205821_at | 457.5 | 243 | 9684.2 | 45.4 | 37.4 | killer cell lectin-like receptor subfamily K, member 1 | KLRK1 |
| 206233_at | 245.2 | 162.6 | 1798.1 | 5.9 | 37.4 | UDP-Gal:betaGlcNAc beta 1,4-galactosyltransferase, polypeptide 6 | B4GALT6 |
| 206574_s_at | 244.7 | 135.8 | 2612.2 | 8.3 | 37.4 | protein tyrosine phosphatase type IVA, member 3 | PTP4A3 |
| 201363_s_at | 313.2 | 120.7 | 1430.5 | 98.9 | 37.0 | influenza virus NS1A binding protein | IVNS1ABP |
| 203254_s_at | 297.5 | 188.7 | 1554.2 | 131.8 | 37.0 | talin 1 | TLN1 |
| 206343_s_at | 20.8 | 8.8 | 1783.2 | 5.1 | 37.0 | neuregulin 1 | NRG1 |
| 208594_x_at | 398.6 | 305.3 | 3235.8 | 170.4 | 37.0 | leukocyte immunoglobulin-like receptor, subfamily A (with TM domain), member 6 | LILRA6 |
| 210030_at | 46.4 | 13.8 | 557.9 | 9.9 | 37.0 | — | — |
| 213854_at | 323.8 | 36.7 | 1730.3 | 26 | 37.0 | synaptogyrin 1 | SYNGR1 |
| 215299_x_at | 681.9 | 407.1 | 4249.4 | 370.6 | 37.0 | sulfotransferase family, cytosolic, 1A, phenol-preferring, member 1 | SULT1A1 |
| 220285_at | 932.1 | 658.1 | 4858.2 | 331.9 | 37.0 | chromosome 9 open reading frame 77 | C9orf77 |
| 220684_at | 244.3 | 156.4 | 1550.4 | 83.4 | 37.0 | T-box 21 | TBX21 |
| 221747_at | 332.6 | 46.9 | 5156.1 | 40.1 | 37.0 | Tensin 1 /// Tensin 1 | TNS1 |
| 204513_s_at | 515.9 | 363 | 4569.4 | 120.1 | 37.0 | engulfment and cell motility 1 (ced-12 homolog, C. elegans) | ELMO1 |
| 208109_s_at | 57.6 | 9.4 | 790.8 | 4.4 | 37.0 | chromosome 15 open reading frame 5 /// chromosome 15 open reading frame 5 | C15orf5 |
| 213364_s_at | 220.2 | 97.9 | 1125.3 | 36.8 | 37.0 | sorting nexin 1 | SNX1 |
| 203949_at | 269.1 | 88 | 44296 | 25 | 37.0 | myeloperoxidase | MPO |
| 201109_s_at | 26.2 | 13.5 | 1803 | 3.3 | 37.0 | thrombospondin 1 | THBS1 |
| 205983_at | 581 | 207.2 | 7380 | 21.6 | 37.0 | dipeptidase 1 (renal) | DPEP1 |
| 218742_at | 406.8 | 167.4 | 2459.7 | 21.9 | 37.0 | nuclear prelamin A recognition factor-like | NARFL |
| 212828_at | 257.9 | 134.8 | 2422.8 | 27.5 | 37.0 | synaptojanin 2 | SYNJ2 |
| 209576_at | 205.7 | 169.9 | 1733.8 | 11.3 | 37.0 | guanine nucleotide binding protein (G protein), alpha inhibiting activity polypeptide 1 | GNAI1 |
| 212526_at | 62.9 | 14.9 | 996.9 | 3 | 37.0 | spastic paraplegia 20, spartin (Troyer syndrome) | SPG20 |
| 205463_s_at | 139.4 | 41.4 | 3342.1 | 5.5 | 37.0 | platelet-derived growth factor alpha polypeptide | PDGFA |
| 203988_s_at | 226.8 | 20 | 1797.6 | 12.4 | 36.7 | fucosyltransferase 8 (alpha (1,6) fucosyltransferase) | FUT8 |
| 212181_s_at | 595.8 | 508.9 | 7196.3 | 373.3 | 36.7 | nudix (nucleoside diphosphate linked moiety X)-type motif 4 | NUDT4 |
| 214255_at | 161.3 | 24.5 | 2123.3 | 18.3 | 36.7 | ATPase, Class V, type 10A | ATP10A |
| 213063_at | 305.7 | 237 | 1454.3 | 91.9 | 36.7 | nuclear protein UKp68 | FLJ11806 |
| 209210_s_at | 88.1 | 16.6 | 1212.8 | 4.9 | 36.7 | pleckstrin homology domain containing, family C (with FERM domain) member 1 | PLEKHC1 |
| 204401_at | 175.2 | 51.2 | 2120.8 | 12 | 36.7 | potassium intermediate/small conductance calcium-activated channel, subfamily N, member 4 | KCNN4 |
| 201848_s_at | 151.7 | 93.2 | 778.4 | 7.9 | 36.7 | BCL2/adenovirus E1B 19 kDa interacting protein 3 | BNIP3 |
| 214453_s_at | 296.5 | 109.3 | 6049.8 | 43.3 | 36.7 | interferon-induced protein 44 | IFI44 |
| 218892_at | 149.5 | 36.5 | 863.8 | 12.8 | 36.7 | dachsous 1 (Drosophila) | DCHS1 |
| 201324_at | 94.7 | 14.1 | 3238.4 | 3.7 | 36.7 | epithelial membrane protein 1 | EMP1 |
| 201029_s_at | 4746 | 2562.3 | 29103.9 | 689.6 | 36.7 | CD99 antigen | CD99 |
| 203038_at | 353 | 73.2 | 5596.8 | 6.7 | 36.7 | protein tyrosine phosphatase, receptor type, K | PTPRK |
| 218035_s_at | 174.4 | 73.7 | 1360.7 | 16.9 | 36.7 | RNA-binding protein | FLJ20273 |
| 203029_s_at | 22.1 | 12.1 | 1684 | 9.2 | 36.3 | protein tyrosine phosphatase, receptor type, N polypeptide 2 | PTPRN2 |
| 203040_s_at | 462.5 | 424.8 | 20562.7 | 233.3 | 36.3 | hydroxymethylbilane synthase | HMBS |
| 211876_x_at | 22.8 | 6 | 700.3 | 5.1 | 36.3 | protocadherin gamma subfamily A, 12 /// protocadherin gamma subfamily A, 11 /// protocadherin gamma subfamily A, 10 /// protocadherin gamma subfamily A, 6 /// protocadherin gamma subfamily A, 5 /// protocadherin gamma subfamily A, 3 | PCDHGA12 /// PCDHGA11 /// PCDHGA10 /// PCDHGA6 /// PCDHGA5 /// PCDHGA3 |

TABLE 1-continued

Probe sets overexpressed in 25% of more of B-lineage ALL cases (n = 270) as compared to normal bone marrow CD19+CD10+ cells from 4 healthy donors

| probe set ID | CD10+ CD19+ max | CD10+ CD19+ min | ALL max | ALL min | % ALL over expressed | Title | Symbol |
| --- | --- | --- | --- | --- | --- | --- | --- |
| 216298_at | 85.4 | 4 | 508.1 | 3.8 | 36.3 | T cell receptor gamma constant 2 | LOC442535 |
| 219701_at | 38.1 | 4.3 | 619.8 | 2.4 | 36.3 | tropomodulin 2 (neuronal) | TMOD2 |
| 221081_s_at | 358 | 48.4 | 2899.8 | 32.4 | 36.3 | DENN/MADD domain containing 2D | DENND2D |
| 209963_s_at | 127.9 | 49.4 | 1950.4 | 17.8 | 36.3 | erythropoietin receptor | EPOR |
| 217096_at | 43 | 9.2 | 442.9 | 3.5 | 36.3 | piccolo (presynaptic cytomatrix protein) | PCLO |
| 217820_s_at | 138.3 | 13.4 | 1021.9 | 6.3 | 36.3 | enabled homolog (*Drosophila*) | ENAH |
| 205390_s_at | 29.7 | 26.3 | 3939.1 | 9.5 | 36.3 | ankyrin 1, erythrocytic /// ankyrin 1, erythrocytic | ANK1 |
| 206366_x_at | 44 | 24.7 | 564.3 | 6 | 36.3 | chemokine (C motif) ligand 2 | XCL2 |
| 211568_at | 19.9 | 3.1 | 728.8 | 1.5 | 36.3 | brain-specific angiogenesis inhibitor 3 | BAI3 |
| 213894_at | 96 | 24.3 | 2885.9 | 6.1 | 36.3 | KIAA0960 protein | KIAA0960 |
| 212314_at | 339.9 | 155.7 | 7986.2 | 55.6 | 36.3 | KIAA0746 protein | KIAA0746 |
| 222136_x_at | 519.1 | 310.1 | 2538.9 | 98.6 | 36.3 | zinc finger protein 43 (HTF6) | ZNF43 |
| 205159_at | 439.5 | 343.6 | 2239.7 | 154.7 | 36.3 | colony stimulating factor 2 receptor, beta, low-affinity (granulocyte-macrophage) /// colony stimulating factor 2 receptor, beta, low-affinity (granulocyte-macrophage) | CSF2RB |
| 220789_s_at | 101.1 | 70.6 | 573.6 | 29 | 36.3 | transforming growth factor beta regulator 4 | TBRG4 |
| 204891_s_at | 418.3 | 189 | 5581.2 | 30.7 | 36.3 | lymphocyte-specific protein tyrosine kinase | LCK |
| 212443_at | 263.3 | 138.7 | 2162 | 17.1 | 36.3 | neurobeachin-like 2 | NBEAL2 |
| 202992_at | 34.6 | 19.2 | 645.1 | 3.7 | 36.3 | complement component 7 | C7 |
| 210435_at | 45.6 | 22.2 | 280.1 | 2.7 | 36.3 | neighbor of BRCA1 gene 2 | NBR2 |
| 202630_at | 200.3 | 121.9 | 895.5 | 73 | 35.9 | amyloid beta precursor protein (cytoplasmic tail) binding protein 2 | APPBP2 |
| 203381_s_at | 29.3 | 10.4 | 1129.3 | 5.6 | 35.9 | apolipoprotein E | APOE |
| 212095_s_at | 47.9 | 11 | 574.8 | 7.8 | 35.9 | mitochondrial tumor suppressor 1 | MTUS1 |
| 212151_at | 114.4 | 30.4 | 10825.3 | 16.5 | 35.9 | Pre-B-cell leukemia transcription factor 1 | PBX1 |
| 213994_s_at | 9.7 | 3.2 | 676 | 2.1 | 35.9 | spondin 1, extracellular matrix protein | SPON1 |
| 218762_at | 53.7 | 24.8 | 851.9 | 17.7 | 35.9 | zinc finger protein 574 | ZNF574 |
| 219149_x_at | 129 | 42.5 | 571.6 | 38.9 | 35.9 | debranching enzyme homolog 1 (*S. cerevisiae*) | DBR1 |
| 205862_at | 23.7 | 2.3 | 422 | 1 | 35.9 | GREB1 protein | GREB1 |
| 211450_s_at | 1390 | 769.9 | 6721.5 | 168 | 35.9 | mutS homolog 6 (*E. coli*) | MSH6 |
| 213882_at | 117.5 | 19 | 636.6 | 5.8 | 35.9 | TM2 domain containing 1 | TM2D1 |
| 215842_at | 43.1 | 5.5 | 1086.9 | 2.7 | 35.9 | ATPase, Class VI, type 11A | ATP11A |
| 216565_x_at | 484.6 | 268.2 | 3433.7 | 128.6 | 35.9 | similar to Interferon-induced transmembrane protein 3 (Interferon-inducible protein 1-8U) | LOC391020 |
| 220577_at | 283.9 | 196.6 | 1308.8 | 83 | 35.9 | GTPase, very large interferon inducible 1 | GVIN1 |
| 207968_s_at | 679.1 | 449.9 | 2961.8 | 79.5 | 35.9 | MADS box transcription enhancer factor 2, polypeptide C (myocyte enhancer factor 2C) | MEF2C |
| 212761_at | 621.5 | 511.4 | 4998.4 | 101.8 | 35.9 | transcription factor 7-like 2 (T-cell specific, HMG-box) | TCF7L2 |
| 217067_s_at | 20.2 | 4.4 | 741.1 | 1.9 | 35.9 | dentin matrix acidic phosphoprotein | DMP1 |
| 212979_s_at | 100.9 | 40.9 | 523.5 | 4.8 | 35.9 | KIAA0738 gene product | KIAA0738 |
| 218402_s_at | 945 | 647.6 | 5332.1 | 139.5 | 35.9 | Hermansky-Pudlak syndrome 4 | HPS4 |
| 219048_at | 189.5 | 37.2 | 963.8 | 12.3 | 35.9 | phosphatigylinositol glycan, class N | PIGN |
| 221558_s_at | 4751.5 | 2901.3 | 16261.4 | 242.4 | 35.9 | lymphoid enhancer-binding factor 1 | LEF1 |
| 201189_s_at | 357.3 | 98 | 2314 | 12.8 | 35.9 | inositol 1,4,5-triphosphate receptor, type 3 | ITPR3 |
| 202540_s_at | 165.2 | 26.9 | 835.4 | 20.7 | 35.9 | 3-hydroxy-3-methylglutaryl-Coenzyme A reductase | HMGCR |
| 210655_s_at | 89.9 | 21.2 | 6692.2 | 10.7 | 35.6 | forkhead box O3A | FOXO3A |
| 213395_at | 126 | 7.5 | 1760 | 9.8 | 35.6 | megalencephalic leukoencephalopathy with subcortical cysts 1 | MLC1 |
| 203574_at | 307.6 | 223.4 | 9812.8 | 43.7 | 35.6 | nuclear factor, interleukin 3 regulated | NFIL3 |
| 210615_at | 40.3 | 12.7 | 335.3 | 3.2 | 35.6 | neuropilin 1 | NRP1 |
| 202833_s_at | 107.1 | 24.3 | 1493.7 | 8.1 | 35.6 | serpin peptidase inhibitor, clade A (alpha-1 antiproteinase, antitrypsin), member 1 | SERPINA1 |
| 205098_at | 220.8 | 141.3 | 2242.5 | 36.1 | 35.6 | chemokine (C-C motif) receptor 1 | CCR1 |
| 220922_s_at | 43.1 | 19 | 1787.1 | 6.8 | 35.6 | sperm protein associated with the nucleus, X-linked, family member A1 /// SPANX family, member B1 /// SPANX family, member A2 /// SPANX family, member C /// SPANX family, member B2 | SPANXA1 /// SPANXB1 /// SPANXA2 /// SPANXC /// SPANXB2 |
| 218656_s_at | 124.8 | 34.5 | 1094.7 | 9.4 | 35.6 | lipoma HMGIC fusion partner | LHFP |
| 201341_at | 245.6 | 58.5 | 1313.2 | 65.5 | 35.2 | ectodermal-neural cortex (with BTB-like domain) | ENC1 |
| 202039_at | 2536.6 | 1152.1 | 12225.9 | 882.4 | 35.2 | TGFB1-induced anti-apoptotic factor 1 /// myosin XVIIIA | TIAF1 /// MYO18A |
| 202441_at | 514.4 | 310.1 | 3817.2 | 227.7 | 35.2 | SPFH domain family, member 1 | SPFH1 |
| 204158_s_at | 312.4 | 27.1 | 2026.7 | 13.6 | 35.2 | T-cell, immune regulator 1, ATPase, H+ transporting, lysosomal V0 protein a isoform 3 | TCIRG1 |
| 204417_at | 307.3 | 192.3 | 1291 | 152.9 | 35.2 | galactosylceramidase (Krabbe disease) | GALC |
| 205702_at | 212.7 | 167 | 922.4 | 94.3 | 35.2 | putative homeodomain transcription factor 1 | PHTF1 |
| 208664_s_at | 378.6 | 46.8 | 2577.1 | 15.2 | 35.2 | tetratricopeptide repeat domain 3 | TTC3 |
| 220024_s_at | 202.4 | 25.4 | 3704.4 | 12.4 | 35.2 | periaxin | PRX |
| 204643_s_at | 168.2 | 37.5 | 838.5 | 13.6 | 35.2 | cytosolic ovarian carcinoma antigen 1 | COVA1 |
| 213530_at | 176.9 | 104.4 | 968.1 | 41 | 35.2 | RAB3 GTPase activating protein subunit 1 (catalytic) | RAB3GAP1 |
| 216286_at | 135.2 | 15.4 | 784.3 | 5.9 | 35.2 | UDP-Gal:betaGlcNAc beta 1,4-galactosyltransferase, polypeptide 6 | B4GALT6 |

TABLE 1-continued

Probe sets overexpressed in 25% of more of B-lineage ALL cases (n = 270) as compared to normal bone marrow CD19⁺CD10⁺ cells from 4 healthy donors

| probe set ID | CD10+ CD19+ max | CD10+ CD19+ min | ALL max | ALL min | % ALL over expressed | Title | Symbol |
|---|---|---|---|---|---|---|---|
| 212641_at | 243.9 | 104.7 | 1762.8 | 21.2 | 35.2 | human immunodeficiency virus type I enhancer binding protein 2 | HIVEP2 |
| 214752_x_at | 448.9 | 347.9 | 3063.9 | 126.4 | 35.2 | filamin A, alpha (actin binding protein 280) | FLNA |
| 206032_at | 133.4 | 56 | 2028.8 | 4.8 | 35.2 | desmocollin 3 | DSC3 |
| 213663_s_at | 23.4 | 8.2 | 259.6 | 1.8 | 35.2 | hypothetical LOC389275 | LOC389275 |
| 219211_at | 152.2 | 33.4 | 1800.2 | 9.8 | 35.2 | ubiquitin specific peptidase 18 | USP18 |
| 213839_at | 142 | 94.1 | 2828.6 | 11.4 | 35.2 | KIAA0500 protein | KIAA0500 |
| 208818_s_at | 1135.7 | 934.7 | 4507 | 488.8 | 34.8 | catechol-O-methyltransferase | COMT |
| 211434_s_at | 60.3 | 16.5 | 825.4 | 10.2 | 34.8 | chemokine (C-C motif) receptor-like 2 | CCRL2 |
| 213715_s_at | 28 | 9.2 | 404.3 | 5.2 | 34.8 | ankyrin repeat domain 47 | ANKRD47 |
| 217542_at | 143 | 9.9 | 1123.1 | 8.2 | 34.8 | Mdm2, transformed 3T3 cell double minute 2, p53 binding protein (mouse) | MDM2 |
| 217753_s_at | 5938.3 | 4006.8 | 25428.5 | 2076.8 | 34.8 | ribosomal protein S26 /// 40S ribosomal protein S26-like /// similar to 40S ribosomal protein S26 | RPS26 /// RPS26L /// LOC440440 |
| 204467_s_at | 171.2 | 51.3 | 13693.2 | 12.8 | 34.8 | synuclein, alpha (non A4 component of amyloid precursor) /// synuclein, alpha (non A4 component of amyloid precursor) | SNCA |
| 204712_at | 14.4 | 5.4 | 195.8 | 1.3 | 34.8 | WNT inhibitory factor 1 | WIF1 |
| 213797_at | 225.5 | 42.7 | 3486.1 | 14.5 | 34.8 | radical S-adenosyl methionine domain containing 2 | RSAD2 |
| 218311_at | 138.3 | 67.8 | 1156.1 | 19.2 | 34.8 | mitogen-activated protein kinase kinase kinase kinase 3 | MAP4K3 |
| 203063_at | 576.5 | 303.1 | 3994.1 | 63.5 | 34.8 | protein phosphatase 1F (PP2C domain containing) | PPM1F |
| 221221_s_at | 240.4 | 149 | 1298.1 | 18.7 | 34.8 | kelch-like 3 (Drosophila) | KLHL3 |
| 217110_s_at | 36.7 | 7.1 | 2577.8 | 1.9 | 34.8 | mucin 4, tracheobronchial | MUC4 |
| 201904_s_at | 39.3 | 16.3 | 1431.6 | 8.9 | 34.4 | CTD (carboxy-terminal domain, RNA polymerase II, polypeptide A) small phosphatase-like | CTDSPL |
| 202017_at | 94.7 | 21 | 750.8 | 12.3 | 34.4 | epoxide hydrolase 1, microsomal (xenobiotic) | EPHX1 |
| 203964_at | 1081 | 748.9 | 3821.7 | 503 | 34.4 | N-myc (and STAT) interactor | NMI |
| 207100_s_at | 251.9 | 14 | 2082.2 | 22.6 | 34.4 | vesicle-associated membrane protein 1 (synaptobrevin 1) | VAMP1 |
| 207413_s_at | 92.2 | 21.6 | 661.3 | 11.3 | 34.4 | sodium channel, voltage-gated, type V, alpha (long QT syndrome 3) | SCN5A |
| 207734_at | 261.8 | 151 | 1265.9 | 82.4 | 34.4 | lymphocyte transmembrane adaptor 1 | LAX1 |
| 221274_s_at | 276.7 | 29 | 1206.4 | 24.3 | 34.4 | lectin, mannose-binding 2-like /// lectin, mannose-binding 2-like | LMAN2L |
| 208361_s_at | 180.4 | 65.5 | 728.9 | 18.9 | 34.4 | polymerase (RNA) III (DNA directed) polypeptide D, 44 kDa | POLR3D |
| 210972_x_at | 758.2 | 554.4 | 24206.5 | 214.3 | 34.4 | T cell receptor alpha locus /// T cell receptor delta variable 2 /// T cell receptor alpha variable 20 /// T cell receptor alpha joining 17 /// T cell receptor alpha constant | TRA@ /// TRDV2 /// TRAV20 /// TRAJ17 /// TRAC |
| 204849_at | 810.8 | 215 | 11702.5 | 5.4 | 34.4 | transcription factor-like 5 (basic helix-loop-helix) | TCFL5 |
| 206400_at | 31.9 | 13.4 | 575.3 | 5 | 34.4 | lectin, galactoside-binding, soluble, 7 (galectin 7) | LGALS7 |
| 214667_s_at | 101.6 | 35 | 998 | 11.4 | 34.4 | tumor protein p53 inducible protein 11 | TP53I11 |
| 220532_s_at | 54.2 | 13.7 | 777.4 | 3.8 | 34.4 | LR8 protein | LR8 |
| 201616_s_at | 22.8 | 6.6 | 1425.1 | 2.1 | 34.4 | caldesmon 1 | CALD1 |
| 203910_at | 179.7 | 83.8 | 10198.4 | 9.4 | 34.4 | Rho GTPase activating protein 29 | ARHGAP29 |
| 215761_at | 164 | 112 | 967.7 | 19.1 | 34.4 | Dmx-like 2 | DMXL2 |
| 201579_at | 158.1 | 58.3 | 5413.2 | 7.1 | 34.4 | FAT tumor suppressor homolog 1 (Drosophila) | FAT |
| 212589_at | 175.6 | 39.9 | 1058.4 | 5.8 | 34.4 | Sterol carrier protein 2 | SCP2 |
| 210765_at | 39.6 | 13.3 | 346.5 | 12.3 | 34.1 | CSE1 chromosome segregation 1-like (yeast) | CSE1L |
| 214370_at | 14.7 | 3.3 | 1290.2 | 3.3 | 34.1 | S100 calcium binding protein A8 (calgranulin A) | S100A8 |
| 221900_at | 24.3 | 10.2 | 428.4 | 6.6 | 34.1 | collagen, type VIII, alpha 2 | COL8A2 |
| 203115_at | 130.9 | 23.7 | 5913.7 | 11.8 | 34.1 | ferrochelatase (protoporphyria) | FECH |
| 203335_at | 364.4 | 171.5 | 12858.3 | 46.7 | 34.1 | phytanoyl-CoA hydroxylase (Refsum disease) | PHYH |
| 212959_s_at | 740.4 | 459.9 | 6222 | 203 | 34.1 | N-acetylglucosamine-1-phosphate transferase, alpha and beta subunits | GNPTAB |
| 221182_at | 23.5 | 5.1 | 327.6 | 1.8 | 34.1 | chromosome 1 open reading frame 129 | C1orf129 |
| 202565_s_at | 206.9 | 161 | 1008.3 | 92.6 | 33.7 | supervillin | SVIL |
| 205538_at | 53.5 | 15.2 | 482.7 | 10.8 | 33.7 | coronin, actin binding protein, 2A | CORO2A |
| 210904_s_at | 100.9 | 9.1 | 1814.7 | 17.2 | 33.7 | interleukin 13 receptor, alpha 1 | IL13RA1 |
| 214094_at | 57.8 | 25.4 | 508.9 | 17.1 | 33.7 | far upstream element (FUSE) binding protein 1 | FUBP1 |
| 216737_at | 26 | 2.1 | 239.6 | 1.4 | 33.7 | CDNA: FLJ20872 fis, clone ADKA02604 | — |
| 219668_at | 38.9 | 16.6 | 450 | 8.5 | 33.7 | ganglioside-induced differentiation-associated protein 1-like 1 | GDAP1L1 |
| 202308_at | 143 | 38 | 917.9 | 16.8 | 33.7 | sterol regulatory element binding transcription factor 1 | SREBF1 |
| 205264_at | 213.8 | 47.3 | 1503.1 | 17.1 | 33.7 | CD3E antigen, epsilon polypeptide associated protein | CD3EAP |
| 207677_s_at | 947.3 | 692.2 | 4262.2 | 272.6 | 33.7 | neutrophil cytosolic factor 4, 40 kDa /// neutrophil cytosolic factor 4, 40 kDa | NCF4 |
| 208949_s_at | 310.6 | 81.7 | 38822.2 | 26 | 33.7 | lectin, galactoside-binding, soluble, 3 (galectin 3) /// galectin-3 internal gene | LGALS3 /// GALIG |
| 206145_at | 149.5 | 39.7 | 9642.4 | 9.1 | 33.7 | Rhesus blood group-associated glycoprotein | RHAG |
| 209570_s_at | 74.1 | 28.9 | 1641.8 | 6 | 33.7 | DNA segment on chromosome 4 (unique) 234 expressed sequence | D4S234E |
| 212554_at | 57.1 | 22.7 | 603.1 | 3.7 | 33.7 | CAP, adenylate cyclase-associated protein, 2 (yeast) | CAP2 |

TABLE 1-continued

Probe sets overexpressed in 25% of more of B-lineage ALL cases (n = 270) as compared to normal bone marrow CD19+CD10+ cells from 4 healthy donors

| probe set ID | CD10+ CD19+ max | CD10+ CD19+ min | ALL max | ALL min | % ALL over ex-pressed | Title | Symbol |
|---|---|---|---|---|---|---|---|
| 206650_at | 41.2 | 15.7 | 306.3 | 8.6 | 33.3 | IQ motif containing C | IQCC |
| 219529_at | 18.7 | 4.6 | 1679.1 | 3.4 | 33.3 | chloride intracellular channel 3 | CLIC3 |
| 211366_x_at | 813.4 | 586.8 | 4143.1 | 273.4 | 33.3 | caspase 1, apoptosis-related cysteine peptidase (interleukin 1, beta, convertase) | CASP1 |
| 215648_at | 103.5 | 27.2 | 615.5 | 9.1 | 33.3 | — | — |
| 202086_at | 1340.7 | 562.8 | 24405.6 | 74.3 | 33.3 | myxovirus (influenza virus) resistance 1, interferon-inducible protein p78 (mouse) /// myxovirus (influenza virus) resistance 1, interferon-inducible protein p78 (mouse) | MX1 |
| 205728_at | 33.5 | 6.4 | 1607.1 | 2.1 | 33.3 | CDNA clone IMAGE: 4811759 | — |
| 211902_x_at | 419.5 | 303.6 | 8249.5 | 116.8 | 33.3 | T cell receptor alpha locus | TRA@ |
| 213764_s_at | 5.3 | 2.5 | 694.3 | 0.6 | 33.3 | microfibrillar associated protein 5 | MFAP5 |
| 211102_s_at | 251.5 | 164.5 | 1535.4 | 6.7 | 33.3 | leukocyte immunoglobulin-like receptor, subfamily A (with TM domain), member 2 | LILRA2 |
| 205573_s_at | 53.1 | 8.9 | 1291.8 | 4.9 | 33.0 | sorting nexin 7 | SNX7 |
| 209407_s_at | 339.6 | 126.1 | 1400.4 | 139.1 | 33.0 | deformed epidermal autoregulatory factor 1 (Drosophila) | DEAF1 |
| 212264_s_at | 284.9 | 94.7 | 1688.2 | 55.8 | 33.0 | KIAA0261 | KIAA0261 |
| 214567_s_at | 14 | 5.7 | 436 | 5.5 | 33.0 | chemokine (C motif) ligand 1 /// chemokine (C motif) ligand 2 | XCL1 /// XCL2 |
| 222216_s_at | 311.4 | 48.4 | 1334.9 | 51.3 | 33.0 | mitochondrial ribosomal protein L17 | MRPL17 |
| 203757_s_at | 220.7 | 22.3 | 7715.1 | 10.1 | 33.0 | carcinoembryonic antigen-related cell adhesion molecule 6 (non-specific cross reacting antigen) | CEACAM6 |
| 204039_at | 129.9 | 49.4 | 2825.4 | 20.1 | 33.0 | CCAAT/enhancer binding protein (C/EBP), alpha | CEBPA |
| 220576_at | 80.2 | 13.7 | 750.9 | 5.9 | 33.0 | GPI deacylase | PGAP1 |
| 216747_at | 70 | 20 | 562.1 | 9.1 | 33.0 | amyloid beta (A4) precursor protein-binding, family B, member 2 (Fe65-like) | APBB2 |
| 202273_at | 43.6 | 22.7 | 1188.9 | 9 | 33.0 | platelet-derived growth factor receptor, beta polypeptide | PDGFRB |
| 203987_at | 185.2 | 97.5 | 2062 | 29.6 | 33.0 | frizzled homolog 6 (Drosophila) | FZD6 |
| 216280_s_at | 47.4 | 17 | 349.9 | 3.5 | 33.0 | Dicer1, Dcr-1 homolog (Drosophila) | DICER1 |
| 206831_s_at | 67.5 | 18.8 | 520.8 | 5.7 | 33.0 | arylsulfatase D | ARSD |
| 200096_s_at | 1044 | 670.1 | 3796 | 382.6 | 32.6 | ATPase, H+ transporting, lysosomal 9 kDa, V0 subunit e /// ATPase, H+ transporting, lysosomal 9 kDa, V0 subunit e | ATP6V0E |
| 206067_s_at | 24.2 | 4.9 | 1338.9 | 4 | 32.6 | Wilms tumor 1 | WT1 |
| 208056_s_at | 1111.8 | 533.9 | 6352.1 | 315.6 | 32.6 | core-binding factor, runt domain, alpha subunit 2; translocated to, 3 | CBFA2T3 |
| 209288_s_at | 141.9 | 7.4 | 2379.5 | 6.1 | 32.6 | CDC42 effector protein (Rho GTPase binding) 3 | CDC42EP3 |
| 210915_x_at | 669.4 | 434.1 | 13605.2 | 260.8 | 32.6 | T cell receptor beta variable 19 /// T cell receptor beta constant 1 | TRBV19 /// TRBC1 |
| 217758_s_at | 636.8 | 342.6 | 3167.8 | 370.7 | 32.6 | SM-11044 binding protein | SMBP |
| 219593_at | 40.1 | 12.7 | 419.5 | 8.4 | 32.6 | solute carrier family 15, member 3 | SLC15A3 |
| 203428_s_at | 442.8 | 159.9 | 1857.4 | 70.3 | 32.6 | ASF1 anti-silencing function 1 homolog A (S. cerevisiae) | ASF1A |
| 208908_s_at | 270.4 | 47.7 | 2051.6 | 23.8 | 32.6 | calpastatin | CAST |
| 218081_at | 150.9 | 22.7 | 1249.2 | 6.8 | 32.6 | chromosome 20 open reading frame 27 | C20orf27 |
| 218660_at | 151.5 | 37.7 | 2348.1 | 14.6 | 32.6 | dysferlin, limb girdle muscular dystrophy 2B (autosomal recessive) | DYSF |
| 219869_s_at | 393.7 | 317.3 | 2196.2 | 66.5 | 32.6 | solute carrier family 39 (zinc transporter), member 8 | SLC39A8 |
| 213558_at | 225.6 | 48.5 | 22160 | 12.8 | 32.6 | piccolo (presynaptic cytomatrix protein) | PCLO |
| 220121_at | 77.8 | 17.7 | 503.4 | 6.6 | 32.6 | lines homolog 1 (Drosophila) | LINS1 |
| 65517_at | 118.5 | 62.4 | 747 | 23.3 | 32.6 | adaptor-related protein complex 1, mu 2 subunit | AP1M2 |
| 203450_at | 161.7 | 73.9 | 561.9 | 19.6 | 32.6 | PKD2 interactor, golgi and endoplasmic reticulum associated 1 | PGEA1 |
| 201849_at | 125.2 | 45.5 | 920.7 | 9.2 | 32.6 | BCL2/adenovirus E1B 19 kDa interacting protein 3 | BNIP3 |
| 211626_x_at | 395 | 173.7 | 1625.1 | 14.7 | 32.6 | v-ets erythroblastosis virus E26 oncogene like (avian) /// v-ets erythroblastosis virus E26 oncogene like (avian) | ERG |
| 215382_x_at | 41.6 | 31.4 | 920.6 | 6.9 | 32.6 | tryptase alpha/beta 1 | TPSAB1 |
| 214757_at | 69.6 | 28.4 | 397.8 | 7.6 | 32.6 | CDNA clone IMAGE: 3456494 | — |
| 202718_at | 113.1 | 58.5 | 4105.7 | 4.9 | 32.6 | insulin-like growth factor binding protein 2, 36 kDa | IGFBP2 |
| 200979_at | 323.9 | 250.3 | 1611.6 | 244.2 | 32.2 | Mitogen-activated protein kinase kinase kinase 15 /// CDNA FLJ34891 fis, clone NT2NE2017562 | MAP3K15 |
| 203739_at | 583.5 | 248.5 | 2923 | 270.5 | 32.2 | zinc finger protein 217 | ZNF217 |
| 204411_at | 64.1 | 24.9 | 654.9 | 17.7 | 32.2 | kinesin family member 21B | KIF21B |
| 212814_at | 250.7 | 121.8 | 1055.7 | 132.4 | 32.2 | KIAA0828 protein | KIAA0828 |
| 212830_at | 423.1 | 227.9 | 2842.9 | 199.4 | 32.2 | EGF-like-domain, multiple 5 | EGFL5 |
| 217790_s_at | 58.1 | 9 | 507.9 | 6.5 | 32.2 | signal sequence receptor, gamma (translocon-associated protein gamma) | SSR3 |
| 219684_at | 196.8 | 23.5 | 1058.6 | 20.7 | 32.2 | 28 kD interferon responsive protein | IFRG28 |
| 221656_s_at | 90.5 | 15.2 | 619 | 7.6 | 32.2 | Rho guanine nucleotide exchange factor (GEF) 10-like | ARHGEF10L |
| 221757_at | 465.1 | 292.9 | 3099.2 | 216.1 | 32.2 | HGFL gene /// HGFL gene | MGC17330 |
| 206127_at | 356.6 | 70.3 | 1993.9 | 23.1 | 32.2 | ELK3, ETS-domain protein (SRF accessory protein 2) | ELK3 |
| 216026_s_at | 686 | 510.8 | 3365 | 21.1 | 32.2 | polymerase (DNA directed), epsilon | POLE |
| 220329_s_at | 127.5 | 83.2 | 656.2 | 19.9 | 32.2 | chromosome 6 open reading frame 96 | C6orf96 |
| 202887_s_at | 1419.8 | 658.6 | 11347.5 | 32.1 | 32.2 | DNA-damage-inducible transcript 4 | DDIT4 |

TABLE 1-continued

Probe sets overexpressed in 25% of more of B-lineage ALL cases (n = 270) as compared to normal bone marrow CD19+CD10+ cells from 4 healthy donors

| probe set ID | CD10+ CD19+ max | CD10+ CD19+ min | ALL max | ALL min | % ALL over expressed | Title | Symbol |
| --- | --- | --- | --- | --- | --- | --- | --- |
| 207621_s_at | 159.4 | 62.9 | 2413.2 | 13.3 | 32.2 | phosphatidylethanolamine N-methyltransferase | PEMT |
| 209776_s_at | 31 | 19.7 | 397.5 | 5.2 | 32.2 | solute carrier family 19 (folate transporter), member 1 | SLC19A1 |
| 204793_at | 209.4 | 154.8 | 1899.3 | 12.8 | 32.2 | G protein-coupled receptor associated sorting protein 1 | GPRASP1 |
| 204115_at | 371.9 | 300.5 | 4663.6 | 3.3 | 32.2 | guanine nucleotide binding protein (G protein), gamma 11 | GNG11 |
| 202948_at | 47.7 | 6.3 | 591.8 | 3.8 | 31.9 | interleukin 1 receptor, type I | IL1R1 |
| 205885_s_at | 1000.2 | 455.9 | 5752.2 | 323.3 | 31.9 | integrin, alpha 4 (antigen CD49D, alpha 4 subunit of VLA4 receptor) | ITGA4 |
| 206359_at | 21.1 | 7 | 299.7 | 7.2 | 31.9 | suppressor of cytokine signaling 3 | SOCS3 |
| 1438_at | 111.7 | 31.1 | 746.6 | 15.3 | 31.9 | EPH receptor B3 | EPHB3 |
| 208637_x_at | 505.3 | 198.4 | 3743.8 | 95.3 | 31.9 | actinin, alpha 1 | ACTN1 |
| 209167_at | 150.4 | 12.8 | 2836 | 5.8 | 31.9 | glycoprotein M6B | GPM6B |
| 211657_at | 313.7 | 63.9 | 10789 | 22.5 | 31.9 | carcinoembryonic antigen-related cell adhesion molecule 6 (non-specific cross reacting antigen) | CEACAM6 |
| 210705_s_at | 189.1 | 119.2 | 849.2 | 12.6 | 31.9 | tripartite motif-containing 5 | TRIM5 |
| 221529_s_at | 222 | 44.4 | 4666.8 | 13.3 | 31.9 | plasmalemma vesicle associated protein | PLVAP |
| 218806_s_at | 287.1 | 204.7 | 1924.9 | 23.3 | 31.9 | vav 3 oncogene | VAV3 |
| 202789_at | 266.4 | 176.7 | 1223.4 | 20.9 | 31.9 | phospholipase C, gamma 1 | PLCG1 |
| 209170_s_at | 197.8 | 44.6 | 3675.7 | 4.5 | 31.9 | glycoprotein M6B | GPM6B |
| 203726_s_at | 56.5 | 18.7 | 2318.4 | 11.7 | 31.5 | laminin, alpha 3 | LAMA3 |
| 204006_s_at | 166.9 | 19.8 | 2149.5 | 10.6 | 31.5 | Fc fragment of IgG, low affinity IIIa, receptor (CD16a) /// Fc fragment of IgG, low affinity IIIb, receptor (CD16b) | FCGR3A /// FCGR3B |
| 204232_at | 313.8 | 222.3 | 4420.7 | 144.8 | 31.5 | Fc fragment of IgE, high affinity I, receptor for; gamma polypeptide | FCER1G |
| 219120_at | 180.4 | 15.2 | 667 | 26.2 | 31.5 | hypothetical protein FLJ21945 | FLJ21945 |
| 219354_at | 92.7 | 35.5 | 482.9 | 27.5 | 31.5 | hypothetical protein FLJ11078 | FLJ11078 |
| 202888_s_at | 63.4 | 11.5 | 749.5 | 5.1 | 31.5 | alanyl (membrane) aminopeptidase (aminopeptidase N, aminopeptidase M, microsomal aminopeptidase, CD13, p150) | ANPEP |
| 203650_at | 49.3 | 6.5 | 324.9 | 2.7 | 31.5 | protein C receptor, endothelial (EPCR) | PROCR |
| 214353_at | 50.1 | 16.6 | 321.3 | 8.2 | 31.5 | Cadherin, EGF LAG seven-pass G-type receptor 1 (flamingo homolog, Drosophila) | CELSR1 |
| 212613_at | 304.4 | 35 | 1511.8 | 8.7 | 31.5 | butyrophilin, subfamily 3, member A2 | BTN3A2 |
| 206762_at | 115.6 | 25.7 | 4277.4 | 9.9 | 31.5 | potassium voltage-gated channel, shaker-related subfamily, member 5 | KCNA5 |
| 213218_at | 166.7 | 123.6 | 656.9 | 19.5 | 31.5 | zinc finger protein 187 | ZNF187 |
| 218087_s_at | 47.4 | 9.3 | 1490.3 | 0.9 | 31.5 | sorbin and SH3 domain containing 1 | SORBS1 |
| 204174_at | 1237 | 842 | 13270.9 | 119 | 31.5 | arachidonate 5-lipoxygenase-activating protein | ALOX5AP |
| 217022_s_at | 1283.9 | 273.1 | 35058.2 | 6.6 | 31.5 | immunoglobulin heavy constant alpha 1 /// immunoglobulin heavy constant alpha 2 (A2m marker) /// hypothetical protein MGC27165 | IGHA1 /// IGHA2 /// MGC27165 |
| 203435_s_at | 3792.8 | 2101.1 | 15156.8 | 14.9 | 31.5 | membrane metallo-endopeptidase (neutral endopeptidase, enkephalinase, CALLA, CD10) | MME |
| 202219_at | 30.5 | 13.8 | 7056.9 | 9.1 | 31.1 | solute carrier family 6 (neurotransmitter transporter, creatine), member 8 | SLC6A8 |
| 202809_s_at | 1265.5 | 710 | 7400.2 | 512 | 31.1 | chromosome 1 open reading frame 60 | C1orf60 |
| 203476_at | 140.1 | 8.3 | 3079.9 | 12.4 | 31.1 | trophoblast glycoprotein | TPBG |
| 203662_s_at | 44.7 | 19.3 | 3171.4 | 12.3 | 31.1 | tropomodulin 1 | TMOD1 |
| 213294_at | 660.6 | 489.1 | 4962.7 | 346.1 | 31.1 | Coiled-coil domain containing 75 | CCDC75 |
| 209474_s_at | 59.7 | 14.6 | 449.6 | 6.8 | 31.1 | ectonucleoside triphosphate diphosphohydrolase 1 | ENTPD1 |
| 211462_s_at | 75.1 | 13.4 | 784.2 | 4.4 | 31.1 | transducin (beta)-like 1Y-linked | TBL1Y |
| 214277_at | 21.5 | 2 | 356.2 | 0.5 | 31.1 | COX11 homolog, cytochrome c oxidase assembly protein (yeast) /// COX11 homolog, cytochrome c oxidase assembly protein (yeast) pseudogene | COX11 /// COX11P |
| 217264_s_at | 72.4 | 31.9 | 487.4 | 9.2 | 31.1 | sodium channel, nonvoltage-gated 1 alpha | SCNN1A |
| 214110_s_at | 28.3 | 16.8 | 809.3 | 6.8 | 31.1 | Similar to lymphocyte-specific protein 1 | LOC440886 |
| 202125_s_at | 447.1 | 312.2 | 8793.8 | 278.3 | 30.7 | amyotrophic lateral sclerosis 2 (juvenile) chromosome region, candidate 3 | ALS2CR3 |
| 203972_s_at | 257.9 | 191.8 | 834.8 | 107.8 | 30.7 | peroxisomal biogenesis factor 3 | PEX3 |
| 204655_at | 243.8 | 157.3 | 2562.6 | 116.7 | 30.7 | chemokine (C-C motif) ligand 5 /// chemokine (C-C motif) ligand 5 | CCL5 |
| 205565_s_at | 178.6 | 49.2 | 911.6 | 28.9 | 30.7 | frataxin | FXN |
| 206135_at | 9.3 | 4.6 | 1153 | 2.3 | 30.7 | suppression of tumorigenicity 18 (breast carcinoma) (zinc finger protein) | ST18 |
| 206488_s_at | 109.2 | 11.5 | 6444.4 | 9.5 | 30.7 | CD36 antigen (collagen type I receptor, thrombospondin receptor) | CD36 |
| 210451_at | 23.3 | 9.8 | 1635.2 | 7.6 | 30.7 | pyruvate kinase, liver and RBC | PKLR |
| 210703_at | 51.1 | 8.6 | 287.8 | 8.2 | 30.7 | — | — |
| 212647_at | 42.7 | 16.4 | 523.9 | 10.9 | 30.7 | related RAS viral (r-ras) oncogene homolog | RRAS |
| 213964_x_at | 23.1 | 2.6 | 511.9 | 2.7 | 30.7 | Chromosome 10 open reading frame 95 | C10orf95 |
| 219360_s_at | 13 | 7.5 | 2377.6 | 5.6 | 30.7 | transient receptor potential cation channel, subfamily M, member 4 | TRPM4 |
| 221484_at | 431 | 310.7 | 4031.6 | 189 | 30.7 | UDP-Gal:betaGlcNAc beta 1,4-galactosyltransferase, polypeptide 5 | B4GALT5 |

TABLE 1-continued

Probe sets overexpressed in 25% of more of B-lineage ALL cases (n = 270) as compared to normal bone marrow CD19⁺CD10⁺ cells from 4 healthy donors

| probe set ID | CD10+ CD19+ max | CD10+ CD19+ min | ALL max | ALL min | % ALL over expressed | Title | Symbol |
|---|---|---|---|---|---|---|---|
| 222084_s_at | 9.9 | 5.6 | 249.1 | 3.7 | 30.7 | SET binding factor 1 | SBF1 |
| 205926_at | 294.3 | 150.8 | 1725.2 | 62.9 | 30.7 | interleukin 27 receptor, alpha | IL27RA |
| 206304_at | 51.8 | 24.1. | 1450.1 | 8.8 | 30.7 | myosin binding protein H | MYBPH |
| 210683_at | 5.9 | 1.7 | 332.1 | 0.6 | 30.7 | neurturin | NRTN |
| 215650_at | 92.7 | 20.3 | 695.3 | 8.3 | 30.7 | — | — |
| 217147_s_at | 63.7 | 6 | 1595.6 | 2.4 | 30.7 | T cell receptor associated transmembrane adaptor 1 | TRAT1 |
| 202456_s_at | 40.8 | 21 | 1242.7 | 9.6 | 30.7 | zyg-11 homolog B (*C. elegans*)-like | ZYG11BL |
| 213012_at | 202.8 | 116 | 771.6 | 36.3 | 30.7 | neural precursor cell expressed, developmentally down-regulated 4 | NEDD4 |
| 207513_s_at | 241.5 | 181.8 | 833.3 | 84.5 | 30.7 | zinc finger protein 189 | ZNF189 |
| 204620_s_at | 208.6 | 169.4 | 12708.4 | 18.5 | 30.7 | chondroitin sulfate proteoglycan 2 (versican) | CSPG2 |
| 211574_s_at | 383.8 | 195.8 | 1584.4 | 46.6 | 30.7 | membrane cofactor protein (CD46, trophoblast-lymphocyte cross-reactive antigen) | MCP |
| 219683_at | 56.8 | 24.9 | 707.8 | 2.2 | 30.7 | frizzled homolog 3 (Drosophila) | FZD3 |
| 213005_s_at | 177.3 | 116.5 | 6672.7 | 8.4 | 30.7 | ankyrin repeat domain 15 | ANKRD15 |
| 218468_s_at | 105.2 | 33.7 | 4564 | 4.3 | 30.7 | gremlin 1, cysteine knot superfamily, homolog (*Xenopus laevis*) | GREM1 |
| 222154_s_at | 275.4 | 128.6 | 13569 | 12.1 | 30.7 | DNA polymerase-transactivated protein 6 | DNAPTP6 |
| 210663_s_at | 44.4 | 15.8 | 1257.6 | 8.7 | 30.4 | kynureninase (L-kynurenine hydrolase) | KYNU |
| 211600_at | 5593.8 | 3335.9 | 31276.5 | 2421.9 | 30.4 | — | — |
| 212216_at | 212.7 | 31.6 | 957.9 | 23.4 | 30.4 | prolyl endopeptidase-like | PREPL |
| 212848_s_at | 64.8 | 19.9 | 2991.6 | 11.2 | 30.4 | chromosome 9 open reading frame 3 | C9orf3 |
| 213800_at | 24.7 | 7.3 | 326.6 | 6 | 30.4 | complement factor H | CFH |
| 219540_at | 137.6 | 17.3 | 531.1 | 11.2 | 30.4 | zinc finger protein 267 | ZNF267 |
| 203471_s_at | 454.6 | 222.9 | 2688 | 73.5 | 30.4 | pleckstrin | PLEK |
| 204548_at | 21.1 | 13.4 | 813.5 | 6.4 | 30.4 | steroidogenic acute regulator | STAR |
| 215064_at | 76.1 | 17.5 | 473.1 | 8.3 | 30.4 | Sterol-C5-desaturase (ERG3 delta-5-desaturase homolog, fungal)-like | SC5DL |
| 204439_at | 215.3 | 10 | 10754 | 4.7 | 30.4 | interferon-induced protein 44-like | IFI44L |
| 210975_x_at | 181.1 | 69.3 | 824.9 | 28.2 | 30.4 | Fas-activated serine/threonine kinase | FASTK |
| 213698_at | 489.6 | 393.5 | 1567.9 | 83.7 | 30.4 | zinc finger, MYM-type 6 | ZMYM6 |
| 218469_at | 139 | 97.9 | 4088.8 | 7.9 | 30.4 | gremlin 1, cysteine knot superfamily, homolog (*Xenopus laevis*) | GREM1 |
| 201655_s_at | 49.3 | 8.6 | 641.1 | 6.8 | 30.0 | heparan sulfate proteoglycan 2 (perlecan) | HSPG2 |
| 210074_at | 63.6 | 7.6 | 303.9 | 8.1 | 30.0 | cathepsin L2 | CTSL2 |
| 212466_at | 26.2 | 5.6 | 657.5 | 4 | 30.0 | sprouty-related, EVH1 domain containing 2 | SPRED2 |
| 213521_at | 776.2 | 547.8 | 4117 | 383.4 | 30.0 | Protein tyrosine phosphatase, non-receptor type 18 (brain-derived) | PTPN18 |
| 218229_s_at | 435 | 234.6 | 2198.6 | 176.2 | 30.0 | pogo transposable element with KRAB domain | POGK |
| 209663_s_at | 23.6 | 14.4 | 324.8 | 6.9 | 30.0 | integrin, alpha 7 | ITGA7 |
| 219731_at | 317.6 | 207.2 | 1712.3 | 61.6 | 30.0 | weakly similar to zinc finger protein 195 | FLJ34077 |
| 221195_at | 36 | 8.2 | 262.1 | 3.5 | 30.0 | PTD016 protein | LOC51136 |
| 204276_at | 105.8 | 23.9 | 706.7 | 6.8 | 30.0 | thymidine kinase 2, mitochondrial | TK2 |
| 206090_s_at | 176.7 | 107.4 | 666.5 | 50.4 | 30.0 | disrupted in schizophrenia 1 | DISC1 |
| 206618_at | 45 | 13.6 | 282.2 | 5.2 | 30.0 | interleukin 18 receptor 1 | IL18R1 |
| 214666_x_at | 123.3 | 45.9 | 565.4 | 9.5 | 30.0 | iron-responsive element binding protein 2 | IREB2 |
| 204821_at | 222.6 | 133.8 | 1084.6 | 32 | 30.0 | butyrophilin, subfamily 3, member A3 | BTN3A3 |
| 47560_at | 204.3 | 86 | 991.2 | 25.8 | 30.0 | latrophilin 1 | LPHN1 |
| 209356_x_at | 118 | 25.8 | 815.1 | 10.6 | 30.0 | EGF-containing fibulin-like extracellular matrix protein 2 | EFEMP2 |
| 216167_at | 18.5 | 8.4 | 225.8 | 2.6 | 30.0 | leucine rich repeat neuronal 5 | LRRN5 |
| 32402_s_at | 85.9 | 53.2 | 334.4 | 16.9 | 30.0 | symplekin | SYMPK |
| 213355_at | 116.3 | 14.9 | 832.8 | 4.9 | 30.0 | ST3 beta-galactoside alpha-2,3-sialyltransferase 6 | ST3GAL6 |
| 37986_at | 105.5 | 41.3 | 1787.6 | 5.1 | 30.0 | erythropoietin receptor | EPOR |
| 200994_at | 616.5 | 375 | 2982.3 | 255.3 | 29.6 | Importin 7 | IPO7 |
| 202265_at | 590.9 | 220.6 | 8430.4 | 244.1 | 29.6 | polycomb group ring finger 4 | PCGF4 |
| 211917_s_at | 63.6 | 5.6 | 415.6 | 5.7 | 29.6 | prolactin receptor /// prolactin receptor | PRLR |
| 219470_x_at | 154.2 | 87.6 | 1374.8 | 53.1 | 29.6 | cyclin J | CCNJ |
| 220676_at | 52.2 | 7.7 | 313 | 4.8 | 29.6 | ADAM metallopeptidase with thrombospondin type 1 motif, 8 | ADAMTS8 |
| 200859_x_at | 686.3 | 476.2 | 4868.3 | 194.6 | 29.6 | filamin A, alpha (actin binding protein 280) | FLNA |
| 200887_s_at | 1051.4 | 588.9 | 8128.3 | 154.8 | 29.6 | signal transducer and activator of transcription 1, 91 kDa | STAT1 |
| 204150_at | 216.4 | 53 | 10597.1 | 14.1 | 29.6 | stabilin 1 | STAB1 |
| 220396_at | 197.7 | 48.5 | 1749.4 | 19.2 | 29.6 | — | — |
| 221042_s_at | 100.7 | 16 | 1322 | 7.4 | 29.6 | calmin (calponin-like, transmembrane) | CLMN |
| 218686_s_at | 54.6 | 49.1 | 1557.5 | 19.7 | 29.6 | rhomboid family 1 (*Drosophila*) | RHBDF1 |
| 206682_at | 78.9 | 23.6 | 445.7 | 6.2 | 29.6 | C-type lectin domain family 10, member A | CLEC10A |
| 208273_at | 128.8 | 65.6 | 524.1 | 11.5 | 29.6 | zinc finger protein 695 | ZNF695 |
| 208614_s_at | 514.9 | 365.6 | 5706.7 | 64.1 | 29.6 | filamin B, beta (actin binding protein 278) | FLNB |
| 214735_at | 167.4 | 65.5 | 2571 | 7 | 29.6 | phosphoinositide-binding protein PIP3-E | PIP3-E |
| 200659_s_at | 472.5 | 151.4 | 4886.9 | 87 | 29.3 | prohibitin | PHB |
| 215222_x_at | 1112.1 | 652.9 | 4103.5 | 671.1 | 29.3 | microtubule-actin crosslinking factor 1 | MACF1 |

TABLE 1-continued

Probe sets overexpressed in 25% of more of B-lineage ALL cases (n = 270) as compared to normal bone marrow CD19+CD10+ cells from 4 healthy donors

| probe set ID | CD10+ CD19+ max | CD10+ CD19+ min | ALL max | ALL min | % ALL over expressed | Title | Symbol |
|---|---|---|---|---|---|---|---|
| 203043_at | 851.8 | 563 | 4757.6 | 206.9 | 29.3 | zinc finger, BED-type containing 1 | ZBED1 |
| 212739_s_at | 663 | 261.3 | 3017 | 109.5 | 29.3 | non-metastatic cells 4, protein expressed in | NME4 |
| 219767_s_at | 305.3 | 259.4 | 1419.8 | 86.3 | 29.3 | crystallin, zeta (quinone reductase)-like 1 | CRYZL1 |
| 209671_x_at | 641.5 | 291.3 | 22825.7 | 60.1 | 29.3 | T cell receptor alpha locus /// T cell receptor alpha locus /// T cell receptor alpha constant /// cell receptor alpha constant | TRA@ /// TRAC |
| 211597_s_at | 176.8 | 29.1 | 5111.3 | 8.3 | 29.3 | homeodomain-only protein /// homeodomain-only protein | HOP |
| 221370_at | 108.6 | 41.1 | 551.4 | 16.6 | 29.3 | kruppel-like zinc finger factor X17 | LOC377064 |
| 221641_s_at | 343.8 | 229.3 | 2829.3 | 42.4 | 29.3 | acyl-CoA thioesterase 9 | ACOT9 |
| 212976_at | 27.3 | 12 | 286.2 | 1.8 | 29.3 | leucine rich repeat containing 8 family, member B | LRRC8B |
| 207190_at | 29.8 | 24.9 | 782.1 | 6.4 | 29.3 | zinc finger, ZZ-type with EF-hand domain 1 | ZZEF1 |
| 203434_s_at | 3344.3 | 2134.2 | 13818.9 | 3.4 | 29.3 | membrane metallo-endopeptidase (neutral endopeptidase, enkephalinase, CALLA, CD10) | MME |
| 206940_s_at | 811.4 | 463.5 | 11867.2 | 33.2 | 29.3 | POU domain, class 4, transcription factor 1 | POU4F1 |
| 208454_s_at | 166.5 | 23 | 1452.4 | 18.8 | 28.9 | plasma glutamate carboxypeptidase | PGCP |
| 211372_s_at | 30.8 | 11.7 | 750.5 | 6.1 | 28.9 | interleukin 1 receptor, type II | IL1R2 |
| 211743_s_at | 96.8 | 14.7 | 29321.7 | 12.2 | 28.9 | proteoglycan 2, bone marrow (natural killer cell activator, eosinophil granule major basic protein) /// proteoglycan 2, bone marrow (natural killer cell activator, eosinophil granule major basic protein) | PRG2 |
| 216037_x_at | 368.2 | 206.5 | 1613 | 120.8 | 28.9 | transcription factor 7-like 2 (T-cell specific, HMG-box) | TCF7L2 |
| 218921_at | 227.6 | 40.7 | 1358.9 | 53.8 | 28.9 | single immunoglobulin and toll-interleukin 1 receptor (TIR) domain | SIGIRR |
| 38487_at | 289.4 | 82.3 | 13184.4 | 50.7 | 28.9 | stabilin 1 | STAB1 |
| 200813_s_at | 666.6 | 416.6 | 2386 | 63.5 | 28.9 | platelet-activating factor acetylhydrolase, isoform Ib, alpha subunit 45 kDa | PAFAH1B1 |
| 219864_s_at | 22.3 | 4.3 | 294.6 | 2 | 28.9 | Down syndrome critical region gene 1-like 2 | DSCR1L2 |
| 208680_at | 8265.5 | 6447.7 | 43425.5 | 1422 | 28.9 | peroxiredoxin 1 | PRDX1 |
| 219451_at | 178.6 | 31 | 1373.2 | 5.9 | 28.9 | methionine sulfoxide reductase B2 | MSRB2 |
| 204007_at | 195.7 | 116.9 | 1789.5 | 26.7 | 28.9 | Fc fragment of IgG, low affinity IIIb, receptor (CD16b) | FCGR3B |
| 216333_x_at | 53 | 28.1 | 1476.8 | 6.4 | 28.9 | tenascin XB | TNXB |
| 215442_s_at | 12 | 4.8 | 444.7 | 1.5 | 28.9 | thyroid stimulating hormone receptor | TSHR |
| 202838_at | 653.7 | 432.9 | 3736.2 | 70.3 | 28.9 | fucosidase, alpha-L-1, tissue | FUCA1 |
| 204505_s_at | 315.2 | 265.2 | 13524 | 32.7 | 28.9 | erythrocyte membrane protein band 4.9 (dematin) | EPB49 |
| 221912_s_at | 199.3 | 117.4 | 734.2 | 19.8 | 28.9 | coiled-coil domain containing 28B | CCDC28B |
| 219564_at | 103.3 | 17.6 | 1219.7 | 8.8 | 28.5 | potassium inwardly-rectifying channel, subfamily J, member 16 | KCNJ16 |
| 204482_at | 26.5 | 16.4 | 433.9 | 7.7 | 28.5 | claudin 5 (transmembrane protein deleted in velocardiofacial syndrome) | CLDN5 |
| 212486_s_at | 139.3 | 14.3 | 766.1 | 4.1 | 28.5 | FYN oncogene related to SRC, FGR, YES | FYN |
| 215646_s_at | 42.5 | 5.4 | 6886.2 | 2.5 | 28.5 | chondroitin sulfate proteoglycan 2 (versican) /// chondroitin sulfate proteoglycan 2 (versican) /// | CSPG2 |
| 216833_x_at | 278.3 | 162.2 | 23091.1 | 19.7 | 28.5 | glycophorin B (includes Ss blood group) /// glycophorin E | GYPB /// GYPE |
| 214945_at | 97.6 | 72.1 | 821.6 | 4.1 | 28.5 | NY-REN-7 antigen /// similar to KIAA0752 protein | NY-REN-7 /// LOC389347 |
| 202877_s_at | 193.8 | 23.9 | 1033 | 19.1 | 28.1 | complement component 1, q subcomponent, receptor 1 /// complement component 1, q subcomponent, receptor 1 | C1QR1 |
| 210340_s_at | 34 | 4.5 | 280.4 | 3.5 | 28.1 | colony stimulating factor 2 receptor, alpha, low-affinity (granulocyte-macrophage) | CSF2RA |
| 221059_s_at | 276.9 | 165.1 | 3040.2 | 105.5 | 28.1 | coactosin-like 1 (Dictyostelium) | COTL1 |
| 203482_at | 349.4 | 302.5 | 1426.7 | 139.9 | 28.1 | chromosome 10 open reading frame 6 | C10orf6 |
| 206023_at | 13.1 | 6.9 | 366.1 | 3.4 | 28.1 | neuromedin U | NMU |
| 43511_s_at | 419 | 243.3 | 1829 | 96.1 | 28.1 | MRNA; cDNA DKFZp762M127 (from clone DKFZp762M127) | — |
| 204689_at | 917.2 | 831.8 | 4085.4 | 104.7 | 28.1 | hematopoietically expressed homeobox | HHEX |
| 213385_at | 150.6 | 28.5 | 2256.5 | 8 | 28.1 | Chimerin (chimaerin) 2 | CHN2 |
| 201911_s_at | 120.3 | 20 | 853.8 | 6.4 | 28.1 | FERM, RhoGEF (ARHGEF) and pleckstrin domain protein 1 (chondrocyte-derived) | FARP1 |
| 213856_at | 84.7 | 15.7 | 403.4 | 5.1 | 28.1 | CD47 antigen (Rh-related antigen, integrin-associated signal transducer) | CD47 |
| 213953_at | 49.5 | 15.7 | 693.1 | 3.2 | 28.1 | keratin 20 | KRT20 |
| 203139_at | 746 | 321.6 | 4394 | 102.3 | 28.1 | death-associated protein kinase 1 | DAPK1 |
| 213451_x_at | 52 | 41.4 | 1626 | 9 | 28.1 | tenascin XB | TNXB |
| 220530_at | 49.1 | 17.1 | 414.9 | 3.7 | 28.1 | — | |
| 220952_s_at | 168 | 141.6 | 1240.3 | 6 | 28.1 | pleckstrin homology domain containing, family A member 5 | PLEKHA5 |
| 202671_s_at | 203.5 | 102.2 | 2003.4 | 5.7 | 28.1 | pyridoxal (pyridoxine, vitamin B6) kinase | PDXK |
| 202665_s_at | 835.1 | 582.7 | 3306.9 | 384.7 | 27.8 | Wiskott-Aldrich syndrome protein interacting protein | WASPIP |
| 204866_at | 211.5 | 75.7 | 1149.6 | 72.8 | 27.8 | PHD finger protein 16 | PHF16 |
| 207063_at | 34.8 | 6.4 | 444.4 | 3.7 | 27.8 | chromosome Y open reading frame 14 | CYorf14 |
| 207605_x_at | 713.7 | 490.7 | 3210.3 | 279.1 | 27.8 | zinc finger protein 117 (HPF9) | ZNF117 |
| 208805_at | 6471.6 | 4957.8 | 25767.8 | 2603.4 | 27.8 | proteasome (prosome, macropain) subunit, alpha type, 6 | PSMA6 |
| 209135_at | 56.4 | 3 | 536.8 | 2.4 | 27.8 | aspartate beta-hydroxylase | ASPH |

TABLE 1-continued

Probe sets overexpressed in 25% of more of B-lineage ALL cases (n = 270) as compared to normal bone marrow CD19+CD10+ cells from 4 healthy donors

| probe set ID | CD10+ CD19+ max | CD10+ CD19+ min | ALL max | ALL min | % ALL over expressed | Title | Symbol |
|---|---|---|---|---|---|---|---|
| 213696_s_at | 144.5 | 47.7 | 666.6 | 30.8 | 27.8 | mediator of RNA polymerase II transcription, subunit 8 homolog (yeast) | MED8 |
| 216071_x_at | 702.9 | 347 | 2780 | 381.2 | 27.8 | mediator of RNA polymerase II transcription, subunit 12 homolog (yeast) | MED12 |
| 218181_s_at | 372 | 256.6 | 1267 | 170.4 | 27.8 | mitogen-activated protein kinase kinase kinase kinase 4 | MAP4K4 |
| 218781_at | 767.9 | 476.7 | 4153.5 | 332.5 | 27.8 | SMC6 structural maintenance of chromosomes 6-like 1 (yeast) | SMC6L1 |
| 220582_at | 100.2 | 14.2 | 522.5 | 9.2 | 27.8 | — | — |
| 202018_s_at | 36.7 | 13.7 | 38822.7 | 5.7 | 27.8 | lactotransferrin | LTF |
| 201162_at | 751 | 32.6 | 11849.6 | 15.7 | 27.8 | insulin-like growth factor binding protein 7 | IGFBP7 |
| 207802_at | 10.5 | 4.1 | 4963.3 | 0.9 | 27.8 | cysteine-rich secretory protein 3 | CRISP3 |
| 220798_x_at | 85.6 | 13.9 | 721.7 | 4.1 | 27.8 | plasticity-related gene 2 | PRG2 |
| 203411_s_at | 190.1 | 23.1 | 2250.7 | 8.1 | 27.8 | lamin A/C | LMNA |
| 208862_s_at | 248.5 | 93.1 | 1480.8 | 35.8 | 27.8 | catenin (cadherin-associated protein), delta 1 | CTNND1 |
| 217257_at | 37.2 | 4.5 | 228.7 | 1.9 | 27.8 | Stathmin 1/oncoprotein 18 | STMN1 |
| 221352_at | 80.5 | 23.1 | 489.8 | 8.4 | 27.8 | DNA binding protein for surfactant protein B | HUMBINDC |
| 201701_s_at | 152.7 | 104.7 | 748.9 | 9.5 | 27.8 | progesterone receptor membrane component 2 | PGRMC2 |
| 218141_at | 151 | 82.4 | 5427.4 | 15.3 | 27.8 | likely ortholog of mouse ubiquitin-conjugating enzyme E2-230K | E2-230K |
| 201188_s_at | 243.2 | 136.8 | 1625 | 29.1 | 27.8 | inositol 1,4,5-triphosphate receptor, type 3 | ITPR3 |
| 208405_s_at | 2539.4 | 1613.7 | 19923.7 | 888.6 | 27.4 | CD164 antigen, sialomucin | CD164 |
| 211819_s_at | 95 | 5 | 1000 | 3.4 | 27.4 | sorbin and SH3 domain containing 1 | SORBS1 |
| 213556_at | 105 | 10.3 | 946.4 | 7.8 | 27.4 | similar to R28379_1 | LOC390940 |
| 208033_s_at | 95.8 | 15.5 | 1150.3 | 6.3 | 27.4 | AT-binding transcription factor 1 | ATBF1 |
| 209272_at | 284.7 | 193.5 | 1317.9 | 33.7 | 27.4 | NGFI-A binding protein 1 (EGR1 binding protein 1) | NAB1 |
| 209604_s_at | 296.1 | 106.9 | 5495.4 | 27.4 | 27.4 | GATA binding protein 3 | GATA3 |
| 220010_at | 30.8 | 7.5 | 4146.7 | 3.3 | 27.4 | KCNE1-like | KCNE1L |
| 218017_s_at | 210.9 | 40.1 | 1100.6 | 19.4 | 27.4 | transmembrane protein 76 | TMEM76 |
| 203398_s_at | 72.1 | 24.1 | 553.6 | 6.4 | 27.4 | UDP-N-acetyl-alpha-D-galactosamine:polypeptide N-acetylgalactosaminyltransferase 3 (GalNAc-T3) | GALNT3 |
| 203577_at | 89.1 | 17.9 | 472.5 | 5.5 | 27.4 | general transcription factor IIH, polypeptide 4, 52 kDa | GTF2H4 |
| 220252_x_at | 399.1 | 132.7 | 2976.4 | 33.6 | 27.4 | chromosome X open reading frame 21 | CXorf21 |
| 204882_at | 679.5 | 332.4 | 3947.9 | 30.2 | 27.4 | Rho GTPase activating protein 25 | ARHGAP25 |
| 205557_at | 40.4 | 29.5 | 14658 | 6.3 | 27.4 | bactericidal/permeability-increasing protein | BPI |
| 202966_at | 51.1 | 20.6 | 440.5 | 3 | 27.4 | calpain 6 | CAPN6 |
| 206761_at | 182.3 | 81.9 | 2348 | 11.1 | 27.4 | CD96 antigen | CD96 |
| 200931_s_at | 1317.9 | 900.8 | 6524.3 | 471.1 | 27.0 | vinculin | VCL |
| 203469_s_at | 47.2 | 16.6 | 512.7 | 11.4 | 27.0 | cyclin-dependent kinase (CDC2-like) 10 | CDK10 |
| 205987_at | 249.7 | 16 | 7020.6 | 9.7 | 27.0 | CD1C antigen, c polypeptide | CD1C |
| 207668_x_at | 2269.9 | 1931.1 | 10249.1 | 1036.8 | 27.0 | protein disulfide isomerase family A, member 6 | PDIA6 |
| 208167_s_at | 54.3 | 6.5 | 1014.3 | 4.6 | 27.0 | matrix metallopeptidase 16 (membrane-inserted) | MMP16 |
| 216672_s_at | 12.4 | 6.2 | 212.7 | 4.2 | 27.0 | myelin transcription factor 1-like | MYT1L |
| 218275_at | 99.3 | 19.2 | 384 | 10.7 | 27.0 | solute carrier family 25 (mitochondrial carrier, dicarboxylate transporter), member 10 | SLC25A10 |
| 202169_s_at | 601.6 | 377.7 | 1966.2 | 166.7 | 27.0 | aminoadipate-semialdehyde dehydrogenase-phosphopantetheinyl transferase | AASDHPPT |
| 204846_at | 70.3 | 15.1 | 733.6 | 6.7 | 27.0 | ceruloplasmin (ferroxidase) | CP |
| 212623_at | 414.1 | 261 | 1305.9 | 112.5 | 27.0 | transmembrane protein 41B | TMEM41B |
| 214582_at | 252.1 | 143.6 | 1684.1 | 43.7 | 27.0 | phosphodiesterase 3B, cGMP-inhibited | PDE3B |
| 220030_at | 20.9 | 3.5 | 364.3 | 1.5 | 27.0 | serine/threonine/tyrosine kinase 1 | STYK1 |
| 218454_at | 207.2 | 52.4 | 12684.2 | 21.7 | 27.0 | hypothetical protein FLJ22662 | FLJ22662 |
| 219467_at | 181.6 | 129.5 | 614.8 | 36.9 | 27.0 | hypothetical protein FLJ20125 | FLJ20125 |
| 209122_at | 542.2 | 267.6 | 8508.3 | 60.5 | 27.0 | adipose differentiation-related protein | ADFP |
| 218019_s_at | 483.5 | 320.9 | 4313.3 | 154.2 | 27.0 | pyridoxal (pyridoxine, vitamin B6) kinase | PDXK |
| 216174_at | 178.7 | 87.5 | 794.5 | 18.1 | 27.0 | hepatocellular carcinoma-related HCRP1 | HCRP1 |
| 216033_s_at | 503.1 | 258.6 | 2491.8 | 22 | 27.0 | FYN oncogene related to SRC, FGR, YES | FYN |
| 206785_s_at | 46.3 | 11.1 | 345.9 | 2.3 | 27.0 | killer cell lectin-like receptor subfamily C, member /// killer cell lectin-like receptor subfamily C, member 2 | KLRC1 /// KLRC2 |
| 213712_at | 86.4 | 15 | 1058.3 | 3 | 27.0 | elongation of very long chain fatty acids (FEN1/Elo2, SUR4/Elo3, yeast)-like 2 | ELOVL2 |
| 204518_s_at | 35.7 | 27.8 | 1300.7 | 8.2 | 27.0 | peptidylprolyl isomerase C (cyclophilin C) | PPIC |
| 203922_s_at | 312.1 | 123.8 | 1877.8 | 77.6 | 26.7 | cytochrome b-245, beta polypeptide (chronic granulomatous disease) | CYBB |
| 204669_s_at | 173.3 | 18.2 | 2477.9 | 12 | 26.7 | ring finger protein 24 | RNF24 |
| 209081_s_at | 26.6 | 7.7 | 800.2 | 5.9 | 26.7 | collagen, type XVIII, alpha 1 | COL18A1 |
| 212352_s_at | 1654.9 | 932.1 | 8879.8 | 606.1 | 26.7 | transmembrane emp24-like trafficking protein 10 (yeast) | TMED10 |
| 214706_at | 185.9 | 36.8 | 735.8 | 20.7 | 26.7 | zinc finger protein 200 | ZNF200 |
| 201703_s_at | 679.9 | 445.1 | 2195.6 | 91.2 | 26.7 | protein phosphatase 1, regulatory subunit 10 | PPP1R10 |
| 203929_s_at | 85.4 | 34.9 | 576.4 | 17.3 | 26.7 | microtubule-associated protein tau | MAPT |
| 209331_s_at | 583.4 | 270.7 | 2420 | 106.1 | 26.7 | MYC associated factor X | MAX |
| 209879_at | 211.8 | 114.5 | 2395.8 | 43.1 | 26.7 | selectin P ligand | SELPLG |
| 212230_at | 128.2 | 40.7 | 1062.4 | 14.4 | 26.7 | phosphatidic acid phosphatase type 2B | PPAP2B |
| 218904_s_at | 112.6 | 24 | 782.4 | 11.4 | 26.7 | chromosome 9 open reading frame 40 | C9orf40 |

TABLE 1-continued

Probe sets overexpressed in 25% of more of B-lineage ALL cases (n = 270) as compared to normal bone marrow CD19+CD10+ cells from 4 healthy donors

| probe set ID | CD10+ CD19+ max | CD10+ CD19+ min | ALL max | ALL min | % ALL over expressed | Title | Symbol |
|---|---|---|---|---|---|---|---|
| 208438_s_at | 186.8 | 44.4 | 2461.2 | 11.1 | 26.7 | Gardner-Rasheed feline sarcoma viral (v-fgr) oncogene homolog | FGR |
| 210222_s_at | 56.5 | 13.7 | 351.5 | 5.1 | 26.7 | reticulon 1 | RTN1 |
| 213157_s_at | 62.7 | 32.2 | 547.2 | 9.7 | 26.7 | KIAA0523 protein | KIAA0523 |
| 89476_r_at | 210.9 | 132 | 981.1 | 48.9 | 26.7 | aminopeptidase-like 1 | NPEPL1 |
| 209434_s_at | 143 | 85.4 | 597.2 | 12.4 | 26.7 | phosphoribosyl pyrophosphate amidotransferase | PPAT |
| 206235_at | 669.4 | 314.9 | 4071.6 | 82 | 26.7 | ligase IV, DNA, ATP-dependent | LIG4 |
| 204863_s_at | 160.9 | 119.4 | 837.1 | 8.5 | 26.7 | interleukin 6 signal transducer (gp130, oncostatin M receptor) | IL6ST |
| 206591_at | 1526.9 | 1040 | 15016.2 | 19.7 | 26.7 | recombination activating gene 1 | RAG1 |
| 207339_s_at | 2085.6 | 1712.7 | 24613.4 | 77.1 | 26.7 | lymphotoxin beta (TNF superfamily, member 3) | LTB |
| 202907_s_at | 582.8 | 409.4 | 2160.4 | 481.3 | 26.3 | nibrin | NBN |
| 204725_s_at | 425.6 | 347.8 | 1967.1 | 211.3 | 26.3 | NCK adaptor protein 1 | NCK1 |
| 206828_at | 116.6 | 15.5 | 1426.5 | 10.7 | 26.3 | TXK tyrosine kinase | TXK |
| 209082_s_at | 125.9 | 14.9 | 1409.2 | 12.6 | 26.3 | collagen, type XVIII, alpha 1 | COL18A1 |
| 210612_s_at | 49.5 | 6.4 | 918.1 | 3.6 | 26.3 | synaptojanin 2 | SYNJ2 |
| 212179_at | 1307.2 | 522 | 5366.7 | 338.9 | 26.3 | chromosome 6 open reading frame 111 | C6orf111 |
| 212268_at | 550.5 | 299 | 11730.6 | 232.6 | 26.3 | serpin peptidase inhibitor, clade B (ovalbumin), member 1 | SERPINB1 |
| 213126_at | 31.5 | 10.2 | 218.7 | 6.2 | 26.3 | mediator of RNA polymerase II transcription, subunit 8 homolog (yeast) | MED8 |
| 218446_s_at | 129.4 | 15.8 | 573.3 | 14.2 | 26.3 | family with sequence similarity 18, member B | FAM18B |
| 220667_at | 40.1 | 5.2 | 458.2 | 4 | 26.3 | — | — |
| 200827_at | 111.6 | 46.7 | 675.1 | 21.4 | 26.3 | procollagen-lysine 1, 2-oxoglutarate 5-dioxygenase 1 | PLOD1 |
| 203632_s_at | 31 | 14.2 | 798.1 | 6.3 | 26.3 | G protein-coupled receptor, family C, group 5, member B | GPRC5B |
| 206302_s_at | 441 | 298.4 | 9153.7 | 39.5 | 26.3 | nudix (nucleoside diphosphate linked moiety X)-type motif 4 /// nudix (nucleoside diphosphate linked moiety X)-type motif 4 pseudogene 1 | NUDT4 /// NUDT4P1 |
| 207703_at | 50.8 | 10.5 | 406.9 | 4 | 26.3 | neuroligin 4, Y-linked | NLGN4Y |
| 220405_at | 89.5 | 32.1 | 556.7 | 6.6 | 26.3 | syntrophin, gamma 1 | SNTG1 |
| 216317_x_at | 150 | 32.7 | 12972.6 | 12.5 | 26.3 | Rhesus blood group, CcEe antigens | RHCE |
| 207851_s_at | 108.7 | 26.6 | 679.3 | 8.1 | 26.3 | insulin receptor | INSR |
| 208492_at | 60.2 | 22.3 | 287.9 | 7.8 | 26.3 | regulatory factor X-associated protein | RFXAP |
| 218232_at | 91.8 | 45.1 | 1938.4 | 8 | 26.3 | complement component 1, q subcomponent, alpha polypeptide | C1QA |
| 209815_at | 167.6 | 45 | 3201 | 3.4 | 26.3 | patched homolog (Drosophila) | PTCH |
| 200871_s_at | 2085.5 | 1361.6 | 14505.4 | 683.1 | 25.9 | prosaposin (variant Gaucher disease and variant metachromatic leukodystrophy) | PSAP |
| 200889_s_at | 527.4 | 422 | 2478.5 | 212.3 | 25.9 | signal sequence receptor, alpha (translocon-associated protein alpha) | SSR1 |
| 207341_at | 128.8 | 16.4 | 22403.2 | 11.7 | 25.9 | proteinase 3 (serine proteinase, neutrophil, Wegener granulomatosis autoantigen) | PRTN3 |
| 208420_x_at | 347.2 | 224.8 | 1303.3 | 145.3 | 25.9 | suppressor of Ty 6 homolog (S. cerevisiae) | SUPT6H |
| 210016_at | 148.8 | 7.3 | 3757.5 | 6.9 | 25.9 | myelin transcription factor 1-like | MYT1L |
| 213435_at | 36.6 | 5.8 | 4632.2 | 5.3 | 25.9 | SATB family member 2 | SATB2 |
| 217367_s_at | 127.2 | 38.5 | 675.7 | 33.7 | 25.9 | zinc fingers and homeoboxes 3 | ZHX3 |
| 219346_at | 56.7 | 4.2 | 502.5 | 4.9 | 25.9 | leucine rich repeat and fibronectin type III domain containing 3 | LRFN3 |
| 200816_s_at | 1030.3 | 550.4 | 3684.2 | 240.8 | 25.9 | platelet-activating factor acetylhydrolase, isoform Ib, alpha subunit 45 kDa | PAFAH1B1 |
| 204858_s_at | 143.8 | 32.9 | 992.8 | 16.2 | 25.9 | endothelial cell growth factor 1 (platelet-derived) | ECGF1 |
| 214634_at | 78.2 | 15.8 | 514.9 | 6.9 | 25.9 | — | — |
| 217695_x_at | 114.1 | 25.5 | 1056.8 | 8.9 | 25.9 | — | — |
| 211071_s_at | 904.7 | 682.7 | 4373.1 | 322.4 | 25.9 | myeloid/lymphoid or mixed-lineage leukemia (trithorax homolog, Drosophila); translocated to, 11 /// myeloid/lymphoid or mixed-lineage leukemia (trithorax homolog, Drosophila); translocated to, 11 | MLLT11 |
| 212895_s_at | 563.7 | 455.4 | 2422.8 | 191.8 | 25.9 | active BCR-related gene | ABR |
| 206165_s_at | 89.7 | 34.9 | 467.2 | 7.9 | 25.9 | chloride channel, calcium activated, family member 2 | CLCA2 |
| 206914_at | 45.4 | 11.4 | 322.1 | 3.4 | 25.9 | class-I MHC-restricted T cell associated molecule | CRTAM |
| 221246_x_at | 217.6 | 148.6 | 2307.1 | 20 | 25.9 | tensin 1 /// tensin 1 | TNS1 |
| 201380_at | 278.8 | 197.5 | 1221 | 150.2 | 25.6 | cartilage associated protein | CRTAP |
| 216633_s_at | 45 | 7.7 | 306.4 | 4 | 25.6 | phospholipase C-like 3 | PLCL3 |
| 221501_x_at | 3049 | 2089.6 | 13557 | 1205 | 25.6 | hypothetical protein LOC339047 | LOC339047 |
| 45297_at | 130.3 | 38.8 | 1920.1 | 21.3 | 25.6 | EH-domain containing 2 | EHD2 |
| 202911_at | 2201.5 | 1372.6 | 8710.3 | 645.7 | 25.6 | mutS homolog 6 (E. coli) | MSH6 |
| 211342_x_at | 784.7 | 489.5 | 3356.7 | 191.2 | 25.6 | mediator of RNA polymerase II transcription, subunit 12 homolog (yeast) | MED12 |
| 218445_at | 81.9 | 36.9 | 733.8 | 13.2 | 25.6 | H2A histone family, member Y2 | H2AFY2 |
| 202557_at | 245.1 | 168.8 | 2210.8 | 33.3 | 25.6 | stress 70 protein chaperone, microsome-associated, 60 kDa | STCH |

TABLE 1-continued

Probe sets overexpressed in 25% of more of B-lineage ALL cases (n = 270) as compared to normal bone marrow CD19+CD10+ cells from 4 healthy donors

| probe set ID | CD10+ CD19+ max | CD10+ CD19+ min | ALL max | ALL min | % ALL over expressed | Title | Symbol |
|---|---|---|---|---|---|---|---|
| 200890_s_at | 365.9 | 300.3 | 1698.2 | 54 | 25.6 | signal sequence receptor, alpha (translocon-associated protein alpha) | SSR1 |
| 215882_at | 66.6 | 16.5 | 312.9 | 6.9 | 25.6 | Centrosomal protein 152 kDa | CEP152 |
| 219602_s_at | 160.6 | 75.9 | 1545.3 | 11.6 | 25.6 | family with sequence similarity 38, member B | FAM38B |
| 207402_at | 77.6 | 19.7 | 440.4 | 4.3 | 25.6 | zinc finger protein 132 (clone pHZ-12) | ZNF132 |
| 218346_s_at | 682.6 | 523.1 | 11846.5 | 178.6 | 25.6 | sestrin 1 | SESN1 |
| 200952_s_at | 210.9 | 49.5 | 3997.6 | 13 | 25.6 | cyclin D2 | CCND2 |
| 203608_at | 957 | 649.2 | 5837.5 | 26.7 | 25.6 | aldehyde dehydrogenase 5 family, member A1 (succinate-semialdehyde dehydrogenase) | ALDH5A1 |
| 218862_at | 291.5 | 69 | 2508.3 | 21.1 | 25.6 | ankyrin repeat and SOCS box-containing 13 | ASB13 |
| 218472_s_at | 154.4 | 91.3 | 793.1 | 9.4 | 25.6 | pelota homolog (Drosophila) | PELO |
| 201743_at | 67.2 | 16.5 | 1571.8 | 5.8 | 25.6 | CD14 antigen /// CD14 antigen | CD14 |
| 202669_s_at | 135.9 | 25.9 | 1724 | 10 | 25.6 | ephrin-B2 | EFNB2 |
| 218804_at | 64.8 | 5.8 | 2319 | 0.7 | 25.6 | transmembrane protein 16A | TMEM16A |
| 202403_s_at | 154.9 | 62.3 | 1745.3 | 9.2 | 25.6 | collagen, type I, alpha 2 | COL1A2 |
| 204014_at | 10.9 | 7.3 | 504.9 | 2.6 | 25.6 | dual specificity phosphatase 4 | DUSP4 |
| 213959_s_at | 69.6 | 41.5 | 719 | 2.8 | 25.6 | KIAA1005 protein | KIAA1005 |
| 219759_at | 415.7 | 208.8 | 3312.2 | 14.4 | 25.6 | leukocyte-derived arginine aminopeptidase | LRAP |
| 204445_s_at | 613.4 | 374.9 | 3692.5 | 11.5 | 25.6 | arachidonate 5-lipoxygenase | ALOX5 |
| 208542_x_at | 25.5 | 8.2 | 342.1 | 5.1 | 25.2 | zinc finger protein 208 | ZNF208 |
| 212198_s_at | 551.4 | 331.2 | 1856.6 | 315.1 | 25.2 | transmembrane 9 superfamily protein member 4 | TM9SF4 |
| 212203_x_at | 2643.1 | 932.3 | 13245.4 | 931 | 25.2 | interferon induced transmembrane protein 3 (1-8U) | IFITM3 |
| 216040_x_at | 150.4 | 37.2 | 761.3 | 22 | 25.2 | CDNA FLJ14073 fis, clone HEMBB1001812 | — |
| 218045_x_at | 14.8 | 6.1 | 528.4 | 4.1 | 25.2 | parathymosin | PTMS |
| 218546_at | 35.7 | 13.4 | 844.5 | 6.8 | 25.2 | chromosome 1 open reading frame 115 | C1orf115 |
| 219364_at | 35.3 | 18 | 376.4 | 11.1 | 25.2 | likely ortholog of mouse D11lgp2 | LGP2 |
| 204413_at | 67.7 | 31 | 410.9 | 13.9 | 25.2 | TNF receptor-associated factor 2 | TRAF2 |
| 205400_at | 209.8 | 62.9 | 1064.9 | 26.4 | 25.2 | Wiskott-Aldrich syndrome (eczema-thrombocytopenia) | WAS |
| 209684_at | 126.1 | 19.5 | 1033.7 | 9.4 | 25.2 | Ras and Rab interactor 2 | RIN2 |
| 213510_x_at | 403.9 | 267.7 | 1583.6 | 42.9 | 25.2 | TL132 protein | LOC220594 |
| 221584_s_at | 75.5 | 27.7 | 536.4 | 6.7 | 25.2 | potassium large conductance calcium-activated channel, subfamily M, alpha member 1 | KCNMA1 |
| 222078_at | 51.2 | 19.6 | 743.7 | 7.2 | 25.2 | Hyperpolarization activated cyclic nucleotide-gated potassium channel 3 | HCN3 |
| 202687_s_at | 168.8 | 60.4 | 2096 | 16.1 | 25.2 | tumor necrosis factor (ligand) superfamily, member 10 /// tumor necrosis factor (ligand) superfamily, member 10 | TNFSF10 |
| 203102_s_at | 543.5 | 357 | 2600.5 | 61.1 | 25.2 | mannosyl (alpha-1,6-)-glycoprotein beta-1,2-N-acetylglucosaminyltransferase | MGAT2 |
| 207269_at | 201.2 | 140.2 | 50844.5 | 26.2 | 25.2 | defensin, alpha 4, corticostatin | DEFA4 |
| 214393_at | 51.3 | 14.2 | 951.1 | 3.8 | 25.2 | hypothetical protein LOC284062 | LOC284062 |
| 220713_at | 153.5 | 131.7 | 1002 | 27.8 | 25.2 | Chromosome 11 open reading frame 49 | C11orf49 |
| 206983_at | 98.4 | 40.3 | 1311.9 | 4.3 | 25.2 | chemokine (C-C motif) receptor 6 | CCR6 |
| 220416_at | 88.4 | 44.1 | 3159.1 | 3.4 | 25.2 | ATPase, Class I, type 8B, member 4 | ATP8B4 |
| 204349_at | 108 | 6.7 | 412.9 | 6.6 | 24.8 | cofactor required for Sp1 transcriptional activation, subunit 9, 33 kDa | CRSP9 |
| 205718_at | 208.5 | 12.1 | 3223.5 | 10.9 | 24.8 | integrin, beta 7 | ITGB7 |
| 210774_s_at | 3772.2 | 3234.2 | 41868.2 | 1733.7 | 24.8 | nuclear receptor coactivator 4 | NCOA4 |
| 212552_at | 1213.9 | 967.9 | 6135.2 | 553.6 | 24.8 | hippocalcin-like 1 | HPCAL1 |
| 202598_at | 650 | 437.8 | 5525.2 | 129 | 24.8 | S100 calcium binding protein A13 | S100A13 |
| 204414_at | 27.6 | 5 | 243.4 | 1.9 | 24.8 | like-glycosyltransferase | LARGE |
| 210128_s_at | 183 | 38.2 | 1125.8 | 18.6 | 24.8 | leukotriene B4 receptor | LTB4R |
| 212217_at | 273.7 | 155.4 | 836.9 | 60.3 | 24.8 | prolyl endopeptidase-like | PREPL |
| 210738_s_at | 22.2 | 4.5 | 251.4 | 1.3 | 24.8 | solute carrier family 4, sodium bicarbonate cotransporter, member 4 | SLC4A4 |
| 202599_s_at | 2080.2 | 919.5 | 11117.1 | 95.4 | 24.8 | nuclear receptor interacting protein 1 | NRIP1 |
| 205795_at | 30.2 | 14.8 | 1096.1 | 2.6 | 24.8 | neurexin 3 | NRXN3 |
| 206372_at | 50 | 23.6 | 1704 | 5.3 | 24.8 | myogenic factor 6 (herculin) | MYF6 |
| 206231_at | 289.9 | 145.6 | 1890.7 | 37.6 | 24.8 | potassium intermediate/small conductance calcium-activated channel, subfamily N, member 1 | KCNN1 |
| 209169_at | 136.9 | 40.3 | 1283.6 | 3.5 | 24.8 | glycoprotein M6B | GPM6B |
| 208981_at | 738.3 | 406.5 | 5037.4 | 25.6 | 24.8 | platelet/endothelial cell adhesion molecule (CD31 antigen) | PECAM1 |

TABLE 2

Probesets underexpressed in 25% of more of B-lineage ALL cases (n = 270) as compared to normal bone marrow CD19+CD10+ cells from 4 healthy donors

| probe set ID | CD10+ CD19+ max | CD10+ CD19+ min | ALL max | ALL min | % ALL under expressed | Title | Symbol |
|---|---|---|---|---|---|---|---|
| 202388_at | 29835.8 | 25562.5 | 9759.4 | 10.9 | 100 | regulator of G-protein signalling 2, 24 kDa | RGS2 |
| 204207_s_at | 4433.5 | 3175.3 | 1223.2 | 332.7 | 100 | RNA guanylyltransferase and 5'-phosphatase | RNGTT |
| 204208_at | 3110 | 1717.1 | 772.2 | 18.6 | 100 | RNA guanylyltransferase and 5'-phosphatase | RNGTT |
| 201853_s_at | 12593.8 | 6539 | 3519.8 | 478.8 | 100 | cell division cycle 25B | CDC25B |
| 202626_s_at | 5962.8 | 4459.4 | 4793.6 | 161.8 | 99 | v-yes-1 Yamaguchi sarcoma viral related oncogene homolog | LYN |
| 205942_s_at | 2204.8 | 1110.2 | 623.9 | 6.3 | 99 | acyl-CoA synthetase medium-chain family member 3 | ACSM3 |
| 207540_s_at | 5984.8 | 4323.6 | 2507.6 | 34.6 | 99 | spleen tyrosine kinase | SYK |
| 206046_at | 1778.2 | 1399.6 | 3305.2 | 24.2 | 99 | ADAM metallopeptidase domain 23 | ADAM23 |
| 210377_at | 1677 | 767.9 | 656.8 | 6.9 | 99 | acyl-CoA synthetase medium-chain family member 3 | ACSM3 |
| 210754_s_at | 6524.5 | 5533.3 | 5518.6 | 119.3 | 98 | v-yes-1 Yamaguchi sarcoma viral related oncogene homolog | LYN |
| 201465_s_at | 1499.1 | 591.2 | 823.4 | 6.2 | 98 | v-jun sarcoma virus 17 oncogene homolog (avian) | JUN |
| 203927_at | 1369.3 | 1138.5 | 916.8 | 67.1 | 97 | nuclear factor of kappa light polypeptide gene enhancer in B-cells inhibitor, epsilon | NFKBIE |
| 211639_x_at | 3276 | 2582.8 | 14470.8 | 9.9 | 97 | Isolate Black93 immunoglobulin heavy chain variable region (IGVH) /// Isolate Black93 immunoglobulin heavy chain variable region (IGVH) | — |
| 216834_at | 8959.4 | 2947.1 | 7948.4 | 3.6 | 97 | regulator of G-protein signalling 1 | RGS1 |
| 207574_s_at | 6491.2 | 3330.7 | 5589.1 | 23.7 | 96 | growth arrest and DNA-damage-inducible, beta | GADD45B |
| 209305_s_at | 7175.5 | 3216.3 | 4660.8 | 35.8 | 96 | growth arrest and DNA-damage-inducible, beta | GADD45B |
| 211633_x_at | 3257.1 | 1593.6 | 1815.9 | 9.4 | 96 | Immunoglobulin heavy constant gamma 1 | IGHG1 |
| 213419_at | 1983.8 | 877.8 | 809.5 | 4 | 96 | amyloid beta (A4) precursor protein-binding, family B, member 2 (Fe65-like) | APBB2 |
| 217168_s_at | 6948.2 | 4299.7 | 9008.6 | 277 | 96 | homocysteine-inducible, endoplasmic reticulum stress-inducible, ubiquitin-like domain member 1 | HERPUD1 |
| 213808_at | 1370.8 | 704.8 | 6121.1 | 3.6 | 96 | ADAM metallopeptidase domain 23 | ADAM23 |
| 201044_x_at | 4997.4 | 1908.8 | 4534.7 | 6.1 | 96 | dual specificity phosphatase 1 | DUSP1 |
| 201416_at | 19683.9 | 13224.7 | 36012.1 | 314.4 | 96 | SRY (sex determining region Y)-box 4 | SOX4 |
| 205297_s_at | 17637 | 11257.6 | 8701 | 19.1 | 96 | CD79B antigen (immunoglobulin-associated beta) | CD79B |
| 221986_s_at | 1516.8 | 1088.1 | 1221.8 | 8.2 | 96 | kelch-like 24 (Drosophila) | KLHL24 |
| 203036_s_at | 377.2 | 246.6 | 424.5 | 7.5 | 96 | metastasis suppressor 1 | MTSS1 |
| 209304_x_at | 5576.4 | 2633.1 | 4811.7 | 23.5 | 96 | growth arrest and DNA-damage-inducible, beta | GADD45B |
| 202191_s_at | 5953.1 | 2637.8 | 2695.5 | 15.6 | 95 | growth arrest-specific 7 | GAS7 |
| 215949_x_at | 2781.1 | 1745.5 | 3036.2 | 10.6 | 95 | immunoglobulin heavy constant mu | IGHM |
| 211650_x_at | 3663.2 | 1700.3 | 18473.5 | 9.6 | 95 | IgG heavy chain variable region (Vh26) /// IgG heavy chain variable region (Vh26) | — |
| 214623_at | 1081.8 | 683.7 | 927 | 6.8 | 94 | split hand/foot malformation (ectrodactyly) type 3 pseudogene 1 | SHFM3P1 |
| 216491_x_at | 7328.1 | 6235.1 | 10541.5 | 7.6 | 94 | immunoglobulin heavy constant mu | IGHM |
| 211637_x_at | 68887 | 4946.8 | 11825.7 | 12.2 | 94 | Immunoglobulin heavy chain variable region (VH IV family) from IgM rheumatoid factor | — |
| 214522_x_at | 1124.3 | 1009.1 | 1334.7 | 7.2 | 94 | histone 1, H3d | HIST1H3D |
| 40148_at | 1381.9 | 627.4 | 593.3 | 4.4 | 94 | amyloid beta (A4) precursor protein-binding, family B, member 2 (Fe65-like) | APBB2 |
| 220668_s_at | 2345.6 | 1514.1 | 5694.5 | 21.5 | 94 | DNA (cytosine-5-)-methyltransferase 3 beta | DNMT3B |
| 204730_at | 4967.4 | 2864 | 8362.2 | 16.1 | 93 | regulating synaptic membrane exocytosis 3 | RIMS3 |
| 214916_x_at | 14343.8 | 6892.4 | 17677.2 | 82.3 | 93 | immunoglobulin heavy locus | IGH@ |
| 218205_s_at | 19891.4 | 12578.8 | 17879.7 | 801.3 | 93 | MAP kinase interacting serine/threonine kinase 2 | MKNK2 |
| 202988_s_at | 2636.3 | 560.9 | 2173.7 | 2.9 | 93 | regulator of G-protein signalling 1 | RGS1 |
| 206864_s_at | 1273.7 | 714.7 | 857.8 | 1.8 | 93 | harakiri, BCL2 interacting protein (contains only BH3 domain) | HRK |
| 210150_s_at | 1324.2 | 1056 | 1372.4 | 5 | 93 | laminin, alpha 5 | LAMA5 |
| 214973_x_at | 6122 | 2443.4 | 7633.2 | 10.1 | 93 | immunoglobulin heavy constant delta | IGHD |
| 217281_x_at | 3751.2 | 1876.2 | 4004.5 | 5.9 | 93 | Isolate Rice94 immunoglobulin heavy chain variable region (IGVH) | — |
| 214669_x_at | 8995.8 | 5783 | 18674.6 | 159.4 | 93 | Immunoglobulin kappa variable 1-5 | IGKC |
| 209062_x_at | 1688.2 | 1275.6 | 1789.8 | 32.3 | 92 | nuclear receptor coactivator 3 | NCOA3 |
| 221496_s_at | 1497.2 | 419.1 | 773.1 | 6.1 | 92 | transducer of ERBB2, 2 | TOB2 |
| 216510_x_at | 3545 | 1371.3 | 10120.1 | 4.8 | 92 | immunoglobulin heavy constant alpha 1 /// immunoglobulin heavy constant delta /// immunoglobulin heavy constant gamma 1 | IGHA1 /// IGHD /// IGHG1 /// IGHM |
| 204562_at | 17170.2 | 7589.8 | 8919.6 | 61.1 | 92 | interferon regulatory factor 4 | IRF4 |
| 201779_s_at | 4113.5 | 2884 | 2079.7 | 439.5 | 91 | ring finger protein 13 | RNF13 |
| 211849_s_at | 1289 | 694.5 | 544.9 | 13 | 91 | RNA guanylyltransferase and 5'-phosphatase | RNGTT |
| 216986_s_at | 1767 | 1088.9 | 1045.9 | 26.5 | 91 | interferon regulatory factor 4 | IRF4 |
| 201303_at | 11275.3 | 6684.6 | 4953 | 869.3 | 91 | DEAD (Asp-Glu-Ala-Asp) box polypeptide 48 | DDX48 |
| 211798_x_at | 3202.8 | 1844.7 | 2570.4 | 13 | 91 | immunoglobulin lambda joining 3 | IGLJ3 |
| 212985_at | 1998.5 | 948.9 | 1367.1 | 5 | 91 | Hypothetical protein FLJ14001 | FLJ14001 |
| 213593_s_at | 2902.3 | 1697.1 | 1429.1 | 15 | 91 | Transformer-2 alpha | TRA2A |

TABLE 2-continued

Probesets underexpressed in 25% of more of B-lineage ALL cases (n = 270) as compared to normal bone marrow CD19+CD10+ cells from 4 healthy donors

| probe set ID | CD10+ CD19+ max | CD10+ CD19+ min | ALL max | ALL min | % ALL under expressed | Title | Symbol |
|---|---|---|---|---|---|---|---|
| 216557_x_at | 4084.7 | 1926.7 | 9300.4 | 89.7 | 91 | immunoglobulin heavy constant alpha 1 /// immunoglobulin heavy constant gamma 1 /// immunoglobulin heavy constant gamma 3 | IGHA1 /// IGHG1 /// IGHG3 |
| 210693_at | 647 | 223.3 | 700.9 | 6.5 | 91 | signal peptide peptidase-like 2B | SPPL2B |
| 217360_x_at | 679 | 447.1 | 853.8 | 5.2 | 91 | immunoglobulin heavy constant alpha 1 /// immunoglobulin heavy constant gamma 1 /// immunoglobulin heavy constant gamma 3 | IGHA1 /// IGHG1 /// IGHG3 |
| 204440_at | 4557.9 | 1759.5 | 9729.2 | 47.8 | 91 | CD83 antigen (activated B lymphocytes, immunoglobulin superfamily) | CD83 |
| 203865_s_at | 2572.5 | 1405.4 | 3163.5 | 7.1 | 90 | adenosine deaminase, RNA-specific, B1 (RED1 homolog rat) | ADARB1 |
| 215121_x_at | 38082.2 | 24742.4 | 97827.3 | 411.9 | 90 | immunoglobulin lambda locus | IGL@ |
| 212942_s_at | 1062.1 | 467.7 | 871.1 | 6.3 | 90 | KIAA1199 | KIAA1199 |
| 204786_s_at | 1394.1 | 633.2 | 626.5 | 7.3 | 90 | interferon (alpha, beta and omega) receptor 2 | IFNAR2 |
| 210172_at | 2090.8 | 1430.9 | 2185.8 | 19.3 | 90 | splicing factor 1 | SF1 |
| 213511_s_at | 8132.9 | 5082.3 | 4143.4 | 404.6 | 90 | myotubularin related protein 1 | MTMR1 |
| 221985_at | 1969.6 | 1635.9 | 1694.5 | 229.7 | 90 | kelch-like 24 (*Drosophila*) | KLHL24 |
| 203751_x_at | 6801.2 | 2457.2 | 9483.9 | 3.2 | 89 | jun D proto-oncogene | JUND |
| 205466_s_at | 456.1 | 371.8 | 864.3 | 2.5 | 89 | heparan sulfate (glucosamine) 3-O-sulfotransferase 1 | HS3ST1 |
| 207993_s_at | 767.8 | 450 | 542.3 | 9 | 89 | calcium binding protein P22 | CHP |
| 208553_at | 538.7 | 230 | 415.9 | 5.2 | 89 | histone 1, H1e | HIST1H1E |
| 213638_at | 2518.5 | 972.3 | 1773.4 | 7.5 | 89 | phosphatase and actin regulator 1 | PHACTR1 |
| 202779_s_at | 4064.5 | 2660.1 | 7091.4 | 94 | 89 | ubiquitin-conjugating enzyme E2S | UBE2S |
| 212350_at | 4326.3 | 3443.9 | 2686.8 | 395.3 | 89 | TBC1 (tre-2/USP6, BUB2, cdc16) domain family, member 1 | TBC1D1 |
| 214777_at | 2535.8 | 914.1 | 3431.5 | 11 | 88 | Ig rearranged kappa-chain mRNA V-J1-region, hybridoma AE6-5, 5' end | — |
| 221909_at | 512.9 | 332.3 | 781.3 | 8.1 | 88 | hypothetical protein FLJ14627 | FLJ14627 |
| 216401_x_at | 2337.3 | 950.1 | 2657.3 | 16.9 | 87 | Ig rearranged kappa-chain mRNA V-J1-region, hybridoma AE6-5, 5' end /// Immunoglobulin kappa constant | LOC400969 /// IGKC |
| 219878_s_at | 867.1 | 176.2 | 962.9 | 4.9 | 87 | Kruppel-like factor 13 | KLF13 |
| 221807_s_at | 2186.5 | 1302.7 | 2491.7 | 10.9 | 87 | hypothetical protein PP2447 | PP2447 |
| 201668_x_at | 1020.2 | 570.7 | 1370.6 | 10.9 | 87 | myristoylated alanine-rich protein kinase C substrate | MARCKS |
| 203589_s_at | 901 | 779.9 | 1067.2 | 30.8 | 87 | transcription factor Dp-2 (E2F dimerization partner 2) | TFDP2 |
| 219202_at | 1964.6 | 1420.8 | 1763.9 | 17 | 87 | rhomboid, veinlet-like 6 (*Drosophila*) | RHBDL6 |
| 221969_at | 13313.2 | 10083.4 | 9494.5 | 125.3 | 87 | Paired box gene 5 (B-cell lineage specific activator) | PAX5 |
| 211649_x_at | 1586.1 | 762.4 | 1034 | 13.7 | 86 | Immunoglobulin heavy constant mu /// Immunoglobulin heavy constant mu | IGHM |
| 216095_x_at | 7254.6 | 3992.8 | 3149.7 | 298 | 86 | myotubularin related protein 1 | MTMR1 |
| 215379_x_at | 14893.2 | 7687.7 | 37246.9 | 354.3 | 86 | immunoglobulin lambda locus | IGL@ |
| 214326_x_at | 5238.4 | 1687 | 6719.1 | 4.4 | 86 | jun D proto-oncogene | JUND |
| 215907_at | 3754.8 | 2954.9 | 4524.6 | 76.9 | 86 | BTB and CNC homology 1, basic leucine zipper transcription factor 2 | BACH2 |
| 202409_at | 2262.9 | 492.3 | 35487.2 | 16.3 | 86 | putative insulin-like growth factor II associated protein | LOC492304 |
| 216560_x_at | 683.9 | 251.9 | 19290.6 | 10.3 | 86 | Immunoglobulin lambda constant 1 (Mcg marker) /// Immunoglobulin lambda joining 3 | IGLC1 /// IGLC2 |
| 204255_s_at | 1219.3 | 464.5 | 772 | 11.8 | 86 | vitamin D (1,25-dihydroxyvitamin D3) receptor | VDR |
| 205861_at | 6899.6 | 4313.1 | 13176.4 | 51.1 | 86 | Spi-B transcription factor (Spi-1/PU.1 related) /// Spi-B transcription factor (Spi-1/PU.1 related) | SPIB |
| 212451_at | 1861.4 | 829.1 | 774.2 | 27.7 | 86 | KIAA0256 gene product | KIAA0256 |
| 213998_s_at | 1316.7 | 735.7 | 2193 | 5.7 | 86 | DEAD (Asp-Glu-Ala-Asp) box polypeptide 17 | DDX17 |
| 214455_at | 1162.4 | 460.7 | 831.8 | 4.9 | 86 | histone 1, H2bc | HIST1H2BC |
| 213668_s_at | 1789.5 | 1185.1 | 4590.5 | 11.1 | 86 | SRY (sex determining region Y)-box 4 | SOX4 |
| 213575_at | 2193.8 | 846.7 | 1062.3 | 9.6 | 85 | Transformer-2 alpha | TRA2A |
| 216430_x_at | 248.7 | 105 | 730.6 | 7.1 | 85 | Immunoglobulin lambda chain variable region (IGVL gene)region, (IGL) | IGLV3-25 /// IGLC2 |
| 206641_at | 318.9 | 157 | 1268 | 4.5 | 85 | tumor necrosis factor receptor superfamily, member 17 | TNFRSF17 |
| 220319_s_at | 3796.9 | 2721.9 | 24534.1 | 150.8 | 85 | myosin regulatory light chain interacting protein | MYLIP |
| 201473_at | 5254.1 | 1979.2 | 4775.3 | 52 | 84 | jun B proto-oncogene | JUNB |
| 205805_s_at | 916.2 | 495.5 | 1461.5 | 5.1 | 84 | receptor tyrosine kinase-like orphan receptor 1 | ROR1 |
| 207521_s_at | 1861 | 1427.3 | 2469.7 | 5.6 | 84 | ATPase, Ca++ transporting, ubiquitous | ATP2A3 |
| 214911_s_at | 5800.8 | 3632.4 | 5237.4 | 190.2 | 84 | bromodomain containing 2 | BRD2 |
| 219752_at | 2390.6 | 1237.6 | 1756 | 18.2 | 84 | RAS protein activator like 1 (GAP1 like) | RASAL1 |
| 44790_s_at | 8505.4 | 3748.8 | 8257.3 | 6 | 84 | chromosome 13 open reading frame 18 | C13orf18 |
| 206478_at | 2360.6 | 1769.8 | 5876.1 | 86.6 | 84 | KIAA0125 | KIAA0125 |
| 210180_s_at | 2174.2 | 823.3 | 3334.9 | 9.1 | 84 | splicing factor, arginine/serine-rich 10 (transformer 2 homolog, *Drosophila*) | SFRS10 |
| 217677_at | 3478.3 | 922.5 | 920 | 20.2 | 84 | pleckstrin homology domain containing, family A (phosphoinositide binding specific) member 2 | PLEKHA2 |
| 221671_x_at | 31680.7 | 22551 | 62604.2 | 824.8 | 84 | immunoglobulin kappa constant /// immunoglobulin kappa variable 1-5 | IGKC /// IGKV1-5 |

TABLE 2-continued

Probesets underexpressed in 25% of more of B-lineage ALL cases (n = 270) as compared to normal bone marrow CD19+CD10+ cells from 4 healthy donors

| probe set ID | CD10+ CD19+ max | CD10+ CD19+ min | ALL max | ALL min | % ALL under expressed | Title | Symbol |
|---|---|---|---|---|---|---|---|
| 211644_x_at | 3855.6 | 1621.8 | 10586.8 | 15.6 | 84 | immunoglobulin kappa constant /// immunoglobulin kappa constant | IGKC |
| 203796_s_at | 1878.7 | 1512.3 | 1760.6 | 15 | 83 | B-cell CLL/lymphoma 7A | BCL7A |
| 209398_at | 16587.4 | 5879.3 | 9073.2 | 152.8 | 83 | histone 1, H1c | HIST1H1C |
| 214975_s_at | 2134.4 | 976.2 | 807.9 | 12.8 | 83 | myotubularin related protein 1 | MTMR1 |
| 216984_x_at | 2571.9 | 1074.1 | 61397.8 | 14.5 | 83 | Immunoglobulin lambda joining 3 | IGLC2 |
| 213811_x_at | 9733.6 | 8324.7 | 8071.6 | 756.7 | 83 | transcription factor 3 (E2A immunoglobulin enhancer binding factors E12/E47) | TCF3 |
| 214472_at | 2531.2 | 829.1 | 2678.5 | 4.6 | 83 | histone 1, H3d | HIST1H3D |
| 209457_at | 1335.3 | 711.6 | 3666.5 | 15.2 | 83 | dual specificity phosphatase 5 | DUSP5 |
| 203588_s_at | 1599.5 | 1292.4 | 3992.3 | 37.4 | 83 | transcription factor Dp-2 (E2F dimerization partner 2) | TFDP2 |
| 201022_s_at | 2376.3 | 1884.5 | 4537.8 | 55.5 | 83 | destrin (actin depolymerizing factor) | DSTN |
| 204642_at | 1707.9 | 798.1 | 1750.6 | 10.6 | 83 | endothelial differentiation, sphingolipid G-protein-coupled receptor, 1 | EDG1 |
| 221651_x_at | 33345.6 | 22787.2 | 65363 | 833.2 | 83 | immunoglobulin kappa constant /// immunoglobulin kappa variable 1-5 | IGKC /// IGKV1-5 |
| 205967_at | 35751.3 | 3512.1 | 6722.1 | 343.1 | 82 | histone 1, H4c | HIST1H4C |
| 209138_x_at | 29357.3 | 20677.1 | 73861.4 | 288.6 | 82 | Immunoglobulin lambda constant 1 (Mcg marker) /// Dehydrogenase/reductase (SDR family) member 4 like 2 /// Immunoglobulin lambda joining 3 | IGLV3-25 /// DHRS4 /// IGLC2 |
| 220377_at | 1115.8 | 527 | 2828.2 | 5.7 | 82 | chromosome 14 open reading frame 110 | C14orf110 |
| 201464_x_at | 6805.8 | 3623.8 | 8372.6 | 35.1 | 82 | v-jun sarcoma virus 17 oncogene homolog (avian) | JUN |
| 209558_s_at | 2068 | 1613.9 | 2686.7 | 18.5 | 82 | huntingtin interacting protein-1-related | HIP1R |
| 204254_s_at | 659.8 | 405.3 | 772.5 | 11.3 | 81 | vitamin D (1,25-dihydroxyvitamin D3) receptor | VDR |
| 217783_s_at | 13626.2 | 9959.4 | 22889.8 | 1046.7 | 81 | yippee-like 5 (*Drosophila*) | YPEL5 |
| 218611_at | 3234.4 | 2084.7 | 3865.9 | 198.3 | 81 | immediate early response 5 | IER5 |
| 201670_s_at | 1189.3 | 856.9 | 1989.8 | 3.5 | 81 | myristoylated alanine-rich protein kinase C substrate | MARCKS |
| 211641_x_at | 3555.3 | 1451.3 | 3293 | 36.3 | 81 | Isolate Middle91 immunoglobulin heavy chain variable region (IGVH) /// Isolate Middle91 immunoglobulin heavy chain variable region (IGVH) | — |
| 211643_x_at | 1996.9 | 1433.2 | 2681 | 50.1 | 81 | Immunoglobulin kappa variable 1-5 /// Immunoglobulin kappa variable 1-5 | IGKC |
| 211881_x_at | 2614.2 | 1336 | 2124.8 | 29.4 | 81 | immunoglobulin lambda joining 3 | IGLJ3 |
| 216365_x_at | 631.9 | 215.9 | 904.6 | 7.3 | 81 | Immunoglobulin lambda constant 1 (Mcg marker) | IGLV3-25 |
| 208995_at | 1294.9 | 882 | 2851.1 | 26.5 | 81 | titin | TTN |
| 214768_x_at | 1795.5 | 1077.9 | 8676.1 | 16.2 | 81 | (clone TR1.6VL) anti-thyroid peroxidase monoclonal autoantibody IgK chain, V region | — |
| 201466_s_at | 921.5 | 787.9 | 2738.4 | 9.6 | 81 | v-jun sarcoma virus 17 oncogene homolog (avian) | JUN |
| 221841_s_at | 2789.2 | 1790.6 | 11750.7 | 11.4 | 81 | Kruppel-like factor 4 (gut) | KLF4 |
| 216576_x_at | 1975.4 | 979.2 | 3352.2 | 16.5 | 81 | Immunoglobulin kappa light chain variable region (IGKV gene), clone 25 | — |
| 211655_at | 212 | 201.8 | 745.9 | 3.1 | 81 | Immunoglobulin lambda joining 3 | IGLC2 |
| 203973_s_at | 1408.8 | 859.5 | 4658 | 6.9 | 81 | CCAAT/enhancer binding protein (C/EBP), delta | CEBPD |
| 204315_s_at | 946.5 | 492.1 | 525.7 | 8.3 | 80 | G-2 and S-phase expressed 1 | GTSE1 |
| 222045_s_at | 857.3 | 586.8 | 1247.2 | 11.5 | 80 | chromosome 20 open reading frame 67 | C20orf67 |
| 201462_at | 414.5 | 295.2 | 1052.3 | 7.3 | 80 | secernin 1 | SCRN1 |
| 221766_s_at | 790.1 | 490.7 | 5906.6 | 5 | 80 | family with sequence similarity 46, member A | FAM46A |
| 208937_s_at | 968.9 | 404.1 | 1480.6 | 6.7 | 80 | inhibitor of DNA binding 1, dominant negative helix-loop-helix protein | ID1 |
| 209374_s_at | 37136 | 23220 | 48689.7 | 660.5 | 80 | immunoglobulin heavy constant mu | IGHM |
| 219517_at | 1979.2 | 948.8 | 1150.7 | 14.8 | 80 | elongation factor RNA polymerase II-like 3 | ELL3 |
| 214677_x_at | 32140.2 | 22901.4 | 67468.9 | 346.5 | 80 | immunoglobulin lambda locus | IGL@ |
| 211199_s_at | 334.7 | 174.5 | 751.5 | 5.8 | 80 | inducible T-cell co-stimulator ligand | ICOSLG |
| 210776_x_at | 13331.7 | 9144.1 | 9907.6 | 669.1 | 80 | transcription factor 3 (E2A immunoglobulin enhancer binding factors E12/E47) | TCF3 |
| 218473_s_at | 5608.8 | 4109.8 | 8071.4 | 522.8 | 80 | glycosyltransferase 25 domain containing 1 | GLT25D1 |
| 221239_s_at | 1531.7 | 693 | 3556 | 18 | 80 | Fc receptor-like 2 /// Fc receptor-like 2 | FCRL2 |
| 217258_x_at | 1046.5 | 523.9 | 4342.2 | 8.9 | 80 | Clone ds1-1 immunoglobulin lambda chain VJ region, (IGL) | — |
| 205148_s_at | 385.7 | 200.8 | 687.1 | 7 | 79 | chloride channel 4 | CLCN4 |
| 219463_at | 3214.4 | 1350.9 | 13373 | 14.1 | 79 | chromosome 20 open reading frame 103 | C20orf103 |
| 200920_s_at | 38532.8 | 16690.8 | 33740.6 | 861.8 | 79 | B-cell translocation gene 1, anti-proliferative | BTG1 |
| 216356_x_at | 631.4 | 390.7 | 536.4 | 12.7 | 79 | BAI1-associated protein 3 | BAIAP3 |
| 222044_at | 1249.2 | 664 | 2083.4 | 26.9 | 79 | — | — |
| 202946_s_at | 2248.1 | 1707.1 | 6129.4 | 60.2 | 79 | BTB (POZ) domain containing 3 | BTBD3 |
| 207038_at | 281.4 | 238.9 | 300.4 | 6.2 | 79 | solute carrier family 16 (monocarboxylic acid transporters), member 6 | SLC16A6 |
| 207237_at | 956.6 | 465.4 | 1294 | 12.3 | 79 | potassium voltage-gated channel, shaker-related subfamily, member 3 | KCNA3 |
| 217384_x_at | 612.4 | 304.7 | 911.3 | 4.8 | 79 | similar to immunoglobulin M chain | LOC388255 |
| 209324_s_at | 2041.9 | 708.8 | 6688.9 | 12.5 | 79 | regulator of G-protein signalling 16 | RGS16 |
| 204121_at | 408.3 | 367.7 | 1061.5 | 6 | 79 | growth arrest and DNA-damage-inducible, gamma | GADD45G |
| 203942_s_at | 361 | 171.6 | 475.7 | 4.3 | 78 | MAP/microtubule affinity-regulating kinase 2 | MARK2 |

TABLE 2-continued

Probesets underexpressed in 25% of more of B-lineage ALL cases (n = 270) as compared to normal bone marrow CD19+CD10+ cells from 4 healthy donors

| probe set ID | CD10+ CD19+ max | CD10+ CD19+ min | ALL max | ALL min | % ALL under expressed | Title | Symbol |
|---|---|---|---|---|---|---|---|
| 222313_at | 349.6 | 202.6 | 841.7 | 2.6 | 78 | CCR4-NOT transcription complex, subunit 2 | CNOT2 |
| 219978_s_at | 4662.1 | 2406.5 | 3581.7 | 46.1 | 78 | nucleolar and spindle associated protein 1 | NUSAP1 |
| 213931_at | 1964.2 | 1049.6 | 5069 | 8.8 | 78 | inhibitor of DNA binding 2, dominant negative helix-loop-helix protein /// inhibitor of DNA binding 2B, dominant negative helix-loop-helix protein | ID2 /// ID2B |
| 206394_at | 389.7 | 292.1 | 888.7 | 5.1 | 78 | myosin binding protein C, fast type | MYBPC2 |
| 202625_at | 2660.4 | 1441.8 | 2664.1 | 42.3 | 77 | v-yes-1 Yamaguchi sarcoma viral related oncogene homolog /// v-yes-1 Yamaguchi sarcoma viral related oncogene homolog | LYN |
| 209795_at | 7502.8 | 6458.6 | 16301.1 | 31.6 | 77 | CD69 antigen (p60, early T-cell activation antigen) | CD69 |
| 204165_at | 4862.1 | 2495.5 | 6203 | 70.3 | 77 | WAS protein family, member 1 | WASF1 |
| 219041_s_at | 5504.8 | 3685.5 | 4616.5 | 468.6 | 77 | replication initiator 1 | REPIN1 |
| 219471_at | 12565.2 | 5971.3 | 13508.4 | 33.2 | 77 | chromosome 13 open reading frame 18 | C13orf18 |
| 220066_at | 375.4 | 86.3 | 382.2 | 2.5 | 77 | caspase recruitment domain family, member 15 | CARD15 |
| 212575_at | 144.6 | 44.4 | 292.7 | 3.8 | 77 | chromosome 19 open reading frame 6 | C19orf6 |
| 212970_at | 2128.3 | 1091.9 | 1609.5 | 75.3 | 77 | Hypothetical protein FLJ14001 | FLJ14001 |
| 219518_s_at | 1488.3 | 893.3 | 1512 | 9.8 | 77 | elongation factor RNA polymerase II-like 3 | ELL3 |
| 222015_at | 633 | 193.6 | 914.6 | 21.6 | 77 | Casein kinase 1, epsilon | CSNK1E |
| 209579_s_at | 3990.3 | 2660.8 | 3384 | 170.6 | 76 | methyl-CpG binding domain protein 4 | MBD4 |
| 210024_s_at | 2119.7 | 1680.2 | 3640.3 | 12.3 | 76 | ubiquitin-conjugating enzyme E2E 3 (UBC4/5 homolog, yeast) | UBE2E3 |
| 216542_x_at | 2645.8 | 1678.4 | 2673.3 | 163.1 | 76 | immunoglobulin heavy constant gamma 1 (G1m marker) /// /// hypothetical protein MGC27165 | IGHG1 /// MGC27165 |
| 219396_s_at | 5460.4 | 2755.9 | 13298.1 | 16.4 | 76 | nei endonuclease VIII-like 1 (E. coli) | NEIL1 |
| 205413_at | 743.7 | 198.2 | 2539.4 | 1.6 | 76 | metallophosphoesterase domain containing 2 | MPPED2 |
| 204936_at | 372.7 | 152.6 | 479 | 8.4 | 76 | mitogen-activated protein kinase kinase kinase kinase 2 | MAP4K2 |
| 211640_x_at | 1068.2 | 595 | 957.6 | 5.2 | 76 | Immunoglobulin heavy variable 1-69 /// Immunoglobulin heavy variable 1-69 | IGHV1-69 |
| 219474_at | 738.5 | 237.1 | 669.4 | 4.3 | 76 | TPA-induced transmembrane protein | TTMP |
| 215918_s_at | 559.5 | 394.8 | 1953.4 | 7 | 76 | spectrin, beta, non-erythrocytic 1 | SPTBN1 |
| 208549_x_at | 18830.4 | 15231.4 | 27927.9 | 3006.9 | 75 | prothymosin, alpha | PTMA |
| 204004_at | 706.5 | 501.8 | 1864.2 | 8.2 | 75 | PRKC, apoptosis, WT1, regulator | PAWR |
| 212225_at | 5240.5 | 2651.9 | 5996.8 | 16.3 | 75 | eukaryotic translation initiation factor 1 | EIF1 |
| 209994_s_at | 625.3 | 379 | 769.6 | 6.1 | 74 | ATP-binding cassette, sub-family B (MDR/TAP), member 1 /// ATP-binding cassette, sub-family B (MDR/TAP), member 4 | ABCB1 /// ABCB4 |
| 204621_s_at | 690.7 | 254.2 | 6807.8 | 3.7 | 74 | nuclear receptor subfamily 4, group A, member 2 | NR4A2 |
| 203749_s_at | 1201.3 | 388.8 | 736.1 | 6.7 | 74 | retinoic acid receptor, alpha | RARA |
| 208610_s_at | 3729.1 | 1815 | 3999.5 | 60.7 | 74 | serine/arginine repetitive matrix 2 | SRRM2 |
| 210282_at | 261.2 | 213.2 | 366.3 | 1 | 74 | zinc finger protein 198 | ZNF198 |
| 214860_at | 430.9 | 222.1 | 490 | 4.6 | 74 | solute carrier family 9 (sodium/hydrogen exchanger), member 7 | SLC9A7 |
| 217227_x_at | 1602.6 | 756.2 | 2441.6 | 23 | 74 | Rearranged Humigla1L1 gene encoding IgG light chain | — |
| 201951_at | 279.8 | 226.8 | 738.3 | 2.9 | 74 | activated leukocyte cell adhesion molecule | ALCAM |
| 205692_s_at | 4324.2 | 2887.3 | 3686 | 27.6 | 74 | CD38 antigen (p45) | CD38 |
| 213986_s_at | 841.4 | 593.5 | 1076.9 | 4.5 | 74 | chromosome 19 open reading frame 6 | C19orf6 |
| 211634_x_at | 5224.7 | 1694.7 | 4720.7 | 20.3 | 73 | immunoglobulin heavy constant mu /// immunoglobulin heavy constant mu | IGHM |
| 81737_at | 646.3 | 446.2 | 770.6 | 7.4 | 73 | SLC7A5 pseudogene /// Hypothetical protein LOC440345 /// Homo sapiens, clone IMAGE: 4271781 | LOC388221 /// LOC440345 |
| 202083_s_at | 317.7 | 183.4 | 1605 | 2.4 | 73 | SEC14-like 1 (S. cerevisiae) | SEC14L1 |
| 219737_s_at | 11684.4 | 7378.1 | 14726.6 | 16.7 | 73 | protocadherin 9 | PCDH9 |
| 220719_at | 1481 | 469.5 | 797 | 6.9 | 73 | hypothetical protein FLJ13769 | FLJ13769 |
| 208785_s_at | 4134.8 | 3677.7 | 13593.6 | 594.9 | 73 | microtubule-associated protein 1 light chain 3 beta | MAP1LC3B |
| 209191_at | 2880.1 | 1467.9 | 6610.5 | 8.6 | 73 | tubulin, beta 6 | TUBB6 |
| 217148_x_at | 4052.1 | 2173.6 | 58163.1 | 58 | 73 | immunoglobulin lambda variable 2-14 | IGLV2-14 |
| 210130_s_at | 974.7 | 577.8 | 889.6 | 18.4 | 73 | transmembrane 7 superfamily member 2 | TM7SF2 |
| 213311_s_at | 1408 | 1130.2 | 1200.8 | 15.6 | 73 | KIAA1049 protein | KIAA1049 |
| 205484_at | 938.8 | 533 | 2842.4 | 25 | 73 | signaling threshold regulating transmembrane adaptor 1 | SIT1 |
| 218857_s_at | 1156.2 | 560.9 | 1331.2 | 15.2 | 72 | asparaginase like 1 | ASRGL1 |
| 219692_at | 551 | 246 | 718.4 | 9.5 | 72 | kringle containing transmembrane protein 2 | KREMEN2 |
| 201041_s_at | 31896.4 | 27090.3 | 35352.9 | 639.6 | 72 | dual specificity phosphatase 1 | DUSP1 |
| 201353_s_at | 1792.5 | 1125.4 | 1363.6 | 42.7 | 72 | bromodomain adjacent to zinc finger domain, 2A | BAZ2A |
| 209876_at | 1164.7 | 741.6 | 933.9 | 25.3 | 72 | G protein-coupled receptor kinase interactor 2 | GIT2 |
| 211908_x_at | 840.4 | 383.1 | 1279.8 | 10.5 | 72 | IgG heavy chain variable region (Vh26) /// IgG heavy chain variable region (Vh26) | — |
| 213309_at | 2887.6 | 2012.8 | 3909 | 51.6 | 72 | phospholipase C-like 2 | PLCL2 |
| 215176_x_at | 5352.9 | 2060.8 | 9753.4 | 29.7 | 72 | Immunoglobulin kappa light chain variable region (IGKV gene), clone 25 | — |
| 222158_s_at | 1538.1 | 1024.4 | 8371.1 | 33.7 | 72 | chromosome 1 open reading frame 121 | C1orf121 |
| 214696_at | 673.2 | 368 | 3256.6 | 4.3 | 72 | hypothetical protein MGC14376 | MGC14376 |
| 212886_at | 3206.4 | 1651.1 | 5457.4 | 89.7 | 71 | DKFZP434C171 protein | DKFZP434C171 |

TABLE 2-continued

Probesets underexpressed in 25% of more of B-lineage ALL cases (n = 270) as compared to normal bone marrow CD19+CD10+ cells from 4 healthy donors

| probe set ID | CD10+ CD19+ max | CD10+ CD19+ min | ALL max | ALL min | % ALL under expressed | Title | Symbol |
|---|---|---|---|---|---|---|---|
| 222145_at | 925.4 | 605.5 | 1445 | 7.4 | 71 | Hypothetical protein LOC440345 | LOC440345 |
| 215692_s_at | 715.3 | 222.9 | 1591.7 | 3.7 | 71 | metallophosphoesterase domain containing 2 | MPPED2 |
| 218319_at | 1039.6 | 480.7 | 2475.8 | 2.4 | 71 | pellino homolog 1 (*Drosophila*) | PELI1 |
| 201738_at | 4836.6 | 3578.5 | 6966.7 | 648.1 | 71 | translation factor sui1 homolog | GC20 |
| 202165_at | 1200.4 | 799.6 | 1456 | 40.8 | 71 | protein phosphatase 1, regulatory (inhibitor) subunit 2 | PPP1R2 |
| 202283_at | 2098.9 | 1138.5 | 3262.7 | 13.2 | 71 | serpin peptidase inhibitor, clade F (alpha-2 antiplasmin, pigment epithelium derived factor), member 1 | SERPINF1 |
| 208621_s_at | 4972.8 | 2805.7 | 15342.9 | 32.8 | 71 | villin 2 (ezrin) | VIL2 |
| 213394_at | 1188.9 | 875 | 6923.8 | 15.5 | 71 | mitogen activated protein kinase binding protein 1 | MAPKBP1 |
| 213718_at | 834.5 | 527.1 | 1336.4 | 14.3 | 70 | RNA binding motif protein 4 | RBM4 |
| 222258_s_at | 686 | 179 | 908.7 | 4.5 | 70 | SH3-domain binding protein 4 | SH3BP4 |
| 202241_at | 1454.6 | 748.6 | 2493.8 | 15.4 | 70 | tribbles homolog 1 (*Drosophila*) | TRIB1 |
| 208616_s_at | 10243.9 | 8059.6 | 9030.6 | 2120.1 | 70 | protein tyrosine phosphatase type IVA, member 2 | PTP4A2 |
| 210281_s_at | 603 | 419.9 | 1173.4 | 10.5 | 70 | zinc finger protein 198 | ZNF198 |
| 221755_at | 619.1 | 525.1 | 1257 | 7.8 | 70 | EH domain binding protein 1-like 1 | EHBP1L1 |
| 222315_at | 717.8 | 189.5 | 3569.7 | 7.5 | 70 | Potassium inwardly-rectifying channel, subfamily J, member 15 | KCNJ15 |
| 201961_s_at | 409.1 | 306.2 | 506 | 10.4 | 70 | ring finger protein 41 | RNF41 |
| 202864_s_at | 2177.6 | 1438.3 | 2327.6 | 71.3 | 70 | nuclear antigen Sp100 | SP100 |
| 204681_s_at | 1024.3 | 453.5 | 1395.2 | 8.1 | 70 | Rap guanine nucleotide exchange factor (GEF) 5 | RAPGEF5 |
| 208018_s_at | 4580.1 | 1787.4 | 3725.6 | 34.5 | 70 | hemopoietic cell kinase | HCK |
| 208078_s_at | 7552.5 | 1852.9 | 12086.4 | 22 | 70 | SNF1-like kinase /// SNF1-like kinase | SNF1LK |
| 211635_x_at | 5284 | 1353.9 | 4018.2 | 17.2 | 70 | Immunoglobulin heavy variable 1-69 /// Immunoglobulin heavy variable 1-69 | IGHV1-69 |
| 212827_at | 26342.6 | 20722.2 | 42899.7 | 451.6 | 70 | immunoglobulin heavy constant mu /// immunoglobulin heavy constant mu | IGHM |
| 91703_at | 987.4 | 806.9 | 1421.1 | 18.6 | 70 | EH domain binding protein 1-like 1 | EHBP1L1 |
| 202082_s_at | 736.6 | 531.1 | 1740.6 | 7.7 | 70 | SEC14-like 1 (*S. cerevisiae*) | SEC14L1 |
| 209711_at | 2282.7 | 1650.5 | 4802 | 123.6 | 70 | solute carrier family 35 (UDP-glucuronic acid/UDP-N-acetylgalactosamine dual transporter), member D1 | SLC35D1 |
| 209765_at | 1649 | 1006.1 | 1671.7 | 25 | 69 | ADAM metallopeptidase domain 19 (meltrin beta) | ADAM19 |
| 209189_at | 18298 | 8625.6 | 23154.4 | 27.1 | 69 | v-fos FBJ murine osteosarcoma viral oncogene homolog | FOS |
| 214836_x_at | 6042.5 | 2307.2 | 9640.9 | 95.8 | 69 | immunoglobulin kappa constant /// immunoglobulin kappa variable 1-5 | IGKC /// IGKV1-5 |
| 211645_x_at | 4806.7 | 1366.1 | 6733.2 | 32.1 | 69 | Immunoglobulin kappa light chain (IGKV) mRNA variable region, joining region, and constant region /// Immunoglobulin kappa light chain (IGKV) mRNA variable region, joining region, and constant region | — |
| 220046_s_at | 9791.7 | 5330.2 | 18566.8 | 700.8 | 69 | cyclin L1 | CCNL1 |
| 222067_x_at | 5113.8 | 2281.1 | 5150.2 | 71 | 69 | histone 1, H2bd | HIST1H2BD |
| 201739_at | 1031.8 | 566.7 | 15238.3 | 9.4 | 69 | serum/glucocorticoid regulated kinase | SGK |
| 201792_at | 3894.1 | 2225.8 | 6769.2 | 32.7 | 68 | AE binding protein 1 | AEBP1 |
| 213476_x_at | 4760.7 | 3613.7 | 8249 | 538.4 | 68 | tubulin, beta 3 | TUBB3 |
| 214290_s_at | 37691.1 | 15264.6 | 33965.1 | 608.2 | 68 | histone 2, H2aa | HIST2H2AA |
| 214708_at | 244.2 | 114.9 | 451.8 | 4.4 | 68 | syntrophin, beta 1 (dystrophin-associated protein A1, 59 kDa, basic component 1) | SNTB1 |
| 218612_s_at | 1028.2 | 575 | 970.5 | 27.3 | 68 | tumor suppressing subtransferable candidate 4 | TSSC4 |
| 218696_at | 3446.9 | 3255.1 | 8935 | 148.1 | 68 | eukaryotic translation initiation factor 2-alpha kinase 3 | EIF2AK3 |
| 200846_s_at | 6661.4 | 5681.8 | 8018 | 491.9 | 68 | protein phosphatase 1, catalytic subunit, alpha isoform | PPP1CA |
| 201392_s_at | 1306 | 739.6 | 1220.5 | 7 | 68 | insulin-like growth factor 2 receptor | IGF2R |
| 208576_at | 282.8 | 114.3 | 298.8 | 3.6 | 68 | histone 1, H3b | HIST1H3B |
| 204192_at | 13251.7 | 5624.7 | 10302.9 | 225.6 | 67 | CD37 antigen | CD37 |
| 208091_s_at | 4116.6 | 2073.2 | 3069.3 | 124.4 | 67 | EGFR-coamplified and overexpressed protein /// EGFR-coamplified and overexpressed protein | ECOP |
| 215214_at | 1058.7 | 400.8 | 17480.7 | 5 | 67 | Immunoglobulin lambda constant 1 (Mcg marker) /// Immunoglobulin lambda joining 3 | IGLV3-25 /// IGLC2 |
| 217378_x_at | 2616.1 | 1178.5 | 7662.5 | 21 | 67 | similar to Ig kappa chain precursor V region (orphon V108) - human (fragment) | LOC391427 |
| 207704_s_at | 1084.8 | 780.1 | 1241.6 | 15.7 | 67 | growth arrest-specific 7 | GAS7 |
| 218100_s_at | 1189.7 | 690.8 | 2508 | 51.4 | 67 | estrogen-related receptor beta like 1 | ESRRBL1 |
| 202147_s_at | 1318.9 | 508.9 | 1610.5 | 9.8 | 67 | interferon-related developmental regulator 1 | IFRD1 |
| 208727_s_at | 9260.1 | 1361 | 4138.1 | 45.2 | 67 | cell division cycle 42 (GTP binding protein, 25 kDa) | CDC42 |
| 216706_x_at | 207 | 79.7 | 368.5 | 6.9 | 67 | Active Ig mu-chain mRNA V-region (VDJ), 5' end, clone mu-11-8 | — |
| 219751_at | 310.6 | 231.6 | 420.2 | 5.3 | 67 | hypothetical protein FLJ21148 | FLJ21148 |
| 215092_s_at | 361.3 | 186.8 | 1137.8 | 11.4 | 67 | nuclear factor of activated T-cells 5, tonicity-responsive | NFAT5 |
| 219577_s_at | 1163.9 | 833.6 | 3119.6 | 54.9 | 67 | ATP-binding cassette, sub-family A (ABC1), member 7 | ABCA7 |
| 202733_at | 4530.6 | 1589.5 | 2513.1 | 12.8 | 66 | procollagen-proline, 2-oxoglutarate 4-dioxygenase (proline 4-hydroxylase), alpha polypeptide II | P4HA2 |
| 207819_s_at | 806.5 | 550.4 | 1100.7 | 8 | 66 | ATP-binding cassette, sub-family B (MDR/TAP), member 4 | ABCB4 |
| 211944_at | 1418.4 | 805 | 1310.1 | 17.6 | 66 | BAT2 domain containing 1 | BAT2D1 |
| 200702_s_at | 1386.6 | 561.8 | 1982.9 | 16.2 | 66 | DEAD (Asp-Glu-Ala-Asp) box polypeptide 24 | DDX24 |
| 203752_s_at | 21461.8 | 16988.4 | 36043.8 | 2627.2 | 66 | jun D proto-oncogene | JUND |

TABLE 2-continued

Probesets underexpressed in 25% of more of B-lineage ALL cases (n = 270) as compared to normal bone marrow CD19+CD10+ cells from 4 healthy donors

| probe set ID | CD10+ CD19+ max | CD10+ CD19+ min | ALL max | ALL min | % ALL under expressed | Title | Symbol |
|---|---|---|---|---|---|---|---|
| 210640_s_at | 260.5 | 106.6 | 2653.6 | 8.5 | 66 | G protein-coupled receptor 30 | GPR30 |
| 217320_at | 311.9 | 147.1 | 738.6 | 3.4 | 66 | Ig rearranged gamma-chain mRNA V-region, 5' end of cds (from clone S9P16) | — |
| 205780_at | 605.3 | 143 | 1884.3 | 6.7 | 66 | BCL2-interacting killer (apoptosis-inducing) | BIK |
| 202844_s_at | 853.6 | 453 | 685.1 | 11.7 | 66 | ralA binding protein 1 | RALBP1 |
| 217198_x_at | 779.9 | 452.7 | 1188.6 | 8.5 | 66 | immunoglobulin heavy locus /// immunoglobulin heavy constant delta /// immunoglobulin heavy constant gamma 1 (G1m marker) | IGH@ /// IGHD /// IGHG1 |
| 218404_at | 346 | 122.8 | 533.2 | 7.7 | 66 | sorting nexin 10 | SNX10 |
| 209372_x_at | 576.3 | 131.3 | 1377.7 | 9.4 | 66 | tubulin, beta 2 | TUBB2 |
| 202719_s_at | 545 | 356.5 | 1245.4 | 9.5 | 66 | testis derived transcript (3 LIM domains) | TES |
| 207535_s_at | 658.4 | 446.7 | 721.3 | 6.6 | 65 | nuclear factor of kappa light polypeptide gene enhancer in B-cells 2 (p49/p100) | NFKB2 |
| 208523_x_at | 1864.9 | 1135.7 | 2759 | 62.3 | 65 | histone 1, H2bi | HIST1H2BI |
| 210240_s_at | 3675.6 | 1394.4 | 1846.6 | 53.4 | 65 | cyclin-dependent kinase inhibitor 2D (p19, inhibits CDK4) | CDKN2D |
|  | 739.8 | 222 | 515.3 | 5.6 | 65 | immunoglobulin kappa constant /// similar to Ig kappa chain | IGKC /// LOC339562 |
| 216066_at | 391.6 | 229.2 | 542.8 | 11.9 | 65 | ATP-binding cassette, sub-family A (ABC1), member 1 | ABCA1 |
| 211226_at | 100.1 | 57.9 | 246.2 | 3.5 | 65 | galanin receptor 2 | GALR2 |
| 204215_at | 4073.8 | 3830.3 | 3926.3 | 401.2 | 64 | chromosome 7 open reading frame 23 | C7orf23 |
| 219341_at | 430.1 | 138.9 | 707.8 | 4.9 | 64 | ceroid-lipofuscinosis, neuronal 8 (epilepsy, progressive with mental retardation) | CLN8 |
| 220603_s_at | 1196.8 | 787.4 | 1233.3 | 44.1 | 64 | multiple C2-domains with two transmembrane regions 2 | MCTP2 |
| 201669_s_at | 1969.4 | 891 | 4075.8 | 3.3 | 64 | myristoylated alanine-rich protein kinase C substrate | MARCKS |
| 202819_s_at | 986.9 | 863.2 | 2552.4 | 30.6 | 64 | transcription elongation factor B (SIII), polypeptide 3 (110 kDa, elongin A) | TCEB3 |
| 201243_s_at | 300.7 | 171.1 | 474.3 | 8.1 | 64 | ATPase, Na+/K+ transporting, beta 1 polypeptide | ATP1B1 |
| 209154_at | 4487.1 | 1728.6 | 2541.9 | 178.4 | 64 | Tax1 (human T-cell leukemia virus type I) binding protein 3 | TAX1BP3 |
| 215946_x_at | 8832.4 | 6771.2 | 13320.6 | 297.3 | 64 | similar to omega protein | LOC91353 |
| 217179_x_at | 1514.4 | 959 | 1819.1 | 28.8 | 64 | (clone 9F2L) Ig rearranged L-chain mRNA V-region, 5' end | — |
| 201021_s_at | 1894.7 | 1359.4 | 4252.5 | 62.6 | 64 | destrin (actin depolymerizing factor) | DSTN |
| 204005_s_at | 231.6 | 143.2 | 471.2 | 1.6 | 64 | PRKC, apoptosis, WT1, regulator | PAWR |
| 217963_s_at | 1003.1 | 479 | 7490.1 | 17.3 | 64 | nerve growth factor receptor (TNFRSF16) associated protein 1 | NGFRAP1 |
| 201917_s_at | 2035.5 | 1564.9 | 2933.3 | 216.1 | 64 | solute carrier family 25, member 36 | SLC25A36 |
| 208490_x_at | 2965.2 | 2315 | 4156.3 | 66.3 | 64 | histone 1, H2bf | HIST1H2BF |
| 211868_x_at | 1153.8 | 685.2 | 2705.6 | 16.7 | 64 | immunoglobulin heavy constant alpha 1 /// immunoglobulin heavy constant gamma 1 (G1m marker) /// immunoglobulin heavy constant gamma 3 (G3m marker) | IGHA1 /// IGHG1 /// IGHG3 |
| 206865_at | 544.2 | 280.4 | 1736.8 | 8.4 | 64 | Harakiri, BCL2 interacting protein (contains only BH3 domain) | HRK |
| 202354_s_at | 635.7 | 559.8 | 888.1 | 10.2 | 63 | general transcription factor IIF, polypeptide 1, 74 kDa | GTF2F1 |
| 203505_at | 2678.1 | 1046.2 | 2299.6 | 7.7 | 63 | ATP-binding cassette, sub-family A (ABC1), member 1 | ABCA1 |
| 212574_x_at | 1371.7 | 942.9 | 1732.6 | 23.8 | 63 | chromosome 19 open reading frame 6 | C19orf6 |
| 212826_s_at | 19729.1 | 15012.9 | 19642.3 | 1648.1 | 63 | solute carrier family 25 (mitochondrial carrier; adenine nucleotide translocator), member 6 | SLC25A6 |
| 222024_s_at | 1582.5 | 1143.2 | 5119 | 28.3 | 63 | A kinase (PRKA) anchor protein 13 | AKAP13 |
| 202166_s_at | 2057.9 | 1473.3 | 1443 | 170.4 | 63 | protein phosphatase 1, regulatory (inhibitor) subunit 2 | PPP1R2 |
| 207492_at | 1232.9 | 853.9 | 975.7 | 44.3 | 63 | N-glycanase 1 | NGLY1 |
| 215777_at | 634.9 | 229.3 | 19107.3 | 4.6 | 63 | IgV lambda [human, chronic lymphocytic leukemia case P87, mRNA Partial Mutant, 237 nt] | — |
| 205734_s_at | 1450.1 | 47.1 | 593 | 2.8 | 62 | AF4/FMR2 family, member 3 | AFF3 |
| 208244_at | 651 | 427.8 | 885.3 | 13.6 | 62 | bone morphogenetic protein 3 (osteogenic) | BMP3 |
| 208685_x_at | 5013.2 | 3634.6 | 4652.7 | 168.3 | 62 | bromodomain containing 2 | BRD2 |
| 209020_at | 3058.3 | 1661.6 | 4878.3 | 377.5 | 62 | chromosome 20 open reading frame 111 | C20orf111 |
| 209761_s_at | 4503.7 | 3048.2 | 3929.8 | 514.6 | 62 | SP110 nuclear body protein | SP110 |
| 213002_at | 730.9 | 613.7 | 1010.8 | 24.9 | 62 | Myristoylated alanine-rich protein kinase C substrate | MARCKS |
| 215785_s_at | 6233.1 | 4436.7 | 6694.4 | 199.8 | 62 | cytoplasmic FMR1 interacting protein 2 | CYFIP2 |
| 216971_s_at | 371.8 | 154.2 | 741.3 | 4.4 | 62 | plectin 1, intermediate filament binding protein 500 kDa | PLEC1 |
| 38340_at | 3343.8 | 2368.3 | 4903.3 | 346.7 | 62 | huntingtin interacting protein-1-related | HIP1R |
| 202723_s_at | 6466.4 | 4219.6 | 17277.3 | 134 | 62 | forkhead box O1A (rhabdomyosarcoma) | FOXO1A |
| 201235_s_at | 2025.4 | 1288.6 | 2444 | 15.1 | 62 | BTG family, member 2 | BTG2 |
| 205655_at | 403.5 | 276.4 | 727.1 | 3.4 | 62 | Mdm4, transformed 3T3 cell double minute 4, p53 binding protein (mouse) | MDM4 |
| 219505_at | 2737.3 | 2243.7 | 4093.5 | 42.1 | 62 | cat eye syndrome chromosome region, candidate 1 | CECR1 |
| 215621_at | 1006.6 | 621.9 | 5610.5 | 9.2 | 62 | immunoglobulin heavy constant delta | IGHD |
| 200790_at | 8522.6 | 5203 | 11216.3 | 281.2 | 61 | ornithine decarboxylase 1 | ODC1 |
| 216541_x_at | 892.6 | 313.8 | 927.6 | 7 | 61 | immunoglobulin heavy constant gamma 1 /// immunoglobulin heavy constant gamma 3 | IGHG1 /// IGHG3 |
| 202503_s_at | 11012.2 | 8769.1 | 10879.3 | 475.6 | 61 | KIAA0101 | KIAA0101 |

TABLE 2-continued

Probesets underexpressed in 25% of more of B-lineage ALL cases (n = 270) as compared to normal bone marrow CD19+CD10+ cells from 4 healthy donors

| probe set ID | CD10+ CD19+ max | CD10+ CD19+ min | ALL max | ALL min | % ALL under expressed | Title | Symbol |
|---|---|---|---|---|---|---|---|
| 204081_at | 717.2 | 168.4 | 1091.9 | 14.4 | 61 | neurogranin (protein kinase C substrate, RC3) | NRGN |
| 207838_x_at | 981.8 | 649.4 | 1635 | 10.6 | 61 | pre-B-cell leukemia transcription factor interacting protein 1 | PBXIP1 |
| 209682_at | 2478.1 | 1025.2 | 2193.7 | 129.8 | 61 | Cas-Br-M (murine) ecotropic retroviral transforming sequence b | CBLB |
| 202773_s_at | 431.4 | 216.8 | 451.7 | 5.7 | 61 | splicing factor, arginine/serine-rich 8 (suppressor-of-white-apricot homolog, Drosophila) | SFRS8 |
| 214469_at | 1051.2 | 408.8 | 2077.8 | 6.9 | 61 | histone 1, H2ae | HIST1H2AE |
| 218302_at | 925.2 | 657.8 | 1130.3 | 10.9 | 61 | presenilin enhancer 2 homolog (C. elegans) | PSENEN |
| 201688_s_at | 2138.1 | 1206.6 | 7186 | 9 | 61 | tumor protein D52 | TPD52 |
| 204961_s_at | 2274 | 1590.8 | 2420.1 | 6.6 | 60 | neutrophil cytosolic factor 1 (47 kDa, chronic granulomatous disease, autosomal 1) | NCF1 |
| 208527_x_at | 2428.2 | 1698.4 | 3233.1 | 139.5 | 60 | histone 1, H2be | HIST1H2BE |
| 218280_x_at | 14912.4 | 4785.1 | 11736.4 | 394.9 | 60 | histone 2, H2aa | HIST2H2AA |
| 220085_at | 1071.5 | 318.2 | 880.2 | 5.2 | 60 | helicase, lymphoid-specific | HELLS |
| 215498_s_at | 5844.9 | 3004.3 | 21628.8 | 326.9 | 60 | mitogen-activated protein kinase kinase 3 /// mitogen-activated protein kinase kinase 3 | MAP2K3 |
| 204152_s_at | 1746.6 | 983.2 | 1317.7 | 9.3 | 60 | manic fringe homolog (Drosophila) | MFNG |
| 204790_at | 1686.5 | 945.9 | 2070.3 | 17.7 | 60 | SMAD, mothers against DPP homolog 7 (Drosophila) | SMAD7 |
| 210594_x_at | 1508.6 | 819.7 | 1369.8 | 61 | 60 | myelin protein zero-like 1 | MPZL1 |
| 212587_s_at | 7477.2 | 2952.5 | 8415.8 | 35.6 | 60 | protein tyrosine phosphatase, receptor type, C | PTPRC |
| 213015_at | 2233.4 | 966.7 | 1632.3 | 119.4 | 60 | Bobby sox homolog (Drosophila) | BBX |
| 215908_at | 637.4 | 160.6 | 619 | 6.2 | 60 | Membrane-associated ring finger (C3HC4) 6 | MARCH6 |
| 205666_at | 525.6 | 174.3 | 567.5 | 9.9 | 60 | flavin containing monooxygenase 1 | FMO1 |
| 209760_at | 6164.9 | 4460.5 | 9469.1 | 632 | 60 | KIAA0922 protein | KIAA0922 |
| 212487_at | 1468.3 | 1046.3 | 1280 | 61.7 | 60 | KIAA0553 protein | KIAA0553 |
| 214084_x_at | 2283.5 | 1604.9 | 2794.8 | 21.7 | 60 | neutrophil cytosolic factor 1 (47 kDa, chronic granulomatous disease, autosomal 1) | NCF1 |
| 216300_at | 400.9 | 157 | 421 | 6.3 | 60 | retinoic acid receptor, alpha | RARA |
| 216503_s_at | 373 | 304.1 | 446.9 | 10 | 60 | myeloid/lymphoid or mixed-lineage leukemia (trithorax homolog, Drosophila); translocated to, 10 | MLLT10 |
| 220369_at | 473.2 | 186.1 | 566.3 | 18.4 | 60 | KIAA2010 | KIAA2010 |
| 216853_x_at | 771.7 | 402.8 | 3033.3 | 17.9 | 60 | Immunoglobulin lambda joining 3 | IGLJ3 |
| 209318_x_at | 773.2 | 451.5 | 845.6 | 6.2 | 59 | pleiomorphic adenoma gene-like 1 | PLAGL1 |
| 217184_s_at | 719.1 | 381.7 | 1070.9 | 10.8 | 59 | leukocyte tyrosine kinase | LTK |
| 217975_at | 407.1 | 252.5 | 1308.6 | 5 | 59 | WW domain binding protein 5 | WBP5 |
| 201291_s_at | 4378.2 | 1215.3 | 2993.2 | 12.6 | 59 | topoisomerase (DNA) II alpha 170 kDa | TOP2A |
| 208900_s_at | 2917.2 | 890.6 | 2375.6 | 13.1 | 59 | topoisomerase (DNA) I | TOP1 |
| 215224_at | 345.8 | 184.4 | 398.1 | 7 | 59 | ribosomal protein L23 | RPL23 |
| 216027_at | 257.2 | 92.1 | 269.6 | 2.5 | 59 | thioredoxin domain containing 13 | TXNDC13 |
| 202768_at | 5278.9 | 656.8 | 12292.3 | 16 | 59 | FBJ murine osteosarcoma viral oncogene homolog B | FOSB |
| 201216_at | 10786 | 7362.1 | 9271.5 | 913.1 | 59 | endoplasmic reticulum protein 29 | ERP29 |
| 209715_at | 658.5 | 505.7 | 607 | 27 | 59 | chromobox homolog 5 (HP1 alpha homolog, Drosophila) | CBX5 |
| 221520_s_at | 1580.8 | 714 | 2876.9 | 23.1 | 59 | cell division cycle associated 8 | CDCA8 |
| 201690_s_at | 1828.9 | 1315 | 5834.8 | 18.5 | 59 | tumor protein D52 | TPD52 |
| 201890_at | 3517.3 | 1900 | 4008 | 18.4 | 58 | ribonucleotide reductase M2 polypeptide | RRM2 |
| 209204_at | 276.6 | 190.6 | 497.6 | 7 | 58 | LIM domain only 4 | LMO4 |
| 215589_at | 174.9 | 104.6 | 490.4 | 2.4 | 58 | SMAD specific E3 ubiquitin protein ligase 1 | SMURF1 |
| 216054_x_at | 1967 | 1230.6 | 11056.3 | 205 | 58 | myosin, light polypeptide 4, alkali; atrial, embryonic | MYL4 |
| 200917_s_at | 548.2 | 419.2 | 713 | 5.3 | 58 | signal recognition particle receptor ('docking protein') | SRPR |
| 202332_at | 2393.6 | 1053.4 | 1876.3 | 54.6 | 58 | casein kinase 1, epsilon | CSNK1E |
| 205548_s_at | 1716.9 | 1128.9 | 3271.5 | 10.1 | 58 | BTG family, member 3 | BTG3 |
| 205511_at | 431.6 | 250.6 | 588.5 | 4 | 57 | hypothetical protein FLJ10038 | FLJ10038 |
| 205735_s_at | 350.5 | 129.7 | 531.1 | 5.4 | 57 | AF4/FMR2 family, member 3 | AFF3 |
| 221234_s_at | 7856.5 | 4916.3 | 9481.5 | 67.1 | 57 | BTB and CNC homology 1, basic leucine zipper transcription factor 2 /// BTB and CNC homology 1, basic leucine zipper transcription factor 2 | BACH2 |
| 216905_s_at | 170.4 | 52.4 | 353.3 | 2.2 | 57 | suppression of tumorigenicity 14 (colon carcinoma, matriptase, epithin) | ST14 |
| 202340_x_at | 1678.5 | 281.2 | 5316.6 | 16.4 | 57 | nuclear receptor subfamily 4, group A, member 1 | NR4A1 |
| 215108_x_at | 104.7 | 27.2 | 980.8 | 1 | 57 | trinucleotide repeat containing 9 | TNRC9 |
| 220331_at | 469.3 | 340.8 | 1727.5 | 10.2 | 57 | cytochrome P450, family 46, subfamily A, polypeptide 1 | CYP46A1 |
| 210656_at | 195.3 | 105.3 | 313 | 2.4 | 57 | embryonic ectoderm development | EED |
| 210872_x_at | 1054.2 | 636.6 | 910.4 | 15.6 | 57 | growth arrest-specific 7 | GAS7 |
| 212430_at | 3874.3 | 2227.6 | 7014.2 | 368 | 57 | RNA-binding region (RNP1, RRM) containing 1 /// RNA-binding region (RNP1, RRM) containing 1 | RNPC1 |
| 213517_at | 1773.3 | 845.4 | 1174.7 | 110.1 | 57 | Poly(rC) binding protein 2 | PCBP2 |
| 215925_s_at | 4238.1 | 1888.1 | 4968.5 | 9.1 | 57 | CD72 antigen | CD72 |
| 203725_at | 1583.5 | 1262.3 | 6711.6 | 30.6 | 57 | growth arrest and DNA-damage-inducible, alpha | GADD45A |
| 212113_at | 899.1 | 423.6 | 830.4 | 18.9 | 56 | hypothetical LOC552889 | LOC552889 |
| 213502_x_at | 10063.7 | 7408.9 | 8939.7 | 480.7 | 56 | similar to bK246H3.1 (immunoglobulin lambda-like polypeptide 1, pre-B-cell specific) | LOC91316 |
| 215078_at | 455.7 | 188.4 | 853.5 | 4.3 | 56 | superoxide dismutase 2, mitochondrial | SOD2 |
| 216969_s_at | 816.1 | 494 | 706.4 | 7.2 | 56 | kinesin family member 22 | KIF22 |

TABLE 2-continued

Probesets underexpressed in 25% of more of B-lineage ALL cases (n = 270) as compared to normal bone marrow CD19+CD10+ cells from 4 healthy donors

| probe set ID | CD10+ CD19+ max | CD10+ CD19+ min | ALL max | ALL min | % ALL under expressed | Title | Symbol |
|---|---|---|---|---|---|---|---|
| 203290_at | 583.9 | 388.9 | 21095.6 | 8.8 | 56 | major histocompatibility complex, class II, DQ alpha 1 /// major histocompatibility complex, class II, DQ alpha 1 | HLA-DQA1 |
| 218002_s_at | 198.9 | 94 | 1519.6 | 3.1 | 56 | chemokine (C—X—C motif) ligand 14 | CXCL14 |
| 212130_x_at | 31870.8 | 22675.5 | 92658.7 | 4959.1 | 56 | eukaryotic translation initiation factor 1 | EIF1 |
| 212016_s_at | 2144.1 | 2025.9 | 3775 | 76.9 | 56 | polypyrimidine tract binding protein 1 | PTBP1 |
| 216997_x_at | 1772.9 | 1068.2 | 5808.1 | 4.3 | 56 | transducin-like enhancer of split 4 (E(sp1) homolog, Drosophila) | TLE4 |
| 210088_x_at | 1798.2 | 1214.6 | 12113 | 204 | 56 | myosin, light polypeptide 4, alkali; atrial, embryonic | MYL4 |
| 205347_s_at | 1244.6 | 606 | 5245.4 | 39.6 | 56 | thymosin-like 8 | TMSL8 |
| 201876_at | 484.2 | 398.4 | 5375.3 | 7.9 | 56 | paraoxonase 2 | PON2 |
| 206459_s_at | 211.3 | 121.1 | 330.1 | 8.5 | 55 | wingless-type MMTV integration site family, member 2B | WNT2B |
| 206555_s_at | 2931.4 | 1311.7 | 1416.1 | 161.1 | 55 | THUMP domain containing 1 | THUMPD1 |
| 208702_x_at | 2780.2 | 2063.1 | 4542.2 | 112.7 | 55 | amyloid beta (A4) precursor-like protein 2 | APLP2 |
| 215513_at | 257.1 | 198.6 | 438.5 | 9 | 55 | hydatidiform mole associated and imprinted | HYMAI |
| 215635_at | 149.7 | 90.2 | 256.5 | 1.1 | 55 | Phosphodiesterase 8A | PDE8A |
| 219437_s_at | 1153.5 | 478.4 | 1406 | 14.9 | 55 | ankyrin repeat domain 11 | ANKRD11 |
| 208960_s_at | 3772.2 | 1315.2 | 23071.2 | 15.1 | 55 | Kruppel-like factor 6 | KLF6 |
| 203037_s_at | 3407.9 | 1492.7 | 5965.9 | 63.7 | 55 | metastasis suppressor 1 | MTSS1 |
| 205449_at | 708.6 | 491.6 | 845.1 | 8 | 55 | SAC3 domain containing 1 | SAC3D1 |
| 208615_s_at | 4008.2 | 2618.2 | 3219.2 | 469.2 | 55 | protein tyrosine phosphatase type IVA, member 2 | PTP4A2 |
| 217591_at | 922.4 | 388 | 1491 | 11.9 | 55 | SKI-like | SKIL |
| 222238_s_at | 700.1 | 271.8 | 1836.4 | 12.1 | 55 | polymerase (DNA directed), mu | POLM |
| 218856_at | 2635.9 | 933.8 | 6067.9 | 16.2 | 55 | tumor necrosis factor receptor superfamily, member 21 | TNFRSF21 |
| 201996_s_at | 1068.9 | 397.4 | 809.9 | 12.1 | 54 | spen homolog, transcriptional regulator (Drosophila) | SPEN |
| 209069_s_at | 36623.3 | 24646.6 | 44984.8 | 3477.8 | 54 | H3 histone, family 3B (H3.3B) | H3F3B |
| 209262_s_at | 502.8 | 224.7 | 533.8 | 9.3 | 54 | nuclear receptor subfamily 2, group F, member 6 | NR2F6 |
| 213730_x_at | 5090.4 | 3880.5 | 4655.5 | 407.8 | 54 | transcription factor 3 (E2A immunoglobulin enhancer binding factors E12/E47) | TCF3 |
| 213742_at | 887.4 | 515.1 | 1080.7 | 24.7 | 54 | splicing factor, arginine/serine-rich 11 | SFRS11 |
| 221586_s_at | 766.3 | 451.4 | 862.6 | 4.3 | 54 | E2F transcription factor 5, p130-binding | E2F5 |
| 209773_s_at | 4102.1 | 2963.2 | 9386.6 | 273.9 | 54 | ribonucleotide reductase M2 polypeptide | RRM2 |
| 205931_s_at | 126.3 | 78.6 | 567.7 | 5.1 | 54 | cAMP responsive element binding protein 5 | CREB5 |
| 215223_s_at | 1802.3 | 683.2 | 13374.5 | 24.7 | 54 | superoxide dismutase 2, mitochondrial | SOD2 |
| 212094_at | 298.8 | 175.7 | 14501.7 | 3.3 | 54 | paternally expressed 10 | PEG10 |
| 204794_at | 978.6 | 131 | 765.5 | 9.1 | 54 | dual specificity phosphatase 2 | DUSP2 |
| 207186_s_at | 3198.9 | 2048.3 | 3694.6 | 175.4 | 54 | fetal Alzheimer antigen | FALZ |
| 208515_at | 273.2 | 147.1 | 314.1 | 2.7 | 54 | histone 1, H2bm | HIST1H2BM |
| 216278_at | 693.4 | 224.7 | 773.7 | 8.1 | 54 | KIAA0256 gene product | KIAA0256 |
| 201689_s_at | 1240 | 836.8 | 3977.5 | 5.6 | 54 | tumor protein D52 | TPD52 |
| 208547_at | 214.9 | 70.7 | 717.9 | 4.1 | 54 | histone 1, H2bb | HIST1H2BB |
| 202021_x_at | 31691.4 | 21494.5 | 85265.8 | 4111 | 54 | eukaryotic translation initiation factor 1 | EIF1 |
| 211789_s_at | 1245.2 | 392.4 | 2084.4 | 3.9 | 54 | MondoA | MONDOA |
| 216211_at | 706.9 | 446.7 | 969.5 | 4.1 | 54 | Chromosome 10 open reading frame 18 | C10orf18 |
| 216855_s_at | 762.9 | 453.7 | 745.5 | 9.6 | 54 | heterogeneous nuclear ribonucleoprotein U (scaffold attachment factor A) | HNRPU |
| 217729_s_at | 4929.7 | 2647.3 | 3119.9 | 82.2 | 54 | amino-terminal enhancer of split | AES |
| 205398_s_at | 853.6 | 471.2 | 2255.6 | 15.6 | 54 | SMAD, mothers against DPP homolog 3 (Drosophila) | SMAD3 |
| 219582_at | 1125.1 | 657.8 | 2626.9 | 26 | 54 | opioid growth factor receptor-like 1 | OGFRL1 |
| 221658_s_at | 346.4 | 188.1 | 872.7 | 10.9 | 54 | interleukin 21 receptor | IL21R |
| 201101_s_at | 3208.5 | 2063.6 | 5635 | 67 | 53 | BCL2-associated transcription factor 1 | BCLAF1 |
| 209759_s_at | 615.2 | 547.2 | 916.5 | 19.2 | 53 | dodecenoyl-Coenzyme A delta isomerase (3,2 trans-enoyl-Coenzyme A isomerase) | DCI |
| 213134_x_at | 2196 | 1367.7 | 3628.9 | 34.2 | 53 | BTG family, member 3 | BTG3 |
| 213973_at | 550.6 | 326.5 | 905.3 | 23 | 53 | ribosome binding protein 1 homolog 180 kDa (dog) | RRBP1 |
| 218247_s_at | 1742.4 | 1256.3 | 2236.9 | 23.3 | 53 | ring finger and KH domain containing 2 | RKHD2 |
| 220084_at | 64.6 | 18.9 | 377.2 | 0.9 | 53 | chromosome 14 open reading frame 105 | C14orf105 |
| 205020_s_at | 673.7 | 395.9 | 7567.1 | 10.8 | 53 | ADP-ribosylation factor-like 4 | ARL4 |
| 203431_s_at | 811.1 | 664 | 1444.9 | 5 | 53 | Rho GTPase-activating protein | RICS |
| 203647_s_at | 1905.8 | 1751.4 | 2621.7 | 99.7 | 53 | ferredoxin 1 | FDX1 |
| 206967_at | 509.1 | 418.5 | 824.2 | 16.3 | 53 | cyclin T1 | CCNT1 |
| 211067_s_at | 1610.4 | 1150.4 | 2029.1 | 14.7 | 53 | growth arrest-specific 7 /// growth arrest-specific 7 | GAS7 |
| 219079_at | 1986.5 | 1349.2 | 2656.9 | 282.9 | 53 | cytochrome b5 reductase 4 | CYB5R4 |
| 200796_s_at | 824.2 | 351.7 | 2316.3 | 7.2 | 53 | myeloid cell leukemia sequence 1 (BCL2-related) | MCL1 |
| 206885_x_at | 754.9 | 476.8 | 2066.3 | 16.3 | 53 | growth hormone 1 | GH1 |
| 215499_at | 3466.8 | 2239.5 | 12058.5 | 356.5 | 53 | mitogen-activated protein kinase kinase 3 /// mitogen-activated protein kinase kinase 3 | MAP2K3 |
| 209774_x_at | 167.5 | 75.2 | 481.9 | 5.5 | 53 | chemokine (C—X—C motif) ligand 2 | CXCL2 |
| 210830_s_at | 331 | 242.4 | 5046.2 | 7.2 | 53 | paraoxonase 2 | HIST4PON2 |
| 208580_x_at | 822 | 213.3 | 1069.5 | 7.8 | 53 | histone 1, H4k /// histone 1, H4j | HIST1H4J |
| 210450_at | 1833.4 | 612.6 | 1191.4 | 5.2 | 53 | hypothetical protein LOC90925 | LOC90925 |
| 213649_at | 5388.1 | 2999.2 | 6475.2 | 472.9 | 53 | splicing factor, arginine/serine-rich 7, 35 kDa | SFRS7 |
| 220012_at | 781.5 | 388.1 | 895 | 12.3 | 53 | ERO1-like beta (S. cerevisiae) | ERO1LB |

TABLE 2-continued

Probesets underexpressed in 25% of more of B-lineage ALL cases (n = 270) as compared to normal bone marrow CD19+CD10+ cells from 4 healthy donors

| probe set ID | CD10+ CD19+ max | CD10+ CD19+ min | ALL max | ALL min | % ALL under expressed | Title | Symbol |
|---|---|---|---|---|---|---|---|
| 201502_s_at | 17163.8 | 10773.5 | 46569.3 | 853.9 | 53 | nuclear factor of kappa light polypeptide gene enhancer in B-cells inhibitor, alpha | NFKBIA |
| 202818_s_at | 1643 | 1085.6 | 4783.7 | 230.2 | 53 | transcription elongation factor B (SIII), polypeptide 3 (110 kDa, elongin A) | TCEB3 |
| 214007_s_at | 517.6 | 394.4 | 1224.7 | 16.4 | 53 | PTK9 protein tyrosine kinase 9 | PTK9 |
| 219057_at | 364 | 227.5 | 767.7 | 21.2 | 53 | rabaptin, RAB GTPase binding effector protein 2 | RABEP2 |
| 213566_at | 684.1 | 410.2 | 4352.6 | 6.8 | 53 | ribonuclease, RNase A family, k6 /// ribonuclease, RNase A family, k6 | RNASE6 |
| 201242_s_at | 194.3 | 113.3 | 318.9 | 2 | 52 | ATPase, Na+/K+ transporting, beta 1 polypeptide | ATP1B1 |
| 213042_s_at | 1042.3 | 539.7 | 1179.2 | 4.5 | 52 | ATPase, Ca++ transporting, ubiquitous | ATP2A3 |
| 214095_at | 257.5 | 138.9 | 356.9 | 7.2 | 52 | serine hydroxymethyltransferase 2 (mitochondrial) | SHMT2 |
| 219555_s_at | 830 | 381.5 | 1573.2 | 14 | 52 | uncharacterized bone marrow protein BM039 | BM039 |
| 217276_x_at | 863.2 | 308.8 | 1969.2 | 9.4 | 52 | serine hydrolase-like 2 | SERHL2 |
| 204141_at | 1257.3 | 269.4 | 15893 | 2.8 | 52 | tubulin, beta 2 | TUBB2 |
| 203504_s_at | 1918.4 | 1199.3 | 2847.2 | 124.2 | 52 | ATP-binding cassette, sub-family A (ABC1), member 1 | ABCA1 |
| 208930_s_at | 2787.7 | 728.6 | 3337.9 | 10.9 | 52 | interleukin enhancer binding factor 3, 90 kDa | ILF3 |
| 209088_s_at | 1844.7 | 948.9 | 2377.1 | 140.9 | 52 | ubinuclein 1 | UBN1 |
| 211899_s_at | 588.9 | 278.8 | 1062.4 | 11.9 | 52 | TNF receptor-associated factor 4 | TRAF4 |
| 214308_s_at | 241.8 | 183.2 | 350.9 | 11.2 | 52 | homogentisate 1,2-dioxygenase (homogentisate oxidase) | HGD |
| 219179_at | 562.2 | 418 | 933.6 | 4.7 | 52 | dapper, antagonist of beta-catenin, homolog 1 (*Xenopus laevis*) | DACT1 |
| 213345_at | 540.7 | 335.9 | 1086.5 | 12.4 | 52 | nuclear factor of activated T-cells, cytoplasmic, calcineurin-dependent 4 | NFATC4 |
| 216248_s_at | 910.5 | 287.2 | 10463.2 | 5 | 52 | nuclear receptor subfamily 4, group A, member 2 | NR4A2 |
| 210395_x_at | 2016.7 | 1139 | 13375.5 | 213.8 | 52 | myosin, light polypeptide 4, alkali; atrial, embryonic | MYL4 |
| 211138_s_at | 1347.3 | 650.6 | 2154.6 | 40.2 | 51 | kynurenine 3-monooxygenase (kynurenine 3-hydroxylase) | KMO |
| 215392_at | 411.6 | 224.1 | 466 | 1.2 | 51 | Multiple inositol polyphosphate histidine phosphatase, 1 | MINPP1 |
| 215623_x_at | 607.6 | 323.7 | 813.1 | 5.5 | 51 | SMC4 structural maintenance of chromosomes 4-like 1 (yeast) | SMC4L1 |
| 218033_s_at | 461.4 | 291.7 | 498.6 | 14.3 | 51 | stannin | SNN |
| 214464_at | 199.1 | 35.8 | 733.4 | 2.9 | 51 | CDC42 binding protein kinase alpha (DMPK-like) | CDC42BPA |
| 216373_at | 190.6 | 96.3 | 404.2 | 1.2 | 51 | Hypothetical protein FLJ90013 | FLJ90013 |
| 200712_s_at | 2609.1 | 2080.3 | 3286.1 | 434.4 | 51 | microtubule-associated protein, RP/EB family, member 1 | MAPRE1 |
| 203919_at | 814.8 | 488.1 | 776.7 | 5.8 | 51 | transcription elongation factor A (SII), 2 | TCEA2 |
| 209750_at | 673.3 | 407.6 | 807.5 | 22.5 | 51 | nuclear receptor subfamily 1, group D, member 2 | NR1D2 |
| 212774_at | 5871.1 | 4225.9 | 6384.8 | 284.6 | 51 | zinc finger protein 238 | ZNF238 |
| 218260_at | 865.6 | 711.6 | 2892 | 20.5 | 51 | cross-immune reaction antigen PCIA1 | PCIA1 |
| 205671_s_at | 689 | 503.6 | 2229.6 | 8.3 | 51 | major histocompatibility complex, class II, DO beta | HLA-DOB |
| 201846_s_at | 2714 | 1876.5 | 4890.4 | 179.1 | 51 | RING1 and YY1 binding protein | RYBP |
| 202076_at | 2724 | 2258.9 | 4525.3 | 417.2 | 51 | baculoviral IAP repeat-containing 2 | BIRC2 |
| 202782_s_at | 2320.6 | 1102 | 1432.9 | 118.5 | 51 | skeletal muscle and kidney enriched inositol phosphatase | SKIP |
| 208077_at | 930.8 | 569.3 | 1293.3 | 14.6 | 51 | chromosome 9 open reading frame 38 | C9orf38 |
| 215188_at | 589.7 | 221 | 424.2 | 4.9 | 51 | serine/threonine kinase 24 (STE20 homolog, yeast) | STK24 |
| 218811_at | 699.2 | 349.3 | 916.1 | 7.5 | 51 | chromosome 7 open reading frame 19 | C7orf19 |
| 220937_s_at | 1450 | 620.9 | 2138.9 | 14.3 | 51 | ST6 (alpha-N-acetyl-neuraminyl-2,3-beta-galactosyl-1,3)-N-acetylgalactosaminide alpha-2,6-sialyltransferase 4 | ST6GALNAC4 |
| 203243_s_at | 262.6 | 108.2 | 615.8 | 1.5 | 51 | PDZ and LIM domain 5 | PDLIM5 |
| 221551_x_at | 987.7 | 682.4 | 2015.3 | 21.6 | 51 | ST6 (alpha-N-acetyl-neuraminyl-2,3-beta-galactosyl-1,3)-N-acetylgalactosaminide alpha-2,6-sialyltransferase 4 | ST6GALNAC4 |
| 217234_s_at | 7979 | 3102 | 19092.8 | 29.1 | 51 | villin 2 (ezrin) | VIL2 |
| 208069_x_at | 577.9 | 384.2 | 1644.2 | 10.1 | 51 | chorionic somatomammotropin hormone 1 (placental lactogen) /// chorionic somatomammotropin hormone 2 /// chorionic somatomammotropin hormone-like 1 /// growth hormone 1 /// growth hormone 2 | CSH1 /// CSH2 /// CSHL1 /// GH1 /// GH2 |
| 200648_s_at | 1761.8 | 951.5 | 5262.9 | 3 | 51 | glutamate-ammonia ligase (glutamine synthetase) | GLUL |
| 210889_s_at | 343.6 | 180 | 1849.1 | 7.1 | 51 | Fc fragment of IgG, low affinity IIb, receptor (CD32) | FCGR2B |
| 203628_at | 410.3 | 208.3 | 1386.3 | 5.2 | 51 | insulin-like growth factor 1 receptor | IGF1R |
| 201793_x_at | 690.1 | 311.4 | 855.6 | 12.2 | 50 | chromosome 1 open reading frame 16 | C1orf16 |
| 215357_s_at | 706.9 | 619 | 983.5 | 23.8 | 50 | polymerase (DNA-directed), delta interacting protein 3 | POLDIP3 |
| 201925_s_at | 1190.3 | 834.1 | 2621.5 | 29 | 50 | decay accelerating factor for complement (CD55, Cromer blood group system) | DAF |
| 213747_at | 217.4 | 155.9 | 505.8 | 5.6 | 50 | — | — |
| 213122_at | 1063.1 | 507 | 4660.5 | 12.5 | 50 | TSPY-like 5 | TSPYL5 |
| 200783_s_at | 3283.3 | 2555.7 | 3636.6 | 276.3 | 50 | stathmin 1/oncoprotein 18 | STMN1 |
| 209713_s_at | 309.2 | 247.8 | 624.8 | 8.5 | 50 | solute carrier family 35 (UDP-glucuronic acid/UDP-N-acetylgalactosamine dual transporter), member D1 | SLC35D1 |
| 206675_s_at | 117.8 | 82.7 | 259.1 | 2 | 50 | SKI-like | SKIL |
| 205397_x_at | 380.7 | 98.7 | 1241 | 10.8 | 50 | SMAD, mothers against DPP homolog 3 (*Drosophila*) | SMAD3 |
| 209151_x_at | 1522.5 | 934.4 | 1986 | 8 | 50 | transcription factor 3 (E2A immunoglobulin enhancer binding factors E12/E47) | TCF3 |
| 218724_s_at | 1079.1 | 581.3 | 1009.7 | 20.5 | 50 | TGFB-induced factor 2 (TALE family homeobox) | TGIF2 |
| 219990_at | 521.6 | 393.4 | 1001 | 5.4 | 50 | E2F transcription factor 8 | E2F8 |

TABLE 2-continued

Probesets underexpressed in 25% of more of B-lineage ALL cases (n = 270) as compared to normal bone marrow CD19+CD10+ cells from 4 healthy donors

| probe set ID | CD10+ CD19+ max | CD10+ CD19+ min | ALL max | ALL min | % ALL under expressed | Title | Symbol |
|---|---|---|---|---|---|---|---|
| 216412_x_at | 475 | 198.6 | 1291.7 | 9.7 | 50 | Clone ds1-1 immunoglobulin lambda chain VJ region, (IGL) | — |
| 202393_s_at | 3382 | 1512.9 | 8593.5 | 160.2 | 50 | Kruppel-like factor 10 | KLF10 |
| 214826_at | 216.5 | 166.3 | 473.3 | 6 | 50 | 2'-phosphodiesterase | 2'-PDE |
| 202464_s_at | 625.6 | 494.3 | 4013.6 | 9 | 50 | 6-phosphofructo-2-kinase/fructose-2,6-biphosphatase 3 | PFKFB3 |
| 206195_x_at | 230 | 164.5 | 436.5 | 8.5 | 49 | growth hormone 2 | GH2 |
| 210448_s_at | 6937.5 | 1830 | 13603.4 | 33.3 | 49 | purinergic receptor P2X, ligand-gated ion channel, 5 | P2RX5 |
| 214516_at | 260 | 99.8 | 440.2 | 4.6 | 49 | histone 1, H4b | HIST1H4B |
| 207106_s_at | 519.4 | 285.3 | 1063.1 | 6.8 | 49 | leukocyte tyrosine kinase | LTK |
| 208046_at | 274 | 104.8 | 701.7 | 7.9 | 49 | histone 1, H4a | HIST1H4A |
| 215284_at | 406.3 | 296.3 | 1224.3 | 7.9 | 49 | Sorting nexin 9 | SNX9 |
| 204285_s_at | 3741 | 3031.1 | 25815.9 | 127.7 | 49 | phorbol-12-myristate-13-acetate-induced protein 1 | PMAIP1 |
| 201499_s_at | 6299 | 4419.1 | 7502.7 | 892.6 | 49 | ubiquitin specific peptidase 7 (herpes virus-associated) | USP7 |
| 202240_at | 964.4 | 607.7 | 1358.9 | 23.8 | 49 | polo-like kinase 1 (Drosophila) | PLK1 |
| 213887_s_at | 1776 | 1213.9 | 1430.7 | 56.8 | 49 | polymerase (RNA) II (DNA directed) polypeptide E, 25 kDa | POLR2E |
| 214056_at | 550.7 | 294.7 | 690.3 | 7.3 | 49 | Myeloid cell leukemia sequence 1 (BCL2-related) | MCL1 |
| 217230_at | 471.6 | 59.2 | 695.4 | 7 | 49 | villin 2 (ezrin) | VIL2 |
| 203391_at | 497.4 | 170.6 | 1012.4 | 17.2 | 49 | FK506 binding protein 2, 13 kDa | FKBP2 |
| 219681_s_at | 487.9 | 328.9 | 1101 | 4.4 | 49 | RAB11 family interacting protein 1 (class I) | RAB11FIP1 |
| 210387_at | 3080.5 | 1587.3 | 7883.1 | 12.2 | 49 | histone 1, H2bg | HIST1H2BG |
| 219839_x_at | 442.9 | 211.3 | 1486.8 | 7.6 | 49 | T-cell leukemia/lymphoma 1B /// T-cell leukemia/lymphoma 6 | TCL1B /// TCL6 |
| 206413_s_at | 1611.3 | 892.6 | 34444.7 | 23.8 | 49 | T-cell leukemia/lymphoma 1B /// T-cell leukemia/lymphoma 6 | TCL1B /// TCL6 |
| 208546_x_at | 1652.9 | 954.3 | 1981.3 | 32.4 | 49 | histone 1, H2bh | HIST1H2BH |
| 209753_s_at | 1802.8 | 1211.1 | 2265.4 | 188.5 | 49 | thymopoietin | TMPO |
| 214712_at | 364 | 86.8 | 327.1 | 1.6 | 49 | — | — |
| 216207_x_at | 4775.2 | 3222.6 | 9161.2 | 398.9 | 49 | immunoglobulin kappa variable 1D-13 | IGKV1D-13 |
| 219961_s_at | 434.9 | 261.5 | 641.1 | 16.1 | 49 | chromosome 20 open reading frame 19 | C20orf19 |
| 220987_s_at | 1908.9 | 838.2 | 1462.1 | 109.5 | 49 | chromosome 11 open reading frame 17 /// chromosome 11 open reading frame 17 /// NUAK family, SNF1-like kinase, 2 /// NUAK family, SNF1-like kinase, 2 | C11orf17 /// NUAK2 |
| 219659_at | 126.6 | 72.7 | 996.1 | 5.9 | 49 | ATPase, aminophospholipid transporter-like, Class I, type 8A, member 2 | ATP8A2 |
| 202379_s_at | 5195.1 | 2436.4 | 4839.2 | 148.8 | 48 | natural killer-tumor recognition sequence | NKTR |
| 210791_s_at | 793 | 342.6 | 1070.1 | 8.1 | 48 | Rho GTPase-activating protein | RICS |
| 212665_at | 1742.4 | 925.9 | 2080.5 | 229.1 | 48 | TCDD-inducible poly(ADP-ribose) polymerase | TIPARP |
| 206660_at | 14361.7 | 8315 | 29213.5 | 26.9 | 48 | immunoglobulin lambda-like polypeptide 1 | IGLL1 |
| 220400_at | 220.9 | 123.6 | 457.5 | 5.5 | 48 | vacuolar protein sorting 13B (yeast) | VPS13B |
| 202014_at | 2765 | 1272.3 | 17225.8 | 37.9 | 48 | protein phosphatase 1, regulatory (inhibitor) subunit 15A | PPP1R15A |
| 212611_at | 1669.7 | 1156.8 | 8728.6 | 150.2 | 48 | deltex 4 homolog (Drosophila) | DTX4 |
| 205769_at | 310.3 | 192.6 | 1536.6 | 4.7 | 48 | solute carrier family 27 (fatty acid transporter), member 2 | SLC27A2 |
| 209269_s_at | 1196.2 | 890 | 1180.9 | 131.4 | 48 | Spleen tyrosine kinase | SYK |
| 209469_at | 217.3 | 34 | 256.4 | 2.1 | 48 | glycoprotein M6A | GPM6A |
| 213939_s_at | 619.7 | 451.4 | 1008 | 6.7 | 48 | rap2 interacting protein x | RIPX |
| 215338_s_at | 1640.9 | 956.8 | 1577.3 | 16.6 | 48 | natural killer-tumor recognition sequence | NKTR |
| 216645_at | 600.6 | 427.4 | 745.3 | 24.2 | 48 | — | — |
| 219340_s_at | 689.7 | 323.6 | 994.5 | 9.6 | 48 | ceroid-lipofuscinosis, neuronal 8 (epilepsy, progressive with mental retardation) | CLN8 |
| 221004_s_at | 3633.1 | 1929.3 | 6469.8 | 15.2 | 48 | integral membrane protein 2C /// integral membrane protein 2C | ITM2C |
| 206665_s_at | 477.7 | 197.9 | 4662.1 | 3A | 48 | BCL2-like 1 | BCL2L1 |
| 206255_at | 1042.3 | 700 | 3332.5 | 7.8 | 48 | B lymphoid tyrosine kinase | BLK |
| 202208_s_at | 548.3 | 385.1 | 2457.6 | 10.6 | 48 | ADP-ribosylation factor-like 7 | ARL7 |
| 201236_s_at | 5477.4 | 4515.7 | 4123.8 | 551.1 | 47 | BTG family, member 2 | BTG2 |
| 207002_s_at | 378.3 | 188.2 | 433.3 | 2 | 47 | pleiomorphic adenoma gene-like 1 | PLAGL1 |
| 207798_s_at | 201.9 | 76 | 526.5 | 2.7 | 47 | ataxin 2-like | ATXN2L |
| 214554_at | 396.1 | 163.7 | 871.2 | 3.2 | 47 | histone 1, H2al | HIST1H2AL |
| 220001_at | 284.9 | 175.2 | 4940.2 | 8 | 47 | peptidyl arginine deiminase, type IV | PADI4 |
| 212457_at | 667.9 | 310.9 | 1110 | 18.1 | 47 | transcription factor binding to IGHM enhancer 3 | TFE3 |
| 213061_s_at | 953.9 | 821.8 | 1418.2 | 114.7 | 47 | N-terminal asparagine amidase | NTAN1 |
| 218529_at | 515.8 | 310.3 | 522.9 | 27.8 | 47 | CD320 antigen | CD320 |
| 202871_at | 481.2 | 246.6 | 1360.7 | 14.4 | 47 | TNF receptor-associated factor 4 | TRAF4 |
| 215891_s_at | 318.1 | 138.6 | 781.1 | 5.9 | 47 | GM2 ganglioside activator | GM2A |
| 215200_x_at | 1026.2 | 273.1 | 4081.9 | 12.7 | 47 | Villin 2 (ezrin) | VIL2 |
| 206342_x_at | 481.2 | 311.1 | 3521.6 | 8.3 | 47 | iduronate 2-sulfatase (Hunter syndrome) | IDS |
| 202479_s_at | 707.9 | 486.7 | 5353.1 | 9.3 | 47 | tribbles homolog 2 (Drosophila) | TRIB2 |
| 217849_s_at | 141.2 | 44 | 919.4 | 3.9 | 47 | CDC42 binding protein kinase beta (DMPK-like) | CDC42BPB |
| 210506_at | 134.1 | 84.3 | 855.2 | 5.1 | 47 | fucosyltransferase 7 (alpha (1,3) fucosyltransferase) | FUT7 |
| 205023_at | 205.3 | 58.5 | 370.3 | 4.3 | 47 | RAD51 homolog (RecA homolog, E. coli) (S. cerevisiae) | RAD51 |
| 206632_s_at | 937.4 | 353 | 856.9 | 2.9 | 47 | apolipoprotein B mRNA editing enzyme, catalytic polypeptide-like 3B | APOBEC3B |

TABLE 2-continued

Probesets underexpressed in 25% of more of B-lineage ALL cases (n = 270) as compared to normal bone marrow CD19+CD10+ cells from 4 healthy donors

| probe set ID | CD10+ CD19+ max | CD10+ CD19+ min | ALL max | ALL min | % ALL under expressed | Title | Symbol |
|---|---|---|---|---|---|---|---|
| 211947_s_at | 1169 | 170.5 | 1508.8 | 10.9 | 47 | BAT2 domain containing 1 | BAT2D1 |
| 206314_at | 158.9 | 90 | 323.8 | 4.4 | 47 | zinc finger protein 167 | ZNF167 |
| 219313_at | 154.4 | 116.7 | 380.8 | 4.8 | 47 | hypothetical protein DKFZp434C0328 | DKFZp434C0328 |
| 205544_s_at | 215.9 | 129 | 5833.9 | 10.1 | 47 | complement component (3d/Epstein Barr virus) receptor 2 | CR2 |
| 206951_at | 606.2 | 340.8 | 663.5 | 12.3 | 46 | histone 1, H4e | HIST1H4E |
| 212620_at | 509.8 | 199.8 | 1165.4 | 15 | 46 | zinc finger protein 609 | ZNF609 |
| 212240_s_at | 2426.9 | 1923.9 | 8975.2 | 277.2 | 46 | phosphoinositide-3-kinase, regulatory subunit 1 (p85 alpha) | PIK3R1 |
| 205425_at | 861.5 | 365.5 | 1018.8 | 4.3 | 46 | huntingtin interacting protein 1 | HIP1 |
| 217390_x_at | 755 | 553.5 | 779.3 | 23.7 | 46 | — | — |
| 220609_at | 617 | 260.1 | 601.4 | 4.7 | 46 | hypothetical protein LOC202181 | LOC202181 |
| 221491_x_at | 1553.3 | 699.6 | 2570 | 2.5 | 46 | major histocompatibility complex, class II, DR beta 1 /// major histocompatibility complex, class II, DR beta 1 /// major histocompatibility complex, class II, DR beta 3 /// major histocompatibility complex, class II, DR beta 3 /// major histocompatibility complex, class II, DR beta 4 /// major histocompatibility complex, class II, DR beta 4 | HLA-DRB1 /// HLA-DRB3 /// HLA-DRB4 |
| 217536_x_at | 136.5 | 46.7 | 276.9 | 0.9 | 46 | — | — |
| 212227_x_at | 30362 | 21224.4 | 93725.6 | 4332.2 | 46 | eukaryotic translation initiation factor 1 | EIF1 |
| 205922_at | 313.3 | 65.8 | 1335.5 | 6.8 | 46 | vanin 2 /// vanin 2 | VNN2 |
| 204684_at | 476.7 | 190.9 | 3423.4 | 8.5 | 46 | neuronal pentraxin I | NPTX1 |
| 214786_at | 427.6 | 294.4 | 1480.2 | 7.1 | 46 | mitogen-activated protein kinase kinase kinase 1 | MAP3K1 |
| 215721_at | 375.9 | 288.8 | 1301.2 | 5.2 | 46 | immunoglobulin heavy constant gamma 1 (G1m marker) | IGHG1 |
| 205768_s_at | 175.3 | 98.1 | 836.9 | 3.6 | 46 | solute carrier family 27 (fatty acid transporter), member 2 | SLC27A2 |
| 201397_at | 1061.9 | 740.5 | 1765.5 | 23.8 | 46 | phosphoglycerate dehydrogenase | PHGDH |
| 211022_s_at | 375.1 | 227.3 | 427.8 | 6.7 | 46 | alpha thalassemia/mental retardation syndrome X-linked (RAD54 homolog, S. cerevisiae) | ATRX |
| 220797_at | 216.3 | 169.9 | 429.9 | 3.8 | 46 | hypothetical protein MGC3329 | MGC3329 |
| 208705_s_at | 6796.1 | 6040.4 | 20022 | 1065.6 | 46 | eukaryotic translation initiation factor 5 | EIF5 |
| 213780_at | 134.2 | 77.1 | 476.5 | 5.7 | 46 | Full-length cDNA clone CS0DI027YJ05 of Placenta Cot 25-normalized of Homo sapiens (human) | — |
| 216456_at | 667.5 | 279 | 2544.7 | 3.1 | 46 | Protocadherin 9 | PCDH9 |
| 37028_at | 5364.5 | 1966.1 | 20132.4 | 281 | 46 | protein phosphatase 1, regulatory (inhibitor) subunit 15A | PPP1R15A |
| 219855_at | 691.1 | 115.1 | 1950.7 | 15 | 46 | nudix (nucleoside diphosphate linked moiety X)-type motif 11 | NUDT11 |
| 201411_s_at | 805.9 | 399.3 | 863.9 | 7.5 | 45 | pleckstrin homology domain containing, family B (evectins) member 2 | PLEKHB2 |
| 201926_s_at | 1353.7 | 877.4 | 2551.7 | 26.8 | 45 | decay accelerating factor for complement (CD55, Cromer blood group system) | DAF |
| 202095_at | 1357.7 | 1007.1 | 2523.9 | 21.7 | 45 | baculoviral IAP repeat-containing 5 (survivin) | BIRC5 |
| 207904_s_at | 448.8 | 304.7 | 583.5 | 9.7 | 45 | leucyl/cystinyl aminopeptidase | LNPEP |
| 211865_s_at | 349.3 | 223.2 | 651.6 | 6.6 | 45 | fizzy/cell division cycle 20 related 1 (Drosophila) | FZR1 |
| 213281_at | 841.7 | 540.7 | 984.1 | 28.2 | 45 | — | — |
| 214108_at | 510.5 | 345.5 | 990.6 | 23.5 | 45 | MYC associated factor X | MAX |
| 219709_x_at | 423 | 326.4 | 666.2 | 6.8 | 45 | chromosome 16 open reading frame 24 | C16orf24 |
| 219996_at | 424 | 247.1 | 427.5 | 7.9 | 45 | ankyrin repeat and SOCS box-containing 7 | ASB7 |
| 220220_at | 321.7 | 221.7 | 595.8 | 3.4 | 45 | hypothetical protein FLJ10120 | FLJ10120 |
| 222263_at | 512.1 | 304.2 | 770.4 | 17.1 | 45 | solute carrier family 35, member E1 | SLC35E1 |
| 209193_at | 3851.9 | 2313.1 | 9601.8 | 305.9 | 45 | pim-1 oncogene /// pim-1 oncogene | PIM1 |
| 208786_s_at | 5397.9 | 3573.9 | 16076.1 | 661.2 | 45 | microtubule-associated protein 1 light chain 3 beta | MAP1LC3B |
| 209325_s_at | 875.7 | 433.6 | 2078.9 | 10.7 | 45 | regulator of G-protein signalling 16 | RGS16 |
| 221054_s_at | 405.2 | 125.6 | 890.2 | 2.4 | 45 | T-cell leukemia/lymphoma 6 | TCL6 |
| 203954_x_at | 112.4 | 104 | 394.1 | 9.6 | 45 | claudin 3 | CLDN3 |
| 205214_at | 696.7 | 515.9 | 3489 | 16.2 | 45 | serine/threonine kinase 17b (apoptosis-inducing) | STK17B |
| 201393_s_at | 1577.7 | 1059.6 | 1740.6 | 12.7 | 45 | insulin-like growth factor 2 receptor | IGF2R |
| 212027_at | 1333 | 485.9 | 996.2 | 18.9 | 45 | RNA binding motif protein 25 | RBM25 |
| 213669_at | 844.5 | 573.2 | 991 | 8.8 | 45 | FCH domain only 1 | FCHO1 |
| 214542_x_at | 506.2 | 283.5 | 898.1 | 10.8 | 45 | histone 1, H2ai | HIST1H2AI |
| 217236_x_at | 710.2 | 459.7 | 761.3 | 23.6 | 45 | Immunoglobulin heavy constant gamma 1 (G1m marker) | IGHG1 |
| 205901_at | 667.9 | 295.2 | 1855 | 15.2 | 45 | prepronociceptin | PNOC |
| 212291_at | 925.7 | 468.1 | 1971.1 | 11.8 | 45 | homeodomain interacting protein kinase 1 | HIPK1 |
| 205803_s_at | 161.9 | 108.6 | 503.3 | 2.2 | 45 | transient receptor potential cation channel, subfamily C, member 1 | TRPC1 |
| 220266_s_at | 900.9 | 355.1 | 6496.8 | 11.3 | 45 | Kruppel-like factor 4 (gut) | KLF4 |
| 215330_at | 211.7 | 109.6 | 776.5 | 5.7 | 45 | Hypothetical protein FLJ43663 | FLJ43663 |
| 214043_at | 266.7 | 154.3 | 3097.2 | 5.6 | 45 | Protein tyrosine phosphatase, receptor type, D | PTPRD |
| 201979_s_at | 812.1 | 513.7 | 906.9 | 9.9 | 44 | protein phosphatase 5, catalytic subunit | PPP5C |
| 203479_s_at | 588.2 | 244.4 | 715.9 | 15.1 | 44 | OTU domain containing 4 | OTUD4 |
| 204908_s_at | 1879.3 | 431.4 | 2716.8 | 7.4 | 44 | B-cell CLL/lymphoma 3 | BCL3 |
| 209559_at | 347.6 | 145.1 | 483.7 | 8.8 | 44 | huntingtin interacting protein-1-related | HIP1R |
| 209718_at | 483 | 361.1 | 707.2 | 9.7 | 44 | kleisin beta | hCAP-H2 |
| 212588_at | 3482.7 | 2298.1 | 6552 | 94.9 | 44 | protein tyrosine phosphatase, receptor type, C | PTPRC |
| 218434_s_at | 956.1 | 383.5 | 3026.3 | 9.4 | 44 | acetoacetyl-CoA synthetase | AACS |

TABLE 2-continued

Probesets underexpressed in 25% of more of B-lineage ALL cases (n = 270) as compared to normal bone marrow CD19+CD10+ cells from 4 healthy donors

| probe set ID | CD10+ CD19+ max | CD10+ CD19+ min | ALL max | ALL min | % ALL under expressed | Title | Symbol |
|---|---|---|---|---|---|---|---|
| 214581_x_at | 729.6 | 320.5 | 3228.7 | 3.1 | 44 | tumor necrosis factor receptor superfamily, member 21 | TNFRSF21 |
| 213172_at | 108.6 | 53.6 | 428.6 | 3.8 | 44 | tetratricopeptide repeat domain 9 | TTC9 |
| 202478_at | 1685.6 | 710.2 | 14010.6 | 14.2 | 44 | tribbles homolog 2 (Drosophila) | TRIB2 |
| 218523_at | 1581.8 | 585.8 | 2999.4 | 34.4 | 44 | phospholysine phosphohistidine inorganic pyrophosphate phosphatase | LHPP |
| 220324_at | 121.8 | 96.4 | 227.5 | 2.6 | 44 | chromosome 6 open reading frame 155 | C6orf155 |
| 203320_at | 2769.4 | 1553.3 | 5905.3 | 148.9 | 44 | lymphocyte adaptor protein | LNK |
| 216518_at | 205.1 | 116.7 | 515.1 | 4.4 | 44 | MRNA; cDNA DKFZp564E233 (from clone DKFZp564E233) | — |
| 220809_at | 135.3 | 66.2 | 449.4 | 3.5 | 44 | hypothetical protein FLJ14327 | FLJ14327 |
| 206802_at | 233.8 | 138.6 | 478 | 10.2 | 44 | paired box gene 5 (B-cell lineage specific activator) | PAX5 |
| 212478_at | 661.4 | 318.8 | 1868.1 | 9.3 | 44 | hypothetical protein FLJ13910 | FLJ13910 |
| 217209_at | 165.2 | 118.6 | 446.2 | 12.2 | 44 | — | — |
| 204719_at | 102.2 | 52.9 | 338 | 1.8 | 44 | ATP-binding cassette, sub-family A (ABC1), member 8 | ABCA8 |
| 209982_s_at | 155.3 | 109.2 | 1350.3 | 4.7 | 44 | neurexin 2 | NRXN2 |
| 201780_s_at | 1014 | 631.5 | 772.5 | 40.1 | 44 | ring finger protein 13 | RNF13 |
| 209153_s_at | 12253.8 | 5691 | 8812.5 | 552.7 | 44 | transcription factor 3 (E2A immunoglobulin enhancer binding factors E12/E47) | TCF3 |
| 209754_s_at | 1401.8 | 705.4 | 1593.9 | 16.7 | 44 | thymopoietin | TMPO |
| 211404_s_at | 1362.9 | 833 | 2347.3 | 22.9 | 44 | amyloid beta (A4) precursor-like protein 2 | APLP2 |
| 212073_at | 730.4 | 433.9 | 766.1 | 8.7 | 44 | casein kinase 2, alpha 1 polypeptide | CSNK2A1 |
| 214190_x_at | 591 | 240.2 | 730.7 | 5.6 | 44 | golgi associated, gamma adaptin ear containing, ARF binding protein 2 | GGA2 |
| 214422_at | 250.7 | 58.5 | 306.9 | 2.1 | 44 | RAD23 homolog B (S. cerevisiae) | RAD23B |
| 215083_at | 681.3 | 386.7 | 923.9 | 9.7 | 44 | Paraspeckle component 1 | PSPC1 |
| 216067_at | 321.2 | 122 | 372.9 | 4.1 | 44 | — | — |
| 216218_s_at | 1014.3 | 670.6 | 1657.5 | 30.6 | 44 | phospholipase C-like 2 | PLCL2 |
| 222309_at | 281.3 | 147 | 1126.8 | 2.9 | 44 | Chromosome 6 open reading frame 62 | C6orf62 |
| 210993_s_at | 4684 | 2723.7 | 16961 | 7.3 | 44 | SMAD, mothers against DPP homolog 1 (Drosophila) | SMAD1 |
| 200916_at | 5108.1 | 1744.3 | 6584.8 | 62.5 | 43 | transgelin 2 | TAGLN2 |
| 208947_s_at | 452.8 | 239.9 | 528.5 | 9.1 | 43 | regulator of nonsense transcripts 1 | RENT1 |
| 210717_at | 366.1 | 204.6 | 486.9 | 4.4 | 43 | Ubiquitin-conjugating enzyme E2D 2 (UBC4/5 homolog, yeast) | UBE2D2 |
| 217284_x_at | 1056.8 | 484.7 | 2082.6 | 16.8 | 43 | serine hydrolase-like | SERHL |
| 217684_at | 311.6 | 169.8 | 536.7 | 12.3 | 43 | thymidylate synthetase | TYMS |
| 218435_at | 1320.3 | 790.5 | 1286.5 | 9.1 | 43 | DnaJ (Hsp40) homolog, subfamily C, member 15 | DNAJC15 |
| 219279_at | 952.4 | 771.3 | 2004.7 | 24.3 | 43 | dedicator of cytokinesis 10 | DOCK10 |
| 222337_at | 144.1 | 74.4 | 405.1 | 7.2 | 43 | Nardilysin (N-arginine dibasic convertase) | NRD1 |
| 203896_s_at | 116.5 | 34.3 | 890.2 | 2.2 | 43 | phospholipase C, beta 4 | PLCB4 |
| 201072_s_at | 973.3 | 734.6 | 1263 | 53.5 | 43 | SWI/SNF related, matrix associated, actin dependent regulator of chromatin, subfamily c, member 1 | SMARCC1 |
| 204269_at | 1830.9 | 1064.3 | 3312.7 | 151.8 | 43 | pim-2 oncogene | PIM2 |
| 208795_s_at | 4268.9 | 3568.4 | 4893.9 | 592.1 | 43 | MCM7 minichromosome maintenance deficient 7 (S. cerevisiae) | MCM7 |
| 212345_s_at | 2299.8 | 1709.5 | 2604.3 | 251.9 | 43 | cAMP responsive element binding protein 3-like 2 | CREB3L2 |
| 215164_at | 965.1 | 508.4 | 1611.4 | 4.7 | 43 | Transcription factor 4 | TCF4 |
| 218927_s_at | 1032.4 | 762.2 | 1817.1 | 17.2 | 43 | carbohydrate (chondroitin 4) sulfotransferase 12 | CHST12 |
| 217274_x_at | 1238.9 | 796.9 | 3380 | 97.2 | 43 | myosin, light polypeptide 4, alkali; atrial, embryonic | MYL4 |
| 205620_at | 173.8 | 72.8 | 322.6 | 6.7 | 43 | coagulation factor X | F10 |
| 208583_x_at | 1234.3 | 766.5 | 1297.9 | 37.6 | 43 | histone 1, H2aj | HIST1H2AJ |
| 211921_x_at | 47312.2 | 33664.3 | 58378.1 | 7053.1 | 43 | prothymosin, alpha (gene sequence 28) /// prothymosin, alpha (gene sequence 28) | PTMA |
| 219072_at | 480.8 | 422.9 | 746.5 | 26 | 43 | B-cell CLL/lymphoma 7C | BCL7C |
| 216466_at | 87.7 | 47.4 | 333.5 | 1.6 | 43 | neuron navigator 3 | NAV3 |
| 214774_x_at | 114.6 | 17.3 | 1325.4 | 0.6 | 43 | trinucleotide repeat containing 9 | TNRC9 |
| 200681_at | 5619.1 | 3222.4 | 4088.7 | 914.6 | 42 | glyoxalase I | GLO1 |
| 202825_at | 566.4 | 326.3 | 1090.4 | 12.8 | 42 | solute carrier family 25 (mitochondrial carrier; adenine nucleotide translocator), member 4 | SLC25A4 |
| 216508_x_at | 5910.3 | 3567.4 | 6310.2 | 494.6 | 42 | high-mobility group box 1 | HMGB1 |
| 220764_at | 195.7 | 132.2 | 293.8 | 6.7 | 42 | protein phosphatase 4, regulatory subunit 2 | PPP4R2 |
| 212420_at | 2900.9 | 2182.6 | 6708 | 168.7 | 42 | E74-like factor 1 (ets domain transcription factor) | ELF1 |
| 212758_s_at | 646.9 | 184.1 | 1585.5 | 9 | 42 | transcription factor 8 (represses interleukin 2 expression) | TCF8 |
| 220374_at | 339.7 | 241.8 | 682.4 | 12.6 | 42 | BTB (POZ) domain containing 5 | BTBD5 |
| 200616_s_at | 946 | 343.2 | 927.7 | 12.4 | 42 | KIAA0152 | KIAA0152 |
| 205205_at | 982.8 | 305.4 | 1182.4 | 10.7 | 42 | v-rel reticuloendotheliosis viral oncogene homolog B, nuclear factor of kappa light polypeptide gene enhancer in B-cells 3 (avian) | RELB |
| 207943_x_at | 543 | 330.3 | 625.4 | 8.5 | 42 | pleiomorphic adenoma gene-like 1 | PLAGL1 |
| 209038_s_at | 345 | 152.6 | 668 | 8.1 | 42 | EH-domain containing 1 | EHD1 |
| 210666_at | 372.9 | 43.1 | 289.3 | 10.2 | 42 | iduronate 2-sulfatase (Hunter syndrome) | IDS |
| 212122_at | 182.5 | 81.3 | 264 | 3 | 42 | ras homolog gene family, member Q | RHOQ |
| 212684_at | 397 | 337.6 | 629.4 | 14.1 | 42 | zinc finger protein 3 (A8-51) | ZNF3 |
| 215269_at | 990.5 | 519.8 | 1185.3 | 15.4 | 42 | transmembrane protein 1 | TMEM1 |

TABLE 2-continued

Probesets underexpressed in 25% of more of B-lineage ALL cases (n = 270) as compared to normal bone marrow CD19+CD10+ cells from 4 healthy donors

| probe set ID | CD10+ CD19+ max | CD10+ CD19+ min | ALL max | ALL min | % ALL under expressed | Title | Symbol |
|---|---|---|---|---|---|---|---|
| 216422_at | 274 | 122.3 | 399.5 | 6.9 | 42 | proliferation-associated 2G4, 38 kDa | PA2G4 |
| 221043_at | 524.2 | 318.4 | 711.7 | 12.9 | 42 | — | — |
| 221952_x_at | 17836.4 | 16373.5 | 17116.4 | 2216.8 | 42 | TRM5 tRNA methyltransferase 5 homolog (S. cerevisiae) | TRMT5 |
| 203590_at | 680.5 | 506.9 | 1718.3 | 21.6 | 42 | dynein, cytoplasmic, light intermediate polypeptide 2 | DNCLI2 |
| 208703_s_at | 1557.7 | 1261.2 | 3450.2 | 133.7 | 42 | amyloid beta (A4) precursor-like protein 2 | APLP2 |
| 210362_x_at | 328.4 | 126.9 | 723.2 | 5.6 | 42 | promyelocytic leukemia | PML |
| 214852_x_at | 154.4 | 107.8 | 362.4 | 6 | 42 | vacuolar protein sorting 13A (yeast) | VPS13A |
| 217418_x_at | 4552.9 | 1979.4 | 25689 | 63.2 | 42 | membrane-spanning 4-domains, subfamily A, member 1 | MS4A1 |
| 202192_s_at | 3906.7 | 2433.3 | 4114.9 | 274.1 | 41 | growth arrest-specific 7 | GAS7 |
| 203376_at | 3692.7 | 2663 | 3142.2 | 506 | 41 | cell division cycle 40 homolog (yeast) | CDC40 |
| 209470_s_at | 212.6 | 93.7 | 341.2 | 1.4 | 41 | glycoprotein M6A | GPM6A |
| 212529_at | 297.1 | 117 | 559.5 | 8.7 | 41 | hypothetical protein FLJ30656 | FLJ30656 |
| 215159_s_at | 466 | 342.8 | 742.5 | 6.5 | 41 | NAD kinase | NADK |
| 201565_s_at | 5880.2 | 1727.4 | 19822.8 | 47.1 | 41 | inhibitor of DNA binding 2, dominant negative helix-loop-helix protein | ID2 |
| 213299_at | 179.6 | 60.8 | 529.2 | 4.1 | 41 | zinc finger and BTB domain containing 7A | ZBTB7A |
| 208245_at | 104.5 | 67 | 842.3 | 1.6 | 41 | RAB9, member RAS oncogene family, pseudogene 1 | RAB9P1 |
| 204346_s_at | 1584.9 | 1272.1 | 2423.3 | 129.2 | 41 | Ras association (RalGDS/AF-6) domain family 1 | RASSF1 |
| 209478_at | 1031.7 | 918 | 1260.3 | 41.6 | 41 | stimulated by retinoic acid 13 homolog (mouse) | STRA13 |
| 210115_at | 633.5 | 354.8 | 928.7 | 9 | 41 | ribosomal protein L39-like | RPL39L |
| 210218_s_at | 510.7 | 252.4 | 430.8 | 8.7 | 41 | nuclear antigen Sp100 | SP100 |
| 210407_at | 483.2 | 237.4 | 667 | 4.8 | 41 | protein phosphatase 1A (formerly 2C), magnesium-dependent, alpha isoform | PPM1A |
| 212026_s_at | 384.9 | 198.5 | 582.4 | 10.9 | 41 | exocyst complex component 7 | EXOC7 |
| 218401_s_at | 959 | 552.1 | 927.4 | 73.5 | 41 | zinc finger protein 281 | ZNF281 |
| 222378_at | 210.6 | 121.7 | 441.6 | 5.2 | 41 | Hypothetical protein FLJ43663 | FLJ43663 |
| 207631_at | 165.8 | 85.7 | 337 | 7.7 | 41 | neighbor of BRCA1 gene 2 | NBR2 |
| 211151_x_at | 667.6 | 384.3 | 2032.1 | 6 | 41 | growth hormone 1 | GH1 |
| 43427_at | 201.2 | 143.7 | 621.5 | 9.3 | 41 | acetyl-Coenzyme A carboxylase beta | ACACB |
| 216361_s_at | 279.2 | 87.6 | 690.4 | 2 | 41 | MYST histone acetyltransferase (monocytic leukemia) 3 | MYST3 |
| 219135_s_at | 356.2 | 262.9 | 1031.1 | 9.5 | 41 | hypothetical protein FLJ12681 | FLJ12681 |
| 208476_s_at | 185.2 | 147.7 | 735.6 | 6.5 | 41 | FERM domain containing 4A | FRMD4A |
| 213954_at | 101 | 74.4 | 325.1 | 3.3 | 41 | KIAA0888 protein | KIAA0888 |
| 212592_at | 806.3 | 485.3 | 15583.5 | 8.7 | 41 | Immunoglobulin J polypeptide, linker protein for immunoglobulin alpha and mu polypeptides | IGJ |
| 202005_at | 443.9 | 239.8 | 814 | 25.5 | 41 | suppression of tumorigenicity 14 (colon carcinoma, matriptase, epithin) | ST14 |
| 202487_s_at | 9563.8 | 8094.3 | 9690.7 | 1623.9 | 41 | H2A histone family, member V | H2AFV |
| 204484_at | 3918.2 | 2035.4 | 3075.3 | 59.7 | 41 | phosphoinositide-3-kinase, class 2, beta polypeptide | PIK3C2B |
| 206707_x_at | 3161.2 | 1759 | 4423.4 | 183.3 | 41 | chromosome 6 open reading frame 32 | C6orf32 |
| 214243_s_at | 993.5 | 280.2 | 1457.1 | 10 | 41 | serine hydrolase-like | SERHL |
| 214481_at | 430 | 143.5 | 665.5 | 3.9 | 41 | histone 1, H2am | HIST1H2AM |
| 217576_x_at | 630.6 | 373 | 947.5 | 13.1 | 41 | son of sevenless homolog 2 (Drosophila) | SOS2 |
| 222322_at | 254.5 | 79.2 | 429.9 | 1.6 | 41 | Transcribed locus | — |
| 203833_s_at | 873.1 | 695.6 | 1838 | 91.8 | 41 | trans-golgi network protein 2 | TGOLN2 |
| 200719_at | 1366.7 | 1017.2 | 3859 | 22.4 | 41 | S-phase kinase-associated protein 1A (p19A) | SKP1A |
| 216277_at | 135.1 | 67.5 | 619.8 | 5 | 41 | BUB1 budding uninhibited by benzimidazoles 1 homolog (yeast) | BUB1 |
| 200772_x_at | 41243 | 33563.5 | 53587.8 | 7692.7 | 40 | prothymosin, alpha (gene sequence 28) | PTMA |
| 204048_s_at | 369 | 251.6 | 684.4 | 6.3 | 40 | phosphatase and actin regulator 2 | PHACTR2 |
| 204074_s_at | 1098.2 | 494.2 | 737.2 | 17.2 | 40 | glycine-, glutamate-, thienylcyclohexylpiperidine-binding protein | GlyBP |
| 208719_s_at | 2411.4 | 187.5 | 3784 | 6.1 | 40 | DEAD (Asp-Glu-Ala-Asp) box polypeptide 17 | DDX17 |
| 214743_at | 2864.9 | 2185.8 | 3477.7 | 461.9 | 40 | cut-like 1, CCAAT displacement protein (Drosophila) | CUTL1 |
| 214834_at | 152.8 | 61.7 | 287.8 | 2.7 | 40 | HBII-437 C/D box snoRNA /// HBII-13 snoRNA | HBII-437 /// HBII-13 |
| 215802_at | 699.1 | 240.8 | 742.6 | 5 | 40 | Transducin-like enhancer of split 1 (E(sp1) homolog, Drosophila) | TLE1 |
| 203233_at | 1017 | 703 | 2086.3 | 21.8 | 40 | interleukin 4 receptor | IL4R |
| 220879_at | 356.5 | 218.2 | 837.1 | 28.7 | 40 | — | — |
| 201283_s_at | 289.1 | 87.5 | 329 | 6.7 | 40 | OGT(O-Glc-NAc transferase)-interacting protein 106 KDa | OIP106 |
| 203395_s_at | 309 | 220.9 | 380.9 | 8.2 | 40 | hairy and enhancer of split 1, (Drosophila) | HES1 |
| 204524_at | 692.2 | 215.4 | 649.7 | 9.2 | 40 | 3-phosphoinositide dependent protein kinase-1 | PDPK1 |
| 215615_x_at | 217.3 | 119 | 406.9 | 4.4 | 40 | — | — |
| 217650_x_at | 526.7 | 320 | 665.4 | 16.1 | 40 | ST3 beta-galactoside alpha-2,3-sialyltransferase 2 | ST3GAL2 |
| 218039_at | 4736 | 3722.6 | 7499 | 402.9 | 40 | nucleolar and spindle associated protein 1 | NUSAP1 |
| 221654_s_at | 2225.9 | 1866.2 | 3238.5 | 454.2 | 40 | ubiquitin specific peptidase 3 | USP3 |
| 205193_at | 417.5 | 181 | 1462.3 | 21.6 | 40 | v-maf musculoaponeurotic fibrosarcoma oncogene homolog F (avian) | MAFF |
| 206100_at | 490.7 | 264.8 | 1235.7 | 8.9 | 40 | carboxypeptidase M | CPM |
| 219703_at | 211.4 | 170.9 | 493.9 | 3.6 | 40 | meiosis-specific nuclear structural 1 | MNS1 |
| 206204_at | 74.9 | 46.7 | 814.1 | 1.8 | 40 | growth factor receptor-bound protein 14 | GRB14 |
| 204115_at | 371.9 | 300.5 | 4663.6 | 3.3 | 40 | guanine nucleotide binding protein (G protein), gamma 11 | GNG11 |

TABLE 2-continued

Probesets underexpressed in 25% of more of B-lineage ALL cases (n = 270) as compared to normal bone marrow CD19+CD10+ cells from 4 healthy donors

| probe set ID | CD10+ CD19+ max | CD10+ CD19+ min | ALL max | ALL min | % ALL under expressed | Title | Symbol |
|---|---|---|---|---|---|---|---|
| 202879_s_at | 768.3 | 396.1 | 815.9 | 10.9 | 40 | pleckstrin homology, Sec7 and coiled-coil domains 1(cytohesin 1) | PSCD1 |
| 205346_at | 310.7 | 138.4 | 420.8 | 8.9 | 40 | ST3 beta-galactoside alpha-2,3-sialyltransferase 2 | ST3GAL2 |
| 213940_s_at | 1325.5 | 781.7 | 2148.6 | 5.4 | 40 | formin binding protein 1 | FNBP1 |
| 214030_at | 552.5 | 218.8 | 766.3 | 9.2 | 40 | hypothetical protein DKFZp667G2110 | DKFZp667G2110 |
| 219312_s_at | 287.3 | 230 | 531.5 | 5.7 | 40 | zinc finger and BTB domain containing 10 | ZBTB10 |
| 219534_x_at | 307.9 | 42 | 561.3 | 3.2 | 40 | cyclin-dependent kinase inhibitor 1C (p57, Kip2) | CDKN1C |
| 221848_at | 429.1 | 362.1 | 661.7 | 24.7 | 40 | zinc finger, CCCH-type with G patch domain | ZGPAT |
| 203467_at | 368 | 154.2 | 751.9 | 8 | 40 | phosphomannomutase 1 | PMM1 |
| 205024_s_at | 1179.4 | 755.8 | 1567.1 | 28.5 | 39 | RAD51 homolog (RecA homolog, E. coli) (S. cerevisiae) | RAD51 |
| 208808_s_at | 14054.5 | 11679.2 | 14451.9 | 1436.6 | 39 | high-mobility group box 2 | HMGB2 |
| 208928_at | 387.9 | 161.8 | 547.1 | 9.6 | 39 | P450 (cytochrome) oxidoreductase | POR |
| 209447_at | 1248.8 | 638.5 | 1546.1 | 14.3 | 39 | spectrin repeat containing, nuclear envelope 1 | SYNE1 |
| 212105_s_at | 1088.6 | 498.6 | 1463.7 | 13.4 | 39 | DEAH (Asp-Glu-Ala-His) box polypeptide 9 | DHX9 |
| 214665_s_at | 3166 | 2307.8 | 3142.1 | 334.7 | 39 | calcium binding protein P22 | CHP |
| 221628_at | 326.8 | 98.4 | 548.3 | 8.3 | 39 | cytokine-like nuclear factor n-pac | N-PAC |
| 204646_at | 418.5 | 299.3 | 1102.6 | 6.2 | 39 | dihydropyrimidine dehydrogenase | DPYD |
| 205081_at | 1999.9 | 1137.4 | 6452.3 | 8.4 | 39 | cysteine-rich protein 1 (intestinal) | CRIP1 |
| 206877_at | 122 | 40.9 | 918.6 | 6 | 39 | MAX dimerization protein 1 | MXD1 |
| 212651_at | 285.2 | 84.9 | 1297.4 | 4.8 | 39 | Rho-related BTB domain containing 1 | RHOBTB1 |
| 214251_s_at | 603.2 | 285.5 | 1741.8 | 4.1 | 39 | nuclear mitotic apparatus protein 1 | NUMA1 |
| 201962_s_at | 1277.2 | 637.4 | 1078.1 | 24.4 | 39 | ring finger protein 41 | RNF41 |
| 204183_s_at | 383.8 | 245.7 | 428 | 9.8 | 39 | adrenergic, beta, receptor kinase 2 | ADRBK2 |
| 205267_at | 12559.7 | 5949 | 10129.5 | 195.1 | 39 | POU domain, class 2, associating factor 1 | POU2AF1 |
| 209501_at | 706.2 | 547.4 | 1404.7 | 21.9 | 39 | cerebellar degeneration-related protein 2, 62 kDa | CDR2 |
| 215779_s_at | 1882.7 | 716.6 | 3292.8 | 15.4 | 39 | histone 1, H2bg | HIST1H2BG |
| 219507_at | 748.8 | 521.7 | 755.7 | 23 | 39 | arginine/serine-rich coiled-coil 1 | RSRC1 |
| 221908_at | 523.4 | 234.3 | 943.1 | 13.8 | 39 | Transmembrane protein 118 | TMEM118 |
| 208325_s_at | 664.6 | 384.2 | 1413.3 | 12.8 | 39 | A kinase (PRKA) anchor protein 13 | AKAP13 |
| 209803_s_at | 109.2 | 47.7 | 258.5 | 1.7 | 39 | pleckstrin homology-like domain, family A, member 2 | PHLDA2 |
| 7592_s_at | 106 | 47.9 | 252.5 | 4.4 | 39 | hyperpolarization activated cyclic nucleotide-gated potassium channel 2 | HCN2 |
| 205489_at | 1211.9 | 581.2 | 3410.5 | 45.9 | 39 | crystallin, mu | CRYM |
| 202102_s_at | 4917.3 | 2139.9 | 4161.3 | 206.4 | 39 | bromodomain containing 4 | BRD4 |
| 209461_x_at | 392 | 219.8 | 510.5 | 10.2 | 39 | WD repeat domain 18 | WDR18 |
| 210778_s_at | 746.7 | 571.2 | 1009.9 | 9.4 | 39 | MAX dimerization protein 4 | MXD4 |
| 213062_at | 944.9 | 662 | 1245.4 | 21.2 | 39 | N-terminal asparagine amidase | NTAN1 |
| 213996_at | 1935.9 | 1006.9 | 1599.5 | 31.4 | 39 | yippee-like 1 (Drosophila) | YPEL1 |
| 55583_at | 356.5 | 228.2 | 491.2 | 34.9 | 39 | dedicator of cytokinesis 6 | DOCK6 |
| 217626_at | 183.5 | 73.9 | 598.9 | 8.1 | 39 | aldo-keto reductase family 1, member C1 /// aldo-keto reductase family 1, member C2 | AKR1C1 /// AKR1C2 |
| 219951_s_at | 175.7 | 117.5 | 603 | 6.9 | 39 | chromosome 20 open reading frame 12 | C20orf12 |
| 205830_at | 121.3 | 64 | 421.7 | 2.2 | 39 | calmegin | CLGN |
| 213156_at | 498.5 | 259.4 | 517.5 | 4 | 38 | MRNA; cDNA DKFZp586B211 (from clone DKFZp586B211) /// Homo sapiens, clone IMAGE: 4214654, mRNA | — |
| 216621_at | 567.5 | 296.2 | 664.1 | 12.4 | 38 | Rho-associated, coiled-coil containing protein kinase 1 | ROCK1 |
| 217268_at | 92.9 | 29 | 371.7 | 0.8 | 38 | RAB7, member RAS oncogene family | RAB7 |
| 210491_at | 137.5 | 98.5 | 538.1 | 3.2 | 38 | — | — |
| 203126_at | 439.7 | 366.7 | 1524.8 | 6 | 38 | inositol(myo)-1(or 4)-monophosphatase 2 | IMPA2 |
| 212254_s_at | 162 | 121.3 | 552.2 | 4.5 | 38 | dystonin | DST |
| 202146_at | 882.7 | 430.7 | 853.4 | 27.8 | 38 | interferon-related developmental regulator 1 | IFRD1 |
| 204975_at | 1069.6 | 427.3 | 1016.3 | 13 | 38 | epithelial membrane protein 2 | EMP2 |
| 205426_s_at | 453.2 | 267.2 | 650.8 | 11.7 | 38 | huntingtin interacting protein 1 | HIP1 |
| 209182_s_at | 993.6 | 330.7 | 1620.7 | 9.7 | 38 | chromosome 10 open reading frame 10 | C10orf10 |
| 218194_at | 5628.1 | 2372.6 | 5536 | 376.4 | 38 | REX2, RNA exonuclease 2 homolog (S. cerevisiae) | REXO2 |
| 217204_at | 190.3 | 82.6 | 408.3 | 2.2 | 38 | Mitochondrial translational release factor 1-like | MTRF1L |
| 219922_s_at | 331 | 157.2 | 854.4 | 3.2 | 38 | latent transforming growth factor beta binding protein 3 | LTBP3 |
| 213537_at | 2955.4 | 1564.6 | 10603.5 | 32.8 | 38 | major histocompatibility complex, class II, DP alpha 1 | HLA-DPA1 |
| 214230_at | 333.3 | 172.9 | 3101.8 | 6.6 | 38 | cell division cycle 42 (GTP binding protein, 25 kDa) | CDC42 |
| 209156_s_at | 133.3 | 51.3 | 605.9 | 4.2 | 38 | collagen, type VI, alpha 2 | COL6A2 |
| 205306_x_at | 1281.1 | 521.1 | 1837.7 | 62.9 | 37 | kynurenine 3-monooxygenase (kynurenine 3-hydroxylase) | KMO |
| 208184_s_at | 1225.2 | 677 | 1209.5 | 24.7 | 37 | transmembrane protein 1 | TMEM1 |
| 212492_s_at | 1554.5 | 674.1 | 1671.1 | 79.6 | 37 | jumonji domain containing 2B | JMJD2B |
| 213106_at | 1975.6 | 946.3 | 1743.3 | 150.2 | 37 | ATPase, aminophospholipid transporter (APLT), Class I, type 8A, member 1 | ATP8A1 |
| 219286_s_at | 1929.7 | 1420.7 | 2353.4 | 39 | 37 | RNA binding motif protein 15 | RBM15 |
| 204840_s_at | 116.6 | 22.2 | 405.6 | 0.4 | 37 | early endosome antigen 1, 162 kD | EEA1 |
| 219651_at | 158 | 50.8 | 472.4 | 3.7 | 37 | developmental pluripotency associated 4 | DPPA4 |
| 210356_x_at | 4859.8 | 2065.7 | 27465.2 | 118.8 | 37 | membrane-spanning 4-domains, subfamily A, member 1 | MS4A1 |
| 201367_s_at | 3841.3 | 440.5 | 3294.3 | 4.4 | 37 | zinc finger protein 36, C3H type-like 2 | ZFP36L2 |
| 205436_s_at | 5772.5 | 3401.4 | 8416.8 | 129.1 | 37 | H2A histone family, member X | H2AFX |

TABLE 2-continued

Probesets underexpressed in 25% of more of B-lineage ALL cases (n = 270) as compared to normal bone marrow CD19+CD10+ cells from 4 healthy donors

| probe set ID | CD10+ CD19+ max | CD10+ CD19+ min | ALL max | ALL min | % ALL under expressed | Title | Symbol |
|---|---|---|---|---|---|---|---|
| 211672_s_at | 1173.9 | 986.1 | 1802.1 | 18.1 | 37 | actin related protein 2/3 complex, subunit 4, 20 kDa /// actin related protein 2/3 complex, subunit 4, 20 kDa | ARPC4 |
| 212459_x_at | 788.8 | 562.7 | 1530.9 | 53.5 | 37 | succinate-CoA ligase, GDP-forming, beta subunit | SUCLG2 |
| 212520_s_at | 2137.8 | 1356.8 | 2927.7 | 140.6 | 37 | SWI/SNF related, matrix associated, actin dependent regulator of chromatin, subfamily a, member 4 | SMARCA4 |
| 215169_at | 403.8 | 77.6 | 459.2 | 3.4 | 37 | solute carrier family 35, member E2 | SLC35E2 |
| 215781_s_at | 303.2 | 111.1 | 458.5 | 4.7 | 37 | topoisomerase (DNA) III beta | TOP3B |
| 220589_s_at | 302.3 | 168.9 | 504.6 | 10.4 | 37 | uncharacterized hematopoietic stem/progenitor cells protein MDS028 | MDS028 |
| 222001_x_at | 1020.4 | 723 | 2006.4 | 11 | 37 | LOC440669 | LOC440669 |
| 205423_at | 1750.2 | 1333.8 | 3693.6 | 144.7 | 37 | adaptor-related protein complex 1, beta 1 subunit | AP1B1 |
| 219371_s_at | 8724.6 | 5051.9 | 18217 | 451.6 | 37 | Kruppel-like factor 2 (lung) | KLF2 |
| 205471_s_at | 235.8 | 104.3 | 1645.6 | 3.7 | 37 | dachshund homolog 1 (Drosophila) | DACH1 |
| 36711_at | 454.5 | 125.8 | 4719.8 | 2.7 | 37 | v-maf musculoaponeurotic fibrosarcoma oncogene homolog F (avian) | MAFF |
| 209184_s_at | 3447.1 | 1380.2 | 19735.9 | 1851 | 37 | insulin receptor substrate 2 | IRS2 |
| 216080_s_at | 1763.4 | 1541.1 | 12130.1 | 26.7 | 37 | fatty acid desaturase 3 | FADS3 |
| 206551_x_at | 1941.3 | 1090.3 | 1840.1 | 94.2 | 37 | kelch-like 24 (Drosophila) | KLHL24 |
| 209118_s_at | 6782.7 | 4027.8 | 10974.1 | 496.1 | 37 | tubulin, alpha 3 | TUBA3 |
| 209592_s_at | 1061.5 | 830.1 | 1149.1 | 63.4 | 37 | WD repeat domain 68 | WDR68 |
| 211997_x_at | 55066.4 | 40842.6 | 74824.4 | 4914.8 | 37 | H3 histone, family 3B (H3.3B) | H3F3B |
| 204680_s_at | 531.6 | 492.2 | 1100 | 70.2 | 37 | Rap guanine nucleotide exchange factor (GEF) 5 | RAPGEF5 |
| 210360_s_at | 351.1 | 241.1 | 706 | 6 | 37 | metastasis suppressor 1 | MTSS1 |
| 219995_s_at | 67.8 | 22.6 | 234.6 | 0.4 | 37 | hypothetical protein FLJ13841 | FLJ13841 |
| 211141_at | 113.6 | 76.1 | 433.7 | 4 | 37 | CCR4-NOT transcription complex, subunit 3 | CNOT3 |
| 204244_s_at | 989.7 | 431.6 | 816 | 5.8 | 36 | activator of S phase kinase | ASK |
| 207740_s_at | 1081.5 | 677 | 1204.7 | 20.3 | 36 | nucleoporin 62 kDa | NUP62 |
| 209235_at | 934.8 | 339.2 | 1405.7 | 21.7 | 36 | chloride channel 7 | CLCN7 |
| 214829_at | 520.5 | 150.3 | 618.9 | 2 | 36 | aminoadipate-semialdehyde synthase | AASS |
| 216012_at | 3285.1 | 822.5 | 2116.6 | 164.8 | 36 | Unidentified mRNA, partial sequence | — |
| 208579_x_at | 6232.3 | 2992.5 | 13423.9 | 240.5 | 36 | H2B histone family, member S | H2BFS |
| 212609_s_at | 309.3 | 116.3 | 677.5 | 5.3 | 36 | V-akt murine thymoma viral oncogene homolog 3 (protein kinase B, gamma) | AKT3 |
| 215768_at | 206.3 | 134.9 | 520.2 | 5.6 | 36 | SRY (sex determining region Y)-box 5 | SOX5 |
| 216224_s_at | 227.1 | 178.7 | 506 | 12.9 | 36 | histone deacetylase 6 | HDAC6 |
| 220297_at | 133.8 | 90.5 | 314 | 8.7 | 36 | BTB (POZ) domain containing 7 | BTBD7 |
| 218785_s_at | 120.6 | 74.9 | 459.4 | 3.1 | 36 | RAB, member RAS oncogene family-like 5 | RABL5 |
| 217263_x_at | 190 | 129.4 | 767.3 | 9.1 | 36 | runt-related transcription factor 1 (acute myeloid leukemia 1; aml1 oncogene) | RUNX1 |
| 201629_s_at | 1512.1 | 1043.6 | 2486.8 | 52.9 | 36 | acid phosphatase 1, soluble | ACP1 |
| 201679_at | 514.4 | 351.2 | 759.1 | 8.6 | 36 | arsenate resistance protein ARS2 | ARS2 |
| 201745_at | 908.2 | 601.1 | 1718.6 | 130.1 | 36 | PTK9 protein tyrosine kinase 9 | PTK9 |
| 202870_s_at | 2228.1 | 1100.3 | 4341.3 | 56.3 | 36 | CDC20 cell division cycle 20 homolog (S. cerevisiae) | CDC20 |
| 208107_s_at | 594.2 | 283.2 | 834.1 | 11.6 | 36 | exonuclease NEF-sp /// exonuclease NEF-sp | LOC81691 |
| 209257_s_at | 2342.4 | 961.4 | 2637.3 | 83.1 | 36 | chondroitin sulfate proteoglycan 6 (bamacan) | CSPG6 |
| 213810_s_at | 392.9 | 168.6 | 563.2 | 11 | 36 | Chromosome 6 open reading frame 166 | C6orf166 |
| 213947_s_at | 1435.9 | 1019.4 | 2459.7 | 55.1 | 36 | nucleoporin 210 kDa | NUP210 |
| 214160_at | 213.7 | 108.9 | 377.8 | 7 | 36 | — | — |
| 215720_s_at | 432.1 | 288.8 | 825 | 6.5 | 36 | nuclear transcription factor Y, alpha | NFYA |
| 217785_s_at | 386.1 | 113.6 | 458.8 | 7 | 36 | SNARE protein Ykt6 | YKT6 |
| 207057_at | 275.7 | 163.6 | 909.8 | 5.2 | 36 | solute carrier family 16 (monocarboxylic acid transporters), member 7 | SLC16A7 |
| 209446_s_at | 190 | 110.3 | 394.6 | 4.8 | 36 | — | — |
| 201482_at | 401 | 314.2 | 1198.1 | 30.8 | 36 | quiescin Q6 | QSCN6 |
| 214242_at | 128.5 | 56.6 | 458 | 4.8 | 36 | Mannosidase, alpha, class 1A, member 2 | MAN1A2 |
| 219208_at | 114.6 | 37.6 | 281 | 3.8 | 36 | F-box protein 11 | FBXO11 |
| 221125_s_at | 479.4 | 282.6 | 2029.4 | 22.5 | 36 | potassium large conductance calcium-activated channel, subfamily M beta member 3 | KCNMB3 |
| 211884_s_at | 433.9 | 339.7 | 719.6 | 10 | 36 | class II, major histocompatibility complex, transactivator | CIITA |
| 219646_at | 607 | 193.7 | 653.3 | 10 | 36 | hypothetical protein FLJ20186 | FLJ20186 |
| 204198_s_at | 1516.7 | 621.8 | 4598.1 | 16 | 36 | runt-related transcription factor 3 | RUNX3 |
| 220958_at | 245.4 | 213.8 | 499 | 8.5 | 36 | unc-51-like kinase 4 (C. elegans) | ULK4 |
| 222179_at | 238.6 | 189 | 550.6 | 10.6 | 36 | — | — |
| 212249_at | 431.4 | 395.5 | 1226.3 | 13.1 | 36 | phosphoinositide-3-kinase, regulatory subunit 1 (p85 alpha) | PIK3R1 |
| 208518_s_at | 126.8 | 86.6 | 604.3 | 7.5 | 36 | period homolog 2 (Drosophila) | PER2 |
| 211238_at | 102.8 | 72.7 | 447 | 3.6 | 36 | ADAM metallopeptidase domain 7 | ADAM7 |
| 200706_s_at | 2637 | 1168.1 | 2666 | 19.5 | 35 | lipopolysaccharide-induced TNF factor | LITAF |
| 200921_s_at | 12107.4 | 6043.1 | 18371.9 | 274.8 | 35 | B-cell translocation gene 1, anti-proliferative | BTG1 |
| 202705_at | 2491.5 | 1661.2 | 4425.3 | 26.5 | 35 | cyclin B2 | CCNB2 |
| 207078_at | 466.5 | 233.5 | 708.3 | 4.5 | 35 | mediator of RNA polymerase II transcription, subunit 6 homolog (yeast) | MED6 |

TABLE 2-continued

Probesets underexpressed in 25% of more of B-lineage ALL cases (n = 270) as compared to normal bone marrow CD19+CD10+ cells from 4 healthy donors

| probe set ID | CD10+ CD19+ max | CD10+ CD19+ min | ALL max | ALL min | % ALL under expressed | Title | Symbol |
|---|---|---|---|---|---|---|---|
| 207522_s_at | 6423.6 | 2981.6 | 5910.6 | 75.5 | 35 | ATPase, Ca++ transporting, ubiquitous | ATP2A3 |
| 209464_at | 1253.5 | 825.7 | 1454.9 | 84.5 | 35 | aurora kinase B | AURKB |
| 211647_x_at | 501.3 | 285.6 | 536.8 | 8.4 | 35 | Immunoglobulin heavy constant mu /// Immunoglobulin heavy constant mu | IGHM |
| 211998_at | 10496.3 | 4591.7 | 15151.5 | 702.8 | 35 | H3 histone, family 3B (H3.3B) | H3F3B |
| 212142_at | 1054.9 | 612.5 | 1543.4 | 69.3 | 35 | MCM4 minichromosome maintenance deficient 4 (*S. cerevisiae*) | MCM4 |
| 213691_at | 365.7 | 283.3 | 623.9 | 24.4 | 35 | — | — |
| 200810_s_at | 4607 | 3204.4 | 9656.1 | 380.4 | 35 | cold inducible RNA binding protein | CIRBP |
| 201006_at | 375.3 | 235.7 | 940.5 | 8.9 | 35 | peroxiredoxin 2 | PRDX2 |
| 208704_x_at | 3138 | 2390.2 | 6336.7 | 329 | 35 | amyloid beta (A4) precursor-like protein 2 | APLP2 |
| 214970_s_at | 151.6 | 83.9 | 396.6 | 3.1 | 35 | ST6 beta-galactosamide alpha-2,6-sialyltranferase 1 | ST6GAL1 |
| 41577_at | 756.4 | 535.7 | 4896.8 | 15.2 | 35 | protein phosphatase 1, regulatory (inhibitor) subunit 16B | PPP1R16B |
| 200853_at | 11838.3 | 7861.6 | 13501 | 1153 | 35 | H2A histone family, member Z | H2AFZ |
| 204612_at | 578.4 | 413.9 | 864.9 | 14.9 | 35 | protein kinase (cAMP-dependent, catalytic) inhibitor alpha | PKIA |
| 205406_s_at | 280.5 | 215.1 | 477.6 | 4.1 | 35 | sperm autoantigenic protein 17 | SPA17 |
| 208918_s_at | 1625.2 | 1160.2 | 1821 | 66.2 | 35 | NAD kinase | NADK |
| 212700_x_at | 382.6 | 287.1 | 543.5 | 19.2 | 35 | pleckstrin homology domain containing, family M (with RUN domain) member 1 | PLEKHM1 |
| 213229_at | 1470.2 | 945.1 | 2296.5 | 38.7 | 35 | Dicer1, Dcr-1 homolog (*Drosophila*) | DICER1 |
| 214405_at | 299.6 | 112.6 | 432.8 | 3.9 | 35 | CUG triplet repeat, RNA binding protein 2 | CUGBP2 |
| 215984_s_at | 360.6 | 181.1 | 484.1 | 9.6 | 35 | ADP-ribosylation factor related protein 1 | ARFRP1 |
| 216101_at | 338.3 | 223.6 | 553.7 | 12.7 | 35 | Hypothetical protein LOC283755 | LOC283755 |
| 222366_at | 1123.1 | 633.7 | 1108.5 | 107.5 | 35 | Activity-dependent neuroprotector | ADNP |
| 209053_s_at | 1604.8 | 927.6 | 3584.9 | 27.4 | 35 | Wolf-Hirschhorn syndrome candidate 1 | WHSC1 |
| 217784_at | 442.5 | 209.6 | 2269.5 | 16.8 | 35 | SNARE protein Ykt6 | YKT6 |
| 210279_at | 1545.9 | 595.5 | 3675 | 9.7 | 35 | G protein-coupled receptor 18 | GPR18 |
| 219785_s_at | 152.6 | 84.4 | 584.7 | 3.9 | 35 | F-box protein 31 | FBXO31 |
| 41397_at | 321.1 | 264.6 | 939.1 | 12.2 | 35 | hypothetical protein LOC55565 | LOC55565 |
| 220799_at | 139.2 | 44.1 | 500.8 | 2.7 | 35 | glial cells missing homolog 2 (*Drosophila*) | GCM2 |
| 208072_s_at | 4341.9 | 2975.7 | 14061.5 | 145.3 | 35 | diacylglycerol kinase, delta 130 kDa | DGKD |
| 213580_at | 96 | 72.6 | 341.5 | 3 | 35 | — | — |
| 220842_at | 104.2 | 82.3 | 458.1 | 4.6 | 35 | Abelson helper integration site | AHI1 |
| 220450_at | 706.7 | 410.9 | 2373.9 | 13 | 35 | — | — |
| 210932_s_at | 157.8 | 61.9 | 314.6 | 3 | 34 | ring finger protein (C3H2C3 type) 6 | RNF6 |
| 212079_s_at | 714.5 | 393.5 | 900.7 | 6.9 | 34 | myeloid/lymphoid or mixed-lineage leukemia (trithorax homolog, *Drosophila*) | MLL |
| 213036_x_at | 6399.2 | 4049.5 | 6841.1 | 79.3 | 34 | ATPase, Ca++ transporting, ubiquitous | ATP2A3 |
| 213726_x_at | 7796.1 | 5120 | 13306.9 | 910.2 | 34 | tubulin, beta, 2 | TUBB2 |
| 214041_x_at | 6122.7 | 1995.5 | 4462.5 | 365.8 | 34 | Ribosomal protein L37a | RPL37A |
| 214463_x_at | 1049.2 | 311 | 1545.7 | 16.6 | 34 | histone 1, H4k /// histone 1, H4j | HIST1H4K /// HIST1H4J |
| 214557_at | 170.5 | 55.5 | 277.9 | 2.4 | 34 | pituitary tumor-transforming 2 | PTTG2 |
| 215339_at | 149.9 | 25.5 | 249.9 | 1.4 | 34 | natural killer-tumor recognition sequence | NKTR |
| 222352_at | 327.4 | 242.8 | 480.9 | 12.4 | 34 | F-box protein 31 | FBXO31 |
| 205003_at | 222.6 | 145.7 | 554.2 | 3.2 | 34 | dedicator of cytokinesis 4 | DOCK4 |
| 210610_at | 235.6 | 157 | 554.7 | 15.4 | 34 | carcinoembryonic antigen-related cell adhesion molecule 1 (biliary glycoprotein) | CEACAM1 |
| 212019_at | 180.4 | 108.3 | 415.5 | 2.8 | 34 | ribosomal L1 domain containing 1 | RSL1D1 |
| 213674_x_at | 2559.9 | 1457.1 | 7346.2 | 20.9 | 34 | immunoglobulin heavy constant delta | IGHD |
| 217697_at | 169 | 105.4 | 535.4 | 2.7 | 34 | FYN oncogene related to SRC, FGR, YES | FYN |
| 205301_s_at | 112.2 | 99.8 | 329.2 | 6.8 | 34 | 8-oxoguanine DNA glycosylase | OGG1 |
| 218949_s_at | 3172.1 | 2003.8 | 7319.2 | 179.9 | 34 | glutaminyl-tRNA synthase (glutamine-hydrolyzing)-like 1 | QRSL1 |
| 201498_at | 2576.2 | 1649.1 | 2581.9 | 338 | 34 | Unknown protein | USP7 |
| 201678_s_at | 3884.7 | 2665.8 | 3904 | 398.1 | 34 | DC12 protein | DC12 |
| 215581_s_at | 554.5 | 340.7 | 728.1 | 5.6 | 34 | MCM3 minichromosome maintenance deficient 3 (*S. cerevisiae*) associated protein | MCM3AP |
| 220018_at | 412.3 | 263.1 | 462.6 | 4.9 | 34 | Cas-Br-M (murine) ecotropic retroviral transforming sequence-like 1 | CBLL1 |
| 220286_at | 354.5 | 271 | 686.7 | 18.3 | 34 | myotubularin related protein 10 | MTMR10 |
| 222150_s_at | 3354 | 1546.8 | 3922.1 | 23.6 | 34 | hypothetical protein LOC54103 | LOC54103 |
| 66053_at | 271.2 | 83.3 | 409.2 | 4.2 | 34 | heterogeneous nuclear ribonucleoprotein U-like 2 | HNRPUL2 |
| 204947_at | 723.2 | 647 | 1959.6 | 45.5 | 34 | E2F transcription factor 1 | E2F1 |
| 215006_at | 1050.5 | 675.3 | 2162 | 55.9 | 34 | — | — |
| 220328_at | 168.9 | 122.6 | 339.6 | 4.4 | 34 | polyhomeotic like 3 (*Drosophila*) | PHC3 |
| 221976_s_at | 149.4 | 108.1 | 825.1 | 5.5 | 34 | Hepatoma-derived growth factor, related protein 3 | HDGFRP3 |
| 202387_at | 1578.7 | 1163.7 | 8122.2 | 230.8 | 34 | BCL2-associated athanogene /// BCL2-associated athanogene | BAG1 |
| 203760_s_at | 923.5 | 364.7 | 2249.3 | 14.1 | 34 | Src-like-adaptor /// Src-like-adaptor | SLA |
| 204324_s_at | 181.4 | 92.4 | 623 | 7.3 | 34 | golgi phosphoprotein 4 | GOLPH4 |
| 221276_s_at | 163.9 | 135.8 | 455.1 | 4.3 | 34 | syncoilin, intermediate filament 1 /// syncoilin, intermediate filament 1 | SYNC1 |
| 215407_s_at | 96.3 | 67.7 | 288.5 | 4.4 | 34 | astrotactin 2 | ASTN2 |

TABLE 2-continued

Probesets underexpressed in 25% of more of B-lineage ALL cases (n = 270) as compared to normal bone marrow CD19+CD10+ cells from 4 healthy donors

| probe set ID | CD10+ CD19+ max | CD10+ CD19+ min | ALL max | ALL min | % ALL under expressed | Title | Symbol |
|---|---|---|---|---|---|---|---|
| 210393_at | 418.7 | 136.2 | 3640.2 | 12.5 | 34 | leucine-rich repeat-containing G protein-coupled receptor 5 | LGR5 |
| 200671_s_at | 1392.9 | 702.6 | 2278.6 | 8.7 | 34 | spectrin, beta, non-erythrocytic 1 | SPTBN1 |
| 202589_at | 17240.3 | 13462.3 | 20596.6 | 380.9 | 34 | thymidylate synthetase | TYMS |
| 203742_s_at | 743 | 677.9 | 1213.6 | 7 | 34 | thymine-DNA glycosylase | TDG |
| 219624_at | 223.1 | 129.3 | 345.4 | 5.6 | 34 | BCL2-associated athanogene 4 | BAG4 |
| 76897_s_at | 236.7 | 80.5 | 371.7 | 3.4 | 34 | KIAA0674 | KIAA0674 |
| 204826_at | 534.2 | 443.9 | 1446.3 | 37.3 | 34 | cyclin F | CCNF |
| 210517_s_at | 3300.7 | 1353.1 | 9242.7 | 11 | 34 | A kinase (PRKA) anchor protein (gravin) 12 | AKAP12 |
| 211039_at | 168.1 | 70.9 | 868.7 | 7 | 34 | cholinergic receptor, nicotinic, alpha polypeptide 1 (muscle) /// cholinergic receptor, nicotinic, alpha polypeptide 1 (muscle) | CHRNA1 |
| 219778_at | 102.8 | 76.6 | 310.6 | 2.8 | 34 | zinc finger protein, multitype 2 | ZFPM2 |
| 207573_x_at | 11632.8 | 10131.6 | 12633.1 | 2167.8 | 33 | ATP synthase, H+ transporting, mitochondrial F0 complex, subunit g | ATP5L |
| 211919_s_at | 29614.3 | 23208.6 | 54252.2 | 1497.1 | 33 | chemokine (C—X—C motif) receptor 4 /// chemokine (C—X—C motif) receptor 4 | CXCR4 |
| 211936_at | 9520.1 | 4084.9 | 9404.7 | 325.9 | 33 | heat shock 70 kDa protein 5 (glucose-regulated protein, 78 kDa) | HSPA5 |
| 219876_s_at | 314.1 | 140 | 513.2 | 9 | 33 | hypotheticalprotein DKFZp434M0331 | DKFZp434M0331 |
| 221557_s_at | 728.3 | 173.4 | 1429.9 | 6.4 | 33 | lymphoid enhancer-binding factor 1 | LEF1 |
| 201085_s_at | 3189.8 | 1357.3 | 13637.2 | 73 | 33 | SON DNA binding protein | SON |
| 201586_s_at | 8569.9 | 5652.5 | 17622.8 | 1201.6 | 33 | splicing factor proline/glutamine-rich (polypyrimidine tract binding protein associated) | SFPQ |
| 212733_at | 2061.3 | 1548.7 | 5477 | 216.4 | 33 | KIAA0226 | KIAA0226 |
| 217930_s_at | 284.2 | 214.8 | 636.1 | 9.5 | 33 | toll interacting protein | TOLLIP |
| 202509_s_at | 258 | 105.5 | 790.5 | 11.1 | 33 | tumor necrosis factor, alpha-induced protein 2 | TNFAIP2 |
| 209936_at | 357.6 | 274.7 | 869.6 | 6.4 | 33 | RNA binding motif protein 5 | RBM5 |
| 214284_s_at | 193 | 132 | 753.1 | 5.6 | 33 | Fibroblast growth factor 18 | FGF18 |
| 215820_x_at | 210.4 | 160 | 460.9 | 5.9 | 33 | sorting nexin 13 | SNX13 |
| 206700_s_at | 1479.6 | 229 | 4109.1 | 15.1 | 33 | Smcy homolog, Y-linked (mouse) | SMCY |
| 204262_s_at | 194 | 123.5 | 506.5 | 7.3 | 33 | presenilin 2 (Alzheimer disease 4) | PSEN2 |
| 204049_s_at | 168.2 | 135.5 | 479.6 | 7.5 | 33 | phosphatase and actin regulator 2 | PHACTR2 |
| 207781_s_at | 194.5 | 118.1 | 751 | 1.1 | 33 | zinc finger protein 6 (CMPX1) | ZNF6 |
| 205712_at | 235.6 | 181 | 1105.9 | 6.4 | 33 | protein tyrosine phosphatase, receptor type, D | PTPRD |
| 204114_at | 864.4 | 304.3 | 4631.7 | 12 | 33 | nidogen 2 (osteonidogen) | NID2 |
| 202412_s_at | 2463.6 | 945.5 | 1998.4 | 58.6 | 33 | ubiquitin specific peptidase 1 | USP1 |
| 202575_at | 280.6 | 207.3 | 482 | 13.4 | 33 | cellular retinoic acid binding protein 2 | CRABP2 |
| 205249_at | 225.3 | 75.4 | 367.7 | 11.7 | 33 | early growth response 2 (Krox-20 homolog, Drosophila) | EGR2 |
| 219237_s_at | 509.8 | 349.6 | 583.8 | 10 | 33 | DnaJ (Hsp40) homolog, subfamily B, member 14 | DNAJB14 |
| 203331_s_at | 1079.1 | 847.9 | 2665.7 | 30.2 | 33 | inositol polyphosphate-5-phosphatase, 145 kDa | INPP5D |
| 214615_at | 257.5 | 190.8 | 516.5 | 7.4 | 33 | purinergic receptor P2Y, G-protein coupled, 10 | P2RY10 |
| 205632_s_at | 1124.2 | 750.9 | 2645.1 | 88.4 | 33 | phosphatidylinositol-4-phosphate 5-kinase, type I, beta | PIP5K1B |
| 214984_at | 147.5 | 93.4 | 521.2 | 2 | 33 | PI-3-kinase-related kinase SMG-1 | SMG1 |
| 202732_at | 876.3 | 589.3 | 2260.7 | 28.7 | 33 | protein kinase (cAMP-dependent, catalytic) inhibitor gamma | PKIG |
| 213538_at | 2967.3 | 1774.8 | 9703.8 | 472.3 | 33 | SON DNA binding protein | SON |
| 210592_s_at | 4102.2 | 3018.5 | 15575.9 | 276.3 | 33 | spermidine/spermine N1-acetyltransferase | SAT |
| 214254_at | 118.5 | 73.8 | 391.7 | 4.1 | 33 | melanoma antigen family A, 4 | MAGEA4 |
| 209465_x_at | 88.2 | 60.5 | 352.3 | 3.3 | 33 | pleiotrophin (heparin binding growth factor 8, neurite growth-promoting factor 1) | PTN |
| 221980_at | 140 | 114.6 | 428.9 | 12.9 | 33 | Elastin microfibril interfacer 2 | EMILIN2 |
| 205617_at | 348.8 | 147.5 | 454.9 | 6.4 | 33 | proline rich Gla (G-carboxyglutamic acid) 2 | PRRG2 |
| 212382_at | 4841.3 | 2575.4 | 7602.8 | 80.3 | 33 | Transcription factor 4 | TCF4 |
| 213146_at | 580.7 | 260.3 | 1033.7 | 9.3 | 33 | — | — |
| 215016_x_at | 293 | 100.3 | 581.8 | 4.1 | 33 | dystonin | DST |
| 215464_s_at | 1495.7 | 546 | 891 | 15.1 | 33 | Tax1 (human T-cell leukemia virus type I) binding protein 3 | TAX1BP3 |
| 219233_s_at | 742.2 | 542 | 1209.2 | 18.8 | 33 | gasdermin-like | GSDML |
| 220843_s_at | 286.7 | 139.9 | 402.3 | 5.6 | 33 | WD repeats and SOF1 domain containing | WDSOF1 |
| 206566_at | 139.4 | 84.4 | 328.6 | 3.9 | 33 | solute carrier family 7 (cationic amino acid transporter, y+ system), member 1 | SLC7A1 |
| 209037_s_at | 441.2 | 245.2 | 1038.9 | 9.6 | 33 | EH-domain containing 1 | EHD1 |
| 204525_at | 119.9 | 94.7 | 373.2 | 1.3 | 33 | PHD finger protein 14 | PHF14 |
| 207604_s_at | 498.4 | 299.6 | 1302.9 | 6 | 33 | solute carrier family 4, sodium bicarbonate cotransporter, member 7 | SLC4A7 |
| 218480_at | 322.2 | 291.5 | 680.8 | 22.7 | 33 | hypothetical protein FLJ21839 | FLJ21839 |
| 215112_x_at | 62.4 | 14.6 | 597.2 | 0.3 | 33 | MCF.2 cell line derived transforming sequence-like 2 | MCF2L2 |
| 207462_at | 263 | 165.5 | 1053.5 | 5.7 | 33 | glycine receptor, alpha 2 | GLRA2 |
| 207334_s_at | 239.9 | 113.8 | 971.7 | 5.8 | 33 | transforming growth factor, beta receptor II (70/80 kDa) | TGFBR2 |
| 220570_at | 180.4 | 89.6 | 3075.1 | 7 | 33 | resistin | RETN |
| 213745_at | 87.6 | 50.3 | 363.4 | 2.4 | 33 | attractin-like 1 | ATRNL1 |
| 202533_s_at | 711 | 317.8 | 704.1 | 12.5 | 32 | dihydrofolate reductase | DHFR |
| 203795_s_at | 3293 | 2438.1 | 5241.7 | 239.2 | 32 | B-cell CLL/lymphoma 7A | BCL7A |

TABLE 2-continued

Probesets underexpressed in 25% of more of B-lineage ALL cases (n = 270) as compared to normal bone marrow CD19+CD10+ cells from 4 healthy donors

| probe set ID | CD10+ CD19+ max | CD10+ CD19+ min | ALL max | ALL min | % ALL under expressed | Title | Symbol |
|---|---|---|---|---|---|---|---|
| 211200_s_at | 374.4 | 97.7 | 390.5 | 4.4 | 32 | EF-hand calcium binding domain 2 | EFCAB2 |
| 212629_s_at | 983.6 | 762.4 | 1470.6 | 49.1 | 32 | protein kinase N2 | PKN2 |
| 218262_at | 765.3 | 563.6 | 1191.6 | 48.3 | 32 | hypothetical protein FLJ22318 | FLJ22318 |
| 218802_at | 2316.7 | 1822.3 | 2483.5 | 42.4 | 32 | hypothetical protein FLJ20647 | FLJ20647 |
| 222032_s_at | 461.1 | 241.6 | 508.1 | 13.7 | 32 | Unknown protein | USP7 |
| 206997_s_at | 210.7 | 71.6 | 498.5 | 7.4 | 32 | heparan sulfate 6-O-sulfotransferase 1 | HS6ST1 |
| 213922_at | 481.2 | 199.2 | 1028.1 | 2.3 | 32 | tau tubulin kinase 2 | TTBK2 |
| 60084_at | 281 | 130 | 624.4 | 5 | 3 | cylindromatosis (turban tumor syndrome) | CYLD |
| 207712_at | 163 | 88 | 395.3 | 4 | 3 | B melanoma antigen | BAGE |
| 216709_at | 153.8 | 103.2 | 482.7 | 6.5 | 3 | Hypothetical gene supported by BC013370; BC034583 | LOC400655 |
| 205385_at | 124.8 | 79.1 | 691.4 | 8.7 | 3 | Mdm2, transformed 3T3 cell double minute 2, p53 binding protein (mouse) | MDM2 |
| 209524_at | 432.4 | 154.3 | 1100.3 | 3.9 | 3 | hepatoma-derived growth factor, related protein 3 | HDGFRP3 |
| 204688_a | 283.8 | 139.5 | 1709.8 | 5.6 | 3 | sarcoglycan, epsilon | SGCE |
| 212092_at | 323.4 | 177.7 | 27725.6 | 6.4 | 3 | paternally expressed 10 | PEG10 |
| 203317_at | 1832.1 | 859.6 | 1426.6 | 133.2 | 3 | pleckstrin and Sec7 domain containing 4 | PSD4 |
| 204335_at | 487.2 | 62.9 | 856 | 8.4 | 3 | hypothetical protein FLJ10374 | FLJ10374 |
| 208548_at | 162.5 | 66.9 | 324.4 | 3.4 | 3 | interferon, alpha 6 | IFNA6 |
| 208608_s_at | 337.6 | 133.3 | 587.1 | 10.4 | 3 | syntrophin, beta 1 (dystrophin-associated protein A1, 59 kDa, basic component 1) | SNTB1 |
| 214305_s_at | 4659 | 3426.8 | 5099.6 | 498.5 | 3 | splicing factor 3b, subunit 1, 155 kDa | SF3B1 |
| 214744_s_at | 279.5 | 117.4 | 349.2 | 7.6 | 3 | Similar to Zgc: 73149 protein | LOC442209 |
| 219814_at | 450.4 | 149.4 | 788.7 | 10 | 3 | muscleblind-like 3 (*Drosophila*) | MBNL3 |
| 205840_x_at | 798.1 | 421.9 | 2064.1 | 14.2 | 3 | growth hormone 1 | GH1 |
| 210961_s_at | 171.3 | 91.8 | 415.9 | 3.7 | 3 | adrenergic, alpha-1D-, receptor | ADRA1D |
| 211192_s_at | 431 | 237.8 | 881.3 | 8.3 | 3 | CD84 antigen (leukocyte antigen) | CD84 |
| 213799_s_at | 370.5 | 198.3 | 755 | 14.3 | 3 | protein tyrosine phosphatase, receptor type, A | PTPRA |
| 220729_at | 151.5 | 60.7 | 336.3 | 2.6 | 3 | — | — |
| 207238_s_at | 2281.5 | 1823 | 5647.1 | 43.2 | 3 | protein tyrosine phosphatase, receptor type, C | PTPRC |
| 214971_s_at | 275.6 | 125.8 | 787.6 | 7.8 | 3 | ST6 beta-galactosamide alpha-2,6-sialyltransferase 1 | ST6GAL1 |
| 213988_s_at | 943.7 | 577.2 | 4736.9 | 24.4 | 3 | spermidine/spermine N1-acetyltransferase | SAT |
| 201584_s_at | 5701.3 | 3803.1 | 5988.4 | 552.8 | 3 | DEAD (Asp-Glu-Ala-Asp) box polypeptide 39 | DDX39 |
| 205308_at | 426.6 | 135.5 | 505.4 | 3.9 | 3 | chromosome 8 open reading frame 70 | C8orf70 |
| 208977_x_at | 9681.5 | 5369.7 | 14888.5 | 972 | 3 | tubulin, beta, 2 | TUBB2 |
| 210466_s_at | 5244.2 | 3388 | 6177 | 820.6 | 3 | SERPINE1 mRNA binding protein 1 | SERBP1 |
| 213725_x_at | 1418.9 | 780.6 | 1815.3 | 69.9 | 3 | hypothetical protein LOC283824 | LOC283824 |
| 218176_at | 1009.6 | 548.2 | 1460.3 | 10.6 | 3 | melanoma antigen family F, 1 | MAGEF1 |
| 41037_at | 189.6 | 101.1 | 356.3 | 6.6 | 3 | TEA domain family member 4 | TEAD4 |
| 207470_at | 181.1 | 83.8 | 435.3 | 3.2 | 3 | hypothetical protein DKFZp566H0824 | DKFZp566H0824 |
| 209083_at | 3910.9 | 3369.5 | 9674.6 | 516.6 | 3 | coronin, actin binding protein, 1A | CORO1A |
| 210741_at | 116 | 54.2 | 258.8 | 2.9 | 3 | Rho guanine nucleotide exchange factor (GEF) 12 | ARHGEF12 |
| 219106_s_at | 83.2 | 24.4 | 781.6 | 1.2 | 3 | kelch repeat and BTB (POZ) domain containing 10 | KBTBD10 |
| 33646_g_at | 325.7 | 251.1 | 1119.4 | 4.5 | 3 | GM2 ganglioside activator | GM2A |
| 215002_at | 116.2 | 32 | 583.2 | 2 | 31 | KIAA0220-like protein /// hypothetical gene LOC283846 /// hypothetical protein 348162 /// NPIP-like locus /// hypothetical protein LOC440345 /// PI-3-kinase-related kinase SMG-1 pseudogene | LOC23117 /// DKFZp547E087 /// LOC348162 /// LOC388221 /// LOC440345 /// LOC440354 |
| 209526_s_at | 622.2 | 426.6 | 1995 | 9.3 | 31 | hepatoma-derived growth factor, related protein 3 | HDGFRP3 |
| 201005_at | 6598.1 | 4694.1 | 25569.7 | 11.4 | 31 | CD9 antigen (p24) | CD9 |
| 206247_at | 1394.4 | 1038.9 | 1334.3 | 166.5 | 31 | MHC class I polypeptide-related sequence B | MICB |
| 212315_s_at | 453.7 | 257.2 | 856.9 | 11.4 | 31 | nucleoporin 210 kDa | NUP210 |
| 215855_at | 732.8 | 504.4 | 1338.6 | 36.5 | 31 | TATA element modulatory factor 1 | TMF1 |
| 218992_at | 547.1 | 338.7 | 925.8 | 19.4 | 31 | chromosome 9 open reading frame 46 | C9orf46 |
| 222023_at | 270 | 146.6 | 382 | 3.6 | 31 | A kinase (PRKA) anchor protein 13 | AKAP13 |
| 207829_s_at | 305.6 | 252.4 | 665.6 | 31.3 | 31 | BCL2/adenovirus E1B 19 kDa interacting protein 1 | BNIP1 |
| 215728_s_at | 353.9 | 258.2 | 713.1 | 16.8 | 31 | acyl-CoA thioesterase 7 | ACOT7 |
| 218279_s_at | 217.1 | 138.9 | 700.8 | 3.3 | 31 | histone 2, H2aa | HIST2H2AA |
| 220623_s_at | 152.1 | 108.2 | 339.2 | 4.7 | 31 | testis specific, 10 | TSGA10 |
| 203245_s_at | 253.2 | 176 | 590.9 | 10.2 | 31 | FLJ35348 | FLJ35348 |
| 203298_s_at | 2224.3 | 1657 | 4931.3 | 308.5 | 31 | Jumonji, AT rich interactive domain 2 | JARID2 |
| 208622_s_at | 8534.4 | 2241.9 | 17271.3 | 137.7 | 31 | villin 2 (ezrin) | VIL2 |
| 209388_at | 861.1 | 717.7 | 2495.5 | 65.9 | 31 | poly(A) polymerase alpha | PAPOLA |
| 222074_at | 197.2 | 71.6 | 1101.8 | 2.2 | 31 | uroporphyrinogen decarboxylase | UROD |
| 211299_s_at | 235.5 | 221.3 | 561.1 | 9.5 | 31 | flotillin 2 | FLOT2 |
| 214240_at | 152.7 | 133.8 | 416.1 | 9.6 | 31 | galanin | GAL |
| 215037_s_at | 900.5 | 530.2 | 6759 | 19.6 | 31 | BCL2-like 1 | BCL2L1 |
| 215163_at | 177.2 | 41.2 | 971.9 | 4.6 | 31 | — | — |

TABLE 2-continued

Probesets underexpressed in 25% of more of B-lineage ALL cases (n = 270) as compared to normal bone marrow CD19+CD10+ cells from 4 healthy donors

| probe set ID | CD10+ CD19+ max | CD10+ CD19+ min | ALL max | ALL min | % ALL under expressed | Title | Symbol |
|---|---|---|---|---|---|---|---|
| 215694_at | 113.4 | 92.2 | 345 | 3.2 | 31 | spermatogenesis associated 5-like 1 | SPATA5L1 |
| 219073_s_at | 282.2 | 200.3 | 1001.9 | 3.4 | 31 | oxysterol binding protein-like 10 | OSBPL10 |
| 214337_at | 63.6 | 30.2 | 363.5 | 1.6 | 31 | coatomer protein complex, subunit alpha | COPA |
| 207339_s_at | 2085.6 | 1712.7 | 24613.4 | 77.1 | 31 | lymphotoxin beta (TNF superfamily, member 3) | LTB |
| 201580_s_at | 1692.5 | 1189.9 | 1675.7 | 160.3 | 31 | thioredoxin domain containing 13 | TXNDC13 |
| 201694_s_at | 2112.8 | 467.7 | 3888.6 | 23.7 | 31 | early growth response 1 | EGR1 |
| 207999_s_at | 667.3 | 514.6 | 836 | 69.8 | 31 | adenosine deaminase, RNA-specific, B1 (RED1 homolog rat) | ADARB1 |
| 212744_at | 279.5 | 267 | 498.4 | 11 | 31 | Bardet-Biedl syndrome 4 | BBS4 |
| 212810_s_at | 873.7 | 577.3 | 931.9 | 28.4 | 31 | solute carrier family 1 (glutamate/neutral amino acid transporter), member 4 | SLC1A4 |
| 217203_at | 192.4 | 68.4 | 327.3 | 3.5 | 31 | — | — |
| 217893_s_at | 1798.4 | 767.9 | 2805.8 | 20.5 | 31 | chromosome 1 open reading frame 108 | C1orf108 |
| 220529_at | 580.9 | 275.3 | 598.2 | 22.9 | 31 | hypothetical protein FLJ11710 | FLJ11710 |
| 221436_s_at | 693.1 | 377.3 | 1276.4 | 10 | 31 | cell division cycle associated 3 /// cell division cycle associated 3 | CDCA3 |
| 206919_at | 185.6 | 109.2 | 552.5 | 3 | 31 | ELK4, ETS-domain protein (SRF accessory protein 1) | ELK4 |
| 210928_at | 179.2 | 64.4 | 491.1 | 6.8 | 31 | CCR4-NOT transcription complex, subunit 2 | CNOT2 |
| 217602_at | 183 | 98.6 | 704.3 | 3.7 | 31 | peptidylprolyl isomerase A (cyclophilin A) | PPIA |
| 213523_at | 555.5 | 373.4 | 1967.5 | 13.8 | 31 | cyclin E1 | CCNE1 |
| 204362_at | 872 | 628.3 | 3033.3 | 9.9 | 31 | src family associated phosphoprotein 2 | SCAP2 |
| 204686_at | 255 | 163.7 | 1166.5 | 5.3 | 31 | insulin receptor substrate 1 | IRS1 |
| 214627_at | 398 | 173.9 | 5293.7 | 16.9 | 31 | eosinophil peroxidase | EPX |
| 215139_at | 95.2 | 54.9 | 314.1 | 3.6 | 31 | Rho guanine nucleotide exchange factor (GEF) 10 | ARHGEF10 |
| 215767_at | 119 | 73.9 | 582.8 | 4.6 | 31 | chromosome 2 open reading frame 10 | C2orf10 |
| 203827_at | 148.4 | 66.5 | 727 | 3.9 | 31 | WD40 repeat protein Interacting with phosphoInositides of 49 kDa | WIPI49 |
| 201364_s_at | 1746.5 | 1321.9 | 2921.9 | 120.9 | 30 | ornithine decarboxylase antizyme 2 | OAZ2 |
| 202413_s_at | 4532.3 | 3194.3 | 4483.5 | 763.6 | 30 | ubiquitin specific peptidase 1 | USP1 |
| 202971_s_at | 851 | 538 | 1188.6 | 8.7 | 30 | dual-specificity tyrosine-(Y)-phosphorylation regulated kinase 2 | DYRK2 |
| 205367_at | 2237.6 | 1328.9 | 3421.3 | 68.2 | 30 | adaptor protein with pleckstrin homology and src homology 2 domains | APS |
| 208076_at | 558.8 | 407.3 | 705.1 | 12.5 | 30 | histone 1, H4d | HIST1H4D |
| 209152_s_at | 3493.2 | 1505.9 | 2674.6 | 248.4 | 30 | transcription factor 3 (E2A immunoglobulin enhancer binding factors E12/E47) | TCF3 |
| 212525_s_at | 908.7 | 543.6 | 1204.8 | 13.5 | 30 | H2A histone family, member X | H2AFX |
| 215024_at | 355.8 | 228.8 | 464.7 | 9 | 30 | chromosome 7 open reading frame 28B | C7orf28B |
| 219426_at | 570 | 329.1 | 586.4 | 42.2 | 30 | eukaryotic translation initiation factor 2C, 3 | EIF2C3 |
| 222349_x_at | 185.8 | 110.7 | 350.5 | 8.6 | 30 | ring finger protein 126 pseudogene 1 | RNF126P1 |
| 204935_at | 112.6 | 32.6 | 258.5 | 1.9 | 30 | protein tyrosine phosphatase, non-receptor type 2 | PTPN2 |
| 215992_s_at | 226.5 | 128.2 | 899.5 | 7.8 | 30 | Rap guanine nucleotide exchange factor (GEF) 2 | RAPGEF2 |
| 209967_s_at | 134.8 | 43 | 415.7 | 5.5 | 30 | cAMP responsive element modulator | CREM |
| 204286_s_at | 1054.4 | 645.4 | 6785.1 | 27 | 30 | phorbol-12-myristate-13-acetate-induced protein 1 | PMAIP1 |
| 206390_x_at | 349.1 | 275 | 5566.7 | 21.4 | 30 | platelet factor 4 (chemokine (C—X—C motif) ligand 4) | PF4 |
| 220270_at | 142.4 | 102.5 | 516.2 | 5.9 | 30 | tudor domain containing 4 | TDRD4 |
| 204396_s_at | 363.5 | 249.8 | 3619.7 | 4.4 | 30 | G protein-coupled receptor kinase 5 | GRK5 |
| 202305_s_at | 1106 | 859.8 | 1483.5 | 59.9 | 30 | fasciculation and elongation protein zeta 2 (zygin II) | FEZ2 |
| 203297_s_at | 3578.4 | 2269.2 | 4416 | 249.5 | 30 | Jumonji, AT rich interactive domain 2 | JARID2 |
| 203311_s_at | 1645.4 | 1021.3 | 3135 | 78.6 | 30 | ADP-ribosylation factor 6 | ARF6 |
| 206965_at | 214.2 | 123.3 | 370.6 | 3.3 | 30 | Kruppel-like factor 12 | KLF12 |
| 208903_at | 848.2 | 783.6 | 1237.4 | 131.2 | 30 | Ribosomal protein S28 | RPS28 |
| 210050_at | 282.7 | 138 | 358.7 | 6.7 | 30 | triosephosphate isomerase 1 | TPI1 |
| 214656_x_at | 1723.7 | 865.9 | 1324.6 | 76.4 | 30 | myosin IC | MYO1C |
| 218913_s_at | 1248 | 564.3 | 1373.8 | 39.5 | 30 | GEM interacting protein | GMIP |
| 219840_s_at | 837.2 | 186.2 | 1234.8 | 8 | 30 | T-cell leukemia/lymphoma 6 | TCL6 |
| 205350_at | 194.6 | 78.9 | 417.2 | 8.8 | 30 | cellular retinoic acid binding protein 1 | CRABP1 |
| 206886_x_at | 816.4 | 315.5 | 2779.8 | 7.6 | 30 | growth hormone 1 | GH1 |
| 218851_s_at | 212 | 137 | 784.1 | 12.2 | 30 | WD repeat domain 33 | WDR33 |
| 201593_s_at | 2313.9 | 2053.5 | 5467.5 | 439.2 | 30 | likely ortholog of mouse immediate early response, erythropoietin 4 | LEREPO4 |
| 215212_at | 272 | 129.7 | 714.5 | 3.1 | 30 | CDNA FLJ12091 fis, clone HEMBB1002582 | — |
| 206361_at | 220.1 | 126 | 661.1 | 13 | 30 | G protein-coupled receptor 44 | GPR44 |
| 206489_s_at | 121.6 | 61.4 | 543.2 | 4.5 | 30 | discs, large (Drosophila) homolog-associated protein 1 | DLGAP1 |
| 202576_s_at | 828.5 | 524.2 | 1222.5 | 32.9 | 30 | DEAD (Asp-Glu-Ala-As) box polypeptide 19B /// DEAD (Asp-Glu-Ala-As) box polypeptide 19A /// DDX19-DDX19L protein | DDX19B /// DDX19A /// DDX19-DDX19L |
| 204982_at | 759.2 | 306.6 | 1312 | 18.5 | 30 | G protein-coupled receptor kinase interactor 2 | GIT2 |
| 209181_s_at | 2471.5 | 1445.9 | 3301 | 370.2 | 30 | Rab geranylgeranyltransferase, beta subunit | RABGGTB |
| 212119_at | 1486.3 | 1058.8 | 1840.8 | 181.7 | 30 | ras homolog gene family, member Q | RHOQ |
| 213971_s_at | 1705.5 | 1190 | 1646.9 | 278 | 30 | suppressor of zeste 12 homolog (Drosophila) | SUZ12 |
| 214314_s_at | 247.2 | 109.9 | 261.2 | 1.5 | 30 | eukaryotic translation initiation factor 5B | EIF5B |

TABLE 2-continued

Probesets underexpressed in 25% of more of B-lineage ALL cases (n = 270) as compared to normal bone marrow CD19+CD10+ cells from 4 healthy donors

| probe set ID | CD10+ CD19+ max | CD10+ CD19+ min | ALL max | ALL min | % ALL under expressed | Title | Symbol |
|---|---|---|---|---|---|---|---|
| 217914_at | 795.6 | 473.5 | 1574.4 | 36.4 | 30 | two pore segment channel 1 | TPCN1 |
| 219537_x_at | 612.7 | 151.4 | 710.1 | 10.7 | 30 | delta-like 3 (*Drosophila*) | DLL3 |
| 219892_at | 406.1 | 301.3 | 693.9 | 12.7 | 30 | transmembrane 6 superfamily member 1 | TM6SF1 |
| 200906_s_at | 196.9 | 84.1 | 443.8 | 5.7 | 30 | palladin | KIAA0992 |
| 213963_s_at | 296.6 | 119.6 | 722.2 | 9.6 | 30 | Sin3A-associated protein, 30 kDa | SAP30 |
| 33148_at | 202.2 | 153.4 | 456.9 | 5.9 | 30 | zinc finger RNA binding protein | ZFR |
| 212715_s_at | 313 | 179.1 | 744.1 | 6.8 | 30 | microtubule associated monoxygenase, calponin and LIM domain containing 3 | MICAL3 |
| 203845_at | 1062.2 | 644.3 | 5682 | 75.2 | 30 | p300/CBP-associated factor | PCAF |
| 216961_s_at | 162.2 | 126 | 401 | 11.5 | 30 | RPA interacting protein | RIP |
| 219841_at | 178.9 | 78.2 | 389.7 | 4.2 | 30 | activation-induced cytidine deaminase | AICDA |
| 216065_at | 170.2 | 63.4 | 574.6 | 4.9 | 30 | — | — |
| 220602_s_at | 180 | 97.5 | 579.2 | 6.4 | 30 | hypothetical protein FLJ22795 /// hypothetical protein FLJ90297 /// LOC388161 | FLJ22795 /// LOC388152 /// LOC388161 |
| 202391_at | 2179.6 | 964.3 | 13386.3 | 154.3 | 30 | brain abundant, membrane attached signal protein 1 | BASP1 |
| 216260_at | 100.5 | 73.4 | 440.8 | 4.9 | 30 | Dicer1, Dcr-1 homolog (*Drosophila*) | DICER1 |
| 200675_at | 12263.9 | 7362.2 | 14130.7 | 1142.6 | 29 | CD81 antigen (target of antiproliferative antibody 1) | CD81 |
| 209041_s_at | 876.8 | 610.3 | 1024.8 | 15 | 29 | ubiquitin-conjugating enzyme E2G 2 (UBC7 homolog, yeast) | UBE2G2 |
| 209060_x_at | 1380 | 753.8 | 1224.4 | 112.6 | 29 | nuclear receptor coactivator 3 | NCOA3 |
| 211279_at | 287.2 | 194.6 | 367.2 | 11 | 29 | nuclear respiratory factor 1 | NRF1 |
| 212680_x_at | 2180.1 | 1447 | 3705 | 43.5 | 29 | protein phosphatase 1, regulatory (inhibitor) subunit 14B | PPP1R14B |
| 214338_at | 292.1 | 245.2 | 539.1 | 11.6 | 29 | DnaJ (Hsp40) homolog, subfamily B, member 12 | DNAJB12 |
| 214838_at | 911.6 | 592.2 | 1570.7 | 30.9 | 29 | SFT2 domain containing 2 | SFT2D2 |
| 216350_s_at | 654.8 | 237.3 | 1216.9 | 11.5 | 29 | zinc finger protein 10 | ZNF10 |
| 78330_at | 539.8 | 377.5 | 856.9 | 42 | 29 | zinc finger protein 335 | ZNF335 |
| 211996_s_at | 8974.6 | 6702.7 | 21416.6 | 985.7 | 29 | KIAA0220-like protein /// hypothetical gene LOC283846 /// hypothetical protein 348162 /// PI-3-kinase-related kinase SMG-1 pseudogene /// similar to the PI-3-kinase-related kinase SMG-1 family pseudogene 2 | LOC23117 /// DKFZp547E087 /// LOC348162 /// LOC440354 /// LOC613037 |
| 215554_at | 111.1 | 48.1 | 454.1 | 2.4 | 29 | glycosylphosphatidylinositol specific phospholipase D1 | GPLD1 |
| 208348_s_at | 116.4 | 38 | 303.5 | 3.3 | 29 | Cas-Br-M (murine) ecotropic retroviral transforming sequence b | CBLB |
| 222205_x_at | 137.1 | 109.4 | 502.2 | 5.7 | 29 | Similar to hypothetical protein FLJ38374 | LOC400840 |
| 212750_at | 930.6 | 632 | 6690.7 | 15.9 | 29 | protein phosphatase 1, regulatory (inhibitor) subunit 16B | PPP1R16B |
| 39729_at | 1792.3 | 1477.1 | 23054 | 26.2 | 29 | peroxiredoxin 2 | PRDX2 |
| 201810_s_at | 1070.1 | 610.6 | 10902 | 33.6 | 29 | SH3-domain binding protein 5 (BTK-associated) | SH3BP5 |
| 202716_at | 2019.7 | 1174.5 | 1578.2 | 117.1 | 29 | protein tyrosine phosphatase, non-receptor type 1 | PTPN1 |
| 202781_s_at | 1392.7 | 858.7 | 1351.8 | 120.4 | 29 | skeletal muscle and kidney enriched inositol phosphatase | SKIP |
| 204817_at | 1160.2 | 785.1 | 1589.1 | 61.1 | 29 | extra spindle poles like 1 (*S. cerevisiae*) | ESPL1 |
| 214508_x_at | 418.7 | 356.9 | 732.4 | 21.5 | 29 | cAMP responsive element modulator | CREM |
| 215151_at | 278.2 | 98.2 | 400.7 | 6.6 | 29 | dedicator of cytokinesis 10 | DOCK10 |
| 221521_s_at | 1660.7 | 1195.7 | 2488.9 | 12.3 | 29 | DNA replication complex GINS protein PSF2 | Pfs2 |
| 203068_at | 278.5 | 56.5 | 1212.6 | 10.2 | 29 | kelch-like 21 (*Drosophila*) | KLHL21 |
| 205590_at | 1491.4 | 641.4 | 3396.4 | 11.1 | 29 | RAS guanyl releasing protein 1 (calcium and DAG-regulated) | RASGRP1 |
| 216449_x_at | 1656.1 | 608.9 | 3772 | 27.5 | 29 | tumor rejection antigen (gp96) 1 | TRA1 |
| 208068_x_at | 663.4 | 497.8 | 1784.6 | 30.3 | 29 | chorionic somatomammotropin hormone 1 (placental lactogen) /// chorionic somatomammotropin hormone 2 /// chorionic somatomammotropin hormone-like 1 /// growth hormone 1 /// growth hormone 2 | CSH1 /// CSH2 /// CSHL1 /// GH1 /// GH2 |
| 218888_s_at | 386.1 | 148.1 | 1168.2 | 5.5 | 29 | neuropilin (NRP) and tolloid (TLL)-like 2 | NETO2 |
| 221261_x_at | 492.8 | 164.3 | 1704.3 | 9.4 | 29 | melanoma antigen family D, 4 /// melanoma antigen family D, 4 | MAGED4 |
| 207772_s_at | 153.2 | 86.3 | 593.2 | 3.7 | 29 | HMT1 hnRNP methyltransferase-like 4 (*S. cerevisiae*) | HRMT1L4 |
| 215931_s_at | 180.6 | 43.6 | 533.8 | 5.3 | 29 | ADP-ribosylation factor guanine nucleotide-exchange factor 2 (brefeldin A-inhibited) | ARFGEF2 |
| 216184_s_at | 163.6 | 106.5 | 770.8 | 5.9 | 29 | regulating synaptic membrane exocytosis 1 | RIMS1 |
| 201718_s_at | 523.7 | 433.5 | 1918.3 | 9.7 | 29 | erythrocyte membrane protein band 4.1-like 2 | EPB41L2 |
| 220359_s_at | 546.9 | 178.5 | 15891.5 | 3.9 | 29 | cyclic AMP-regulated phosphoprotein, 21 kD | ARPP-21 |
| 201868_s_at | 147.6 | 120.5 | 611.9 | 3.7 | 29 | transducin (beta)-like 1X-linked | TBL1X |
| 202289_s_at | 157 | 84 | 1169.5 | 5.2 | 29 | transforming, acidic coiled-coil containing protein 2 | TACC2 |
| 220059_at | 777.8 | 473.2 | 9891.4 | 15.3 | 29 | BCR downstream signaling 1 | BRDG1 |
| 200704_at | 2127.5 | 1314.5 | 3636.2 | 50.4 | 29 | lipopolysaccharide-induced TNF factor | LITAF |
| 201396_s_at | 517.4 | 358.8 | 590.4 | 20.8 | 29 | small glutamine-rich tetratricopeptide repeat (TPR)-containing, alpha | SGTA |
| 201625_s_at | 730.7 | 607.5 | 1053.5 | 75.3 | 29 | insulin induced gene 1 | INSIG1 |

TABLE 2-continued

Probesets underexpressed in 25% of more of B-lineage ALL cases (n = 270) as compared to normal bone marrow CD19+CD10+ cells from 4 healthy donors

| probe set ID | CD10+ CD19+ max | CD10+ CD19+ min | ALL max | ALL min | % ALL under expressed | Title | Symbol |
|---|---|---|---|---|---|---|---|
| 201730_s_at | 3624.8 | 1911 | 4999.2 | 138.9 | 29 | translocated promoter region (to activated MET oncogene) | TPR |
| 207124_s_at | 422.6 | 208.9 | 510 | 13.9 | 29 | guanine nucleotide binding protein (G protein), beta 5 | GNB5 |
| 209052_s_at | 1267.4 | 568.8 | 2199.3 | 13.7 | 29 | Wolf-Hirschhorn syndrome candidate 1 | WHSC1 |
| 212035_s_at | 759.8 | 598.6 | 1203.5 | 58.5 | 29 | exocyst complex component 7 | EXOC7 |
| 215174_at | 249 | 135.5 | 491.3 | 8.6 | 29 | flavin containing monooxygenase 6 | FMO6 |
| 217370_x_at | 1147.3 | 737 | 1707.2 | 38.8 | 29 | fusion (involved in t(12; 16) in malignant liposarcoma) | FUS |
| 218812_s_at | 880.9 | 570.1 | 1354.3 | 76.4 | 29 | chromosome 7 open reading frame 19 | C7orf19 |
| 219094_at | 316.3 | 236.8 | 547.6 | 6.6 | 29 | armadillo repeat containing 8 | ARMC8 |
| 219174_at | 142.9 | 17.2 | 203.5 | 2.2 | 29 | coiled-coil domain containing 2 | CCDC2 |
| 221745_at | 849 | 567.4 | 1216.1 | 16.3 | 29 | WD repeat domain 68 | WDR68 |
| 215234_at | 198.1 | 112.5 | 396.3 | 7.1 | 29 | MRNA, trapped exon e1b7, DCR1-16.0, | — |
| 216573_at | 204.4 | 57.2 | 559.1 | 4.7 | 29 | Clone ds1-1 immunoglobulin lambda chain VJ region, (IGL) | — |
| 40837_at | 435.6 | 331 | 1225.2 | 34.9 | 29 | transducin-like enhancer of split 2 (E(sp1) homolog, Drosophila) | TLE2 |
| 203857_s_at | 1302.4 | 844.3 | 3509 | 46.3 | 29 | protein disulfide isomerase family A, member 5 | PDIA5 |
| 211088_s_at | 230 | 164.8 | 555.7 | 7.6 | 29 | polo-like kinase 4 (Drosophila) /// polo-like kinase 4 (Drosophila) | PLK4 |
| 211475_s_at | 2071.5 | 1680.1 | 8077 | 413 | 29 | BCL2-associated athanogene | BAG1 |
| 217127_at | 112.2 | 61.5 | 291.3 | 2 | 29 | cystathionase (cystathionine gamma-lyase) | CTH |
| 202286_s_at | 153.5 | 76.9 | 659.7 | 7.4 | 29 | tumor-associated calcium signal transducer 2 | TACSTD2 |
| 207517_at | 131.2 | 61 | 680.2 | 4.1 | 29 | laminin, gamma 2 | LAMC2 |
| 220784_s_at | 110.7 | 31.1 | 319.1 | 1.8 | 29 | urotensin 2 | UTS2 |
| 221152_at | 131.1 | 81.2 | 448 | 2.8 | 29 | collagen, type VIII, alpha 1 | COL8A1 |
| 207894_s_at | 269.4 | 156.9 | 687.1 | 21.3 | 29 | T-cell leukemia/lymphoma 6 | TCL6 |
| 201942_s_at | 133.4 | 82.9 | 588.8 | 4.7 | 29 | carboxypeptidase D | CPD |
| 206935_at | 54.9 | 18.9 | 294.4 | 0.8 | 29 | protocadherin 8 | PCDH8 |
| 211341_at | 1031 | 133.9 | 10201.6 | 2.1 | 29 | POU domain, class 4, transcription factor 1 | POU4F1 |
| 201598_s_at | 1332.6 | 1111.7 | 2082.9 | 189.5 | 28 | inositol polyphosphate phosphatase-like 1 | INPPL1 |
| 202769_at | 2932.9 | 1532.5 | 3398 | 190.4 | 28 | Cyclin G2 | CCNG2 |
| 202900_s_at | 1820.3 | 1430.3 | 2398.2 | 109.6 | 28 | nucleoporin 88 kDa | NUP88 |
| 203113_s_at | 12072.1 | 8841.5 | 11404.7 | 1180.8 | 28 | eukaryotic translation elongation factor 1 delta (guanine nucleotide exchange protein) | EEF1D |
| 207499_x_at | 922.1 | 720.5 | 1197.2 | 51.5 | 28 | smooth muscle cell associated protein-1 | SMAP-1 |
| 209535_s_at | 889.7 | 507.2 | 808.6 | 65.3 | 28 | — | — |
| 211352_s_at | 940.2 | 324.4 | 918.2 | 9.3 | 28 | nuclear receptor coactivator 3 | NCOA3 |
| 213286_at | 422.7 | 215.1 | 583.7 | 12.7 | 28 | zinc finger RNA binding protein | ZFR |
| 214052_x_at | 476.4 | 225.6 | 618.2 | 6.3 | 28 | BAT2 domain containing 1 | BAT2D1 |
| 214336_s_at | 1446.5 | 518.3 | 1121.1 | 62.6 | 28 | coatomer protein complex, subunit alpha | COPA |
| 215509_s_at | 771.4 | 220.1 | 1118.4 | 11 | 28 | BUB1 budding uninhibited by benzimidazoles 1 homolog (yeast) | BUB1 |
| 217966_s_at | 290.5 | 157.6 | 489.7 | 7.8 | 28 | chromosome 1 open reading frame 24 | C1orf24 |
| 219207_at | 373.8 | 241.9 | 568.8 | 6.8 | 28 | hypothetical protein FLJ21128 | FLJ21128 |
| 221611_s_at | 254.3 | 148.8 | 390.6 | 11.1 | 28 | PHD finger protein 7 | PHF7 |
| 211274_at | 165.9 | 85.1 | 342.9 | 8.3 | 28 | T-box 1 | TBX1 |
| 208023_at | 181.6 | 76.3 | 382.3 | 5.6 | 28 | tumor necrosis factor receptor superfamily, member 4 | TNFRSF4 |
| 216872_at | 120 | 52.7 | 514.8 | 1.8 | 28 | Hr44 antigen | HR44 |
| 203836_s_at | 444.9 | 329.7 | 1706 | 6.6 | 28 | mitogen-activated protein kinase kinase kinase 5 | MAP3K5 |
| 214651_s_at | 115.1 | 59.9 | 7233.4 | 3 | 28 | homeo box A9 | HOXA9 |
| 201843_s_at | 109.6 | 78.2 | 7630.9 | 4.4 | 28 | EGF-containing fibulin-like extracellular matrix protein 1 | EFEMP1 |
| 203241_at | 1066.4 | 834.5 | 1885.9 | 152.9 | 28 | UV radiation resistance associated gene | UVRAG |
| 204970_s_at | 749.8 | 468.4 | 1127.1 | 41.9 | 28 | v-maf musculoaponeurotic fibrosarcoma oncogene homolog G (avian) | MAFG |
| 214941_s_at | 2325.5 | 1206.9 | 2919.2 | 73.8 | 28 | formin binding protein 3 | FNBP3 |
| 216279_at | 188.3 | 103.8 | 303 | 5.3 | 28 | zinc finger protein 272 | ZNF272 |
| 218810_at | 797.5 | 275.2 | 968.6 | 25.1 | 28 | zinc finger CCCH-type containing 12A | ZC3H12A |
| 219717_at | 769.6 | 568.7 | 1382.9 | 72.7 | 28 | hypothetical protein FLJ20280 | FLJ20280 |
| 221664_s_at | 763.3 | 449.2 | 1121.6 | 24.1 | 28 | F11 receptor | F11R |
| 221154_at | 188.5 | 47.7 | 392.8 | 1.3 | 28 | tripartite motif-containing 49 | TRIM49 |
| 222320_at | 188.7 | 62.2 | 779 | 0.4 | 28 | Cell division cycle 73, Paf1/RNA polymerase II complex component, homolog (S. cerevisiae) | CDC73 |
| 203876_s_at | 221.3 | 182.3 | 484.9 | 18.2 | 28 | matrix metallopeptidase 11 (stromelysin 3) | MMP11 |
| 214295_at | 178.6 | 121.5 | 991 | 6.2 | 28 | KIAA0485 protein | KIAA0485 |
| 202859_x_at | 705.3 | 181.2 | 4322.1 | 10.9 | 28 | interleukin 8 | IL8 |
| 212336_at | 118.4 | 40.8 | 347.3 | 3.1 | 28 | erythrocyte membrane protein band 4.1-like 1 | EPB41L1 |
| 218834_s_at | 183.7 | 97.4 | 471.7 | 10.5 | 28 | heat shock 70 kDa protein 5 (glucose-regulated protein, 78 kDa) binding protein 1 | HSPA5BP1 |
| 205612_at | 119.4 | 66.5 | 613.8 | 1.8 | 28 | multimerin 1 | MMRN1 |
| 213400_s_at | 404 | 207.8 | 1760.6 | 11.7 | 28 | transducin (beta)-like 1X-linked | TBL1X |
| 208983_s_at | 634.7 | 438 | 5148 | 13.9 | 28 | platelet/endothelial cell adhesion molecule (CD31 antigen) | PECAM1 |
| 201309_x_at | 2136.9 | 1690.7 | 3920.1 | 205.2 | 27 | chromosome 5 open reading frame 13 | C5orf13 |

TABLE 2-continued

Probesets underexpressed in 25% of more of B-lineage ALL cases (n = 270) as compared to normal bone marrow CD19+CD10+ cells from 4 healthy donors

| probe set ID | CD10+ CD19+ max | CD10+ CD19+ min | ALL max | ALL min | % ALL under expressed | Title | Symbol |
|---|---|---|---|---|---|---|---|
| 202154_x_at | 3521.2 | 1931.5 | 5268.2 | 196.6 | 27 | tubulin, beta 3 | TUBB3 |
| 203318_s_at | 1287.8 | 861.9 | 2184.2 | 162.8 | 27 | zinc finger protein 148 (pHZ-52) | ZNF148 |
| 207556_s_at | 1040.9 | 730.5 | 1867.1 | 30.2 | 27 | diacylglycerol kinase, zeta 104 kDa | DGKZ |
| 209610_s_at | 1038.3 | 584.6 | 1530.4 | 53.6 | 27 | solute carrier family 1 (glutamate/neutral amino acid transporter), member 4 | SLC1A4 |
| 210605_s_at | 357.4 | 171.9 | 630.5 | 12.2 | 27 | milk fat globule-EGF factor 8 protein | MFGE8 |
| 213182_x_at | 210.3 | 28.2 | 399 | 4.5 | 27 | cyclin-dependent kinase inhibitor 1C (p57, Kip2) | CDKN1C |
| 216983_s_at | 314.4 | 198.1 | 530.3 | 12.5 | 27 | zinc finger protein 224 | ZNF224 |
| 217924_at | 374.4 | 211 | 591.3 | 11.3 | 27 | chromosome 6 open reading frame 106 | C6orf106 |
| 218219_s_at | 826.9 | 399 | 920.1 | 13.4 | 27 | LanC lantibiotic synthetase component C-Like 2 (bacterial) | LANCL2 |
| 218981_at | 146.5 | 90.6 | 269.5 | 1.2 | 27 | ACN9 homolog (S. cerevisiae) | ACN9 |
| 219339_s_at | 483.5 | 242.8 | 515.2 | 9.8 | 27 | euchromatic histone-lysine N-methyltransferase 1 | EHMT1 |
| 221262_s_at | 209.5 | 80.6 | 360.8 | 5 | 27 | solute carrier family 2 (facilitated glucose transporter), member 11 /// solute carrier family 2 (facilitated glucose transporter), member 11 | SLC2A11 |
| 221546_at | 307.2 | 156.8 | 524.4 | 10.8 | 27 | PRP18 pre-mRNA processing factor 18 homolog (yeast) | PRPF18 |
| 35436_at | 470.9 | 214.4 | 673.4 | 19.5 | 27 | golgi autoantigen, golgin subfamily a, 2 | GOLGA2 |
| 208851_s_at | 350.1 | 209.5 | 747.3 | 15.8 | 27 | Thy-1 cell surface antigen | THY1 |
| 209201_x_at | 27920.9 | 22826.8 | 56196.9 | 1417.6 | 27 | chemokine (C—X—C motif) receptor 4 | CXCR4 |
| 221829_s_at | 2947.8 | 1924.8 | 7554.1 | 350.5 | 27 | transportin 1 | TNPO1 |
| 222063_s_at | 151 | 55.8 | 320.1 | 2.5 | 27 | CDP-diacylglycerol synthase (phosphatidate cytidylyltransferase) 1 | CDS1 |
| 216108_at | 117.4 | 38.8 | 248.7 | 4.4 | 27 | Transcribed locus, weakly similar to NP_055301.1 neuronal thread protein AD7c-NTP [Homo sapiens] | — |
| 217585_at | 133.6 | 76.5 | 392.2 | 4.7 | 27 | nebulette | NEBL |
| 211771_s_at | 231.6 | 49.6 | 938.8 | 6.4 | 27 | POU domain, class 2, transcription factor 2 /// POU domain, class 2, transcription factor 2 | POU2F2 |
| 215609_at | 160.3 | 126.1 | 450.3 | 6.3 | 27 | START domain containing 7 | STARD7 |
| 202953_at | 104.2 | 88 | 968.1 | 9.6 | 27 | complement component 1, q subcomponent, beta polypeptide | C1QB |
| 201710_at | 2306.4 | 789.5 | 2974.5 | 27.5 | 27 | v-myb myeloblastosis viral oncogene homolog (avian)-like 2 | MYBL2 |
| 203377_s_at | 1193.9 | 412.3 | 871.2 | 27.2 | 27 | cell division cycle 40 homolog (yeast) | CDC40 |
| 212085_at | 16661.8 | 13263.8 | 21255.3 | 1445.2 | 27 | solute carrier family 25 (mitochondrial carrier, adenine nucleotide translocator), member 6 | SLC25A6 |
| 217094_s_at | 478.9 | 218.5 | 431.3 | 12.8 | 27 | itchy homolog E3 ubiquitin protein ligase (mouse) | ITCH |
| 218418_s_at | 3248.2 | 1177.9 | 4104.1 | 69.6 | 27 | ankyrin repeat domain 25 | ANKRD25 |
| 202545_at | 554 | 284.5 | 2142.8 | 20.2 | 27 | protein kinase C, delta | PRKCD |
| 203263_s_at | 351.6 | 271.3 | 737 | 8.3 | 27 | Cdc42 guanine nucleotide exchange factor (GEF) 9 | ARHGEF9 |
| 203653_s_at | 408.8 | 335.3 | 883.7 | 8.1 | 27 | coilin | COIL |
| 206850_at | 540.4 | 204.2 | 1160.3 | 16.3 | 27 | RAS-related on chromosome 22 | RRP22 |
| 207526_s_at | 205 | 117.9 | 519.5 | 4.7 | 27 | interleukin 1 receptor-like 1 | IL1RL1 |
| 215203_at | 847.9 | 423.2 | 2505.9 | 52 | 27 | golgi autoantigen, golgin subfamily a, 4 | GOLGA4 |
| 217607_x_at | 225 | 134.6 | 475.7 | 2 | 27 | eukaryotic translation initiation factor 4 gamma, 2 | EIF4G2 |
| 220140_s_at | 442.2 | 264.5 | 1143.6 | 19.5 | 27 | sorting nexin 11 | SNX11 |
| 220296_at | 283.9 | 169.2 | 806 | 13.1 | 27 | UDP-N-acetyl-alpha-D-galactosamine:polypeptide N-acetylgalactosaminyltransferase 10 (GalNAc-T10) | GALNT10 |
| 205547_s_at | 358.7 | 262.2 | 1771 | 11.8 | 27 | transgelin | TAGLN |
| 207479_at | 130.3 | 26.9 | 503.6 | 1.7 | 27 | — | |
| 211538_s_at | 335.4 | 178.3 | 6151.6 | 10.9 | 27 | heat shock 70 kDa protein 2 | HSPA2 |
| 217302_at | 201.1 | 124.7 | 577.8 | 8.8 | 27 | olfactory receptor, family 2, subfamily F, member 2 | OR2F2 |
| 220550_at | 126.2 | 51.7 | 542.1 | 2.6 | 27 | F-box protein 4 | FBXO4 |
| 207357_s_at | 235 | 109.4 | 1081.7 | 9.9 | 27 | UDP-N-acetyl-alpha-D-galactosamine:polypeptide N-acetylgalactosaminyltransferase 10 (GalNAc-T10) | GALNT10 |
| 212392_s_at | 203.4 | 152.7 | 545 | 11.9 | 27 | phosphodiesterase 4D interacting protein (myomegalin) | PDE4DIP |
| 213606_s_at | 198.8 | 76.2 | 989.3 | 1.2 | 27 | Rho GDP dissociation inhibitor (GDI) alpha | ARHGDIA |
| 202040_s_at | 1505.6 | 1348.4 | 2800 | 323.2 | 27 | Jumonji, AT rich interactive domain 1A (RBBP2-like) | JARID1A |
| 202588_at | 475.2 | 260 | 665.6 | 33.5 | 27 | adenylate kinase 1 | AK1 |
| 203272_s_at | 767.6 | 394.4 | 820.6 | 38.4 | 27 | tumor suppressor candidate 2 | TUSC2 |
| 203869_at | 227.4 | 154.5 | 412.2 | 7.5 | 27 | ubiquitin specific peptidase 46 | USP46 |
| 205315_s_at | 583.5 | 457.3 | 879.7 | 21.4 | 27 | syntrophin, beta 2 (dystrophin-associated protein A1, 59 kDa, basic component 2) | SNTB2 |
| 208503_s_at | 955.4 | 562.3 | 1110.6 | 62.7 | 27 | GATA zinc finger domain containing 1 | GATAD1 |
| 208506_at | 187.1 | 113.7 | 296.6 | 3.6 | 27 | histone 1, H3f | HIST1H3F |
| 208859_s_at | 717.8 | 264.6 | 975.1 | 8.1 | 27 | alpha thalassemia/mental retardation syndrome X-linked (RAD54 homolog, S. cerevisiae) | ATRX |
| 208879_x_at | 523 | 396.2 | 924.3 | 10.8 | 27 | chromosome 20 open reading frame 14 | C20orf14 |
| 212794_s_at | 6236.8 | 2719.2 | 8965.8 | 303 | 27 | KIAA1033 | KIAA1033 |
| 213223_at | 1355.5 | 995.3 | 1388.8 | 48.2 | 27 | ribosomal protein L28 | RPL28 |
| 213879_at | 680.6 | 451.6 | 1000.1 | 31.2 | 27 | SMT3 suppressor of mif two 3 homolog 2 (yeast) | SUMO2 |
| 215001_s_at | 6297.3 | 4027 | 11499.9 | 107.4 | 27 | glutamate-ammonia ligase (glutamine synthetase) | GLUL |
| 217208_s_at | 515.6 | 370 | 839.4 | 18.8 | 27 | discs, large homolog 1 (Drosophila) | DLG1 |
| 217480_x_at | 3170.5 | 1483.4 | 3437.3 | 282.6 | 27 | similar to Ig kappa chain | LOC339562 |
| 217813_s_at | 845.4 | 613.1 | 1204.4 | 48.6 | 27 | spindlin | SPIN |

TABLE 2-continued

Probesets underexpressed in 25% of more of B-lineage ALL cases (n = 270) as compared to normal bone marrow CD19+CD10+ cells from 4 healthy donors

| probe set ID | CD10+ CD19+ max | CD10+ CD19+ min | ALL max | ALL min | % ALL under expressed | Title | Symbol |
|---|---|---|---|---|---|---|---|
| 219148_at | 688.6 | 300.2 | 1139.4 | 16.5 | 27 | PDZ binding kinase | PBK |
| 220068_at | 11799.9 | 7578.4 | 22254.1 | 78.9 | 27 | pre-B lymphocyte gene 3 | VPREB3 |
| 221051_s_at | 249.1 | 122 | 462.4 | 4.6 | 27 | integrin beta 1 binding protein 3 | ITGB1BP3 |
| 222165_x_at | 844.1 | 506 | 1300 | 14.9 | 27 | chromosome 9 open reading frame 16 | C9orf16 |
| 213751_at | 255.7 | 70.7 | 596.5 | 5.5 | 27 | hypothetical protein LOC284352 | LOC284352 |
| 218012_at | 2264.7 | 844.4 | 8541.7 | 53 | 27 | TSPY-like 2 | TSPYL2 |
| 219264_s_at | 432 | 188.2 | 1178.5 | 5.9 | 27 | protein phosphatase 2 (formerly 2A), regulatory subunit B", beta | PPP2R3B |
| 219994_at | 886.4 | 477.3 | 2329.5 | 31 | 27 | amyloid beta (A4) precursor protein-binding, family B, member 1 interacting protein | APBB1IP |
| 206142_at | 224.2 | 87 | 536.9 | 2.2 | 27 | zinc finger protein 135 (clone pHZ-17) | ZNF135 |
| 217332_at | 166 | 71.5 | 865.4 | 3.5 | 27 | Hypothetical LOC387937 | LOC387937 |
| 211751_at | 89.3 | 37.7 | 420.3 | 2.9 | 27 | phosphodiesterase 4D interacting protein (myomegalin) /// phosphodiesterase 4D interacting protein (myomegalin) | PDE4DIP |
| 201204_s_at | 331.7 | 173.1 | 1773.8 | 14 | 27 | CDNA FLJ41000 fis, clone UTERU2016761, highly similar to Homo sapiens ES/130 mRNA | — |
| 204792_s_at | 112 | 62.2 | 323.3 | 4.1 | 27 | WD and tetratricopeptide repeats 2 | WDTC2 |
| 211463_at | 123.6 | 54.9 | 349.5 | 4 | 27 | Zic family member 4 | ZIC4 |
| 208690_s_at | 6571.5 | 4976.5 | 24492 | 198.6 | 27 | PDZ and LIM domain 1 (elfin) | PDLIM1 |
| 221037_s_at | 61.6 | 35.4 | 551.3 | 0.5 | 27 | solute carrier family 25 (mitochondrial carrier; adenine nucleotide translocator), member 31 /// solute carrier family 25 (mitochondrial carrier; adenine nucleotide translocator), member 31 | SLC25A31 |
| 206686_at | 178 | 98.2 | 624.3 | 13.7 | 27 | pyruvate dehydrogenase kinase, isoenzyme 1 | PDK1 |
| 201161_s_at | 15493.5 | 6381.9 | 21619.5 | 36.5 | 26 | cold shock domain protein A | CSDA |
| 203832_at | 3801 | 1803.9 | 4672 | 216.6 | 26 | enolase 1, (alpha) /// small nuclear ribonucleoprotein polypeptide F | ENO1 /// SNRPF |
| 208919_s_at | 2456.4 | 1631.2 | 2454.9 | 404.3 | 26 | NAD kinase | NADK |
| 209308_s_at | 1454.5 | 1070.9 | 1764.3 | 94.4 | 26 | BCL2/adenovirus E1B 19 kDa interacting protein 2 | BNIP2 |
| 209336_at | 509.8 | 276 | 745.3 | 15.7 | 26 | PWP2 periodic tryptophan protein homolog (yeast) | PWP2H |
| 211085_s_at | 605.3 | 105.9 | 474.3 | 3.6 | 26 | serine/threonine kinase 4 /// serine/threonine kinase 4 | STK4 |
| 212078_s_at | 932.1 | 633.4 | 1296.9 | 54.9 | 26 | myeloid/lymphoid or mixed-lineage leukemia (trithorax homolog, Drosophila) | MLL |
| 218906_x_at | 513.8 | 291.8 | 771.3 | 24.2 | 26 | kinesin light chain 2 | KLC2 |
| 219833_s_at | 519.5 | 357.9 | 862.3 | 8.4 | 26 | EF-hand domain (C-terminal) containing 1 | EFHC1 |
| 90610_at | 3305.2 | 2444.1 | 2899 | 500.2 | 26 | leucine-rich repeats and calponin homology (CH) domain containing 4 | LRCH4 |
| 204180_s_at | 596.7 | 442.4 | 1360.7 | 53.5 | 26 | zinc finger protein 297B | ZNF297B |
| 219213_at | 336.6 | 193.6 | 1089.7 | 15.2 | 26 | junctional adhesion molecule 2 | JAM2 |
| 205106_at | 185 | 127.5 | 477.4 | 17.3 | 26 | mature T-cell proliferation 1 | MTCP1 |
| 215669_at | 218.9 | 124.5 | 1632.2 | 7.2 | 26 | major histocompatibility complex, class II, DR beta 4 | HLA-DRB4 |
| 208511_at | 264.1 | 220 | 656.1 | 11.5 | 26 | pituitary tumor-transforming 3 | PTTG3 |
| 213906_at | 210.5 | 99.7 | 700.2 | 5.6 | 26 | v-myb myeloblastosis viral oncogene homolog (avian)-like 1 | MYBL1 |
| 216070_at | 96 | 60.7 | 453 | 1.9 | 26 | ATPase, Na+/K+ transporting, beta 1 polypeptide | ATP1B1 |
| 221674_s_at | 165.4 | 84.5 | 539.1 | 11.1 | 26 | chordin | CHRD |
| 215901_at | 117.6 | 99 | 461 | 3.6 | 26 | zinc finger protein 81 (HFZ20) | ZNF81 |
| 217085_at | 70.6 | 36.4 | 382.5 | 2.3 | 26 | Solute carrier family 14 (urea transporter), member 2 | SLC14A2 |
| 205376_at | 93.9 | 65.4 | 516.9 | 2.1 | 26 | inositol polyphosphate-4-phosphatase, type II, 105 kDa | INPP4B |
| 208096_s_at | 76.5 | 45.3 | 480.1 | 3.1 | 26 | collagen, type XXI, alpha 1 /// collagen, type XXI, alpha 1 | COL21A1 |
| 205933_at | 434.8 | 329.6 | 2712.4 | 9.5 | 26 | SET binding protein 1 | SETBP1 |
| 204446_s_at | 2632.3 | 1297.5 | 12918.8 | 3.8 | 26 | arachidonate 5-lipoxygenase | ALOX5 |
| 201518_at | 1663.8 | 1366.3 | 2814.1 | 80.4 | 26 | chromobox homolog 1 (HP1 beta homolog Drosophila) | CBX1 |
| 202407_s_at | 689.2 | 443.7 | 649.4 | 8.1 | 26 | PRP31 pre-mRNA processing factor 31 homolog (yeast) | PRPF31 |
| 202937_x_at | 632.3 | 314 | 1072.3 | 19.1 | 26 | CGI-96 protein | CGI-96 |
| 203362_s_at | 1114.5 | 849.3 | 2198.2 | 97 | 26 | MAD2 mitotic arrest deficient-like 1 (yeast) | MAD2L1 |
| 208750_s_at | 2763.3 | 1990.4 | 4772.1 | 326.7 | 26 | ADP-ribosylation factor 1 | ARF1 |
| 210458_s_at | 140.3 | 64.3 | 256.2 | 1.9 | 26 | TRAF family member-associated NFKB activator | TANK |
| 210633_x_at | 3072.4 | 2422 | 4202.8 | 624.1 | 26 | keratin 10 (epidermolytic hyperkeratosis; keratosis palmaris et plantaris) | KRT10 |
| 211804_s_at | 761.5 | 573.6 | 1161.4 | 27.6 | 26 | cyclin-dependent kinase 2 | CDK2 |
| 213548_s_at | 604.8 | 443 | 972.2 | 22.9 | 26 | hypothetical protein H41 | H41 |
| 217157_x_at | 1340.3 | 507.1 | 1638.1 | 29.4 | 26 | IGK mRNA for immunoglobulin kappa light chain VLJ region, partial cds, clone: K142 | — |
| 219131_at | 276.1 | 193.2 | 503.7 | 22.3 | 26 | UbiA prenyltransferase domain containing 1 | UBIAD1 |
| 219366_at | 442.9 | 229.7 | 607.7 | 18.4 | 26 | apoptosis, caspase activation inhibitor | AVEN |
| 219807_x_at | 1785.1 | 1074.6 | 1756 | 54.9 | 26 | RAB4B, member RAS oncogene family | RAB4B |
| 221734_at | 583.9 | 329.7 | 1064.7 | 32.7 | 26 | hypothetical protein MGC12103 | LOC133619 |
| 222082_at | 382.4 | 342.7 | 743.2 | 13 | 26 | zinc finger and BTB domain containing 7A | ZBTB7A |
| 41386j_at | 2681.1 | 1537.2 | 3237.1 | 299.7 | 26 | — | — |
| 203753_at | 5156.3 | 3589.5 | 11739.6 | 100.6 | 26 | transcription factor 4 | TCF4 |
| 206530_at | 440.9 | 314.6 | 1126.1 | 26.8 | 26 | RAB30, member RAS oncogene family | RAB30 |
| 211514_at | 184.3 | 57.5 | 481.6 | 6.7 | 26 | receptor interacting protein kinase 5 | RIPK5 |

TABLE 2-continued

Probesets underexpressed in 25% of more of B-lineage ALL cases (n = 270) as compared to normal bone marrow CD19+CD10+ cells from 4 healthy donors

| probe set ID | CD10+ CD19+ max | CD10+ CD19+ min | ALL max | ALL min | % ALL under expressed | Title | Symbol |
|---|---|---|---|---|---|---|---|
| 216894_x_at | 256 | 28.2 | 537.5 | 3.6 | 26 | cyclin-dependent kinase inhibitor 1C (p57, Kip2) | CDKN1C |
| 220898_at | 253.3 | 172.7 | 581.6 | 6.1 | 26 | — | |
| 46142_at | 786.4 | 434.8 | 1628.2 | 19.2 | 26 | hypothetical protein FLJ12681 | FLJ12681 |
| 214443_at | 248.3 | 149.3 | 1045.7 | 9.7 | 26 | poliovirus receptor | PVR |
| 220702_at | 484.2 | 331.2 | 1135.3 | 11.6 | 26 | — | |
| 208180_s_at | 481.3 | 295.3 | 1335.4 | 3.3 | 26 | histone 1, H4h | HIST1H4H |
| 207228_at | 160.2 | 88 | 418.2 | 10.3 | 26 | protein kinase, cAMP-dependent, catalytic, gamma | PRKACG |
| 204257_at | 1371.7 | 1160.5 | 6143 | 100.4 | 26 | fatty acid desaturase 3 | FADS3 |
| 205420_at | 90.8 | 54.9 | 421.3 | 2.7 | 26 | peroxisomal biogenesis factor 7 | PEX7 |
| 213582_at | 106.3 | 74.3 | 395.4 | 1.6 | 26 | ATPase, Class VI, type 11A | ATP11A |
| 213222_at | 324.3 | 226.9 | 1351.7 | 3.6 | 26 | phospholipase C, beta 1 (phosphoinositide-specific) | PLCB1 |
| 220893_at | 128.5 | 44.9 | 548.2 | 4.2 | 26 | uncharacterized gastric protein ZA52P | LOC57399 |
| 210848_at | 153.2 | 122.9 | 459.4 | 5.4 | 26 | — | |
| 214649_s_at | 130.4 | 97.7 | 420 | 3.5 | 26 | myotubularin related protein 2 | MTMR2 |
| 209825_s_at | 519.7 | 444.7 | 1963.8 | 8 | 26 | uridine-cytidine kinase 2 | UCK2 |
| 200914_x_at | 913.4 | 714.2 | 983.4 | 106.9 | 26 | kinectin 1 (kinesin receptor) | KTN1 |
| 203787_at | 3369.3 | 2320.4 | 4268 | 120.7 | 26 | single-stranded DNA binding protein 2 | SSBP2 |
| 205932_s_at | 529.7 | 159.8 | 978.8 | 11.1 | 26 | msh homeo box homolog 1 (Drosophila) | MSX1 |
| 207700_s_at | 2273.6 | 996.5 | 1781 | 167.3 | 26 | nuclear receptor coactivator 3 | NCOA3 |
| 210461_s_at | 570.6 | 262.9 | 974.7 | 43.7 | 26 | actin binding LIM protein 1 | ABLIM1 |
| 213186_at | 473.6 | 342.9 | 532 | 9.9 | 26 | zinc finger DAZ interacting protein 3 | DZIP3 |
| 214738_s_at | 607.5 | 372.4 | 1062 | 13.5 | 26 | NIMA (never in mitosis gene a)-related kinase 9 | NEK9 |
| 218774_at | 539.9 | 338.8 | 850.7 | 24.2 | 26 | decapping enzyme, scavenger | DCPS |
| 218908_at | 525.1 | 270.4 | 786.4 | 17.6 | 26 | alveolar soft part sarcoma chromosome region, candidate 1 | ASPSCR1 |
| 211386_at | 286.8 | 178.2 | 604.1 | 5 | 26 | hypothetical protein MGC12488 | MGC12488 |
| 211177_s_at | 344.7 | 152.3 | 781.9 | 16.1 | 26 | thioredoxin reductase 2 | TXNRD2 |
| 215117_at | 661.4 | 193.7 | 1613.1 | 2.8 | 26 | recombination activating gene 2 | RAG2 |
| 206166_s_at | 157.6 | 100.6 | 383.3 | 8.1 | 26 | chloride channel, calcium activated, family member 2 | CLCA2 |
| 211620_x_at | 292.2 | 158.1 | 710.2 | 5.8 | 26 | runt-related transcription factor 1 (acute myeloid leukemia 1; aml1 oncogene) | RUNX1 |
| 214828_s_at | 268.6 | 174.9 | 680.9 | 10.9 | 26 | similar to CGI-96 | dJ222E13.2 |
| 209125_at | 133.6 | 97.9 | 826.3 | 5.4 | 26 | keratin 6A /// keratin 6C /// keratin 6E | KRT6A /// KRT6C /// KRT6E |
| 219666_at | 924.1 | 459.5 | 7946.9 | 14.9 | 26 | membrane-spanning 4-domains, subfamily A, member 6A | MS4A6A |
| 35974_at | 3454.6 | 2149.4 | 18984.7 | 227.5 | 26 | lymphoid-restricted membrane protein | LRMP |
| 208015_at | 324.6 | 243.5 | 3779.8 | 5 | 26 | SMAD, mothers against DPP homolog 1 (Drosophila) | SMAD1 |
| 202718_at | 113.1 | 58.5 | 4105.7 | 4.9 | 26 | insulin-like growth factor binding protein 2, 36 kDa | IGFBP2 |
| 203401_at | 837 | 652.7 | 1491.4 | 29.4 | 25 | phosphoribosyl pyrophosphate synthetase 2 | PRPS2 |
| 203907_s_at | 2033.9 | 1446.6 | 3024.1 | 138 | 25 | IQ motif and Sec7 domain 1 | IQSEC1 |
| 205017_s_at | 339.5 | 185.8 | 617.6 | 12.6 | 25 | muscleblind-like 2 (Drosophila) | MBNL2 |
| 208248_x_at | 3004.5 | 1846.7 | 5417.3 | 311.7 | 25 | amyloid beta (A4) precursor-like protein 2 | APLP2 |
| 213007_at | 1438.7 | 874.5 | 1714.6 | 104.6 | 25 | hypothetical protein FLJ10719 | FLJ10719 |
| 216187_x_at | 9608.3 | 6081 | 10136.8 | 1384.5 | 25 | Kinesin 2 | KNS2 |
| 218308_at | 2167.3 | 1016.3 | 2296.8 | 32.3 | 25 | transforming, acidic coiled-coil containing protein 3 | TACC3 |
| 219203_at | 407.8 | 60.7 | 564.5 | 13.9 | 25 | chromosome 14 open reading frame 122 | C14orf122 |
| 222027_at | 535.7 | 147 | 680 | 13.7 | 25 | Nuclear casein kinase and cyclin-dependent kinase substrate 1 | NUCKS1 |
| 206408_at | 211 | 62.4 | 454.5 | 6.6 | 25 | leucine rich repeat transmembrane neuronal 2 | LRRTM2 |
| 213623_at | 330.1 | 213.7 | 833 | 8.8 | 25 | kinesin family member 3A | KIF3A |
| 215459_at | 317 | 169.2 | 668 | 7.5 | 25 | Tax1 (human T-cell leukemia virus type I) binding protein 3 | TAX1BP3 |
| 206079_at | 343.8 | 180.7 | 938.1 | 11.4 | 25 | choroideremia-like (Rab escort protein 2) | CHML |
| 208465_at | 135.9 | 43.4 | 1907.9 | 7.2 | 25 | glutamate receptor, metabotropic 2 | GRM2 |
| 61732_r_at | 83.1 | 23.6 | 198.2 | 0.3 | 25 | coiled-coil domain containing 2 | CCDC2 |
| 64900_at | 95.8 | 29.2 | 263.9 | 3 | 25 | carbohydrate (N-acetylglucosamine 6-O) sulfotransferase 5 /// hypothetical protein MGC15429 | CHST5 /// MGC15429 |
| 215653_at | 66.6 | 14.5 | 411.1 | 0.3 | 25 | Glypican 5 | GPC5 |
| 208054_at | 83.6 | 43.8 | 792.6 | 2.8 | 25 | hect domain and RLD 4 | HERC4 |
| 219948_x_at | 55.7 | 18.7 | 366 | 1 | 25 | UDP glucuronosyltransferase 2 family, polypeptide A3 | UGT2A3 |
| 208394_x_at | 81.2 | 54.2 | 1063.4 | 2.3 | 25 | endothelial cell-specific molecule 1 | ESM1 |
| 207555_s_at | 356.3 | 210.5 | 600.8 | 14.6 | 25 | thromboxane A2 receptor | TBXA2R |
| 208319_s_at | 2462.3 | 1579.7 | 4284.6 | 231.2 | 25 | RNA binding motif (RNP1, RRM) protein 3 | RBM3 |
| 208415_x_at | 2728.8 | 1776.8 | 2291.1 | 315.2 | 25 | inhibitor of growth family, member 1 | ING1 |
| 209878_s_at | 832.2 | 497.4 | 1166.4 | 19.8 | 25 | v-rel reticuloendotheliosis viral oncogene homolog A, nuclear factor of kappa light polypeptide gene enhancer in B-cells 3, p65 (avian) | RELA |
| 212475_at | 260.3 | 199.7 | 517.2 | 18.7 | 25 | KIAA0241 protein | KIAA0241 |
| 212867_at | 1495.5 | 1330.8 | 1768.6 | 356.9 | 25 | Nuclear receptor coactivator 2 /// Nuclear receptor coactivator 2 | NCOA2 |
| 213351_s_at | 489.6 | 270.8 | 934.5 | 9.5 | 25 | transmembrane and coiled-coil domain family 1 | TMCC1 |

TABLE 2-continued

Probesets underexpressed in 25% of more of B-lineage ALL cases (n = 270) as compared to normal bone marrow CD19+CD10+ cells from 4 healthy donors

| probe set ID | CD10+ CD19+ max | CD10+ CD19+ min | ALL max | ALL min | % ALL under expressed | Title | Symbol |
|---|---|---|---|---|---|---|---|
| 214447_at | 467.1 | 178.1 | 514.6 | 7.8 | 25 | v-ets erythroblastosis virus E26 oncogene homolog 1 (avian) | ETS1 |
| 214861_at | 273.2 | 180.4 | 482.4 | 8.3 | 25 | jumonji domain containing 2C | JMJD2C |
| 215415_s_at | 378.9 | 114.3 | 474.7 | 7.7 | 25 | lysosomal trafficking regulator | LYST |
| 216172_at | 429.1 | 230.1 | 708.1 | 23.5 | 25 | Exosome component 2 | EXOSC2 |
| 219971_at | 237.9 | 51.2 | 428 | 6.2 | 25 | interleukin 21 receptor | IL21R |
| 210057_at | 163.6 | 112.5 | 892.7 | 2.5 | 25 | PI-3-kinase-related kinase SMG-1 | SMG1 |
| 212949_at | 375.3 | 184.4 | 766.8 | 20.7 | 25 | barren homolog (*Drosophila*) | BRRN1 |
| 220674_at | 323.7 | 255.8 | 689.3 | 6.1 | 25 | hypothetical protein FLJ22814 | FLJ22814 |
| 63825_at | 491.4 | 340.1 | 1073.4 | 14.8 | 25 | — | — |
| 203334_at | 444 | 238.8 | 946.9 | 17.3 | 25 | DEAH (Asp-Glu-Ala-His) box polypeptide 8 | DHX8 |
| 209145_s_at | 251.4 | 105.7 | 544.1 | 9.8 | 25 | core-binding factor, runt domain, alpha subunit 2; translocated to, 2 | CBFA2T2 |
| 216898_s_at | 139.4 | 62.3 | 546.7 | 2.9 | 25 | collagen, type IV, alpha 3 (Goodpasture antigen) | COL4A3 |
| 219181_at | 218.6 | 128.5 | 1224.7 | 4.1 | 25 | lipase, endothelial | LIPG |
| 221606_s_at | 156.6 | 78.7 | 352 | 3.4 | 25 | nucleosomal binding protein 1 | NSBP1 |
| 205577_at | 361.7 | 123.3 | 1258.9 | 10.9 | 25 | phosphorylase, glycogen; muscle (McArdle syndrome, glycogen storage disease type V) | PYGM |
| 217505_at | 84 | 10.4 | 833.9 | 0.6 | 25 | kelch-like 23 (*Drosophila*) | KLHL23 |
| 208961_s_at | 5616 | 1346.2 | 20947.3 | 27.6 | 25 | Kruppel-like factor 6 | KLF6 |
| 217787_s_at | 322.8 | 234.4 | 1316.5 | 6.6 | 25 | UDP-N-acetyl-alpha-D-galactosamine:polypeptide N-acetylgalactosaminyltransferase 2 (GalNAc-T2) | GALNT2 |
| 207575_at | 148 | 70.7 | 549.6 | 7 | 25 | golgi autoantigen, golgin subfamily a, 6 | GOLGA6/ |
| 206556_at | 102.7 | 72.1 | 364.7 | 7.4 | 25 | clusterin-like 1 (retinal) | CLUL1 |
| 211646_at | 69.8 | 34.3 | 452.3 | 2.7 | 25 | Similar to KIAA1501 protein /// Similar to KIAA1501 protein | LOC388248 |
| 213836_s_at | 140 | 94.2 | 467.8 | 8.7 | 25 | WD40 repeat protein Interacting with phosphoInositides of 49 kDa | WIPI49 |
| 216498_at | 96.5 | 66.5 | 393.4 | 4.2 | 25 | — | — |
| 219157_at | 991.2 | 639.9 | 6082.6 | 20.2 | 25 | kelch-like 2, Mayven (*Drosophila*) | KLHL2 |
| 214282_at | 60.3 | 31.1 | 462.2 | 0.3 | 25 | Hermansky-Pudlak syndrome 3 | HPS3 |

Normal" Controls

In one embodiment, a "normal control" used in the methods and kits of the invention are taken from a subject, or pool of subjects diagnosed and validated as "normal." As discussed elsewhere herein, the corresponding predictive markers which are assayed in these samples can include, but are not limited to, CD19, CD10, CD34, CD45, CD38, CD24, CD44, CD58, CD73, CD15, CD200, CD66c, CD123, CD86, CD72, CD13, CD33, CD79b, HSPB1, BCL2, CD164, CD304, CD97, CD99, CD102 and CD300a or combinations thereof. In embodiments of the invention, specimens from normal controls correspond to blood or bone marrow specimens classified as nonmalignant, benign, and/or other conditions that are not considered to be indicative of clinical disease.

In specific embodiments, it may be necessary to phenotypically differentiate "hematogones" in normal controls from leukemic cells in ALL specimens. Hematogones are benign lymphoid precursors whose morphology and immunophenotype are similar to the blasts found in ALL, but are considered distinctive from cells indicative of MRD or ALL. Hematogone cells are more commonly found in pediatric bone marrow aspirates following therapy.

It is recognized that the accuracy of detecting and diagnosing minimal residual disease in ALL leukemia will vary based on the strength of the correlation between the expression levels of the differentially expressed genes when compared to normal controls. When the values in the expression profiles represent the expression levels of genes whose expression is strongly correlated with the physiologic condition, it may be possible to use a fewer number of values in the expression profile and still obtain an acceptable level of diagnostic or prognostic accuracy.

RNA Expression Profiling

The values in the expression profiles of the invention are measurements representing the absolute or the relative expression level of differentially expressed genes. The expression levels of marker genes may be determined by any method known in the art for assessing the expression level of an RNA molecule in a specimen. For example, expression levels of RNA may be monitored using a membrane blot (such as used in hybridization analysis such as Northern, Southern, dot, and the like), or microwells, sample tubes, gels, beads or fibers (or any solid support comprising bound nucleic acids). See U.S. Pat. Nos. 5,770,722, 5,874,219, 5,744,305, 5,677,195 and 5,445,934, which are expressly incorporated herein by reference. Gene expression detection may also comprise nucleic acid probes in solution. Expression levels of RNA may also be monitored using the reverse transcriptase polymerase chain reaction (e.g., TaqMan®).

In one embodiment, microarrays are used to measure the values to be included in the expression profiles. Microarrays are particularly well suited for this purpose because of the reproducibility between different experiments. DNA microarrays provide one method for the simultaneous measurement of the expression levels of large numbers of genes. Each array consists of a reproducible pattern of capture probes attached to a solid support. Labeled RNA or DNA is hybridized to complementary probes on the array and then detected by laser scanning. Hybridization intensities for each probe on the array are determined and converted to a quantitative value representing relative gene expression levels. See, TABLE 1 and TABLE 2. See also, U.S. Pat. Nos.

6,040,138, 5,800,992 and 6,020,135, 6,033,860, and 6,344,316, which are incorporated herein by reference. High-density oligonucleotide arrays are particularly useful for determining the gene expression profile for a large number of RNA's in a sample.

In one approach, total mRNA isolated from cells taken from the subject is converted to labeled cDNA and then hybridized to an oligonucleotide array. Each specimen is hybridized to a separate array. Relative transcript levels are calculated by reference to appropriate controls present on the array and in the sample.

Embodiments of the invention, can include, but are not limited to, the detection of mRNA expression with probes specific for genes shown in TABLE 1 comprising genes overexpressed in B-lineage ALL. Other embodiments of the invention, can include, but are not limited to, the detection of mRNA expression with probes specific for genes shown in TABLE 2 comprising genes underexpressed in B-lineage ALL.

In embodiments of the invention, an expression profile is generated by the detection of nucleic acid corresponding to the expression of mRNA from a specimen. As a first step, a specimen is contacted with a set of probes to CD19 and CD10, wherein a first probe specifically binds to CD19 and a second probe specifically binds to CD10. As a second step a CD19+/CD10+ cell is isolated from said specimen. As a third step, an expression level of at least two gene products encoding CD38, CD24, CD44, CD58, CD73, CD15, CD200, CD66c, CD123, CD86, CD72, CD13, CD33, CD79b, HSPB1, BCL2, CD164, CD304, CD97, CD99, CD102 or CD300a is determined in said CD19+/CD10+ isolated cell population from step two. As a forth step, an expression profile is generated of the CD19+/CD10+ cells of step two. The expression profile of step four, displaying a modulated level of at least one gene product, is indicative of minimal residual disease in acute lymphoblastic leukemia. In embodiments of the invention, modulation of the gene product detected from gene products encoding CD38, CD24, CD44, CD58, CD73, CD15, CD200, CD66c, CD123, CD86, CD72, CD13, CD33, CD79b, HSPB1, BCL2, CD164, CD304, CD97, CD99, CD102 and CD300a, relative to a normal control, is indicative of minimal residual disease in acute lymphoblastic leukemia.

As is well understood in the art and in yet other embodiments of the invention, various subsets of cells can be isolated for analysis, for example, it may be advantageous to compare CD19+, CD10− cells. In yet other embodiments, other combinations of probes may be included in the first step, for example, CD19, CD10, CD45, and CD34. For example, the subpopulations of cells that can be isolated by contacting a specimen with probes to markers CD19, CD10, CD45, and CD34 can include, but are not limited to: CD19+, CD10+, CD45+, and CD34+ cells; CD19+, CD10−, CD45+, and CD34+ cells; CD19+, CD10−, CD45−, and CD34+ cells; CD19+, CD10−, CD45+, and CD34−; CD19+, CD10+, CD45−, and CD34+ cells; CD19+, CD10+, CD45+, and CD34−; and CD19+, CD10+, CD45−, and CD34− cells. All of the preceeding subpopulations of cell can be isolated by contacting the specimen with said plurality of probes, but in addition, modulated activity of any one probe of that combination could also be selected thereby increasing the number of subpoplations analysed. The design of assays to optimize detection conditions and determining cell sorting conditions is standard and well within the routine capabilities of those of ordinary skill in the art.

In embodiments of the invention, determining the expression profile of the specimen that is CD10+/CD19+ further comprises probe combinations comprising (a) CD38, CD24, and CD44; (b) CD38, CD58, and CD44; (c) CD38, CD73, and CD15; (d) CD38, CD200, and CD44; (e) CD66c, CD123, and CD86; (f) CD72, CD13, and CD33; or (g) CD79b, HSPB1, and Bcl-2. In embodiments of the invention said modulated level comprises overexpression of CD44, CD58, CD73, CD200, CD86, HSPB1, BCL2, CD164, CD97, CD99, or CD300a and/or the underexpression of CD38, CD72, or CD79b, relative to a normal control.

In embodiments of the invention, determining the expression level of a gene product in cells expressing each of CD19, CD10, CD34, and CD45, can further comprise probes to detect at least four, five, six, seven, eight, nine, ten, eleven, twelve, thirteen, fourteen, fifteen, sixteen, seventeen, eighteen, nineteen, twenty, twenty-one, or twenty-two markers comprising: CD38, CD24, CD44, CD58, CD73, CD15, CD200, CD66c, CD123, CD86, CD72, CD13, CD33, CD79b, HSPB1, BCL2, CD164, CD304, CD97, CD99, CD102 or CD300a.

Protein Expression Profile and Antibody Detection

In other embodiments, the values in the expression profile are obtained by measuring the abundance of the protein products of the differentially-expressed genes. The abundance of these protein products can be determined, for example, using antibodies specific for the protein products of the differentially-expressed genes. The term "antibody" as used herein refers to an immunoglobulin molecule or immunologically active portion thereof, i.e., an antigen-binding portion. Examples of immunologically active portions of immunoglobulin molecules include F(ab) and F(ab')$_2$ fragments, which can be generated by treating the antibody with an enzyme such as pepsin.

The terms "antibody" and "antibodies" broadly encompass naturally occurring forms of antibodies and recombinant antibodies such as single-chain antibodies, chimeric and humanized antibodies and multi-specific antibodies as well as fragments and derivatives of all of the foregoing, which fragments and derivatives have at least an antigenic binding site (e.g., Fab', F(ab)$_2$, Fv, single chain antibodies, diabodies). Antibody derivatives may comprise a protein or chemical moiety conjugated to the antibody.

In embodiments of the invention, the antibody can be a polyclonal, monoclonal, or recombinant, e.g., a chimeric or humanized, fully human, non-human (e.g., murine, or single chain antibody). The term "monoclonal antibody" as used herein refers to an antibody obtained from a population of substantially homogeneous antibodies, i.e., the individual antibodies comprising the population are identical except for possible naturally-occurring mutations that may be present in minor amounts.

The term "polyclonal antibody" as used herein refers to an antibody obtained from a population of heterogeneous antibodies derived from a multiple B cell response to an antigen which will recognize a variety of epitopes on the antigen. Polyclonal antibodies can be prepared by immunizing a suitable subject (e.g., rabbit, goat, mouse, or other mammal) with a marker protein immunogen. The antibody titer in the immunized subject can be monitored over time by standard techniques, such as with an enzyme linked immunosorbent assay (ELISA) using immobilized biomarker protein. At an appropriate time after immunization, e.g., when the antibody titers are highest, antibody-producing cells can be obtained from the subject and used to prepare monoclonal antibodies by standard techniques, such as the hybridoma technique originally described by Kohler and Milstein, C. (1975) *Nature* 256:495-497, the human B cell hybridoma technique (Kozbor, et al. (1983) *Immunol. Today* 4:72), the EBVhybridoma technique (Cole, et al. (1985) in Monoclonal Antibodies and Cancer Therapy, ed. Reisfeld and Sell (Alan R. Liss, Inc., New York, N.Y.), pp. 77-96) or trioma techniques. The technology for producing hybridomas is well known (see generally Coligan, et al. eds. (1994) Current Protocols in Immunology (John Wiley & Sons, Inc., New York, N.Y.); Galfre et al. (1977) *Nature* 266:550-52; Kenneth (1980) in Monoclonal Antibodies: A New Dimension In Biological Analyses (Plenum Publishing Corp., NY); and Lerner (1981) *Yale J. Biol. Med.*, 54:387 402).

As an alternative to preparing monoclonal antibody-secreting hybridomas, a monoclonal antibody can be identified and isolated by screening a recombinant combinatorial immunoglobulin library (e.g., an antibody phage display library) with a marker protein to thereby isolate immunoglobulin library members that bind the marker protein. Kits for generating and screening phage display libraries are commercially available (e.g., the Pharmacia Recombinant Phage Antibody System, Catalog No. 27-9400-01; and the Stratagene SurfZAP™ Phage Display Kit, Catalog No. 240612). Additionally, examples of methods and reagents particularly amenable for use in generating and screening antibody display library can be found in, for example, U.S. Pat. No. 5,223,409; PCT Publication Nos. WO 92/18619; WO 91/17271; WO 92/20791; WO 92/15679; 93/01288; WO 92/01047; 92/09690; and 90/02809; Fuchs et al. (1991) Bio/Technology 9:1370-1372; Hay et al. (1992) *Hum. Antibod. Hybridomas* 3:81-85; Huse et al. (1989) Science 246: 1275-1281; Griffiths et al. (1993) *EMBO J.* 12:725-734.

Antigen-binding fragments and variants of the monoclonal antibodies disclosed herein are contemplated and within the scope of the present invention. Such variants, for example, will retain the desired binding properties of the parent antibody. Methods for making antibody fragments and variants are generally available in the art. For example, amino acid sequence variants of a monoclonal antibody described herein can be prepared by mutations in the cloned DNA sequence encoding the antibody of interest. Methods for mutagenesis and nucleotide sequence alterations are well known in the art. See, for example, Walker and Gaastra, eds. (1983) Techniques in Molecular Biology (MacMillan Publishing Company, New York); Kunkel (1985) Proc. Natl. Acad. Sci. USA 82:488-492; Kunkel et al. (1987) Methods Enzymol. 154:367-382; Sambrook et al. (1989) Molecular Cloning: A Laboratory Manual (Cold Spring Harbor, N.Y.); U.S. Pat. No. 4,873,192; and the references cited therein; herein incorporated by reference. Guidance as to appropriate amino acid substitutions that do not affect biological activity of the polypeptide of interest may be found in the model of Dayhoff et al. (1978) in Atlas of Protein Sequence and Structure (Natl. Biomed. Res. Found., Washington, D.C.), herein incorporated by reference. Conservative substitutions, such as exchanging one amino acid with another having similar properties, may be preferred.

Preferably, variants of an antibody to a reference marker will have amino acid sequences that have at least 70% or 75% sequence identity, preferably at least 80% or 85% sequence identity, more preferably at least 90%, 91%, 92%, 93%, 94% or 95% sequence identity to the amino acid sequence for the reference antibody molecule, or to a shorter portion of the reference antibody molecule. More preferably, the molecules share at least 96%, 97%, 98% or 99% sequence identity. For purposes of the present invention, percent sequence identity is determined using the Smith-Waterman homology search algorithm using an affine gap search with a gap open penalty of 12 and a gap extension penalty of 2, BLOSUM matrix of 62. The Smith-Waterman homology search algorithm is taught in Smith and Waterman (1981) Adv. Appl. Math. 2:482-489. A variant may, for example, differ from the reference antibody by as few as 1 to 15 amino acid residues, as few as 1 to 10 amino acid residues, such as 6-10, as few as 5, as few as 4, 3, 2, or even 1 amino acid residue.

In embodiments of the invention, an antibody can be used to detect the marker or protein product of a differentially expressed gene in order to evaluate the abundance and pattern of expression of the protein. These antibodies can also be used diagnostically to monitor protein expression levels over time as part of a clinical monitoring procedure, e.g., determine the efficacy of a given therapy and reoccurrence of disease.

In embodiments of the invention, antibodies specifically bind to and detect markers comprising CD44, BCL2, HSPB1, CD73, CD24, CD123, CD72, CD86, CD200, CD79b, CD164, CD304, CD97, CD102, CD99, CD300a, CD130, PBX1, CTNNA1, ITGB7, CD69, or CD49f.

In embodiments of the invention antibodies specifically bind to and detect markers comprising CD19, CD10, CD34, CD45, CD38, CD24, CD44, CD58, CD73, CD15, CD200, CD66c, CD123, CD86, CD72, CD13, CD33, CD79b, HSPB1, BCL2, CD164, CD304, CD97, CD99, CD102 or CD300a.

Embodiments of the invention include antibodies described in TABLE 3, TABLE 4, and TABLE 5.

Optical Detection Methods:

Detection of antibodies can be facilitated by coupling (i.e., physically linking) the antibody to a detectable substance (i.e., antibody labeling). Examples of detectable substances include various enzymes, prosthetic groups, fluorescent materials (fluorophores, flurochromes), luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of fluorophores/flurochromes, include phycoerythrin (PE), fluorescein isothiocyanate (FITC), peridinin-chlorophyll (PerCP), allophycocyanin (APC), R-phycoerythrin conjugated with cyanine dye (PE-Cy7), allophycocyanin-cyanine tandem (APC-H7), coumarin dye (Horizon v450), sulphonyl chloride (Texas Red), cyanine (CY3, CY5, Cy7), FAM, JOE, TAMRA, TET, VIC, rhodamine; an example of a luminescent material includes luminol; examples of bioluminescent materials include luciferase, luciferin, and aequorin, and examples of suitable radioactive material include $^{125}$I, $^{131}$I, $^{35}$S or $^{3}$H. The skilled artisan will understand that additional moieties may be suitable for the method of the invention.

A detectable moiety generally refers in one embodiment to a composition or moiety that is detectable by spectroscopic, photochemical, biochemical, immunochemical, electromagnetic, radiochemical or chemical means such as fluorescence, chemifluorescence, or chemiluminescence, or any other appropriate means. The terms "fluorophore" and "fluorochrome" are defined as a chemical group, or component of a molecule that causes a molecule to be fluorescent. It is a functional group in a molecule which will absorb energy of a specific wavelength and re-emit energy at a different (but equally specific) wavelength. A fluorophore/fluorchrome can refer to various fluorescent substances, including dyes, used in fluorescence microscopy or flow cytometry to stain specimens. The terms fluorophore" and "fluorochrome" are herein used interchangeably.

Fluorochromes may be conjugated to antibodies, proteins, polypeptides, peptides, or nucleotide probes which specifically bind to antigens, proteins, polypeptides, peptides, polysaccharides, DNA, or RNA sequences. Thus, binding of an antibody, protein, polypeptide, peptide, or nucleotide probe to an antigen, protein, polypeptide, peptide, polysaccharide, DNA, or RNA may be detected by measuring a signal generated from a fluorochrome by flow cytometry, or any suitable optical imaging technique. Detection of a signal may indicate binding, whereas lack of detection of a signal may indicate lack of binding.

Methods and compositions for detectably labeling nucleic acid probes, such as oligonucleotides, DNA-RNA hybrids, etc. are well known in the art. See, e.g., U.S. Pat. Nos. 6,316,230; 6,297,016; 6,316,610; 6,060,240; 6,150,107; and 6,028,290, each of which is hereby incorporated by reference in their entirety.

The compositions of the invention further comprise monoclonal antibodies and variants and fragments thereof that specifically bind to marker proteins of interest, thereby forming a detectable complex. The monoclonal antibodies may be labeled with a detectable substance to facilitate marker protein detection in the sample. Such antibodies find use in practicing the methods of the invention. Monoclonal antibodies having the binding characteristics of the antibodies disclosed herein are also encompassed by the present invention. Compositions further comprise antigen-binding variants and fragments of the monoclonal antibodies.

In embodiments of the invention, a probe is an antibody, including but not limited to a whole antibody molecule, a F(ab')$_2$, Fab', Fv, Fd', or Fd fragment. In yet other embodiments, an antibody can be conjugated with a detectable moiety, wherein the detectable moiety can be, for example, a fluorophore, a chromophore, a radionuclide, or an enzyme. In embodiments of the invention a fluorophore can for example, can be, but is not limited to, phycoerythrin (PE), fluorescein isothiocyanate (FITC), peridinin-chlorophyll (PerCP), allophycocyanin (APC), R-phycoerythrin conjugated with cyanine dye (PE-Cy7), allophycocyanin-cyanine tandem (APC-H7), and coumarin dye (Horizon v450). Detection of complexes formed between an antibody probe and marker can be achieved by an optical detection technique, including, but not limited to flow cytometry and microscopy.

"Cell staining" when used in reference to an antibody means that the antibody recognizes an marker and binds to marker in the specimen forming a complex, thereby "labeling" or otherwise "staining" the cell expressing the marker to make it visible and/or detectable by microscopy or flow cytometry. Combinations of antibodies can be collectively added a specimen and thereby "stain the cell" for later analysis by visualization with a flow cytometer or microscope, for example. One of skill in the art could determine whether a cell expressed a specific protein based on the level of antibody that bound to the cell using standard methods.

The methods of the invention can also be used in immunofluorescence histochemistry. This technique involves the use of antibodies labeled with various fluorophores to detect substances within a specimen. In exemplary embodiments a pathologist can derive a great deal of morphological information of diagnostic value by examining a specimen from a subject by microscope. Immunohistochemistry is particularly relevant to, for example, the early diagnosis of cancer or pre-acute states such as minimal residual disease in ALL. Combinations of fluorophores or other detectable labels can be used by the methods on this invention, thereby greatly increasing the number of distinguishable signals in multicolor protocols.

In another embodiment, the method employs flow cytometry. In another embodiment, in a peripheral blood sample or blood sample, lymphocyte, monocyte and granulocyte populations can be defined on the basis of forward and side scatter. Forward and side scatter are used in one embodiment to exclude debris and dead cells.

Flow cytometry is an optical technique that analyzes particles or cells in a fluid mixture based on their optical characteristics, via the use of a flow cytometer (See, for example, Shapiro, "Practical Flow Cytometry," Third Ed. (Alan R. Liss, Inc., 1995); and Melamed et al. "Flow Cytometry and Sorting," Second Ed. (Wiley-Liss 1990)). Flow cytometers hydrodynamically focus a fluid suspension of particles/cells into a thin stream so that they flow down the stream in substantially single file and pass through an examination zone. A focused light beam, such as a laser beam illuminates the particles as they flow through the examination zone. Optical detectors within the flow cytometer measure certain characteristics of the light as it interacts with the particles/cells. Commonly used flow cytometers such as the Becton-Dickinson Immunocytometry Systems "FACSCAN" (San Jose, Calif.) can measure forward light scatter (generally correlated with the refractive index and size of the particle/cell being illuminated), side light scatter (generally correlated with the cell granularity), and particle fluorescence at one or more wavelengths. Data acquisition and analysis can be done using FASCALIBER® LSRII flow cytometers (Becton Dickinson), and CELLQUEST Pro™, BD FACSDiVa™ software (both from Becton Dickinson), FLowJo software (Tree Star, Ashland, Oreg.) and/or KALUZA™ software (Beckman Coulter, Miami, Fla.) (Campana, D. (2009) *Hematol Oncol Clin North Am.* 23; 1083-98, vii).

In embodiments of the invention, determining an expression profile of a specimen is generated using combinations of probes that bind specifically to CD10, CD19, CD34, and CD45, wherein combinations comprise (a) CD10, CD19, CD34, CD45, CD38, CD24, and CD44; (b) CD10, CD19, CD34, CD45, CD38, CD58, and CD44; (c) CD10, CD19, CD34, CD45, CD38, CD73, and CD15; (d) CD10, CD19, CD34, CD45, CD38, CD200, and CD44; (e) CD10, CD19, CD34, CD45, CD66c, CD123, and CD86; (f) CD10, CD19, CD34, CD45, CD72, CD13, and CD33; or (g) CD10, CD19, CD34, CD45, CD79b, HSPB1, and Bcl-2.

In other embodiments of the invention, antibodies can be directly conjugated for simultaneous detection. For example, a method of the invention can comprise antibodies directly conjugated to a detectable fluorochrome for simultaneous detection of a plurality of markers wherein: CD34 is conjugated to PerCP, CD19 is conjugated to APC, CD10 is conjugated to PE-Cy5, CD45 is coupled to APC-H7, CD38 is conjugated to FITC, CD24 is conjugated to PE, CD44 is conjugated to Horizon v450, CD58 is conjugated to PE, CD73 is conjugated to PE, CD15 is conjugated to Horizon v450, CD200 is conjugated to PE, CD66c is conjugated to FITC, CD123 is conjugated to PE, CD86 is conjugated to Horizon v450, CD72 is conjugated to FITC, CD13 is conjugated to PE, CD33 is conjugated to v450, CD79b is conjugated to FITC, HSPB1 is conjugated to PE, and Bcl2 is conjugated to Horizon V450. The skilled artisan will understand that any one antibody marker can be coupled to any fluorochrome for use in combination with any other antibody, and that preferred combinations can be used simultaneously with other antibody markers by the selection of different combinations of antibodies labeled with different flurochromes.

TABLE 3 shows exemplary marker combinations for detection of MRD in B-lineage ALL incorporating the top 10 differentially expressed markers including CD24, CD44, CD73, CD200, CD123, CD86, CD72, CD79b, HSPB1, and Bcl2.

TABLE 3

Marker combinations used for MRD studies in B-lineage ALL incorporating the top 10 differentially expressed markers discovered in this study (in italics)

| FITC | PE | PerCP | APC | PE-Cy7 | APC-H7 | Horizon v450 |
|------|------|-------|------|--------|--------|--------------|
| CD38 | *CD24* | CD34 | CD19 | CD10 | CD45 | *CD44* |
| CD38 | CD58 | CD34 | CD19 | CD10 | CD45 | *CD44* |
| CD38 | *CD73* | CD34 | CD19 | CD10 | CD45 | CD15 |
| CD38 | *CD200* | CD34 | CD19 | CD10 | CD45 | *CD44* |
| CD66c | *CD123* | CD34 | CD19 | CD10 | CD45 | CD86 |
| *CD72* | CD13 | CD34 | CD19 | CD10 | CD45 | CD33 |
| *CD79b* | *HSPB1* | CD34 | CD19 | CD10 | CD45 | *Bcl2* |

Cell Sorting and Selection of Subpopulations of Cells in a Specimen

Multiparameter flow cytometric cell analysis can be used as part of the methods of this invention. The simultaneous analysis of multiple predictive parameters using flow cytometry is known to those of skill in the art. In one embodiment, the population of cells to be analyzed is contacted with a panel of antibodies directed against distinct cell surface markers, under conditions effective to allow antibody probe binding. The antibodies employed can be monoclonal antibodies, and can, in another embodiment, be labeled in a manner to allow their subsequent detection.

In embodiments of the invention, fluorochromes can be excited by at least two different lasers to give off light of at least four different wavelengths, with the potential, for simultaneous analysis of at least four different markers. An additional two parameters include two light scattering parameters; direct and orthogonal, or side-scattering capability which can be analyzed concurrently with antibody detection, thereby allowing for cell analysis on the basis of at least 6 parameters. In embodiments of the invention at least five, six, seven, eight, nine, ten, eleven, or twelve different antibody probes, can be used simultaneously, thereby allowing for cell analysis on the basis of at least seven, eight, nine, ten, eleven, twelve, thirteen, or fourteen different parameters.

Multiparameter cell sorting can be used in an embodiment of the invention to isolate cells based on a specific expression profile. For example, in one embodiment cell sorting analysis can be achieved using fluorescence-activated flow cytometry, by methods well described in the art. In one embodiment cells can be sorted based on the co-expression of markers CD19 and CD10, wherein in combination with the expression of CD19 and CD10 the expression of other markers can be interrogated. In another embodiment of the invention, mRNA expression profiles can be generated from a purified population of CD19+ and CD10+ cells isolated from a subject specimen for the purpose of diagnosing minimal residual disease.

As is well understood in the art and in yet other embodiments of the invention, various subsets of cells can be isolated for analysis, for example, it may be advantageous to compare CD19+, CD10+ cells and CD19+, CD10− cells. Both subpopulations can be isolated by contacting the specimen with probes to CD19 and CD10, whereas in one condition cells are positively selected (CD19+, CD10+), and in the later, are negatively selected (CD19+, CD10−). Likewise, in yet other embodiments, other combinations of probes may be included in a first step, for example, CD19, CD10, CD45, and CD34, wherein modulated levels of CD45 and CD34 may be reflected in the subsets that are isolated. For example, the subpopulations of cells that could be isolated by contacting a specimen with probes to markers CD19, CD10, CD45, and CD34 could include, but are not limited to: CD19+, CD10+, CD45+, and CD34+ cells; CD19+, CD10−, CD45+, and CD34+ cells; CD19+, CD10−, CD45−, and CD34+ cells; CD19+, CD10−, CD45+, and CD34−; CD19+, CD10+, CD45−, and CD34+ cells; CD19+, CD10+, CD45+, and CD34−; and CD19+, CD10+, CD45−, and CD34− cells. All the preceeding subpopulations of cell could be isolated from by contacting the specimen with said probes, but in addition, using flow cytometry for example, modulated activity could representative of a spectrum of expression to negative to positive, and also be selected. The number of potential subpopulations analyzed could thereby increase the number of subpoplations analysed. The design of assays to optimize detection conditions and determining cell sorting conditions to isolate specific subpopulations of cells is standard and well within the routine capabilities of those of ordinary skill in the art.

In yet other embodiments of the invention, enrichment of specific subpopulations of cells can be achieved by other methods as well. For example a wide variety of magnetic bead separation and isolation procedures can be used to selectively negatively and positively enrich samples for specific subpopulations of cells. For example, in some embodiments a mixture of magnetic beads coupled to lineage specific antibodies can be used to deplete, T cells, NK cells, monocytes, platelets, dendritic cells, granulocytes and erythrocytes, thereby negatively isolating B cells. The skilled artisan will understand that combinations of different antibodies can be used alone or in combination, and in multiple successive rounds of isolation, to positively and/or negatively select for subpopulations of cells.

One of skill in the art will recognize that optimization of reagents and conditions, for example, antibody titer and parameters for detection of antigen-antibody binding, is needed to maximize the signal to noise ratio for a particular antibody. Antibody concentrations that maximize specific binding to the markers of the invention and minimize non-specific binding (or "background") will be determined. In particular embodiments, appropriate antibody titers are determined by initially testing various antibody dilutions on patient serum samples. The design of assays to optimize antibody titer and detection conditions is standard and well within the routine capabilities of those of ordinary skill in the art. Some antibodies require additional optimization to reduce background and/or to increase specificity and sensitivity.

The skilled artisan will recognize that optimization of multiparameter assays designed to detect a plurality of antibody probes simultaneously will be necessary. In embodiments of the invention, maximization of signal to noise ratio, as well an optimization of fluorochrome combinations will be necessary for each of the antibody probes combinations. Conjugated-antibody concentrations that maximize specific binding to the markers of the invention and minimize non-specific binding (or "background") will be determined with other such conjugated antibody probes as is known in the art. The design of assays to optimize and compensate the signals detected for the various conjugated antibodies is standard and well within the routine capabilities of those of ordinary skill in the art. Some antibodies require additional optimization to reduce background and/or to increase specificity and sensitivity.

Antibody and Nucleic Acid Probes to Target Genes

The antibodies used to practice the invention are selected to have high specificity for the marker proteins of interest. Methods for making antibodies and for selecting appropriate antibodies are known in the art. In some embodiments, commercial antibodies directed to specific marker proteins may be used to practice the invention (see TABLE 4). The antibodies of the invention may be selected on the basis of desirable staining of cytological, rather than histological, samples. That is, in particular embodiments the antibodies are selected with the desired combination in mind and for binding specificity.

The markers and combinations of markers of the invention include genes or proteins that are selectively expressed, overexpressed or underexpressed in leukemia, and specifically in ALL, as defined herein above, and may be combined with known markers as well as those presently unknown in the art. In particular embodiments, markers are intracellular proteins, secreted proteins or proteins that are predicted to encode membranous proteins with transmembrane segments and extracellular domains. In some embodiments of the invention, probes can detect markers that are polypeptides expressed at the surface of the cell. In other embodiments, probes can detect markers that are polypeptides expressed intracellularly. In still other embodiments, probes detect markers that are polynucleotides. In still other embodiments, kits and methods of invention can comprise probes that can detect markers that include polypeptides and polynucleotides.

The methods of the invention can comprise MRD detection by gene array with preferred combinations of markers. MRD detection can be combined, for example, with at least 3 different marker combinations. Embodiments of the invention, can include, but are not limited to, the detection of mRNA expression with probes specific for genes shown in TABLE 1 comprising genes overexpressed in B-lineage ALL. Other embodiments of the invention, can include, but are not limited to, the detection of mRNA expression with probes specific for genes shown in TABLE 2 comprising genes underexpressed in B-lineage ALL.

Embodiments of the invention can include, but are not limited to, compositions and methods related to the detection of new markers for minimal residual disease (MRD) comprising: CD44, BCL2, HSPB1, CD73, CD24, CD123, CD72, CD86, CD200, CD79b, CD164, CD304, CD97, CD102, CD99, CD300a, CD130, PBX1, CTNNA1, ITGB7, CD69, or CD49f.

In yet other embodiments, diagnosing minimal residual disease in a sample taken from a subject can comprise the detection of combinations of markers including, but not limited to markers CD19, CD10, CD34, and CD45, in combination with markers comprising CD44, BCL2, HSPB1, CD73, CD24, CD123, CD72, CD86, CD200, CD79b, CD164, CD304, CD97, CD102, CD99, CD300a, CD130, PBX1, CTNNA1, ITGB7, CD69, or CD49f.

In yet other embodiments, diagnosing minimal residual disease in a sample taken from a subject can comprise the detection of combinations of markers including, but not limited to: CD19, CD10, CD34, and CD45, in combination with markers comprising CD38, CD24, CD44, CD58, CD73, CD15, CD200, CD66c, CD123, CD86, CD72, CD13, CD33, CD79b, HSPB1, BCL2, CD164, CD304, CD97, CD99, CD102 or CD300a.

"CD" or "cluster designation" refers to a system to classify cell markers defining cells based on what molecules are present on their surface. These "cell markers" or "markers" are often used to associate cells with certain immune functions. While using one CD molecule to define populations is uncommon (though a few examples exist), combining markers is often used to identify cell types with very specific characteristics within the immune system. The system was originally intended for the classification of the monoclonal antibodies (mAbs) generated by different laboratories around the world against epitopes on the surface molecules of leukocytes (white blood cells). Since then, the use of the CD nomenclature has expanded to include many other cell types, and more than 320 CD unique clusters and subclusters have been identified. In some instances CD antigens are expressed only at certain stages of development or under certain conditions, for example after cell activation or in certain disease conditions. Unlike the morphological criteria used in classical hematology for the description of specific developmental stages of lymphocytes, the use of monoclonal antibodies, and the "CD" marker annotation, allows the objective and precise analysis and standardized typing of mature and immature normal and malignant cells of all hematopoietic cell lineages. Antibodies that recognize cell surface markers can also be referred to by the CD designation. The CD designation can help to delineate the biologic traits that distinguish normal immune and hematopoietic cells from their malignant counterparts, which is of fundamental importance in understanding hematological malignancies.

The CD designation of molecules is often used to identify cells and expression patterns detected by various applications including flow cytometry. Very generally, cell populations can be defined using a '+' or '−' a symbol to indicate whether a certain cell fraction expresses or lacks a CD molecule. For example, a "CD34+, CD31−" cell is one that expresses CD34, but not CD31. This exemplary CD combination typically corresponds to a stem cell, opposed to a fully-differentiated endothelial cell. Therefore, generally speaking, use of CD with a number X, as in "CDX," can refer to a protein that in humans is encoded by the CDX gene, for example. Markers can be referred to by their CD designation, but can also be referred to by the gene or encoded protein name. Antibodies recognizing specific proteins can also be referred to by the CD number of the marker that is recognized.

CD34 (cluster designation 34) encompasses the human gene at locus 1q32 corresponding to sequences having GENBANK® Accession Nos: NM_001773, NP_001764.1. The protein is a monomeric cell surface antigen with a molecular mass of approximately 110 kDa that is selectively expressed on human hematopoietic progenitor cells.

CD19 (cluster designation 19) encompasses the human gene at locus 16p11.2 corresponding to sequences having GENBANK® Accession Nos: NM_01178098 and NP_001171569.1. CD19 is a cell surface molecule expressed only by B lymphocytes and follicular dendritic cells of the hematopoietic system. It is the earliest of the B-lineage-restricted antigens to be expressed and is present on most pre-B cells and most non-T-cell acute lymphocytic leukemia cells and B-cell type chronic lymphocytic leukemia cells (Tedder and Isaacs, 1989. *J. Immun.* 143: 712-717).

CD10 (cluster designation 10) encompasses the human gene at locus 3q21-q27 corresponding to sequences GEN-BANK® Accession Nos: NM_000902 and NP_000893.2. The protein is also known as "membrane metallo-endopeptidase (MME)" or "common acute lymphocytic leukemia antigen (CALLA)." The common acute lymphocytic leukemia antigen (CALLA) is an important cell surface marker in the diagnosis of human acute lymphocytic leukemia (ALL). It is present on leukemic cells of pre-B phenotype, which represents 85% of cases of ALL. The CALLA gene encodes a 100 kDa type II transmembrane glycoprotein Barker et al. (1989) *J. Immun.* 142: 283-287.

CD45 (cluster designation 45), encompasses the human gene at locus 1q31-q32 corresponding to sequences having GENBANK® Accession Nos: NM_002838, NP_002829.2. CD45 is also called B220; CD45R; GP180; LCA; LY5; and T200. It is a membrane-bound protein tyrosine phosphatase expressed in various isoforms, of between 180 and 220 kDa in size. CD45 is expressed on virtually all leukocytes, including myeloid and lymphoid precursors in bone marrow and mature lymphocytes in lymph nodes. CD45 (T200) is expressed on all hematopoietic cells except mature red cells and their immediate progenitors. It is not found, however, on other differentiated tissues; thus, it can be used as an antigenic marker with which to identify undifferentiated hematopoietic tumors.

CD38 (cluster designation 38) encompasses the human gene at locus 4p15.32 corresponding to sequences having GENBANK® Accession Nos: NM_001775.2, NP_001766.2, as set forth in SEQ ID NO: 1 and SEQ ID NO:2, respectively. CD38 is commonly used as a human leukocyte differentiation marker and is a novel multifunctional ectoenzyme widely expressed in cells and tissues especially in leukocytes. CD38 also functions in cell adhesion, signal transduction and calcium signaling. It has been demonstrated to be involved in the synthesis and hydrolysis of Cyclic ADP-ribose (cADPR) (Takasawa et al. (1993). *J. Biol. Chem.* 268: 26052-26054, 1993). Cyclic ADP-ribose is generated in pancreatic islets by glucose stimulation, serving as a second messenger for Ca(2+) mobilization in the endoplasmic reticulum for secretion of insulin (Takasawa et al. (1993) *Science* 259: 370-373).

CD24 (cluster designation 24) encompasses the human gene at locus 6q21 corresponding to sequences having GENBANK® Accession Nos: NM_013230, NP_037362.1, as set forth in SEQ ID NO: 3 and SEQ ID NO:4, respectively. CD24 is also known as "small cell lung carcinoma cluster 4 antigen" Studies with monoclonal antibodies indicate that most other hematopoietic cells, including T cells, monocytes, red blood cells, and platelets, seem not to express the CD24 antigen. CD24 has been implicated in both activation and differentiation of B lymphocytes because its expression pattern changes at critical times during B-cell development. In some embodiments, the variants detected encompass an epitope recognized by the antibody derived from clone ML5 which reacts with a 35-45 kDa two-chain glycoprotein (see TABLE 4, BD Pharmingen™ Cat. NO. 555428) (Schlossman et al. ed. (1995) *Leukocyte Typing V: White Cell Differentiation Antigens*. New York: Oxford University Press).

CD44 (cluster designation 44) encompasses the human gene at locus 11p13 corresponding to sequences having GENBANK® Accession Nos: NM_000610, NP_000601.3, as set forth in SEQ ID NO:5 and SEQ ID NO:6, respectively. It is also known as "Indian blood group" antigen. It is a receptor for hyaluronic acid and can also interact with other ligands, such as osteopontin, collagens, and matrix metalloproteinases (MMPs). This integral cell membrane glycoprotein participates in a wide variety of cellular functions including lymphocyte activation, recirculation and homing, hematopoiesis, and tumor metastasis (Aruffo et al. (1990) *Cell* 61: 1303-1313). In some embodiments, the variants detected encompass an epitope recognized by the antibody derived from clone 515 which reacts with a 85 kDa glycoprotein expressed on leukocytes, erythrocytes, epithelial cells and weakly on platelets (see TABLE 4, BD Pharmingen™, Cat. NO. 5500989) (Patel et al. "CD44 Workshop Panel Report" In: Kishimoto et al, ed. (1997) *Leukocyte Typing Vi: White Cell Differentiation Antigens*. New York: Garland Publishing Inc: 373-375).

CD58 (cluster designation 58) encompasses the human gene at locus 1p13 corresponding to sequences having GENBANK® Accession Nos: NM_001779, NP_001770.1, as set forth in SEQ ID NO:7 and SEQ ID NO:8, respectively. CD58 is also known as "lymphocyte function-associated antigen (LFA3)". The CD58 gene encodes a CD2 receptor. The presence of these both CD2 and CD58 antigens on opposing cells optimizes immune recognition, facilitating contacts between helper T lymphocytes and antigen-presenting cells as well as between cytolytic effectors and target cells (Wang et al. (1999) *Cell* 97: 791-803).

CD73 (cluster designation 73) encompasses the human gene at locus 6q14-q21 corresponding to sequences having GENBANK® Accession Nos: NM_002526 and NP_002517.1, as set forth in SEQ ID NO:9 and SEQ ID NO:10, respectively. CD73 is a membrane-bound enzyme also known as "ecto-5-prime-nucleotidase," and is expressed on subsets of B-cells and T-cells as well as other cell types. The enzyme is used as a marker of lymphocyte differentiation. CD73 is thought to function as a cell adhesion molecule and to mediate lymphocyte binding to endothelial cells (Airas, L. et al. (1995) *J. Exp. Med.* 182(2): 1603-8) and adhesion between B-cells and follicular dendritic cells (Airas and Jalkanen (1996) *Blood.* 88(5):1755-64). In some embodiments, the variants detected encompass an eptitope recognized by the antibody derived from clone AD2 which reacts with a 70 kDa glycosyl phosphatidylinositol (GPI)-anchored glycoprotein expressed on subsets of T and B lymphocytes, follicular dendritic cells, epithelial cells, and endothelial cells (see TABLE 4, BD Pharmingen™, Cat. NO. 550257) (Schlossman et al. ed. (1995) *Leukocyte Typing V: White Cell Differentiation Antigens*. New York: Oxford University Press).

CD15 (cluster designation 15) encompasses the human gene at locus 11q12-qter corresponding to sequences having GENBANK® Accession Nos: NM_002033 and NP_002024.1, as set forth in SEQ ID NO:11 and SEQ ID NO:12, respectively. CD15 expresses a protein also known as "fucosyltransferase 4 (alpha (1,3)," "myeloid-specific fucosyltransferase," "ELAM ligand fucosyltransferase," and "galactoside 3-L-fucosyltransferase." The product of this gene transfers fucose to N-acetyllactosamine polysaccharides to generate fucosylated carbohydrate structures. CD15 catalyzes the synthesis of the non-sialylated antigen, Lewis x (CD15).

CD200 (cluster designation 200) encompasses the human gene located at locus 3q12-q13 corresponding to sequences having GENBANK® Accession Nos: NM_001004196 and NP_001004196.2, as set forth in SEQ ID NO:13 and SEQ ID NO:14, respectively. CD200 was identified as a type II membrane glycoprotein expressed on a number of cell types relevant to the inflammatory and immune cascade, including dendritic cells, endothelial cells, and activated T cells. In some embodiments, the variants detected encompass an eptitope recognized by the antibody derived from clone MRC OX-104 which recognizes a 40-45 kDa membrane glycoprotein expressed on resting and activated T cells and B cells, as well as a subset of CD34+ progenitor cells, but not on NK cells, monocytes, granulocytes, or platelets (see TABLE 4, BD Pharmingen™, Cat. NO. 552475) (Mason et al. ed. (2002) *Leukocyte Typing VII*. New York: Oxford University Press).

CD66c (cluster designation 66c) encompasses the human gene at locus 19q13.1-q13.2 corresponding to sequences having GENBANK® Accession Nos: NM_002483 and NP_002474.3, as set forth in SEQ ID NO:15 and SEQ ID NO:16, respectively. CD66c is also known as "carcinoembryonic antigen-related cell adhesion molecule." CD66c is one of the most widely used tumor markers in serum immunoassay determinations of carcinoma.

CD123 (cluster designation 123) encompasses the human gene at loci Xp22.3 and Yp13.3 corresponding to sequences having GENBANK® Accession Nos: NM_002183 and NP_002174.1, as set forth in SEQ ID NO:17 and SEQ ID NO:18, respectively. CD123 is also known as the low affinity receptor for IL-3 encoding an interleukin 3 specific subunit of a heterodimeric cytokine receptor. The receptor is comprised of a ligand specific alpha subunit and a signal transducing beta subunit shared by the receptors for interleukin 3 (IL3), colony stimulating factor 2 (CSF2/GM-CSF), and interleukin 5 (IL5). CD123 is expressed on a subset of peripheral blood dendritic cells, progenitor cells, monocytes, eosinophils, basophils, and hematopoietic cells, such as erythroid cells and B cells. In some embodiments, the variants detected encompass an epitope recognized by the antibody derived from clone 9F5 which reacts to the α-chain of the interleukin-3 receptor (IL-3Rα) expressed on a subset of peripheral blood dendritic cells, on a subset of progenitor cells, monocytes, eosinophils, and basophils (see TABLE 4, BD Pharmingen™, Cat. NO. 303545) (Sun et al. (1996) *Blood*. 87: 88-92).

CD86 (cluster designation 86) encompasses the human gene at locus 3q21 corresponding to sequences having GENBANK® Accession Nos: NM_006889 and NP_008820.3, as set forth in SEQ ID NO:19 and SEQ ID NO:20, respectively. CD86 encodes a type I membrane protein that is a member of the immunoglobulin superfamily. This protein is expressed by antigen-presenting cells, and it is the ligand for two proteins at the cell surface of T cells: CD28 antigen and cytotoxic T-lymphocyte-associated protein 4. Binding of this protein with CD28 antigen is a co-stimulatory signal for activation of the T-cell. In some embodiments, the variants detected encompass an epitope recognized by the antibody derived from clone 2331 (FUN-1) which recognizes a 75 kDa cell surface protein expressed primarily on monocytes and activated B cells (see TABLE 4, BD Pharmingen™, Cat. NO. 555658) (Nozawa et al. (1993) *J Path*. 169(3):309-315).

CD72 (cluster designation 72) encompasses the human gene at locus 9p13.3 corresponding to sequences having GENBANK® Accession Nos: NM_001782 and NP_001773.1, as set forth in SEQ ID NO:21 and SEQ ID NO:22, respectively. CD72 is expressed on B cells and is the ligand for CD5. CD5 and/or CD72 engagement delivers critical co-stimulatory signals to B cells. It has been suggested that CD72 is a key molecule in regulating mature B cell differentiation, particularly in preventing the differentiation of naïve B cells into plasma cells (Yamazaki et al. (2005) *Eur. J. Immunol.*). In some embodiments, the variants detected encompass an epitope recognized by the antibody derived from clone JA-117 which reacts with a 39-43 kDa type II integral membrane protein expressed on B cells from early precursor stages through mature B cells, although not on plasma cells (see TABLE 4, BD Pharmingen™, Cat. NO. 555918) (Schlossman et al. ed. (1995) *Leukocyte Typing V. White Cell Differentiation Antigens*. New York: Oxford University Press).

CD13 (cluster designation 13) encompasses the human gene at locus 15q25-q26 corresponding to sequences having GENBANK® Accession Nos: NM_001150 and NP_001141.2, as set forth in SEQ ID NO:23 and SEQ ID NO:24, respectively. CD13 encodes a surface antigen glycoprotein of about 150 kDa, also known as "aminopeptidase-N." CD13 is an enzyme thought to be involved in the metabolism of regulatory peptides expressed by diverse cell types, including small intestinal and renal tubular epithelial cells, macrophages, granulocytes, and synaptic membranes from the CNS. Defects in this gene appear to be a cause of various types of leukemia or lymphoma.

CD79b (cluster designation 79b) encompasses the human gene at locus 17q23 corresponding to sequences having GENBANK® Accession Nos: NM_000626 and NP_000617.1, as set forth in SEQ ID NO:25 and SEQ ID NO:26, respectively. CD79b is a B lymphocyte antigen receptor that is a multimeric complex that includes the antigen specific component, surface immunoglobulin (Ig). Surface Ig non-covalently associates with two other proteins, Ig-alpha and Ig-beta, which are necessary for expression and function of the B-cell antigen receptor. The CD79b gene encodes the Ig-beta protein of the B-cell antigen component. In some embodiments, the variants detected encompass an epitope recognized by the antibody derived from clone AT107-2 which recognizes an immunogen peptide containing 20 amino acid residues derived from murine CD79b (NP_032365.1, NM_008339.2). The antibody is cross reactive with human, rat, pig, and dog CD79b (see TABLE 4, AbDserotec, Cat. NO. MCA2209FT) (Dornan et al. (2009) *Blood*. 114:2721-9; Vendel et al. (2009) *J. Immunol*. 182: 1509-17).

CD33 (cluster designation 33) encompasses the human gene at locus 19q13.41 corresponding to sequences having GENBANK® Accession Nos: NM_001082618.1 and NP_001076087.1, as set forth in SEQ ID NO:27 and SEQ ID NO:28, respectively. CD33, or Siglec-3 is a transmembrane receptor expressed on cells of myeloid lineage. It is usually considered myeloid-specific, but it can also be found on some lymphoid cells. CD33 has been implicated in the negative regulation of cell proliferation of normal or leukemic myeloid cells. (Vitale et al. (1999) *PNAS*. 96, 15091-15096).

HSPB1 encompasses the human gene at locus 7q11.23 corresponding to sequences having GENBANK® Accession Nos: NM_001540 and NP_001531.1. HSPB1, as set forth in SEQ ID NO:29 and SEQ ID NO:30, respectively, is a gene that encodes the intercellular heat shock 27 kDa protein. Expression of this gene is induced by environmental stress and developmental changes. The encoded protein is involved in stress resistance and actin organization and translocates from the cytoplasm to the nucleus upon stress induction. Synthesis of the small (27-kDa) HSP has been shown to be correlated with the acquisition of thermotolerance. In some embodiments, the variants detected encompass an epitope recognized by antibody HSP27, clone G3.1 conjugated to biotin that recognizes a 24-27 kDa hsp27 protein (early called 24K) expressed on approximately 50% of breast carcinomas and drug resistant cancer cells (See TABLE 4, Thermo Scientific, Cat. NO. MS-101-BO, -B1, or -B, for biotin labeled). In other embodiments, the variants encompass the eptitope recognized by the antibody HSPB1 derived from G3.1, conjugated to PE (see TABLE 4, Stressgen, Cat. NO. SPA-800PE) (Edward et al. (1980) *Biochem Biophys Research Commun.* 93:804-812; Ciocca et al. (1991) *Breast Cancer Research and Treatment.* 20:33-42).

Bcl-2 (B-cell lymphoma 2) encompasses the human gene at locus 18q21.3 corresponding to sequences having GENBANK® Accession Nos: NM_000633 and NM_000657, and NP_000624.2 and NP_000648.2, as set forth in SEQ ID NO:31 and SEQ ID NO:33, and SEQ ID NO:32 and SEQ ID NO:34, respectively. This gene encodes an integral outer mitochondrial membrane protein that blocks the apoptotic death of some cells such as lymphocytes. Bcl-2 derives its name from B-cell lymphoma 2, as it is the second member of a range of proteins initially described in chromosomal translocations involving chromosomes 14 and 18 in follicular lymphomas. Constitutive expression of BCL2, such as in the case of translocation of BCL2 to Ig heavy chain locus, is thought to be the cause of follicular lymphoma. The Bcl-2 gene has been implicated in a number of cancers, including melanoma, breast, prostate, and lung carcinomas. It is also thought to be involved in resistance to conventional cancer treatment. Two transcript variants, produced by alternate splicing, differ in their C-terminal ends. In some embodiments, the variants detected encompass an eptitope recognized by the antibody derived from clone 100 which is expressed in lymphocytes and monocytes but not appreciably in granulocytes (see TABLE 4, Invitrogen, Cat. NO. MHBLC014) (Hill et al. (1996) *Blood.* 88:1046).

CD164 (cluster designation 164) encompasses the human gene at locus 6q21 corresponding to sequences having GENBANK® Accession Nos: NM_006016 and NP_006007.2, as set forth in SEQ ID NO:35 and SEQ ID NO:36, respectively. CD164 is a type-I integral transmembrane sialomucin that functions as an adhesion receptor. Sialomucins are a heterogeneous group of secreted or membrane-associated mucins that appear to play two key but opposing roles in vivo: first as cytoprotective or anti-adhesive agents, and second as adhesion receptors. In some embodiments, the variants detected encompass an eptitope recognized by the antibody derived from clone N6B6 which recognizes a 80-90 kDa mucin-like molecule present on CD34+ progenitor cells during the early stages of B cell, erythroid cell and myelomonocytic cell development. It is also expressed on epithelial cells, peripheral blood monocytes and weakly on lymphocytes (see TABLE 4, BD Pharmingen™, Cat. NO. 551298) (Watt et al. (1998). *Blood* 92 (3):849-66; and Zannettino et al. (1998). *Blood.* 92 (8):2613-28).

CD304 (cluster designation 304) encompasses the human gene at locus 10p12 corresponding to sequences having GENBANK® Accession Nos: NM_001024628 and NP_001019799.1, as set forth in SEQ ID NO:37 and SEQ ID NO:38, respectively. CD304 is also known as "NRP1," "Neuropilin-1 (NP-1)," and "BDCA-4," and encodes a protein with numerous functions. On neurons, it is a receptor for axon growth guidance class-3 semaphorins SEMA3A and plexin-1. On endothelial and some tumor cells it is a VEGF165 receptor, and on plasmacytoid dendritic cells it has a similar role to CD303 but does not decrease interferon production upon activation. In some embodiments, the variants detected encompass an eptitope recognized by the antibody derived from clone AD5-17F6 (see TABLE 4, Miltenyi Biotec Cat. NO. 130-090-533) (Dzionek, A., et al. (2000) *J. Immunol.* 165:6037-6046.)

CD97 (cluster designation 97) encompasses the human gene at locus 19p13 corresponding to sequences having GENBANK® Accession Nos: NM_078481 and NP_510966.1, as set forth in SEQ ID NO:39 and SEQ ID NO:40, respectively. The encoded product is a glycoprotein present on the surface of most activated leukocytes and spans the membrane seven times, which is a defining feature of G protein-coupled receptors. The protein has an extended extracellular region with several N-terminal epidermal growth factor (EGF)-like domains, which mediate binding to its cellular ligand, decay accelerating factor (DAF, CD55), a regulatory protein of the complement cascade. The presence of structural features characteristic of extracellular matrix proteins and transmembrane proteins suggests that this protein is a receptor involved in both cell adhesion and signaling processes early after leukocyte activation. Alternative splicing has been observed for this gene and three variants have been found. In some embodiments, the variants detected encompass an eptitope recognized by the antibody derived from clone VIM3b which recognizes a triplet of membrane proteins of 74, 80 and 89 kDa strongly expressed on phytohemagglutinin (PHA)-activated T and B cells, virtually all monocytes and granulocytes, and several cell lines including HL-60, THP-1, and K562. It is weakly expressed on resting lymphocytes (see TABLE 4, BD Pharmingen™, Cat. NO. 555774) (Schlossman, et al. ed. (1995) *Leukocyte Typing V.* New York: Oxford University Press).

CD99 (cluster designation 99) encompasses the human gene at loci Xp22.32 and Yp11.3 corresponding to sequences having GENBANK® Accession Nos: NM_001122898 and NP_001116370.1, as set forth in SEQ ID NO:41 and SEQ ID NO:42, respectively. CD99 is a cell surface glycoprotein involved in leukocyte migration, T-cell adhesion, ganglioside GM1 and transmembrane protein transport, and T cell death by a caspase-independent pathway. Two transcript variants encoding different isoforms have been found for this gene. This variant 2 lacks an alternate in-frame exon compared to variant 1. The resulting isoform 2 has the same N- and C-termini but is shorter compared to isoform 1. In some embodiments, the variants detected encompass an eptitope recognized by the antibody derived from clone TU 12 which recognizes a 32 kDa sialoglycoprotein expressed on all leukocyte lineages, although is differentially expressed during T and B-lymphoid and granulocytic development, with higher densities being expressed during early hematopoietic stages (see TABLE 4, BD Pharmingen™, Cat. NO. 555689) (Knapp et al, ed. (1989) *Leucocyte Typing IV.* New York: Oxford University Press; 1989).

CD102 (cluster designation 102) encompasses the human gene at locus 17q23-q25 corresponding to sequences having GENBANK® Accession Nos: NM_000873 and NP_000864.2, as set forth in SEQ ID NO:43 and SEQ ID NO:44, respectively. CD102 is also known as intercellular adhesion molecule 2 (ICAM-2). This variant (5) differs in the 5' UTR compared to variant 1. All five variants encode the same protein. The protein encoded by this gene is a member of the intercellular adhesion molecule (ICAM) family. All ICAM proteins are type-I transmembrane glycoproteins, contain 2-9 immunoglobulin-like C2-type domains, and bind to the leukocyte adhesion LFA-1 protein. This protein may play a role in lymphocyte recirculation by blocking LFA-1-dependent cell adhesion. CD102 mediates adhesive interactions important for antigen-specific immune response, NK-cell mediated clearance, lymphocyte recirculation, and other cellular interactions important for immune response and surveillance. In some embodiments, the variants detected encompass an eptitope recognized by the antibody derived from clone CBR-IC/2 which recognizes a type-I membrane glycoprotein with an approximate molecular weight of 55-65 kDa expressed on vascular endothelial cells, lymphocytes, monocytes, but not on granuloctyes. (see TABLE 4, BD Pharmingen™, Cat. NO. 558080) (Barclay et al. ed. (1997) *The Leukocyte Antigen FactsBook*. San Diego: Academic Press).

CD300a (cluster designation 300a) encompasses the human gene at locus 17q25.2 corresponding to sequences having GENBANK® Accession Nos: NM_007261 and NP_009192.2, as set forth in SEQ ID NO:45 and SEQ ID NO:46, respectively. CD300a also known as "inhibitory receptor protein (IRp60)" is a surface molecule of 60 kDa expressed by all human natural killer (NK) cells. The IRp60 gene, encodes a molecule that is highly O- and N-glycosylated, belonging to the immunoglobulin superfamily (Ig-SF). The ligand of the CD300a is still unknown but IRp60 does not appear to recognize HLA-class I molecules. In some embodiments, the variants detected encompass an eptitope recognized by the antibody derived from clone E59.126 expressed on T lymphocyte subsets, monocytes, and granulocytes (see TABLE 4, Beckman Coulter Cat. NO. A22328).

Intracellular Protein Targets

In some embodiments of the invention, the expression of intracellular proteins, for example, BCL2 and HSPB1, are detected using flow cytometry by first permeablizing the cell surface membrane to allow access of antibody through the membrane. In one embodiment a permeabilization reagent, such as those containing various surfactants (e.g., saponin, Triton X-100, Tween-20, N-acyl sarcosine, etc) or organic solvents (e.g., alcohols, acetone) or other similar solution, is used. A permeabilization reagent is optimally used in a sufficient amount enabling penetration of antibodies to the intercellular space, while substantially preserving the cellular membrane. Ideally, the permeabilizing agent creates apertures in the cell membrane without affecting the gross morphology of the cell such that flow cytometric light scattering characteristics of the cell are not affected. Such methods of permeabilizing cells are well known in the art.

In embodiments of the invention, the cell may be fixed prior to or during permeabilization to maintain the integrity of the cell. Methods of fixation are also well known in the art. In some embodiments, fixation and permeabilization can be combined. An example of a fixation/permeabilizing agent is INTRAPREP™ (Beckman Coulter, Inc.) which comprises 5.5% v/v formaldehyde as a fixation reagent and a phosphate buffered saline (PBS)-saponin-based permeabilization reagent.

TABLE 4

Antibodies against the new markers

| Marker | Antibody | Clone | Conjugate | Source | Catalogue # | Positive Control | Negative Control* |
|---|---|---|---|---|---|---|---|
| CD44 | CD44 | 515 | PE | BD Biosciences | 550989 | Lymphocytes, monocytes | Jurkat cell line |
| BCL2 | Anti-Human Bcl-2 | 100 | PE | Invitrogen | MHBCL04 | Lymphocytes, monocytes | Ramos cell line |
| HSPB1 | HSP27 | G3.1 | Biotin | Lab Vision Corporation | MS-101 | Monocytes | Lymphocytes |
| HSPB1 | HSP27 | G3.1 | PE | Stressgen | SPA-800PE | Monocytes | Lymphocytes |
| CD73 | CD73 | AD2 | PE | BD Biosciences | 550257 | Lymphocyte subset | Monocytes |
| CD24 | CD24 | ML5 | PE | BD Biosciences | 555428 | B lymphocytes | T lymphocytes |
| CD123 | CD123 | 9F5 | PE | BD Biosciences | 340545 | Monocytes | T lymphocytes |
| CD72 | CD72 | J4-117 | FITC | BD Biosciences | 555918 | B lymphocytes | T lymphocytes |
| CD86 | CD86 | 2331 | PE | BD Biosciences | 555658 | Monocytes | Lymphocytes |
| CD200 | CD200 | MRC OX-104 | PE | BD Biosciences | 552475 | B lymphocytes | Monocytes |
| CD79B | CD79b | AT107-2 | FITC | Serotec | MCA2209F | B lymphocytes | T lymphocytes |
| CD164 | CD164 | N6B6 | PE | BD Biosciences | 551298 | Monocytes | Granulocytes |
| CD304 | CD304 | AD5-17F6 | PE | Miltenyi Biotec inc | 130-090-533 | Dendritic cells (doubled with CD123) | Lymphocytes |
| CD97 | CD97 | VIM3b | PE | BD Biosciences | 555774 | Monocytes | Lymphocytes |
| ITG7 | Anti-Human Integrin 7 | FIB504 | PE | BD Biosciences | 555945 | Lymphocyte subset | Lymphocyte subset |
| CD102 | CD102 | CBR-IC2/2 | PE | BD Biosciences | 558080 | Monocytes, lymphocytes | Granulocytes |
| CD99 | CD99 | TU12 | PE | BD Biosciences | 555689 | T-ALL | Granulocytes |
| CD300a | Anti-IRp60 | E59.126 | PE | Beckman Coulter | A22328 | Monocytes, lymphocyte subset | Lymphocyte subset |
| CD130 | CD130 | AM64 | PE | BD Biosciences | 555757 | Monocytes, lymphocyte subset | B lymphocytes |
| PBX1 | PBX1 | 4A2 | None | Abnova | H00005087-M01 | Cell line 697 | Lymphocytes |
| CTNNA1 | Anti-Human | 1G5 | None | Abcam | Ab17259 | Monocytes | Lymphocytes |
| CD69 | CD69 | L78 | PE | BD Biosciences | 341652 | Activated lymphocytes | Non-activated lymphocytes |
| CD49f | CD49f | GoH3 | PE | BD Biosciences | 555736 | Monocytes | Subset of lymphocytes |
| EPOR | Anti-Human Epo-R | 38409 | PE | R&D Systems | FAB307P | Subset of erythroblasts | Lymphocytes |
| CD1c | CD1c | AD5-8E7 | PE | Miltenyi Biotec | 130-090-508 | B lymphocyte subset | Granulocytes |
| BCL11B | Anti-Human BCL11B | 25B6 | None | Abcam | Ab18465 | Jurkat cell line | NALM6 cell line |

TABLE 4-continued

Antibodies against the new markers

| Marker | Antibody | Clone | Conjugate | Source | Catalogue # | Positive Control | Negative Control* |
|---|---|---|---|---|---|---|---|
| CD120a | CD120a | H398 | PE | Serotec | MCA1340PE | Monocytes | Lymphocyte subsets |
| CD37 | CD37 | BL14 | PE | Beckman Coulter | IM0458 | B lymphocytes | T lymphocytes |
| CD62L | CD62L | SK11 | PE | BD Biosciences | 341012 | Monocytes, lymphoid subset | Lymphoid subset |
| CD132 | CD132 | AG184 | PE | BD Biosciences | 555900 | Monocytes, lymphocyte subset | Lymphocyte subset |
| CD83 | CD83 | HB15a | PE | Beckman Coulter | IM2218 | Tonsillar lymphocyte subset | Resting lymphocytes |
| IL13RA1 | Anti-Human IL-13 Receptor.1 | GM-1C8 | None | Abcam | Ab3772 | Monocytes | Lymphocytes |

Secondary antibodies/reagent

| | | | | | | | |
|---|---|---|---|---|---|---|---|
| Goat F(Ab')2 Anti-Mouse IgG2a | | | PE | Southern Biotechnology Associates | 1082-09 | | |
| Goat F(Ab')2 Anti-Mouse IgG1 | | | FITC | Southern Biotechnology Associates | 1072-02 | | |
| Goat F(Ab')2 Anti-Mouse IgG1 | | | FITC | Southern Biotechnology Associates | 1072-02 | | |
| Goat F(ab')2 Anti-Rat IgG Fc | | | PE | Jackson Immuno-Research Laboratories | 112-116-071 | | |
| Streptavidin | | | PE | Jackson Immuno-Research Laboratories | 016-110-084 | | |

*Dim or no expression

TABLE 5

Standard marker combinations used to monitor MRD in childhood B-lineage ALL

| FITC | PE | PerCP | APC |
|---|---|---|---|
| CD58 | CD10 | CD34 | CD19 |
| CD38 | CD10 | CD34 | CD19 |
| CD45 | CD10 | CD34 | CD19 |
| anti-TdT | CD10 | CD34 | CD19 |
| CD13 | CD10 | CD34 | CD19 |
| anti-TdT* | anti-IgM | CD34 | CD19 |
| CD66c | CD10 | CD34 | CD19 |
| CD33 | CD10 | CD34 | CD19 |
| CD15 | CD10 | CD34 | CD19 |

*TdT, terminal deoxynucleotidyl transferase

RNA Expression Profiling:

In other embodiments, the expression of a marker of interest is detected at the nucleic acid level. Nucleic acid-based techniques for assessing expression are well known in the art and include, for example, determining the level of marker mRNA in a specimen taken from a patient. Many expression detection methods use isolated RNA. Generally, blood, serum, or tissue samples can readily be processed using techniques well known to those of skill in the art, such as, for example, the single-step RNA isolation process of Chomczynski (1989, U.S. Pat. No. 4,843,155).

Isolated mRNA can be used in hybridization or amplification assays that include, but are not limited to, Southern or Northern analyses, polymerase chain reaction analyses and probe arrays. One method for the detection of mRNA levels involves contacting the isolated mRNA with a nucleic acid molecule (probe) that can hybridize to the mRNA encoded by the gene being detected. The nucleic acid probe can be, for example, a full-length cDNA, or a portion thereof, such as an oligonucleotide of at least 7, 15, 30, 50, 100, 250 or 500 nucleotides in length and sufficient to specifically hybridize under stringent conditions to an mRNA or genomic DNA encoding a marker of the present invention. Hybridization of an mRNA with the probe indicates that the marker in question is being expressed.

In one embodiment, the mRNA is immobilized on a solid surface and contacted with a probe, for example by running the isolated mRNA on an agarose gel and transferring the mRNA from the gel to a membrane, such as nitrocellulose. In an alternative embodiment, the probe(s) are immobilized on a solid surface and the mRNA is contacted with the probe(s), for example, in an Affymetrix gene chip array. A skilled artisan can readily adapt known mRNA detection methods for use in detecting the level of mRNA encoded by the markers of the present invention.

An alternative method for determining the level of marker mRNA in a sample involves the process of nucleic acid amplification, e.g., by RT-PCR (the experimental embodiment set forth in Mullis, 1987, U.S. Pat. No. 4,683,202), ligase chain reaction (Barany (1991) *Proc. Natl. Acad. Sci. USA* 88:189-193), self sustained sequence replication (Guatelli et al. (1990) *Proc. Natl. Acad. Sci. USA* 87:1874-1878), transcriptional amplification system (Kwoh et al. (1989) *Proc. Natl. Acad. Sci. USA* 86:1173-1177), Q-Beta Replicase (Lizardi et al. (1988) *Bio/Technology* 6:1197), rolling circle replication (Lizardi et al. U.S. Pat. No. 5,854,033) or any other nucleic acid amplification method, followed by the detection of the amplified molecules using techniques well known to those of skill in the art. These detection schemes are especially useful for the detection of nucleic acid molecules if such molecules are present in very low numbers. In particular aspects of the invention, marker expression is assessed by quantitative fluorogenic RT-PCR (i.e., the TaqMan® System). Such methods typically utilize pairs of oligonucleotide primers that are specific for the marker of interest. Methods for designing oligonucleotide primers specific for a known sequence are well known in the art.

Marker expression levels of RNA may be monitored using a membrane blot (such as used in hybridization analysis such as Northern, Southern, dot, and the like), or microwells, sample tubes, gels, beads or fibers (or any solid support comprising bound nucleic acids). See U.S. Pat. Nos. 5,770,722, 5,874,219, 5,744,305, 5,677,195 and 5,445,934, which are incorporated herein by reference. The detection of marker expression may also comprise using nucleic acid probes in solution.

In one embodiment of the invention, microarrays are used to detect marker expression. Microarrays are particularly well suited for this purpose because of the reproducibility between different experiments. DNA microarrays provide one method for the simultaneous measurement of the expression levels of large numbers of genes. Each array consists of a reproducible pattern of capture probes attached to a solid support. Labeled RNA or DNA is hybridized to complementary probes on the array and then detected by laser scanning. Hybridization intensities for each probe on the array are determined and converted to a quantitative value representing relative gene expression levels. See, U.S. Pat. Nos. 6,040,138, 5,800,992 and 6,020,135, 6,033,860, and 6,344,316, which are incorporated herein by reference. High-density oligonucleotide arrays are particularly useful for determining the gene expression profile for a large number of RNA's in a sample.

Techniques for the synthesis of these arrays using mechanical synthesis methods are described in, e.g., U.S. Pat. No. 5,384,261, incorporated herein by reference in its entirety for all purposes. Although a planar array surface is preferred, the array may be fabricated on a surface of virtually any shape or even a multiplicity of surfaces. Arrays may be peptides or nucleic acids on beads, gels, polymeric surfaces, fibers such as fiber optics, glass or any other appropriate substrate, see U.S. Pat. Nos. 5,770,358, 5,789,162, 5,708,153, 6,040,193 and 5,800,992, each of which is hereby incorporated in its entirety for all purposes. Arrays may be packaged in such a manner as to allow for diagnostics or other manipulation of an all-inclusive device. See, for example, U.S. Pat. Nos. 5,856,174 and 5,922,591 herein incorporated by reference.

In one approach, total mRNA isolated from a specimen is converted to labeled cRNA and then hybridized to an oligonucleotide array. Each specimen is hybridized to a separate array. Relative transcript levels may be calculated by reference to appropriate controls present on the array and in the sample. In one embodiment of the invention, RNA can be isolated from a subpopulation of cells with a characteristic expression profile, for example, cells co-expressing markers CD19 and CD10.

In embodiments of the invention, an expression profile can comprise values corresponding to gene expression detected by mRNA expression levels where the expression of many genes can be analyzed simultaneously and interpreted in one sample. In embodiments of the invention, an mRNA probe set can include probes corresponding to those in TABLE 1 and TABLE 2. Embodiments of the invention, include but are not limited to the detection of markers and combinations of markers in TABLE 1 comprising genes overexpressed in B-lineage ALL. Embodiments of the invention, include but are not limited to the detection of markers and combinations of markers in TABLE 2 comprising genes underexpressed in B-lineage ALL.

Embodiments of the invention can include, but are not limited to, compositions and methods related to the detection of new markers for the detection of minimal residual disease (MRD) comprising: CD44, BCL2, HSPB1, CD73, CD24, CD123, CD72, CD86, CD200, CD79b, CD164, CD304, CD97, CD102, CD99, CD300a, CD130, PBX1, CTNNA1, ITGB7, CD69, or CD49f.

In embodiments of the invention, an expression profile is generated by the detection of nucleic acid corresponds to the expression of mRNA. Embodiments of the method comprise a method of diagnosing minimal residual disease in a subject by obtaining a specimen from the subject. The specimen is contacted with a plurality of probes, wherein each of the probes specifically binds to a distinct marker, wherein a first probe specifically binds to CD19 and a second probe specifically binds to CD10. A CD19+/CD10+ cell is isolated from the specimen. An expression level of at least one, two, three, four, five, six or more gene products expressed in said CD19+, CD10+ cell is determined, wherein the at least one, two, three, four, five, six or more gene products encode CD38, CD24, CD44, CD58, CD73, CD15, CD200, CD66c, CD123, CD86, CD72, CD13, CD33, CD79b, HSPB1, BCL2, CD164, CD304, CD97, CD99, CD102 or CD300a. An expression profile is then generated by combining the expression values of the gene products. In such methods, the expression of CD19 and CD10 and a modulated level of at least one gene products encoding CD38, CD24, CD44, CD58, CD73, CD15, CD200, CD66c, CD123, CD86, CD72, CD13, CD33, CD79b, HSPB1, BCL2, CD164, CD304, CD97, CD99, CD102, or CD300a relative to a normal control is indicative of minimal residual disease in acute lymphoblastic leukemia.

Other embodiments of the method comprise contacting a specimen with a plurality of probes to detect expression levels of markers comprising CD19 and CD10 and at least four, five, six, seven, eight, nine, ten, eleven, twelve, thirteen, fourteen, fifteen, sixteen, seventeen, eighteen, nineteen, twenty, twenty-one, or twenty-two markers comprising: CD38, CD24, CD44, CD58, CD73, CD15, CD200, CD66c, CD123, CD86, CD72, CD13, CD33, CD79b, HSPB1, BCL2, CD164, CD304, CD97, CD99, CD102 or CD300a.

In embodiments of the invention, determining the expression profile of a specimen that is CD10+/CD19+ further comprises probe combinations comprising (a) CD38, CD24, and CD44; (b) CD38, CD58, and CD44; (c) CD38, CD73, and CD15; (d) CD38, CD200, and CD44; (e) CD66c, CD123, and CD86; (f) CD72, CD13, and CD33; or (g) CD79b, HSPB1, and Bcl-2.

In yet other embodiments of the invention, a kit for detecting minimal residual disease in a subject is disclosed. The kit can comprise a plurality of antibodies, antibody fragments, or molecular probes wherein each antibody, antibody fragment, or molecular probe is reactive to each of markers CD10, CD19, CD34, and CD45, and at least one additional of antibody, antibody fragment, or molecular probe that specifically binds to at least one additional marker comprising CD38, CD24, CD44, CD58, CD73, CD15, CD200, CD66c, CD123, CD86, CD72, CD13, CD33, CD79b, HSPB1, BCL2, CD164, CD304, CD97, CD99, CD102 or CD300a. The kit can include at least one antibody, antibody fragment, or molecular probe that is detectably labeled. Embodiments of the invention include detectable labels, which can be, but are not limited to a radiolabel, a fluorophore, a peptide, an enzyme, a quantum dot, or a combination thereof.

In embodiments of the invention, a kit can comprise combinations of probes comprising (a) CD10, CD19, CD34, CD45, CD38, CD24, and CD44; (b) CD10, CD19, CD34, CD45, CD38, CD58, and CD44; (c) CD10, CD19, CD34, CD45, CD38, CD73, and CD15; (d) CD10, CD19, CD34, CD45, CD38, CD200, and CD44; (e) CD10, CD19, CD34, CD45, CD66c, CD123, and CD86; (f) CD10, CD19, CD34, CD45, CD72, CD13, and CD33; or (g) CD10, CD19, CD34, CD45, CD79b, HSPB1, and Bcl-2.

Data and Expression Profile Analysis

Any method known in the art for comparing two or more data sets to detect similarity and/or variance between them may be used to compare a subject expression profile to a normal expression profile. To determine whether two or more expression profiles show statistically significant similarity and/or variance, statistical tests may be performed to determine whether any differences between the expression profiles are likely to have been achieved by a random event. Methods for comparing gene expression profiles to determine whether they share statistically significant similarity or variance are known in the art and also reviewed in Holloway et al. (2002) *Nature Genetics Suppl.* 32:481-89, Churchill (2002) *Nature Genetics Suppl.* 32:490-95, Quackenbush (2002) *Nature Genetics Suppl.* 32: 496-501; Slonim (2002) *Nature Genetics Suppl.* 32:502-08; and Chuaqui et at (2002) *Nature Genetics Suppl.* 32:509-514; each of which is herein incorporated by reference in its entirety.

An expression profile is "distinguishable" or "statistically distinguishable" from a normal control expression profile according to the invention if the two expression profiles do not share statistically significant similarity.

Kits for Detection of Minimal Residual Disease

Kits for practicing the screening and diagnostic methods of the invention are further provided. The kits of the invention may also include methods for use in diagnosing minimal residual disease in ALL, detecting or diagnosing ALL, monitoring disease status in a patient for the recurrence of ALL, or monitoring the efficacy of a treatment for ALL. These methods are described elsewhere herein.

As used herein, "kit" refers to a set of reagents for the purpose of performing the method embodiments of the invention, more particularly, the detection of minimal residual disease in patient specimens. The term "kit" is intended to mean any manufacture (e.g., a package or a container) comprising at least one reagent, e.g., an antibody, a nucleic acid probe, etc. for specifically detecting the expression of a marker of the invention. The kit may be promoted, distributed, or sold as a unit for performing the methods of the present invention. Additionally, the kits may contain a package insert describing the kit and methods for its use.

In embodiments of the invention, expression of markers can be assessed at the protein level or nucleic acid level, or both in combination. In some embodiments, expression of protein expression is detected using specific antibody probes. Expression of identified markers can also be detected by nucleic acid based techniques, including, for example, hybridization and RT-PCR. Expression can be evaluated in a variety of specimens taken from the body including, but not limited to, blood cells or bone marrow cells, and cellular products extracted from blood and bone marrow cells, including, but not limited to protein and RNA extracted from blood and bone marrow cells.

The kit can comprise a plurality of antibodies, antibody fragments, or molecular probes wherein each antibody, antibody fragment, or molecular probe is specific for CD10, CD19, CD34, CD45, CD38, CD58, CD15, CD66c, CD13, CD33, CD44, BCL2, HSPB1, CD73, CD24, CD123, CD72, CD86, CD200, CD79b, CD164, CD304, CD97, CD102, CD99, CD300a, CD130, PBX1, CTNNA1, ITGB7, CD69, or CD49f.

The kit can comprise a plurality of antibodies, antibody fragments, or molecular probes wherein each antibody, antibody fragment, or molecular probe is reactive to each of markers CD10, CD19, CD34, and CD45, and at least one additional antibody, antibody fragment, or molecular probe that specifically binds to at least one additional marker comprising CD44, BCL2, HSPB1, CD73, CD24, CD123, CD72, CD86, CD200, CD79b, CD164, CD304, CD97, CD102, CD99, CD300a, CD130, PBX1, CTNNA1, ITGB7, CD69, or CD49f.

The kit can comprise a plurality of antibodies, antibody fragments, or molecular probes wherein each antibody, antibody fragment, or molecular probe is reactive to each of markers CD10, CD19, CD34, and CD45, and at least one additional antibody, antibody fragment, or molecular probe that specifically binds to at least one additional marker comprising CD38, CD24, CD44, CD58, CD73, CD15, CD200, CD66c, CD123, CD86, CD72, CD13, CD33, CD79b, HSPB1, BCL2, CD164, CD304, CD97, CD99, CD102 or CD300a. The kit can include at least one antibody, antibody fragment, or molecular probe that is detectably labeled. Embodiments of the invention include detectable labels, which can be, but are not limited to a radiolabel, a fluorophore, a peptide, an enzyme, a quantum dot, or a combination thereof.

In embodiments of the invention, a kit can comprise combinations of probes comprising (a) CD10, CD19, CD34, CD45, CD38, CD24, and CD44; (b) CD10, CD19, CD34, CD45, CD38, CD58, and CD44; (c) CD10, CD19, CD34, CD45, CD38, CD73, and CD15; (d) CD10, CD19, CD34, CD45, CD38, CD200, and CD44; (e) CD10, CD19, CD34, CD45, CD66c, CD123, and CD86; (f) CD10, CD19, CD34, CD45, CD72, CD13, and CD33; or (g) CD10, CD19, CD34, CD45, CD79b, HSPB1, and Bcl-2.

In yet another embodiment, a kit can comprises an array having a substrate with a plurality of addresses, where each address has a capture probe that can specifically bind a nucleic acid molecule comprising CD38, CD58, CD66c, CD79b, CD164, CD44, BCL2, HSPB1, CD72, CD73, CD24, CD123, CD86, CD200, CD304, CD97, CD99, CD102 or CD300a.

The methods of the invention can comprise MRD detection by gene array with preferred combinations of probes to specific markers. MRD detection can be combined, for example, with at least 3 different probes. Embodiments of the invention, can include, but are not limited to, the detection of mRNA expression with probes specific for genes shown in TABLE 1 comprising genes overexpressed in B-lineage ALL. Other embodiments of the invention, can include, but are not limited to, the detection of mRNA expression with probes specific for genes shown in TABLE 2 comprising genes underexpressed in B-lineage ALL.

One of skill in the art will further appreciate that any or all steps in the screening and diagnostic methods of the invention could be implemented by personnel or, alternatively, performed in an automated fashion. For example, the methods can be performed in an automated, semi-automated, or manual fashion, and as one-step or multi-step processes. Furthermore, the methods disclosed herein can also be combined with other methods known or later developed to permit a more accurate identification of patients having an increased likelihood of having minimal residual disease or a more reliable diagnosis of ALL.

The article "a" and "an" are used herein to refer to one or more than one (i.e., to at least one) of the grammatical object of the article. By way of example, "an element" means one or more element.

Throughout the specification the word "comprising," or variations such as "comprises" or "comprising," will be understood to imply the inclusion of a stated element, integer or step, or group of elements, integers or steps, but not the exclusion of any other element, integer or step, or group of elements, integers or steps.

Embodiments of the present invention are further defined in the following Examples. It should be understood that these Examples are given by way of illustration only. From the above discussion and these Examples, one skilled in the art can ascertain the essential characteristics of this invention, and without departing from the spirit and scope thereof, can make various changes and modifications of the embodiments of the invention to adapt it to various usages and conditions. Thus, various modifications of the embodiments of the invention, in addition to those shown and described herein, will be apparent to those skilled in the art from the foregoing description. Such modifications are also intended to fall within the scope of the appended claims.

EXPERIMENTAL

Patients

Bone marrow samples were collected at presentation from 470 patients aged <1 to 18 years with newly diagnosed B-lineage ALL; 270 samples were included in genome-wide gene expression studies, and 200 were tested to validate the gene expression findings by flow cytometry. Bone marrow samples were obtained during therapy in 51 patients and samples obtained at relapse in 9. The diagnosis of B-lineage ALL was unequivocal and based on morphology, cytochemistry and cell marker expression. To determine gene expression and immunophenotype of normal lymphoid progenitors, bone marrow samples were collected from 22 healthy donors aged 2-25 yrs (median, 10 yrs) during the harvest of bone marrow for stem cell transplantation, and bone marrow samples obtained from 27 patients with B-lineage ALL, 7 with T-lineage ALL and 5 with acute myeloid leukemia (AML) during therapy.

Sample Preparation

Leukemic and normal mononuclear cells were collected after centrifugation on a density gradient (AccuPrep, Nycomed, Oslo, Norway) and washed three times in phosphate-buffered saline (PBS). Leukemic cells used in gene expression studies were cryopreserved. Normal bone marrow CD19+ cells used for gene expression analysis were first enriched using a MACS separation system (Miltenyi Biotec, Auburn, Calif.) from fresh samples, yielding>98% CD19+ cell purity. Cells were then stained with anti-CD19 conjugated to phycoerythrin (PE) and anti-CD10 conjugated to fluorescein isothiocyanate (FITC; both from Becton Dickinson, San Jose, Calif.) and CD19+CD10+ cells were sorted using a Mono high-speed fluorescence-activated cell sorter (CYTOMATION®, Fort Collins, Colo.). All samples were processed or cryopreserved within 5 hours of collection.

Flow Cytometric Analysis and MRD Studies

Flow cytometry using the antibodies listed in TABLES 3-5 were used to verify the differential expression of gene products in ALL cells. In most tests, the antibodies were used in combination with anti-CD19 conjugated to allophycocyanin (APC), anti-CD10 conjugated to either FITC or PE, and anti-CD34 conjugated to peridinin chlorophyll protein (PerCP). Isotype-matched nonreactive antibodies were used as controls. For cell staining, monunucleated cells were washed in PBS containing 0.5% bovine serum albumin and 0.5% sodium azide (PBSA), mixed with rabbit serum to block surface Fc receptors, incubated with the antibodies for 10 minutes at 20° C. in the dark, washed twice in PBSA and fixed with 0.5% paraformaldehyde. For intracellular markers, cells were permeabilized and fixed before exposure to antibodies using a permeablization reagent 8E. Measurements of antibody labeling were performed by multiparameter flow cytometry, using a FACSCALIBER® flow cytometer (Becton Dickinson, San Jose, Calif.).

Studies of MRD by flow cytometry were performed using combinations of monoclonal antibodies that identified leukemia-associated immunophenotypes determined at diagnosis. Cell staining was essentially performed as described above, using a combination of 4 markers simultaneously (see TABLE 4) and, where indicated, with 6-marker combinations (SEE TABLE 3). Data acquisition and analysis was done as previously described, using BD FACSCALIBER™ LSRII flow cytometers (Becton Dickinson), BD CELLQUEST Pro™, BD FACSDiVa™ software (both from Becton Dickinson), FlowJo software (Tree Star, Ashland, Oreg.) and/or Kaluza™ software (Beckman Coulter, Miami, Fla.). Determination of MRD by PCR amplification of immunoglobulin and T-cell receptor genes was done as previously described (Stow. P. (2010) *Blood.* 115:4657-4663). The results of MRD studies by the two methods were recorded independently.

Example 1. Identification of Genes Differentially Expressed in Leukemic and Normal Immature B Cells Gene Expression Arrays Studies A first-generation gene array study was previously performed (Chen et al. (2001) *Blood.* 97:2115-2120) and as previously described (Ross et al. (2003) *Blood.* 102:2951-2959). In Chen et al., diagnostic ALL samples from 4 patients were compared to CD19+ CD10+ bone marrow immature B cells taken from 2 healthy donors. The array contained probes for approximately 4000 genes.

In an embodiment of the invention, a gene expression array probing over 23,000 genes was used to screen a larger set of samples, including 270 cases of B-lineage ALL. The B-lineage ALLs encompassed the spectrum of genetic abnormalities occurring in ALL and were included to specifically identify other prognostic markers. Briefly, total RNA was isolated from freshly thawed B-lineage ALL cells and flow sorted normal CD19+CD10+ cells using the TRIZOL® reagent (Invitrogen, Carlsbad, Calif.). After generating cDNA, biotin-labeled cRNA was prepared according to the protocols of Affymetrix (Santa Clara, Calif.). The solutions were hybridized to HG-U133A oligonucleotide microarrays (Affymetrix). After staining with phycoerythrin-conjugated streptavidin, the arrays were read with a laser confocal scanner (Agilent, Palo Alto, Calif.). Signal values were computed from the image files using Affymetrix GeneChip® Operating Software. Intensity values for a total of 22,283 probe sets on the U133A microarray were obtained (See Affymetrix Data Sheet (Part No. 701484 Rev. 4 (2003-2004), Santa Clara, Calif., USA, GeneChip® Human Genome U133A 2.0 Array, Part Nos. #900471, 468, 469)

Expression data was generated using genome-wide expression data detected from 270 B-lineage ALL samples and CD19+CD10+ lymphoid progenitors obtained from the bone marrow of 4 healthy donors. Of the 23,000 genes compared, a total of 133 probe sets (corresponding to 112 genes, TABLE 1) had signals higher than 2-fold of the highest value obtained among normal CD19+CD10+ cells in 75% or more of ALL cases studied. Conversely, 192 probe sets (corresponding to 165, TABLE 2) had signals at least 50% lower than the lowest signal among the normal CD19+ CD10+ cells in 75% or more of ALL cases. When the criteria for inclusion was extended to genes that were differentially expressed in at least 25% of ALL cases, 1405 probe sets were over-expressed and 1474 were under-expressed. The results are summarized in TABLES 1 and 2.

Among the genes that were differentially expressed, some had been previously identified as abnormally expressed in ALL cells. For example, CD58 was over-expressed in 81.9% of cases (See also Chen J. S., et al. (2001) *Blood.* 97:2115-2120), and WT1 in 32.6% of cases (See also Ogawa et al. (2002) *Blood.* 101:1698-1704) whereas PAX5 was under-expressed in 86.7% and CD38 in 73.7% of cases (See also Coustan-Smith et al. (2002) *Blood.* 100:52-58). Among the 23 ALL specimens with MLL gene rearrangements, 100% over-expressed galectin-1 and 91.3% under-expressed CD10, characteristic features of this subset of ALL (See also Juszczynski et al. (2010) *Clin Cancer Res.* 16:2122-2130; Pui et al. (1994) *J. Clin. Oncol.* 12:909-915); most of these cases also over-expressed a cohort of genes (e.g., FLT3, LMO2, ADAM10, MEIS1) previously reported to be associated with MLL-rearranged leukemia (see also Ferrando et al. (2003) *Blood.* 102:262-268).

All 26 cases with TCF3-PBX1 over-expressed PBX1 (See also Kamps et al. (1991). *Genes Dev.* 5:358-368), and, among the 62 cases with ETV6-RUNX1, 46.8% over-expressed CD13 and 29.0% CD33 (Baruchel et al. (1997) *Br J HaematoL* 99:101-106).

Example 2. Validation of Gene Expression Array Results by Flow Cytometry

Among the genes differentially expressed by gene array analysis, there were some already widely used for MRD studies by flow cytometry, i.e., CD58, CD38, CD13, and CD34, suggesting the possibility that other useful markers could be present among the remaining genes (Basso et al. (2009) *J Clin Oncol.* 27:5168-5174; Lucio et al. (2001) *Leukemia.* 15:1185-1192; Chen et al. (2001) *Blood.* 97:2115-2120; Coustan-Smith et al. (2002) *Blood.* 100:52-58).

To prioritize genes for validation by flow cytometry, an initial inclusion criteria was applied: a) differential expression in at least 25% of cases of ALL, or 40% of cases of a genetic subtype of ALL; b) over-expression in leukemic cells by at least 3-fold of the maximum value in normal cells, or under-expression by 3-fold of the minimum value in normal cells; and c) commercial availability of specific antibodies conjugated to fluorochromes suitable for flow cytometry. Guided by these criteria, 30 genes (25 overexpressed in ALL and 5 underexpressed) were selected (TABLE 6) and compared to determine whether the differential expression measured by microarray analysis at the mRNA level corresponded to differential expression of the encoded proteins.

After confirming the specificity of the antibodies with known positive and negative target cells (TABLE 6), the antibodies were tested for reactivity using ALL samples obtained at diagnosis (n=200) and leukemia-free bone marrow samples (n=61). Importantly, comparisons included not only bone marrow specimens from healthy donors (n=22) but also bone marrow from children with ALL (MRD-negative according to PCR amplification of antigen-receptor genes) and AML (MRD negative by flow cytometry) during chemotherapy (n=39), some with a high proportion of hematogones. When the overall expression in the ALL versus normal CD19+ CD10+ B-cell progenitor groups were compared the difference in overall expression was statistically significant (P<0.05) for 13 of the 30 markers tested. Additionally, 11 of the proteins encoded by the over-expressed genes were expressed at a significantly higher level in B-lineage ALL cells, while 2 of the 5 proteins encoded by under-expressed genes had a significantly lower expression (FIG. 1).

TABLE 6

Expression level in ALL cells and normal CD19+CD10+ cells of the genes selected for study

| Probeset | Gene symbol/CD number | Range expression in normal CD19+ CD10+ (n = 4)[1] Min | Max | Range expression in ALL (n = 270)[1] Min | Max | % ALL cases with higher/lower expression |
|---|---|---|---|---|---|---|
| | | Overexpressed in ALL | | | | |
| 203685_at | BCL2 | 149.1 | 229 | 150.1 | 5203.8 | 90% |
| 201841_s_at | HSPB1 | 15.6 | 302 | 36.4 | 8938.9 | 87% |
| 207643_s_at | TNFRSF1A/CD120a | 94.4 | 234.7 | 28 | 3029.5 | 84% |
| 209933_s_at | CD300A | 59.1 | 126.1 | 29.3 | 1481.7 | 81% |
| 202910_s_at | CD97 | 149.2 | 303.4 | 31.5 | 6537 | 80% |
| 212298_at | NRP1/CD304 | 5.6 | 10.6 | 3.3 | 2155.1 | 80% |
| 204563_at | SELL/CD62L | 288.1 | 415.7 | 205 | 16680.8 | 79% |
| 210916_s_at | CD44 | 40.8 | 109.2 | 18.8 | 4864.2 | 78% |
| 215177_s_at | ITGA6/CD49f | 31.5 | 145.9 | 14.6 | 12400.9 | 75% |
| 209583_s_at | CD200 | 313.2 | 423.9 | 42.3 | 3955.4 | 72% |
| 203939_at | NT5E/CD73 | 54.3 | 121.1 | 5 | 5133.9 | 67% |
| 213620_s_at | ICAM2/CD102 | 871.1 | 983 | 233.8 | 7321.1 | 65% |
| 210895_s_at | CD86 | 31.9 | 106.9 | 13.6 | 1392.7 | 60% |

TABLE 6-continued

Expression level in ALL cells and normal CD19+CD10+ cells of the genes selected for study

| Probeset | Gene symbol/CD number | Range expression in normal CD19+ CD10+ (n = 4)[1] | | Range expression in ALL (n = 270)[1] | | % ALL cases with higher/lower expression |
|---|---|---|---|---|---|---|
| | | Min | Max | Min | Max | |
| 204116_at | IL2RG/CD132 | 604 | 1213.2 | 574.9 | 8123.4 | 56% |
| 201028_s_at | CD99 | 1148.8 | 2047.8 | 325.4 | 19384.2 | 50% |
| 201887_at | IL13RA1 | 81.2 | 159.2 | 30.4 | 2829.5 | 41% (59% of BCR-ABL1) |
| 208654_s_at | CD164 | 754.9 | 1274.4 | 667.6 | 15234.8 | 39% (71% of hyperdiploid; 59% of BCR-ABL1) |
| 209963_s_at | EPOR | 49.4 | 127.9 | 17.8 | 1950.4 | 36% |
| 212151_at | PBX1 | 30.4 | 114.4 | 16.5 | 10825.3 | 36% (100% of TCF3-PBX1) |
| 205987_at | CD1C | 16 | 249.7 | 9.7 | 7020.6 | 27% (71% of hyperdiploid) |
| 204863_s_at | IL6ST/CD130 | 119.4 | 160.9 | 8.5 | 837.1 | 27% |
| 205718_at | ITGB7 | 12.1 | 208.5 | 10.9 | 3223.5 | 25% (50% of BCR-ABL1) |
| 206148_at | IL3RA/CD123 | 53.6 | 260.6 | 18.7 | 3497.2 | 22% (71% of hyperdiploid) |
| 208651_x_at | CD24 | 3125.7 | 4310.4 | 258.6 | 14231.4 | 17% (54% of TCF3-PBX1) |
| 209617_s_at | CTNNA1 | 23.3 | 68.7 | 6 | 424.5 | 9% (40.3% of ETV6-RUNX1) |
| Underexpressed in ALL | | | | | | |
| 205297_s_at | CD79B | 11257.6 | 17637 | 19.1 | 8701 | 96% |
| 204440_at | CD83 | 1759.5 | 4557.9 | 47.8 | 9729.2 | 91% |
| 209795_at | CD69 | 6458.6 | 7502.8 | 31.6 | 16301.1 | 77% |
| 204192_at | CD37 | 5624.7 | 13251.7 | 225.6 | 10302.9 | 67% (81% of ETV6-RUNX1) |
| 215925_s_at | CD72 | 1888.1 | 4238.1 | 9.1 | 4968.5 | 57% |

[1]Data expressed as units calculated by MAS5.0 to a median target intensity of 500.

Figure 2:
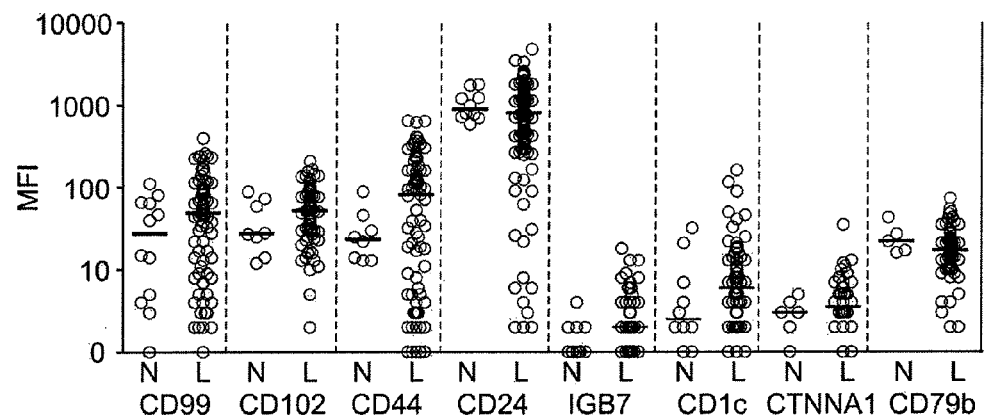
FIG. 2 shows a comparison of the relative mean fluorescence intensity of immunophenotypic markers expressed in ALL cells and CD19$^+$CD10$^+$ B-cell progenitors as determined by flow cytometry.
Figure 2:
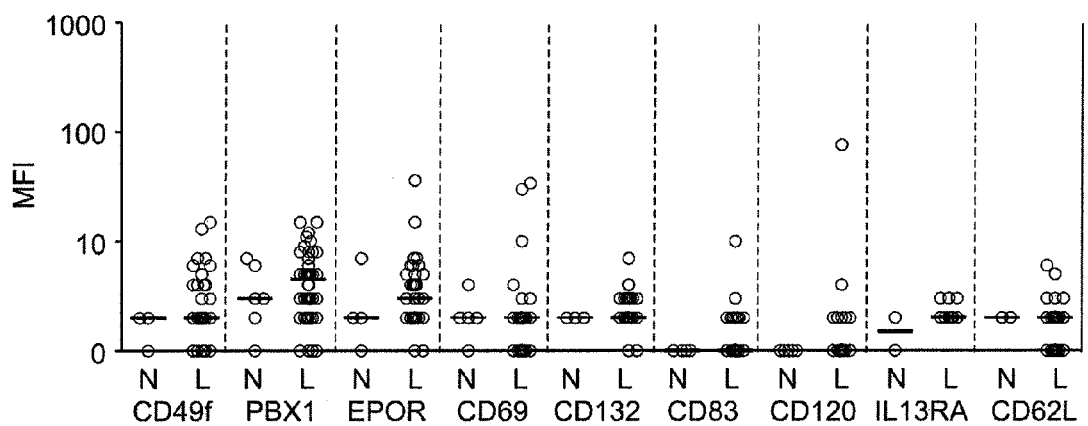

FIG. 1 shows the differential expression of markers in ALL cells compared to CD19+ CD10+ B cell progenitors. Shown are mean fluorescence intensity (MFI) values obtained in CD19+ leukemic lymphoblasts from bone marrow samples of patients with newly diagnosed ALL ("L") and bone marrow CD19+CD10+ cells from healthy donors or from patients with leukemia in remission and no evidence of MRD ("N"). Each symbol indicates results of one sample; horizontal bars correspond to median values within each group For the remaining 17 markers, the difference in overall expression between ALL cells and normal B-cell progenitors was not statistically significant (FIG. 2). FIG. 2 shows markers that were not expressed at levels significantly different (P>0.05) in ALL cells and CD19+CD10+ B-cell progenitors as determined by flow cytometry. Shown are mean fluorescence intensity (MFI) values obtained in CD19+ leukemic lymphoblasts from bone marrow samples of patients with newly diagnosed ALL ("L") and bone marrow CD19+CD10+ cells from healthy donors or from patients with leukemia in remission and no evidence of MRD ("N"). Each symbol indicates results of one sample; horizontal bars correspond to median values within each group.

However, some these later markers were found to be overexpressed when the mean fluorescent intensity MFI values were compared to normal controls. For example, in some cases the MFI values of a marker in ALL specimens was higher than the highest mean fluorescence intensity (MFI) value recorded among normal B-cell progenitors. In other ALL specimens, markers were found to be underexpressed in ALL cells. For markers that were under-expressed in ALL cells, for example, specimens had at least 50% lower MFI values compared to the lowest MFI measured in normal B-cell progenitors. Using MFI levels as a criteria for differential expression, a substantial proportion of ALL cases expressed markers whose MFI values that were higher or lower than that of normal B cell progenitors. Overall, 22 of the 30 markers were found differentially expressed in 5%-81.4% (median, 35%) of cases These results are summarized in TABLE 6.

For example, CD44 was differentially expressed in 81.4% cases studied, BCL2 was over-expressed in 76.6%, HSPB1 (heat shock protein 27) in 63.4% and CD73 in 54.5%. Notably, CD44 and CD24 were over-expressed in some cases and under-expressed in others. Importantly, some of the markers, such as CD97, CD99 and CD102 appeared to be over-expressed in a much larger proportion of cases when the comparisons included only resting bone marrow samples. However, when regenerating specimens rich in hematogones were included, it became clear that expression in leukemic cells for many of these cases was not outside the range of normality. Of the 30 markers studied, only 8 (EPOR, CD1c, CD120a, CD37, CD62L, CD132, CD83 and IL13RA1) showed no clear differential expression by the above criteria and were excluded from further studies.

Example 3: Validation of the New Markers for MRD Detection

To determine the reliability of the new markers to identify leukemic cells in clinical samples, 128 bone marrow samples were collected during treatment (46 during or at the end of remission induction therapy and 82 during post-remission therapy) from 51 patients with B-lineage ALL in whom expression of the markers on the leukemic cells had been measured at diagnosis. The markers included in these studies were the top 16 differentially expressed markers listed in TABLE 7, for a total of 258 tests.

Figure 3:
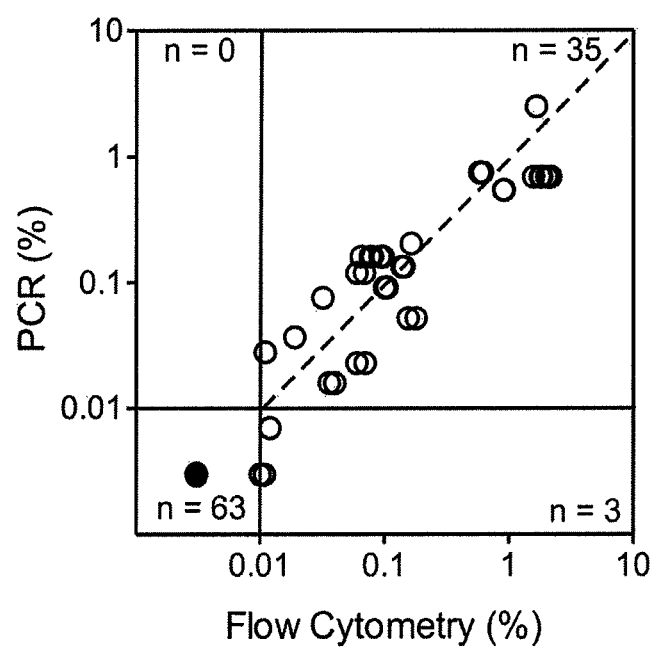
FIG. 3 shows a comparison of new markers to standard markers using flow cytometry.

Newly identified markers (TABLE 3, 4) were compared to standard marker combinations presently used in for MRD detection (TABLE 5). Using a threshold of 0.01% ALL cells to define MRD positivity, no discordant results were observed except for one comparison in which MRD was negative with the standard markers and 0.012% with the new markers. Overall, there was an excellent correlation in MRD estimates between new and standard markers (r=0.9816, P<0.0001 by Spearman's regression analysis of the MRD-positive tests; FIG. 3).

FIG. 3 graphically illustrates the relationship between results of MRD monitoring using flow cytometry targeting the new markers and those of PCR amplification of antigen-receptor genes. Each symbol on the graph represents results obtained by 4-color flow cytometry including antibodies against CD19, CD10, CD34 and one of the new markers; r=0.8178, P<0.0001 by Spearman's regression analysis of the positive MRD results. The dashed line is the line of identity.

In a subset of 52 samples from 18 patients studied with some of the markers (CD44, BCL2, HSPB1, CD73, CD24, CD123, CD86, CD200, CD304, CD97, CD99,

TABLE 7

Expression of the new markers in ALL cells relative to their expression in bone marrow CD19+ CD10+ cells from healthy individuals as determined by flow cytometry

| Marker | Number of ALL cases studied | Number of cases with overexpression (%)[1] | Number of cases with underexpression (%)[2] |
|---|---|---|---|
| CD44 | 86 | 46 (53.5%) | 24 (27.9%) |
| BCL2 | 77 | 59 (76.6%) | — |
| HSPB1 | 93 | 59 (63.4%) | — |
| CD73 | 77 | 42 (54.5%) | — |
| CD24 | 139 | 16 (11.5%) | 55 (39.6%) |
| CD123 | 142 | 72 (50.7%) | — |
| CD72 | 45 | — | 22 (48.9%) |
| CD86 | 135 | 63 (46.7%) | — |
| CD200 | 95 | 41 (43.2%) | — |
| CD79b | 74 | — | 31 (41.9%) |
| CD164 | 75 | 31 (41.3%) | — |
| CD304 | 129 | 37 (28.7%) | — |
| CD97 | 81 | 22 (27.2%) | — |
| CD102 | 76 | 15 (19.7%) | 2 (2.6%) |
| CD99 | 77 | 17 (22.1%) | — |
| CD300A | 92 | 18 (19.6%) | — |
| CD130 | 71 | 12 (16.9%) | — |
| PBX1 | 64 | 4 (11.8%) | — |
| CTNNA1 | 44 | 4 (9.1%) | — |
| ITGB7 | 90 | 7 (7.8%) | — |
| CD69 | 33 | 2 (6.1%) | — |
| CD49f | 38 | 2 (5.3%) | — |
| EPOR | 45 | 2 (4.4%) | — |
| CD1C | 86 | 3 (3.5%) | — |
| CD120a | 35 | 1 (<2.9%) | — |
| CD37 | 46 | 1 (<2.2%) | — |
| CD62L | 34 | 0 | — |
| CD132 | 33 | 0 | — |
| CD83 | 33 | 0 | — |
| IL13RA1 | 10 | 0 | — |

[1] Number of ALL cases that expressed the indicated marker at levels higher than the highest mean fluorescence intensity (MFI) value recorded among normal B-cell progenitors, and had an MFI higher than 10.
[2] Number of ALL cases that expressed the indicated marker at levels lower than the lowest MFI measured in normal B-cell progenitors, excluded cases in which a marker had an MFI lower than 10 on normal B-cell progenitors.

CD102 and CD300a), MRD estimates by PCR amplification of clonally rearranged immunoglobulin and T-cell receptor genes were also available. Using the threshold of 0.01% ALL cells to define MRD positivity, MRD was negative (<0.01%) by flow cytometry and PCR analysis in 35 of the 52 samples studied. By contrast, MRD was ≥0.01% according to both methods in 15 samples. Two additional samples had MRD≥0.01% by flow cytometry while PCR showed detectable signals but below the 0.01% threshold: 0.007% and 0.003%. Among the 101 tests performed, MRD was <0.01% by flow cytometry in 63 and ≥0.01% in 38, with a good correlation in the MRD positive estimates by the two techniques (r=0.8178, P<0.0001). Two samples had MRD≥0.01% by flow cytometry (1 tested with two markers) and also had positive PCR but below the 0.01% threshold.

Figure 4:
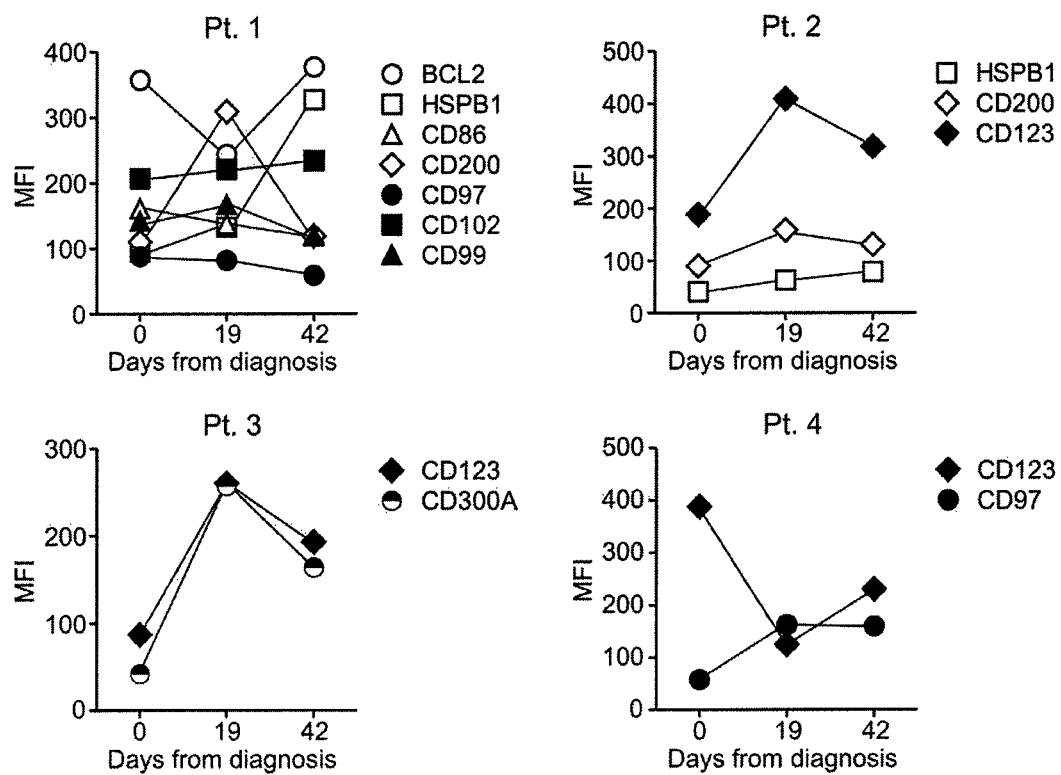
FIG. 4 graphically illustrates the expression of the new markers before, during, and at the end of remission induction therapy.

To determine stability of the new markers during the course of the disease, a prerequisite for reliable MRD tracking (Gaipa et al. (2005) Leukemia. 19:49-56) the level of expression was compared to that recorded during MRD monitoring in 10 patients who had persistent MRD during remission induction therapy (day 19 and 42 from diagnosis). FIG. 4 illustrates the results obtained in 4 representative cases showing the expression of the new markers before, during and at the end of remission induction therapy.

The long-term stability of the markers was assessed by comparing the immunophenotype of paired samples collected at diagnosis and relapse from nine patients whose leukemic cells at diagnosis expressed some of the newly identified markers identified. In FIG. 4 symbols indicate mean fluorescence intensity (MFI) of each marker as measured on ALL cells at diagnosis and on residual leukemic lymphoblasts detected on days 19 and 42 of remission induction therapy. At all time points, all markers were expressed at levels that exceeded those measured in normal CD19+CD10+ cells. Although levels of expression fluctuated during therapy, they consistently remained outside the range of normality in all cases studied.

As shown in TABLE 8, abnormal marker expression at diagnosis reverted to expression within the normal range at relapse in 7 of 55 (12.7%) of comparisons. In the remaining cases, marker expression remained abnormal. Importantly, in all 9 patients studied at least one marker remained abnormally expressed at relapse. In 58 additional comparisons where the markers at diagnosis were within the normal range, there were 10 instances (17.2%) in which expression became abnormal at relapse. These results suggest that false-negative results due to phenotypic shifts affecting these markers would be unlikely.

TABLE 8

Expression of new markers in paired samples of B-lineage ALL collected at diagnosis (D) and at relapse (R)[1]

| Marker | Patient 1 D | Patient 1 R | Patient 2 D | Patient 2 R | Patient 3 D | Patient 3 R | Patient 4 D | Patient 4 R | Patient 5 D | Patient 5 R | Patient 6 D | Patient 6 R | Patient 7 D | Patient 7 R | Patient 8 D | Patient 8 R | Patient 9 D | Patient 9 R |
|---|---|---|---|---|---|---|---|---|---|---|---|---|---|---|---|---|---|---|
| CD44 | — | — | 233 | 235 | 372 | —[2] | 325 | —[2] | — | — | — | — | 3 | 4 | 208 | 93 | 292 | 307 |
| BCL2 | 254 | 249 | 240 | 262 | — | — | 286 | 326 | 144 | 137 | 332 | 562 | 150 | 151 | 87 | 137 | 273 | 188 |
| HSPB1 | 18 | 47 | 44 | 94 | — | 74[3] | 169 | 143 | 141 | 165 | 64 | 351 | 23 | 267 | 15 | 158 | 80 | 36 |
| CD73 | 30 | 39 | 37 | 64 | 56 | 149 | 29 | 105 | — | — | 95 | 30 | 33 | —[2] | 168 | 33 | 103 | 63 |
| CD24 | — | — | 338 | 504 | — | 333[3] | 204 | 146 | 104 | 2 | — | 277[3] | — | — | — | — | — | 77[3] |
| CD123 | — | — | 62 | 31 | — | — | 45 | 133 | — | — | — | — | — | — | — | — | — | 25[3] |
| CD72 | 6 | 7 | NT | NT | NT | NT | — | — | — | — | 5 | 3 | 8 | 13 | 6 | 6 | 4 | 4 |
| CD86 | — | — | 26 | 23 | — | — | 33 | —[2] | — | — | — | — | — | — | — | — | — | — |
| CD200 | 86 | 65 | 107 | 88 | — | — | 80 | 201 | 260 | 154 | — | — | 102 | 126 | — | 72[3] | 83 | —[2] |
| CD164 | — | — | 18 | 49 | — | — | — | — | — | — | — | — | — | 29[3] | NT | NT | NT | NT |
| CD97 | — | — | 119 | 53 | — | — | 84 | 200 | — | — | — | — | — | 54[3] | — | — | — | — |
| CD102 | — | — | — | — | — | — | 96 | 92 | — | — | — | — | — | 100[3] | — | — | — | 136[3] |
| CD99 | — | — | — | — | — | — | — | 329[3] | 184 | —[2] | 124 | —[2] | — | — | — | — | 122 | 488 |

Figure 5:
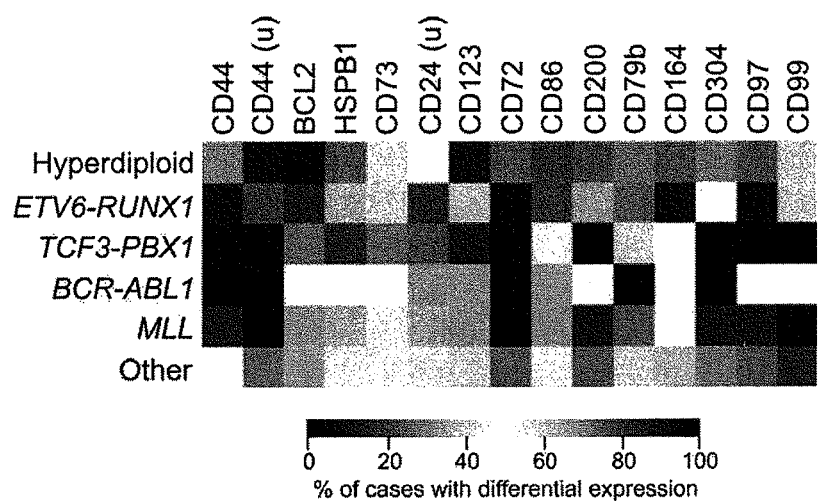
FIG. 5 is a heatmap showing the percentage of cases among the main genetic subtypes of childhood ALL in which the markers studied were differentially expressed by flow cytometry.

NT, not tested
[1] Values indicate MFI as determined by flow cytometry. Dash indicates MFI within the normal range
[2] Significant change in expression: from abnormal expression at diagnosis to expression within the normal range at relapse
[3] Significant change in expression: from expression within the normal range at diagnosis to abnormal expression at relapse Example 4. Association of the New Markers with Genetic Subtypes of ALL The new markers used in embodiments of the invention were associated with known genetic subtypes of ALL, including hyperdiploidy (51-65 chromosomes), ETV6-RUNX1, TCF3-PBX1, BCR-ABL1, or MLL gene rearrangements. FIG. 5 shows the results of this analysis as a heat map including markers that were differentially expressed in at least 20% of cases. The heatmap graphically displays the percentage of cases among the main genetic subtypes of childhood ALL in which the markers studied were differentially expressed by flow cytometry. Percentages refer to cases in which each marker was over-expressed in ALL cases as compared to CD19+CD10+ cells from non-leukemic bone marrow samples; markers under-expressed in ALL cells are indicated by "u".

Expression of some markers was clearly related to ALL genetic subtype. For example, among hyperdiploid (51-65 chromosomes) ALL cases, there was a significantly higher prevalence of CD123 ($P<0.0001$ by Fisher's exact test), CD86 ($P<0.0001$), CD200 ($P=0.0003$) and CD97 ($P<0.0001$) overexpression as compared to the other cases without this genetic abnormality. Among cases with ETV6-RUNX1, there was a higher prevalence of CD200 over-expression ($P<0.0001$), and of CD44 ($P<0.0001$), CD72 ($P=0.0073$) and CD79b ($P=0.0109$) under-expression. Finally, abnormal expression of CD164 was most prevalent among cases lacking all the genetic abnormalities analyzed ($P=0.002$).

Example 5: Comparisons Between New Markers and Established Leukemia-Associated Immunophenotypes In a proportion of patients with ALL, MRD cannot currently be monitored because of the lack of suitable immunophenotypes differentiating ALL from normal controls. (Campana (2009) *Hematol. Oncol Clin North Am.* 23:1083-98, vii; Bruggemann et al. (2010) *Leukemia.* 24:521-535) In other patients, leukemic cells express only one set of markers, and have an increased risk of false-negative MRD results due to immunophenotypic shifts (Coustan-Smith et al. (1998) *Lancet.* 351:550-554). The availability of the additional markers of embodiments of the invention enables MRD studies in patients whose ALL cells currently lack suitable leukemia-associated immunophenotypes and minimize the risk of false-negative results.

Using a method of the invention, expression profiling was used to evaluate 171 ALL diagnostic samples including: 11 subjects lacking detectable leukemia-associated immunophenotypes with the standard panel of antibodies; and another 37 subjects having only one immunophenotypic abnormality detectable with the standard panel.

In contrast to the standard method, the method of the present invention detected a phenotypic abnormality indicative of MRD in all of the 11 cases previously lacking a leukemia-associated immunophenotype. Moreover, the method of the present invention identified additional abnormalities in 36 of the 37 cases with one standard abnormality. Thus, the new markers substantially improved the potential for flow cytometric monitoring of MRD in 47 of 48 cases that could not be adequately studied previously. The number of new markers differentially expressed ranged from two to twelve (median, six). In 45 of the 47 cases, one or more markers were expressed at levels that exceeded by at least two-fold the normal range, allowing a particularly clear identification of ALL cells.

The availability of additional markers of leukemia improved the resolution of leukemic and normal cells during flow cytometric analysis. This was clearly demonstrated in experiments in which mixtures of leukemia and normal cells were analyzed using either one standard phenotypic abnormality (e.g., under-expression of CD38), or additional abnormalities revealed by the new markers. An example of such an experiment is shown in FIG. 6.

Figure 6:
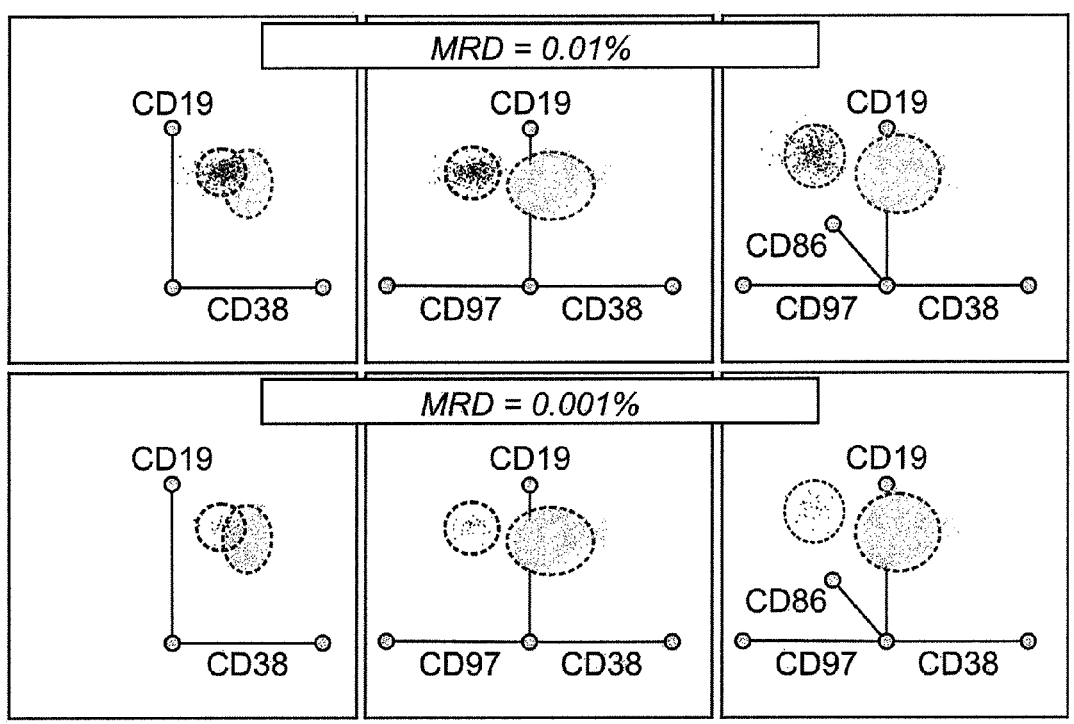
FIG. 6 is a graphic depiction of additional leukemia-associated markers that can improve resolution of MRD.

FIG. 6 shows an example of the comparison of flow cytometric data from 5 non-leukemic bone marrow samples cells (gray dots) and one diagnostic ALL sample (black dots) that were merged and analyzed as radial plots using the KALUZA™ software after selecting all CD19+ CD10+ CD34+ cells. Mixtures containing 0.01% ALL cells (top row) and 0.001% ALL cells (bottom row) are shown. Under-expression of CD38 alone, a standard MRD marker, could not discriminate well between ALL cells and normal CD19+ CD10+ CD34+ cells (left panels) in this case; the discrimination was improved by analyzing expression of CD97 (middle panels), and further improved by the inclusion of CD86 and the use of a 3-dimensional space (right panels). Using embodiments of the invention improve the discrimination between normal and leukemic CD19+, CD10+, CD34+ cells thereby allowing the unequivocal detection of ALL cells at a level of 0.001%.

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

That which is claimed:

1. A method of diagnosing and treating minimal residual disease in a subject comprising:
   (a) contacting a specimen comprising a plurality of markers obtained from a patient with a plurality of probes, wherein the specimen is selected from the group consisting of blood cells, bone marrow cells, and cellular products that are derived from blood and bone marrow cells: and wherein each of said plurality of probes specifically binds to a single marker, wherein a first probe specifically binds to the single marker CD19, a second probe specifically binds to the single marker CD10, a third probe specifically binds to the single marker CD34, a fourth probe specifically binds to the single marker CD45, and at least two additional probes that specifically bind to any two of the single markers selected from the group consisting of CD38, CD24, CD44, CD58, CD73, CD15, CD200, CD123, CD86, CD72, CD13, CD33, CD79b, HSPB1, BCL2, CD164, CD304, CD97, CD99, CD102, or CD300a, wherein each of said plurality of probes that specifically bind to a single marker comprises a detectable moiety;
   (b) detecting a complex formed between each of said plurality of probes in step (a) with said plurality of markers, wherein a value is generated corresponding to an expression level of each of said single markers;
   (c) generating an expression profile by combining the values generated in step (b); wherein the expression of CD19, and the differential expression of CD10, CD34 and CD45, and the differential expression of at least two additional markers selected from the group consisting of CD38, CD24, CD44, CD58, CD73, CD15, CD200, CD123, CD86, CD72, CD13, CD33, CD79b, HSPB1, BCL2, CD164, CD304, CD97, CD99, CD102, and CD300a relative to the expression profile for a plurality of the same markers in a normal control is indicative of minimal residual disease in acute lymphoblastic leukemia (ALL), and (d) administering to the patient having at least one leukemic cell detected among 100,000 normal cells an effective amount of a therapy for treating minimal residual disease in ALL.

2. The method of claim 1, wherein said plurality of probes further comprises at least three additional probes, wherein each of the at least three additional probes specifically bind to a single marker selected from the group consisting of CD38, CD24, CD44, CD58, CD73, CD15, CD200, CD66c, CD123, CD86, CD72, CD13, CD33, CD79b, HSPB1, BCL2, CD164, CD304, CD97, CD99, CD102 and CD300a.

3. The method of claim 1, wherein said differential expression comprises an overexpression of at least one of the single markers selected from the group consisting of CD44, CD58, CD73, CD200, CD86, HSPB1, BCL2, CD164, CD97, CD99, and CD300a and/or an underexpression of at least one of the single markers selected from the group consisting of CD38, CD72, and CD79b, relative to expression level of the same single marker in a normal control.

4. The method of claim 1, wherein the at least two additional probes that selectively bind a single marker are CD38 and CD44.

5. The method of claim 1, wherein cells in the specimen are permeabilized prior to contacting the specimen with the plurality of probes which specifically bind to the single markers.

6. The method of claim 1, wherein at least one of the plurality of probes is an antibody.

7. The method of claim 1, wherein said detecting utilizes an optical detection technique.

8. The method of claim 7, wherein said optical detection technique is flow cytometry.

9. The method of claim 7, wherein said optical detection technique is microscopy.

10. The method of claim 1, wherein said detectable moiety is selected from the group consisting of a fluorophore, a chromophore, a radionuclide, and an enzyme.

* * * * *

UNITED STATES PATENT AND TRADEMARK OFFICE
CERTIFICATE OF CORRECTION

PATENT NO.        : 9,777,332 B2
APPLICATION NO.   : 14/005921
DATED             : October 3, 2017
INVENTOR(S)       : Campana et al.

It is certified that error appears in the above-identified patent and that said Letters Patent is hereby corrected as shown below:

In the Specification

In Column 1, under the heading "FEDERALLY SPONSORED RESEARCH OR DEVELOPMENT," at Lines 7-11, the text "This invention was made with support under United States Government Grant CA60419 awarded by the National Institutes of Health. The United States Government has certain rights in this invention.." should be changed to --This invention was made with government support under grant CA060419 awarded by the National Institutes of Health. The government has certain rights in the invention.--

Signed and Sealed this
Twenty-second Day of January, 2019

Andrei Iancu
*Director of the United States Patent and Trademark Office*

```
                          SEQUENCE LISTING

<160> NUMBER OF SEQ ID NOS: 46

<210> SEQ ID NO 1
<211> LENGTH: 1494
<212> TYPE: DNA
<213> ORGANISM: Homo Sapiens
<220> FEATURE:
<221> NAME/KEY: CDS
<222> LOCATION: (108)...(1010)
<220> FEATURE:
<221> NAME/KEY: misc_feature
<222> LOCATION: (0)...(0)
<223> OTHER INFORMATION: CD38

<400> SEQUENCE: 1
agtgaaacag aaggggaggt gcagtttcag aacccagcca gcctctctct tgctgcctag    60
cctcctgccg gcctcatctt cgcccagcca accccgcctg gagccct atg gcc aac   116
                                                   Met Ala Asn
                                                     1 tgc gag ttc agc ccg gtg tcc ggg gac aaa ccc tgc tgc cgg ctc tct   164
Cys Glu Phe Ser Pro Val Ser Gly Asp Lys Pro Cys Cys Arg Leu Ser
         5                  10                  15 agg aga gcc caa ctc tgt ctt ggc gtc agt atc ctg gtc ctg atc ctc   212
Arg Arg Ala Gln Leu Cys Leu Gly Val Ser Ile Leu Val Leu Ile Leu
 20                  25                  30                  35 gtc gtg gtg ctc gcg gtg gtc gtc ccg agg tgg cgc cag cag tgg agc   260
Val Val Val Leu Ala Val Val Val Pro Arg Trp Arg Gln Gln Trp Ser
                     40                  45                  50 ggt ccg ggc acc acc aag cgc ttt ccc gag acc gtc ctg gcg cga tgc   308
Gly Pro Gly Thr Thr Lys Arg Phe Pro Glu Thr Val Leu Ala Arg Cys
                 55                  60                  65 gtc aag tac act gaa att cat cct gag atg aga cat gta gac tgc caa   356
Val Lys Tyr Thr Glu Ile His Pro Glu Met Arg His Val Asp Cys Gln
             70                  75                  80 agt gta tgg gat gct ttc aag ggt gca ttt att tca aaa cat cct tgc   404
Ser Val Trp Asp Ala Phe Lys Gly Ala Phe Ile Ser Lys His Pro Cys
         85                  90                  95 aac att act gaa gaa gac tat cag cca cta atg aag ttg gga act cag   452
Asn Ile Thr Glu Glu Asp Tyr Gln Pro Leu Met Lys Leu Gly Thr Gln
100                 105                 110                 115 acc gta cct tgc aac aag att ctt ctt tgg agc aga ata aaa gat ctg   500
Thr Val Pro Cys Asn Lys Ile Leu Leu Trp Ser Arg Ile Lys Asp Leu
                    120                 125                 130 gcc cat cag ttc aca cag gtc cag cgg gac atg ttc acc ctg gag gac   548
Ala His Gln Phe Thr Gln Val Gln Arg Asp Met Phe Thr Leu Glu Asp
                135                 140                 145 acg ctg cta ggc tac ctt gct gat gac ctc aca tgg tgt ggt gaa ttc   596
Thr Leu Leu Gly Tyr Leu Ala Asp Asp Leu Thr Trp Cys Gly Glu Phe
            150                 155                 160 aac act tcc aaa ata aac tat caa tct tgc cca gac tgg aga aag gac   644
Asn Thr Ser Lys Ile Asn Tyr Gln Ser Cys Pro Asp Trp Arg Lys Asp
        165                 170                 175
```

```
tgc agc aac aac cct gtt tca gta ttc tgg aaa acg gtt tcc cgc agg      692
Cys Ser Asn Asn Pro Val Ser Val Phe Trp Lys Thr Val Ser Arg Arg
180                 185                 190                 195 ttt gca gaa gct gcc tgt gat gtg gtc cat gtg atg ctc aat gga tcc      740
Phe Ala Glu Ala Ala Cys Asp Val Val His Val Met Leu Asn Gly Ser
                200                 205                 210 cgc agt aaa atc ttt gac aaa aac agc act ttt ggg agt gtg gaa gtc      788
Arg Ser Lys Ile Phe Asp Lys Asn Ser Thr Phe Gly Ser Val Glu Val
            215                 220                 225 cat aat ttg caa cca gag aag gtt cag aca cta gag gcc tgg gtg ata      836
His Asn Leu Gln Pro Glu Lys Val Gln Thr Leu Glu Ala Trp Val Ile
        230                 235                 240 cat ggt gga aga gaa gat tcc aga gac tta tgc cag gat ccc acc ata      884
His Gly Gly Arg Glu Asp Ser Arg Asp Leu Cys Gln Asp Pro Thr Ile
    245                 250                 255 aaa gag ctg gaa tcg att ata agc aaa agg aat att caa ttt tcc tgc      932
Lys Glu Leu Glu Ser Ile Ile Ser Lys Arg Asn Ile Gln Phe Ser Cys
260                 265                 270                 275 aag aat atc tac aga cct gac aag ttt ctt cag tgt gtg aaa aat cct      980
Lys Asn Ile Tyr Arg Pro Asp Lys Phe Leu Gln Cys Val Lys Asn Pro
                280                 285                 290 gag gat tca tct tgc aca tct gag atc tga gccagtcgct gtggttgttt       1030
Glu Asp Ser Ser Cys Thr Ser Glu Ile
                295                 300 tagctccttg actccttgtg gtttatgtca tcatacatga ctcagcatac ctgctggtgc   1090
agagctgaag attttggagg gtcctccaca ataaggtcaa tgccagagac ggaagccttt   1150
ttccccaaag tcttaaaata acttatatca tcagcatacc tttattgtga tctatcaata   1210
gtcaagaaaa attattgtat aagattagaa tgaaaattgt atgttaagtt acttcacttt   1270
aattctcatg tgatcctttt atgttattta tatattggta acatcctttc tattgaaaaa   1330
tcaccacacc aaacctctct tattagaaca ggcaagtgaa gaaaagtgaa tgctcaagtt   1390
tttcagaaag cattacattt ccaaatgaat gaccttgttg catgatgtat ttttgtaccc   1450
ttcctacaga tagtcaaacc ataaacttca tggtcatggg taaa                    1494

<210> SEQ ID NO 2
<211> LENGTH: 300
<212> TYPE: PRT
<213> ORGANISM: Homo Sapiens

<400> SEQUENCE: 2

Met Ala Asn Cys Glu Phe Ser Pro Val Ser Gly Asp Lys Pro Cys Cys
1               5                   10                  15

Arg Leu Ser Arg Arg Ala Gln Leu Cys Leu Gly Val Ser Ile Leu Val
            20                  25                  30

Leu Ile Leu Val Val Leu Ala Val Val Pro Arg Trp Arg Gln
        35                  40                  45

Gln Trp Ser Gly Pro Gly Thr Thr Lys Arg Phe Pro Glu Thr Val Leu
    50                  55                  60

Ala Arg Cys Val Lys Tyr Thr Glu Ile His Pro Glu Met Arg His Val
65                  70                  75                  80

Asp Cys Gln Ser Val Trp Asp Ala Phe Lys Gly Ala Phe Ile Ser Lys
                85                  90                  95

His Pro Cys Asn Ile Thr Glu Glu Asp Tyr Gln Pro Leu Met Lys Leu
            100                 105                 110

Gly Thr Gln Thr Val Pro Cys Asn Lys Ile Leu Leu Trp Ser Arg Ile
        115                 120                 125
```

```
Lys Asp Leu Ala His Gln Phe Thr Gln Val Gln Arg Asp Met Phe Thr
        130                 135                 140

Leu Glu Asp Thr Leu Leu Gly Tyr Leu Ala Asp Leu Thr Trp Cys
145                 150                 155                 160

Gly Glu Phe Asn Thr Ser Lys Ile Asn Tyr Gln Ser Cys Pro Asp Trp
                    165                 170                 175

Arg Lys Asp Cys Ser Asn Asn Pro Val Ser Val Phe Trp Lys Thr Val
                180                 185                 190

Ser Arg Arg Phe Ala Glu Ala Ala Cys Asp Val Val His Val Met Leu
            195                 200                 205

Asn Gly Ser Arg Ser Lys Ile Phe Asp Lys Asn Ser Thr Phe Gly Ser
210                 215                 220

Val Glu Val His Asn Leu Gln Pro Glu Lys Val Gln Thr Leu Glu Ala
225                 230                 235                 240

Trp Val Ile His Gly Gly Arg Glu Asp Ser Arg Asp Leu Cys Gln Asp
                    245                 250                 255

Pro Thr Ile Lys Glu Leu Glu Ser Ile Ile Ser Lys Arg Asn Ile Gln
                260                 265                 270

Phe Ser Cys Lys Asn Ile Tyr Arg Pro Asp Lys Phe Leu Gln Cys Val
            275                 280                 285

Lys Asn Pro Glu Asp Ser Ser Cys Thr Ser Glu Ile
290                 295                 300

<210> SEQ ID NO 3
<211> LENGTH: 2194
<212> TYPE: DNA
<213> ORGANISM: Homo Sapiens
<220> FEATURE:
<221> NAME/KEY: CDS
<222> LOCATION: (111)...(353)
<220> FEATURE:
<221> NAME/KEY: misc_feature
<222> LOCATION: (0)...(0)
<223> OTHER INFORMATION: CD24

<400> SEQUENCE: 3
gggtctcgcc ggctcgccgc gctccccacc ttgcctgcgc ccgcccggag ccagcggttc      60
tccaagcacc cagcatcctg ctagacgcgc gcgcaccga cggagggac atg ggc         116
                                                    Met Gly
                                                      1 aga gca atg gtg gcc agg ctc ggg ctg ggg ctg ctg ctg ctg gca ctg      164
Arg Ala Met Val Ala Arg Leu Gly Leu Gly Leu Leu Leu Leu Ala Leu
          5                  10                  15 ctc cta ccc acg cag att tat tcc agt gaa aca aca act gga act tca      212
Leu Leu Pro Thr Gln Ile Tyr Ser Ser Glu Thr Thr Thr Gly Thr Ser
     20                  25                  30 agt aac tcc tcc cag agt act tcc aac tct ggg ttg gcc cca aat cca      260
Ser Asn Ser Ser Gln Ser Thr Ser Asn Ser Gly Leu Ala Pro Asn Pro
 35                  40                  45                  50 act aat gcc acc acc aag gcg gct ggt ggt gcc ctg cag tca aca gcc      308
Thr Asn Ala Thr Thr Lys Ala Ala Gly Gly Ala Leu Gln Ser Thr Ala
             55                  60                  65 agt ctc ttc gtg gtc tca ctc tct ctt ctg cat ctc tac tct taa         353
Ser Leu Phe Val Val Ser Leu Ser Leu Leu His Leu Tyr Ser
                 70                  75                  80 gagactcagg ccaagaaacg tcttctaaat ttccccatct tctaaaccca atccaaatgg    413
cgtctggaag tccaatgtgg caaggaaaaa caggtcttca tcgaatctac taattccaca   473
```

```
ccttttattg acacagaaaa tgttgagaat cccaaatttg attgatttga agaacatgtg      533
agaggtttga ctagatgatg gatgccaata ttaaatctgc tggagtttca tgtacaagat      593
gaaggagagg caacatccaa aatagttaag acatgatttc cttgaatgtg gcttgagaaa      653
tatggacact taatactacc ttgaaaataa gaatagaaat aaaggatggg attgtggaat      713
ggagattcag ttttcatttg gttcattaat tctataaggc cataaaacag gtaatataaa      773
aagcttccat gattctattt atatgtacat gagaaggaac ttccaggtgt tactgtaatt      833
cctcaacgta ttgtttcgac agcactaatt taatgccgat atactctaga tgaagtttta      893
cattgttgag ctattgctgt tctcttggga actgaactca ctttcctcct gaggctttgg      953
atttgacatt gcatttgacc ttttatgtag taattgacat gtgccagggc aatgatgaat     1013
gagaatctac ccccagatcc aagcatcctg agcaactctt gattatccat attgagtcaa     1073
atggtaggca tttcctatca cctgtttcca ttcaacaaga gcactacatt catttagcta     1133
aacggattcc aaagagtaga attgcattga ccacgactaa tttcaaaatg cttttattta     1193
ttattatttt ttagacagtc tcactttgtc gcccaggccg gagtgcagtg gtgcgatctc     1253
agatcagtgt accatttgcc tcccgggctc aagcgattct cctgcctcag cctcccaagt     1313
agctgggatt acaggcacct gccaccatgc ccggctaatt tttgtaattt tagtagagac     1373
agggtttcac catgttgccc aggctggttt cgaactcctg acctcaggtg atccacccgc     1433
ctcggcctcc caaagtgctg ggattacagg cttgagcccc cgcgcccagc catcaaaatg     1493
ctttttattt ctgcatatgt tgaatacttt ttacaattta aaaaaatgat ctgttttgaa     1553
ggcaaaattg caaatcttga aattaagaag gcaaaaatgt aaaggagtca aaactataaa     1613
tcaagtattt gggaagtgaa gactggaagc taatttgcat taaattcaca aacttttata     1673
ctctttctgt atatacattt ttttctttta aaaacaact atggatcaga atagccacat      1733
ttagaacact ttttgttatc agtcaatatt tttagatagt tagaacctgg tcctaagcct     1793
aaaagtgggc ttgattctgc agtaaatctt ttacaactgc ctcgacacac ataaaccttt     1853
ttaaaaatag acactccccg aagtcttttg ttcgcatggt cacacactga tgcttagatg     1913
ttccagtaat ctaatatggc cacagtagtc ttgatgacca aagtccttt ttccatctt      1973 tagaaaacta catgggaaca aacagatcga acagttttga agctactgtg tgtgtgaatg     2033
aacactcttg ctttattcca gaatgctgta catctatttt ggattgtata ttgtgttttgt    2093 gtatttacgc tttgattcat agtaacttct tatggaattg atttgcattg aacacaaact     2153
gtaaataaaa agaaatggct gaaagagcaa aaaaaaaaa a                          2194
```

<210> SEQ ID NO 4
<211> LENGTH: 80
<212> TYPE: PRT
<213> ORGANISM: Homo Sapiens

<400> SEQUENCE: 4

```
Met Gly Arg Ala Met Val Ala Arg Leu Gly Leu Gly Leu Leu Leu Leu
 1               5                  10                  15

Ala Leu Leu Leu Pro Thr Gln Ile Tyr Ser Ser Glu Thr Thr Thr Gly
             20                  25                  30

Thr Ser Ser Asn Ser Ser Gln Thr Ser Asn Ser Gly Leu Ala Pro
         35                  40                  45

Asn Pro Thr Asn Ala Thr Thr Lys Ala Ala Gly Gly Ala Leu Gln Ser
     50                  55                  60

Thr Ala Ser Leu Phe Val Val Ser Leu Ser Leu Leu His Leu Tyr Ser
```

<210> SEQ ID NO 5
<211> LENGTH: 5748
<212> TYPE: DNA
<213> ORGANISM: Homo Sapiens
<220> FEATURE:
<221> NAME/KEY: CDS
<222> LOCATION: (435)...(2663)
<220> FEATURE:
<221> NAME/KEY: misc_feature
<222> LOCATION: (0)...(0)
<223> OTHER INFORMATION: CD44

<400> SEQUENCE: 5

```
gagaagaaag ccagtgcgtc tctgggcgca ggggccagtg gggctcggag gcacaggcac      60
cccgcgacac tccaggttcc ccgacccacg tccctggcag ccccgattat ttacagcctc     120
agcagagcac ggggcggggg cagaggggcc cgcccgggag ggctgctact tcttaaaacc     180
tctgcgggct gcttagtcac agccccccctt gcttgggtgt gtccttcgct cgctccctcc     240
ctccgtctta ggtcactgtt ttcaaccctcg aataaaaact gcagccaact tccgaggcag     300
cctcattgcc cagcggaccc cagcctctgc caggttcggt ccgccatcct cgtcccgtcc     360
tccgccggcc cctgccccgc gcccagggat cctccagctc ctttcgcccg cgccctccgt     420
tcgctccgga cacc atg gac aag ttt tgg tgg cac gca gcc tgg gga ctc        470
              Met Asp Lys Phe Trp Trp His Ala Ala Trp Gly Leu
                1               5                  10 tgc ctc gtg ccg ctg agc ctg gcg cag atc gat ttg aat ata acc tgc        518
Cys Leu Val Pro Leu Ser Leu Ala Gln Ile Asp Leu Asn Ile Thr Cys
         15                  20                  25 cgc ttt gca ggt gta ttc cac gtg gag aaa aat ggt cgc tac agc atc        566
Arg Phe Ala Gly Val Phe His Val Glu Lys Asn Gly Arg Tyr Ser Ile
     30                  35                  40 tct cgg acg gag gcc gct gac ctc tgc aag gct ttc aat agc acc ttg        614
Ser Arg Thr Glu Ala Ala Asp Leu Cys Lys Ala Phe Asn Ser Thr Leu
45                  50                  55                  60 ccc aca atg gcc cag atg gag aaa gct ctg agc atc gga ttt gag acc        662
Pro Thr Met Ala Gln Met Glu Lys Ala Leu Ser Ile Gly Phe Glu Thr
                 65                  70                  75 tgc agg tat ggg ttc ata gaa ggg cac gtg gtg att ccc cgg atc cac        710
Cys Arg Tyr Gly Phe Ile Glu Gly His Val Val Ile Pro Arg Ile His
         80                  85                  90 ccc aac tcc atc tgt gca gca aac aac aca ggg gtg tac atc ctc aca        758
Pro Asn Ser Ile Cys Ala Ala Asn Asn Thr Gly Val Tyr Ile Leu Thr
     95                 100                 105 tcc aac acc tcc cag tat gac aca tat tgc ttc aat gct tca gct cca        806
Ser Asn Thr Ser Gln Tyr Asp Thr Tyr Cys Phe Asn Ala Ser Ala Pro
110                 115                 120 cct gaa gaa gat tgt aca tca gtc aca gac ctg ccc aat gcc ttt gat        854
Pro Glu Glu Asp Cys Thr Ser Val Thr Asp Leu Pro Asn Ala Phe Asp
125                 130                 135                 140 gga cca att acc ata act att gtt aac cgt gat ggc acc cgc tat gtc        902
Gly Pro Ile Thr Ile Thr Ile Val Asn Arg Asp Gly Thr Arg Tyr Val
                145                 150                 155 cag aaa gga gaa tac aga acg aat cct gaa gac atc tac ccc agc aac        950
Gln Lys Gly Glu Tyr Arg Thr Asn Pro Glu Asp Ile Tyr Pro Ser Asn
        160                 165                 170 cct act gat gat gac gtg agc agc ggc tcc tcc agt gaa agg agc agc        998
Pro Thr Asp Asp Asp Val Ser Ser Gly Ser Ser Ser Glu Arg Ser Ser
    175                 180                 185
```

```
act tca gga ggt tac atc ttt tac acc ttt tct act gta cac ccc atc    1046
Thr Ser Gly Gly Tyr Ile Phe Tyr Thr Phe Ser Thr Val His Pro Ile
    190             195                 200 cca gac gaa gac agt ccc tgg atc acc gac agc aca gac aga atc cct    1094
Pro Asp Glu Asp Ser Pro Trp Ile Thr Asp Ser Thr Asp Arg Ile Pro
205             210                 215                 220 gct acc act ttg atg agc act agt gct aca gca act gag aca gca acc    1142
Ala Thr Thr Leu Met Ser Thr Ser Ala Thr Ala Thr Glu Thr Ala Thr
                225                 230                 235 aag agg caa gaa acc tgg gat tgg ttt tca tgg ttg ttt cta cca tca    1190
Lys Arg Gln Glu Thr Trp Asp Trp Phe Ser Trp Leu Phe Leu Pro Ser
                240                 245                 250 gag tca aag aat cat ctt cac aca aca aca caa atg gct ggt acg tct    1238
Glu Ser Lys Asn His Leu His Thr Thr Thr Gln Met Ala Gly Thr Ser
            255                 260                 265 tca aat acc atc tca gca ggc tgg gag cca aat gaa gaa aat gaa gat    1286
Ser Asn Thr Ile Ser Ala Gly Trp Glu Pro Asn Glu Glu Asn Glu Asp
270                 275                 280 gaa aga gac aga cac ctc agt ttt tct gga tca ggc att gat gat gat    1334
Glu Arg Asp Arg His Leu Ser Phe Ser Gly Ser Gly Ile Asp Asp Asp
285                 290                 295                 300 gaa gat ttt atc tcc agc acc att tca acc aca cca cgg gct ttt gac    1382
Glu Asp Phe Ile Ser Ser Thr Ile Ser Thr Thr Pro Arg Ala Phe Asp
                305                 310                 315 cac aca aaa cag aac cag gac tgg acc cag tgg aac cca agc cat tca    1430
His Thr Lys Gln Asn Gln Asp Trp Thr Gln Trp Asn Pro Ser His Ser
                320                 325                 330 aat ccg gaa gtg cta ctt cag aca acc aca agg atg act gat gta gac    1478
Asn Pro Glu Val Leu Leu Gln Thr Thr Thr Arg Met Thr Asp Val Asp
            335                 340                 345 aga aat ggc acc act gct tat gaa gga aac tgg aac cca gaa gca cac    1526
Arg Asn Gly Thr Thr Ala Tyr Glu Gly Asn Trp Asn Pro Glu Ala His
350                 355                 360 cct ccc ctc att cac cat gag cat cat gag gaa gaa gag acc cca cat    1574
Pro Pro Leu Ile His His Glu His His Glu Glu Glu Glu Thr Pro His
365                 370                 375                 380 tct aca agc aca atc cag gca act cct agt agt aca acg gaa gaa aca    1622
Ser Thr Ser Thr Ile Gln Ala Thr Pro Ser Ser Thr Thr Glu Glu Thr
                385                 390                 395 gct acc cag aag gaa cag tgg ttt ggc aac aga tgg cat gag gga tat    1670
Ala Thr Gln Lys Glu Gln Trp Phe Gly Asn Arg Trp His Glu Gly Tyr
                400                 405                 410 cgc caa aca ccc aaa gaa gac tcc cat tcg aca aca ggg aca gct gca    1718
Arg Gln Thr Pro Lys Glu Asp Ser His Ser Thr Thr Gly Thr Ala Ala
            415                 420                 425 gcc tca gct cat acc agc cat cca atg caa gga agg aca aca cca agc    1766
Ala Ser Ala His Thr Ser His Pro Met Gln Gly Arg Thr Thr Pro Ser
430                 435                 440 cca gag gac agt tcc tgg act gat ttc ttc aac cca atc tca cac ccc    1814
Pro Glu Asp Ser Ser Trp Thr Asp Phe Phe Asn Pro Ile Ser His Pro
445                 450                 455                 460 atg gga cga ggt cat caa gca gga aga agg atg gat atg gac tcc agt    1862
Met Gly Arg Gly His Gln Ala Gly Arg Arg Met Asp Met Asp Ser Ser
                465                 470                 475 cat agt ata acg ctt cag cct act gca aat cca aac aca ggt ttg gtg    1910
His Ser Ile Thr Leu Gln Pro Thr Ala Asn Pro Asn Thr Gly Leu Val
            480                 485                 490 gaa gat ttg gac agg aca gga cct ctt tca atg aca acg cag cag agt    1958
Glu Asp Leu Asp Arg Thr Gly Pro Leu Ser Met Thr Thr Gln Gln Ser
            495                 500                 505
```

```
aat tct cag agc ttc tct aca tca cat gaa ggc ttg gaa gaa gat aaa         2006
Asn Ser Gln Ser Phe Ser Thr Ser His Glu Gly Leu Glu Glu Asp Lys
    510                 515                 520 gac cat cca aca act tct act ctg aca tca agc aat agg aat gat gtc         2054
Asp His Pro Thr Thr Ser Thr Leu Thr Ser Ser Asn Arg Asn Asp Val
525                 530                 535                 540 aca ggt gga aga aga gac cca aat cat tct gaa ggc tca act act tta         2102
Thr Gly Gly Arg Arg Asp Pro Asn His Ser Glu Gly Ser Thr Thr Leu
                545                 550                 555 ctg gaa ggt tat acc tct cat tac cca cac acg aag gaa agc agg acc         2150
Leu Glu Gly Tyr Thr Ser His Tyr Pro His Thr Lys Glu Ser Arg Thr
            560                 565                 570 ttc atc cca gtg acc tca gct aag act ggg tcc ttt gga gtt act gca         2198
Phe Ile Pro Val Thr Ser Ala Lys Thr Gly Ser Phe Gly Val Thr Ala
        575                 580                 585 gtt act gtt gga gat tcc aac tct aat gtc aat cgt tcc tta tca gga         2246
Val Thr Val Gly Asp Ser Asn Ser Asn Val Asn Arg Ser Leu Ser Gly
    590                 595                 600 gac caa gac aca ttc cac ccc agt ggg ggg tcc cat acc act cat gga         2294
Asp Gln Asp Thr Phe His Pro Ser Gly Gly Ser His Thr Thr His Gly
605                 610                 615                 620 tct gaa tca gat gga cac tca cat ggg agt caa gaa ggt gga gca aac         2342
Ser Glu Ser Asp Gly His Ser His Gly Ser Gln Glu Gly Gly Ala Asn
                625                 630                 635 aca acc tct ggt cct ata agg aca ccc caa att cca gaa tgg ctg atc         2390
Thr Thr Ser Gly Pro Ile Arg Thr Pro Gln Ile Pro Glu Trp Leu Ile
            640                 645                 650 atc ttg gca tcc ctc ttg gcc ttg gct ttg att ctt gca gtt tgc att         2438
Ile Leu Ala Ser Leu Leu Ala Leu Ala Leu Ile Leu Ala Val Cys Ile
        655                 660                 665 gca gtc aac agt cga aga agg tgt ggg cag aag aaa aag cta gtg atc         2486
Ala Val Asn Ser Arg Arg Arg Cys Gly Gln Lys Lys Lys Leu Val Ile
    670                 675                 680 aac agt ggc aat gga gct gtg gag gac aga aag cca agt gga ctc aac         2534
Asn Ser Gly Asn Gly Ala Val Glu Asp Arg Lys Pro Ser Gly Leu Asn
685                 690                 695                 700 gga gag gcc agc aag tct cag gaa atg gtg cat ttg gtg aac aag gag         2582
Gly Glu Ala Ser Lys Ser Gln Glu Met Val His Leu Val Asn Lys Glu
                705                 710                 715 tcg tca gaa act cca gac cag ttt atg aca gct gat gag aca agg aac         2630
Ser Ser Glu Thr Pro Asp Gln Phe Met Thr Ala Asp Glu Thr Arg Asn
            720                 725                 730 ctg cag aat gtg gac atg aag att ggg gtg taa cacctacacc attatcttgg       2683
Leu Gln Asn Val Asp Met Lys Ile Gly Val
        735                 740 aaagaaacaa ccgttggaaa cataaccatt acagggagct gggacactta acagatgcaa       2743
tgtgctactg attgtttcat tgcgaatctt ttttagcata aaattttcta ctcttttgt        2803 tttttgtgtt ttgttcttta aagtcaggtc caatttgtaa aaacagcatt gctttctgaa       2863
attagggccc aattaataat cagcaagaat ttgatcgttc cagttcccac ttggaggcct       2923
ttcatccctc gggtgtgcta tggatggctt ctaacaaaaa ctacacatat gtattcctga       2983
tcgccaacct ttcccccacc agctaaggac atttcccagg gttaataggg cctggtccct       3043
gggaggaaat ttgaatgggt ccatttttgcc cttccatagc ctaatccctg ggcattgctt      3103
tccactgagg ttgggggttg gggtgtacta gttacacatc ttcaacagac cccctctaga       3163 aattttttcag atgcttctgg gagacaccca aagggtgaag ctatttatct gtagtaaact      3223
```

```
atttatctgt gttttttgaaa tattaaaccc tggatcagtc ctttgatcag tataattttt   3283
taaagttact ttgtcagagg cacaaaaggg tttaaactga ttcataataa atatctgtac   3343
ttcttcgatc ttcacctttt gtgctgtgat tcttcagttt ctaaaccagc actgtctggg   3403
tccctacaat gtatcaggaa gagctgagaa tggtaaggag actcttctaa gtcttcatct   3463
cagagaccct gagttcccac tcagacccac tcagccaaat ctcatggaag accaaggagg   3523
gcagcactgt ttttgttttt tgtttttttgt tttttttttt tgacactgtc caaaggtttt   3583
ccatcctgtc ctggaatcag agttggaagc tgaggagctt cagcctcttt tatggtttaa   3643
tggccacctg ttctctcctg tgaaaggctt tgcaaagtca cattaagttt gcatgacctg   3703
ttatccctgg ggcctatttt catagaggct ggccctatta gtgatttcca aaacaatat   3763 ggaagtgcct tttgatgtct tacaataaga gaagaagcca atggaaatga aagagattgg   3823
caaaggggaa ggatgatgcc atgtagatcc tgtttgacat ttttatggct gtatttgtaa   3883
acttaaacac accagtgtct gttcttgatg cagttgctat ttaggatgag ttaagtgcct   3943
ggggagtccc tcaaaaggtt aaagggattc ccatcattgg aatcttatca ccagataggc   4003
aagtttatga ccaaacaaga gagtactggc tttatcctct aacctcatat tttctcccac   4063
ttggcaagtc cttttgtggca tttattcatc agtcagggtg tccgattggt cctagaactt   4123
ccaaaggctg cttgtcatag aagccattgc atctataaag caacggctcc tgttaaatgg   4183
tatctccttt ctgaggctcc tactaaaagt catttgttac ctaaacttat gtgcttaaca   4243
ggcaatgctt ctcagaccac aaagcagaaa gaagaagaaa agctcctgac taaatcaggg   4303
ctgggcttag acagagttga tctgtagaat atctttaaag gagagatgtc aactttctgc   4363
actattccca gcctctgctc ctccctgtct accctctccc ctccctctct ccctccactt   4423
caccccacaa tcttgaaaaa cttcctttct cttctgtgaa catcattggc cagatccatt   4483
ttcagtggtc tggatttctt tttatttttct tttcaacttg aaagaaactg gacattaggc   4543
cactatgtgt tgttactgcc actagtgttc aagtgcctct tgttttccca gagatttcct   4603
gggtctgcca gaggcccaga caggctcact caagctcttt aactgaaaag caacaagcca   4663
ctccaggaca aggttcaaaa tggttacaac agcctctacc tgtcgcccca gggagaaagg   4723
ggtagtgata caagtctcat agccagagat ggttttccac tccttctaga tattcccaaa   4783
aagaggctga acaggaggt tattttcaat tttattttgg aattaaatac ttttttccct   4843
ttattactgt tgtagtccct cacttggata tacctctgtt ttcacgatag aaataaggga   4903
ggtctagagc ttctattcct tggccattgt caacggagag ctggccaagt cttcacaaac   4963
ccttgcaaca ttgcctgaag tttatggaat aagatgtatt ctcactccct tgatctcaag   5023
ggcgtaactc tggaagcaca gcttgactac acgtcattt taccaatgat tttcaggtga   5083
cctgggctaa gtcatttaaa ctgggtcttt ataaagtaa aaggccaaca tttaattatt   5143
ttgcaaagca acctaagagc taagatgta atttttcttg caattgtaaa tcttttgtgt   5203
ctcctgaaga cttcccttaa aattagctct gagtgaaaaa tcaaaagaga caaagacat   5263 cttcgaatcc atatttcaag cctggtagaa ttggcttttc tagcagaacc tttccaaaag   5323
ttttatattg agattcataa caacaccaag aattgatttt gtagccaaca ttcattcaat   5383
actgttatat cagaggagta ggagagagga acatttgac ttatctggaa aagcaaaatg   5443
tacttaagaa taagaataac atggtccatt caccttatg ttatagatat gtctttgtgt   5503
aaatcatttg ttttgagttt tcaaagaata gcccattgtt cattcttgtg ctgtacaatg   5563
accactgtta ttgttacttt gactttcag agcacaccct tcctctggtt tttgtatatt   5623
```

```
tattgatgga tcaataataa tgaggaaagc atgatatgta tattgctgag ttgaaagcac    5683
ttattggaaa atattaaaag gctaacatta aagactaaa  ggaaacagaa aaaaaaaaaa    5743
aaaaa                                                                5748
```

<210> SEQ ID NO 6
<211> LENGTH: 742
<212> TYPE: PRT
<213> ORGANISM: Homo Sapiens

<400> SEQUENCE: 6

```
Met Asp Lys Phe Trp Trp His Ala Ala Trp Gly Leu Cys Leu Val Pro
  1               5                  10                  15

Leu Ser Leu Ala Gln Ile Asp Leu Asn Ile Thr Cys Arg Phe Ala Gly
                 20                  25                  30

Val Phe His Val Glu Lys Asn Gly Arg Tyr Ser Ile Ser Arg Thr Glu
             35                  40                  45

Ala Ala Asp Leu Cys Lys Ala Phe Asn Ser Thr Leu Pro Thr Met Ala
         50                  55                  60

Gln Met Glu Lys Ala Leu Ser Ile Gly Phe Glu Thr Cys Arg Tyr Gly
 65                  70                  75                  80

Phe Ile Glu Gly His Val Val Ile Pro Arg Ile His Pro Asn Ser Ile
                 85                  90                  95

Cys Ala Ala Asn Asn Thr Gly Val Tyr Ile Leu Thr Ser Asn Thr Ser
            100                 105                 110

Gln Tyr Asp Thr Tyr Cys Phe Asn Ala Ser Ala Pro Pro Glu Glu Asp
        115                 120                 125

Cys Thr Ser Val Thr Asp Leu Pro Asn Ala Phe Asp Gly Pro Ile Thr
    130                 135                 140

Ile Thr Ile Val Asn Arg Asp Gly Thr Arg Tyr Val Gln Lys Gly Glu
145                 150                 155                 160

Tyr Arg Thr Asn Pro Glu Asp Ile Tyr Pro Ser Asn Pro Thr Asp Asp
                165                 170                 175

Asp Val Ser Ser Gly Ser Ser Ser Glu Arg Ser Ser Thr Ser Gly Gly
            180                 185                 190

Tyr Ile Phe Tyr Thr Phe Ser Thr Val His Pro Ile Pro Asp Glu Asp
        195                 200                 205

Ser Pro Trp Ile Thr Asp Ser Thr Asp Arg Ile Pro Ala Thr Thr Leu
    210                 215                 220

Met Ser Thr Ser Ala Thr Ala Thr Glu Thr Ala Thr Lys Arg Gln Glu
225                 230                 235                 240

Thr Trp Asp Trp Phe Ser Trp Leu Phe Leu Pro Ser Glu Ser Lys Asn
                245                 250                 255

His Leu His Thr Thr Thr Gln Met Ala Gly Thr Ser Ser Asn Thr Ile
            260                 265                 270

Ser Ala Gly Trp Glu Pro Asn Glu Glu Asn Glu Asp Glu Arg Asp Arg
        275                 280                 285

His Leu Ser Phe Ser Gly Ser Gly Ile Asp Asp Asp Glu Asp Phe Ile
    290                 295                 300

Ser Ser Thr Ile Ser Thr Thr Pro Arg Ala Phe Asp His Thr Lys Gln
305                 310                 315                 320

Asn Gln Asp Trp Thr Gln Trp Asn Pro Ser His Ser Asn Pro Glu Val
                325                 330                 335

Leu Leu Gln Thr Thr Thr Arg Met Thr Asp Val Asp Arg Asn Gly Thr
```

```
               340             345             350
Thr Ala Tyr Glu Gly Asn Trp Asn Pro Glu Ala His Pro Pro Leu Ile
            355                 360                 365

His His Glu His His Glu Glu Glu Thr Pro His Ser Thr Ser Thr
370                 375                 380

Ile Gln Ala Thr Pro Ser Ser Thr Thr Glu Glu Thr Ala Thr Gln Lys
385                 390                 395                 400

Glu Gln Trp Phe Gly Asn Arg Trp His Glu Gly Tyr Arg Gln Thr Pro
                405                 410                 415

Lys Glu Asp Ser His Ser Thr Thr Gly Thr Ala Ala Ala Ser Ala His
            420                 425                 430

Thr Ser His Pro Met Gln Gly Arg Thr Thr Pro Ser Pro Glu Asp Ser
        435                 440                 445

Ser Trp Thr Asp Phe Phe Asn Pro Ile Ser His Pro Met Gly Arg Gly
    450                 455                 460

His Gln Ala Gly Arg Arg Met Asp Met Asp Ser Ser His Ser Ile Thr
465                 470                 475                 480

Leu Gln Pro Thr Ala Asn Pro Asn Thr Gly Leu Val Glu Asp Leu Asp
                485                 490                 495

Arg Thr Gly Pro Leu Ser Met Thr Thr Gln Gln Ser Asn Ser Gln Ser
            500                 505                 510

Phe Ser Thr Ser His Glu Gly Leu Glu Glu Asp Lys Asp His Pro Thr
        515                 520                 525

Thr Ser Thr Leu Thr Ser Ser Asn Arg Asn Asp Val Thr Gly Gly Arg
    530                 535                 540

Arg Asp Pro Asn His Ser Glu Gly Ser Thr Thr Leu Leu Glu Gly Tyr
545                 550                 555                 560

Thr Ser His Tyr Pro His Thr Lys Glu Ser Arg Thr Phe Ile Pro Val
                565                 570                 575

Thr Ser Ala Lys Thr Gly Ser Phe Gly Val Thr Ala Val Thr Val Gly
            580                 585                 590

Asp Ser Asn Ser Asn Val Asn Arg Ser Leu Ser Gly Asp Gln Asp Thr
        595                 600                 605

Phe His Pro Ser Gly Gly Ser His Thr Thr His Gly Ser Glu Ser Asp
    610                 615                 620

Gly His Ser His Gly Ser Gln Glu Gly Gly Ala Asn Thr Thr Ser Gly
625                 630                 635                 640

Pro Ile Arg Thr Pro Gln Ile Pro Glu Trp Leu Ile Ile Leu Ala Ser
                645                 650                 655

Leu Leu Ala Leu Ala Leu Ile Leu Ala Val Cys Ile Ala Val Asn Ser
            660                 665                 670

Arg Arg Arg Cys Gly Gln Lys Lys Lys Leu Val Ile Asn Ser Gly Asn
        675                 680                 685

Gly Ala Val Glu Asp Arg Lys Pro Ser Gly Leu Asn Gly Glu Ala Ser
    690                 695                 700

Lys Ser Gln Glu Met Val His Leu Val Asn Lys Glu Ser Ser Glu Thr
705                 710                 715                 720

Pro Asp Gln Phe Met Thr Ala Asp Glu Thr Arg Asn Leu Gln Asn Val
                725                 730                 735

Asp Met Lys Ile Gly Val
            740

<210> SEQ ID NO 7
```

```
<211> LENGTH: 1153
<212> TYPE: DNA
<213> ORGANISM: Homo Sapiens
<220> FEATURE:
<221> NAME/KEY: CDS
<222> LOCATION: (122)...(874)
<220> FEATURE:
<221> NAME/KEY: misc_feature
<222> LOCATION: (0)...(0)
<223> OTHER INFORMATION: CD58

<400> SEQUENCE: 7
```

| | | | | |
|---|---|---|---|---|
| gggccgccgg ctgccagccc agggcggggc ggagccctac ttctggccga ccgcgtaggc | | | | 60 |
| ggtgcttgaa cttagggctg cttgtggctg ggcactcgcg cagaggccgg cccgacgagc | | | | 120 |

| c atg gtt gct ggg agc gac gcg ggg cgg gcc ctg ggg gtc ctc agc gtg | 169 |
|---|---|
| Met Val Ala Gly Ser Asp Ala Gly Arg Ala Leu Gly Val Leu Ser Val | |
| 1               5                  10                 15 | |

| gtc tgc ctg ctg cac tgc ttt ggt ttc atc agc tgt ttt tcc caa caa | 217 |
|---|---|
| Val Cys Leu Leu His Cys Phe Gly Phe Ile Ser Cys Phe Ser Gln Gln | |
|         20                  25                  30 | |

| ata tat ggt gtt gtg tat ggg aat gta act ttc cat gta cca agc aat | 265 |
|---|---|
| Ile Tyr Gly Val Val Tyr Gly Asn Val Thr Phe His Val Pro Ser Asn | |
|     35                  40                  45 | |

| gtg cct tta aaa gag gtc cta tgg aaa aaa caa aag gat aaa gtt gca | 313 |
|---|---|
| Val Pro Leu Lys Glu Val Leu Trp Lys Lys Gln Lys Asp Lys Val Ala | |
| 50                  55                  60 | |

| gaa ctg gaa aat tct gaa ttc aga gct ttc tca tct ttt aaa aat agg | 361 |
|---|---|
| Glu Leu Glu Asn Ser Glu Phe Arg Ala Phe Ser Ser Phe Lys Asn Arg | |
| 65                  70                  75                  80 | |

| gtt tat tta gac act gtg tca ggt agc ctc act atc tac aac tta aca | 409 |
|---|---|
| Val Tyr Leu Asp Thr Val Ser Gly Ser Leu Thr Ile Tyr Asn Leu Thr | |
|             85                  90                  95 | |

| tca tca gat gaa gat gag tat gaa atg gaa tcg cca aat att act gat | 457 |
|---|---|
| Ser Ser Asp Glu Asp Glu Tyr Glu Met Glu Ser Pro Asn Ile Thr Asp | |
|                 100                 105                 110 | |

| acc atg aag ttc ttt ctt tat gtg ctt gag tct ctt cca tct ccc aca | 505 |
|---|---|
| Thr Met Lys Phe Phe Leu Tyr Val Leu Glu Ser Leu Pro Ser Pro Thr | |
|         115                 120                 125 | |

| cta act tgt gca ttg act aat gga agc att gaa gtc caa tgc atg ata | 553 |
|---|---|
| Leu Thr Cys Ala Leu Thr Asn Gly Ser Ile Glu Val Gln Cys Met Ile | |
| 130                 135                 140 | |

| cca gag cat tac aac agc cat cga gga ctt ata atg tac tca tgg gat | 601 |
|---|---|
| Pro Glu His Tyr Asn Ser His Arg Gly Leu Ile Met Tyr Ser Trp Asp | |
| 145                 150                 155                 160 | |

| tgt cct atg gag caa tgt aaa cgt aac tca acc agt ata tat ttt aag | 649 |
|---|---|
| Cys Pro Met Glu Gln Cys Lys Arg Asn Ser Thr Ser Ile Tyr Phe Lys | |
|                 165                 170                 175 | |

| atg gaa aat gat ctt cca caa aaa ata cag tgt act ctt agc aat cca | 697 |
|---|---|
| Met Glu Asn Asp Leu Pro Gln Lys Ile Gln Cys Thr Leu Ser Asn Pro | |
|         180                 185                 190 | |

| tta ttt aat aca aca tca tca atc att ttg aca acc tgt atc cca agc | 745 |
|---|---|
| Leu Phe Asn Thr Thr Ser Ser Ile Ile Leu Thr Thr Cys Ile Pro Ser | |
|     195                 200                 205 | |

| agc ggt cat tca aga cac aga tat gca ctt ata ccc ata cca tta gca | 793 |
|---|---|
| Ser Gly His Ser Arg His Arg Tyr Ala Leu Ile Pro Ile Pro Leu Ala | |
| 210                 215                 220 | |

| gta att aca aca tgt att gtg ctg tat atg aat ggt att ctg aaa tgt | 841 |
|---|---|
| Val Ile Thr Thr Cys Ile Val Leu Tyr Met Asn Gly Ile Leu Lys Cys | |
| 225                 230                 235                 240 | |

| gac aga aaa cca gac aga acc aac tcc aat tga ttggtaacag aagatgaaga | 894 |
|---|---|
| Asp Arg Lys Pro Asp Arg Thr Asn Ser Asn | |

```
                     245                 250
caacagcata actaaattat tttaaaaact aaaaagccat ctgatttctc atttgagtat    954
tacaattttt gaacaactgt tggaaatgta acttgaagca gctgctttaa gaagaaatac   1014
ccactaacaa agaacaagca ttagttttgg ctgtcatcaa cttattatat gactaggtgc   1074 ttgcttttt tgtcagtaaa ttgttttac tgatgatgta gatactttg taaataaatg     1134 taaatatgta cacaagtga                                                 1153
```

```
<210> SEQ ID NO 8
<211> LENGTH: 250
<212> TYPE: PRT
<213> ORGANISM: Homo Sapiens

<400> SEQUENCE: 8

Met Val Ala Gly Ser Asp Ala Gly Arg Ala Leu Gly Val Leu Ser Val
 1               5                  10                  15

Val Cys Leu Leu His Cys Phe Gly Phe Ile Ser Cys Phe Ser Gln Gln
            20                  25                  30

Ile Tyr Gly Val Val Tyr Gly Asn Val Thr Phe His Val Pro Ser Asn
        35                  40                  45

Val Pro Leu Lys Glu Val Leu Trp Lys Lys Gln Lys Asp Lys Val Ala
    50                  55                  60

Glu Leu Glu Asn Ser Glu Phe Arg Ala Phe Ser Ser Phe Lys Asn Arg
65                  70                  75                  80

Val Tyr Leu Asp Thr Val Ser Gly Ser Leu Thr Ile Tyr Asn Leu Thr
                85                  90                  95

Ser Ser Asp Glu Asp Glu Tyr Glu Met Glu Ser Pro Asn Ile Thr Asp
            100                 105                 110

Thr Met Lys Phe Phe Leu Tyr Val Leu Glu Ser Leu Pro Ser Pro Thr
        115                 120                 125

Leu Thr Cys Ala Leu Thr Asn Gly Ser Ile Glu Val Gln Cys Met Ile
    130                 135                 140

Pro Glu His Tyr Asn Ser His Arg Gly Leu Ile Met Tyr Ser Trp Asp
145                 150                 155                 160

Cys Pro Met Glu Gln Cys Lys Arg Asn Ser Thr Ser Ile Tyr Phe Lys
                165                 170                 175

Met Glu Asn Asp Leu Pro Gln Lys Ile Gln Cys Thr Leu Ser Asn Pro
            180                 185                 190

Leu Phe Asn Thr Thr Ser Ser Ile Ile Leu Thr Thr Cys Ile Pro Ser
        195                 200                 205

Ser Gly His Ser Arg His Arg Tyr Ala Leu Ile Pro Ile Pro Leu Ala
    210                 215                 220

Val Ile Thr Thr Cys Ile Val Leu Tyr Met Asn Gly Ile Leu Lys Cys
225                 230                 235                 240

Asp Arg Lys Pro Asp Arg Thr Asn Ser Asn
                245                 250

<210> SEQ ID NO 9
<211> LENGTH: 4086
<212> TYPE: DNA
<213> ORGANISM: Homo Sapiens
<220> FEATURE:
<221> NAME/KEY: CDS
<222> LOCATION: (557)...(2281)
<220> FEATURE:
<221> NAME/KEY: misc_feature
<222> LOCATION: (0)...(0)
```

-continued

<223> OTHER INFORMATION: CD73

<400> SEQUENCE: 9

```
actcctcctc tctgcccctc agctcgctca tctttcttcc cgccccctct cttttccttc    60
tttggttctt tgaagtgatg agctagcgca accacaaacc atacattcct tttgtagaaa   120
aacccgtgcc tcgaatgagg cgagactcag agaggaccca ggcgcggggc ggacccctcc   180
aattccttcc tcgcgccccc gaaagagcgg cgcaccagca gccgaactgc cggcgcccag   240 gctcctggt ccggccggga tgcggccggt accgctcccc gccgggaac aacctctcca    300 ctcttcctgc agggagctgg tgccagccga cagccgcgcc agggccgctc cgggtaccag   360
ggtcggatcg ggtgacgtcg cgaacttgcg cctggccgcc aagccggcct ccaggctgaa   420
gaaggacccg ccccggcctt gacccgggcc ccgcccctcc agccggggca ccgagccccg   480
gccctagctg ctcgccccta ctcgccggca ctcgccggc tcgcccgctt cgcacccag    540 ttcacgcgcc acagct atg tgt ccc cga gcc gcg cgg gcg ccc gcg acg cta   592
              Met Cys Pro Arg Ala Ala Arg Ala Pro Ala Thr Leu
                1               5                  10
```

```
ctc ctc gcc ctg ggc gcg gtg ctg tgg cct gcg gct ggc gcc tgg gag     640
Leu Leu Ala Leu Gly Ala Val Leu Trp Pro Ala Ala Gly Ala Trp Glu
        15                  20                  25
```

```
ctt acg att ttg cac acc aac gac gtg cac agc cgg ctg gag cag acc     688
Leu Thr Ile Leu His Thr Asn Asp Val His Ser Arg Leu Glu Gln Thr
 30                  35                  40
```

```
agc gag gac tcc agc aag tgc gtc aac gcc agc cgc tgc atg ggt ggc     736
Ser Glu Asp Ser Ser Lys Cys Val Asn Ala Ser Arg Cys Met Gly Gly
 45                  50                  55                  60
```

```
gtg gct cgg ctc ttc acc aag gtt cag cag atc cgc cgc gcc gaa ccc     784
Val Ala Arg Leu Phe Thr Lys Val Gln Gln Ile Arg Arg Ala Glu Pro
                 65                  70                  75
```

```
aac gtg ctg ctg ctg gac gcc ggc gac cag tac cag ggc act atc tgg     832
Asn Val Leu Leu Leu Asp Ala Gly Asp Gln Tyr Gln Gly Thr Ile Trp
         80                  85                  90
```

```
ttc acc gtg tac aag ggc gcc gag gtg gcg cac ttc atg aac gcc ctg     880
Phe Thr Val Tyr Lys Gly Ala Glu Val Ala His Phe Met Asn Ala Leu
             95                 100                 105
```

```
cgc tac gat gcc atg gca ctg gga aat cat gaa ttt gat aat ggt gtg     928
Arg Tyr Asp Ala Met Ala Leu Gly Asn His Glu Phe Asp Asn Gly Val
 110                 115                 120
```

```
gaa gga ctg atc gag cca ctc ctc aaa gag gcc aaa ttt cca att ctg     976
Glu Gly Leu Ile Glu Pro Leu Leu Lys Glu Ala Lys Phe Pro Ile Leu
125                 130                 135                 140
```

```
agt gca aac att aaa gca aag ggg cca cta gca tct caa ata tca gga    1024
Ser Ala Asn Ile Lys Ala Lys Gly Pro Leu Ala Ser Gln Ile Ser Gly
                145                 150                 155
```

```
ctt tat ttg cca tat aaa gtt ctt cct gtt ggt gat gaa gtt gtg gga    1072
Leu Tyr Leu Pro Tyr Lys Val Leu Pro Val Gly Asp Glu Val Val Gly
         160                 165                 170
```

```
atc gtt gga tac act tcc aaa gaa acc cct ttt ctc tca aat cca ggg    1120
Ile Val Gly Tyr Thr Ser Lys Glu Thr Pro Phe Leu Ser Asn Pro Gly
             175                 180                 185
```

```
aca aat tta gtg ttt gaa gat gaa atc act gca tta caa cct gaa gta    1168
Thr Asn Leu Val Phe Glu Asp Glu Ile Thr Ala Leu Gln Pro Glu Val
 190                 195                 200
```

```
gat aag tta aaa act cta aat gtg aac aaa att att gca ctg gga cat    1216
Asp Lys Leu Lys Thr Leu Asn Val Asn Lys Ile Ile Ala Leu Gly His
205                 210                 215                 220
```

```
tcg ggt ttt gaa atg gat aaa ctc atc gct cag aaa gtg agg ggt gtg    1264
Ser Gly Phe Glu Met Asp Lys Leu Ile Ala Gln Lys Val Arg Gly Val
```

```
            Ser Gly Phe Glu Met Asp Lys Leu Ile Ala Gln Lys Val Arg Gly Val
                            225                 230                 235 gac gtc gtg gtg gga gga cac tcc aac aca ttt ctt tac aca ggc aat             1312
Asp Val Val Val Gly Gly His Ser Asn Thr Phe Leu Tyr Thr Gly Asn
            240                 245                 250 cca cct tcc aaa gag gtg cct gct ggg aag tac cca ttc ata gtc act             1360
Pro Pro Ser Lys Glu Val Pro Ala Gly Lys Tyr Pro Phe Ile Val Thr
            255                 260                 265 tct gat gat ggg cgg aag gtt cct gta gtc cag gcc tat gct ttt ggc             1408
Ser Asp Asp Gly Arg Lys Val Pro Val Val Gln Ala Tyr Ala Phe Gly
            270                 275                 280 aaa tac cta ggc tat ctg aag atc gag ttt gat gaa aga gga aac gtc             1456
Lys Tyr Leu Gly Tyr Leu Lys Ile Glu Phe Asp Glu Arg Gly Asn Val
285                 290                 295                 300 atc tct tcc cat gga aat ccc att ctt cta aac agc agc att cct gaa             1504
Ile Ser Ser His Gly Asn Pro Ile Leu Leu Asn Ser Ser Ile Pro Glu
                305                 310                 315 gat cca agc ata aaa gca gac att aac aaa tgg agg ata aaa ttg gat             1552
Asp Pro Ser Ile Lys Ala Asp Ile Asn Lys Trp Arg Ile Lys Leu Asp
            320                 325                 330 aat tat tct acc cag gaa tta ggg aaa aca att gtc tat ctg gat ggc             1600
Asn Tyr Ser Thr Gln Glu Leu Gly Lys Thr Ile Val Tyr Leu Asp Gly
            335                 340                 345 tcc tct caa tca tgc cgc ttt aga gaa tgc aac atg ggc aac ctg att             1648
Ser Ser Gln Ser Cys Arg Phe Arg Glu Cys Asn Met Gly Asn Leu Ile
350                 355                 360 tgt gat gca atg att aac aac aac ctg aga cac acg gat gaa atg ttc             1696
Cys Asp Ala Met Ile Asn Asn Asn Leu Arg His Thr Asp Glu Met Phe
365                 370                 375                 380 tgg aac cac gta tcc atg tgc att tta aat gga ggt ggt atc cgg tcg             1744
Trp Asn His Val Ser Met Cys Ile Leu Asn Gly Gly Gly Ile Arg Ser
                385                 390                 395 ccc att gat gaa cgc aac aat ggc aca att acc tgg gag aac ctg gct             1792
Pro Ile Asp Glu Arg Asn Asn Gly Thr Ile Thr Trp Glu Asn Leu Ala
            400                 405                 410 gct gta ttg ccc ttt gga ggc aca ttt gac cta gtc cag tta aaa ggt             1840
Ala Val Leu Pro Phe Gly Gly Thr Phe Asp Leu Val Gln Leu Lys Gly
            415                 420                 425 tcc acc ctg aag aag gcc ttt gag cat agc gtg cac cgc tac ggc cag             1888
Ser Thr Leu Lys Lys Ala Phe Glu His Ser Val His Arg Tyr Gly Gln
430                 435                 440 tcc act gga gag ttc ctg cag gtg ggc gga atc cat gtg gtg tat gat             1936
Ser Thr Gly Glu Phe Leu Gln Val Gly Gly Ile His Val Val Tyr Asp
445                 450                 455                 460 ctt tcc cga aaa cct gga gac aga gta gtc aaa tta gat gtt ctt tgc             1984
Leu Ser Arg Lys Pro Gly Asp Arg Val Val Lys Leu Asp Val Leu Cys
                465                 470                 475 acc aag tgt cga gtg ccc agt tat gac cct ctc aaa atg gac gag gta             2032
Thr Lys Cys Arg Val Pro Ser Tyr Asp Pro Leu Lys Met Asp Glu Val
            480                 485                 490 tat aag gtg atc ctc cca aac ttc ctg gcc aat ggt gga gat ggg ttc             2080
Tyr Lys Val Ile Leu Pro Asn Phe Leu Ala Asn Gly Gly Asp Gly Phe
            495                 500                 505 cag atg ata aaa gat gaa tta tta aga cat gac tct ggt gac caa gat             2128
Gln Met Ile Lys Asp Glu Leu Leu Arg His Asp Ser Gly Asp Gln Asp
            510                 515                 520 atc aac gtg gtt tct aca tat atc tcc aaa atg aaa gta att tat cca             2176
Ile Asn Val Val Ser Thr Tyr Ile Ser Lys Met Lys Val Ile Tyr Pro
525                 530                 535                 540
```

| gca Ala | gtt Val | gaa Glu | ggt Gly | cgg Arg 545 | atc Ile | aag Lys | ttt Phe | tcc Ser | aca Thr 550 | gga Gly | agt Ser | cac His | tgc Cys | cat His 555 | gga Gly | 2224 |

| agc Ser | ttt Phe | tct Ser | tta Leu | ata Ile 560 | ttt Phe | ctt Leu | tca Ser | ctt Leu | tgg Trp 565 | gca Ala | gtg Val | atc Ile | ttt Phe | gtt Val 570 | tta Leu | 2272 | tac caa tag ccaaaaattc tccttgcctt taatgtgtga aactgcattt    2321
Tyr Gln tttcaagtga gattcaaatc tgcctttttag gacctggctt tgtgacagca aaaaccatct    2381
ttacaggctc ctagaagctg aaggttagag cattataaaa tgaagagaca gacatgatta    2441
ctcagggtca gcaacctagt gagttagaaa aaaaattaac atagggccct ataaggagaa    2501
agccaactat gttaagttta cgtgtccaaa ttttaatgaa attttactaa caattttaaa    2561
ccatatttt cttcttcata tccatttcta atccatcaaa cagcttatgt ttacataaaa    2621
ttttatcatt cacaaggaag ttttaagcac actgtctcat ttgatatcca caacttattt    2681
ttggtaggaa agagagatgt ttttcccacc tgtcagatga aaaaactgaa gctcaaaaag    2741
ggttgacttg accatacagc taatgctgac agatccaaga cctagaccta ggtcttttga    2801
actcaagtcc agcattctca actatatcaa gttactgttc agaatactta atatctcctc    2861
tcttcataat tatcaatagc cccaagctca tggatgacaa atctctgctt tatttcttgt    2921
ctctatttt tcactttata gctcctgtta taatagcaag tttaatggta taaacacagg    2981
ataccatcct ctcttgcaac acccatgtgc ctttgatgag tcaggtagca agctgtagta    3041
gataatgaga aaggccagag gctgcaaaag acagtcaaag gacacgagag aaaggaaggg    3101
gaagaacagg actccaggac tgtttttatat tatagaaaag caagagctaa agagcattta    3161
cacatgttaa acagatactt gttaagcata gtgcctgaca cacggcatta gctgttattt    3221
tatgagattc catcagctct gcctctgtcc tctttcttct aacatgaagg tatcatgaga    3281
agagaacctt ctaacataag ctgtaattct aaacctgcac ttgtccctct ccagcaagag    3341
gctagcactg aattcattct actcatacta cacacccagt tatggaatgt ccagagttct    3401
cgaagaaaat aaatgacttt aggaagaggt atacatttt taagtcgctc tgcctccaaa    3461
tctgaacagt cactgtaaat cattcttaag cccagatatg agaacttctg ctggaaagtg    3521
ggaccctctg agtgggtggt cagaaaatac ccatgctgat gaaatgacct atgcccaaag    3581
aacaaatact taacgtggga gtggaaccac atgagcctgc tcagctctgc ataagtaatt    3641
caagaaatgg gaggcttcac cttaaaaaca gtgtgcaaat ggcagctaga ggttttgata    3701
ggaagtatgt ttgtttctta gtgtttacaa atattaagta ctcttgatac aaaatatact    3761
tttaaacttc ataaccttt tataaaagtt gttgcagcaa aataatagcc tcggttctat    3821
gcatatatgg attagctata aaaaatgtca ataagattgt acaaggaaaa ttagagaaag    3881
tcacatttag ggtttatttt ttacacttgg ccagtaaaat agggtaaatc ctattagaat    3941
tttttaaaga acttttttta agtttcctaa atctgtgtgt gtattgtgaa gtggtataag    4001
aaatgacttt gaaccacttt gcaattgtag attcccaaca ataaaattga agataagctc    4061
tttggtcaaa aaaaaaaaaa aaaaa                                         4086

<210> SEQ ID NO 10
<211> LENGTH: 574
<212> TYPE: PRT
<213> ORGANISM: Homo Sapiens

<400> SEQUENCE: 10

```
Met Cys Pro Arg Ala Ala Arg Ala Pro Ala Thr Leu Leu Ala Leu
 1               5                  10                  15

Gly Ala Val Leu Trp Pro Ala Ala Gly Ala Trp Glu Leu Thr Ile Leu
            20                  25                  30

His Thr Asn Asp Val His Ser Arg Leu Glu Gln Thr Ser Glu Asp Ser
            35                  40                  45

Ser Lys Cys Val Asn Ala Ser Arg Cys Met Gly Gly Val Ala Arg Leu
 50                  55                  60

Phe Thr Lys Val Gln Gln Ile Arg Arg Ala Glu Pro Asn Val Leu Leu
 65                  70                  75                  80

Leu Asp Ala Gly Asp Gln Tyr Gln Gly Thr Ile Trp Phe Thr Val Tyr
                85                  90                  95

Lys Gly Ala Glu Val Ala His Phe Met Asn Ala Leu Arg Tyr Asp Ala
                100                 105                 110

Met Ala Leu Gly Asn His Glu Phe Asp Asn Gly Val Glu Gly Leu Ile
            115                 120                 125

Glu Pro Leu Leu Lys Glu Ala Lys Phe Pro Ile Leu Ser Ala Asn Ile
            130                 135                 140

Lys Ala Lys Gly Pro Leu Ala Ser Gln Ile Ser Gly Leu Tyr Leu Pro
145                 150                 155                 160

Tyr Lys Val Leu Pro Val Gly Asp Glu Val Val Gly Ile Val Gly Tyr
                165                 170                 175

Thr Ser Lys Glu Thr Pro Phe Leu Ser Asn Pro Gly Thr Asn Leu Val
            180                 185                 190

Phe Glu Asp Glu Ile Thr Ala Leu Gln Pro Glu Val Asp Lys Leu Lys
            195                 200                 205

Thr Leu Asn Val Asn Lys Ile Ile Ala Leu Gly His Ser Gly Phe Glu
210                 215                 220

Met Asp Lys Leu Ile Ala Gln Lys Val Arg Gly Val Asp Val Val Val
225                 230                 235                 240

Gly Gly His Ser Asn Thr Phe Leu Tyr Thr Gly Asn Pro Pro Ser Lys
                245                 250                 255

Glu Val Pro Ala Gly Lys Tyr Pro Phe Ile Val Thr Ser Asp Asp Gly
                260                 265                 270

Arg Lys Val Pro Val Val Gln Ala Tyr Ala Phe Gly Lys Tyr Leu Gly
            275                 280                 285

Tyr Leu Lys Ile Glu Phe Asp Glu Arg Gly Asn Val Ile Ser Ser His
            290                 295                 300

Gly Asn Pro Ile Leu Leu Asn Ser Ser Ile Pro Glu Asp Pro Ser Ile
305                 310                 315                 320

Lys Ala Asp Ile Asn Lys Trp Arg Ile Lys Leu Asp Asn Tyr Ser Thr
                325                 330                 335

Gln Glu Leu Gly Lys Thr Ile Val Tyr Leu Asp Gly Ser Ser Gln Ser
            340                 345                 350

Cys Arg Phe Arg Glu Cys Asn Met Gly Asn Leu Ile Cys Asp Ala Met
            355                 360                 365

Ile Asn Asn Asn Leu Arg His Thr Asp Glu Met Phe Trp Asn His Val
370                 375                 380

Ser Met Cys Ile Leu Asn Gly Gly Gly Ile Arg Ser Pro Ile Asp Glu
385                 390                 395                 400

Arg Asn Asn Gly Thr Ile Thr Trp Glu Asn Leu Ala Ala Val Leu Pro
            405                 410                 415

Phe Gly Gly Thr Phe Asp Leu Val Gln Leu Lys Gly Ser Thr Leu Lys
```

```
                420              425              430
Lys Ala Phe Glu His Ser Val His Arg Tyr Gly Gln Ser Thr Gly Glu
            435                  440                  445
Phe Leu Gln Val Gly Gly Ile His Val Val Tyr Asp Leu Ser Arg Lys
        450                  455                  460
Pro Gly Asp Arg Val Val Lys Leu Asp Val Leu Cys Thr Lys Cys Arg
465                  470                  475                  480
Val Pro Ser Tyr Asp Pro Leu Lys Met Asp Glu Val Tyr Lys Val Ile
                485                  490                  495
Leu Pro Asn Phe Leu Ala Asn Gly Gly Asp Gly Phe Gln Met Ile Lys
            500                  505                  510
Asp Glu Leu Leu Arg His Asp Ser Gly Asp Gln Asp Ile Asn Val Val
        515                  520                  525
Ser Thr Tyr Ile Ser Lys Met Lys Val Ile Tyr Pro Ala Val Glu Gly
    530                  535                  540
Arg Ile Lys Phe Ser Thr Gly Ser His Cys His Gly Ser Phe Ser Leu
545                  550                  555                  560
Ile Phe Leu Ser Leu Trp Ala Val Ile Phe Val Leu Tyr Gln
                565                  570

<210> SEQ ID NO 11
<211> LENGTH: 6063
<212> TYPE: DNA
<213> ORGANISM: Homo Sapiens
<220> FEATURE:
<221> NAME/KEY: CDS
<222> LOCATION: (284)...(1876)
<223> OTHER INFORMATION: CD15

<400> SEQUENCE: 11
aatccctccc tccggcgggc gtcgctggcg ggtggctagg cccaacggca ggaagccgac      60
gctatcctcc gttccgcggc gccgggtccg ccttccgtct gttctagggc ctgctcctgc     120
gcggcagctg ctttagaagg tctcgagcct cctgtacctt cccagggatg aaccgggcct     180
tccctctgga aggcgagggt tcgggccaca gtgagcgagg gccagggcgg tgggcgcgcg     240
cagagggaaa ccggatcagt tgagagagaa tcaagagtag cgg atg agg cgc ttg      295
                                            Met Arg Arg Leu
                                              1 tgg ggc gcg gcc cgg aag ccc tcg ggc gcg ggc tgg gag aag gag tgg      343
Trp Gly Ala Ala Arg Lys Pro Ser Gly Ala Gly Trp Glu Lys Glu Trp
  5              10                  15                  20 gcg gag gcg ccg cag gag gct ccc ggg gcc tgg tcg ggc cgg ctg ggc      391
Ala Glu Ala Pro Gln Glu Ala Pro Gly Ala Trp Ser Gly Arg Leu Gly
                25                  30                  35 ccc ggg cgc agt gga aga aag gga cgg gcg gtg ccc ggt tgg gcg tcc      439
Pro Gly Arg Ser Gly Arg Lys Gly Arg Ala Val Pro Gly Trp Ala Ser
            40                  45                  50 tgg cca gct cac ctt gcc ctg gcg gct cgc ccc gcc cgg cac ttg gga      487
Trp Pro Ala His Leu Ala Leu Ala Ala Arg Pro Ala Arg His Leu Gly
        55                  60                  65 gga gca ggg cag ggc ccg cgg cct ttg cat tct ggg acc gcc ccc ttc      535
Gly Ala Gly Gln Gly Pro Arg Pro Leu His Ser Gly Thr Ala Pro Phe
    70                  75                  80 cat tcc cgg gcc agc ggc gag cgg cag cga cgg ctg gag ccg cag cta      583
His Ser Arg Ala Ser Gly Glu Arg Gln Arg Arg Leu Glu Pro Gln Leu
85                  90                  95                 100 cag cat gag agc cgg tgc cgc tcc tcc acg cct gcg gac gcg tgg cga      631
Gln His Glu Ser Arg Cys Arg Ser Ser Thr Pro Ala Asp Ala Trp Arg
```

```
                    105                 110                 115
gcg gag gca gcg ctg cct gtt cgc gcc atg ggg gca ccg tgg ggc tcg    679
Ala Glu Ala Ala Leu Pro Val Arg Ala Met Gly Ala Pro Trp Gly Ser
        120                 125                 130 ccg acg gcg gcg gcg ggc ggg cgg cgc ggg tgg cgc cga ggc cgg ggg    727
Pro Thr Ala Ala Ala Gly Gly Arg Arg Gly Trp Arg Arg Gly Arg Gly
        135                 140                 145 ctg cca tgg acc gtc tgt gtg ctg gcg gcc gcc ggc ttg acg tgt acg    775
Leu Pro Trp Thr Val Cys Val Leu Ala Ala Ala Gly Leu Thr Cys Thr
150                 155                 160 gcg ctg atc acc tac gct tgc tgg ggg cag ctg ccg ccg ctg ccc tgg    823
Ala Leu Ile Thr Tyr Ala Cys Trp Gly Gln Leu Pro Pro Leu Pro Trp
165                 170                 175                 180 gcg tcg cca acc ccg tcg cga ccg gtg ggc gtg ctg ctg tgg tgg gag    871
Ala Ser Pro Thr Pro Ser Arg Pro Val Gly Val Leu Leu Trp Trp Glu
                185                 190                 195 ccc ttc ggg ggg cgc gat agc gcc ccg agg ccg ccc cct gac tgc cgg    919
Pro Phe Gly Gly Arg Asp Ser Ala Pro Arg Pro Pro Pro Asp Cys Arg
            200                 205                 210 ctg cgc ttc aac atc agc ggc tgc cgc ctg ctc acc gac cgc gcg tcc    967
Leu Arg Phe Asn Ile Ser Gly Cys Arg Leu Leu Thr Asp Arg Ala Ser
        215                 220                 225 tac gga gag gct cag gcc gtg ctt ttc cac cac cgc gac ctc gtg aag   1015
Tyr Gly Glu Ala Gln Ala Val Leu Phe His His Arg Asp Leu Val Lys
    230                 235                 240 ggg ccc ccc gac tgg ccc ccg ccc tgg ggc atc cag gcg cac act gcc   1063
Gly Pro Pro Asp Trp Pro Pro Pro Trp Gly Ile Gln Ala His Thr Ala
245                 250                 255                 260 gag gag gtg gat ctg cgc gtg ttg gac tac gag gag gcg gcg gcg gcg   1111
Glu Glu Val Asp Leu Arg Val Leu Asp Tyr Glu Glu Ala Ala Ala Ala
                265                 270                 275 gca gaa gcc ctg gcg acc tcc agc ccc agg ccc ccg ggc cag cgc tgg   1159
Ala Glu Ala Leu Ala Thr Ser Ser Pro Arg Pro Pro Gly Gln Arg Trp
            280                 285                 290 gtt tgg atg aac ttc gag tcg ccc tcg cac tcc ccg ggg ctg cga agc   1207
Val Trp Met Asn Phe Glu Ser Pro Ser His Ser Pro Gly Leu Arg Ser
        295                 300                 305 ctg gca agt aac ctc ttc aac tgg acg ctc tcc tac cgg gcg gac tcg   1255
Leu Ala Ser Asn Leu Phe Asn Trp Thr Leu Ser Tyr Arg Ala Asp Ser
310                 315                 320 gac gtc ttt gtg cct tat ggc tac ctc tac ccc aga agc cac ccc ggc   1303
Asp Val Phe Val Pro Tyr Gly Tyr Leu Tyr Pro Arg Ser His Pro Gly
325                 330                 335                 340 gac ccg ccc tca ggc ctg gcc ccg cca ctg tcc agg aaa cag ggg ctg   1351
Asp Pro Pro Ser Gly Leu Ala Pro Pro Leu Ser Arg Lys Gln Gly Leu
                345                 350                 355 gtg gca tgg gtg gtg agc cac tgg gac gag cgc cag gcc cgg gtc cgc   1399
Val Ala Trp Val Val Ser His Trp Asp Glu Arg Gln Ala Arg Val Arg
            360                 365                 370 tac tac cac caa ctg agc caa cat gtg acc gtg gac gtg ttc ggc cgg   1447
Tyr Tyr His Gln Leu Ser Gln His Val Thr Val Asp Val Phe Gly Arg
        375                 380                 385 ggc ggg ccg ggg cag ccg gtg ccc gaa att ggg ctc ctg cac aca gtg   1495
Gly Gly Pro Gly Gln Pro Val Pro Glu Ile Gly Leu Leu His Thr Val
390                 395                 400 gcc cgc tac aag ttc tac ctg gct ttc gag aac tcg cag cac ctg gat   1543
Ala Arg Tyr Lys Phe Tyr Leu Ala Phe Glu Asn Ser Gln His Leu Asp
405                 410                 415                 420 tat atc acc gag aag ctc tgg cgc aac gcg ttg ctc gct ggg gcg gtg   1591
Tyr Ile Thr Glu Lys Leu Trp Arg Asn Ala Leu Leu Ala Gly Ala Val
```

```
                Tyr Ile Thr Glu Lys Leu Trp Arg Asn Ala Leu Leu Ala Gly Ala Val
                            425                 430                 435 ccg gtg gtg ctg ggc cca gac cgt gcc aac tac gag cgc ttt gtg ccc          1639
Pro Val Val Leu Gly Pro Asp Arg Ala Asn Tyr Glu Arg Phe Val Pro
            440                 445                 450 cgc ggc gcc ttc atc cac gtg gac gac ttc cca agt gcc tcc tcc ctg          1687
Arg Gly Ala Phe Ile His Val Asp Asp Phe Pro Ser Ala Ser Ser Leu
            455                 460                 465 gcc tcg tac ctg ctt ttc ctc gac cgc aac ccc gcg gtc tat cgc cgc          1735
Ala Ser Tyr Leu Leu Phe Leu Asp Arg Asn Pro Ala Val Tyr Arg Arg
            470                 475                 480 tac ttc cac tgg cgc cgg agc tac gct gtc cac atc acc tcc ttc tgg          1783
Tyr Phe His Trp Arg Arg Ser Tyr Ala Val His Ile Thr Ser Phe Trp
485                 490                 495                 500 gac gag cct tgg tgc cgg gtg tgc cag gct gta cag agg gct ggg gac          1831
Asp Glu Pro Trp Cys Arg Val Cys Gln Ala Val Gln Arg Ala Gly Asp
                505                 510                 515 cgg ccc aag agc ata cgg aac ttg gcc agc tgg ttc gag cgg tga              1876
Arg Pro Lys Ser Ile Arg Asn Leu Ala Ser Trp Phe Glu Arg
            520                 525                 530 agccgcgctc ccctggaagc gacccagggg aggccaagtt gtcagctttt tgatcctcta        1936
ctgtgcatct ccttgactgc cgcatcatgg gagtaagttc ttcaaacacc cattttgct         1996 ctatgggaaa aaaacgattt accaattaat attactcagc acagagatgg gggcccggtt        2056
tccatatttt ttgcacagct agcaattggg ctcccttgc tgctgatggg catcattgtt         2116 tagggtgaa ggaggggtt cttcctcacc ttgtaaccag tgcagaaatg aaatagctta         2176
gcggcaagaa gccgttgagg cggtttcctg aatttcccca tctgccacag gccatatttg        2236
tggcccgtgc agcttccaaa tctcatacac aactgttccc gattcacgtt tttctggacc       2296
aaggtgaagc aaatttgtgg ttgtagaagg agccttgttg gtggagagtg aaggactgt         2356 ggctgcaggt gggactttgt tgtttggatt cctcacagcc ttggctcctg agaaaggtga       2416
ggagggcagt ccaagagggg ccgctgactt cttttcacaag tactatctgt tccctgtcc       2476 tgtgaatgga agcaaagtgc tggattgtcc ttggaggaaa cttaagatga atacatgcgt       2536
gtacctcact ttcataaga aatgtattcc tgaaaagctg catttaaatc aagtcccaaa        2596
ttcattgact tagggagtt cagtatttaa tgaaacccta tggagaattt atcccttttac       2656 aatgtgaata gtcatctcct aatttgtttc ttctgtcttt atgtttttct ataacctgga       2716
ttttttaaat catattaaaa ttacagatgt gaaaataaag cagaagcaac cttttttccct      2776 cttcccagaa aaccagtctg tgtttacaga cagaagagaa ggaagccata gtgtcacttc       2836
cacacaatta tttatttcat gtctttactg gacctgaaat ttaaactgca atgccagtcc       2896
tgcaggagtg ctggcattac cctctgcaga acagtgaaag gtattgcact acattatgga       2956
atcatgcaaa aggaaaaaaa gtttcatgat atctgttgtt ggcagttttt gtttatctct       3016
gacagttttt agttaaatgt ttagatcctc agaactacat tagtgcctac tattaactta       3076
ctctgtctct tgttaaaggc taaatctgcg cttctccctg gtgccagcag gttcccctca       3136
cagtcaatgc agtggtatag catatcctca catttctagt gcccttgaga ctgtgctatg       3196
gaaccaatct tgaacataca tgcattgact tgacaagtta ctgagtaagc agcatattca       3256
gcaggtgcca ctacatgcct actctgccag acactgagct tggggcccta gggaagatag       3316
agaattatac aaggcaaagt ccttctcttt agggctctta caatctatca cttccaaaaa       3376
gtaaatggtg actgataaaa caattggcag aacctgtttg attactgtga cagtcttaat       3436
```

```
gataccataaa atcaatatta gaaagctagt tgacttaaag cctgaaataa tgggagtttt    3496
ctcctccact tattagaata aggaccctca gtgactaatt attgtgggta gggtcaagat    3556
taactagttt tatacagagt tctgctgtaa atagtcattt tgcatttgat tagtgcagtt    3616
ctctgaatca taaagcaagt tttacctctc tgtacatgtt tttgcagaca tacttgaaaa    3676
gctcacttaa atctaggtgc ttcaattcac tttcttgaga ggacaaatga aaagctgtgg    3736
agaaaatgtc ctcattaaag tattaaagtg tgggcagaat tacaattaca aagtgccagc    3796
caccgaataa agataaaagt tcagttctta aaatgagttt ttatgagata acagtcagtg    3856
atcttggtgt taccgggatt ccacatgggg cagtgggaaa gagttcaggt tttgaaggta    3916
acctagttta gatttgaatt ccagctatgt gacattgggt aaattagtag tagtcctgag    3976
cctcagcgtc ctcatctata aaatgactgg cgaaaatact tcacaagctc attttgagca    4036
ctttaggaag taagtgaaag tacctaaaat agcaggcacc caattgatga tttatatct    4096 tccttctttg cttgcagtga tttcaggatg tcctcatatc tatttatagg tctaaaatta    4156
tatcttaagg tatgttgtag aataaattaa aaggataatc taaatcacca tttagattaa    4216
gcttgacttg caaactagga agaagcacct aggctttctt tgaaaatatt ttttttggttc    4276 gttttggtaa agctctataa attggtatct attattttac caatttttt ttagtattaa    4336 gtccatttag aactaaccat attatttatg gaataattag catgaggaag gtataattgc    4396
attttttttt ttttgagacg gagtcttgca ctgtagcccc agctggactg cagtggcgtg    4456
atcttggctc actgcaacct ccgcctccca ggttcaagcg attctcctgc ctcagcctcc    4516
cgagcagctg agactacagg cgcctgccac cacgcctggc caatttttg tattttagt    4576 agagactgcg tttcaccatg ttgggcaggc tggtcttgaa ctcctgacct tgtgatccac    4636
ctgcctcggc ctctcagaga gctgggatta caggtgtgag ccgccgtgcc cagccattgc    4696
atttttattc acatacacat tgttaatgtg gaacaattta acactaatct catcagagag    4756
cgagatgaat gtggcaattg ctcattttat tttgcatata ttaaattgag taggttcagc    4816
tctaacatac cttaagaaaa atgcatatcg gtgcactgta tgtatttcaa aatgcctttc    4876
ctatgattgt catgtcctcc tttaaggctt ttccctcaaa tttattacaa atttagtatt    4936
tttagtactt gatgactcta attacatgaa tgcacctgga atgacatttg taacagaaga    4996
cggtctgact tgctttcagt attcacaagt tctttccagt ttccaagtct tttcctagca    5056
gtaatttagg ggagacagag gagtttcatg taaagagcat gcagtttgga gtcagaacct    5116
gggtatgact ctgtggcctt gatgaagcaa gttacttaaa ctcttgagtt ttagcttttct    5176 cctttacaat gcatgaatgc ctatccccct acaaaacaaa gattaaatgt gatgatgtat    5236
gccaaggtgc tttgtatatt gtaaagtgct atataattat aagatgttct aaattttcaa    5296
ggatctaaac cagggattgg caaacgtttt tccagggagt aaatatttta cgctttgcat    5356
atataattta tggaggtgtt gagaggatag attagacact tgaagtactc aggatagtgc    5416
ctggcatgta ggaagcacct ggaaaatatt cgctgtgatt accatcagtc cattttaccg    5476
aggaaggagc caaggtccag gcccactgaa ggacttgcat aacattacaa tagcagtggc    5536
agaaccagcc atgcttctgc aaatcacaac ctctttgagc ctctgtcacc tgaactgcaa    5596
aatgagtggg ttagacaaaa tcatctgttg ggacctccta gttccacgtg ctatcattct    5656
actaactggc accctaaggt tgaaagtgct tatctgcttt ccaatgtggc ttccttacag    5716
tctggaactg acaatatgca ggagcagtaa actggcagaa aaccaggaat cagagaagaa    5776
aaatataatt taactttaaa gatgtaaatt atatatatag tatattatat atattttaa    5836
```

```
agctttatat gcctcaaata tcagggaaag gagccaagtc cttggtattt agtttggtga      5896
atacttgcat tgaatacatg tcaagatgtc aagtcatttt tgaatgtgtc tcagggattt      5956
ctatgctaca cattctttta acaaatcaag tatttatgta cacatgttca gattttttga      6016
caaaatgatt aaaataatga gatggaaaat gaaaaaaaaa aaaaaaa                    6063
```

<210> SEQ ID NO 12
<211> LENGTH: 530
<212> TYPE: PRT
<213> ORGANISM: Homo Sapiens

<400> SEQUENCE: 12

```
Met Arg Arg Leu Trp Gly Ala Ala Arg Lys Pro Ser Gly Ala Gly Trp
 1               5                  10                  15

Glu Lys Glu Trp Ala Glu Ala Pro Gln Glu Ala Pro Gly Ala Trp Ser
            20                  25                  30

Gly Arg Leu Gly Pro Gly Arg Ser Gly Arg Lys Gly Arg Ala Val Pro
        35                  40                  45

Gly Trp Ala Ser Trp Pro Ala His Leu Ala Leu Ala Ala Arg Pro Ala
    50                  55                  60

Arg His Leu Gly Gly Ala Gly Gln Gly Pro Arg Pro Leu His Ser Gly
65                  70                  75                  80

Thr Ala Pro Phe His Ser Arg Ala Ser Gly Glu Arg Gln Arg Arg Leu
                85                  90                  95

Glu Pro Gln Leu Gln His Glu Ser Arg Cys Arg Ser Ser Thr Pro Ala
           100                 105                 110

Asp Ala Trp Arg Ala Glu Ala Ala Leu Pro Val Arg Ala Met Gly Ala
       115                 120                 125

Pro Trp Gly Ser Pro Thr Ala Ala Gly Gly Arg Arg Gly Trp Arg
   130                 135                 140

Arg Gly Arg Gly Leu Pro Trp Thr Val Cys Val Leu Ala Ala Ala Gly
145                 150                 155                 160

Leu Thr Cys Thr Ala Leu Ile Thr Tyr Ala Cys Trp Gly Gln Leu Pro
                165                 170                 175

Pro Leu Pro Trp Ala Ser Pro Thr Pro Ser Arg Pro Val Gly Val Leu
            180                 185                 190

Leu Trp Trp Glu Pro Phe Gly Gly Arg Asp Ser Ala Pro Arg Pro Pro
        195                 200                 205

Pro Asp Cys Arg Leu Arg Phe Asn Ile Ser Gly Cys Arg Leu Leu Thr
    210                 215                 220

Asp Arg Ala Ser Tyr Gly Glu Ala Gln Ala Val Leu Phe His His Arg
225                 230                 235                 240

Asp Leu Val Lys Gly Pro Pro Asp Trp Pro Pro Trp Gly Ile Gln
                245                 250                 255

Ala His Thr Ala Glu Glu Val Asp Leu Arg Val Leu Asp Tyr Glu Glu
            260                 265                 270

Ala Ala Ala Ala Glu Ala Leu Ala Thr Ser Ser Pro Arg Pro Pro
        275                 280                 285

Gly Gln Arg Trp Val Trp Met Asn Phe Glu Ser Pro Ser His Ser Pro
    290                 295                 300

Gly Leu Arg Ser Leu Ala Ser Asn Leu Phe Asn Trp Thr Leu Ser Tyr
305                 310                 315                 320

Arg Ala Asp Ser Asp Val Phe Val Pro Tyr Gly Tyr Leu Tyr Pro Arg
                325                 330                 335
```

```
Ser His Pro Gly Asp Pro Pro Ser Gly Leu Ala Pro Pro Leu Ser Arg
            340                 345                 350

Lys Gln Gly Leu Val Ala Trp Val Ser His Trp Asp Glu Arg Gln
        355                 360                 365

Ala Arg Val Arg Tyr Tyr His Gln Leu Ser Gln His Val Thr Val Asp
370                 375                 380

Val Phe Gly Arg Gly Gly Pro Gly Gln Pro Val Pro Glu Ile Gly Leu
385                 390                 395                 400

Leu His Thr Val Ala Arg Tyr Lys Phe Tyr Leu Ala Phe Glu Asn Ser
                405                 410                 415

Gln His Leu Asp Tyr Ile Thr Glu Lys Leu Trp Arg Asn Ala Leu Leu
            420                 425                 430

Ala Gly Ala Val Pro Val Val Leu Gly Pro Asp Arg Ala Asn Tyr Glu
        435                 440                 445

Arg Phe Val Pro Arg Gly Ala Phe Ile His Val Asp Asp Phe Pro Ser
    450                 455                 460

Ala Ser Ser Leu Ala Ser Tyr Leu Leu Phe Leu Asp Arg Asn Pro Ala
465                 470                 475                 480

Val Tyr Arg Arg Tyr Phe His Trp Arg Arg Ser Tyr Ala Val His Ile
                485                 490                 495

Thr Ser Phe Trp Asp Glu Pro Trp Cys Arg Val Cys Gln Ala Val Gln
            500                 505                 510

Arg Ala Gly Asp Arg Pro Lys Ser Ile Arg Asn Leu Ala Ser Trp Phe
        515                 520                 525

Glu Arg
    530

<210> SEQ ID NO 13
<211> LENGTH: 2301
<212> TYPE: DNA
<213> ORGANISM: Homo Sapiens
<220> FEATURE:
<221> NAME/KEY: CDS
<222> LOCATION: (145)...(1029)
<223> OTHER INFORMATION: CD200

<400> SEQUENCE: 13
aaacggagtg gggagaaggg gctagcgagg aggaagaggc gggaggtgcg gcaggggcac        60
aggtgacgct cctcccgcct gcctagcaga gctccaggcg cacatccgca gtcagccacc       120
tcgcgcgcgc ctccaggagc aagg atg gag agg ctg act ctg acc agg aca         171
                            Met Glu Arg Leu Thr Leu Thr Arg Thr
                              1               5 att ggg ggc cct ctc ctt aca gct aca ctc cta gga aag acc acc atc        219
Ile Gly Gly Pro Leu Leu Thr Ala Thr Leu Leu Gly Lys Thr Thr Ile
 10                  15                  20                  25 aat gat tac cag gtg atc agg atg ccc ttc tct cat ctg tct acc tac        267
Asn Asp Tyr Gln Val Ile Arg Met Pro Phe Ser His Leu Ser Thr Tyr
                 30                  35                  40 agc ctg gtt tgg gtc atg gca gca gtg gtg ctg tgc aca gca caa gtg        315
Ser Leu Val Trp Val Met Ala Ala Val Val Leu Cys Thr Ala Gln Val
             45                  50                  55 caa gtg gtg acc cag gat gaa aga gag cag ctg tac aca cct gct tcc        363
Gln Val Val Thr Gln Asp Glu Arg Glu Gln Leu Tyr Thr Pro Ala Ser
         60                  65                  70 tta aaa tgc tct ctg caa aat gcc cag gaa gcc ctc att gtg aca tgg        411
Leu Lys Cys Ser Leu Gln Asn Ala Gln Glu Ala Leu Ile Val Thr Trp
 75                  80                  85
```

| | | |
|---|---|---|
| cag aaa aag aaa gct gta agc cca gaa aac atg gtc acc ttc agc gag<br>Gln Lys Lys Lys Ala Val Ser Pro Glu Asn Met Val Thr Phe Ser Glu<br>90                                95                           100                          105 | | 459 |
| aac cat ggg gtg gtg atc cag cct gcc tat aag gac aag ata aac att<br>Asn His Gly Val Val Ile Gln Pro Ala Tyr Lys Asp Lys Ile Asn Ile<br>                        110                           115                         120 | | 507 |
| acc cag ctg gga ctc caa aac tca acc atc acc ttc tgg aat atc acc<br>Thr Gln Leu Gly Leu Gln Asn Ser Thr Ile Thr Phe Trp Asn Ile Thr<br>            125                           130                         135 | | 555 |
| ctg gag gat gaa ggg tgt tac atg tgt ctc ttc aat acc ttt ggt ttt<br>Leu Glu Asp Glu Gly Cys Tyr Met Cys Leu Phe Asn Thr Phe Gly Phe<br>       140                          145                         150 | | 603 |
| ggg aag atc tca gga acg gcc tgc ctc acc gtc tat gta cag ccc ata<br>Gly Lys Ile Ser Gly Thr Ala Cys Leu Thr Val Tyr Val Gln Pro Ile<br>         155                       160                       165 | | 651 |
| gta tcc ctt cac tac aaa ttc tct gaa gac cac cta aat atc act tgc<br>Val Ser Leu His Tyr Lys Phe Ser Glu Asp His Leu Asn Ile Thr Cys<br>170                         175                       180                       185 | | 699 |
| tct gcc act gcc cgc cca gcc ccc atg gtc ttc tgg aag gtc cct cgg<br>Ser Ala Thr Ala Arg Pro Ala Pro Met Val Phe Trp Lys Val Pro Arg<br>                    190                       195                       200 | | 747 |
| tca ggg att gaa aat agt aca gtg act ctg tct cac cca aat ggg acc<br>Ser Gly Ile Glu Asn Ser Thr Val Thr Leu Ser His Pro Asn Gly Thr<br>               205                        210                       215 | | 795 |
| acg tct gtt acc agc atc ctc cat atc aaa gac cct aag aat cag gtg<br>Thr Ser Val Thr Ser Ile Leu His Ile Lys Asp Pro Lys Asn Gln Val<br>            220                         225                      230 | | 843 |
| ggg aag gag gtg atc tgc cag gtg ctg cac ctg ggg act gtg acc gac<br>Gly Lys Glu Val Ile Cys Gln Val Leu His Leu Gly Thr Val Thr Asp<br>       235                          240                         245 | | 891 |
| ttt aag caa acc gtc aac aaa ggc tat tgg ttt tca gtt ccg cta ttg<br>Phe Lys Gln Thr Val Asn Lys Gly Tyr Trp Phe Ser Val Pro Leu Leu<br>250                         255                       260                       265 | | 939 |
| cta agc att gtt tcc ctg gta att ctt ctc gtc cta atc tca atc tta<br>Leu Ser Ile Val Ser Leu Val Ile Leu Leu Val Leu Ile Ser Ile Leu<br>               270                        275                       280 | | 987 |
| ctg tac tgg aaa cgt cac cgg aat cag gac cga gag ccc taa<br>Leu Tyr Trp Lys Arg His Arg Asn Gln Asp Arg Glu Pro<br>            285                         290 | | 1029 |
| ataagtcaca cagcaccctg aaagtgattc cctggtctac ttgaatttga cacaagagaa | | 1089 |
| aagcaggagg aaaaggggcc attctccaaa ggacctgaaa gagcaaaaga ggtgggagcg | | 1149 |
| aaagccttaa ggatcccacg acttttact gccatctgag ctactcagtg tttgaatccc | | 1209 |
| aagaggaagt cagtttacct ctcaggtctg ttgtaggact tgattttgta aagcaatgcc | | 1269 |
| atgttatgtg gttgaaaggg cactggactt agttagtatc aggagcactg agctcacaga | | 1329 |
| ctgacttggg ctcctactgg tggggacctc tgttagtcac tttacctcat ccaaagtata | | 1389 |
| aaggaattgg accaaataat ttaccacata gctctaaaac ttaatttaaa atgtaattcc | | 1449 |
| agaaaaaaaa agggaataag caaggggga agaattgaaa gagagagaga agaaagaata | | 1509 |
| cagagagctt accttttgcc tttctgttga tgttacatct cttcttccta tgttcttagg | | 1569 |
| tctatgagtc tgtttcccca tcatttggta tctagtccag ttcctgctta ctgctttgct | | 1629 |
| aatagctggc cttgctagaa tccttggttt cactgctgtt cttcatgtgc ttctatgaga | | 1689 |
| tttactccaa cacaaatagg actgaattta ttgtgaagta acattggcaa tcttaactta | | 1749 |
| ttcatttaac ttattttat agctagataa atattgttag tcttagacaa tagctcacat | | 1809 |

-continued

```
tttttgagaa gcatgccctc cctgtccatt tgtcttataa catgacccag ccctatttta    1869
cgtcattcta aattcagcct catataatga aaatacatta tgaaaacaga tgtttaggag    1929
atttcctgta tagcagtcag ccaattcata tgctttgtct ctgctggctt cttttttccat   1989 gcgttaactt ttcccaatag cagaggaggc aaatatgagc atacaatccc tttgttctaa    2049
agatattgtt ccagctagtg gaatgatgtt gaatctttaa taaccataat tagttgcttt    2109
ttcagtatct tctgctttgt ctgtgtctat ccagtggcct aggaattaaa gtgtaagttg    2169
ttttcgctgt taaattggat atttatatat atatatagca agattttcat gtgttattta    2229
attctgtatt gtttcttata tttgtagtaa aatattgaac aattaaaagt gttgactcca    2289
aaaaaaaaaa aa                                                        2301
```

<210> SEQ ID NO 14
<211> LENGTH: 294
<212> TYPE: PRT
<213> ORGANISM: Homo Sapiens

<400> SEQUENCE: 14

```
Met Glu Arg Leu Thr Leu Thr Arg Thr Ile Gly Gly Pro Leu Leu Thr
  1               5                  10                  15

Ala Thr Leu Leu Gly Lys Thr Thr Ile Asn Asp Tyr Gln Val Ile Arg
             20                  25                  30

Met Pro Phe Ser His Leu Ser Thr Tyr Ser Leu Val Trp Val Met Ala
         35                  40                  45

Ala Val Val Leu Cys Thr Ala Gln Val Gln Val Val Thr Gln Asp Glu
     50                  55                  60

Arg Glu Gln Leu Tyr Thr Pro Ala Ser Leu Lys Cys Ser Leu Gln Asn
 65                  70                  75                  80

Ala Gln Glu Ala Leu Ile Val Thr Trp Gln Lys Lys Ala Val Ser
                 85                  90                  95

Pro Glu Asn Met Val Thr Phe Ser Glu Asn His Gly Val Val Ile Gln
            100                 105                 110

Pro Ala Tyr Lys Asp Lys Ile Asn Ile Thr Gln Leu Gly Leu Gln Asn
        115                 120                 125

Ser Thr Ile Thr Phe Trp Asn Ile Thr Leu Glu Asp Glu Gly Cys Tyr
    130                 135                 140

Met Cys Leu Phe Asn Thr Phe Gly Phe Gly Lys Ile Ser Gly Thr Ala
145                 150                 155                 160

Cys Leu Thr Val Tyr Val Gln Pro Ile Val Ser Leu His Tyr Lys Phe
                165                 170                 175

Ser Glu Asp His Leu Asn Ile Thr Cys Ser Ala Thr Ala Arg Pro Ala
            180                 185                 190

Pro Met Val Phe Trp Lys Val Pro Arg Ser Gly Ile Glu Asn Ser Thr
        195                 200                 205

Val Thr Leu Ser His Pro Asn Gly Thr Thr Ser Val Thr Ser Ile Leu
    210                 215                 220

His Ile Lys Asp Pro Lys Asn Gln Val Gly Lys Glu Val Ile Cys Gln
225                 230                 235                 240

Val Leu His Leu Gly Thr Val Thr Asp Phe Lys Gln Thr Val Asn Lys
                245                 250                 255

Gly Tyr Trp Phe Ser Val Pro Leu Leu Leu Ser Ile Val Ser Leu Val
            260                 265                 270

Ile Leu Leu Val Leu Ile Ser Ile Leu Leu Tyr Trp Lys Arg His Arg
        275                 280                 285
```

Asn Gln Asp Arg Glu Pro
            290

<210> SEQ ID NO 15
<211> LENGTH: 2631
<212> TYPE: DNA
<213> ORGANISM: Homo Sapiens
<220> FEATURE:
<221> NAME/KEY: CDS
<222> LOCATION: (150)...(1184)
<223> OTHER INFORMATION: CD66c

<400> SEQUENCE: 15

```
gaccctggga aatgcttcta tccctgagag gaggctcagc acagaaggag gaaggacagc      60
agggccaaca gtcacagcag ccctgaccag agcattcctg gagctcaagc tcctctacaa     120
agaggtggac agagaagaca gcagagacc atg gga ccc ccc tca gcc cct ccc        173
                                Met Gly Pro Pro Ser Ala Pro Pro
                                  1               5 tgc aga ttg cat gtc ccc tgg aag gag gtc ctg ctc aca gcc tca ctt        221
Cys Arg Leu His Val Pro Trp Lys Glu Val Leu Leu Thr Ala Ser Leu
         10                  15                  20 cta acc ttc tgg aac cca ccc acc act gcc aag ctc act att gaa tcc        269
Leu Thr Phe Trp Asn Pro Pro Thr Thr Ala Lys Leu Thr Ile Glu Ser
 25                  30                  35                  40 acg ccg ttc aat gtc gca gag ggg aag gag gtt ctt cta ctc gcc cac        317
Thr Pro Phe Asn Val Ala Glu Gly Lys Glu Val Leu Leu Leu Ala His
                     45                  50                  55 aac ctg ccc cag aat cgt att ggt tac agc tgg tac aaa ggc gaa aga        365
Asn Leu Pro Gln Asn Arg Ile Gly Tyr Ser Trp Tyr Lys Gly Glu Arg
             60                  65                  70 gtg gat ggc aac agt cta att gta gga tat gta ata gga act caa caa        413
Val Asp Gly Asn Ser Leu Ile Val Gly Tyr Val Ile Gly Thr Gln Gln
         75                  80                  85 gct acc cca ggg ccc gca tac agt ggt cga gag aca ata tac ccc aat        461
Ala Thr Pro Gly Pro Ala Tyr Ser Gly Arg Glu Thr Ile Tyr Pro Asn
     90                  95                 100 gca tcc ctg ctg atc cag aac gtc acc cag aat gac aca gga ttc tat        509
Ala Ser Leu Leu Ile Gln Asn Val Thr Gln Asn Asp Thr Gly Phe Tyr
105                 110                 115                 120 acc cta caa gtc ata aag tca gat ctt gtg aat gaa gaa gca acc gga        557
Thr Leu Gln Val Ile Lys Ser Asp Leu Val Asn Glu Glu Ala Thr Gly
                 125                 130                 135 cag ttc cat gta tac ccg gag ctg ccc aag ccc tcc atc tcc agc aac        605
Gln Phe His Val Tyr Pro Glu Leu Pro Lys Pro Ser Ile Ser Ser Asn
             140                 145                 150 aac tcc aac ccc gtg gag gac aag gat gct gtg gcc ttc acc tgt gaa        653
Asn Ser Asn Pro Val Glu Asp Lys Asp Ala Val Ala Phe Thr Cys Glu
         155                 160                 165 cct gag gtt cag aac aca acc tac ctg tgg tgg gta aat ggt cag agc        701
Pro Glu Val Gln Asn Thr Thr Tyr Leu Trp Trp Val Asn Gly Gln Ser
     170                 175                 180 ctc ccg gtc agt ccc agg ctg cag ctg tcc aat ggc aac atg acc ctc        749
Leu Pro Val Ser Pro Arg Leu Gln Leu Ser Asn Gly Asn Met Thr Leu
185                 190                 195                 200 act cta ctc agc gtc aaa agg aac gat gca gga tcc tat gaa tgt gaa        797
Thr Leu Leu Ser Val Lys Arg Asn Asp Ala Gly Ser Tyr Glu Cys Glu
                 205                 210                 215 ata cag aac cca gcg agt gcc aac cgc agt gac cca gtc acc ctg aat        845
Ile Gln Asn Pro Ala Ser Ala Asn Arg Ser Asp Pro Val Thr Leu Asn
             220                 225                 230
```

```
gtc ctc tat ggc cca gat ggc ccc acc att tcc ccc tca aag gcc aat    893
Val Leu Tyr Gly Pro Asp Gly Pro Thr Ile Ser Pro Ser Lys Ala Asn
            235                 240                 245 tac cgt cca ggg gaa aat ctg aac ctc tcc tgc cac gca gcc tct aac    941
Tyr Arg Pro Gly Glu Asn Leu Asn Leu Ser Cys His Ala Ala Ser Asn
        250                 255                 260 cca cct gca cag tac tct tgg ttt atc aat ggg acg ttc cag caa tcc    989
Pro Pro Ala Gln Tyr Ser Trp Phe Ile Asn Gly Thr Phe Gln Gln Ser
265                 270                 275                 280 aca caa gag ctc ttt atc ccc aac atc act gtg aat aat agc gga tcc    1037
Thr Gln Glu Leu Phe Ile Pro Asn Ile Thr Val Asn Asn Ser Gly Ser
            285                 290                 295 tat atg tgc caa gcc cat aac tca gcc act ggc ctc aat agg acc aca    1085
Tyr Met Cys Gln Ala His Asn Ser Ala Thr Gly Leu Asn Arg Thr Thr
        300                 305                 310 gtc acg atg atc aca gtc tct gga agt gct cct gtc ctc tca gct gtg    1133
Val Thr Met Ile Thr Val Ser Gly Ser Ala Pro Val Leu Ser Ala Val
            315                 320                 325 gcc acc gtc ggc atc acg att gga gtg ctg gcc agg gtg gct ctg ata    1181
Ala Thr Val Gly Ile Thr Ile Gly Val Leu Ala Arg Val Ala Leu Ile
330                 335                 340 tag cagccctggt gtattttcga tatttcagga agactggcag attggaccag         1234
accctgaatt cttctagctc ctccaatccc attttatccc atggaaccac taaaaacaag  1294
gtctgctctg ctcctgaagc cctatatgct ggagatggac aactcaatga aaatttaaag  1354
ggaaaaccct caggcctgag gtgtgtgcca ctcagagact tcacctaact agagacaggc  1414
aaactgcaaa ccatggtgag aaattgacga cttcacacta tggacagctt ttcccaagat  1474
gtcaaaacaa gactcctcat catgataagg ctcttacccc cttttaattt gtccttgctt  1534
atgcctgcct ctttcgcttg gcaggatgat gctgtcatta gtatttcaca agaagtagct  1594
tcagagggta acttaacaga gtatcagatc tatcttgtca atcccaacgt tttacataaa  1654
ataagagatc ctttagtgca cccagtgact gacattagca gcatctttaa cacagccgtg  1714
tgttcaaatg tacagtggtc cttttcagag ttggacttct agactcacct gttctcactc  1774
cctgttttaa ttcaacccag ccatgcaatg ccaaataata gaattgctcc ctaccagctg  1834
aacagggagg agtctgtgca gtttctgaca cttgttgttg aacatggcta aatacaatgg  1894
gtatcgctga gactaagttg tagaaattaa caaatgtgct gcttggttaa aatggctaca  1954
ctcatctgac tcattcttta ttctatttta gttggtttgt atcttgccta aggtgcgtag  2014
tccaactctt ggtattaccc tcctaatagt catactagta gtcatactcc ctggtgtagt  2074
gtattctcta aaagctttaa atgtctgcat gcagccagcc atcaaatagt gaatggtctc  2134
tctttggctg gaattacaaa actcagagaa atgtgtcatc aggagaacat cataacccat  2194
gaaggataaa agccccaaat ggtggtaact gataatagca ctaatgcttt aagatttggt  2254
cacactctca cctaggtgag cgcattgagc cagtggtgct aaatgctaca tactccaact  2314
gaaatgttaa ggaagaagat agatccaatt aaaaaaaatt aaaaccaatt taaaaaaaaa  2374
aagaacacag gagattccag tctacttgag ttagcataat acagaagtcc cctctacttt  2434
aacttttaca aaaaagtaac ctgaactaat ctgatgttaa ccaatgtatt tatttctgtg  2494
gttctgtttc cttgttccaa tttgacaaaa cccactgttc ttgtattgta ttgcccaggg  2554
ggagctatca ctgtacttgt agagtggtgc tgctttaatt cataaatcac aaataaaagc  2614
caattagctc tataact                                                 2631
```

-continued

```
<210> SEQ ID NO 16
<211> LENGTH: 344
<212> TYPE: PRT
<213> ORGANISM: Homo Sapiens

<400> SEQUENCE: 16

Met Gly Pro Pro Ser Ala Pro Pro Cys Arg Leu His Val Pro Trp Lys
 1               5                  10                  15

Glu Val Leu Leu Thr Ala Ser Leu Leu Thr Phe Trp Asn Pro Pro Thr
            20                  25                  30

Thr Ala Lys Leu Thr Ile Glu Ser Thr Pro Phe Asn Val Ala Glu Gly
        35                  40                  45

Lys Glu Val Leu Leu Leu Ala His Asn Leu Pro Gln Asn Arg Ile Gly
    50                  55                  60

Tyr Ser Trp Tyr Lys Gly Glu Arg Val Asp Gly Asn Ser Leu Ile Val
 65                  70                  75                  80

Gly Tyr Val Ile Gly Thr Gln Gln Ala Thr Pro Gly Pro Ala Tyr Ser
                85                  90                  95

Gly Arg Glu Thr Ile Tyr Pro Asn Ala Ser Leu Leu Ile Gln Asn Val
            100                 105                 110

Thr Gln Asn Asp Thr Gly Phe Tyr Thr Leu Gln Val Ile Lys Ser Asp
        115                 120                 125

Leu Val Asn Glu Glu Ala Thr Gly Gln Phe His Val Tyr Pro Glu Leu
    130                 135                 140

Pro Lys Pro Ser Ile Ser Ser Asn Asn Ser Asn Pro Val Glu Asp Lys
145                 150                 155                 160

Asp Ala Val Ala Phe Thr Cys Glu Pro Glu Val Gln Asn Thr Thr Tyr
                165                 170                 175

Leu Trp Trp Val Asn Gly Gln Ser Leu Pro Val Ser Pro Arg Leu Gln
            180                 185                 190

Leu Ser Asn Gly Asn Met Thr Leu Thr Leu Leu Ser Val Lys Arg Asn
        195                 200                 205

Asp Ala Gly Ser Tyr Glu Cys Glu Ile Gln Asn Pro Ala Ser Ala Asn
    210                 215                 220

Arg Ser Asp Pro Val Thr Leu Asn Val Leu Tyr Gly Pro Asp Gly Pro
225                 230                 235                 240

Thr Ile Ser Pro Ser Lys Ala Asn Tyr Arg Pro Gly Glu Asn Leu Asn
                245                 250                 255

Leu Ser Cys His Ala Ala Ser Asn Pro Pro Ala Gln Tyr Ser Trp Phe
            260                 265                 270

Ile Asn Gly Thr Phe Gln Gln Ser Thr Gln Glu Leu Phe Ile Pro Asn
        275                 280                 285

Ile Thr Val Asn Asn Ser Gly Ser Tyr Met Cys Gln Ala His Asn Ser
    290                 295                 300

Ala Thr Gly Leu Asn Arg Thr Thr Val Thr Met Ile Thr Val Ser Gly
305                 310                 315                 320

Ser Ala Pro Val Leu Ser Ala Val Ala Thr Val Gly Ile Thr Ile Gly
                325                 330                 335

Val Leu Ala Arg Val Ala Leu Ile
            340

<210> SEQ ID NO 17
<211> LENGTH: 1726
<212> TYPE: DNA
<213> ORGANISM: Homo Sapiens
```

<220> FEATURE:
<221> NAME/KEY: CDS
<222> LOCATION: (350)...(1486)
<223> OTHER INFORMATION: CD123

<400> SEQUENCE: 17

```
gtcaggttca tggttacgaa gctgctgacc ccaggatccc agcccgtggg agagaagggg      60
gtctctgaca gcccccaccc ctccccactg ccagatcctt attgggtctg agtttcaggg     120
gtggggcccc agctggaggt tataaaacag ctcaatcggg gagtacaacc ttcggtttct     180
cttcggggaa agctgctttc agcgcacacg ggaagatatc agaaacatcc taggatcagg     240 acacccccaga tcttctcaac tggaaccacg aaggctgttt cttccacaca gcactttgat   300
ctccatttaa gcaggcacct ctgtcctgcg ttccggagct gcgttcccg atg gtc ctc    358
                                                     Met Val Leu
                                                       1
```

| | | | | | | | | | | | | | | | | |
|---|---|---|---|---|---|---|---|---|---|---|---|---|---|---|---|---|
| ctt | tgg | ctc | acg | ctg | ctc | ctg | atc | gcc | ctg | ccc | tgt | ctc | ctg | caa | acg | 406 |
| Leu | Trp | Leu | Thr | Leu | Leu | Leu | Ile | Ala | Leu | Pro | Cys | Leu | Leu | Gln | Thr | |
| | 5 | | | | 10 | | | | | 15 | | | | | | |

| aag | gaa | gat | cca | aac | cca | cca | atc | acg | aac | cta | agg | atg | aaa | gca | aag | 454 |
|---|---|---|---|---|---|---|---|---|---|---|---|---|---|---|---|---|
| Lys | Glu | Asp | Pro | Asn | Pro | Pro | Ile | Thr | Asn | Leu | Arg | Met | Lys | Ala | Lys | |
| 20 | | | | 25 | | | | | 30 | | | | | 35 | | |

| gct | cag | cag | ttg | acc | tgg | gac | ctt | aac | aga | aat | gtg | acc | gat | atc | gag | 502 |
|---|---|---|---|---|---|---|---|---|---|---|---|---|---|---|---|---|
| Ala | Gln | Gln | Leu | Thr | Trp | Asp | Leu | Asn | Arg | Asn | Val | Thr | Asp | Ile | Glu | |
| | | | 40 | | | | | 45 | | | | | 50 | | | |

| tgt | gtt | aaa | gac | gcc | gac | tat | tct | atg | ccg | gca | gtg | aac | aat | agc | tat | 550 |
|---|---|---|---|---|---|---|---|---|---|---|---|---|---|---|---|---|
| Cys | Val | Lys | Asp | Ala | Asp | Tyr | Ser | Met | Pro | Ala | Val | Asn | Asn | Ser | Tyr | |
| | | 55 | | | | | 60 | | | | | 65 | | | | |

| tgc | cag | ttt | gga | gca | att | tcc | tta | tgt | gaa | gtg | acc | aac | tac | acc | gtc | 598 |
|---|---|---|---|---|---|---|---|---|---|---|---|---|---|---|---|---|
| Cys | Gln | Phe | Gly | Ala | Ile | Ser | Leu | Cys | Glu | Val | Thr | Asn | Tyr | Thr | Val | |
| | 70 | | | | | 75 | | | | | 80 | | | | | |

| cga | gtg | gcc | aac | cca | cca | ttc | tcc | acg | tgg | atc | ctc | ttc | cct | gag | aac | 646 |
|---|---|---|---|---|---|---|---|---|---|---|---|---|---|---|---|---|
| Arg | Val | Ala | Asn | Pro | Pro | Phe | Ser | Thr | Trp | Ile | Leu | Phe | Pro | Glu | Asn | |
| 85 | | | | | 90 | | | | | 95 | | | | | | |

| agt | ggg | aag | cct | tgg | gca | ggt | gcg | gag | aat | ctg | acc | tgc | tgg | att | cat | 694 |
|---|---|---|---|---|---|---|---|---|---|---|---|---|---|---|---|---|
| Ser | Gly | Lys | Pro | Trp | Ala | Gly | Ala | Glu | Asn | Leu | Thr | Cys | Trp | Ile | His | |
| 100 | | | | | 105 | | | | | 110 | | | | | 115 | |

| gac | gtg | gat | ttc | ttg | agc | tgc | agc | tgg | gcg | gta | ggc | ccg | ggg | gcc | ccc | 742 |
|---|---|---|---|---|---|---|---|---|---|---|---|---|---|---|---|---|
| Asp | Val | Asp | Phe | Leu | Ser | Cys | Ser | Trp | Ala | Val | Gly | Pro | Gly | Ala | Pro | |
| | | | | 120 | | | | | 125 | | | | | 130 | | |

| gcg | gac | gtc | cag | tac | gac | ctg | tac | ttg | aac | gtt | gcc | aac | agg | cgt | caa | 790 |
|---|---|---|---|---|---|---|---|---|---|---|---|---|---|---|---|---|
| Ala | Asp | Val | Gln | Tyr | Asp | Leu | Tyr | Leu | Asn | Val | Ala | Asn | Arg | Arg | Gln | |
| | | | 135 | | | | | 140 | | | | | 145 | | | |

| cag | tac | gag | tgt | ctt | cac | tac | aaa | acg | gat | gct | cag | gga | aca | cgt | atc | 838 |
|---|---|---|---|---|---|---|---|---|---|---|---|---|---|---|---|---|
| Gln | Tyr | Glu | Cys | Leu | His | Tyr | Lys | Thr | Asp | Ala | Gln | Gly | Thr | Arg | Ile | |
| | 150 | | | | | 155 | | | | | 160 | | | | | |

| ggg | tgt | cgt | ttc | gat | gac | atc | tct | cga | ctc | tcc | agc | ggt | tct | caa | agt | 886 |
|---|---|---|---|---|---|---|---|---|---|---|---|---|---|---|---|---|
| Gly | Cys | Arg | Phe | Asp | Asp | Ile | Ser | Arg | Leu | Ser | Ser | Gly | Ser | Gln | Ser | |
| | 165 | | | | | 170 | | | | | 175 | | | | | |

| tcc | cac | atc | ctg | gtg | cgg | ggc | agg | agc | gca | gcc | ttc | ggt | atc | ccc | tgc | 934 |
|---|---|---|---|---|---|---|---|---|---|---|---|---|---|---|---|---|
| Ser | His | Ile | Leu | Val | Arg | Gly | Arg | Ser | Ala | Ala | Phe | Gly | Ile | Pro | Cys | |
| 180 | | | | 185 | | | | | 190 | | | | | 195 | | |

| aca | gat | aag | ttt | gtc | gtc | ttt | tca | cag | att | gag | ata | tta | act | cca | ccc | 982 |
|---|---|---|---|---|---|---|---|---|---|---|---|---|---|---|---|---|
| Thr | Asp | Lys | Phe | Val | Val | Phe | Ser | Gln | Ile | Glu | Ile | Leu | Thr | Pro | Pro | |
| | | | | 200 | | | | | 205 | | | | | 210 | | |

| aac | atg | act | gca | aag | tgt | aat | aag | aca | cat | tcc | ttt | atg | cac | tgg | aaa | 1030 |
|---|---|---|---|---|---|---|---|---|---|---|---|---|---|---|---|---|
| Asn | Met | Thr | Ala | Lys | Cys | Asn | Lys | Thr | His | Ser | Phe | Met | His | Trp | Lys | |
| | | | 215 | | | | | 220 | | | | | 225 | | | |

| atg | aga | agt | cat | ttc | aat | cgc | aaa | ttt | cgc | tat | gag | ctt | cag | ata | caa | 1078 |
|---|---|---|---|---|---|---|---|---|---|---|---|---|---|---|---|---|
| Met | Arg | Ser | His | Phe | Asn | Arg | Lys | Phe | Arg | Tyr | Glu | Leu | Gln | Ile | Gln | |

```
aag aga atg cag cct gta atc aca gaa cag gtc aga gac aga acc tcc    1126
Lys Arg Met Gln Pro Val Ile Thr Glu Gln Val Arg Asp Arg Thr Ser
245                 250                 255 ttc cag cta ctc aat cct gga acg tac aca gta caa ata aga gcc cgg    1174
Phe Gln Leu Leu Asn Pro Gly Thr Tyr Thr Val Gln Ile Arg Ala Arg
260                 265                 270                 275 gaa aga gtg tat gaa ttc ttg agc gcc tgg agc acc ccc cag cgc ttc    1222
Glu Arg Val Tyr Glu Phe Leu Ser Ala Trp Ser Thr Pro Gln Arg Phe
                280                 285                 290 gag tgc gac cag gag gag ggc gca aac aca cgt gcc tgg cgg acg tcg    1270
Glu Cys Asp Gln Glu Glu Gly Ala Asn Thr Arg Ala Trp Arg Thr Ser
            295                 300                 305 ctg ctg atc gcg ctg ggg acg ctg ctg gcc ctg gtc tgt gtc ttc gtg    1318
Leu Leu Ile Ala Leu Gly Thr Leu Leu Ala Leu Val Cys Val Phe Val
        310                 315                 320 atc tgc aga agg tat ctg gtg atg cag aga ctc ttt ccc cgc atc cct    1366
Ile Cys Arg Arg Tyr Leu Val Met Gln Arg Leu Phe Pro Arg Ile Pro
    325                 330                 335 cac atg aaa gac ccc atc ggt gac agc ttc caa aac gac aag ctg gtg    1414
His Met Lys Asp Pro Ile Gly Asp Ser Phe Gln Asn Asp Lys Leu Val
340                 345                 350                 355 gtc tgg gag gcg ggc aaa gcc ggc ctg gag gag tgt ctg gtg act gaa    1462
Val Trp Glu Ala Gly Lys Ala Gly Leu Glu Glu Cys Leu Val Thr Glu
                360                 365                 370 gta cag gtc gtg cag aaa act tga gactggggtt cagggcttgt ggggtctgc    1516
Val Gln Val Val Gln Lys Thr
                375 ctcaatctcc ctggccgggc caggcgcctg cacagactgg ctgctggacc tgcgcacgca    1576 gcccaggaat ggacattcct aacgggtggt gggcatggga gatgcctgtg taatttcgtc    1636 cgaagctgcc aggaagaaga acagaacttt gtgtgtttat ttcatgataa agtgattttt    1696 ttttttttaa cccaaaaaaa aaaaaaaaaa                                     1726

<210> SEQ ID NO 18
<211> LENGTH: 378
<212> TYPE: PRT
<213> ORGANISM: Homo Sapiens

<400> SEQUENCE: 18

Met Val Leu Leu Trp Leu Thr Leu Leu Leu Ile Ala Leu Pro Cys Leu
1               5                   10                  15

Leu Gln Thr Lys Glu Asp Pro Asn Pro Pro Ile Thr Asn Leu Arg Met
            20                  25                  30

Lys Ala Lys Ala Gln Gln Leu Thr Trp Asp Leu Asn Arg Asn Val Thr
        35                  40                  45

Asp Ile Glu Cys Val Lys Asp Ala Asp Tyr Ser Met Pro Ala Val Asn
50                  55                  60

Asn Ser Tyr Cys Gln Phe Gly Ala Ile Ser Leu Cys Glu Val Thr Asn
65                  70                  75                  80

Tyr Thr Val Arg Val Ala Asn Pro Pro Phe Ser Thr Trp Ile Leu Phe
                85                  90                  95

Pro Glu Asn Ser Gly Lys Pro Trp Ala Gly Ala Glu Asn Leu Thr Cys
            100                 105                 110

Trp Ile His Asp Val Asp Phe Leu Ser Cys Ser Trp Ala Val Gly Pro
        115                 120                 125

Gly Ala Pro Ala Asp Val Gln Tyr Asp Leu Tyr Leu Asn Val Ala Asn
```

```
              130                 135                 140
Arg Arg Gln Gln Tyr Glu Cys Leu His Tyr Lys Thr Asp Ala Gln Gly
145                 150                 155                 160

Thr Arg Ile Gly Cys Arg Phe Asp Asp Ile Ser Arg Leu Ser Ser Gly
                165                 170                 175

Ser Gln Ser Ser His Ile Leu Val Arg Gly Arg Ser Ala Ala Phe Gly
            180                 185                 190

Ile Pro Cys Thr Asp Lys Phe Val Val Phe Ser Gln Ile Glu Ile Leu
        195                 200                 205

Thr Pro Pro Asn Met Thr Ala Lys Cys Asn Lys Thr His Ser Phe Met
210                 215                 220

His Trp Lys Met Arg Ser His Phe Asn Arg Lys Phe Arg Tyr Glu Leu
225                 230                 235                 240

Gln Ile Gln Lys Arg Met Gln Pro Val Ile Thr Glu Gln Val Arg Asp
                245                 250                 255

Arg Thr Ser Phe Gln Leu Leu Asn Pro Gly Thr Tyr Thr Val Gln Ile
            260                 265                 270

Arg Ala Arg Glu Arg Val Tyr Glu Phe Leu Ser Ala Trp Ser Thr Pro
        275                 280                 285

Gln Arg Phe Glu Cys Asp Gln Glu Glu Gly Ala Asn Thr Arg Ala Trp
290                 295                 300

Arg Thr Ser Leu Leu Ile Ala Leu Gly Thr Leu Leu Ala Leu Val Cys
305                 310                 315                 320

Val Phe Val Ile Cys Arg Arg Tyr Leu Val Met Gln Arg Leu Phe Pro
                325                 330                 335

Arg Ile Pro His Met Lys Asp Pro Ile Gly Asp Ser Phe Gln Asn Asp
            340                 345                 350

Lys Leu Val Val Trp Glu Ala Gly Lys Ala Gly Leu Glu Glu Cys Leu
        355                 360                 365

Val Thr Glu Val Gln Val Val Gln Lys Thr
370                 375

<210> SEQ ID NO 19
<211> LENGTH: 2790
<212> TYPE: DNA
<213> ORGANISM: Homo Sapiens
<220> FEATURE:
<221> NAME/KEY: CDS
<222> LOCATION: (202)...(1173)
<223> OTHER INFORMATION: CD86

<400> SEQUENCE: 19
cccttcctgt atttgagttc taccgtcagt cctggcatta tttctctctc tacaaggagc    60
cttaggaggt acggggagct cgcaaatact ccttttggtt tattcttacc accttgcttc   120
tgtgttcctt gggaatgctg ctgtgcttat gcatctggtc tcttttttgga gctacagtgg  180 acaggcattt gtgacagcac t atg gga ctg agt aac att ctc ttt gtg atg    231
                        Met Gly Leu Ser Asn Ile Leu Phe Val Met
                         1               5                  10 gcc ttc ctg ctc tct ggt gct gct cct ctg aag att caa gct tat ttc    279
Ala Phe Leu Leu Ser Gly Ala Ala Pro Leu Lys Ile Gln Ala Tyr Phe
                15                  20                  25 aat gag act gca gac ctg cca tgc caa ttt gca aac tct caa aac caa    327
Asn Glu Thr Ala Asp Leu Pro Cys Gln Phe Ala Asn Ser Gln Asn Gln
            30                  35                  40 agc ctg agt gag cta gta gta ttt tgg cag gac cag gaa aac ttg gtt    375
Ser Leu Ser Glu Leu Val Val Phe Trp Gln Asp Gln Glu Asn Leu Val
```

|     |     |     |     |     |     |     |     |     |     |     |     |     |     |     |     |      |
|---|---|---|---|---|---|---|---|---|---|---|---|---|---|---|---|---|
|     |     |     | 45  |     |     |     | 50  |     |     |     | 55  |     |     |     |     |      |
| ctg | aat | gag | gta | tac | tta | ggc | aaa | gag | aaa | ttt | gac | agt | gtt | cat | tcc | 423  |
| Leu | Asn | Glu | Val | Tyr | Leu | Gly | Lys | Glu | Lys | Phe | Asp | Ser | Val | His | Ser |      |
|     | 60  |     |     |     | 65  |     |     |     | 70  |     |     |     |     |     |     |      |
| aag | tat | atg | ggc | cgc | aca | agt | ttt | gat | tcg | gac | agt | tgg | acc | ctg | aga | 471  |
| Lys | Tyr | Met | Gly | Arg | Thr | Ser | Phe | Asp | Ser | Asp | Ser | Trp | Thr | Leu | Arg |      |
| 75  |     |     |     |     | 80  |     |     |     | 85  |     |     |     |     |     | 90  |      |
| ctt | cac | aat | ctt | cag | atc | aag | gac | aag | ggc | ttg | tat | caa | tgt | atc | atc | 519  |
| Leu | His | Asn | Leu | Gln | Ile | Lys | Asp | Lys | Gly | Leu | Tyr | Gln | Cys | Ile | Ile |      |
|     |     |     |     | 95  |     |     |     |     | 100 |     |     |     |     | 105 |     |      |
| cat | cac | aaa | aag | ccc | aca | gga | atg | att | cgc | atc | cac | cag | atg | aat | tct | 567  |
| His | His | Lys | Lys | Pro | Thr | Gly | Met | Ile | Arg | Ile | His | Gln | Met | Asn | Ser |      |
|     |     |     | 110 |     |     |     | 115 |     |     |     | 120 |     |     |     |     |      |
| gaa | ctg | tca | gtg | ctt | gct | aac | ttc | agt | caa | cct | gaa | ata | gta | cca | att | 615  |
| Glu | Leu | Ser | Val | Leu | Ala | Asn | Phe | Ser | Gln | Pro | Glu | Ile | Val | Pro | Ile |      |
|     | 125 |     |     |     | 130 |     |     |     | 135 |     |     |     |     |     |     |      |
| tct | aat | ata | aca | gaa | aat | gtg | tac | ata | aat | ttg | acc | tgc | tca | tct | ata | 663  |
| Ser | Asn | Ile | Thr | Glu | Asn | Val | Tyr | Ile | Asn | Leu | Thr | Cys | Ser | Ser | Ile |      |
| 140 |     |     |     |     | 145 |     |     |     | 150 |     |     |     |     |     |     |      |
| cac | ggt | tac | cca | gaa | cct | aag | aag | atg | agt | gtt | ttg | cta | aga | acc | aag | 711  |
| His | Gly | Tyr | Pro | Glu | Pro | Lys | Lys | Met | Ser | Val | Leu | Leu | Arg | Thr | Lys |      |
| 155 |     |     |     |     | 160 |     |     |     | 165 |     |     |     |     |     | 170 |      |
| aat | tca | act | atc | gag | tat | gat | ggt | att | atg | cag | aaa | tct | caa | gat | aat | 759  |
| Asn | Ser | Thr | Ile | Glu | Tyr | Asp | Gly | Ile | Met | Gln | Lys | Ser | Gln | Asp | Asn |      |
|     |     |     | 175 |     |     |     | 180 |     |     |     | 185 |     |     |     |     |      |
| gtc | aca | gaa | ctg | tac | gac | gtt | tcc | atc | agc | ttg | tct | gtt | tca | ttc | cct | 807  |
| Val | Thr | Glu | Leu | Tyr | Asp | Val | Ser | Ile | Ser | Leu | Ser | Val | Ser | Phe | Pro |      |
|     | 190 |     |     |     | 195 |     |     |     | 200 |     |     |     |     |     |     |      |
| gat | gtt | acg | agc | aat | atg | acc | atc | ttc | tgt | att | ctg | gaa | act | gac | aag | 855  |
| Asp | Val | Thr | Ser | Asn | Met | Thr | Ile | Phe | Cys | Ile | Leu | Glu | Thr | Asp | Lys |      |
|     | 205 |     |     |     | 210 |     |     |     | 215 |     |     |     |     |     |     |      |
| acg | cgg | ctt | tta | tct | tca | cct | ttc | tct | ata | gag | ctt | gag | gac | cct | cag | 903  |
| Thr | Arg | Leu | Leu | Ser | Ser | Pro | Phe | Ser | Ile | Glu | Leu | Glu | Asp | Pro | Gln |      |
|     | 220 |     |     |     | 225 |     |     |     | 230 |     |     |     |     |     |     |      |
| cct | ccc | cca | gac | cac | att | cct | tgg | att | aca | gct | gta | ctt | cca | aca | gtt | 951  |
| Pro | Pro | Pro | Asp | His | Ile | Pro | Trp | Ile | Thr | Ala | Val | Leu | Pro | Thr | Val |      |
| 235 |     |     |     |     | 240 |     |     |     | 245 |     |     |     |     |     | 250 |      |
| att | ata | tgt | gtg | atg | gtt | ttc | tgt | cta | att | cta | tgg | aaa | tgg | aag | aag | 999  |
| Ile | Ile | Cys | Val | Met | Val | Phe | Cys | Leu | Ile | Leu | Trp | Lys | Trp | Lys | Lys |      |
|     |     |     |     | 255 |     |     |     | 260 |     |     |     |     | 265 |     |     |      |
| aag | aag | cgg | cct | cgc | aac | tct | tat | aaa | tgt | gga | acc | aac | aca | atg | gag | 1047 |
| Lys | Lys | Arg | Pro | Arg | Asn | Ser | Tyr | Lys | Cys | Gly | Thr | Asn | Thr | Met | Glu |      |
|     |     |     | 270 |     |     |     | 275 |     |     |     | 280 |     |     |     |     |      |
| agg | gaa | gag | agt | gaa | cag | acc | aag | aaa | aga | gaa | aaa | atc | cat | ata | cct | 1095 |
| Arg | Glu | Glu | Ser | Glu | Gln | Thr | Lys | Lys | Arg | Glu | Lys | Ile | His | Ile | Pro |      |
|     | 285 |     |     |     | 290 |     |     |     | 295 |     |     |     |     |     |     |      |
| gaa | aga | tct | gat | gaa | gcc | cag | cgt | gtt | ttt | aaa | agt | tcg | aag | aca | tct | 1143 |
| Glu | Arg | Ser | Asp | Glu | Ala | Gln | Arg | Val | Phe | Lys | Ser | Ser | Lys | Thr | Ser |      |
|     | 300 |     |     |     | 305 |     |     |     | 310 |     |     |     |     |     |     |      |
| tca | tgc | gac | aaa | agt | gat | aca | tgt | ttt | taa | ttaaagagta | | aagcccatac | | | | 1193 |
| Ser | Cys | Asp | Lys | Ser | Asp | Thr | Cys | Phe |     |     |     |     |     |     |     |      |
| 315 |     |     |     |     | 320 |     |     |     |     |     |     |     |     |     |     |      |

| | |
|---|---|
| aagtattcat tttttctacc ctttcctttg taagttcctg gcaacctttt tgatttctt | 1253 |
| ccagaaggca aaaagacatt accatgagta ataagggggc tccaggactc cctctaagtg | 1313 |
| gaatagcctc cctgtaactc cagctctgct ccgtatgcca agaggagact ttaattctct | 1373 |
| tactgcttct tttcacttca gagcacactt atgggccaag cccagcttaa tggctcatga | 1433 |
| cctggaaata aaatttagga ccaatacctc ctccagatca gattcttctc ttaatttcat | 1493 |

```
agattgtgtt ttttttttaa atagacctct caatttctgg aaaactgcct tttatctgcc   1553
cagaattcta agctggtgcc ccactgaatt ttgtgtacct gtgactaaac aactacctcc   1613
tcagtctggg tgggacttat gtatttatga ccttatagtg ttaatatctt gaaacataga   1673
gatctatgta ctgtaatagt gtgattacta tgctctagaa aaagtctac ccctgctaag    1733 gagttctcat ccctctgtca gggtcagtaa ggaaaacggt ggcctagggt acaggcaaca   1793
atgagcagac caacctaaat ttggggaaat taggagaggc agagatagaa cctggagcca   1853
cttctatctg ggctgttgct aatattgagg aggcttgccc cacccaacaa gccatagtgg   1913
agagaactga ataaacagga aaatgccaga gcttgtgaac cctgtttctc ttgaagaact   1973
gactagtgag atggcctggg gaagctgtga agaaccaaa agagatcaca atactcaaaa    2033
gagagagaga gagaaaaaag agagatcttg atccacagaa atacatgaaa tgtctggtct   2093
gtccacccca tcaacaagtc ttgaaacaag caacagatgg atagtctgtc caaatggaca   2153
taagacagac agcagtttcc ctggtggtca gggaggggtt ttggtgatac ccaagttatt   2213
gggatgtcat cttcctggaa gcagagctgg ggagggagag ccatcacctt gataatggga   2273
tgaatggaag gaggcttagg actttccact cctggctgag agaggaagag ctgcaacgga   2333
attaggaaga ccaagacaca gatcacccgg ggcttactta gcctacagat gtcctacggg   2393
aacgtgggct ggcccagcat agggctagca aatttgagtt ggatgattgt ttttgctcaa   2453
ggcaaccaga ggaaacttgc atacagagac agatatactg ggagaaatga ctttgaaaac   2513
ctggctctaa ggtgggatca ctaagggatg gggcagtctc tgcccaaaca taaagagaac   2573
tctggggagc ctgagccaca aaaatgttcc tttattttat gtaaaccctc aagggttata   2633
gactgccatg ctagacaagc ttgtccatgt aatattccca tgttttacc ctgcccctgc    2693 cttgattaga ctcctagcac ctggctagtt tctaacatgt tttgtgcagc acagttttta   2753
ataaatgctt gttacattca tttaaaaaaa aaaaaaa                            2790
```

<210> SEQ ID NO 20
<211> LENGTH: 323
<212> TYPE: PRT
<213> ORGANISM: Homo Sapiens

<400> SEQUENCE: 20

```
Met Gly Leu Ser Asn Ile Leu Phe Val Met Ala Phe Leu Leu Ser Gly
 1               5                  10                  15

Ala Ala Pro Leu Lys Ile Gln Ala Tyr Phe Asn Glu Thr Ala Asp Leu
            20                  25                  30

Pro Cys Gln Phe Ala Asn Ser Gln Asn Gln Ser Leu Ser Glu Leu Val
        35                  40                  45

Val Phe Trp Gln Asp Gln Glu Asn Leu Val Leu Asn Glu Val Tyr Leu
    50                  55                  60

Gly Lys Glu Lys Phe Asp Ser Val His Ser Lys Tyr Met Gly Arg Thr
65                  70                  75                  80

Ser Phe Asp Ser Asp Ser Trp Thr Leu Arg Leu His Asn Leu Gln Ile
                85                  90                  95

Lys Asp Lys Gly Leu Tyr Gln Cys Ile Ile His His Lys Pro Thr
            100                 105                 110

Gly Met Ile Arg Ile His Gln Met Asn Ser Glu Leu Ser Val Leu Ala
        115                 120                 125

Asn Phe Ser Gln Pro Glu Ile Val Pro Ile Ser Asn Ile Thr Glu Asn
    130                 135                 140
```

```
Val Tyr Ile Asn Leu Thr Cys Ser Ser Ile His Gly Tyr Pro Glu Pro
145                 150                 155                 160

Lys Lys Met Ser Val Leu Leu Arg Thr Lys Asn Ser Thr Ile Glu Tyr
                165                 170                 175

Asp Gly Ile Met Gln Lys Ser Gln Asp Asn Val Thr Glu Leu Tyr Asp
            180                 185                 190

Val Ser Ile Ser Leu Ser Val Ser Phe Pro Asp Val Thr Ser Asn Met
        195                 200                 205

Thr Ile Phe Cys Ile Leu Glu Thr Asp Lys Thr Arg Leu Leu Ser Ser
    210                 215                 220

Pro Phe Ser Ile Glu Leu Glu Asp Pro Gln Pro Pro Asp His Ile
225                 230                 235                 240

Pro Trp Ile Thr Ala Val Leu Pro Thr Val Ile Ile Cys Val Met Val
                245                 250                 255

Phe Cys Leu Ile Leu Trp Lys Trp Lys Lys Lys Arg Pro Arg Asn
                260                 265                 270

Ser Tyr Lys Cys Gly Thr Asn Thr Met Glu Arg Glu Glu Ser Glu Gln
            275                 280                 285

Thr Lys Lys Arg Glu Lys Ile His Ile Pro Glu Arg Ser Asp Glu Ala
        290                 295                 300

Gln Arg Val Phe Lys Ser Ser Lys Thr Ser Ser Cys Asp Lys Ser Asp
305                 310                 315                 320

Thr Cys Phe

<210> SEQ ID NO 21
<211> LENGTH: 1548
<212> TYPE: DNA
<213> ORGANISM: Homo Sapiens
<220> FEATURE:
<221> NAME/KEY: CDS
<222> LOCATION: (125)...(1204)
<223> OTHER INFORMATION: CD72

<400> SEQUENCE: 21
aattgctaag ccgtgcagtc acagagggaa cacagagcct agttgtaaac ggacagagac      60
gagaggggca agggaggaca gtggatgaca gggaagacga gtgggggcag agctgctcag     120 gacc atg gct gag gcc atc acc tat gca gat ctg agg ttt gtg aag gct     169
     Met Ala Glu Ala Ile Thr Tyr Ala Asp Leu Arg Phe Val Lys Ala
     1               5                   10                  15 ccc ctg aag aag agc atc tcc agc cgg tta gga cag gac cca ggg gct     217
Pro Leu Lys Lys Ser Ile Ser Ser Arg Leu Gly Gln Asp Pro Gly Ala
            20                  25                  30 gat gat gat ggg gaa atc acc tac gag aat gtt caa gtg ccc gca gtc     265
Asp Asp Asp Gly Glu Ile Thr Tyr Glu Asn Val Gln Val Pro Ala Val
        35                  40                  45 cta ggg gtg ccc tca agc ttg gct tct tct gta cta ggg gac aaa gca     313
Leu Gly Val Pro Ser Ser Leu Ala Ser Ser Val Leu Gly Asp Lys Ala
    50                  55                  60 gcg gtc aag tcg gag cag cca act gcg tcc tgg aga gcc gtg acg tca     361
Ala Val Lys Ser Glu Gln Pro Thr Ala Ser Trp Arg Ala Val Thr Ser
65                  70                  75 cca gct gtc ggg cgg att ctc ccc tgc cgc aca acc tgc ctg cga tac     409
Pro Ala Val Gly Arg Ile Leu Pro Cys Arg Thr Thr Cys Leu Arg Tyr
80                  85                  90                  95 ctc ctg ctc ggc ctg ctc ctc acc tgc ctg ctg tta gga gtg acc gcc     457
Leu Leu Leu Gly Leu Leu Leu Thr Cys Leu Leu Leu Gly Val Thr Ala
                100                 105                 110
```

```
atc tgc ctg gga gtg cgc tat ctg cag gtg tct cag cag ctc cag cag      505
Ile Cys Leu Gly Val Arg Tyr Leu Gln Val Ser Gln Gln Leu Gln Gln
            115                 120                 125 acg aac agg gtt ctg gaa gtc act aac agc agc ctg agg cag cag ctc      553
Thr Asn Arg Val Leu Glu Val Thr Asn Ser Ser Leu Arg Gln Gln Leu
        130                 135                 140 cgc ctc aag ata acg cag ctg gga cag agt gca gag gat ctg cag ggg      601
Arg Leu Lys Ile Thr Gln Leu Gly Gln Ser Ala Glu Asp Leu Gln Gly
145                 150                 155 tcc agg aga gag ctg gcg cag agt cag gaa gca cta cag gtg gaa cag      649
Ser Arg Arg Glu Leu Ala Gln Ser Gln Glu Ala Leu Gln Val Glu Gln
160                 165                 170                 175 agg gct cat cag gcg gcc gaa ggg cag cta cag gcc tgc cag gca gac      697
Arg Ala His Gln Ala Ala Glu Gly Gln Leu Gln Ala Cys Gln Ala Asp
                180                 185                 190 aga cag aag acg aag gag acc ttg caa agt gag gag caa cag agg agg      745
Arg Gln Lys Thr Lys Glu Thr Leu Gln Ser Glu Glu Gln Gln Arg Arg
            195                 200                 205 gcc ttg gag cag aag ctg agc aac atg gag aac aga ctg aag ccc ttc      793
Ala Leu Glu Gln Lys Leu Ser Asn Met Glu Asn Arg Leu Lys Pro Phe
        210                 215                 220 ttc aca tgc ggc tca gca gac acc tgc tgt ccg tcg gga tgg ata atg      841
Phe Thr Cys Gly Ser Ala Asp Thr Cys Cys Pro Ser Gly Trp Ile Met
225                 230                 235 cat cag aaa agc tgc ttt tac atc tca ctt act tca aaa aat tgg cag      889
His Gln Lys Ser Cys Phe Tyr Ile Ser Leu Thr Ser Lys Asn Trp Gln
240                 245                 250                 255 gag agc caa aaa caa tgt gaa act ctg tct tcc aag ctg gcc aca ttc      937
Glu Ser Gln Lys Gln Cys Glu Thr Leu Ser Ser Lys Leu Ala Thr Phe
                260                 265                 270 agt gaa att tat cca caa tca cac tct tac tac ttc tta aat tca ctg      985
Ser Glu Ile Tyr Pro Gln Ser His Ser Tyr Tyr Phe Leu Asn Ser Leu
            275                 280                 285 ttg cca aat ggt ggt tca ggg aat tca tat tgg act ggc ctc agc tct     1033
Leu Pro Asn Gly Gly Ser Gly Asn Ser Tyr Trp Thr Gly Leu Ser Ser
        290                 295                 300 aac aag gat tgg aag ttg act gat gat aca caa cgc act agg act tat     1081
Asn Lys Asp Trp Lys Leu Thr Asp Asp Thr Gln Arg Thr Arg Thr Tyr
305                 310                 315 gct caa agc tca aaa tgt aac aag gta cat aaa act tgg tca tgg tgg     1129
Ala Gln Ser Ser Lys Cys Asn Lys Val His Lys Thr Trp Ser Trp Trp
                320                 325                 330                 335 aca ctg gag tca gag tca tgt aga agt tct ctt ccc tac atc tgt gag     1177
Thr Leu Glu Ser Glu Ser Cys Arg Ser Ser Leu Pro Tyr Ile Cys Glu
            340                 345                 350 atg aca gct ttc agg ttt cca gat tag dacagtcctt tgcactgagt            1224
Met Thr Ala Phe Arg Phe Pro Asp
                355 tgacactcat gccaacaaga acctgtgccc ctccttccta acctgaggcc tggggttcct   1284 cagaccatct ccttcattct gggcagtgcc cagccaccgg ctgacccaca cctgacactt   1344 ccagccagtc tgctgcctgc tccctcttcc tgaaactgga ctgttcctgg gaaaagggtg   1404 aagccacctc tagaagggac tttggcctcc ccccaagaac ttcccatggt agaatgggt    1464 gggggaggag ggcgcacggg ctgagcggat aggggcggcc cggagccagc caggcagttt   1524 tattgaaatc ttttttaaata attg                                         1548
```

<210> SEQ ID NO 22

<211> LENGTH: 359
<212> TYPE: PRT
<213> ORGANISM: Homo Sapiens

<400> SEQUENCE: 22

```
Met Ala Glu Ala Ile Thr Tyr Ala Asp Leu Arg Phe Val Lys Ala Pro
 1               5                   10                  15

Leu Lys Lys Ser Ile Ser Ser Arg Leu Gly Gln Asp Pro Gly Ala Asp
             20                  25                  30

Asp Asp Gly Glu Ile Thr Tyr Glu Asn Val Gln Val Pro Ala Val Leu
         35                  40                  45

Gly Val Pro Ser Ser Leu Ala Ser Ser Val Leu Gly Asp Lys Ala Ala
 50                  55                  60

Val Lys Ser Glu Gln Pro Thr Ala Ser Trp Arg Ala Val Thr Ser Pro
 65                  70                  75                  80

Ala Val Gly Arg Ile Leu Pro Cys Arg Thr Thr Cys Leu Arg Tyr Leu
                 85                  90                  95

Leu Leu Gly Leu Leu Thr Cys Leu Leu Gly Val Thr Ala Ile
                100                 105                 110

Cys Leu Gly Val Arg Tyr Leu Gln Val Ser Gln Gln Leu Gln Gln Thr
                115                 120                 125

Asn Arg Val Leu Glu Val Thr Asn Ser Ser Leu Arg Gln Gln Leu Arg
            130                 135                 140

Leu Lys Ile Thr Gln Leu Gly Gln Ser Ala Glu Asp Leu Gln Gly Ser
145                 150                 155                 160

Arg Arg Glu Leu Ala Gln Ser Gln Glu Ala Leu Gln Val Glu Gln Arg
                165                 170                 175

Ala His Gln Ala Ala Glu Gly Gln Leu Gln Ala Cys Gln Ala Asp Arg
            180                 185                 190

Gln Lys Thr Lys Glu Thr Leu Gln Ser Glu Gln Gln Arg Arg Ala
            195                 200                 205

Leu Glu Gln Lys Leu Ser Asn Met Glu Asn Arg Leu Lys Pro Phe Phe
        210                 215                 220

Thr Cys Gly Ser Ala Asp Thr Cys Cys Pro Ser Gly Trp Ile Met His
225                 230                 235                 240

Gln Lys Ser Cys Phe Tyr Ile Ser Leu Thr Ser Lys Asn Trp Gln Glu
                245                 250                 255

Ser Gln Lys Gln Cys Glu Thr Leu Ser Ser Lys Leu Ala Thr Phe Ser
            260                 265                 270

Glu Ile Tyr Pro Gln Ser His Ser Tyr Tyr Phe Leu Asn Ser Leu Leu
        275                 280                 285

Pro Asn Gly Gly Ser Gly Asn Ser Tyr Trp Thr Gly Leu Ser Ser Asn
    290                 295                 300

Lys Asp Trp Lys Leu Thr Asp Asp Thr Gln Arg Thr Arg Thr Tyr Ala
305                 310                 315                 320

Gln Ser Ser Lys Cys Asn Lys Val His Lys Thr Trp Ser Trp Trp Thr
                325                 330                 335

Leu Glu Ser Glu Ser Cys Arg Ser Ser Leu Pro Tyr Ile Cys Glu Met
            340                 345                 350

Thr Ala Phe Arg Phe Pro Asp
        355
```

<210> SEQ ID NO 23
<211> LENGTH: 3740
<212> TYPE: DNA

<213> ORGANISM: Homo Sapiens
<220> FEATURE:
<221> NAME/KEY: CDS
<222> LOCATION: (293)...(3196)
<223> OTHER INFORMATION: CD13

<400> SEQUENCE: 23

```
gggacggcgg cggcgcagct cggaacccgc cagggtccag ggtccaggtt ccagcgcccg        60
gcggcccagg cacccccga  gcccagctcc acacaccgtt cctggatctc ctctccccag       120
gcggagcgtg ccctgccca  gtccagtgac cttcgcctgt tggagccctg gttaattttt       180
gcccagtctg cctgttgtgg ggctcctccc ctttggggat ataagcccgg cctggggctg       240
ctccgttctc tgcctggcct gaggctccct gagccgcctc ccaccatca cc atg gcc       298
                                                          Met Ala
                                                            1 aag ggc ttc tat att tcc aag tcc ctg ggc atc ctg ggg atc ctc ctg        346
Lys Gly Phe Tyr Ile Ser Lys Ser Leu Gly Ile Leu Gly Ile Leu Leu
        5                  10                 15 ggc gtg gca gcc gtg tgc aca atc atc gca ctg tca gtg gtg tac tcc       394
Gly Val Ala Ala Val Cys Thr Ile Ile Ala Leu Ser Val Val Tyr Ser
    20                  25                  30 cag gag aag aac aag aac gcc aac agc tcc ccc gtg gcc tcc acc acc       442
Gln Glu Lys Asn Lys Asn Ala Asn Ser Ser Pro Val Ala Ser Thr Thr
35                  40                  45                  50 ccg tcc gcc tca gcc acc acc aac ccc gcc tcg gcc acc acc ttg gac       490
Pro Ser Ala Ser Ala Thr Thr Asn Pro Ala Ser Ala Thr Thr Leu Asp
                55                  60                  65 caa agt aaa gcg tgg aat cgt tac cgc ctc ccc aac acg ctg aaa ccc       538
Gln Ser Lys Ala Trp Asn Arg Tyr Arg Leu Pro Asn Thr Leu Lys Pro
            70                  75                  80 gat tcc tac cgg gtg acg ctg aga ccg tac ctc acc ccc aat gac agg       586
Asp Ser Tyr Arg Val Thr Leu Arg Pro Tyr Leu Thr Pro Asn Asp Arg
        85                  90                  95 ggc ctg tac gtt ttt aag ggc tcc agc acc gtc cgt ttc acc tgc aag       634
Gly Leu Tyr Val Phe Lys Gly Ser Ser Thr Val Arg Phe Thr Cys Lys
    100                 105                 110 gag gcc act gac gtc atc atc atc cac agc aag aag ctc aac tac acc       682
Glu Ala Thr Asp Val Ile Ile Ile His Ser Lys Lys Leu Asn Tyr Thr
115                 120                 125                 130 ctc agc cag ggg cac agg gtg gtc ctg cgt ggt gtg gga ggc tcc cag       730
Leu Ser Gln Gly His Arg Val Val Leu Arg Gly Val Gly Gly Ser Gln
                135                 140                 145 ccc ccc gac att gac aag act gag ctg gtg gag ccc acc gag tac ctg       778
Pro Pro Asp Ile Asp Lys Thr Glu Leu Val Glu Pro Thr Glu Tyr Leu
            150                 155                 160 gtg gtg cac ctc aag ggc tcc ctg gtg aag gac agc cag tat gag atg       826
Val Val His Leu Lys Gly Ser Leu Val Lys Asp Ser Gln Tyr Glu Met
        165                 170                 175 gac agc gag ttc gag ggg gag ttg gca gat gac ctg gcg ggc ttc tac       874
Asp Ser Glu Phe Glu Gly Glu Leu Ala Asp Asp Leu Ala Gly Phe Tyr
    180                 185                 190 cgc agc gag tac atg gag ggc aat gtc aga aag gtg gtg gcc act aca       922
Arg Ser Glu Tyr Met Glu Gly Asn Val Arg Lys Val Val Ala Thr Thr
195                 200                 205                 210 cag atg cag gct gca gat gcc cgg aag tcc ttc cca tgc ttc gat gag       970
Gln Met Gln Ala Ala Asp Ala Arg Lys Ser Phe Pro Cys Phe Asp Glu
                215                 220                 225 ccg gcc atg aag gcc gag ttc aac atc acg ctt atc cac ccc aag gac      1018
Pro Ala Met Lys Ala Glu Phe Asn Ile Thr Leu Ile His Pro Lys Asp
            230                 235                 240
```

```
ctg aca gcc ctg tcc aac atg ctt ccc aaa ggt ccc agc acc cca ctt      1066
Leu Thr Ala Leu Ser Asn Met Leu Pro Lys Gly Pro Ser Thr Pro Leu
        245                 250                 255 cca gaa gac ccc aac tgg aat gtc act gag ttc cac acc acg ccc aag      1114
Pro Glu Asp Pro Asn Trp Asn Val Thr Glu Phe His Thr Thr Pro Lys
    260                 265                 270 atg tcc acg tac ttg ctg gcc ttc att gtc agt gag ttc gac tac gtg      1162
Met Ser Thr Tyr Leu Leu Ala Phe Ile Val Ser Glu Phe Asp Tyr Val
275                 280                 285                 290 gag aag cag gca tcc aat ggt gtc ttg atc cgg atc tgg gcc cgg ccc      1210
Glu Lys Gln Ala Ser Asn Gly Val Leu Ile Arg Ile Trp Ala Arg Pro
                295                 300                 305 agt gcc att gcg gcg ggc cac ggc gat tat gcc ctg aac gtg acg ggc      1258
Ser Ala Ile Ala Ala Gly His Gly Asp Tyr Ala Leu Asn Val Thr Gly
            310                 315                 320 ccc atc ctt aac ttc ttt gct ggt cat tat gac aca ccc tac cca ctc      1306
Pro Ile Leu Asn Phe Phe Ala Gly His Tyr Asp Thr Pro Tyr Pro Leu
        325                 330                 335 cca aaa tca gac cag att ggc ctg cca gac ttc aac gcc ggc gcc atg      1354
Pro Lys Ser Asp Gln Ile Gly Leu Pro Asp Phe Asn Ala Gly Ala Met
    340                 345                 350 gag aac tgg gga ctg gtg acc tac cgg gag aac tcc ctg ctg ttc gac      1402
Glu Asn Trp Gly Leu Val Thr Tyr Arg Glu Asn Ser Leu Leu Phe Asp
355                 360                 365                 370 ccc ctg tcc tcc tcc agc agc aac aag gag cgg gtg gtc act gtg att      1450
Pro Leu Ser Ser Ser Ser Ser Asn Lys Glu Arg Val Val Thr Val Ile
                375                 380                 385 gct cat gag ctg gcc cac cag tgg ttc ggg aac ctg gtg acc ata gag      1498
Ala His Glu Leu Ala His Gln Trp Phe Gly Asn Leu Val Thr Ile Glu
            390                 395                 400 tgg tgg aat gac ctg tgg ctg aac gag ggc ttc gcc tcc tac gtg gag      1546
Trp Trp Asn Asp Leu Trp Leu Asn Glu Gly Phe Ala Ser Tyr Val Glu
        405                 410                 415 tac ctg ggt gct gac tat gcg gag ccc acc tgg aac ttg aaa gac ctc      1594
Tyr Leu Gly Ala Asp Tyr Ala Glu Pro Thr Trp Asn Leu Lys Asp Leu
    420                 425                 430 atg gtg ctg aat gat gtg tac cgc gtg atg gca gtg gat gca ctg gcc      1642
Met Val Leu Asn Asp Val Tyr Arg Val Met Ala Val Asp Ala Leu Ala
435                 440                 445                 450 tcc tcc cac ccg ctg tcc aca ccc gcc tcg gag atc aac acg ccg gcc      1690
Ser Ser His Pro Leu Ser Thr Pro Ala Ser Glu Ile Asn Thr Pro Ala
                455                 460                 465 cag atc agt gag ctg ttt gac gcc atc tcc tac agc aag ggc gcc tca      1738
Gln Ile Ser Glu Leu Phe Asp Ala Ile Ser Tyr Ser Lys Gly Ala Ser
            470                 475                 480 gtc ctc agg atg ctc tcc agc ttc ctg tcc gag gac gta ttc aag cag      1786
Val Leu Arg Met Leu Ser Ser Phe Leu Ser Glu Asp Val Phe Lys Gln
        485                 490                 495 ggc ctg gcg tcc tac ctc cac acc ttt gcc tac cag aac acc atc tac      1834
Gly Leu Ala Ser Tyr Leu His Thr Phe Ala Tyr Gln Asn Thr Ile Tyr
    500                 505                 510 ctg aac ctg tgg gac cac ctg cag gag gct gtg aac aac cgg tcc atc      1882
Leu Asn Leu Trp Asp His Leu Gln Glu Ala Val Asn Asn Arg Ser Ile
515                 520                 525                 530 caa ctc ccc acc acc gtg cgg gac atc atg aac cgc tgg acc ctg cag      1930
Gln Leu Pro Thr Thr Val Arg Asp Ile Met Asn Arg Trp Thr Leu Gln
                535                 540                 545 atg ggc ttc ccg gtc atc acg gtg gat acc agc acg ggg acc ctt tcc      1978
Met Gly Phe Pro Val Ile Thr Val Asp Thr Ser Thr Gly Thr Leu Ser
```

-continued

```
                550                 555                 560
cag gag cac ttc ctc ctt gac ccc gat tcc aat gtt acc cgc ccc tca    2026
Gln Glu His Phe Leu Leu Asp Pro Asp Ser Asn Val Thr Arg Pro Ser
            565                 570                 575 gaa ttc aac tac gtg tgg att gtg ccc atc aca tcc atc aga gat ggc    2074
Glu Phe Asn Tyr Val Trp Ile Val Pro Ile Thr Ser Ile Arg Asp Gly
        580                 585                 590 aga cag cag cag gac tac tgg ctg ata gat gta aga gcc cag aac gat    2122
Arg Gln Gln Gln Asp Tyr Trp Leu Ile Asp Val Arg Ala Gln Asn Asp
595                 600                 605                 610 ctc ttc agc aca tca ggc aat gag tgg gtc ctg ctg aac ctc aat gtg    2170
Leu Phe Ser Thr Ser Gly Asn Glu Trp Val Leu Leu Asn Leu Asn Val
            615                 620                 625 acg ggc tat tac cgg gtg aac tac gac gaa gag aac tgg agg aag att    2218
Thr Gly Tyr Tyr Arg Val Asn Tyr Asp Glu Glu Asn Trp Arg Lys Ile
        630                 635                 640 cag act cag ctg cag aga gac cac tcg gcc atc cct gtc atc aat cgg    2266
Gln Thr Gln Leu Gln Arg Asp His Ser Ala Ile Pro Val Ile Asn Arg
    645                 650                 655 gca cag atc att aat gac gcc ttc aac ctg gcc agt gcc cat aag gtc    2314
Ala Gln Ile Ile Asn Asp Ala Phe Asn Leu Ala Ser Ala His Lys Val
660                 665                 670 cct gtc act ctg gcg ctg aac aac acc ctc ttc ctg att gaa gag aga    2362
Pro Val Thr Leu Ala Leu Asn Asn Thr Leu Phe Leu Ile Glu Glu Arg
675                 680                 685                 690 cag tac atg ccc tgg gag gcc gcc ctg agc agc ctg agc tac ttc aag    2410
Gln Tyr Met Pro Trp Glu Ala Ala Leu Ser Ser Leu Ser Tyr Phe Lys
            695                 700                 705 ctc atg ttt gac cgc tcc gag gtc tat ggc ccc atg aag aac tac ctg    2458
Leu Met Phe Asp Arg Ser Glu Val Tyr Gly Pro Met Lys Asn Tyr Leu
        710                 715                 720 aag aag cag gtc aca ccc ctc ttc att cac ttc aga aat aat acc aac    2506
Lys Lys Gln Val Thr Pro Leu Phe Ile His Phe Arg Asn Asn Thr Asn
    725                 730                 735 aac tgg agg gag atc cca gaa aac ctg atg gac cag tac agc gag gtt    2554
Asn Trp Arg Glu Ile Pro Glu Asn Leu Met Asp Gln Tyr Ser Glu Val
740                 745                 750 aat gcc atc agc acc gcc tgc tcc aac gga gtt cca gag tgt gag gag    2602
Asn Ala Ile Ser Thr Ala Cys Ser Asn Gly Val Pro Glu Cys Glu Glu
755                 760                 765                 770 atg gtc tct ggc ctt ttc aag cag tgg atg gag aac ccc aat aat aac    2650
Met Val Ser Gly Leu Phe Lys Gln Trp Met Glu Asn Pro Asn Asn Asn
            775                 780                 785 ccg atc cac ccc aac ctg cgg tcc acc gtc tac tgc aac gct atc gcc    2698
Pro Ile His Pro Asn Leu Arg Ser Thr Val Tyr Cys Asn Ala Ile Ala
        790                 795                 800 cag ggc ggg gag gag gag tgg gac ttc gcc tgg gag cag ttc cga aat    2746
Gln Gly Gly Glu Glu Glu Trp Asp Phe Ala Trp Glu Gln Phe Arg Asn
    805                 810                 815 gcc aca ctg gtc aat gag gct gac aag ctc cgg gca gcc ctg gcc tgc    2794
Ala Thr Leu Val Asn Glu Ala Asp Lys Leu Arg Ala Ala Leu Ala Cys
820                 825                 830 agc aaa gag ttg tgg atc ctg aac agg tac ctg agc tac acc ctg aac    2842
Ser Lys Glu Leu Trp Ile Leu Asn Arg Tyr Leu Ser Tyr Thr Leu Asn
835                 840                 845                 850 ccg gac tta atc cgg aag cag gac gcc acc tct acc atc atc agc att    2890
Pro Asp Leu Ile Arg Lys Gln Asp Ala Thr Ser Thr Ile Ile Ser Ile
            855                 860                 865 acc aac aac gtc att ggg caa ggt ctg gtc tgg gac ttt gtc cag agc    2938
```

```
                                                                    -continued Thr Asn Asn Val Ile Gly Gln Gly Leu Val Trp Asp Phe Val Gln Ser
            870                 875                 880 aac tgg aag aag ctt ttt aac gat tat ggt ggt ggc tcg ttc tcc ttc    2986
Asn Trp Lys Lys Leu Phe Asn Asp Tyr Gly Gly Gly Ser Phe Ser Phe
        885                 890                 895 tcc aac ctc atc cag gca gtg aca cga cga ttc tcc acc gag tat gag    3034
Ser Asn Leu Ile Gln Ala Val Thr Arg Arg Phe Ser Thr Glu Tyr Glu
900                 905                 910 ctg cag cag ctg gag cag ttc aag aag gac aac gag gaa aca ggc ttc    3082
Leu Gln Gln Leu Glu Gln Phe Lys Lys Asp Asn Glu Glu Thr Gly Phe
915                 920                 925                 930 ggc tca ggc acc cgg gcc ctg gag caa gcc ctg gag aag acg aaa gcc    3130
Gly Ser Gly Thr Arg Ala Leu Glu Gln Ala Leu Glu Lys Thr Lys Ala
                935                 940                 945 aac atc aag tgg gtg aag gag aac aag gag gtg gtg ctc cag tgg ttc    3178
Asn Ile Lys Trp Val Lys Glu Asn Lys Glu Val Val Leu Gln Trp Phe
        950                 955                 960 aca gaa aac agc aaa tag tccccagccc ttgaagtcac ccggccccca           3226
Thr Glu Asn Ser Lys
            965 tgcaaggtgc ccacatgtgt ccatcccagc ggctggtgca gggcctccat tcctggagcc  3286 cgaggcacca gtgtcctccc ctcaaggaca aagtctccag cccacgttct ctctgcctgt  3346 gagccagtct agttcctgat gacccaggct gcctgagcac ctcccagccc ctgcccctca  3406 tgccaacccc gccctaggcc tggcatggca cctgtcgccc agtgccctgg ggctgatctc  3466 agggaagccc agctccaggg ccagatgagc agaagctctc gatggacaat gaacggcctt  3526 gctgggggcc gccctgtacc ctctttcacc tttccctaaa gaccctaaat ctgaggaatc  3586 aacaggcag cagatctgta tattttttc taagagaaaa tgtaaataaa ggatttctag   3646 atgaaaaaaa aaaaaaaaaa aaaaaaaaaa aaaaaaaaaa aaaaaaaaaa aaaaaaaaaa  3706 aaaaaaaaaa aaaaaaaaaa aaaaaaaaaa aaaa                             3740

<210> SEQ ID NO 24
<211> LENGTH: 967
<212> TYPE: PRT
<213> ORGANISM: Homo Sapiens

<400> SEQUENCE: 24

Met Ala Lys Gly Phe Tyr Ile Ser Lys Ser Leu Gly Ile Leu Gly Ile
1               5                   10                  15

Leu Leu Gly Val Ala Ala Val Cys Thr Ile Ile Ala Leu Ser Val Val
            20                  25                  30

Tyr Ser Gln Glu Lys Asn Lys Asn Ala Asn Ser Ser Pro Val Ala Ser
        35                  40                  45

Thr Thr Pro Ser Ala Ser Ala Thr Thr Asn Pro Ala Ser Ala Thr Thr
    50                  55                  60

Leu Asp Gln Ser Lys Ala Trp Asn Arg Tyr Arg Leu Pro Asn Thr Leu
65                  70                  75                  80

Lys Pro Asp Ser Tyr Arg Val Thr Leu Arg Pro Tyr Leu Thr Pro Asn
                85                  90                  95

Asp Arg Gly Leu Tyr Val Phe Lys Gly Ser Ser Thr Val Arg Phe Thr
            100                 105                 110

Cys Lys Glu Ala Thr Asp Val Ile Ile Ile His Ser Lys Lys Leu Asn
        115                 120                 125

Tyr Thr Leu Ser Gln Gly His Arg Val Val Leu Arg Gly Val Gly Gly
    130                 135                 140
```

```
Ser Gln Pro Pro Asp Ile Asp Lys Thr Glu Leu Val Glu Pro Thr Glu
145                 150                 155                 160

Tyr Leu Val Val His Leu Lys Gly Ser Leu Val Lys Asp Ser Gln Tyr
                165                 170                 175

Glu Met Asp Ser Glu Phe Glu Gly Glu Leu Ala Asp Asp Leu Ala Gly
            180                 185                 190

Phe Tyr Arg Ser Glu Tyr Met Glu Gly Asn Val Arg Lys Val Val Ala
        195                 200                 205

Thr Thr Gln Met Gln Ala Ala Asp Ala Arg Lys Ser Phe Pro Cys Phe
    210                 215                 220

Asp Glu Pro Ala Met Lys Ala Glu Phe Asn Ile Thr Leu Ile His Pro
225                 230                 235                 240

Lys Asp Leu Thr Ala Leu Ser Asn Met Leu Pro Lys Gly Pro Ser Thr
                245                 250                 255

Pro Leu Pro Glu Asp Pro Asn Trp Asn Val Thr Glu Phe His Thr Thr
            260                 265                 270

Pro Lys Met Ser Thr Tyr Leu Leu Ala Phe Ile Val Ser Glu Phe Asp
        275                 280                 285

Tyr Val Glu Lys Gln Ala Ser Asn Gly Val Leu Ile Arg Ile Trp Ala
    290                 295                 300

Arg Pro Ser Ala Ile Ala Ala Gly His Gly Asp Tyr Ala Leu Asn Val
305                 310                 315                 320

Thr Gly Pro Ile Leu Asn Phe Phe Ala Gly His Tyr Asp Thr Pro Tyr
                325                 330                 335

Pro Leu Pro Lys Ser Asp Gln Ile Gly Leu Pro Asp Phe Asn Ala Gly
            340                 345                 350

Ala Met Glu Asn Trp Gly Leu Val Thr Tyr Arg Glu Asn Ser Leu Leu
        355                 360                 365

Phe Asp Pro Leu Ser Ser Ser Ser Asn Lys Glu Arg Val Val Thr
370                 375                 380

Val Ile Ala His Glu Leu Ala His Gln Trp Phe Gly Asn Leu Val Thr
385                 390                 395                 400

Ile Glu Trp Trp Asn Asp Leu Trp Leu Asn Glu Gly Phe Ala Ser Tyr
                405                 410                 415

Val Glu Tyr Leu Gly Ala Asp Tyr Ala Glu Pro Thr Trp Asn Leu Lys
            420                 425                 430

Asp Leu Met Val Leu Asn Asp Val Tyr Arg Val Met Ala Val Asp Ala
        435                 440                 445

Leu Ala Ser Ser His Pro Leu Ser Thr Pro Ala Ser Glu Ile Asn Thr
    450                 455                 460

Pro Ala Gln Ile Ser Glu Leu Phe Asp Ala Ile Ser Tyr Ser Lys Gly
465                 470                 475                 480

Ala Ser Val Leu Arg Met Leu Ser Ser Phe Leu Ser Glu Asp Val Phe
                485                 490                 495

Lys Gln Gly Leu Ala Ser Tyr Leu His Thr Phe Ala Tyr Gln Asn Thr
            500                 505                 510

Ile Tyr Leu Asn Leu Trp Asp His Leu Gln Glu Ala Val Asn Asn Arg
        515                 520                 525

Ser Ile Gln Leu Pro Thr Thr Val Arg Asp Ile Met Asn Arg Trp Thr
    530                 535                 540

Leu Gln Met Gly Phe Pro Val Ile Thr Val Asp Thr Ser Thr Gly Thr
545                 550                 555                 560
```

-continued

Leu Ser Gln Glu His Phe Leu Leu Asp Pro Asp Ser Asn Val Thr Arg
            565                 570                 575

Pro Ser Glu Phe Asn Tyr Val Trp Ile Val Pro Ile Thr Ser Ile Arg
            580                 585                 590

Asp Gly Arg Gln Gln Gln Asp Tyr Trp Leu Ile Asp Val Arg Ala Gln
            595                 600                 605

Asn Asp Leu Phe Ser Thr Ser Gly Asn Glu Trp Val Leu Leu Asn Leu
            610                 615                 620

Asn Val Thr Gly Tyr Tyr Arg Val Asn Tyr Asp Glu Asn Trp Arg
625                 630                 635                 640

Lys Ile Gln Thr Gln Leu Gln Arg Asp His Ser Ala Ile Pro Val Ile
            645                 650                 655

Asn Arg Ala Gln Ile Ile Asn Asp Ala Phe Asn Leu Ala Ser Ala His
            660                 665                 670

Lys Val Pro Val Thr Leu Ala Leu Asn Asn Thr Leu Phe Leu Ile Glu
            675                 680                 685

Glu Arg Gln Tyr Met Pro Trp Glu Ala Ala Leu Ser Ser Leu Ser Tyr
            690                 695                 700

Phe Lys Leu Met Phe Asp Arg Ser Glu Val Tyr Gly Pro Met Lys Asn
705                 710                 715                 720

Tyr Leu Lys Lys Gln Val Thr Pro Leu Phe Ile His Phe Arg Asn Asn
            725                 730                 735

Thr Asn Asn Trp Arg Glu Ile Pro Glu Asn Leu Met Asp Gln Tyr Ser
            740                 745                 750

Glu Val Asn Ala Ile Ser Thr Ala Cys Ser Asn Gly Val Pro Glu Cys
            755                 760                 765

Glu Glu Met Val Ser Gly Leu Phe Lys Gln Trp Met Glu Asn Pro Asn
            770                 775                 780

Asn Asn Pro Ile His Pro Asn Leu Arg Ser Thr Val Tyr Cys Asn Ala
785                 790                 795                 800

Ile Ala Gln Gly Gly Glu Glu Trp Asp Phe Ala Trp Glu Gln Phe
            805                 810                 815

Arg Asn Ala Thr Leu Val Asn Glu Ala Asp Lys Leu Arg Ala Ala Leu
            820                 825                 830

Ala Cys Ser Lys Glu Leu Trp Ile Leu Asn Arg Tyr Leu Ser Tyr Thr
            835                 840                 845

Leu Asn Pro Asp Leu Ile Arg Lys Gln Asp Ala Thr Ser Thr Ile Ile
            850                 855                 860

Ser Ile Thr Asn Asn Val Ile Gly Gln Gly Leu Val Trp Asp Phe Val
865                 870                 875                 880

Gln Ser Asn Trp Lys Lys Leu Phe Asn Asp Tyr Gly Gly Gly Ser Phe
            885                 890                 895

Ser Phe Ser Asn Leu Ile Gln Ala Val Thr Arg Arg Phe Ser Thr Glu
            900                 905                 910

Tyr Glu Leu Gln Gln Leu Glu Gln Phe Lys Lys Asp Asn Glu Glu Thr
            915                 920                 925

Gly Phe Gly Ser Gly Thr Arg Ala Leu Glu Gln Ala Leu Glu Lys Thr
            930                 935                 940

Lys Ala Asn Ile Lys Trp Val Lys Glu Asn Lys Glu Val Val Leu Gln
945                 950                 955                 960

Trp Phe Thr Glu Asn Ser Lys
            965

```
<210> SEQ ID NO 25
<211> LENGTH: 1300
<212> TYPE: DNA
<213> ORGANISM: Homo Sapiens
<220> FEATURE:
<221> NAME/KEY: CDS
<222> LOCATION: (84)...(773)
<223> OTHER INFORMATION: CD79b

<400> SEQUENCE: 25
ctgcagccgg tgcagttaca cgttttcctc caaggagcct cggacgttgt cacgggtttg      60
gggtcgggga cagagcggtg acc atg gcc agg ctg gcg ttg tct cct gtg ccc    113
                         Met Ala Arg Leu Ala Leu Ser Pro Val Pro
                           1               5                  10 agc cac tgg atg gtg gcg ttg ctg ctg ctc tca gct gag cca gta            161
Ser His Trp Met Val Ala Leu Leu Leu Leu Ser Ala Glu Pro Val
             15                  20                  25 cca gca gcc aga tcg gag gac cgg tac cgg aat ccc aaa ggt agt gct       209
Pro Ala Ala Arg Ser Glu Asp Arg Tyr Arg Asn Pro Lys Gly Ser Ala
                 30                  35                  40 tgt tcg cgg atc tgg cag agc cca cgt ttc ata gcc agg aaa cgg ggc       257
Cys Ser Arg Ile Trp Gln Ser Pro Arg Phe Ile Ala Arg Lys Arg Gly
             45                  50                  55 ttc acg gtg aaa atg cac tgc tac atg aac agc gcc tcc ggc aat gtg       305
Phe Thr Val Lys Met His Cys Tyr Met Asn Ser Ala Ser Gly Asn Val
         60                  65                  70 agc tgg ctc tgg aag cag gag atg gac gag aat ccc cag cag ctg aag       353
Ser Trp Leu Trp Lys Gln Glu Met Asp Glu Asn Pro Gln Gln Leu Lys
 75                  80                  85                  90 ctg gaa aag ggc cgc atg gaa gag tcc cag aac gaa tct ctc gcc acc       401
Leu Glu Lys Gly Arg Met Glu Glu Ser Gln Asn Glu Ser Leu Ala Thr
                 95                 100                 105 ctc acc atc caa ggc atc cgg ttt gag gac aat ggc atc tac ttc tgt       449
Leu Thr Ile Gln Gly Ile Arg Phe Glu Asp Asn Gly Ile Tyr Phe Cys
             110                 115                 120 cag cag aag tgc aac aac acc tcg gag gtc tac cag ggc tgc ggc aca       497
Gln Gln Lys Cys Asn Asn Thr Ser Glu Val Tyr Gln Gly Cys Gly Thr
         125                 130                 135 gag ctg cga gtc atg gga ttc agc acc ttg gca cag ctg aag cag agg       545
Glu Leu Arg Val Met Gly Phe Ser Thr Leu Ala Gln Leu Lys Gln Arg
    140                 145                 150 aac acg ctg aag gat ggt atc atc atg atc cag acg ctg ctg atc atc       593
Asn Thr Leu Lys Asp Gly Ile Ile Met Ile Gln Thr Leu Leu Ile Ile
155                 160                 165                 170 ctc ttc atc atc gtg cct atc ttc ctg ctg gac aag gat gac agc           641
Leu Phe Ile Ile Val Pro Ile Phe Leu Leu Asp Lys Asp Asp Ser
                175                 180                 185 aag gct ggc atg gag gaa gat cac acc tac gag ggc ctg gac att gac       689
Lys Ala Gly Met Glu Glu Asp His Thr Tyr Glu Gly Leu Asp Ile Asp
            190                 195                 200 cag aca gcc acc tat gag gac ata gtg acg ctg cgg aca ggg gaa gtg       737
Gln Thr Ala Thr Tyr Glu Asp Ile Val Thr Leu Arg Thr Gly Glu Val
        205                 210                 215 aag tgg tct gta ggt gag cac cca ggc cag gag tga gagccaggtc            783
Lys Trp Ser Val Gly Glu His Pro Gly Gln Glu
    220                 225 gccccatgac ctgggtgcag gctccctggc tcagtgact gcttcggagc tgcctggctc     843
atggcccaac ccctttcctg gacccccag ctggcctctg aagctggccc accagagctg     903
ccatttgtct ccagcccctg gtccccagct cttgccaaag gcctggagt agaaggacaa    963
```

-continued

```
caggycagca acttggaggg agttctctgg ggatggacgg gacccagcct tctggggtg     1023 ctatgaggtg atccgtcccc acacatggga tgggggaggc agagactggt ccagagcccg     1083
caaatggact cggagccgag ggcctccag cagagcttgg aagggccat ggacccaact       1143 gggcccagga agagccacag gaacatcatt cctctcccgc aaccactccc accccaggga     1203
ggccctggcc tccagtgcct tccccgtgg aataaacggt gtgtcctgag aaaccacaaa      1263
aaaaaaaaaa aaaaaaaaaa aaaaaaaaaa aaaaaa                               1300
```

<210> SEQ ID NO 26
<211> LENGTH: 229
<212> TYPE: PRT
<213> ORGANISM: Homo Sapiens

<400> SEQUENCE: 26

```
Met Ala Arg Leu Ala Leu Ser Pro Val Pro Ser His Trp Met Val Ala
 1               5                  10                  15

Leu Leu Leu Leu Leu Ser Ala Glu Pro Val Pro Ala Ala Arg Ser Glu
             20                  25                  30

Asp Arg Tyr Arg Asn Pro Lys Gly Ser Ala Cys Ser Arg Ile Trp Gln
         35                  40                  45

Ser Pro Arg Phe Ile Ala Arg Lys Arg Gly Phe Thr Val Lys Met His
     50                  55                  60

Cys Tyr Met Asn Ser Ala Ser Gly Asn Val Ser Trp Leu Trp Lys Gln
 65                  70                  75                  80

Glu Met Asp Glu Asn Pro Gln Gln Leu Lys Leu Glu Lys Gly Arg Met
                 85                  90                  95

Glu Glu Ser Gln Asn Glu Ser Leu Ala Thr Leu Thr Ile Gln Gly Ile
            100                 105                 110

Arg Phe Glu Asp Asn Gly Ile Tyr Phe Cys Gln Gln Lys Cys Asn Asn
        115                 120                 125

Thr Ser Glu Val Tyr Gln Gly Cys Gly Thr Glu Leu Arg Val Met Gly
    130                 135                 140

Phe Ser Thr Leu Ala Gln Leu Lys Gln Arg Asn Thr Leu Lys Asp Gly
145                 150                 155                 160

Ile Ile Met Ile Gln Thr Leu Leu Ile Ile Leu Phe Ile Ile Val Pro
                165                 170                 175

Ile Phe Leu Leu Leu Asp Lys Asp Asp Ser Lys Ala Gly Met Glu Glu
            180                 185                 190

Asp His Thr Tyr Glu Gly Leu Asp Ile Asp Gln Thr Ala Thr Tyr Glu
        195                 200                 205

Asp Ile Val Thr Leu Arg Thr Gly Glu Val Lys Trp Ser Val Gly Glu
    210                 215                 220

His Pro Gly Gln Glu
225
```

<210> SEQ ID NO 27
<211> LENGTH: 1085
<212> TYPE: DNA
<213> ORGANISM: Homo Sapiens
<220> FEATURE:
<221> NAME/KEY: CDS
<222> LOCATION: (41)...(754)
<223> OTHER INFORMATION: CD33

<400> SEQUENCE: 27

```
tctgctcaca caggaagccc tggaagctgc ttcctcagac atg ccg ctg ctg cta      55
                                             Met Pro Leu Leu Leu
```

```
                              1               5
ctg ctg ccc ctg ctg tgg gca gac ttg acc cac agg ccc aaa atc ctc    103
Leu Leu Pro Leu Leu Trp Ala Asp Leu Thr His Arg Pro Lys Ile Leu
                    10              15                  20 atc cct ggc act cta gaa ccc ggc cac tcc aaa aac ctg acc tgc tct    151
Ile Pro Gly Thr Leu Glu Pro Gly His Ser Lys Asn Leu Thr Cys Ser
                25              30                  35 gtg tcc tgg gcc tgt gag cag gga aca ccc ccg atc ttc tcc tgg ttg    199
Val Ser Trp Ala Cys Glu Gln Gly Thr Pro Pro Ile Phe Ser Trp Leu
            40              45                  50 tca gct gcc ccc acc tcc ctg ggc ccc agg act act cac tcc tcg gtg    247
Ser Ala Ala Pro Thr Ser Leu Gly Pro Arg Thr Thr His Ser Ser Val
        55              60                  65 ctc ata atc acc cca cgg ccc cag gac cac ggc acc aac ctg acc tgt    295
Leu Ile Ile Thr Pro Arg Pro Gln Asp His Gly Thr Asn Leu Thr Cys
70              75                  80                  85 cag gtg aag ttc gct gga gct ggt gtg act acg gag aga acc atc cag    343
Gln Val Lys Phe Ala Gly Ala Gly Val Thr Thr Glu Arg Thr Ile Gln
                90                  95                  100 ctc aac gtc acc tat gtt cca cag aac cca aca act ggt atc ttt cca    391
Leu Asn Val Thr Tyr Val Pro Gln Asn Pro Thr Thr Gly Ile Phe Pro
            105                 110                 115 gga gat ggc tca ggg aaa caa gag acc aga gca gga gtg gtt cat ggg    439
Gly Asp Gly Ser Gly Lys Gln Glu Thr Arg Ala Gly Val Val His Gly
        120                 125                 130 gcc att gga gga gct ggt gtt aca gcc ctg ctc gct ctt tgt ctc tgc    487
Ala Ile Gly Gly Ala Gly Val Thr Ala Leu Leu Ala Leu Cys Leu Cys
    135                 140                 145 ctc atc ttc ttc ata gtg aag acc cac agg agg aaa gca gcc agg aca    535
Leu Ile Phe Phe Ile Val Lys Thr His Arg Arg Lys Ala Ala Arg Thr
150                 155                 160                 165 gca gtg ggc agg aat gac acc cac cct acc aca ggg tca gcc tcc ccg    583
Ala Val Gly Arg Asn Asp Thr His Pro Thr Thr Gly Ser Ala Ser Pro
                170                 175                 180 aaa cac cag aag aag tcc aag tta cat ggc ccc act gaa acc tca agc    631
Lys His Gln Lys Lys Ser Lys Leu His Gly Pro Thr Glu Thr Ser Ser
            185                 190                 195 tgt tca ggt gcc gcc cct act gtg gag atg gat gag gag ctg cat tat    679
Cys Ser Gly Ala Ala Pro Thr Val Glu Met Asp Glu Glu Leu His Tyr
        200                 205                 210 gct tcc ctc aac ttt cat ggg atg aat cct tcc aag gac acc tcc acc    727
Ala Ser Leu Asn Phe His Gly Met Asn Pro Ser Lys Asp Thr Ser Thr
    215                 220                 225 gaa tac tca gag gtc agg acc cag tga ggaacccaca agagcatcag          774
Glu Tyr Ser Glu Val Arg Thr Gln
230                 235 gctcagctag aagatccaca tcctctacag gtcggggacc aaaggctgat tcttggagat    834 ttaaccccc acaggcaatg ggtttataga cattatgtga gtttcctgct atattaacat    894
catcttagac tttgcaagca gagagtcgtg gaatcaaatc tgtgctcttt catttgctaa    954
gtgtatgatg tcacacaagc tccttaacct tccatgtctc cattttcttc tctgtgaagt    1014
aggtataaga agtcctatct catagggatg ctgtgagcat taaataaagg tacacatgga    1074
aaacaccagt c                                                         1085

<210> SEQ ID NO 28
<211> LENGTH: 237
<212> TYPE: PRT
<213> ORGANISM: Homo Sapiens
```

<400> SEQUENCE: 28

```
Met Pro Leu Leu Leu Leu Pro Leu Leu Trp Ala Asp Leu Thr His
1               5                   10                  15

Arg Pro Lys Ile Leu Ile Pro Gly Thr Leu Glu Pro Gly His Ser Lys
            20                  25                  30

Asn Leu Thr Cys Ser Val Ser Trp Ala Cys Glu Gln Gly Thr Pro Pro
        35                  40                  45

Ile Phe Ser Trp Leu Ser Ala Ala Pro Thr Ser Leu Gly Pro Arg Thr
50                  55                  60

Thr His Ser Ser Val Leu Ile Ile Thr Pro Arg Pro Gln Asp His Gly
65                  70                  75                  80

Thr Asn Leu Thr Cys Gln Val Lys Phe Ala Gly Ala Gly Val Thr Thr
                85                  90                  95

Glu Arg Thr Ile Gln Leu Asn Val Thr Tyr Val Pro Gln Asn Pro Thr
            100                 105                 110

Thr Gly Ile Phe Pro Gly Asp Gly Ser Gly Lys Gln Glu Thr Arg Ala
        115                 120                 125

Gly Val Val His Gly Ala Ile Gly Gly Ala Gly Val Thr Ala Leu Leu
130                 135                 140

Ala Leu Cys Leu Cys Leu Ile Phe Phe Ile Val Lys Thr His Arg Arg
145                 150                 155                 160

Lys Ala Ala Arg Thr Ala Val Gly Arg Asn Asp Thr His Pro Thr Thr
                165                 170                 175

Gly Ser Ala Ser Pro Lys His Gln Lys Lys Ser Lys Leu His Gly Pro
        180                 185                 190

Thr Glu Thr Ser Ser Cys Ser Gly Ala Ala Pro Thr Val Glu Met Asp
    195                 200                 205

Glu Leu His Tyr Ala Ser Leu Asn Phe His Gly Met Asn Pro Ser
210                 215                 220

Lys Asp Thr Ser Thr Glu Tyr Ser Glu Val Arg Thr Gln
225                 230                 235
```

<210> SEQ ID NO 29
<211> LENGTH: 914
<212> TYPE: DNA
<213> ORGANISM: Homo Sapiens
<220> FEATURE:
<221> NAME/KEY: CDS
<222> LOCATION: (156)...(773)
<223> OTHER INFORMATION: HSPB1

<400> SEQUENCE: 29

```
gcatggggag gggcggccct caaacgggtc attgccatta atagagacct caaacaccgc      60
ctgctaaaaa tacccgactg gaggagcata aaagcgcagc cgagcccagc gccccgcact    120
tttctgagca gacgtccaga gcagagtcag ccagc atg acc gag cgc cgc gtc       173
                                       Met Thr Glu Arg Arg Val
                                         1               5 ccc ttc tcg ctc ctg cgg ggc ccc agc tgg gac ccc ttc cgc gac tgg      221
Pro Phe Ser Leu Leu Arg Gly Pro Ser Trp Asp Pro Phe Arg Asp Trp
         10                  15                  20 tac ccg cat agc cgc ctc ttc gac cag gcc ttc ggg ctg ccc cgg ctg      269
Tyr Pro His Ser Arg Leu Phe Asp Gln Ala Phe Gly Leu Pro Arg Leu
        25                  30                  35 ccg gag gag tgg tcg cag tgg tta ggc ggc agc agc tgg cca ggc tac      317
Pro Glu Glu Trp Ser Gln Trp Leu Gly Gly Ser Ser Trp Pro Gly Tyr
    40                  45                  50
```

```
gtg cgc ccc ctg ccc ccc gcc gcc atc gag agc ccc gca gtg gcc gcg        365
Val Arg Pro Leu Pro Pro Ala Ala Ile Glu Ser Pro Ala Val Ala Ala
 55                  60                  65                  70 ccc gcc tac agc cgc gcg ctc agc cgg caa ctc agc agc ggg gtc tcg        413
Pro Ala Tyr Ser Arg Ala Leu Ser Arg Gln Leu Ser Ser Gly Val Ser
                 75                  80                  85 gag atc cgg cac act gcg gac cgc tgg cgc gtg tcc ctg gat gtc aac        461
Glu Ile Arg His Thr Ala Asp Arg Trp Arg Val Ser Leu Asp Val Asn
             90                  95                 100 cac ttc gcc ccg gac gag ctg acg gtc aag acc aag gat ggc gtg gtg        509
His Phe Ala Pro Asp Glu Leu Thr Val Lys Thr Lys Asp Gly Val Val
         105                 110                 115 gag atc acc ggc aag cac gag gag cgg cag gac gag cat ggc tac atc        557
Glu Ile Thr Gly Lys His Glu Glu Arg Gln Asp Glu His Gly Tyr Ile
     120                 125                 130 tcc cgg tgc ttc acg cgg aaa tac acg ctg ccc ccc ggt gtg gac ccc        605
Ser Arg Cys Phe Thr Arg Lys Tyr Thr Leu Pro Pro Gly Val Asp Pro
135                 140                 145                 150 acc caa gtt tcc tcc tcc ctg tcc cct gag ggc aca ctg acc gtg gag        653
Thr Gln Val Ser Ser Ser Leu Ser Pro Glu Gly Thr Leu Thr Val Glu
                155                 160                 165 gcc ccc atg ccc aag cta gcc acg cag tcc aac gag atc acc atc cca        701
Ala Pro Met Pro Lys Leu Ala Thr Gln Ser Asn Glu Ile Thr Ile Pro
            170                 175                 180 gtc acc ttc gag tcg cgg gcc cag ctt ggg ggc cca gaa gct gca aaa        749
Val Thr Phe Glu Ser Arg Ala Gln Leu Gly Gly Pro Glu Ala Ala Lys
        185                 190                 195 tcc gat gag act gcc gcc aag taa agccttagcc cggatgccca cccctgctgc      803
Ser Asp Glu Thr Ala Ala Lys
    200                 205 cgccactggc tgtgcctccc ccgccacctg tgtgttcttt tgatacattt atcttctgtt    863
tttctcaaat aaagttcaaa gcaaccacct gtcaaaaaaa aaaaaaaaaa a              914

<210> SEQ ID NO 30
<211> LENGTH: 205
<212> TYPE: PRT
<213> ORGANISM: Homo Sapiens

<400> SEQUENCE: 30

Met Thr Glu Arg Arg Val Pro Phe Ser Leu Leu Arg Gly Pro Ser Trp
 1               5                  10                  15

Asp Pro Phe Arg Asp Trp Tyr Pro His Ser Arg Leu Phe Asp Gln Ala
                20                  25                  30

Phe Gly Leu Pro Arg Leu Pro Glu Glu Trp Ser Gln Trp Leu Gly Gly
            35                  40                  45

Ser Ser Trp Pro Gly Tyr Val Arg Pro Leu Pro Ala Ala Ile Glu
         50                  55                  60

Ser Pro Ala Val Ala Ala Pro Ala Tyr Ser Arg Ala Leu Ser Arg Gln
 65                  70                  75                  80

Leu Ser Ser Gly Val Ser Glu Ile Arg His Thr Ala Asp Arg Trp
                 85                  90                  95

Val Ser Leu Asp Val Asn His Phe Ala Pro Asp Glu Leu Thr Val Lys
                100                 105                 110

Thr Lys Asp Gly Val Val Glu Ile Thr Gly Lys His Glu Glu Arg Gln
            115                 120                 125

Asp Glu His Gly Tyr Ile Ser Arg Cys Phe Thr Arg Lys Tyr Thr Leu
        130                 135                 140
```

```
Pro Pro Gly Val Asp Pro Thr Gln Val Ser Ser Leu Ser Pro Glu
145                 150                 155                 160

Gly Thr Leu Thr Val Glu Ala Pro Met Pro Lys Leu Ala Thr Gln Ser
            165                 170                 175

Asn Glu Ile Thr Ile Pro Val Thr Phe Glu Ser Arg Ala Gln Leu Gly
            180                 185                 190

Gly Pro Glu Ala Ala Lys Ser Asp Glu Thr Ala Ala Lys
        195                 200                 205

<210> SEQ ID NO 31
<211> LENGTH: 6492
<212> TYPE: DNA
<213> ORGANISM: Homo Sapiens
<220> FEATURE:
<221> NAME/KEY: CDS
<222> LOCATION: (494)...(1213)
<223> OTHER INFORMATION: Bcl2 (alpha)

<400> SEQUENCE: 31
tttctgtgaa gcagaagtct gggaatcgat ctggaaatcc tcctaatttt tactccctct      60
ccccgcgact cctgattcat tgggaagttt caaatcagct ataactggag agtgctgaag     120
attgatggga tcgttgcctt atgcatttgt tttggtttta caaaaaggaa acttgacaga     180
ggatcatgct gtacttaaaa aatacaacat cacagaggaa gtagactgat attaacaata     240
cttactaata ataacgtgcc tcatgaaata aagatccgaa aggaattgga ataaaaattt     300
cctgcatctc atgccaaggg ggaaacacca gaatcaagtg ttccgcgtga ttgaagacac     360 ccctcgtcc aagaatgcaa agcacatcca ataaaatagc tggattataa ctcctcttct     420
ttctctgggg gccgtggggt gggagctggg gcgagaggtg ccgttggccc ccgttgcttt     480
tcctctggga agg atg gcg cac gct ggg aga aca ggg tac gat aac cgg       529
            Met Ala His Ala Gly Arg Thr Gly Tyr Asp Asn Arg
                1               5                   10 gag ata gtg atg aag tac atc cat tat aag ctg tcg cag agg ggc tac      577
Glu Ile Val Met Lys Tyr Ile His Tyr Lys Leu Ser Gln Arg Gly Tyr
        15                  20                  25 gag tgg gat gcg gga gat gtg ggc gcc gcg ccc ccg ggg gcc gcc ccc      625
Glu Trp Asp Ala Gly Asp Val Gly Ala Ala Pro Pro Gly Ala Ala Pro
    30                  35                  40 gca ccg ggc atc ttc tcc tcc cag ccc ggg cac acg ccc cat cca gcc      673
Ala Pro Gly Ile Phe Ser Ser Gln Pro Gly His Thr Pro His Pro Ala
45                  50                  55                  60 gca tcc cgg gac ccg gtc gcc agg acc tcg ccg ctg cag acc ccg gct      721
Ala Ser Arg Asp Pro Val Ala Arg Thr Ser Pro Leu Gln Thr Pro Ala
                65                  70                  75 gcc ccc ggc gcc gcc gcg ggg cct gcg ctc agc ccg gtg cca cct gtg      769
Ala Pro Gly Ala Ala Ala Gly Pro Ala Leu Ser Pro Val Pro Pro Val
            80                  85                  90 gtc cac ctg acc ctc cgc cag gcc ggc gac gac ttc tcc cgc cgc tac      817
Val His Leu Thr Leu Arg Gln Ala Gly Asp Asp Phe Ser Arg Arg Tyr
        95                  100                 105 cgc cgc gac ttc gcc gag atg tcc agc cag ctg cac ctg acg ccc ttc      865
Arg Arg Asp Phe Ala Glu Met Ser Ser Gln Leu His Leu Thr Pro Phe
    110                 115                 120 acc gcg cgg gga cgc ttt gcc acg gtg gtg gag gag ctc ttc agg gac      913
Thr Ala Arg Gly Arg Phe Ala Thr Val Val Glu Glu Leu Phe Arg Asp
125                 130                 135                 140 ggg gtg aac tgg ggg agg att gtg gcc ttc ttt gag ttc ggt ggg gtc      961
Gly Val Asn Trp Gly Arg Ile Val Ala Phe Phe Glu Phe Gly Gly Val
```

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
|     |     |     | 145 |     |     |     |     | 150 |     |     |     |     | 155 |     |     |      |
| atg | tgt | gtg | gag | agc | gtc | aac | cgg | gag | atg | tcg | ccc | ctg | gtg | gac | aac | 1009 |
| Met | Cys | Val | Glu | Ser | Val | Asn | Arg | Glu | Met | Ser | Pro | Leu | Val | Asp | Asn |      |
|     |     |     | 160 |     |     |     |     | 165 |     |     |     |     | 170 |     |     |      |
| atc | gcc | ctg | tgg | atg | act | gag | tac | ctg | aac | cgg | cac | ctg | cac | acc | tgg | 1057 |
| Ile | Ala | Leu | Trp | Met | Thr | Glu | Tyr | Leu | Asn | Arg | His | Leu | His | Thr | Trp |      |
|     |     | 175 |     |     |     |     | 180 |     |     |     |     | 185 |     |     |     |      |
| atc | cag | gat | aac | gga | ggc | tgg | gat | gcc | ttt | gtg | gaa | ctg | tac | ggc | ccc | 1105 |
| Ile | Gln | Asp | Asn | Gly | Gly | Trp | Asp | Ala | Phe | Val | Glu | Leu | Tyr | Gly | Pro |      |
|     | 190 |     |     |     |     | 195 |     |     |     |     | 200 |     |     |     |     |      |
| agc | atg | cgg | cct | ctg | ttt | gat | ttc | tcc | tgg | ctg | tct | ctg | aag | act | ctg | 1153 |
| Ser | Met | Arg | Pro | Leu | Phe | Asp | Phe | Ser | Trp | Leu | Ser | Leu | Lys | Thr | Leu |      |
| 205 |     |     |     | 210 |     |     |     |     | 215 |     |     |     |     | 220 |     |      |
| ctc | agt | ttg | gcc | ctg | gtg | gga | gct | tgc | atc | acc | ctg | ggt | gcc | tat | ctg | 1201 |
| Leu | Ser | Leu | Ala | Leu | Val | Gly | Ala | Cys | Ile | Thr | Leu | Gly | Ala | Tyr | Leu |      |
|     |     |     |     | 225 |     |     |     |     | 230 |     |     |     |     | 235 |     |      |
| ggc | cac | aag | tga | agtcaacatg | cctgccccaa | acaaatatgc | aaaaggttca | | | | | | | | | 1253 |
| Gly | His | Lys |     |     |     |     |     |     |     |     |     |     |     |     |     |      |

```
ctaaagcagt agaaataata tgcattgtca gtgatgtacc atgaaacaaa gctgcaggct    1313
gtttaagaaa aaataacaca catataaaca tcacacacac agacagacac acacacacac    1373
aacaattaac agtcttcagg caaaacgtcg aatcagctat ttactgccaa agggaaatat    1433
catttatttt ttacattatt aagaaaaaaa gatttattta tttaagcag tcccatcaaa     1493
actcctgtct ttggaaatcc gaccactaat tgccaagcac cgcttcgtgt ggctccacct    1553
ggatgttctg tgcctgtaaa catagattcg cttttccatgt tgttggccgg atcaccatct   1613
gaagagcaga cggatggaaa aaggacctga tcattgggga agctggcttt ctggctgctg    1673
gaggctgggg agaaggtgtt cattcacttg catttctttg ccctgggggc tgtgatatta    1733
acagagggag ggttcctgtg ggggggaagtc catgcctccc tggcctgaag aagagactct   1793
ttgcatatga ctcacatgat gcatacctgg tgggaggaaa agagttggga acttcagatg    1853
gacctagtac ccactgagat ttccacgccg aaggacagcg atgggaaaaa tgcccttaaa    1913
tcataggaaa gtattttttt aagctaccaa ttgtgccgag aaaagcattt tagcaattta    1973
tacaatatca tccagtacct taagccctga ttgtgtatat tcatatattt tggatacgca    2033
ccccccaact cccaatactg gctctgtctg agtaagaaac agaatcctct ggaacttgag    2093
gaagtgaaca tttcggtgac ttccgcatca ggaaggctag agttacccag agcatcaggc    2153
cgccacaagt gcctgctttt aggagaccga agtccgcaga acctgcctgt gtcccagctt    2213
ggaggcctgg tcctggaact gagccggggc cctcactggc ctcctccagg atgatcaac     2273
agggcagtgt ggtctccgaa tgtctggaag ctgatggagc tcagaattcc actgtcaaga    2333
aagagcagta gagggtgtg gctgggcctg tcaccctggg gccctccagg taggcccgtt     2393
ttcacgtgga gcatgggagc cacgacccct cttaagacat gtatcactgt agagggaagg    2453
aacagaggcc ctgggcccctt cctatcagaa ggacatggtg aaggctggga acgtgaggag   2513
aggcaatggc cacggcccat tttggctgta gcacatggca cgttggctgt gtggccttgg    2573
cccacctgtg agtttaaagc aaggctttaa atgactttgg agagggtcac aaatcctaaa    2633
agaagcattg aagtgaggtg tcatggatta attgaccct gtctatggaa ttacatgtaa     2693
aacattatct tgtcactgta gtttggtttt atttgaaaac ctgacaaaaa aaagttcca    2753
ggtgtggaat atgggggtta tctgtacatc ctggggcatt aaaaaaaaaa tcaatggtgg    2813
ggaactataa agaagtaaca aaagaagtga catcttcagc aaataaacta ggaaattttt    2873
```

```
ttttcttcca gtttagaatc agccttgaaa cattgatgga ataactctgt ggcattattg    2933
cattatatac catttatctg tattaacttt ggaatgtact ctgttcaatg tttaatgctg    2993
tggttgatat ttcgaaagct gctttaaaaa aatacatgca tctcagcgtt ttttgtttt    3053 taattgtatt tagttatggc ctatacacta tttgtgagca aaggtgatcg ttttctgttt    3113 gagatttta tctcttgatt cttcaaaagc attctgagaa ggtgagataa gccctgagtc    3173
tcagctacct aagaaaaacc tggatgtcac tggccactga ggagctttgt ttcaaccaag    3233
tcatgtgcat ttccacgtca acagaattgt ttattgtgac agtatatct gttgtccctt    3293 tgaccttgtt tcttgaaggt ttcctcgtcc ctgggcaatt ccgcatttaa ttcatggtat    3353
tcaggattac atgcatgttt ggttaaaccc atgagattca ttcagttaaa aatccagatg    3413
gcaaatgacc agcagattca aatctatggt ggtttgacct ttagagagtt gctttacgtg    3473
gcctgtttca acacagaccc acccagagcc ctcctgccct ccttccgcgg gggctttctc    3533
atggctgtcc ttcagggtct tcctgaaatg cagtggtgct tacgctccac caagaaagca    3593
ggaaacctgt ggtatgaagc cagacctccc cggcgggcc cagggaacag aatgatcaga    3653
cctttgaatg attctaattt ttaagcaaaa tattatttta tgaaaggttt acattgtcaa    3713
agtgatgaat atggaatatc caatcctgtg ctgctatcct gccaaaatca ttttaatgga    3773
gtcagtttgc agtatgctcc acgtggtaag atcctccaag ctgctttaga agtaacaatg    3833
aagaacgtga acgtttttaa tataaagcct gttttgtctt ttgttgttgt tcaaacggga    3893
ttcacagagt atttgaaaaa tgtatatata ttaagaggtc acgggggcta attgctggct    3953
ggctgccttt tgctgtgggg ttttgttacc tggtttaat aacagtaaat gtgcccagcc    4013
tcttggcccc agaactgtac agtattgtgg ctgcacttgc tctaagagta gttgatgttg    4073
cattttcctt attgttaaaa acatgttaga agcaatgaat gtatataaaa gcctcaacta    4133
gtcatttttt tctcctcttc ttttttttca ttatatctaa ttattttgca gttgggcaac    4193
agagaaccat ccctattttg tattgaagag ggattcacat ctgcatctta actgctcttt    4253
atgaatgaaa aaacagtcct ctgtatgtac tcctctttac actggccagg gtcagagtta    4313
aatagagtat atgcactttc caaattgggg acaagggctc taaaaaaagc cccaaaggaa    4373
gaagaacatc tgagaacctc ctcggccctc ccagtccctc gctgcacaaa tactccgcaa    4433
gagaggccag aatgacagct gacagggtct atggccatcg ggtcgtctcc gaagatttgg    4493
caggggcaga aaactctggc aggcttaaga tttggaataa agtcacagaa ttaaggaagc    4553
acctcaattt agttcaaaca agacgccaac attctctcca cagctcactt acctctctgt    4613
gttcagatgt ggccttccat ttatatgtga tctttgttt attagtaaat gcttatcatc    4673
taaagatgta gctctggccc agtgggaaaa attaggaagt gattataaat cgagaggagt    4733
tataataatc aagattaaat gtaaataatc agggcaatcc caacacatgt ctagctttca    4793
cctccaggat ctattgagtg aacagaattg caaatagtct ctatttgtaa ttgaacttat    4853
cctaaaacaa atagtttata aatgtgaact taaactctaa ttaattccaa ctgtactttt    4913
aaggcagtgg ctgttttag actttcttat cacttatagt tagtaatgta cacctactct    4973
atcagagaaa aacaggaaag gctcgaaata caagccattc taaggaaatt agggagtcag    5033
ttgaaattct attctgatct tattctgtgg tgtcttttgc agcccagaca aatgtggtta    5093
cacacttttt aagaaataca attctacatt gtcaagctta tgaaggttcc aatcagatct    5153
ttattgttat tcaatttgga tctttcaggg atttttttt taaattatta tgggacaaag    5213
gacatttgtt ggaggggtgg gagggaggaa gaatttttaa atgtaaaaca ttcccaagtt    5273
```

```
tggatcaggg agttggaagt tttcagaata accagaacta agggtatgaa ggacctgtat    5333
tggggtcgat gtgatgcctc tgcgaagaac cttgtgtgac aaatgagaaa cattttgaag    5393
tttgtggtac gacctttaga ttccagagac atcagcatgg ctcaaagtgc agctccgttt    5453
ggcagtgcaa tggtataaat ttcaagctgg atatgtctaa tgggtattta acaataaat     5513 gtgcagtttt aactaacagg atatttaatg acaaccttct ggttggtagg gacatctgtt    5573
tctaaatgtt tattatgtac aatacagaaa aaaattttat aaaattaagc aatgtgaaac    5633
tgaattggag agtgataata caagtccttt agtcttaccc agtgaatcat tctgttccat    5693
gtctttggac aaccatgacc ttggacaatc atgaaatatg catctcactg gatgcaaaga    5753
aaatcagatg gagcatgaat ggtactgtac cggttcatct ggactgcccc agaaaaataa    5813
cttcaagcaa acatcctatc aacaacaagg ttgttctgca taccaagctg agcacagaag    5873
atgggaacac tggtggagga tggaaaggct cgctcaatca gaaaattct  gagactatta    5933 ataaataaga ctgtagtgta gatactgagt aaatccatgc acctaaacct tttggaaaat    5993
ctgccgtggg ccctccagat agctcatttc attaagtttt tccctccaag gtagaatttg    6053
caagagtgac agtggattgc atttcttttg gggaagcttc cttttggtgg ttttgtttat    6113
tataccttct taagttttca accaaggttt gcttttgttt tgagttactg gggttatttt    6173
tgttttaaat aaaaataagt gtacaataag tgtttttgta ttgaaagctt ttgttatcaa    6233
gattttcata cttttacctt ccatggctct ttttaagatt gatactttta agaggtggct    6293
gatattctgc aacactgtac acataaaaaa tacggtaagg atactttaca tggttaaggt    6353
aaagtaagtc tccagttggc caccattagc tataatggca ctttgtttgt gttgttggaa    6413
aaagtcacat tgccattaaa ctttccttgt ctgtctagtt aatattgtga agaaaaataa    6473
agtacagtgt gagatactg                                                 6492

<210> SEQ ID NO 32
<211> LENGTH: 239
<212> TYPE: PRT
<213> ORGANISM: Homo Sapiens

<400> SEQUENCE: 32

Met Ala His Ala Gly Arg Thr Gly Tyr Asp Asn Arg Glu Ile Val Met
  1               5                  10                  15

Lys Tyr Ile His Tyr Lys Leu Ser Gln Arg Gly Tyr Glu Trp Asp Ala
             20                  25                  30

Gly Asp Val Gly Ala Ala Pro Pro Gly Ala Ala Pro Ala Pro Gly Ile
         35                  40                  45

Phe Ser Ser Gln Pro Gly His Thr Pro His Pro Ala Ala Ser Arg Asp
     50                  55                  60

Pro Val Ala Arg Thr Ser Pro Leu Gln Thr Pro Ala Ala Pro Gly Ala
 65                  70                  75                  80

Ala Ala Gly Pro Ala Leu Ser Pro Val Pro Val Val His Leu Thr
                 85                  90                  95

Leu Arg Gln Ala Gly Asp Asp Phe Ser Arg Tyr Arg Arg Asp Phe
            100                 105                 110

Ala Glu Met Ser Ser Gln Leu His Leu Thr Pro Phe Thr Ala Arg Gly
            115                 120                 125

Arg Phe Ala Thr Val Val Glu Glu Leu Phe Arg Asp Gly Val Asn Trp
        130                 135                 140

Gly Arg Ile Val Ala Phe Phe Glu Phe Gly Gly Val Met Cys Val Glu
```

```
145                 150                 155                 160
Ser Val Asn Arg Glu Met Ser Pro Leu Val Asp Asn Ile Ala Leu Trp
                165                 170                 175

Met Thr Glu Tyr Leu Asn Arg His Leu His Thr Trp Ile Gln Asp Asn
            180                 185                 190

Gly Gly Trp Asp Ala Phe Val Glu Leu Tyr Gly Pro Ser Met Arg Pro
        195                 200                 205

Leu Phe Asp Phe Ser Trp Leu Ser Leu Lys Thr Leu Leu Ser Leu Ala
210                 215                 220

Leu Val Gly Ala Cys Ile Thr Leu Gly Ala Tyr Leu Gly His Lys
225                 230                 235

<210> SEQ ID NO 33
<211> LENGTH: 1207
<212> TYPE: DNA
<213> ORGANISM: Homo Sapiens
<220> FEATURE:
<221> NAME/KEY: CDS
<222> LOCATION: (494)...(1111)
<223> OTHER INFORMATION: Bcl2 beta

<400> SEQUENCE: 33
tttctgtgaa gcagaagtct gggaatcgat ctggaaatcc tcctaatttt tactccctct      60
ccccgcgact cctgattcat tgggaagttt caaatcagct ataactggag agtgctgaag     120
attgatggga tcgttgcctt atgcatttgt tttggtttta caaaaaggaa acttgacaga     180
ggatcatgct gtacttaaaa aatcaacat cacagaggaa gtagactgat attaacaata     240
```

```
cttactaata ataacgtgcc tcatgaaata aagatccgaa aggaattgga ataaaaattt     300
cctgcatctc atgccaaggg ggaaacacca gaatcaagtg ttccgcgtga ttgaagacac     360 ccctcgtcc aagaatgcaa agcacatcca ataaatagc tggattataa ctcctcttct      420
ttctctgggg gccgtggggt gggagctggg gcgagaggtg ccgttggccc cgttgctttt    480
tcctctggga agg atg gcg cac gct ggg aga aca ggg tac gat aac cgg     529
             Met Ala His Ala Gly Arg Thr Gly Tyr Asp Asn Arg
                 1               5                  10 gag ata gtg atg aag tac atc cat tat aag ctg tcg cag agg ggc tac      577
Glu Ile Val Met Lys Tyr Ile His Tyr Lys Leu Ser Gln Arg Gly Tyr
            15                  20                  25 gag tgg gat gcg gga gat gtg ggc gcc gcg ccc ccg ggg gcc gcc ccc      625
Glu Trp Asp Ala Gly Asp Val Gly Ala Ala Pro Pro Gly Ala Ala Pro
    30                  35                  40 gca ccg ggc atc ttc tcc tcc cag ccc ggg cac acg ccc cat cca gcc      673
Ala Pro Gly Ile Phe Ser Ser Gln Pro Gly His Thr Pro His Pro Ala
45                  50                  55                  60 gca tcc cgg gac ccg gtc gcc agg acc tcg ccg ctg cag acc ccg gct      721
Ala Ser Arg Asp Pro Val Ala Arg Thr Ser Pro Leu Gln Thr Pro Ala
                65                  70                  75 gcc ccc ggc gcc gcc gcg ggg cct gcg ctc agc ccg gtg cca cct gtg      769
Ala Pro Gly Ala Ala Ala Gly Pro Ala Leu Ser Pro Val Pro Pro Val
            80                  85                  90 gtc cac ctg acc ctc cgc cag gcc ggc gac gac ttc tcc cgc cgc tac      817
Val His Leu Thr Leu Arg Gln Ala Gly Asp Asp Phe Ser Arg Arg Tyr
        95                  100                 105 cgc cgc gac ttc gcc gag atg tcc agc cag ctg cac ctg acg ccc ttc      865
Arg Arg Asp Phe Ala Glu Met Ser Ser Gln Leu His Leu Thr Pro Phe
    110                 115                 120 acc gcg cgg gga cgc ttt gcc acg gtg gtg gag gag ctc ttc agg gac      913
Thr Ala Arg Gly Arg Phe Ala Thr Val Val Glu Glu Leu Phe Arg Asp
```

```
                125                 130                 135                 140
ggg gtg aac tgg ggg agg att gtg gcc ttc ttt gag ttc ggt ggg gtc        961
Gly Val Asn Trp Gly Arg Ile Val Ala Phe Phe Glu Phe Gly Gly Val
                145                 150                 155 atg tgt gtg gag agc gtc aac cgg gag atg tcg ccc ctg gtg gac aac       1009
Met Cys Val Glu Ser Val Asn Arg Glu Met Ser Pro Leu Val Asp Asn
        160                 165                 170 atc gcc ctg tgg atg act gag tac ctg aac cgg cac ctg cac acc tgg       1057
Ile Ala Leu Trp Met Thr Glu Tyr Leu Asn Arg His Leu His Thr Trp
            175                 180                 185 atc cag gat aac gga ggc tgg gta ggt gca ctt ggt gat gtg agt ctg       1105
Ile Gln Asp Asn Gly Gly Trp Val Gly Ala Leu Gly Asp Val Ser Leu
        190                 195                 200 ggc tga ggccacaggt ccgagatgcg ggggttggag tgcgggtggg ctcctggggc        1161
Gly
205 aatgggaggc tgtggagccg gcgaaataaa atcagagttg ttgcta                    1207

<210> SEQ ID NO 34
<211> LENGTH: 205
<212> TYPE: PRT
<213> ORGANISM: Homo Sapiens

<400> SEQUENCE: 34

Met Ala His Ala Gly Arg Thr Gly Tyr Asp Asn Arg Glu Ile Val Met
1               5                   10                  15

Lys Tyr Ile His Tyr Lys Leu Ser Gln Arg Gly Tyr Glu Trp Asp Ala
            20                  25                  30

Gly Asp Val Gly Ala Ala Pro Pro Gly Ala Ala Pro Ala Pro Gly Ile
        35                  40                  45

Phe Ser Ser Gln Pro Gly His Thr Pro His Pro Ala Ala Ser Arg Asp
    50                  55                  60

Pro Val Ala Arg Thr Ser Pro Leu Gln Thr Pro Ala Ala Pro Gly Ala
65                  70                  75                  80

Ala Ala Gly Pro Ala Leu Ser Pro Val Pro Pro Val Val His Leu Thr
                85                  90                  95

Leu Arg Gln Ala Gly Asp Asp Phe Ser Arg Arg Tyr Arg Arg Asp Phe
            100                 105                 110

Ala Glu Met Ser Ser Gln Leu His Leu Thr Pro Phe Thr Ala Arg Gly
        115                 120                 125

Arg Phe Ala Thr Val Val Glu Glu Leu Phe Arg Asp Gly Val Asn Trp
    130                 135                 140

Gly Arg Ile Val Ala Phe Phe Glu Phe Gly Gly Val Met Cys Val Glu
145                 150                 155                 160

Ser Val Asn Arg Glu Met Ser Pro Leu Val Asp Asn Ile Ala Leu Trp
                165                 170                 175

Met Thr Glu Tyr Leu Asn Arg His Leu His Thr Trp Ile Gln Asp Asn
            180                 185                 190

Gly Gly Trp Val Gly Ala Leu Gly Asp Val Ser Leu Gly
        195                 200                 205

<210> SEQ ID NO 35
<211> LENGTH: 3128
<212> TYPE: DNA
<213> ORGANISM: Homo Sapiens
<220> FEATURE:
<221> NAME/KEY: CDS
<222> LOCATION: (182)...(775)
```

<223> OTHER INFORMATION: CD164

<400> SEQUENCE: 35

```
atcgtccgag ccccacctcc ctcctcttcg cccccgcacg ccgaaaacag gggcctctca      60
cgtgacccct gcgcgctccc gcggggagc gtagtctcgg aggcggcgcc gcagggatt      120 gaggggttga ctgagcgttg cgagccttag ctttctcccg aacgccagcg ctgaggacac     180 g atg tcg cgg ctc tcc cgc tca ctg ctt tgg gcc gcc acc tgc ctg ggc     229
  Met Ser Arg Leu Ser Arg Ser Leu Leu Trp Ala Ala Thr Cys Leu Gly
  1               5                   10                  15 gtg ctc tgc gtg ctg tcc gcg gac aag aac acg acc cag cac ccg aac      277
Val Leu Cys Val Leu Ser Ala Asp Lys Asn Thr Thr Gln His Pro Asn
            20                  25                  30 gtg acg act tta gcg ccc atc tcc aac gta acc tcg gcg ccg gtg acg      325
Val Thr Thr Leu Ala Pro Ile Ser Asn Val Thr Ser Ala Pro Val Thr
        35                  40                  45 tcc ctc ccg ctg gtc acc act ccg gca cca gaa acc tgt gaa ggt cga      373
Ser Leu Pro Leu Val Thr Thr Pro Ala Pro Glu Thr Cys Glu Gly Arg
    50                  55                  60 aac agc tgc gtt tcc tgt ttt aat gtt agc gtt gtt aat act acc tgc      421
Asn Ser Cys Val Ser Cys Phe Asn Val Ser Val Val Asn Thr Thr Cys
65                  70                  75                  80 ttt tgg ata gaa tgt aaa gat gag agc tat tgt tca cat aac tca aca      469
Phe Trp Ile Glu Cys Lys Asp Glu Ser Tyr Cys Ser His Asn Ser Thr
                85                  90                  95 gtt agt gat tgt caa gtg ggg aac acg aca gac ttc tgt tcc gtt tcc      517
Val Ser Asp Cys Gln Val Gly Asn Thr Thr Asp Phe Cys Ser Val Ser
            100                 105                 110 acg gcc act cca gtg cca aca gcc aat tct aca gct aaa ccc aca gtt      565
Thr Ala Thr Pro Val Pro Thr Ala Asn Ser Thr Ala Lys Pro Thr Val
        115                 120                 125 cag ccc tcc cct tct aca act tcc aag aca gtt act aca tca ggt aca      613
Gln Pro Ser Pro Ser Thr Thr Ser Lys Thr Val Thr Thr Ser Gly Thr
    130                 135                 140 aca aat aac act gtg act cca acc tca caa cct gtg cga aag tct acc      661
Thr Asn Asn Thr Val Thr Pro Thr Ser Gln Pro Val Arg Lys Ser Thr
145                 150                 155                 160 ttt gat gca gcc agt ttc att gga gga att gtc ctg gtc ttg ggt gtg      709
Phe Asp Ala Ala Ser Phe Ile Gly Gly Ile Val Leu Val Leu Gly Val
                165                 170                 175 cag gct gta att ttc ttt ctt tat aaa ttc tgc aaa tct aaa gaa cga      757
Gln Ala Val Ile Phe Phe Leu Tyr Lys Phe Cys Lys Ser Lys Glu Arg
            180                 185                 190 aat tac cac act ctg taa acagacccat tgaattaata aggactggtg             805
Asn Tyr His Thr Leu
            195 attcatttgt gtaactcact gaagccaaaa tactatcttt taagatgtcc cacatggaag    865 acgctattcc aggatcttta aatttccatg gatgcatata ggatgtttgg gagcatcatc    925 cgtgaagaaa aaatcaatta aatcattgtg ttcaacagga atatttaaaa tattctgcat    985 gaatcctgtg gctgtcttat tttaaatagc tgctgctgtg ggattatatt ttttttcctt   1045 aacatgccaa atataacttt ctgaaagtga tggaaaatgt tgtcttgtgc agacaacatc   1105 atggctcttg gcagtttaaa tttagtaatt ttaatttagt gaacagaatt gagaagaacg   1165 tgccaaatga gaatcaatta ggtggatttt tggctgtcat ttcaaaagtg gaataaattt   1225 attaatttag tagtactaaa tggtatcctt agattaaaat tttgtgcttg ataacagctg   1285 tttttttctac attagaaata agatgccaca caaggaacta cattccagat ttaaagaaat   1345
```

```
gaaaggatac cattagtgtg tataacagat tattgttcat acttgtaaag catcttatgt   1405
cattgagaat ataaagaaca gtgccttaga agacagtgaa aggtaagctc tagcttaatg   1465
tctatgattt gttctttgac attaaggaag gtaaggattg gtcagaggat gtaacttgat   1525
gtgagcagta gtaaacctgt tttagatatc atactgttaa tattttattg aaaatttatt   1585
tcagagcgga gaaacttaag ctaaagtctg ttatacagaa ttgaaagcct tcgtatcttg   1645
aacctcccaa catttttctt atggctgttg aaaagtatag agctaaattg atttaattac   1705
actttccttt gtactttaaa aaaaagtatg ctagcactat tgtaccttga aaggatttcc   1765
accagactgt cttgagtagt gacttctttg gtgaggcaag aaggatatac attattttag   1825
aatcatttac tatttaaatg agacaatcat attattttag aatcatttat tttaaatgag   1885
acaatcattt taagttttaa gataacagaa gtgaccaatg taatttcaca cacctaagg    1945 attttttggt tgatcaggtt actgtagatt tttactgatt gtcctggatg aatagactgt   2005
gcttttctct tttctctccc ttccttcttg gtttcccata gtataataag catgcatact   2065
ttaacttcta tagttttctc ctttagaggg tcgtcttcag ttttagaggt ttacttctcc   2125
cttgcctttg actcattgga ctagtgcaga ggctttaagt agtttaaaat gggcttttgc   2185
ttttctaggt cattaacgtt ttttatttag tttctttagc caatagtggc tgagtttcgc   2245
acttgatttt caatatttta tagtaagaaa tgacaaactg ctttgtttca tttcataaac   2305
aaactctgca tttagataac tattaaaggt tgttaagatg aagatttact gtttctttgt   2365
tactcgttgg tacagctgtt tgttttactt gcacatttgt acatatactt aatgttttca   2425
agtgccttaa ttgtttaaaa tctctggctt caaagtttct tggggaaagg tcggtttacc   2485
tcacattttt tgtttccatt agtaatattc taggtacctc acaaaatgta ttatggtgcc   2545
atggctgtta gtttttagtg agtgctgtag gattaattcg aaaataggca gaattccatt   2605
cctcccaagg tggcaaaaat tagctatact gatgtaattg tcatttacct gggtatgaat   2665
tccctgacac acattcatgt caacatatgt agcaaatttt gtgaaaacat aacaatttga   2725
agcttctgta atttttgagca ctgctctaac aacaagcata atataaaatt agttagattt   2785
tgcaagtcta caaatgagct cttgcaacag aactcacagc cttttactt ttttccccta    2845 actttagcaa tgtagtatct tgagccatta attttttgggt tttttttaaaa tccagaaggt  2905 atatagaaac cttttcagat ttttcatctg atttgttctt gcagatgttc ttctatcaaa   2965 taccttatttt taccttacag atatttgttg cacaggcaga tactgctgta tttagacatt  3025
tctatttcag ttcattaaaa actgcaaaac caatctgtat catgtaccaa actgacttaa   3085
aataaatcta catgtttatt gaattaaaaa aaaaaaaaaa aaa                     3128
```

<210> SEQ ID NO 36
<211> LENGTH: 197
<212> TYPE: PRT
<213> ORGANISM: Homo Sapiens

<400> SEQUENCE: 36

```
Met Ser Arg Leu Ser Arg Ser Leu Leu Trp Ala Ala Thr Cys Leu Gly
 1               5                  10                  15

Val Leu Cys Val Leu Ser Ala Asp Lys Asn Thr Thr Gln His Pro Asn
            20                  25                  30

Val Thr Thr Leu Ala Pro Ile Ser Asn Val Thr Ser Ala Pro Val Thr
        35                  40                  45

Ser Leu Pro Leu Val Thr Thr Pro Ala Pro Glu Thr Cys Glu Gly Arg
```

```
                  50                  55                  60
Asn Ser Cys Val Ser Cys Phe Asn Val Ser Val Val Asn Thr Thr Cys
 65                  70                  75                  80

Phe Trp Ile Glu Cys Lys Asp Glu Ser Tyr Cys Ser His Asn Ser Thr
                 85                  90                  95

Val Ser Asp Cys Gln Val Gly Asn Thr Thr Asp Phe Cys Ser Val Ser
            100                 105                 110

Thr Ala Thr Pro Val Pro Thr Ala Asn Ser Thr Ala Lys Pro Thr Val
        115                 120                 125

Gln Pro Ser Pro Ser Thr Thr Ser Lys Thr Val Thr Thr Ser Gly Thr
    130                 135                 140

Thr Asn Asn Thr Val Thr Pro Thr Ser Gln Pro Val Arg Lys Ser Thr
145                 150                 155                 160

Phe Asp Ala Ala Ser Phe Ile Gly Gly Ile Val Leu Val Leu Gly Val
                165                 170                 175

Gln Ala Val Ile Phe Phe Leu Tyr Lys Phe Cys Lys Ser Lys Glu Arg
            180                 185                 190

Asn Tyr His Thr Leu
        195

<210> SEQ ID NO 37
<211> LENGTH: 2478
<212> TYPE: DNA
<213> ORGANISM: Homo Sapiens
<220> FEATURE:
<221> NAME/KEY: CDS
<222> LOCATION: (524)...(2458)
<223> OTHER INFORMATION: CD304

<400> SEQUENCE: 37
gcagttggtg aaactcctct gtctcccgct catcttttca ttgctcgttc ccctccttcc      60
cgcagacacc cggacctccc ctgggcgcca gctccgcggc tccaacgggt ccagaaacaa     120
gccggatttt ttttttttct tcctggaaat tggctttggt gtgtgttgcc ctacctccct     180
cctccccctc ccacccacag cccccccccg gcctttttt ttttttttt ttttttgag       240 acatggcccg ggcagtggct cctggaagag gaacaagtgt gggaaaaggg agaggaagcc     300
ggagctaaat gacaggatgc aggcgacttg agacacaaaa agagaagcgt cctctcgga      360 tccaggcatt gcctcgctgc tttcttttct ccaagacggg ctgaggattg tacagctcta     420
ggcggagttg ggctcttccg gatcgcttag attctcctct ttgctgcatt tcccccacg      480 tcctcgttct cccgcgtctg cctgcggacc cggagaaggg aga atg gag agg ggg       535
                                              Met Glu Arg Gly
                                              1 ctg ccg ctc ctc tgc gcc gtg ctc gcc ctc gtc ctc gcc ccg gcc ggc       583
Leu Pro Leu Leu Cys Ala Val Leu Ala Leu Val Leu Ala Pro Ala Gly
  5                  10                  15                  20 gct ttt cgc aac gat aaa tgt ggc gat act ata aaa att gaa agc ccc       631
Ala Phe Arg Asn Asp Lys Cys Gly Asp Thr Ile Lys Ile Glu Ser Pro
                 25                  30                  35 ggg tac ctt aca tct cct ggt tat cct cat tct tat cac cca agt gaa       679
Gly Tyr Leu Thr Ser Pro Gly Tyr Pro His Ser Tyr His Pro Ser Glu
             40                  45                  50 aaa tgc gaa tgg ctg att cag gct ccg gac cca tac cag aga att atg       727
Lys Cys Glu Trp Leu Ile Gln Ala Pro Asp Pro Tyr Gln Arg Ile Met
         55                  60                  65 atc aac ttc aac cct cac ttc gat ttg gag gac aga gac tgc aag tat       775
Ile Asn Phe Asn Pro His Phe Asp Leu Glu Asp Arg Asp Cys Lys Tyr
```

-continued

```
            70                  75                  80
gac tac gtg gaa gtc ttc gat gga gaa aat gaa aat gga cat ttt agg    823
Asp Tyr Val Glu Val Phe Asp Gly Glu Asn Glu Asn Gly His Phe Arg
 85                  90                  95                 100 gga aag ttc tgt gga aag ata gcc cct cct cct gtt gtg tct tca ggg    871
Gly Lys Phe Cys Gly Lys Ile Ala Pro Pro Pro Val Val Ser Ser Gly
                    105                 110                 115 cca ttt ctt ttt atc aaa ttt gtc tct gac tac gaa aca cat ggt gca    919
Pro Phe Leu Phe Ile Lys Phe Val Ser Asp Tyr Glu Thr His Gly Ala
                120                 125                 130 gga ttt tcc ata cgt tat gaa att ttc aag aga ggt cct gaa tgt tcc    967
Gly Phe Ser Ile Arg Tyr Glu Ile Phe Lys Arg Gly Pro Glu Cys Ser
            135                 140                 145 cag aac tac aca aca cct agt gga gtg ata aag tcc ccc gga ttc cct   1015
Gln Asn Tyr Thr Thr Pro Ser Gly Val Ile Lys Ser Pro Gly Phe Pro
        150                 155                 160 gaa aaa tat ccc aac agc ctt gaa tgc act tat att gtc ttt gcg cca   1063
Glu Lys Tyr Pro Asn Ser Leu Glu Cys Thr Tyr Ile Val Phe Ala Pro
165                 170                 175                 180 aag atg tca gag att atc ctg gaa ttt gaa agc ttt gac ctg gag cct   1111
Lys Met Ser Glu Ile Ile Leu Glu Phe Glu Ser Phe Asp Leu Glu Pro
                    185                 190                 195 gac tca aat cct cca ggg ggg atg ttc tgt cgc tac gac cgg cta gaa   1159
Asp Ser Asn Pro Pro Gly Gly Met Phe Cys Arg Tyr Asp Arg Leu Glu
                200                 205                 210 atc tgg gat gga ttc cct gat gtt ggc cct cac att ggg cgt tac tgt   1207
Ile Trp Asp Gly Phe Pro Asp Val Gly Pro His Ile Gly Arg Tyr Cys
            215                 220                 225 gga cag aaa aca cca ggt cga atc cga tcc tca tcg ggc att ctc tcc   1255
Gly Gln Lys Thr Pro Gly Arg Ile Arg Ser Ser Ser Gly Ile Leu Ser
        230                 235                 240 atg gtt ttt tac acc gac agc gcg ata gca aaa gaa ggt ttc tca gca   1303
Met Val Phe Tyr Thr Asp Ser Ala Ile Ala Lys Glu Gly Phe Ser Ala
245                 250                 255                 260 aac tac agt gtc ttg cag agc agt gtc tca gaa gat ttc aaa tgt atg   1351
Asn Tyr Ser Val Leu Gln Ser Ser Val Ser Glu Asp Phe Lys Cys Met
                    265                 270                 275 gaa gct ctg ggc atg gaa tca gga gaa att cat tct gac cag atc aca   1399
Glu Ala Leu Gly Met Glu Ser Gly Glu Ile His Ser Asp Gln Ile Thr
                280                 285                 290 gct tct tcc cag tat agc acc aac tgg tct gca gag cgc tcc cgc ctg   1447
Ala Ser Ser Gln Tyr Ser Thr Asn Trp Ser Ala Glu Arg Ser Arg Leu
            295                 300                 305 aac tac cct gag aat ggg tgg act ccc gga gag gat tcc tac cga gag   1495
Asn Tyr Pro Glu Asn Gly Trp Thr Pro Gly Glu Asp Ser Tyr Arg Glu
        310                 315                 320 tgg ata cag gta gac ttg ggc ctt ctg cgc ttt gtc acg gct gtc ggg   1543
Trp Ile Gln Val Asp Leu Gly Leu Leu Arg Phe Val Thr Ala Val Gly
325                 330                 335                 340 aca cag ggc gcc att tca aaa gaa acc aag aag aaa tat tat gtc aag   1591
Thr Gln Gly Ala Ile Ser Lys Glu Thr Lys Lys Lys Tyr Tyr Val Lys
                    345                 350                 355 act tac aag atc gac gtt agc tcc aac ggg gaa gac tgg atc acc ata   1639
Thr Tyr Lys Ile Asp Val Ser Ser Asn Gly Glu Asp Trp Ile Thr Ile
                360                 365                 370 aaa gaa gga aac aaa cct gtt ctc ttt cag gga aac acc aac ccc aca   1687
Lys Glu Gly Asn Lys Pro Val Leu Phe Gln Gly Asn Thr Asn Pro Thr
            375                 380                 385 gat gtt gtg gtt gca gta ttc ccc aaa cca ctg ata act cga ttt gtc   1735
Asp Val Val Val Ala Val Phe Pro Lys Pro Leu Ile Thr Arg Phe Val
```

| | | | | | | | | | | | | | | |
|---|---|---|---|---|---|---|---|---|---|---|---|---|---|---|
| Asp | Val | Val | Ala | Val | Phe | Pro | Lys | Pro | Leu | Ile | Thr | Arg | Phe | Val |
| | 390 | | | | 395 | | | | 400 | | | | | |

```
cga atc aag cct gca act tgg gaa act ggc ata tct atg aga ttt gaa    1783
Arg Ile Lys Pro Ala Thr Trp Glu Thr Gly Ile Ser Met Arg Phe Glu
405                 410                 415                 420 gta tac ggt tgc aag ata aca gat tat cct tgc tct gga atg ttg ggt    1831
Val Tyr Gly Cys Lys Ile Thr Asp Tyr Pro Cys Ser Gly Met Leu Gly
                425                 430                 435 atg gtg tct gga ctt att tct gac tcc cag atc aca tca tcc aac caa    1879
Met Val Ser Gly Leu Ile Ser Asp Ser Gln Ile Thr Ser Ser Asn Gln
            440                 445                 450 ggg gac aga aac tgg atg cct gaa aac atc cgc ctg gta acc agt cgc    1927
Gly Asp Arg Asn Trp Met Pro Glu Asn Ile Arg Leu Val Thr Ser Arg
        455                 460                 465 tct ggc tgg gca ctt cca ccc gca cct cat tcc tac atc aat gag tgg    1975
Ser Gly Trp Ala Leu Pro Pro Ala Pro His Ser Tyr Ile Asn Glu Trp
    470                 475                 480 ctc caa ata gac ctg ggg gag gag aag atc gtg agg ggc atc atc att    2023
Leu Gln Ile Asp Leu Gly Glu Glu Lys Ile Val Arg Gly Ile Ile Ile
485                 490                 495                 500 cag ggt ggg aag cac cga gag aac aag gtg ttc atg agg aag ttc aag    2071
Gln Gly Gly Lys His Arg Glu Asn Lys Val Phe Met Arg Lys Phe Lys
                505                 510                 515 atc ggg tac agc aac aac ggc tcg gac tgg aag atg atc atg gat gac    2119
Ile Gly Tyr Ser Asn Asn Gly Ser Asp Trp Lys Met Ile Met Asp Asp
            520                 525                 530 agc aaa cgc aag gcg aag tct ttt gag ggc aac aac aac tat gat aca    2167
Ser Lys Arg Lys Ala Lys Ser Phe Glu Gly Asn Asn Asn Tyr Asp Thr
        535                 540                 545 cct gag ctg cgg act ttt cca gct ctc tcc acg cga ttc atc agg atc    2215
Pro Glu Leu Arg Thr Phe Pro Ala Leu Ser Thr Arg Phe Ile Arg Ile
    550                 555                 560 tac ccc gag aga gcc act cat ggc gga ctg ggg ctc aga atg gag ctg    2263
Tyr Pro Glu Arg Ala Thr His Gly Gly Leu Gly Leu Arg Met Glu Leu
565                 570                 575                 580 ctg ggc tgt gaa gtg gaa gcc cct aca gct gga ccg acc act ccc aac    2311
Leu Gly Cys Glu Val Glu Ala Pro Thr Ala Gly Pro Thr Thr Pro Asn
                585                 590                 595 ggg aac ttg gtg gat gaa tgt gat gac gac cag gcc aac tgc cac agt    2359
Gly Asn Leu Val Asp Glu Cys Asp Asp Asp Gln Ala Asn Cys His Ser
            600                 605                 610 gga aca ggt gat gac ttc cag ctc aca ggt ggc act gtg ctg gcc       2407
Gly Thr Gly Asp Asp Phe Gln Leu Thr Gly Gly Thr Thr Val Leu Ala
        615                 620                 625 aca gaa aag ccc acg gtc ata gac agc acc ata caa tca ggt atc aaa    2455
Thr Glu Lys Pro Thr Val Ile Asp Ser Thr Ile Gln Ser Gly Ile Lys
    630                 635                 640 taa aatacgaaat gtgacagatt                                          2478

<210> SEQ ID NO 38
<211> LENGTH: 644
<212> TYPE: PRT
<213> ORGANISM: Homo Sapiens

<400> SEQUENCE: 38

Met Glu Arg Gly Leu Pro Leu Leu Cys Ala Val Leu Ala Leu Val Leu
1               5                   10                  15

Ala Pro Ala Gly Ala Phe Arg Asn Asp Lys Cys Gly Asp Thr Ile Lys
            20                  25                  30
```

```
Ile Glu Ser Pro Gly Tyr Leu Thr Ser Pro Gly Tyr Pro His Ser Tyr
             35                  40                  45

His Pro Ser Glu Lys Cys Glu Trp Leu Ile Gln Ala Pro Asp Pro Tyr
 50                  55                  60

Gln Arg Ile Met Ile Asn Phe Asn Pro His Phe Asp Leu Glu Asp Arg
 65                  70                  75                  80

Asp Cys Lys Tyr Asp Tyr Val Glu Val Phe Asp Gly Glu Asn Glu Asn
                 85                  90                  95

Gly His Phe Arg Gly Lys Phe Cys Gly Lys Ile Ala Pro Pro Pro Val
                100                 105                 110

Val Ser Ser Gly Pro Phe Leu Phe Ile Lys Phe Val Ser Asp Tyr Glu
                115                 120                 125

Thr His Gly Ala Gly Phe Ser Ile Arg Tyr Glu Ile Phe Lys Arg Gly
        130                 135                 140

Pro Glu Cys Ser Gln Asn Tyr Thr Thr Pro Ser Gly Val Ile Lys Ser
145                 150                 155                 160

Pro Gly Phe Pro Glu Lys Tyr Pro Asn Ser Leu Glu Cys Thr Tyr Ile
                165                 170                 175

Val Phe Ala Pro Lys Met Ser Glu Ile Ile Leu Glu Phe Glu Ser Phe
                180                 185                 190

Asp Leu Glu Pro Asp Ser Asn Pro Pro Gly Gly Met Phe Cys Arg Tyr
            195                 200                 205

Asp Arg Leu Glu Ile Trp Asp Gly Phe Pro Asp Val Gly Pro His Ile
        210                 215                 220

Gly Arg Tyr Cys Gly Gln Lys Thr Pro Gly Arg Ile Arg Ser Ser Ser
225                 230                 235                 240

Gly Ile Leu Ser Met Val Phe Tyr Thr Asp Ser Ala Ile Ala Lys Glu
                245                 250                 255

Gly Phe Ser Ala Asn Tyr Ser Val Leu Gln Ser Ser Val Ser Glu Asp
                260                 265                 270

Phe Lys Cys Met Glu Ala Leu Gly Met Glu Ser Gly Glu Ile His Ser
            275                 280                 285

Asp Gln Ile Thr Ala Ser Ser Gln Tyr Ser Thr Asn Trp Ser Ala Glu
        290                 295                 300

Arg Ser Arg Leu Asn Tyr Pro Glu Asn Gly Trp Thr Pro Gly Glu Asp
305                 310                 315                 320

Ser Tyr Arg Glu Trp Ile Gln Val Asp Leu Gly Leu Leu Arg Phe Val
                325                 330                 335

Thr Ala Val Gly Thr Gln Gly Ala Ile Ser Lys Glu Thr Lys Lys Lys
            340                 345                 350

Tyr Tyr Val Lys Thr Tyr Lys Ile Asp Val Ser Ser Asn Gly Glu Asp
            355                 360                 365

Trp Ile Thr Ile Lys Glu Gly Asn Lys Pro Val Leu Phe Gln Gly Asn
        370                 375                 380

Thr Asn Pro Thr Asp Val Val Val Ala Val Phe Pro Lys Pro Leu Ile
385                 390                 395                 400

Thr Arg Phe Val Arg Ile Lys Pro Ala Thr Trp Glu Thr Gly Ile Ser
                405                 410                 415

Met Arg Phe Glu Val Tyr Gly Cys Lys Ile Thr Asp Tyr Pro Cys Ser
            420                 425                 430

Gly Met Leu Gly Met Val Ser Gly Leu Ile Ser Asp Ser Gln Ile Thr
        435                 440                 445

Ser Ser Asn Gln Gly Asp Arg Asn Trp Met Pro Glu Asn Ile Arg Leu
```

```
                450             455             460
Val Thr Ser Arg Ser Gly Trp Ala Leu Pro Pro Ala Pro His Ser Tyr
465                 470                 475                 480

Ile Asn Glu Trp Leu Gln Ile Asp Leu Gly Glu Lys Ile Val Arg
                485                 490                 495

Gly Ile Ile Ile Gln Gly Gly Lys His Arg Glu Asn Lys Val Phe Met
            500                 505                 510

Arg Lys Phe Lys Ile Gly Tyr Ser Asn Asn Gly Ser Asp Trp Lys Met
        515                 520                 525

Ile Met Asp Asp Ser Lys Arg Lys Ala Lys Ser Phe Glu Gly Asn Asn
            530                 535                 540

Asn Tyr Asp Thr Pro Glu Leu Arg Thr Phe Pro Ala Leu Ser Thr Arg
545                 550                 555                 560

Phe Ile Arg Ile Tyr Pro Glu Arg Ala Thr His Gly Gly Leu Gly Leu
                565                 570                 575

Arg Met Glu Leu Leu Gly Cys Glu Val Glu Ala Pro Thr Ala Gly Pro
            580                 585                 590

Thr Thr Pro Asn Gly Asn Leu Val Asp Glu Cys Asp Asp Gln Ala
            595                 600                 605

Asn Cys His Ser Gly Thr Gly Asp Asp Phe Gln Leu Thr Gly Gly Thr
            610                 615                 620

Thr Val Leu Ala Thr Glu Lys Pro Thr Val Ile Asp Ser Thr Ile Gln
625                 630                 635                 640

Ser Gly Ile Lys

<210> SEQ ID NO 39
<211> LENGTH: 3500
<212> TYPE: DNA
<213> ORGANISM: Homo Sapiens
<220> FEATURE:
<221> NAME/KEY: CDS
<222> LOCATION: (381)...(2888)
<223> OTHER INFORMATION: CD97

<400> SEQUENCE: 39
caccttcccc tcagagcagc cagccccaac acagaggcca aagggttcgt cagagccaca      60
tggtggaaac tctagcagag ggttttttgaa agcaggttgc acttcattct tactgagtgc     120
acgtgtgtgt gtgtgtgtgt gtgtgtgtgt gtgtgtgtgt gtatgcagcg cccctgggtc     180
tgtgttttta ttgcactttc ctgctggctt ccagctgcac cgccagttcc ggggagggcc     240
ctgggccagc ggctgtccgc cccccctcct tcataaagtc ctggcctcgg acagcctgc      300 acagctgcct agcctgtgga cgggacag ccctgtccca ctcactcttt ccctgccgc       360 tcctgccggc agctccaacc atg gga ggc cgc gtc ttt ctc gca ttc tgt gtc    413
                         Met Gly Gly Arg Val Phe Leu Ala Phe Cys Val
                           1               5                  10 tgg ctg act ctg ccg gga gct gaa acc cag gac tcc agg ggc tgt gcc       461
Trp Leu Thr Leu Pro Gly Ala Glu Thr Gln Asp Ser Arg Gly Cys Ala
        15                  20                  25 cgg tgg tgc cct cag aac tcc tcg tgt gtc aat gcc acc gcc tgt cgc       509
Arg Trp Cys Pro Gln Asn Ser Ser Cys Val Asn Ala Thr Ala Cys Arg
        30                  35                  40 tgc aat cca ggg ttc agc tct ttt tct gag atc atc acc acc ccg acg      557
Cys Asn Pro Gly Phe Ser Ser Phe Ser Glu Ile Ile Thr Thr Pro Thr
    45                  50                  55 gag act tgt gac gac atc aac gag tgt gca aca ccg tcg aaa gtg tca      605
Glu Thr Cys Asp Asp Ile Asn Glu Cys Ala Thr Pro Ser Lys Val Ser
60                  65                  70                  75
```

```
                60                  65                  70                  75
      tgc gga aaa ttc tcg gac tgc tgg aac aca gag ggg agc tac gac tgc         653
      Cys Gly Lys Phe Ser Asp Cys Trp Asn Thr Glu Gly Ser Tyr Asp Cys
                      80                  85                  90 gtg tgc agc ccg gga tat gag cct gtt tct ggg gca aaa aca ttc aag         701
      Val Cys Ser Pro Gly Tyr Glu Pro Val Ser Gly Ala Lys Thr Phe Lys
                  95                 100                 105 aat gag agc gag aac acc tgt caa gat gtg gac gaa tgt cag cag aac         749
      Asn Glu Ser Glu Asn Thr Cys Gln Asp Val Asp Glu Cys Gln Gln Asn
              110                 115                 120 cca agg ctc tgt aaa agc tac ggc acc tgc gtc aac acc ctt ggc agc         797
      Pro Arg Leu Cys Lys Ser Tyr Gly Thr Cys Val Asn Thr Leu Gly Ser
          125                 130                 135 tat acc tgc cag tgc ctg cct ggc ttc aag ttc ata cct gag gat ccg         845
      Tyr Thr Cys Gln Cys Leu Pro Gly Phe Lys Phe Ile Pro Glu Asp Pro
      140                 145                 150                 155 aag gtc tgc aca gat gtg aat gaa tgc acc tcc gga caa aac ccg tgc         893
      Lys Val Cys Thr Asp Val Asn Glu Cys Thr Ser Gly Gln Asn Pro Cys
                      160                 165                 170 cac agc tcc acc cac tgc ctc aac aac gtg ggc agc tat cag tgc cgc         941
      His Ser Ser Thr His Cys Leu Asn Asn Val Gly Ser Tyr Gln Cys Arg
                  175                 180                 185 tgc cgc ccg ggc tgg caa ccg att ccg ggg tcc ccc aat ggc cca aac         989
      Cys Arg Pro Gly Trp Gln Pro Ile Pro Gly Ser Pro Asn Gly Pro Asn
              190                 195                 200 aat acc gtc tgt gaa gat gtg gac gag tgc agc tcc ggg cag cat cag        1037
      Asn Thr Val Cys Glu Asp Val Asp Glu Cys Ser Ser Gly Gln His Gln
          205                 210                 215 tgt gac agc tcc acc gtc tgc ttc aac acc gtg ggt tca tac agc tgc        1085
      Cys Asp Ser Ser Thr Val Cys Phe Asn Thr Val Gly Ser Tyr Ser Cys
      220                 225                 230                 235 cgc tgc cgc cca ggc tgg aag ccc aga cac gga atc ccg aat aac caa        1133
      Arg Cys Arg Pro Gly Trp Lys Pro Arg His Gly Ile Pro Asn Asn Gln
                      240                 245                 250 aag gac act gtc tgt gaa gat atg act ttc tcc acc tgg acc ccg ccc        1181
      Lys Asp Thr Val Cys Glu Asp Met Thr Phe Ser Thr Trp Thr Pro Pro
                  255                 260                 265 cct gga gtc cac agc cag acg ctt tcc cga ttc ttc gac aaa gtc cag        1229
      Pro Gly Val His Ser Gln Thr Leu Ser Arg Phe Phe Asp Lys Val Gln
              270                 275                 280 gac ctg ggc aga gac tcc aag aca agc tca gcc gag gtc acc atc cag        1277
      Asp Leu Gly Arg Asp Ser Lys Thr Ser Ser Ala Glu Val Thr Ile Gln
          285                 290                 295 aat gtc atc aaa ttg gtg gat gaa ctg atg gaa gct cct gga gac gta        1325
      Asn Val Ile Lys Leu Val Asp Glu Leu Met Glu Ala Pro Gly Asp Val
      300                 305                 310                 315 gag gcc ctg gcg cca cct gtc cgg cac ctc ata gcc acc cag ctg ctc        1373
      Glu Ala Leu Ala Pro Pro Val Arg His Leu Ile Ala Thr Gln Leu Leu
                      320                 325                 330 tca aac ctt gaa gat atc atg agg atc ctg gcc aag agc ctg cct aaa        1421
      Ser Asn Leu Glu Asp Ile Met Arg Ile Leu Ala Lys Ser Leu Pro Lys
                  335                 340                 345 ggc ccc ttc acc tac att tcc cct tcg aac aca gag ctg acc ctg atg        1469
      Gly Pro Phe Thr Tyr Ile Ser Pro Ser Asn Thr Glu Leu Thr Leu Met
              350                 355                 360 atc cag gag cgg ggg gac aag aac gtc act atg ggt cag agc agc gca        1517
      Ile Gln Glu Arg Gly Asp Lys Asn Val Thr Met Gly Gln Ser Ser Ala
          365                 370                 375 cgc atg aag ctg aat tgg gct gtg gca gct gga gcc gag gat cca ggc        1565
```

```
                Arg Met Lys Leu Asn Trp Ala Val Ala Ala Gly Ala Glu Asp Pro Gly
                380             385                 390                 395 ccc gcc gtg gcg ggc atc ctc tcc atc cag aac atg acg aca ttg ctg         1613
Pro Ala Val Ala Gly Ile Leu Ser Ile Gln Asn Met Thr Thr Leu Leu
                400                 405                 410 gcc aat gcc tcc ttg aac ctg cat tcc aag aag caa gcc gaa ctg gag         1661
Ala Asn Ala Ser Leu Asn Leu His Ser Lys Lys Gln Ala Glu Leu Glu
                415                 420                 425 gag ata tat gaa agc agc atc cgt ggt gtc caa ctc aga cgc ctc tct         1709
Glu Ile Tyr Glu Ser Ser Ile Arg Gly Val Gln Leu Arg Arg Leu Ser
                430                 435                 440 gcc gtc aac tcc atc ttt ctg agc cac aac aac acc aag gaa ctc aac         1757
Ala Val Asn Ser Ile Phe Leu Ser His Asn Asn Thr Lys Glu Leu Asn
                445                 450                 455 tcc ccc atc ctt ttc gcc ttc tcc cac ctt gag tcc tcc gat ggg gag         1805
Ser Pro Ile Leu Phe Ala Phe Ser His Leu Glu Ser Ser Asp Gly Glu
460                 465                 470                 475 gcg gga aga gac cct cct gcc aag gac gtg atg cct ggg cca cgg cag         1853
Ala Gly Arg Asp Pro Pro Ala Lys Asp Val Met Pro Gly Pro Arg Gln
                480                 485                 490 gag ctg ctc tgt gcc ttc tgg aag agt gac agc gac agg gga ggg cac         1901
Glu Leu Leu Cys Ala Phe Trp Lys Ser Asp Ser Asp Arg Gly Gly His
                495                 500                 505 tgg gcc acc gag ggc tgc cag gtg ctg ggc agc aag aac ggc agc acc         1949
Trp Ala Thr Glu Gly Cys Gln Val Leu Gly Ser Lys Asn Gly Ser Thr
                510                 515                 520 acc tgc caa tgc agc cac ctg agc agc ttt gcg atc ctt atg gct cat         1997
Thr Cys Gln Cys Ser His Leu Ser Ser Phe Ala Ile Leu Met Ala His
525                 530                 535 tat gac gtg gag gac tgg aag ctg acc ctg atc acc agg gtg gga ctg         2045
Tyr Asp Val Glu Asp Trp Lys Leu Thr Leu Ile Thr Arg Val Gly Leu
540                 545                 550                 555 gcg ctg tca ctc ttc tgc ctg ctg ctg tgc atc ctc act ttc ctg ctg         2093
Ala Leu Ser Leu Phe Cys Leu Leu Leu Cys Ile Leu Thr Phe Leu Leu
                560                 565                 570 gtg cgg ccc atc cag ggc tcg cgc acc acc ata cac ctg cac ctc tgc         2141
Val Arg Pro Ile Gln Gly Ser Arg Thr Thr Ile His Leu His Leu Cys
                575                 580                 585 atc tgc ctc ttc gtg ggc tcc acc atc ttc ctg gcc ggc atc gag aac         2189
Ile Cys Leu Phe Val Gly Ser Thr Ile Phe Leu Ala Gly Ile Glu Asn
                590                 595                 600 gaa ggc ggc cag gtg ggg ctg cgc tgc cgc ctg gtg gcc ggg ctg ctg         2237
Glu Gly Gly Gln Val Gly Leu Arg Cys Arg Leu Val Ala Gly Leu Leu
605                 610                 615 cac tac tgt ttc ctg gcc gcc ttc tgc tgg atg agc ctc gaa ggc ctg         2285
His Tyr Cys Phe Leu Ala Ala Phe Cys Trp Met Ser Leu Glu Gly Leu
620                 625                 630                 635 gag ctc tac ttt ctt gtg gtg cgc gtg ttc caa ggc cag ggc ctg agt         2333
Glu Leu Tyr Phe Leu Val Val Arg Val Phe Gln Gly Gln Gly Leu Ser
                640                 645                 650 acg cgc tgg ctc tgc ctg atc ggc tat ggc gtg ccc ctg ctc atc gtg         2381
Thr Arg Trp Leu Cys Leu Ile Gly Tyr Gly Val Pro Leu Leu Ile Val
                655                 660                 665 ggc gtc tcg gct gcc atc tac agc aag ggc tac ggc cgc ccc aga tac         2429
Gly Val Ser Ala Ala Ile Tyr Ser Lys Gly Tyr Gly Arg Pro Arg Tyr
                670                 675                 680 tgc tgg ttg gac ttt gag cag ggc ttc ctc tgg agc ttc ttg gga cct         2477
Cys Trp Leu Asp Phe Glu Gln Gly Phe Leu Trp Ser Phe Leu Gly Pro
                685                 690                 695
```

| | | |
|---|---|---|
| gtg acc ttc atc att ttg tgc aat gct gtt att ttc gtg act acc gtc<br>Val Thr Phe Ile Ile Leu Cys Asn Ala Val Ile Phe Val Thr Thr Val<br>700                      705                    710                    715 | 2525 | |
| tgg aag ctc act cag aag ttt tct gaa atc aat cca gac atg aag aaa<br>Trp Lys Leu Thr Gln Lys Phe Ser Glu Ile Asn Pro Asp Met Lys Lys<br>                    720                    725                    730 | 2573 | |
| tta aag aag gcg agg gcg ctg acc atc acg gcc atc gcg cag ctc ttc<br>Leu Lys Lys Ala Arg Ala Leu Thr Ile Thr Ala Ile Ala Gln Leu Phe<br>             735                    740                    745 | 2621 | |
| ctg ttg ggc tgc acc tgg gtc ttt ggc ctg ttc atc ttc gac gat cgg<br>Leu Leu Gly Cys Thr Trp Val Phe Gly Leu Phe Ile Phe Asp Asp Arg<br>750                      755                    760 | 2669 | |
| agc ttg gtg ctg acc tat gtg ttt acc atc ctc aac tgc ctg cag ggc<br>Ser Leu Val Leu Thr Tyr Val Phe Thr Ile Leu Asn Cys Leu Gln Gly<br>             765                    770                    775 | 2717 | |
| gcc ttc ctc tac ctg ctg cac tgc ctg ctc aac aag aag gtt cgg gaa<br>Ala Phe Leu Tyr Leu Leu His Cys Leu Leu Asn Lys Lys Val Arg Glu<br>780                      785                    790                    795 | 2765 | |
| gaa tac cgg aag tgg gcc tgc cta gtt gct ggg ggg agc aag tac tca<br>Glu Tyr Arg Lys Trp Ala Cys Leu Val Ala Gly Gly Ser Lys Tyr Ser<br>                    800                    805                    810 | 2813 | |
| gaa ttc acc tcc acc acg tct ggc act ggc cac aat cag acc cgg gcc<br>Glu Phe Thr Ser Thr Thr Ser Gly Thr Gly His Asn Gln Thr Arg Ala<br>             815                    820                    825 | 2861 | |
| ctc agg gca tca gag tcc ggc ata tga aggcgcatgg ttctggacgg<br>Leu Arg Ala Ser Glu Ser Gly Ile<br>830                      835 | 2908 | |
| cccagcagct cctgtggcca cagcagcttt gtacacgaag accatccatc ctcccttcgt | 2968 | |
| ccaccactct actccctcca ccctccctcc ctgatcccgt gtgccaccag gagggagtgg | 3028 | |
| cagctatagt ctggcaccaa agtccaggac acccagtggg gtggagtcgg agccactggt | 3088 | |
| cctgctgctg gctgcctctc tgctccacct tgtgacccag ggtggggaca ggggctggcc | 3148 | |
| cagggctgca atgcagcatg ttgccctggc acctgtggcc agtactcggg acagactaag | 3208 | |
| ggcgcttgtc ccatcctgga cttttcctct catgtctttg ctgcagaact gaagagacta | 3268 | |
| ggcgctgggg ctcagcttcc ctcttaagct aagactgatg tcagaggccc catggcgagg | 3328 | |
| cccccttgggg ccactgcctg aggctcacgg tacagaggcc tgccctgcct ggccgggcag | 3388 | |
| gaggttctca ctgttgtgaa ggttgtagac gttgtgtaat gtgtttttat ctgttaaaat | 3448 | |
| ttttcagtgt tgacacttaa aattaaacac atgcatacag aagaaaaaaa aa | 3500 | |

<210> SEQ ID NO 40
<211> LENGTH: 835
<212> TYPE: PRT
<213> ORGANISM: Homo Sapiens

<400> SEQUENCE: 40

Met Gly Gly Arg Val Phe Leu Ala Phe Cys Val Trp Leu Thr Leu Pro
1                       5                              10                          15

Gly Ala Glu Thr Gln Asp Ser Arg Gly Cys Ala Arg Trp Cys Pro Gln
                    20                          25                        30

Asn Ser Ser Cys Val Asn Ala Thr Ala Cys Arg Cys Asn Pro Gly Phe
            35                    40                    45

Ser Ser Phe Ser Glu Ile Ile Thr Thr Pro Thr Glu Thr Cys Asp Asp
    50                    55                    60

Ile Asn Glu Cys Ala Thr Pro Ser Lys Val Ser Cys Gly Lys Phe Ser
65                      70                    75                    80

```
Asp Cys Trp Asn Thr Glu Gly Ser Tyr Asp Cys Val Cys Ser Pro Gly
                85                  90                  95

Tyr Glu Pro Val Ser Gly Ala Lys Thr Phe Lys Asn Glu Ser Glu Asn
            100                 105                 110

Thr Cys Gln Asp Val Asp Glu Cys Gln Gln Asn Pro Arg Leu Cys Lys
            115                 120                 125

Ser Tyr Gly Thr Cys Val Asn Thr Leu Gly Ser Tyr Thr Cys Gln Cys
            130                 135                 140

Leu Pro Gly Phe Lys Phe Ile Pro Glu Asp Pro Lys Val Cys Thr Asp
145                 150                 155                 160

Val Asn Glu Cys Thr Ser Gly Gln Asn Pro Cys His Ser Ser Thr His
                165                 170                 175

Cys Leu Asn Asn Val Gly Ser Tyr Gln Cys Arg Cys Arg Pro Gly Trp
            180                 185                 190

Gln Pro Ile Pro Gly Ser Pro Asn Gly Pro Asn Asn Thr Val Cys Glu
            195                 200                 205

Asp Val Asp Glu Cys Ser Ser Gly Gln His Gln Cys Asp Ser Ser Thr
            210                 215                 220

Val Cys Phe Asn Thr Val Gly Ser Tyr Ser Cys Arg Cys Arg Pro Gly
225                 230                 235                 240

Trp Lys Pro Arg His Gly Ile Pro Asn Asn Gln Lys Asp Thr Val Cys
                245                 250                 255

Glu Asp Met Thr Phe Ser Thr Trp Thr Pro Pro Gly Val His Ser
            260                 265                 270

Gln Thr Leu Ser Arg Phe Phe Asp Lys Val Gln Asp Leu Gly Arg Asp
            275                 280                 285

Ser Lys Thr Ser Ser Ala Glu Val Thr Ile Gln Asn Val Ile Lys Leu
            290                 295                 300

Val Asp Glu Leu Met Glu Ala Pro Gly Asp Val Glu Ala Leu Ala Pro
305                 310                 315                 320

Pro Val Arg His Leu Ile Ala Thr Gln Leu Leu Ser Asn Leu Glu Asp
                325                 330                 335

Ile Met Arg Ile Leu Ala Lys Ser Leu Pro Lys Gly Pro Phe Thr Tyr
            340                 345                 350

Ile Ser Pro Ser Asn Thr Glu Leu Thr Leu Met Ile Gln Glu Arg Gly
            355                 360                 365

Asp Lys Asn Val Thr Met Gly Gln Ser Ser Ala Arg Met Lys Leu Asn
            370                 375                 380

Trp Ala Val Ala Ala Gly Ala Glu Asp Pro Gly Pro Ala Val Ala Gly
385                 390                 395                 400

Ile Leu Ser Ile Gln Asn Met Thr Thr Leu Leu Ala Asn Ala Ser Leu
                405                 410                 415

Asn Leu His Ser Lys Lys Gln Ala Glu Leu Glu Glu Ile Tyr Glu Ser
            420                 425                 430

Ser Ile Arg Gly Val Gln Leu Arg Arg Leu Ser Ala Val Asn Ser Ile
            435                 440                 445

Phe Leu Ser His Asn Asn Thr Lys Glu Leu Asn Ser Pro Ile Leu Phe
            450                 455                 460

Ala Phe Ser His Leu Glu Ser Ser Asp Gly Glu Ala Gly Arg Asp Pro
465                 470                 475                 480

Pro Ala Lys Asp Val Met Pro Gly Pro Arg Gln Glu Leu Leu Cys Ala
                485                 490                 495

Phe Trp Lys Ser Asp Ser Asp Arg Gly Gly His Trp Ala Thr Glu Gly
```

```
                      500                 505                 510
Cys Gln Val Leu Gly Ser Lys Asn Gly Ser Thr Thr Cys Gln Cys Ser
            515                 520                 525

His Leu Ser Ser Phe Ala Ile Leu Met Ala His Tyr Asp Val Glu Asp
        530                 535                 540

Trp Lys Leu Thr Leu Ile Thr Arg Val Gly Leu Ala Leu Ser Leu Phe
545                 550                 555                 560

Cys Leu Leu Leu Cys Ile Leu Thr Phe Leu Leu Val Arg Pro Ile Gln
                565                 570                 575

Gly Ser Arg Thr Thr Ile His Leu His Leu Cys Ile Cys Leu Phe Val
            580                 585                 590

Gly Ser Thr Ile Phe Leu Ala Gly Ile Glu Asn Glu Gly Gly Gln Val
        595                 600                 605

Gly Leu Arg Cys Arg Leu Val Ala Gly Leu Leu His Tyr Cys Phe Leu
    610                 615                 620

Ala Ala Phe Cys Trp Met Ser Leu Glu Gly Leu Glu Leu Tyr Phe Leu
625                 630                 635                 640

Val Val Arg Val Phe Gln Gly Gln Gly Leu Ser Thr Arg Trp Leu Cys
                645                 650                 655

Leu Ile Gly Tyr Gly Val Pro Leu Leu Ile Val Gly Val Ser Ala Ala
            660                 665                 670

Ile Tyr Ser Lys Gly Tyr Gly Arg Pro Arg Tyr Cys Trp Leu Asp Phe
        675                 680                 685

Glu Gln Gly Phe Leu Trp Ser Phe Leu Gly Pro Val Thr Phe Ile Ile
    690                 695                 700

Leu Cys Asn Ala Val Ile Phe Val Thr Thr Val Trp Lys Leu Thr Gln
705                 710                 715                 720

Lys Phe Ser Glu Ile Asn Pro Asp Met Lys Lys Leu Lys Ala Arg
                725                 730                 735

Ala Leu Thr Ile Thr Ala Ile Ala Gln Leu Phe Leu Leu Gly Cys Thr
            740                 745                 750

Trp Val Phe Gly Leu Phe Ile Phe Asp Asp Arg Ser Leu Val Leu Thr
        755                 760                 765

Tyr Val Phe Thr Ile Leu Asn Cys Leu Gln Gly Ala Phe Leu Tyr Leu
    770                 775                 780

Leu His Cys Leu Leu Asn Lys Lys Val Arg Glu Glu Tyr Arg Lys Trp
785                 790                 795                 800

Ala Cys Leu Val Ala Gly Gly Ser Lys Tyr Ser Glu Phe Thr Ser Thr
                805                 810                 815

Thr Ser Gly Thr Gly His Asn Gln Thr Arg Ala Leu Arg Ala Ser Glu
            820                 825                 830

Ser Gly Ile
        835

<210> SEQ ID NO 41
<211> LENGTH: 1207
<212> TYPE: DNA
<213> ORGANISM: Homo Sapiens
<220> FEATURE:
<221> NAME/KEY: CDS
<222> LOCATION: (175)...(684)
<223> OTHER INFORMATION: CD99

<400> SEQUENCE: 41
ggaggccggg gcggggcggg cgcagccggc gctgagcttg cagggccgct cccctcaccc        60
```

```
gcccccttcg agtccccggg cttcgcccca cccggcccgt ggggagtat ctgtcctgcc      120 gccttcgccc acgccctgca ctccgggacc gtccctgcgc gctctgggcg cacc atg        177
                                                              Met
                                                              1 gcc cgc ggg gct gcg ctg gcg ctg ctc ttc ggc ctg ctg ggt gtt            225
Ala Arg Gly Ala Ala Leu Ala Leu Leu Leu Phe Gly Leu Leu Gly Val
            5                   10                  15 ctg gtc gcc gcc ccg gat ggt ggt ttc gat tta tcc gat gcc ctt cct        273
Leu Val Ala Ala Pro Asp Gly Gly Phe Asp Leu Ser Asp Ala Leu Pro
            20                  25                  30 ggg gat gac ttt gac tta gga gat gct gtt gtt gat gga gaa aat gac        321
Gly Asp Asp Phe Asp Leu Gly Asp Ala Val Val Asp Gly Glu Asn Asp
35                  40                  45 gac cca cga cca ccg aac cca ccc aaa ccg atg cca aat cca aac ccc        369
Asp Pro Arg Pro Pro Asn Pro Pro Lys Pro Met Pro Asn Pro Asn Pro
50                  55                  60                  65 aac cac cct agt tcc tcc ggt agc ttt tca gat gct gac ctt gcg gat        417
Asn His Pro Ser Ser Ser Gly Ser Phe Ser Asp Ala Asp Leu Ala Asp
            70                  75                  80 ggc gtt tca ggt gga gaa gga aaa gga ggc agt gat ggt gga ggc agc        465
Gly Val Ser Gly Gly Glu Gly Lys Gly Gly Ser Asp Gly Gly Gly Ser
            85                  90                  95 cac agg aaa gaa ggg gaa gag gcc gac gcc cca ggc gtg atc ccc ggg        513
His Arg Lys Glu Gly Glu Glu Ala Asp Ala Pro Gly Val Ile Pro Gly
            100                 105                 110 att gtg ggg gct gtc gtg gtc gcc gtg gct gga gcc atc tct agc ttc        561
Ile Val Gly Ala Val Val Val Ala Val Ala Gly Ala Ile Ser Ser Phe
115                 120                 125 att gct tac cag aaa aag aag cta tgc ttc aaa gaa aat gca gaa caa        609
Ile Ala Tyr Gln Lys Lys Lys Leu Cys Phe Lys Glu Asn Ala Glu Gln
130                 135                 140                 145 ggg gag gtg gac atg gag agc cac cgg aat gcc aac gca gag cca gct        657
Gly Glu Val Asp Met Glu Ser His Arg Asn Ala Asn Ala Glu Pro Ala
                150                 155                 160 gtt cag cgt act ctt tta gag aaa tag aagattgtcg gcagaaacag              704
Val Gln Arg Thr Leu Leu Glu Lys
                165 cccaggcgtt ggcagcaggg ttagaacagc tgcctgaggc tcctccctga aggacacctg      764 cctgagagca gagatggagg ccttctgttc acggcggatt cttgtttta atcttgcgat       824 gtgctttgct tgttgctggg cggatgatgt ttactaacga tgaattttac atccaaaggg     884 ggataggcac ttggaccccc attctccaag gcccggggg gcggtttccc atgggatgtg      944 aaaggctggc cattattaag tccctgtaac tcaaatgtca accccaccga ggcaccccc    1004 cgtcccccag aatcttggct gtttacaaat cacgtgtcca tcgagcacgt ctgaaacccc    1064 tggtagcccc gacttctttt taattaaaat aaggtaagcc cttcaatttg tttcttcaat    1124 atttctttca tttgtaggga tatttgtttt tcatatcaga ctaataaaaa gaaattagaa    1184 accaaaaaaa aaaaaaaaaa aaa                                             1207

<210> SEQ ID NO 42
<211> LENGTH: 169
<212> TYPE: PRT
<213> ORGANISM: Homo Sapiens

<400> SEQUENCE: 42

Met Ala Arg Gly Ala Ala Leu Ala Leu Leu Leu Phe Gly Leu Leu Gly
1               5                   10                  15
```

```
Val Leu Val Ala Ala Pro Asp Gly Gly Phe Asp Leu Ser Asp Ala Leu
            20                  25                  30

Pro Gly Asp Asp Phe Asp Leu Gly Asp Ala Val Val Asp Gly Glu Asn
                35                  40                  45

Asp Asp Pro Arg Pro Pro Asn Pro Pro Lys Pro Met Pro Asn Pro Asn
 50                  55                  60

Pro Asn His Pro Ser Ser Gly Ser Phe Ser Asp Ala Asp Leu Ala
 65                  70                  75                  80

Asp Gly Val Ser Gly Gly Glu Gly Lys Gly Gly Ser Asp Gly Gly
                85                  90                  95

Ser His Arg Lys Glu Gly Glu Glu Ala Asp Ala Pro Gly Val Ile Pro
                100                 105                 110

Gly Ile Val Gly Ala Val Val Ala Val Ala Gly Ala Ile Ser Ser
            115                 120                 125

Phe Ile Ala Tyr Gln Lys Lys Lys Leu Cys Phe Lys Glu Asn Ala Glu
            130                 135                 140

Gln Gly Glu Val Asp Met Glu Ser His Arg Asn Ala Asn Ala Glu Pro
145                 150                 155                 160

Ala Val Gln Arg Thr Leu Leu Glu Lys
                165
```

<210> SEQ ID NO 43
<211> LENGTH: 1229
<212> TYPE: DNA
<213> ORGANISM: Homo Sapiens
<220> FEATURE:
<221> NAME/KEY: CDS
<222> LOCATION: (233)...(1060)
<223> OTHER INFORMATION: CD102

<400> SEQUENCE: 43

```
gccctgctta tcagcagctt cccagcttcc tctgcctgga ttcttagagg cctggggtcc      60
tagaacgagc tggtgcacgt ggcttcccaa agatctctca gataatgaga ggaaatgcag     120
tcatcagttt gcagaaggct agggattctg gccatagct cagacctgcg cccaccatct     180
ccctccaggc agcccttggc tggtccctgc gagcccgtgg agactgccag ag atg tcc    238
                                                          Met Ser
                                                            1 tct ttc ggt tac agg acc ctg act gtg gcc ctc ttc acc ctg atc tgc      286
Ser Phe Gly Tyr Arg Thr Leu Thr Val Ala Leu Phe Thr Leu Ile Cys
        5                  10                  15 tgt cca gga tcg gat gag aag gta ttc gag gta cac gtg agg cca aag      334
Cys Pro Gly Ser Asp Glu Lys Val Phe Glu Val His Val Arg Pro Lys
     20                 25                  30 aag ctg gcg gtt gag ccc aaa ggg tcc ctc gag gtc aac tgc agc acc      382
Lys Leu Ala Val Glu Pro Lys Gly Ser Leu Glu Val Asn Cys Ser Thr
 35                  40                  45                  50 acc tgt aac cag cct gaa gtg ggt ggt ctg gag acc tct cta gat aag      430
Thr Cys Asn Gln Pro Glu Val Gly Gly Leu Glu Thr Ser Leu Asp Lys
             55                  60                  65 att ctg ctg gac gaa cag gct cag tgg aaa cat tac ttg gtc tca aac      478
Ile Leu Leu Asp Glu Gln Ala Gln Trp Lys His Tyr Leu Val Ser Asn
         70                  75                  80 atc tcc cat gac acg gtc ctc caa tgc cac ttc acc tgc tcc ggg aag      526
Ile Ser His Asp Thr Val Leu Gln Cys His Phe Thr Cys Ser Gly Lys
     85                  90                  95 cag gag tca atg aat tcc aac gtc agc gtg tac cag cct cca agg cag      574
Gln Glu Ser Met Asn Ser Asn Val Ser Val Tyr Gln Pro Pro Arg Gln
 100                 105                 110
```

```
gtc atc ctg aca ctg caa ccc act ttg gtg gct gtg ggc aag tcc ttc       622
Val Ile Leu Thr Leu Gln Pro Thr Leu Val Ala Val Gly Lys Ser Phe
115                 120                 125                 130 acc att gag tgc agg gtg ccc acc gtg gag ccc ctg gac agc ctc acc       670
Thr Ile Glu Cys Arg Val Pro Thr Val Glu Pro Leu Asp Ser Leu Thr
                135                 140                 145 ctc ttc ctg ttc cgt ggc aat gag act ctg cac tat gag acc ttc ggg       718
Leu Phe Leu Phe Arg Gly Asn Glu Thr Leu His Tyr Glu Thr Phe Gly
            150                 155                 160 aag gca gcc cct gct ccg cag gag gcc aca gcc aca ttc aac agc acg       766
Lys Ala Ala Pro Ala Pro Gln Glu Ala Thr Ala Thr Phe Asn Ser Thr
165                 170                 175 gct gac aga gag gat ggc cac cgc aac ttc tcc tgc ctg gct gtg ctg       814
Ala Asp Arg Glu Asp Gly His Arg Asn Phe Ser Cys Leu Ala Val Leu
    180                 185                 190 gac ttg atg tct cgc ggt ggc aac atc ttt cac aaa cac tca gcc ccg       862
Asp Leu Met Ser Arg Gly Gly Asn Ile Phe His Lys His Ser Ala Pro
195                 200                 205                 210 aag atg ttg gag atc tat gag cct gtg tcg gac agc cag atg gtc atc       910
Lys Met Leu Glu Ile Tyr Glu Pro Val Ser Asp Ser Gln Met Val Ile
                215                 220                 225 ata gtc acg gtg gtg tcg gtg ttg ctg tcc ctg ttc gtg aca tct gtc       958
Ile Val Thr Val Val Ser Val Leu Leu Ser Leu Phe Val Thr Ser Val
            230                 235                 240 ctg ctc tgc ttc atc ttc ggc cag cac ttg cgc cag cag cgg atg ggc       1006
Leu Leu Cys Phe Ile Phe Gly Gln His Leu Arg Gln Gln Arg Met Gly
        245                 250                 255 acc tac ggg gtg cga gcg gct tgg agg agg ctg ccc cag gcc ttc cgg       1054
Thr Tyr Gly Val Arg Ala Ala Trp Arg Arg Leu Pro Gln Ala Phe Arg
    260                 265                 270 cca tag caaccatgag tggcatggcc accaccacgg tggtcactgg aactcagtgt        1110
Pro
275 gactcctcag ggttgaggtc cagccctggc tgaaggactg tgacaggcag cagagacttg     1170 ggacattgcc ttttctagcc cgaatacaaa cacctggact taaaaaaaaa aaaaaaaa      1229

<210> SEQ ID NO 44
<211> LENGTH: 275
<212> TYPE: PRT
<213> ORGANISM: Homo Sapiens

<400> SEQUENCE: 44

Met Ser Ser Phe Gly Tyr Arg Thr Leu Thr Val Ala Leu Phe Thr Leu
1               5                   10                  15

Ile Cys Cys Pro Gly Ser Asp Glu Lys Val Phe Glu Val His Val Arg
            20                  25                  30

Pro Lys Lys Leu Ala Val Glu Pro Lys Gly Ser Leu Glu Val Asn Cys
        35                  40                  45

Ser Thr Thr Cys Asn Gln Pro Glu Val Gly Gly Leu Glu Thr Ser Leu
    50                  55                  60

Asp Lys Ile Leu Leu Asp Glu Gln Ala Gln Trp Lys His Tyr Leu Val
65                  70                  75                  80

Ser Asn Ile Ser His Asp Thr Val Leu Gln Cys His Phe Thr Cys Ser
                85                  90                  95

Gly Lys Gln Glu Ser Met Asn Ser Asn Val Ser Val Tyr Gln Pro Pro
            100                 105                 110

Arg Gln Val Ile Leu Thr Leu Gln Pro Thr Leu Val Ala Val Gly Lys
        115                 120                 125
```

```
Ser Phe Thr Ile Glu Cys Arg Val Pro Thr Val Glu Pro Leu Asp Ser
    130                 135                 140

Leu Thr Leu Phe Leu Phe Arg Gly Asn Glu Thr Leu His Tyr Glu Thr
145                 150                 155                 160

Phe Gly Lys Ala Ala Pro Ala Pro Gln Glu Ala Thr Ala Thr Phe Asn
                165                 170                 175

Ser Thr Ala Asp Arg Glu Asp Gly His Arg Asn Phe Ser Cys Leu Ala
                180                 185                 190

Val Leu Asp Leu Met Ser Arg Gly Gly Asn Ile Phe His Lys His Ser
                195                 200                 205

Ala Pro Lys Met Leu Glu Ile Tyr Glu Pro Val Ser Asp Ser Gln Met
    210                 215                 220

Val Ile Ile Val Thr Val Ser Val Leu Leu Ser Leu Phe Val Thr
225                 230                 235                 240

Ser Val Leu Leu Cys Phe Ile Phe Gly Gln His Leu Arg Gln Gln Arg
                245                 250                 255

Met Gly Thr Tyr Gly Val Arg Ala Ala Trp Arg Arg Leu Pro Gln Ala
                260                 265                 270

Phe Arg Pro
    275

<210> SEQ ID NO 45
<211> LENGTH: 1893
<212> TYPE: DNA
<213> ORGANISM: Homo Sapiens
<220> FEATURE:
<221> NAME/KEY: CDS
<222> LOCATION: (322)...(1221)
<223> OTHER INFORMATION: CD300a

<400> SEQUENCE: 45
cggggaagtg agagtcgggg atcagtcctg caagctacgg agtcactaca gggagaggtc        60
tcatcactag aaatagccga agaacctgca gcctcaacca gcgttaagga ggacgtgccg       120
tttctaggga gtcttagtcg gggctcacca gcttcctgca ttttctgacc ggctccagga       180
atagaaccaa agaagctgaa caaggaagc agcgcggcac caagaaaagc agaagtcggg        240
gccttggagg cgtgactttc ccctcgggtc caggtagggc ctggagctgc tgcaagtgcc       300
gcctgtgctg gggaagggac c atg tgg ctg cct tgg gct ctg ttg ctt ctc        351
                       Met Trp Leu Pro Trp Ala Leu Leu Leu Leu
                         1               5                  10 tgg gtc cca gga tgt ttt gct ctg agc aaa tgc agg acc gtg gcg ggc        399
Trp Val Pro Gly Cys Phe Ala Leu Ser Lys Cys Arg Thr Val Ala Gly
                15                  20                  25 ccc gtg ggg gga tcc ctg agt gtg cag tgt ccc tat gag aag gaa cac        447
Pro Val Gly Gly Ser Leu Ser Val Gln Cys Pro Tyr Glu Lys Glu His
            30                  35                  40 agg acc ctc aac aaa tac tgg tgc aga cca cca cag att ttc cta tgt        495
Arg Thr Leu Asn Lys Tyr Trp Cys Arg Pro Pro Gln Ile Phe Leu Cys
        45                  50                  55 gac aag att gtg gag acc aaa ggg tca gca gga aaa agg aac ggc cga        543
Asp Lys Ile Val Glu Thr Lys Gly Ser Ala Gly Lys Arg Asn Gly Arg
    60                  65                  70 gtg tcc atc agg gac agt cct gca aac ctc agc ttc aca gtg acc ctg        591
Val Ser Ile Arg Asp Ser Pro Ala Asn Leu Ser Phe Thr Val Thr Leu
75                  80                  85                  90 gag aat ctc aca gag gag gat gca ggc acc tac tgg tgt ggg gtg gat        639
Glu Asn Leu Thr Glu Glu Asp Ala Gly Thr Tyr Trp Cys Gly Val Asp
                95                  100                 105
```

| | | |
|---|---|---|
| aca cca tgg ctc cga gac ttt cat gat ccc gtt gtc gag gtt gag gtg<br>Thr Pro Trp Leu Arg Asp Phe His Asp Pro Val Val Glu Val Glu Val<br>110                        115                    120 | 687 |
| tcc gtg ttc ccg gca tca acg tca atg aca cct gca agt atc act gcg<br>Ser Val Phe Pro Ala Ser Thr Ser Met Thr Pro Ala Ser Ile Thr Ala<br>125                        130                    135 | 735 |
| gcc aag acc tca aca atc aca act gca ttt cca cct gta tca tcc act<br>Ala Lys Thr Ser Thr Ile Thr Thr Ala Phe Pro Pro Val Ser Ser Thr<br>140                        145                    150 | 783 |
| acc ctg ttt gca gtg ggt gcc acc cac agt gcc agc atc cag gag gaa<br>Thr Leu Phe Ala Val Gly Ala Thr His Ser Ala Ser Ile Gln Glu Glu<br>155                        160                    165                    170 | 831 |
| act gag gag gtg gtg aac tca cag ctc ccg ctc ctc tcc ctg ctg<br>Thr Glu Glu Val Val Asn Ser Gln Leu Pro Leu Leu Leu Ser Leu Leu<br>175                        180                    185 | 879 |
| gca ttg ttg ctg ctt ctg ttg gtg ggg gcc tcc ctg cta gcc tgg agg<br>Ala Leu Leu Leu Leu Leu Leu Val Gly Ala Ser Leu Leu Ala Trp Arg<br>190                        195                    200 | 927 |
| atg ttt cag aaa tgg atc aaa gct ggt gac cat tca gag ctg tcc cag<br>Met Phe Gln Lys Trp Ile Lys Ala Gly Asp His Ser Glu Leu Ser Gln<br>205                        210                    215 | 975 |
| aac ccc aag cag gct gcc acg cag agt gag ctg cac tac gca aat ctg<br>Asn Pro Lys Gln Ala Ala Thr Gln Ser Glu Leu His Tyr Ala Asn Leu<br>220                        225                    230 | 1023 |
| gag ctg ctg atg tgg cct ctg cag gaa aag cca gca cca cca agg gag<br>Glu Leu Leu Met Trp Pro Leu Gln Glu Lys Pro Ala Pro Pro Arg Glu<br>235                        240                    245                    250 | 1071 |
| gtg gag gtg gaa tac agc act gtg gcc tcc ccc agg gaa gaa ctt cac<br>Val Glu Val Glu Tyr Ser Thr Val Ala Ser Pro Arg Glu Glu Leu His<br>255                        260                    265 | 1119 |
| tat gcc tcg gtg gtg ttt gat tct aac acc aac agg ata gct gct cag<br>Tyr Ala Ser Val Val Phe Asp Ser Asn Thr Asn Arg Ile Ala Ala Gln<br>270                        275                    280 | 1167 |
| agg cct cgg gag gag gaa cca gat tca gat tac agt gtg ata agg aag<br>Arg Pro Arg Glu Glu Glu Pro Asp Ser Asp Tyr Ser Val Ile Arg Lys<br>285                        290                    295 | 1215 |
| aca tag gcttttgtcc tgcctcgcca tcggagctct catgggcccc aggaagtcca<br>Thr | 1271 |
| gggacagctc ccttatacct ggcccacgtc cttctcagcc tgccctcgac aacagtgacc | 1331 |
| aacagacagg cagctgggtt tcccaggcca tccctctgtt gccatcagct tgattggctt | 1391 |
| ccccgagggc cagcagggct gggggctccg gagagcagca ggaagcactc ccagccacca | 1451 |
| gtgcctgtca cctctttccc ctttgcccct gcttcatccc agctctgtgt gtggaggaca | 1511 |
| aagcttcttc ctgcgtggct ccaggaaaag atgtggctca cgtaggtggc acctgccaat | 1571 |
| agctttgtca atcacagccc cataggaacg tctggaattg cttgggagtt ggggagaact | 1631 |
| gtcaagaaga gtgaagagag tgccaaagcg gagatctgtt cacctggggg ccatggaggg | 1691 |
| gggacccact aaagatcaag atcaaagatt ctccccatct cacagacaag gaaactgagg | 1751 |
| ccagagggag gagagaattg ctcatggctc cagaactggt ggcaagtttc tctggactct | 1811 |
| taggtttatt tttaatatga aatataaaaa cagtttcaaa tatcttattg agggagaagt | 1871 |
| aaaaacttat ttaaacaatg cc | 1893 |

<210> SEQ ID NO 46
<211> LENGTH: 299
<212> TYPE: PRT
<213> ORGANISM: Homo Sapiens

```
<400> SEQUENCE: 46

Met Trp Leu Pro Trp Ala Leu Leu Leu Trp Val Pro Gly Cys Phe
 1               5                  10                  15

Ala Leu Ser Lys Cys Arg Thr Val Ala Gly Pro Val Gly Gly Ser Leu
            20                  25                  30

Ser Val Gln Cys Pro Tyr Glu Lys Glu His Arg Thr Leu Asn Lys Tyr
        35                  40                  45

Trp Cys Arg Pro Pro Gln Ile Phe Leu Cys Asp Lys Ile Val Glu Thr
    50                  55                  60

Lys Gly Ser Ala Gly Lys Arg Asn Gly Arg Val Ser Ile Arg Asp Ser
65                  70                  75                  80

Pro Ala Asn Leu Ser Phe Thr Val Thr Leu Glu Asn Leu Thr Glu Glu
                85                  90                  95

Asp Ala Gly Thr Tyr Trp Cys Gly Val Asp Thr Pro Trp Leu Arg Asp
            100                 105                 110

Phe His Asp Pro Val Val Glu Val Glu Val Ser Val Phe Pro Ala Ser
        115                 120                 125

Thr Ser Met Thr Pro Ala Ser Ile Thr Ala Ala Lys Thr Ser Thr Ile
    130                 135                 140

Thr Thr Ala Phe Pro Pro Val Ser Ser Thr Thr Leu Phe Ala Val Gly
145                 150                 155                 160

Ala Thr His Ser Ala Ser Ile Gln Glu Glu Thr Glu Glu Val Val Asn
                165                 170                 175

Ser Gln Leu Pro Leu Leu Leu Ser Leu Leu Ala Leu Leu Leu Leu Leu
            180                 185                 190

Leu Val Gly Ala Ser Leu Leu Ala Trp Arg Met Phe Gln Lys Trp Ile
        195                 200                 205

Lys Ala Gly Asp His Ser Glu Leu Ser Gln Asn Pro Lys Gln Ala Ala
    210                 215                 220

Thr Gln Ser Glu Leu His Tyr Ala Asn Leu Glu Leu Leu Met Trp Pro
225                 230                 235                 240

Leu Gln Glu Lys Pro Ala Pro Pro Arg Glu Val Glu Val Glu Tyr Ser
                245                 250                 255

Thr Val Ala Ser Pro Arg Glu Glu Leu His Tyr Ala Ser Val Val Phe
            260                 265                 270

Asp Ser Asn Thr Asn Arg Ile Ala Ala Gln Arg Pro Arg Glu Glu Glu
        275                 280                 285

Pro Asp Ser Asp Tyr Ser Val Ile Arg Lys Thr
290                 295
```